(12) United States Patent
Tanner et al.

(10) Patent No.: US 11,213,356 B2
(45) Date of Patent: Jan. 4, 2022

(54) SYSTEMS AND METHODS FOR POSITIONING AN ELONGATE MEMBER INSIDE A BODY

(71) Applicant: Auris Health, Inc., Redwood City, CA (US)

(72) Inventors: Neal A. Tanner, Burnet, TX (US); Teresa Miller, Palo Alto, CA (US); Christopher M. Sewell, Los Alamos, NM (US); Sean P. Walker, Mountain View, CA (US)

(73) Assignee: Auris Health, Inc., Redwood City, CA (US)

( * ) Notice: Subject to any disclaimer, the term of this patent is extended or adjusted under 35 U.S.C. 154(b) by 137 days.

(21) Appl. No.: 16/746,728

(22) Filed: Jan. 17, 2020

(65) Prior Publication Data
US 2020/0163726 A1    May 28, 2020

Related U.S. Application Data

(63) Continuation of application No. 16/165,375, filed on Oct. 19, 2018, now Pat. No. 10,555,780, which is a
(Continued)

(51) Int. Cl.
*A61B 34/20* (2016.01)
*A61B 34/35* (2016.01)
(Continued)

(52) U.S. Cl.
CPC .............. *A61B 34/20* (2016.02); *A61B 6/12* (2013.01); *A61B 6/4423* (2013.01); *A61B 8/12* (2013.01);
(Continued)

(58) Field of Classification Search
USPC ...................................... 606/1, 130
See application file for complete search history.

(56) References Cited

U.S. PATENT DOCUMENTS

| | | | |
|---|---|---|---|
| 3,572,325 | A | 3/1971 | Bazell et al. |
| 3,807,390 | A | 4/1974 | Ostrowski et al. |
| | | (Continued) | |

FOREIGN PATENT DOCUMENTS

| | | |
|---|---|---|
| CA | 2285342 | 10/1998 |
| CN | 1846181 | 10/2006 |
| | (Continued) | |

OTHER PUBLICATIONS

European Examination Report dated Jan. 27, 2014 for Application No. EP 11761231.7, 4 pgs.
(Continued)

*Primary Examiner* — Nicole F Lavert
(74) *Attorney, Agent, or Firm* — Frost Brown Todd LLC

(57) ABSTRACT

Systems and methods for introducing and driving flexible members in a patient's body are described herein. In one embodiment, a robotic method includes positioning a flexible elongated member that has a preformed configuration, wherein at least a part of the flexible elongated member has a first member disposed around it, and wherein the first member includes a first wire for bending the first member or for maintaining the first member in a bent configuration, releasing at least some tension in the first wire to relax the first member, and advancing the first member distally relative to the flexible elongated member while the first member is in a relaxed configuration.

20 Claims, 194 Drawing Sheets

Related U.S. Application Data continuation of application No. 14/603,836, filed on Jan. 23, 2015, now Pat. No. 10,130,427, which is a continuation of application No. 13/174,536, filed on Jun. 30, 2011, now abandoned.

(60) Provisional application No. 61/482,598, filed on May 4, 2011, provisional application No. 61/384,220, filed on Sep. 17, 2010.

(51) Int. Cl.

| | | |
|---|---|---|
| *A61B 34/00* | (2016.01) | |
| *A61B 46/10* | (2016.01) | |
| *A61B 6/12* | (2006.01) | |
| *A61B 8/00* | (2006.01) | |
| *G06T 19/00* | (2011.01) | |
| *A61B 34/37* | (2016.01) | |
| *A61B 6/00* | (2006.01) | |
| *A61B 8/12* | (2006.01) | |
| *A61B 34/30* | (2016.01) | |
| *A61B 34/10* | (2016.01) | |
| *A61B 90/00* | (2016.01) | |
| *A61B 17/00* | (2006.01) | |
| *A61B 8/08* | (2006.01) | |

(52) U.S. Cl.
CPC ............ *A61B 8/4218* (2013.01); *A61B 34/30* (2016.02); *A61B 34/35* (2016.02); *A61B 34/37* (2016.02); *A61B 34/71* (2016.02); *A61B 34/74* (2016.02); *A61B 46/10* (2016.02); *G06T 19/00* (2013.01); *A61B 6/487* (2013.01); *A61B 8/0841* (2013.01); *A61B 34/25* (2016.02); *A61B 90/361* (2016.02); *A61B 2017/00991* (2013.01); *A61B 2034/102* (2016.02); *A61B 2034/301* (2016.02); *A61B 2034/303* (2016.02); *A61B 2034/715* (2016.02); *A61B 2034/742* (2016.02); *G06T 2210/41* (2013.01)

(56) References Cited

U.S. PATENT DOCUMENTS

| | | |
|---|---|---|
| 3,913,565 A | 10/1975 | Kawahara |
| 4,294,234 A | 10/1981 | Matsuo |
| 4,392,485 A | 7/1983 | Hiltebrandt |
| 4,443,698 A | 4/1984 | Schiffner |
| 4,607,619 A | 8/1986 | Seike et al. |
| 4,690,175 A | 9/1987 | Ouchi et al. |
| 4,706,656 A | 11/1987 | Kubota |
| 4,741,326 A | 5/1988 | Sidall et al. |
| 4,745,908 A | 5/1988 | Wardle |
| 4,748,969 A | 6/1988 | Wardle |
| 4,750,475 A | 6/1988 | Yoshihashi |
| 4,761,073 A | 8/1988 | Meltz et al. |
| 4,771,766 A | 9/1988 | Aoshiro |
| 4,846,791 A | 7/1989 | Hattler et al. |
| 4,869,238 A | 9/1989 | Opie et al. |
| 4,906,496 A | 3/1990 | Hosono et al. |
| 4,907,168 A | 3/1990 | Boggs |
| 4,960,410 A | 10/1990 | Pinchuk |
| 4,967,732 A | 11/1990 | Inoue |
| 4,996,419 A | 2/1991 | Morey |
| 5,003,982 A | 4/1991 | Halperin |
| 5,007,705 A | 4/1991 | Morey et al. |
| 5,050,585 A | 9/1991 | Takahashi |
| 5,066,133 A | 11/1991 | Brienza |
| 5,067,346 A | 11/1991 | Field |
| 5,078,714 A | 1/1992 | Katims |
| 5,083,549 A | 1/1992 | Cho et al. |
| 5,086,401 A | 2/1992 | Glassman et al. |
| 5,106,387 A | 4/1992 | Kittrell et al. |
| 5,108,800 A | 4/1992 | Koo |
| 5,118,931 A | 6/1992 | Udd |
| 5,125,909 A | 6/1992 | Heimberger |
| 5,144,960 A | 9/1992 | Mehra et al. |
| 5,168,864 A | 12/1992 | Shockey |
| 5,217,002 A | 6/1993 | Katsurada |
| 5,251,611 A | 10/1993 | Zehel |
| 5,257,617 A | 11/1993 | Takahashi |
| 5,261,391 A | 11/1993 | Inoue |
| 5,267,339 A | 11/1993 | Yamauchi et al. |
| 5,287,861 A | 2/1994 | Wilk |
| 5,313,934 A | 5/1994 | Wiita et al. |
| 5,341,807 A | 8/1994 | Nardella |
| 5,344,395 A | 9/1994 | Whalen et al. |
| 5,386,818 A | 2/1995 | Schneebaum |
| 5,397,891 A | 3/1995 | Udd et al. |
| 5,401,956 A | 3/1995 | Dunphy et al. |
| 5,433,215 A | 7/1995 | Athanasiou et al. |
| 5,447,529 A | 9/1995 | Marchlinski et al. |
| 5,448,988 A | 9/1995 | Watanabe |
| 5,469,857 A | 11/1995 | Laurent et al. |
| 5,478,330 A | 12/1995 | Imran et al. |
| 5,482,029 A | 1/1996 | Sekiguchi |
| 5,489,270 A | 2/1996 | van Erp |
| 5,492,131 A | 2/1996 | Galel |
| 5,507,725 A | 4/1996 | Savage et al. |
| 5,533,985 A | 7/1996 | Wang |
| 5,549,542 A | 8/1996 | Kovaicheck |
| 5,563,967 A | 10/1996 | Haake |
| 5,580,200 A | 12/1996 | Fullerton |
| 5,591,965 A | 1/1997 | Udd |
| 5,627,927 A | 5/1997 | Udd |
| 5,630,783 A | 5/1997 | Steinberg |
| 5,662,108 A | 9/1997 | Budd et al. |
| 5,673,704 A | 10/1997 | Marchlinski et al. |
| 5,676,653 A | 10/1997 | Taylor et al. |
| 5,681,296 A | 10/1997 | Ishida |
| 5,704,534 A | 1/1998 | Huitema et al. |
| 5,720,775 A | 2/1998 | Larnard |
| 5,722,959 A | 3/1998 | Bierman |
| 5,741,429 A | 4/1998 | Donadio, III |
| 5,749,889 A | 5/1998 | Bacich et al. |
| 5,798,521 A | 8/1998 | Froggatt |
| 5,810,716 A | 9/1998 | Mukherjee et al. |
| 5,828,059 A | 10/1998 | Udd |
| 5,836,874 A | 11/1998 | Swanson et al. |
| 5,836,990 A | 11/1998 | Li |
| 5,845,646 A | 12/1998 | Lernelson |
| 5,873,817 A | 2/1999 | Kokish et al. |
| 5,876,325 A | 3/1999 | Mizuno et al. |
| 5,879,287 A | 3/1999 | Yoshihashi |
| 5,882,347 A | 3/1999 | Mouris-Laan |
| 5,888,191 A | 3/1999 | Akiba |
| 5,891,095 A | 4/1999 | Eggers et al. |
| 5,910,129 A | 6/1999 | Koblish et al. |
| 5,911,694 A | 6/1999 | Ikeda et al. |
| 5,917,978 A | 6/1999 | Rutterman |
| 5,935,079 A | 8/1999 | Swanson et al. |
| 5,938,586 A | 8/1999 | Wilk |
| 5,938,587 A | 8/1999 | Taylor et al. |
| 6,004,271 A | 12/1999 | Moore |
| 6,012,494 A | 1/2000 | Balazs |
| 6,035,082 A | 3/2000 | Murphy et al. |
| 6,061,587 A | 5/2000 | Kucharczyk et al. |
| 6,068,604 A | 5/2000 | Krause et al. |
| 6,069,420 A | 5/2000 | Mizzi et al. |
| 6,096,004 A | 8/2000 | Meglan et al. |
| 6,143,013 A | 11/2000 | Samson et al. |
| 6,144,026 A | 11/2000 | Udd et al. |
| 6,157,853 A | 12/2000 | Blume et al. |
| 6,174,280 B1 | 1/2001 | Oneda |
| 6,197,015 B1 | 3/2001 | Wilson |
| 6,198,974 B1 | 3/2001 | Webster, Jr. |
| 6,201,984 B1 | 3/2001 | Funda et al. |
| 6,215,943 B1 | 4/2001 | Crofts et al. |
| 6,234,958 B1 | 5/2001 | Snoke et al. |
| 6,256,090 B1 | 7/2001 | Chen et al. |
| 6,275,511 B1 | 8/2001 | Pan et al. |
| 6,275,628 B1 | 8/2001 | Jones et al. |
| 6,301,420 B1 | 10/2001 | Greenaway et al. |

(56) References Cited

U.S. PATENT DOCUMENTS

| | | |
|---|---|---|
| 6,315,715 B1 | 11/2001 | Taylor et al. |
| 6,331,181 B1 | 12/2001 | Tierney et al. |
| 6,364,888 B1 | 4/2002 | Niemeyer et al. |
| 6,366,722 B1 | 4/2002 | Murphy et al. |
| 6,381,483 B1 | 4/2002 | Hareyama et al. |
| 6,389,187 B1 | 5/2002 | Greenaway et al. |
| 6,404,497 B1 | 6/2002 | Backman |
| 6,404,956 B1 | 6/2002 | Brennan, III et al. |
| 6,426,796 B1 | 7/2002 | Pulliam et al. |
| 6,436,107 B1 | 8/2002 | Wang et al. |
| 6,464,632 B1 | 10/2002 | Taylor |
| 6,470,205 B2 | 10/2002 | Bosselmann et al. |
| 6,471,710 B1 | 10/2002 | Bucholtz |
| 6,485,411 B1 | 11/2002 | Konstorum |
| 6,491,626 B1 | 12/2002 | Stone et al. |
| 6,530,913 B1 | 3/2003 | Giba et al. |
| 6,537,205 B1 | 3/2003 | Smith |
| 6,544,230 B1 | 4/2003 | Flaherty |
| 6,545,760 B1 | 4/2003 | Froggatt |
| 6,550,342 B2 | 4/2003 | Croteau et al. |
| 6,551,273 B1 | 4/2003 | Olson et al. |
| 6,554,793 B1 | 4/2003 | Pauker et al. |
| 6,569,084 B1 | 5/2003 | Mizuno et al. |
| 6,571,639 B1 | 6/2003 | May et al. |
| 6,610,007 B2 | 8/2003 | Belson et al. |
| 6,611,700 B1 | 8/2003 | Vilsmeier et al. |
| 6,669,709 B1 | 12/2003 | Cohn |
| 6,671,055 B1 | 12/2003 | Wavering et al. |
| 6,697,664 B2 | 2/2004 | Kienzle, III et al. |
| 6,716,178 B1 | 4/2004 | Kilpatrick et al. |
| 6,726,699 B1 | 4/2004 | Wright et al. |
| 6,741,883 B2 | 5/2004 | Gildenberg |
| 6,746,422 B1 | 6/2004 | Noriega |
| 6,749,560 B1 | 6/2004 | Konstorum |
| 6,790,173 B2 | 9/2004 | Saadat |
| 6,796,963 B2 | 9/2004 | Carpenter et al. |
| 6,817,981 B2 | 11/2004 | Luce |
| 6,826,343 B2 | 11/2004 | Davis et al. |
| 6,827,710 B1 | 12/2004 | Mooney et al. |
| 6,827,712 B2 | 12/2004 | Tovey et al. |
| 6,837,846 B2 | 1/2005 | Jaffe |
| 6,850,817 B1 | 2/2005 | Green |
| 6,868,195 B2 | 3/2005 | Fujita |
| 6,876,786 B2 | 4/2005 | Chliaguine et al. |
| 6,888,623 B2 | 5/2005 | Clements |
| 6,892,090 B2 | 5/2005 | Verard et al. |
| 6,898,337 B2 | 5/2005 | Averett et al. |
| 6,905,460 B2 | 6/2005 | Wang et al. |
| 6,908,428 B2 | 6/2005 | Aizenfeld |
| 6,921,362 B2 | 7/2005 | Ouchi |
| 6,923,048 B2 | 8/2005 | Willsch et al. |
| 6,958,035 B2 | 10/2005 | Friedman et al. |
| 6,965,708 B2 | 11/2005 | Luo et al. |
| 6,974,455 B2 | 12/2005 | Garabedian et al. |
| 6,987,897 B2 | 1/2006 | Elster et al. |
| 7,008,401 B2 | 3/2006 | Thompson et al. |
| 7,010,182 B2 | 3/2006 | Pennington |
| 7,038,190 B2 | 5/2006 | Udd et al. |
| 7,042,573 B2 | 5/2006 | Froggatt |
| 7,046,866 B2 | 5/2006 | Sahlgren et al. |
| 7,130,700 B2 | 10/2006 | Gardeski et al. |
| 7,154,081 B1 | 12/2006 | Friedersdorf et al. |
| 7,330,245 B2 | 2/2008 | Froggatt |
| RE40,176 E | 3/2008 | Peshkin et al. |
| 7,371,210 B2 | 5/2008 | Brock |
| 7,404,824 B1 | 7/2008 | Webler et al. |
| 7,538,883 B2 | 5/2009 | Froggatt |
| 7,540,866 B2 | 6/2009 | Viswanathan et al. |
| 7,561,276 B2 | 7/2009 | Boyd |
| 7,594,903 B2 | 9/2009 | Webler et al. |
| 7,645,230 B2 | 1/2010 | Mikkaichi |
| 7,645,231 B2 | 1/2010 | Akiba |
| 7,742,805 B2 | 6/2010 | Furnish et al. |
| 7,772,541 B2 | 8/2010 | Froggatt et al. |
| 7,781,724 B2 | 8/2010 | Childers et al. |
| 7,789,827 B2 | 9/2010 | Landry |
| 7,789,874 B2 | 9/2010 | Yu et al. |
| 7,789,875 B2 | 9/2010 | Brock et al. |
| 7,850,642 B2 | 12/2010 | Moll et al. |
| 7,930,065 B2 | 4/2011 | Larkin et al. |
| 8,046,049 B2 | 10/2011 | Govari et al. |
| 8,050,523 B2 | 11/2011 | Younge et al. |
| 8,052,621 B2 | 11/2011 | Wallace et al. |
| 8,052,636 B2 | 11/2011 | Moll et al. |
| 8,092,397 B2 | 1/2012 | Wallace et al. |
| 8,219,178 B2 | 7/2012 | Smith et al. |
| 8,246,536 B2 | 8/2012 | Ochi |
| 8,290,571 B2 | 10/2012 | Younge et al. |
| 8,317,746 B2 | 11/2012 | Sewell et al. |
| 8,391,957 B2 | 3/2013 | Carlson et al. |
| 8,444,637 B2 | 5/2013 | Podmore et al. |
| 8,460,236 B2 | 6/2013 | Roelle et al. |
| 8,498,691 B2 | 7/2013 | Moll et al. |
| 8,515,215 B2 | 8/2013 | Younge et al. |
| 8,652,030 B2 | 2/2014 | Matsuura et al. |
| 8,657,781 B2 | 2/2014 | Sewell et al. |
| 8,672,837 B2 | 3/2014 | Roelle et al. |
| 8,686,747 B2 | 4/2014 | Berner |
| 8,705,903 B2 | 4/2014 | Younge et al. |
| 8,720,448 B2 | 5/2014 | Romo et al. |
| 8,758,231 B2 | 6/2014 | Bunch et al. |
| 8,811,777 B2 | 8/2014 | Younge et al. |
| 8,818,143 B2 | 8/2014 | Younge et al. |
| 8,827,947 B2 | 9/2014 | Bosman et al. |
| 8,864,655 B2 | 10/2014 | Ramarurthy et al. |
| 9,014,851 B2 | 4/2015 | Wong et al. |
| 9,057,600 B2 | 6/2015 | Walker et al. |
| 9,138,166 B2 | 9/2015 | Wong et al. |
| 9,173,713 B2 | 11/2015 | Hart et al. |
| 9,186,046 B2 | 11/2015 | Ramamurthy et al. |
| 9,186,047 B2 | 11/2015 | Ramamurthy et al. |
| 9,254,123 B2 | 2/2016 | Alvarez et al. |
| 9,271,663 B2 | 3/2016 | Walker et al. |
| 9,283,046 B2 | 3/2016 | Walker et al. |
| 9,289,578 B2 | 3/2016 | Walker et al. |
| 9,314,953 B2 | 4/2016 | Lauer |
| 9,404,734 B2 | 8/2016 | Ramamurthy et al. |
| 9,427,551 B2 | 8/2016 | Leeflang et al. |
| 9,441,954 B2 | 9/2016 | Ramamurthy et al. |
| 9,498,291 B2 | 11/2016 | Balaji et al. |
| 9,498,601 B2 | 11/2016 | Tanner et al. |
| 9,500,472 B2 | 11/2016 | Ramamurthy et al. |
| 9,500,473 B2 | 11/2016 | Ramamurthy et al. |
| 9,504,604 B2 | 11/2016 | Alvarez |
| 9,532,840 B2 | 1/2017 | Wong et al. |
| 9,561,083 B2 | 2/2017 | Yu et al. |
| 9,566,414 B2 | 2/2017 | Wong et al. |
| 9,591,990 B2 | 3/2017 | Chen et al. |
| 9,622,827 B2 | 4/2017 | Yu et al. |
| 9,629,595 B2 | 4/2017 | Walker et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,726,476 B2 | 8/2017 | Ramarnurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,827,061 B2 | 11/2017 | Balaji et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,659 B2 | 3/2018 | Chopra |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |

(56) References Cited

U.S. PATENT DOCUMENTS

| | | |
|---|---|---|
| 10,046,140 B2 | 8/2018 | Kokish et al. |
| 10,080,576 B2 | 9/2018 | Romo et al. |
| 10,123,755 B2 | 11/2018 | Walker et al. |
| 10,130,427 B2 | 11/2018 | Tanner et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,363,103 B2 | 7/2019 | Alvarez et al. |
| 10,376,672 B2 | 8/2019 | Yu |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,463,439 B2 | 11/2019 | Joseph et al. |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,539,478 B2 | 1/2020 | Lin |
| 10,543,048 B2 | 1/2020 | Noonan et al. |
| 10,555,778 B2 | 2/2020 | Ummalaneni et al. |
| 10,555,780 B2 | 2/2020 | Tanner et al. |
| 10,765,487 B2 | 9/2020 | Ho |
| 2001/0004676 A1 | 6/2001 | Ouchi |
| 2001/0009976 A1 | 7/2001 | Panescu et al. |
| 2001/0021843 A1 | 9/2001 | Bosselmann et al. |
| 2001/0029366 A1 | 10/2001 | Swanson et al. |
| 2002/0064330 A1 | 5/2002 | Croteau et al. |
| 2002/0087169 A1 | 7/2002 | Brock et al. |
| 2002/0138009 A1 | 9/2002 | Brockway et al. |
| 2002/0177789 A1 | 11/2002 | Ferry et al. |
| 2003/0036748 A1 | 2/2003 | Cooper et al. |
| 2003/0050649 A1 | 3/2003 | Brock et al. |
| 2003/0055360 A1 | 3/2003 | Zeleznik et al. |
| 2003/0073908 A1 | 4/2003 | Desai |
| 2003/0074011 A1 | 4/2003 | Gilboa et al. |
| 2003/0130564 A1 | 7/2003 | Martone et al. |
| 2003/0135204 A1 | 7/2003 | Lee et al. |
| 2003/0158545 A1 | 8/2003 | Hovda et al. |
| 2003/0163199 A1 | 8/2003 | Chu et al. |
| 2003/0181809 A1 | 9/2003 | Hall et al. |
| 2003/0188585 A1 | 10/2003 | Esser et al. |
| 2003/0195502 A1 | 10/2003 | Garabedian et al. |
| 2003/0195664 A1 | 10/2003 | Nowlin et al. |
| 2004/0015122 A1 | 1/2004 | Zhang et al. |
| 2004/0034282 A1 | 2/2004 | Quaid, III |
| 2004/0034300 A1 | 2/2004 | Verard et al. |
| 2004/0054322 A1 | 3/2004 | Vargas |
| 2004/0068173 A1 | 4/2004 | Viswanathan |
| 2004/0072066 A1 | 4/2004 | Cho et al. |
| 2004/0138525 A1 | 7/2004 | Saadat et al. |
| 2004/0152972 A1 | 8/2004 | Hunter |
| 2004/0165810 A1 | 8/2004 | Fujita |
| 2004/0171929 A1 | 9/2004 | Leitner et al. |
| 2004/0176751 A1 | 9/2004 | Weitzner et al. |
| 2004/0193013 A1 | 9/2004 | Isakawa et al. |
| 2004/0193146 A1 | 9/2004 | Lee et al. |
| 2004/0208413 A1 | 10/2004 | Scandale et al. |
| 2004/0220588 A1 | 11/2004 | Kermode et al. |
| 2004/0249246 A1 | 12/2004 | Campos |
| 2005/0004515 A1 | 1/2005 | Hart et al. |
| 2005/0036140 A1 | 2/2005 | Elster et al. |
| 2005/0054934 A1 | 3/2005 | Furnish et al. |
| 2005/0085728 A1 | 4/2005 | Fukuda |
| 2005/0125005 A1 | 6/2005 | Fujikura |
| 2005/0131279 A1 | 6/2005 | Boulais et al. |
| 2005/0154262 A1 | 7/2005 | Banik et al. |
| 2005/0159646 A1 | 7/2005 | Nordstrom et al. |
| 2005/0159789 A1 | 7/2005 | Brockway et al. |
| 2005/0165366 A1 | 7/2005 | Brustad |
| 2005/0182295 A1 | 8/2005 | Soper et al. |
| 2005/0182330 A1 | 8/2005 | Brockway et al. |
| 2005/0201664 A1 | 9/2005 | Udd et al. |
| 2005/0203382 A1 | 9/2005 | Govari et al. |
| 2005/0222554 A1 | 10/2005 | Wallace et al. |
| 2005/0222581 A1 | 10/2005 | Fischer et al. |
| 2005/0234293 A1 | 10/2005 | Yamamoto |
| 2005/0254575 A1 | 11/2005 | Hannuksela et al. |
| 2005/0256452 A1 | 11/2005 | DeMarchi |
| 2005/0272975 A1 | 12/2005 | McWeeney et al. |
| 2005/0273085 A1 | 12/2005 | Hinman et al. |
| 2005/0288549 A1 | 12/2005 | Mathis |
| 2006/0013523 A1 | 1/2006 | Childers et al. |
| 2006/0025679 A1 | 2/2006 | Viswanathan et al. |
| 2006/0036164 A1 | 2/2006 | Wilson et al. |
| 2006/0036213 A1 | 2/2006 | Viswanathan et al. |
| 2006/0041188 A1 | 2/2006 | Dirusso et al. |
| 2006/0100610 A1 | 5/2006 | Wallace et al. |
| 2006/0111692 A1 | 5/2006 | Hlavka et al. |
| 2006/0142897 A1 | 6/2006 | Green |
| 2006/0161045 A1 | 7/2006 | Merril et al. |
| 2006/0200049 A1 | 9/2006 | Leo et al. |
| 2006/0241368 A1 | 10/2006 | Fichtinger et al. |
| 2006/0264708 A1 | 11/2006 | Horne |
| 2006/0271036 A1 | 11/2006 | Garabedian et al. |
| 2006/0276827 A1 | 12/2006 | Mitelberg et al. |
| 2006/0285638 A1 | 12/2006 | Boese et al. |
| 2006/0293864 A1 | 12/2006 | Soss |
| 2007/0013336 A1 | 1/2007 | Nowlin et al. |
| 2007/0038181 A1 | 2/2007 | Melamud et al. |
| 2007/0060847 A1 | 3/2007 | Leo et al. |
| 2007/0060879 A1 | 3/2007 | Weitzner et al. |
| 2007/0112355 A1 | 5/2007 | Salahieh |
| 2007/0135733 A1 | 6/2007 | Soukup et al. |
| 2007/0135763 A1 | 6/2007 | Musbach et al. |
| 2007/0135803 A1 | 6/2007 | Belson |
| 2007/0156019 A1 | 7/2007 | Larkin et al. |
| 2007/0201793 A1 | 8/2007 | Askins et al. |
| 2007/0265503 A1 | 11/2007 | Schlesinger et al. |
| 2007/0270645 A1 | 11/2007 | Ikeda |
| 2007/0270679 A1 | 11/2007 | Nguyen et al. |
| 2007/0282167 A1 | 12/2007 | Barenboym et al. |
| 2007/0287886 A1 | 12/2007 | Saadat |
| 2008/0009750 A1 | 1/2008 | Aeby et al. |
| 2008/0039255 A1 | 2/2008 | Jinno et al. |
| 2008/0043902 A1 | 2/2008 | Viswanathan et al. |
| 2008/0051629 A1 | 2/2008 | Sugiyama et al. |
| 2008/0065103 A1 | 3/2008 | Cooper et al. |
| 2008/0097293 A1 | 4/2008 | Chin et al. |
| 2008/0108869 A1 | 5/2008 | Sanders et al. |
| 2008/0139887 A1 | 6/2008 | Fitpatrick |
| 2008/0140087 A1 | 6/2008 | Barbagli et al. |
| 2008/0146874 A1 | 6/2008 | Miller |
| 2008/0147089 A1 | 6/2008 | Loh |
| 2008/0177285 A1 | 7/2008 | Brock et al. |
| 2008/0208001 A1 | 8/2008 | Hadani |
| 2008/0212082 A1 | 9/2008 | Froggatt et al. |
| 2008/0218770 A1 | 9/2008 | Moll et al. |
| 2008/0255505 A1 | 10/2008 | Carlson et al. |
| 2008/0300592 A1 | 12/2008 | Weitzner et al. |
| 2009/0054884 A1 | 2/2009 | Farley et al. |
| 2009/0076476 A1 | 3/2009 | Barbagli et al. |
| 2009/0099420 A1 | 4/2009 | Woodley et al. |
| 2009/0123111 A1 | 5/2009 | Udd |
| 2009/0163851 A1 | 6/2009 | Holloway |
| 2009/0247880 A1 | 10/2009 | Naruse et al. |
| 2009/0248039 A1 | 10/2009 | Cooper et al. |
| 2009/0254083 A1 | 10/2009 | Wallace et al. |

(56) References Cited

U.S. PATENT DOCUMENTS

| | | |
|---|---|---|
| 2009/0262109 A1 | 10/2009 | Markowitz et al. |
| 2009/0299344 A1 | 12/2009 | Lee et al. |
| 2009/0306587 A1 | 12/2009 | Milijasevic et al. |
| 2010/0030023 A1 | 2/2010 | Yoshie |
| 2010/0073150 A1 | 3/2010 | Olson et al. |
| 2010/0106140 A1 | 4/2010 | Odland et al. |
| 2010/0114115 A1 | 5/2010 | Schlesinger et al. |
| 2010/0125284 A1 | 5/2010 | Tanner et al. |
| 2010/0130823 A1 | 5/2010 | Ando |
| 2010/0168918 A1 | 7/2010 | Zhao |
| 2010/0217184 A1 | 8/2010 | Koblish et al. |
| 2010/0228191 A1 | 9/2010 | Alvarez et al. |
| 2010/0249497 A1 | 9/2010 | Peine et al. |
| 2010/0249506 A1 | 9/2010 | Prisco et al. |
| 2010/0280525 A1 | 11/2010 | Alvarez et al. |
| 2010/0331856 A1 | 12/2010 | Carlson et al. |
| 2011/0009863 A1 | 1/2011 | Stanislaw |
| 2011/0046441 A1 | 2/2011 | Wiltshire et al. |
| 2011/0077681 A1 | 3/2011 | Nagano |
| 2011/0098533 A1 | 4/2011 | Onoda |
| 2011/0130718 A1 | 6/2011 | Kidd et al. |
| 2011/0148442 A1 | 6/2011 | Berner |
| 2011/0152880 A1 | 6/2011 | Alvarez et al. |
| 2011/0245844 A1 | 10/2011 | Jinno et al. |
| 2011/0261183 A1 | 10/2011 | Ma et al. |
| 2011/0295247 A1 | 12/2011 | Schlesinger et al. |
| 2011/0295248 A1 | 12/2011 | Wallace et al. |
| 2011/0295267 A1 | 12/2011 | Tanner et al. |
| 2011/0295268 A1 | 12/2011 | Roelle et al. |
| 2011/0306836 A1 | 12/2011 | Ohline et al. |
| 2011/0319910 A1 | 12/2011 | Roelle et al. |
| 2012/0071752 A1 | 3/2012 | Sewell |
| 2012/0071821 A1 | 3/2012 | Yu |
| 2012/0071822 A1 | 3/2012 | Romo et al. |
| 2012/0071894 A1 | 3/2012 | Tanner et al. |
| 2012/0071895 A1 | 3/2012 | Stahler et al. |
| 2012/0123327 A1 | 5/2012 | Miller |
| 2012/0136419 A1 | 5/2012 | Zarembo et al. |
| 2012/0143226 A1 | 6/2012 | Belson et al. |
| 2012/0190976 A1 | 7/2012 | Kleinstreuer |
| 2012/0191107 A1 | 7/2012 | Tanner et al. |
| 2012/0239012 A1 | 9/2012 | Laurent et al. |
| 2012/0259244 A1 | 10/2012 | Roberts et al. |
| 2012/0283747 A1 | 11/2012 | Popovic |
| 2012/0289777 A1 | 11/2012 | Chopra |
| 2013/0018400 A1 | 1/2013 | Milton et al. |
| 2013/0030519 A1 | 1/2013 | Tran et al. |
| 2013/0035537 A1 | 2/2013 | Wallace et al. |
| 2013/0085330 A1 | 4/2013 | Ramamurthy et al. |
| 2013/0085331 A1 | 4/2013 | Ramamurthy et al. |
| 2013/0085333 A1 | 4/2013 | Ramamurthy et al. |
| 2013/0090528 A1 | 4/2013 | Ramamurthy et al. |
| 2013/0090530 A1 | 4/2013 | Ramamurthy |
| 2013/0090552 A1 | 4/2013 | Ramamurthy et al. |
| 2013/0109957 A1 | 5/2013 | Hooft et al. |
| 2013/0144116 A1 | 6/2013 | Cooper et al. |
| 2013/0165854 A1 | 6/2013 | Sandhu et al. |
| 2013/0165908 A1 | 6/2013 | Purdy et al. |
| 2013/0165945 A9 | 6/2013 | Roelle |
| 2013/0204124 A1 | 8/2013 | Duindam |
| 2013/0226151 A1 | 8/2013 | Suehara |
| 2013/0303892 A1 | 11/2013 | Zhao |
| 2013/0304091 A1 | 11/2013 | Straehnz et al. |
| 2013/0317276 A1 | 11/2013 | D'Andrea |
| 2013/0317519 A1 | 11/2013 | Romo et al. |
| 2013/0345519 A1 | 12/2013 | Piskun et al. |
| 2014/0012288 A1 | 1/2014 | Darisse |
| 2014/0046313 A1 | 2/2014 | Pederson et al. |
| 2014/0142591 A1 | 5/2014 | Alvarez et al. |
| 2014/0200402 A1 | 7/2014 | Snoke et al. |
| 2014/0235943 A1 | 8/2014 | Paris |
| 2014/0257334 A1 | 9/2014 | Wong et al. |
| 2014/0264081 A1 | 9/2014 | Walker et al. |
| 2014/0275988 A1 | 9/2014 | Walker et al. |
| 2014/0276392 A1 | 9/2014 | Wong et al. |
| 2014/0276394 A1 | 9/2014 | Wong et al. |
| 2014/0276594 A1 | 9/2014 | Tanner et al. |
| 2014/0276646 A1 | 9/2014 | Wong et al. |
| 2014/0276934 A1 | 9/2014 | Balaji et al. |
| 2014/0276937 A1 | 9/2014 | Wong et al. |
| 2014/0277747 A1 | 9/2014 | Walker et al. |
| 2014/0316397 A1 | 10/2014 | Brown |
| 2014/0343416 A1 | 11/2014 | Panescu |
| 2014/0357984 A1 | 12/2014 | Wallace et al. |
| 2014/0364870 A1 | 12/2014 | Alvarez et al. |
| 2015/0031950 A1 | 1/2015 | Drontle et al. |
| 2015/0142013 A1 | 5/2015 | Tanner et al. |
| 2015/0223902 A1 | 8/2015 | Walker et al. |
| 2015/0255782 A1 | 9/2015 | Kim et al. |
| 2015/0265807 A1 | 9/2015 | Park et al. |
| 2015/0375399 A1 | 12/2015 | Chiu et al. |
| 2016/0000414 A1 | 1/2016 | Brown |
| 2016/0001038 A1 | 1/2016 | Romo et al. |
| 2016/0007881 A1 | 1/2016 | Wong et al. |
| 2016/0067009 A1 | 3/2016 | Ramamurthy et al. |
| 2016/0067450 A1 | 3/2016 | Kowshik |
| 2016/0183841 A1 | 6/2016 | Duindam et al. |
| 2016/0202053 A1 | 7/2016 | Walker et al. |
| 2016/0213432 A1 | 7/2016 | Flexman |
| 2016/0227982 A1 | 8/2016 | Takahashi |
| 2016/0228032 A1 | 8/2016 | Walker et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0346049 A1 | 12/2016 | Allen et al. |
| 2016/0372743 A1 | 12/2016 | Cho et al. |
| 2016/0374590 A1 | 12/2016 | Wong et al. |
| 2017/0007337 A1 | 1/2017 | Dan |
| 2017/0065356 A1 | 3/2017 | Balaji et al. |
| 2017/0113019 A1 | 4/2017 | Wong et al. |
| 2017/0119481 A1 | 5/2017 | Romo et al. |
| 2017/0151028 A1 | 6/2017 | Ogawa et al. |
| 2017/0165011 A1 | 6/2017 | Bovay et al. |
| 2017/0202627 A1 | 7/2017 | Sramek et al. |
| 2017/0209073 A1 | 7/2017 | Sramek et al. |
| 2017/0209224 A1 | 7/2017 | Walker et al. |
| 2017/0281218 A1 | 10/2017 | Timm |
| 2017/0290631 A1 | 10/2017 | Lee et al. |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0110839 A1 | 4/2019 | Rafii-Tari et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |

(56) References Cited

U.S. PATENT DOCUMENTS

| | | |
|---|---|---|
| 2019/0298460 A1 | 10/2019 | Al-Jadda |
| 2019/0298465 A1 | 10/2019 | Chin |
| 2019/0307987 A1 | 10/2019 | Yu |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0038128 A1 | 2/2020 | Joseph |
| 2020/0039086 A1 | 2/2020 | Meyer |
| 2020/0046434 A1 | 2/2020 | Graetzel |
| 2020/0046942 A1 | 2/2020 | Alvarez |
| 2020/0054405 A1 | 2/2020 | Schuh |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |

FOREIGN PATENT DOCUMENTS

| | | |
|---|---|---|
| CN | 1857877 | 11/2006 |
| CN | 102316817 | 1/2012 |
| CN | 102458295 | 5/2012 |
| CN | 102665590 | 9/2012 |
| CN | 102711586 | 10/2012 |
| CN | 102973317 | 3/2013 |
| CN | 103767659 | 5/2014 |
| CN | 103930063 | 7/2014 |
| EP | 0 543 539 | 5/1993 |
| EP | 0 776 739 | 6/1997 |
| EP | 0 970 663 | 1/2000 |
| EP | 1 103 223 | 5/2001 |
| EP | 1 442 720 | 8/2004 |
| EP | 0 904 796 | 11/2004 |
| JP | 2006-525087 | 11/2006 |
| JP | 2007-511247 | 5/2007 |
| JP | 2010-046384 | 3/2010 |
| JP | 2011-015992 | 1/2011 |
| JP | 2012-105793 | 6/2012 |
| WO | WO 92/02276 | 2/1992 |
| WO | WO 94/14494 | 7/1994 |
| WO | WO 99/45994 | 9/1999 |
| WO | WO 00/67640 | 11/2000 |
| WO | WO 01/33165 | 5/2001 |
| WO | WO 02/19898 | 3/2002 |
| WO | WO 02/47751 | 6/2002 |
| WO | WO 02/74178 | 9/2002 |
| WO | WO 03/065095 | 8/2003 |
| WO | WO 04/001469 | 12/2003 |
| WO | WO 04/039273 | 5/2004 |
| WO | WO 04/105849 | 12/2004 |
| WO | WO 05/032637 | 4/2005 |
| WO | WO 05/055605 | 6/2005 |
| WO | WO 05/081202 | 9/2005 |
| WO | WO 05/087128 | 9/2005 |
| WO | WO 05/117596 | 12/2005 |
| WO | WO 06/092707 | 9/2006 |
| WO | WO 06/099056 | 9/2006 |
| WO | WO 07/015139 | 2/2007 |
| WO | WO 07/045028 | 4/2007 |
| WO | WO 09/097461 | 6/2007 |
| WO | WO 07/098494 | 8/2007 |
| WO | WO 07/109778 | 9/2007 |
| WO | WO 07/146987 | 12/2007 |
| WO | WO 08/094949 | 8/2008 |
| WO | WO 08/097540 | 8/2008 |
| WO | WO 08/131303 | 10/2008 |
| WO | WO 09/061915 | 5/2009 |
| WO | WO 09/092059 | 7/2009 |
| WO | WO 09/094588 | 7/2009 |
| WO | WO 10/032148 | 3/2010 |
| WO | WO 10/081187 | 7/2010 |
| WO | WO 11/005335 | 1/2011 |
| WO | WO 12/037506 | 3/2012 |
| WO | WO 13/107468 | 7/2013 |
| WO | WO 15/093602 | 12/2013 |
| WO | WO 16/003052 | 1/2016 |

OTHER PUBLICATIONS

European Examination Report dated Jun. 26, 2014 for Application No. EP 11761231.7, 5 pgs.

European Examination Report dated Mar. 23, 2015 for Application No. EP 11761231.7, 4 pgs.

European Examination Report dated Jun. 28, 2018 for Application No. EP 16180007.3, 5 pgs.

"Fiber Optic Interferometer Fabry-Perot," viewed on Dec. 9, 2010, http://physicsanimations.com/sensors/English/interf.htm (5 pages).

"Speciality Guidewires," Retrieved from the Internet: http://www.galtmedical.com/pdf/Guidewires.pdf, retrieved on Jun. 18, 2014 (2 pages).

Abouraddy et al., "Towards multimaterial multifunctional fibres that see, hear, sense, and communicate," Nature Materials, May 2007, pp. 336-342, vol. 6.

Berthold, III, "Historical Review of Microbend Fiber-Optic Sensors," Journal of Lightwave Technology, Jul. 1995, pp. 1193-1199, vol. 13 No. 7.

Blandino et al., "Three-Dimensional Shape Sensing for Inflatable Booms," 46th AIAA/ASME/ASCE/AHS/ASC Structures, Structural Dynamics & Materials Conference, Conference Dates: Apr. 18-21, 2005, Austin, Texas (10 pages).

Capouilliet et al., "A Fiber Bragg Grating Measurement System for Monitoring Optical Fiber Strain," IWCS/FOCUS Internet Conference, Nov. 12-15, 2001 (9 pages).

Childers et al., "Recent developments in the application of optical frequency domain reflectometry to distributed Bragg grating sensing," Luna Innovations and NASA Langley Research Center joint PowerPoint presentation (26 pages).

Danisch et al., "Bend Enhanced Fiber Optic Sensors in a Teleoperation Application," Fiber Optic and Laser Sensors XI, 1993, pp. 73-85, SPIE vol. 2070.

Danisch et al., "Spatially continuous six degree of freedom position and orientation sensor," Sensor Review, 1999, pp. 106-112, vol. 19.

Davis, "Strain Survey of an F/A-18 Stabilator Spindle Using High Density Bragg Grating Arrays," Feb. 2005 (33 pages).

Davis, et al., "Fiber-Optic Bragg Grating Array for Shape and Vibration Mode Sensing," May 1994, pp. 94-102, SPIE vol. 2191.

Duncan et al., "A distributed sensing technique for aerospace applications," Luna innovations, Inc., American Institute of Aeronautics and Astronautics, 2004 (8 pages).

Duncan et al., "Characterization of a fiber optic shape and position sensor," Conference Title: Smart Structures and Materials 2006: Smart Sensor Monitoring Systems and Applications: San Diego, CA, Conference Date: Monday Feb. 27, 2006, Published in: Proc. SPIE, vol. 6167, 616704.

(56) References Cited

OTHER PUBLICATIONS

Duncan et al., "Fiber-optic shape and position sensing," Proceedings of the 5th International Conference on Structural Health Monitoring (2005), Structural Health Monitoring, 2005: Advancements and Challenges for Implementation (8 pages).
Duncan et al., "High-accuracy fiber-optic shape sensing," Conference Title: Sensor Systems and Networks: Phenomena, Technology, and Applications for NOE and Health Monitoring 2007, San Diego, California, USA, Conference Date: Monday Mar. 19, 2007, Published in: Proc. SPIE, vol. 6530 (11 pages).
Duncan et al., "Use of high spatial resolution fiber-optic shape sensors to monitor the shape of deployable space structures," Space Technology and Applications Int.Forum-Staif 2005 (7 pages).
Duncan, "Sensing Shape: Fiber-Bragg-grating sensor arrays monitor shape at a high resolution," Spie's OE Magazine, Sep. 2005, pp. 18-21.
File history of U.S. Pat. No. 5,798,521 (69 pages).
File history of U.S. Pat. No. 6,256,090 (126 pages).
File history of U.S. Pat. No. 6,470,205 (64 pages).
Flockhart et al., "Two-axis bend measurement with Bragg gratings in multicore optical fiber," Optics Letters, Mar. 15, 2003, pp. 387-389, vol. 28 No. 6.
Froggatt et al., "Distributed Fiber-Optic Strain and Temperature Sensors Using Photoinduced Bragg Gratings," Thesis (Masters of Science), Feb. 1995 (22 pages).
Froggatt et al., "Distributed measurement of static strain in an optical fiber with multiple Bragg gratings at nominally equal wavelengths," Applied Optics, Apr. 1, 1998, pp. 1741-1746, vol. 37 No. 10.
Froggatt et al., "High-spatial-resolution distributed strain measurement in optical fiber with Rayleigh scatter," Applied Optics, Apr. 1, 1998, pp. 1735-1740, vol. 37, No. 1O.
Froggatt, "Intracore and extracore examination of fiber gratings with coherent detection," Thesis (PhD), 2000 (156 pages).
Gander et al., "Bend Measurement using multicore optical fiber." Proceedings of OFS-12, Oct. 1997, pp. 166-169.
Gander et al., "Measurement of bending in two dimensions using multicore optical fibre," European Workshop on Optical Fibre Sensors, Jun. 1998, pp. 64-68, SPIE vol. 3483.
Gifford et al., "Swept-wavelength Interferometric Interrogation of Fiber Rayleigh Scatter for Distributed Sensing Applications," Fiber Optic Sensors and Applications V, 2007, p. 67700E-1-67700E-9, Proc. of SPIE vol. 6770.
Grant et al., "investigation of Structural Properties of Carbon-Epoxy Composites using Fiber-Bragg Gratings," Applications of Photonic Technology 5, 2002, pp. 191-199, Proc. of SPIE vol. 4833.
Grobnic et al., "Localized High Birefringence Induced in SMF-28 Fiber by Femtosecond IR Laser Exposure of the Cladding," Journal of Lightwave Technology, Aug. 2007, pp. 1996-2001, vol. 25, No. 8.
Grossman et al., "Development of microbend sensors for pressure, load, displacement measurements in civil engineering," Downloaded from SPIE Digital Library on Nov. 4, 2010, May 1994, pp. 112-125, vol. 2191.
Hayano et al., "Structural Health Monitoring System Using FBG Sensor Simultaneous Detection of Acceleration and Strain," Department of System Design Engineering, Keio University (14 pages).
Heo et al., "Design of TR-EFPI fiber optic pressure sensor for the medical application," Korea Advanced Institute of Science and Technology (6 pages).
Hill et al., "Fiber Bragg Grating Technology Fundamentals and Overview," Journal of Lightwave Technology, Aug. 1997, pp. 1263-1276, vol. 15, No. 8.
Hotate et al., "Proposal and experimental verification of Bragg wavelength distribution measurement within a long-length FBG by synthesis of optical coherence function," Optics Express, May 26, 2008, pp. 7881-7887, vol. 16, No.
Huang et al., "Continuous arbitrary strain profile measurements with fiber bragg gratings," Smart Materials and Structures, 1998, pp. 248-256, vol. 7.
Janssen et al., "Signal averaging in the undergraduate laboratory," Europe Journal of Physics, 1988, pp. 131-134, vol. 9.
Katsuki et al., "The Experimental Research on the Health Monitoring of the Concrete Structures Using Optical Fiber Sensor," BAM international Symposium, Sep. 16-19, 2003 (7 pages).
Kersey et al., "Fiber Grating Sensors," Journal of Lightwave Technology, Aug. 1997, pp. 1442-1463, vol. 15, No. 8.
Kim et al., "Micromachined Fabry-Perot Cavity Pressure Transducer," IEEE Photonics Technology Letters, Dec. 1995, pp. 1471-1473, vol. 7, No. 12.
Kirby et al., "Optimal sensor layout for shape estimation form strain sensors," Smart Structures and Materials, 1995, pp. 367-376, vol. 2444.
Klute et al., "Fiber-optic shape sensing and distributed strain measurements on a morphing chevron," 44th AIAA Aerospace Sciences Meeting and Exhibit, Conference dates: Jan. 9-12, 2006, American Institute of Aeronautics and Astronautics (25 pages).
Kreger et al., "Distributed strain and temperature sensing in plastic optical fiber using Rayleigh scatter," Fiber Optic Sensors and Applications VI, 2009, p. 73160A-1-73160A-8, vol. 7316.
Kreger et al., "High-Resolution Extended Distance Distributed Fiber-Optic Sensing Using Rayleigh Backscatter," Sensor Systems and Networks: Phenomena, Technology, and Applications for NDE and Health Monitoring, 2007, p. 65301R-1-65301R-10, Proc. of SPIE vol. 6530.
Kunzler et al., "Damage Evaluation and Analysis of Composite Pressure Vessels Using Fiber Bragg Gratings to Determine Structural Health" (9 pages).
Lawrence et al., "A Fiber Optic Sensor for Transverse Strain Measurement," Experimental Mechanics, Sep. 1999, pp. 202-209, vol. 39, No. 3.
Lawrence et al., "Multi-Parameter Sensing with Fiber Bragg Gratings," 1996, pp. 24-31, SPIE vol. 2872.
Lee et al., "Intraoperative Use of Duel Fiberoptic Catheter for Simultaneous in Vivo Visualization and Laser Vaporization of Peripheral Atherosclerotic Obstructive Disease," Catheterization and Cardiovascular Diagnosis, 1984, pp. 11-16, vol. 10.
Lequime et al., "Fiber optic pressure and temperature sensor for down-hole applications," Fiber Optic Sensors: Engineering and Applications, 1991, pp. 652-657, Proceedings SPIE vol. 1511.
Lopatin et al., "Distributed Measurement of Strain in Smart Materials Using Rayleigh Scattering," 32 International SAMPE Technical Conference, conference dates: Nov. 5-9, 2000, pp. 231-241.
Maas, "Shape measurement using phase shifting speckle interferometry," Laser Interferometry IV: Computer-Aided Interferometry (1991), 1992, pp. 558-568, SPIE vol. 1553.
MacDonald, "Frequency domain optical reflectometer," Applied Optics, May 15, 1981, pp. 1840-1844, vol. 20, No. 10.
Measures, Raymond et al., "Fiber Optic Strain Sensing", Fiber Optic Smart Structures, 1995, pp. 171-247, John Wiley & Sons Inc.
Mihailov et al., "UV-induced polarization-dependent loss (POL) in tilted fibre Bragg gratings: application of a POL equalizer," IEE Proc.-Optoelectron., Oct./Dec. 2002, pp. 211-216, vol. 149, No. 5/6.
Miller et al., "Fiber-optic shape sensing for flexible structures," Fiber Optic Smart Structures and Skins II, 1989, pp. 399-404, SPIE vol. 1170.
Miller et al., "Shape sensing using distributed fiber optic strain measurements," Second European Workshop on Optical Fibre Sensors, 2004, pp. 528-531, Proc. of SPIE vol. 5502.
Morey, "Fiber-optic braag grating sensors," Fiber Optic and Laser Sensors VII, 1989, pp. 98-107, SPIE vol. 1169.
Ohn et al., "Arbitrary strain profile measurement within fibre gratings using interferometric Fourier transform technique," Electronics Letters, Jul. 3, 1997, pp. 1242-1243, vol. 33, No. 14.
Pinet et al., "True challenges of disposable optical fiber sensors for clinical environment," Third European Workshop on Optical Fibre Sensors, 2007, p. 66191Q-1-66191Q-4, Proc. of SPIE vol. 6619.
Posey et al., "Strain sensing based on coherent Rayleigh scattering in an optical fibre," Electronics Letters, Sep. 28, 2000, pp. 1688-1689, vol. 36, No. 20.
Raum et al., "Performance Analysis of a Fiber-Optic Shape Sensing System," Collection of Technical papers—44th AIAA, 2006, (11 pages).

(56) References Cited

OTHER PUBLICATIONS

Raum, "Error Analysis of Three Dimensional Shape Sensing Algorithm," Apr. 26, 2005 (13 pages).
Reyes et al., "Tunable POL of Twisted-Tilted Fiber Gratings," IEEE Photonics Technology Letters, Jun. 2003, pp. 828-830, vol. 15, No. 6.
Satava, "How the Future of Surgery is Changing: Robotics, telesurgery, surgical simulators and other advanced technologies," May 2006, pp. 2-21.
Sato el al., "Ground strain measuring system using optical fiber sensors," Part of the SPIE Conference on Sensory Phenomena and Measurement Instrumentation for Smart Structures and Materials, Mar. 1999, pp. 470-479, SPIE vol. 3670.
Schreiber et al., "Stress-induced birefringence in large-mode-area micro-structured optical fibers," Optics Express, May 16, 2005, pp. 3637-3646, vol. 13, No. 10.
Schulz et al., "Advanced fiber grating strain sensor systems for bridges, structures, and highways" (11 pages).
Schulz et al., "Health monitoring of adhesive joints using multi-axis fiber grating strain sensor system," (12 pages).
Soller et al., "High resolution optical frequency domain reflectometry for characterization of components and assemblies," Optics Express, Jan. 24, 2005, pp. 666-674, vol. 13, No. 2.
Soller et al., "Optical Frequency Domain Reflectometry for Single- and Multi-Mode Avionics Fiber-Optics Applications," IEEE, 2006, pp. 38-39.
Sorin, Chapter 10: Section 10.5 Optical Reflectometry for Component Characterization: Survey of Different Techniques, pp. 425-429.
Tian et al., "Torsion Measurement Using Fiber Bragg Grating Sensors," Experimental Mechanics, Sep. 2001, pp. 248-253, vol. 41, No. 3.
Trimble, "A successful fiber sensor for medical applications," Fiber Optic Sensors in Medical Diagnostics, 1993, pp. 147-150, SPIE vol. 1886.
Udd et al., "Multidimensional strain field measurements using fiber optic grating sensors," Smart Structures and Materials 2000: Sensory Phenomena and Measurement Instrumentation for Smart Structures and Materials, 2000, pp. 254-262, Proceedings SPIE vol. 3986.
Udd et al., "Progress on developing a multiaxis fiber optic strain sensor," Third Pacific Northwest Fiber Optic Sensor Workshop, 1997, pp. 50-56, Proceedings SPIE vol. 3180.
Udd et al., "Usage of Multi-Axis Fiber Grating Strain Sensors to Support Nondestructive Evaluation of Composite Parts and Adhesive Bond Lines," pp. 1-9.
Udd, "Good Sense," Spie's OE Magazine, Aug. 2002. pp. 27-30.
Walker et al., "Shaping the radiation field of tilted fiber Bragg gratings," J. Opt. Soc. Am. B, May 2005, pp. 962-975, vol. 22, No. 5.
Wippich et al., "Tunable Lasers and Fiber-Braga-Grating Sensors," The Industrial Physicist, Jun./Jul. 2003, pp. 24-27.
Wong et al., "Distributed Bragg grating integrated-optical filters: Synthesis and fabrication," J. Vac. Sci. Technol. B., Nov./Dec. 1995, pp. 2859-2864, vol. 13, No. 6.
Wu et al., Sep. 2003, Fabrication of self-apodized short-length fiber Bragg gratings, Applied Optics, 42(25):5017-5023.
Xu et al., "Miniature fiber optic pressure and temperature sensors," Fiber Optic Sensor Technology and Applications IV, 2005, p. 600403-1-600403-6, Proc. of SPIE vol. 6004.
Xue et al., "Simultaneous Measurement of Stress and Temperature with a Fiber Bragg Grating Based on Loop Thin-Wall Section Beam," Applied Optics, Mar. 2, 2006, pp. 1-16.
Ye et al., "A polarization-maintaining fibre Bragg Grating interrogation system for multi-axis strain sensing," Measurement Science and Technology, 2002, pp. 1446-1449, vol. 13.
Zhang et al., "FBG Sensor Devices for Spatial Shape Detection of Intelligent Colonoscope," Proceedings of the 2004 IEEE International Conference on Robotics & Automation, Apr. 2004, pp. 835-840, Louisiana.
Zhang et al., "Fiber-Bragg-grating-based seismic geophone for oil/gas prospecting," Optical Engineering, Aug. 2006, p. 084404-1-84404-4, vol. 45, No. 8.
Zhang, "Novel shape detection systems based on FBG sensor net for intelligent endoscope," Journal of Shanghai University (English Edition), 2006, pp. 154-155, vol. 10, No. 2.
Extended European Search Report dated May 9, 2017 in patent application No. 16180007.3.
International Search Report for International Patent Application No. PCT/US2006/026218, dated Dec. 12, 2006 (4 pages).
Written Opinion of the International Searching Authority for International Patent Application No. PCT/US2006/026218, dated Dec. 12, 2006 (7 pages).
International Search Report and Written Opinion for International Patent Application No. PCT/US2007/064728, dated Jul. 31, 2007 (13 pages).
International Search Report and Written Opinion for International Patent Application No. PCT/US2008/001505, dated Dec. 3, 2008 (8 pages).
International Search Report and Written Opinion for International Patent Application No. PCT/US2008/060936, dated Nov. 6, 2008 (12 pages).
International Search Report and Written Opinion for International Patent Application No. PCT/US2008/073215, dated Jan. 21, 2009 (12 pages).
International Preliminary Report on Patentability for International Patent Application No. PCT/US2007/062617, report dated Aug. 26, 2008 (7 pages).
International Preliminary Report on Patentabiltiy for International Patent Application No. PCT/US2008/082236, dated May 18, 2010 (10 pp.).
International Search Report and Written Opinion for International Patent Application No. PCT/US2008/082236, dated Oct. 16, 2009 (16 pages).
International Search Report and Written Opinion for International Application No. PCT/US2011/052013, Applicant Hansen Medical, Inc., forms PCT/ISA/210, 220, and 237, dated Mar. 18, 2013 (40 pages).
International Preliminary Report on Patentability for International Application No. PCT/US2011/052013, Applicant Hansen Medical, Inc., forms PCT/ISA/326, 373, and 237, dated Apr. 4, 2013 (32 pages).
Invitation to Pay Additional Fees and Communication Relating to the Results of the Partial International Search, form PCT/ISA/206 and Annex to form PCT/ISA/206, dated Feb. 6, 2012 (9 pages).
Amendment and Response to Non-Final Office Action for related U.S. Appl. No. 11/678,016, filed Dec. 27, 2010 (21 pages).
Non/Final Office Action for related U.S. Appl. No. 11/678,016, dated Aug. 31, 2010 (30 pages).
Papers from file history for Chinese Patent Application No. 200780009956.6 (20 pages).
Papers from file history for U.S. Appl. No. 11/690,116 (45 pages).
Papers from file history for U.S. Appl. No. 12/106,254 (57 pages).
Papers from file history for U.S. Appl. No. 12/507,727 (15 pages).
Papers from prosecution File History for U.S. Appl. No. 11/690,116 (45 pages).

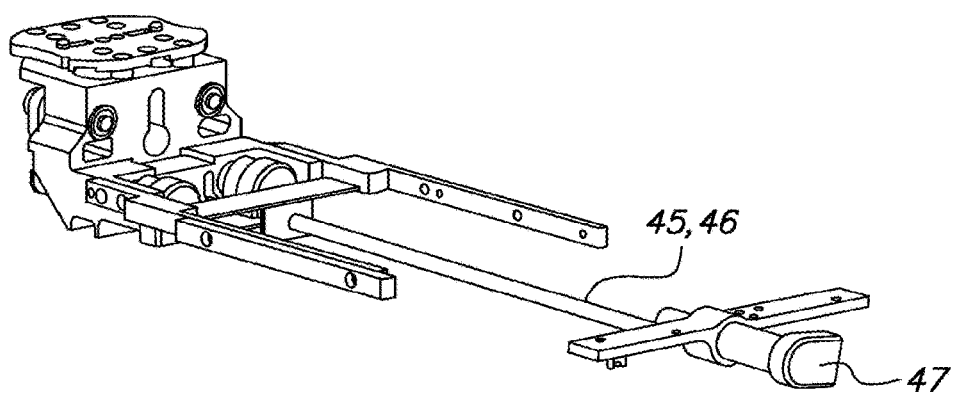
FIG. 10
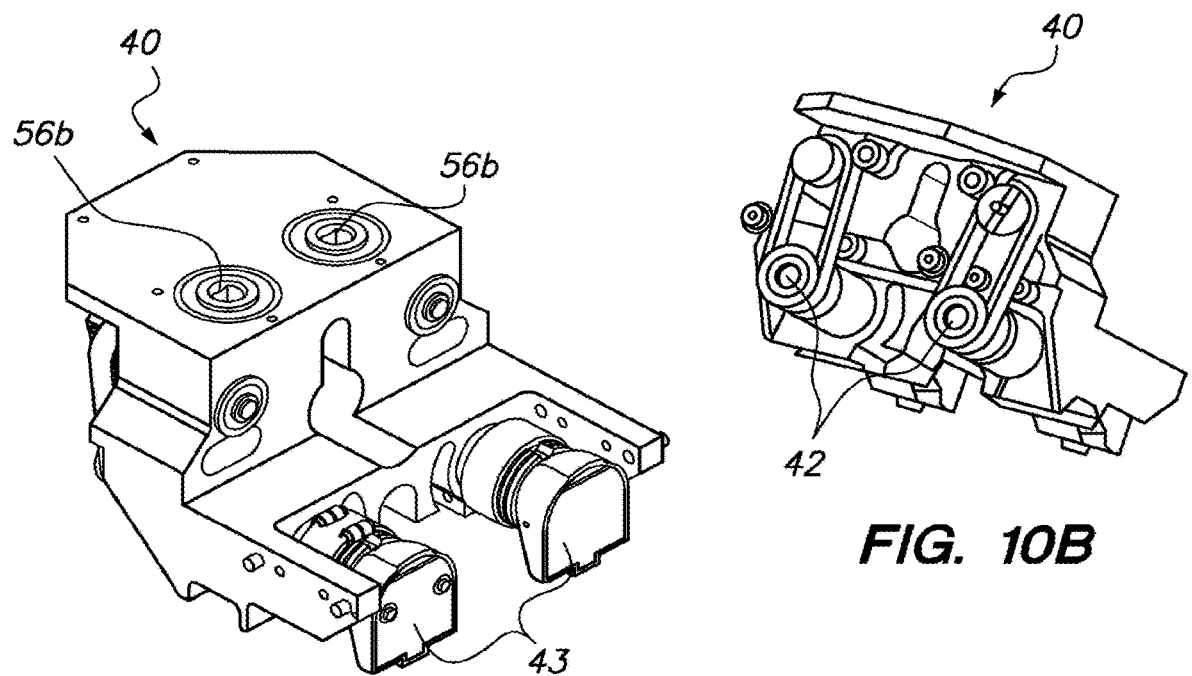
FIG. 10A
FIG. 10B

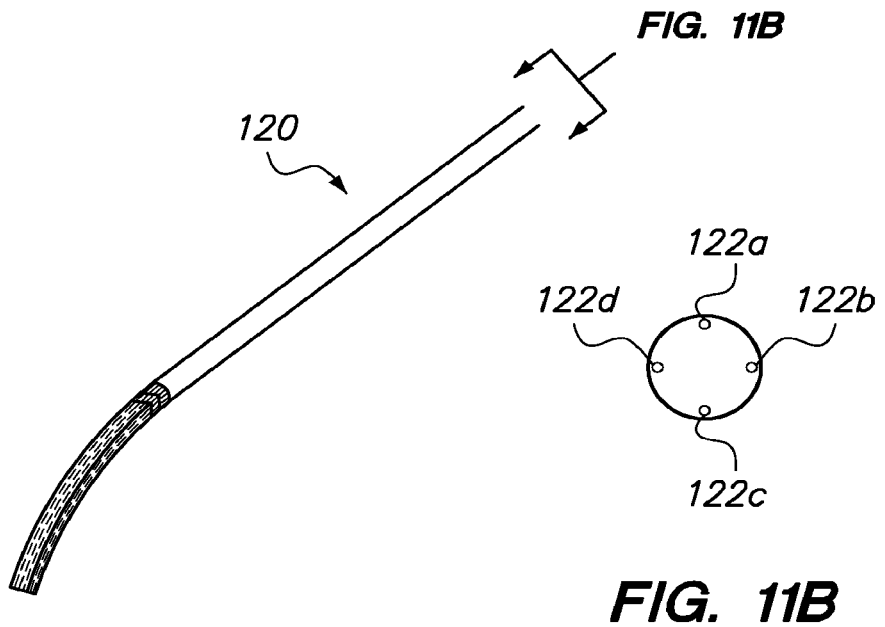
FIG. 11A
FIG. 11B
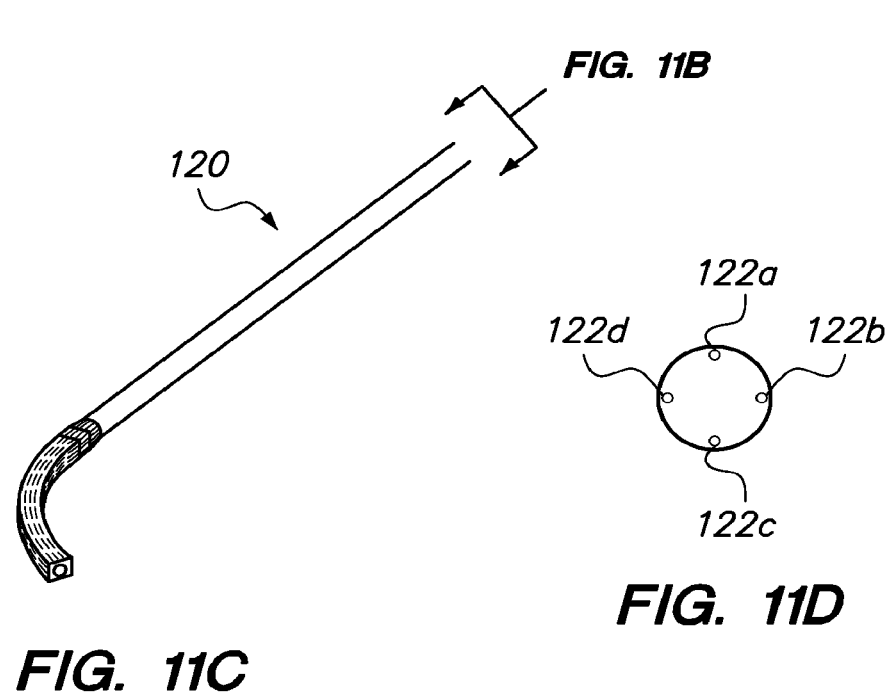
FIG. 11C
FIG. 11D

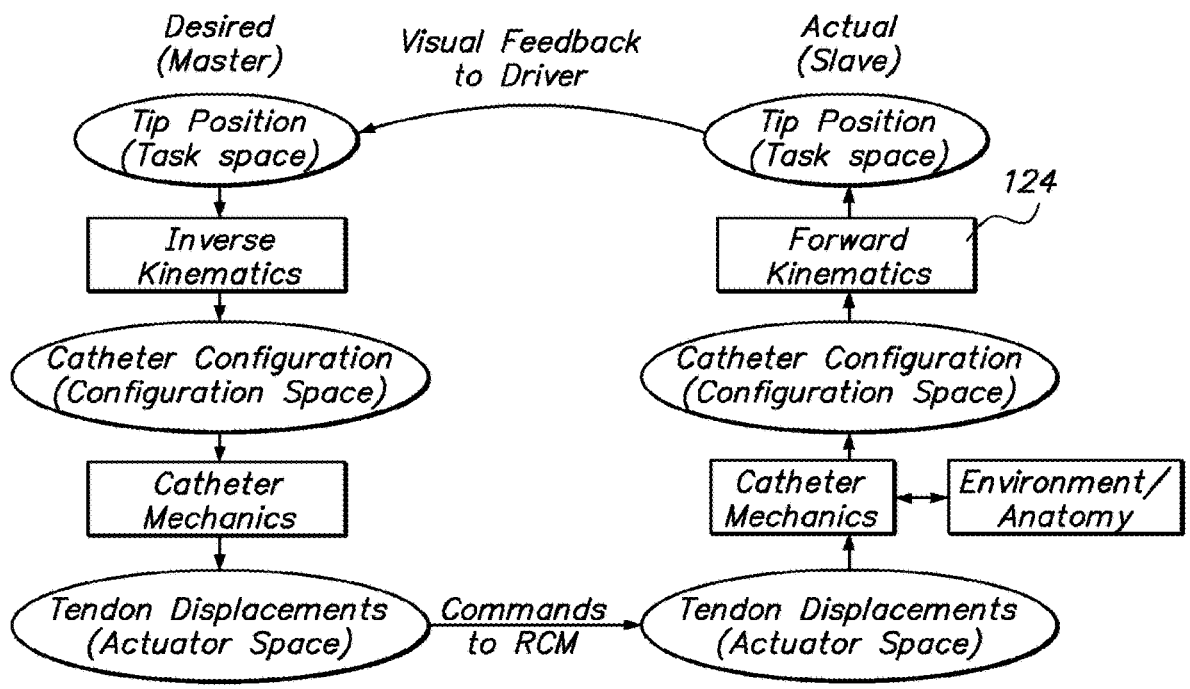
FIG. 12
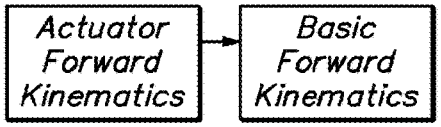
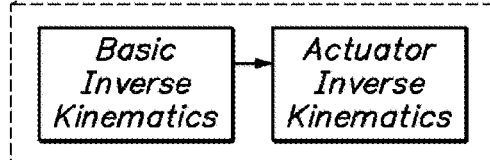
FIG. 13

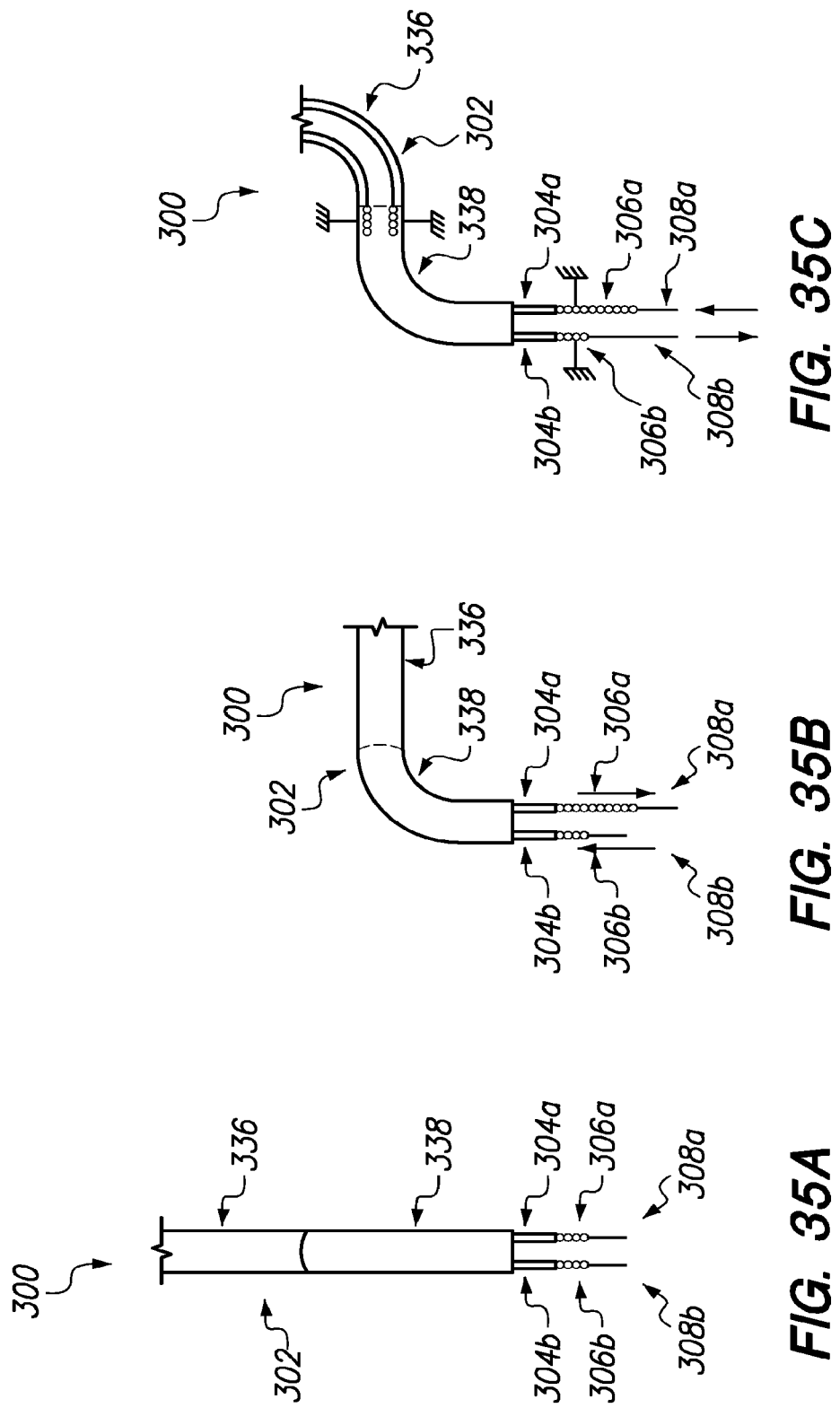

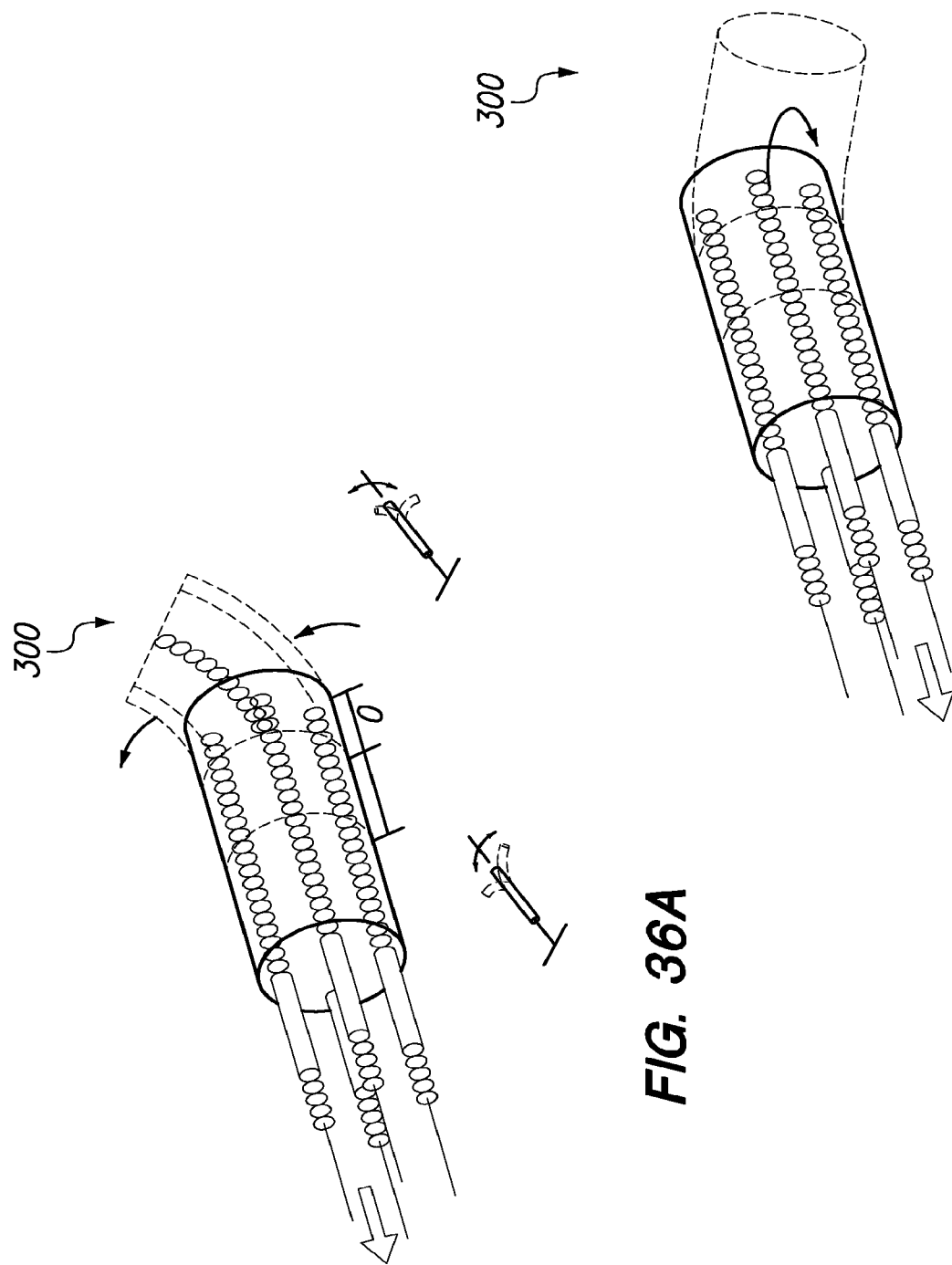

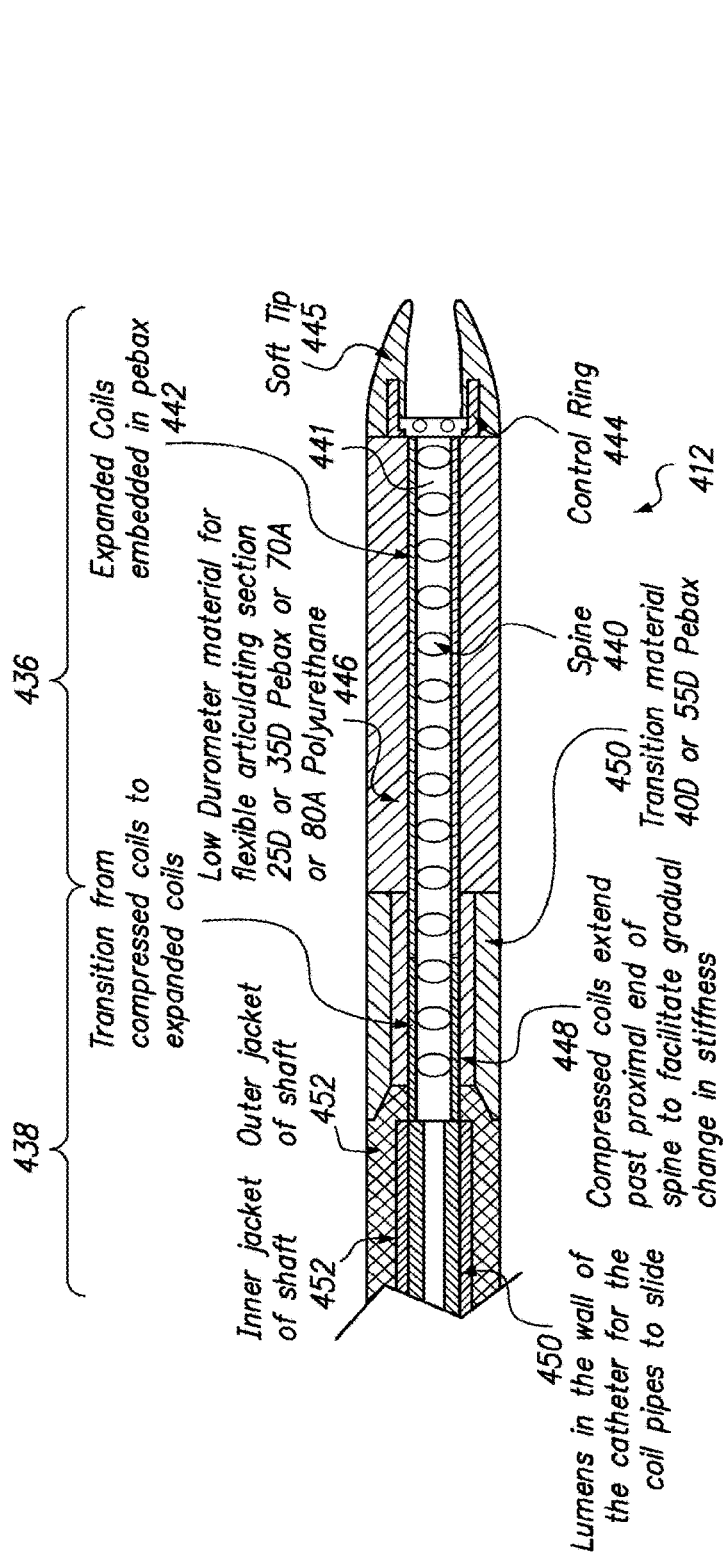
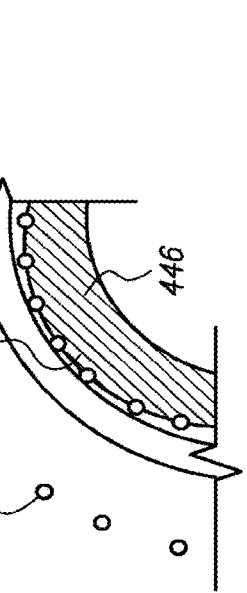
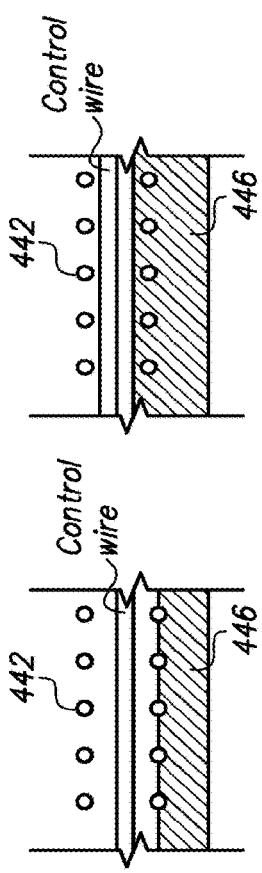

- Liner HDPE/Plexar Co-Ext
- Base braid 30 PPI of .001" x .003"
- Braid over polyimide 40 PPI
- Jacket Pellethane 80A
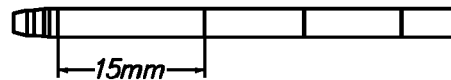
- Liner HDPE/Plexar Co-Ext
- Base braid 30 PPI of .001" x .003"
- Braid over polyimide 40 PPI
- Jacket Pebax 3533
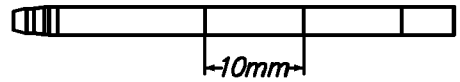
- Liner HDPE/Plexar Co-Ext
- Base braid 30 PPI of .001" x .003"
- Braid over polyimide 40 & PPI 100 PPI
- Jacket Pebax 3533
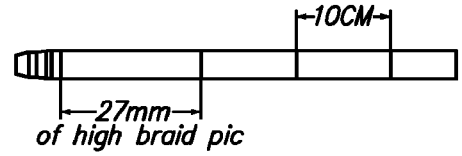
*FIG. 43*
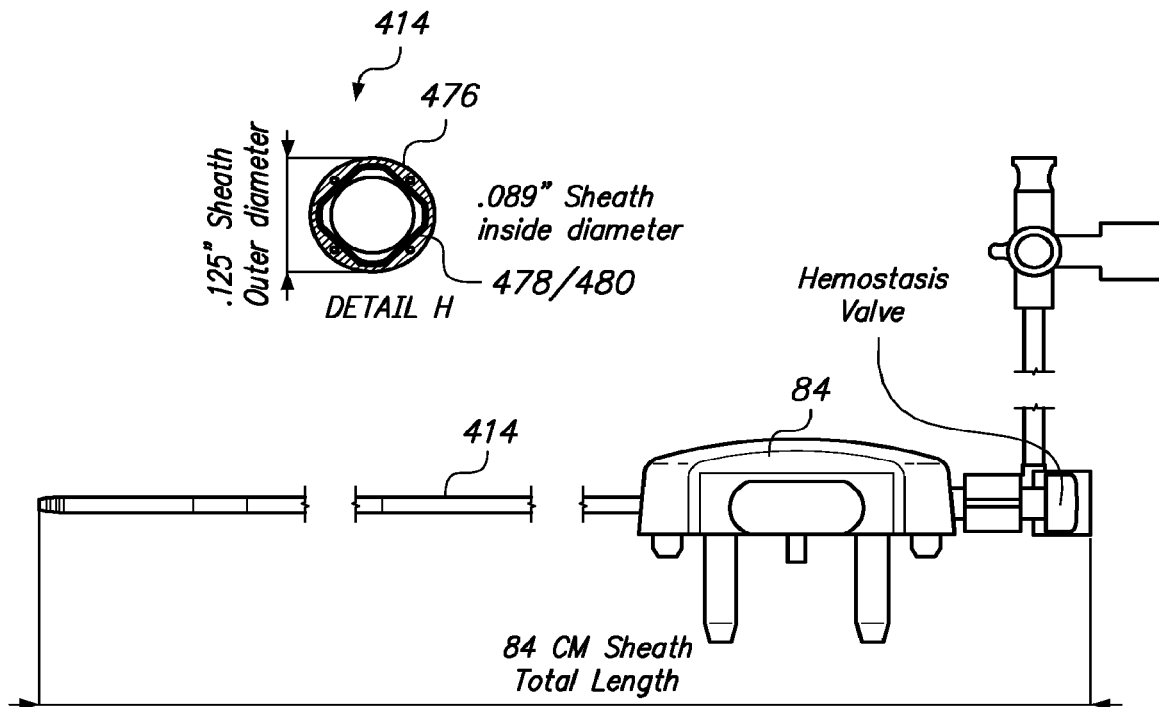
*FIG. 44*

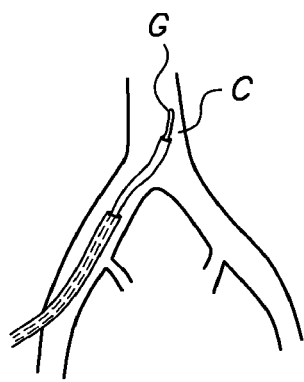
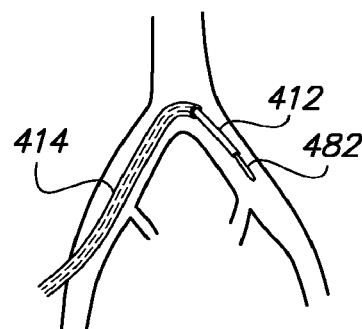
FIG. 45          FIG. 46
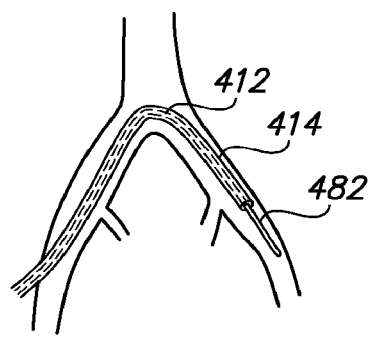
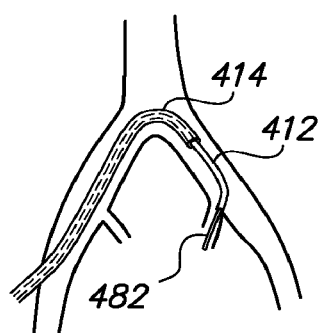
FIG. 47          FIG. 48
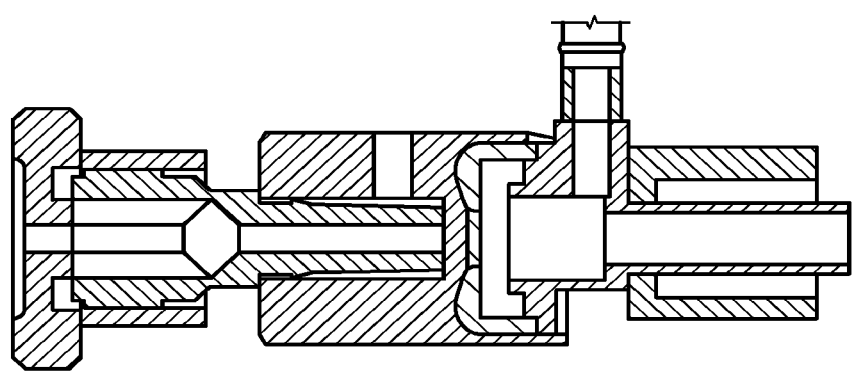
FIG. 49

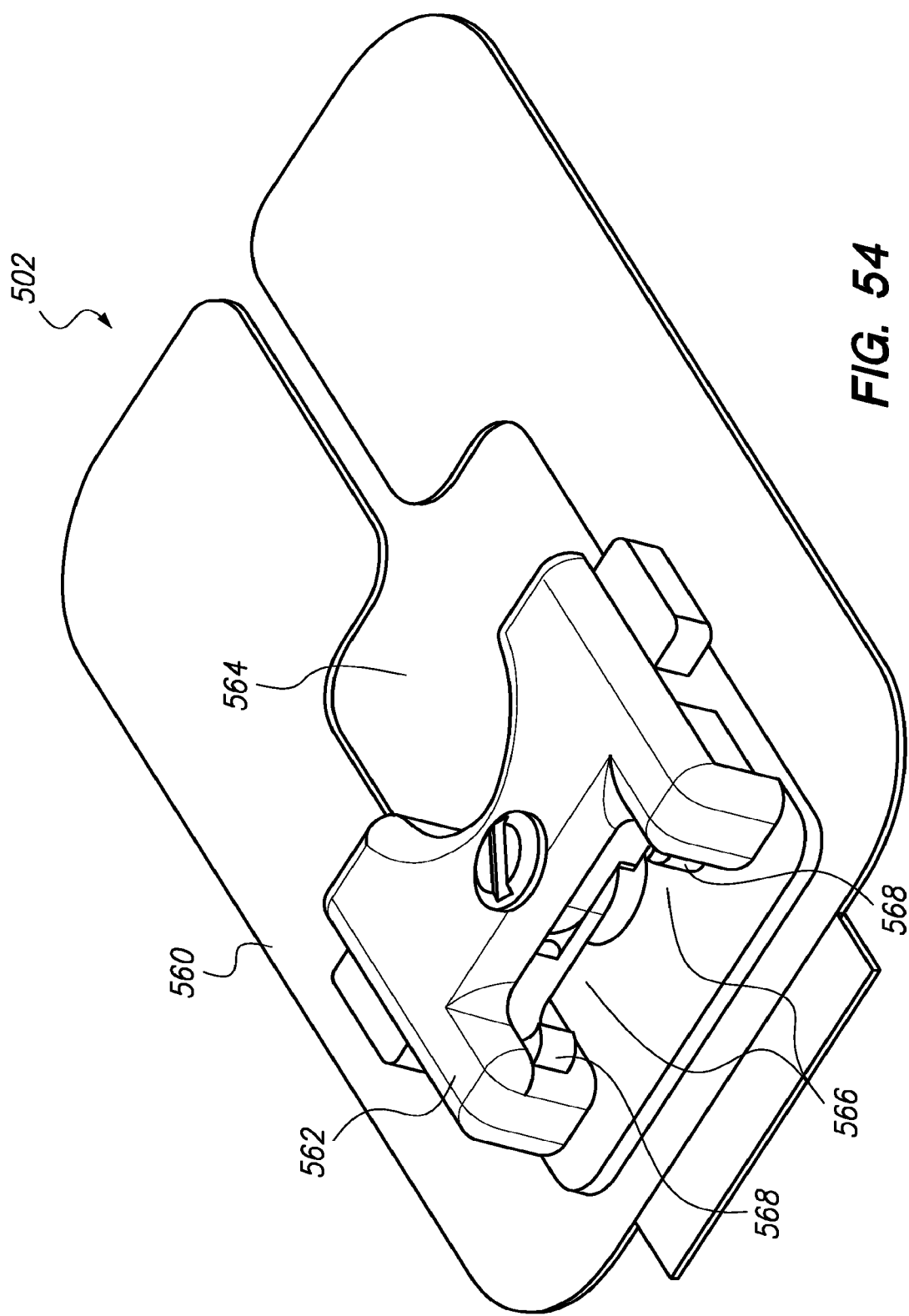

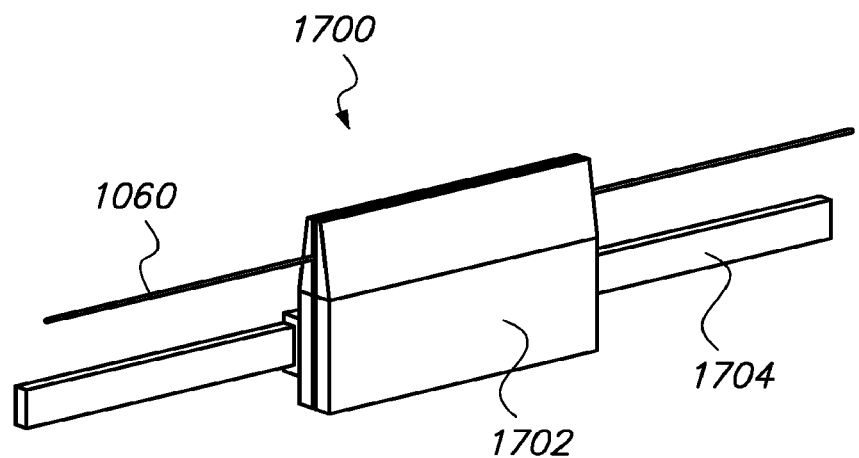
FIG. 96C
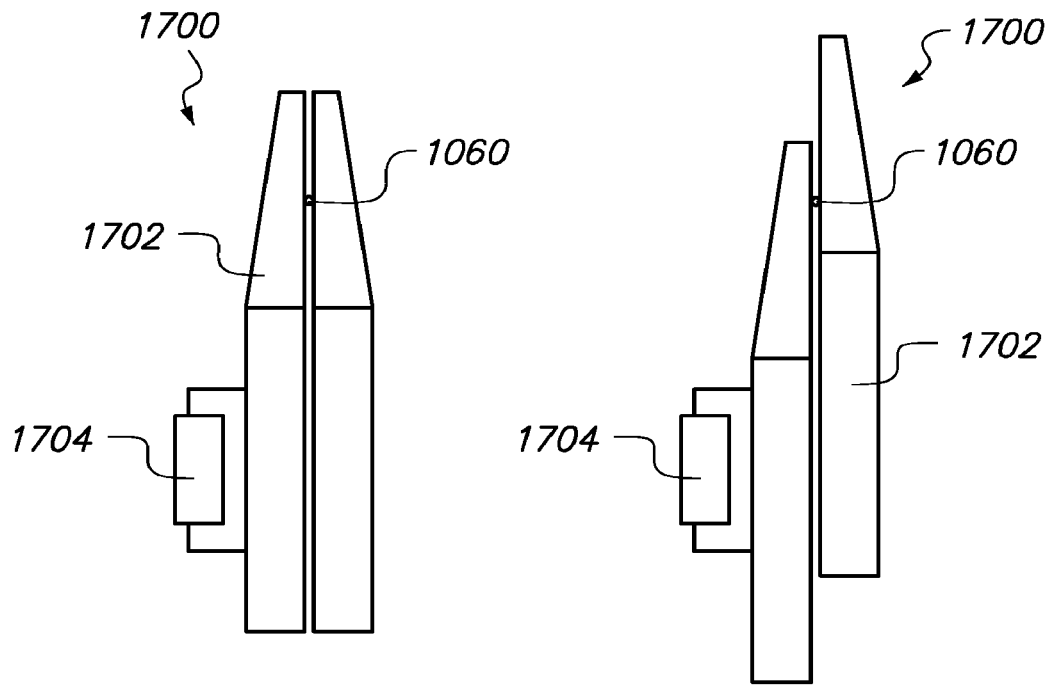
FIG. 96D   FIG. 96E

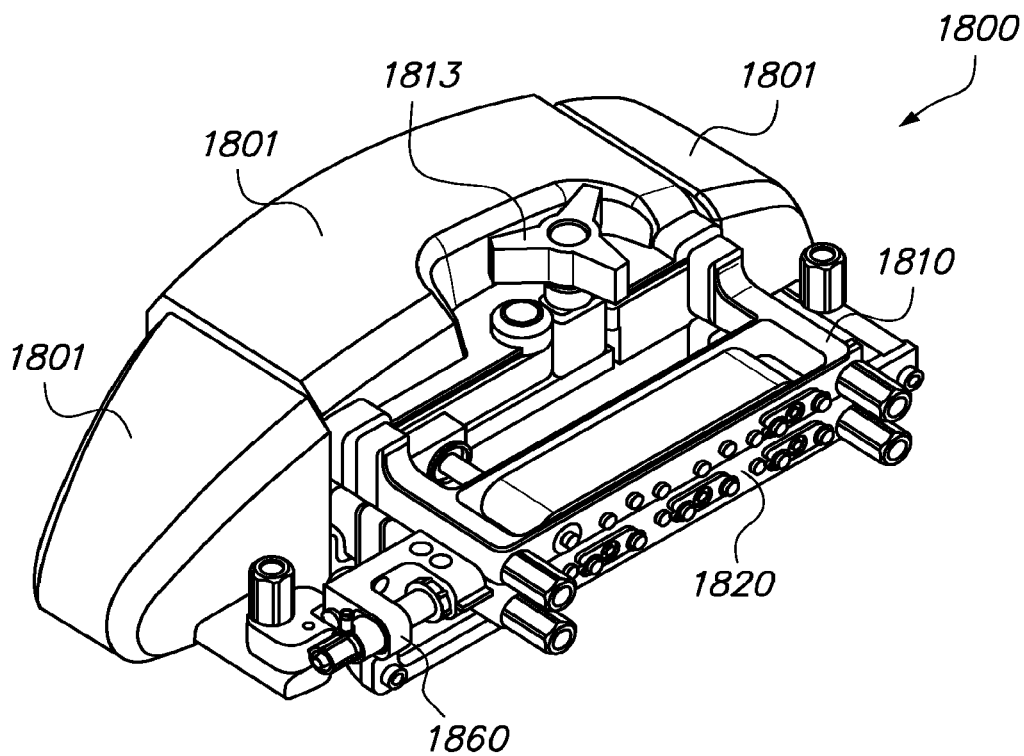
FIG. 97A1
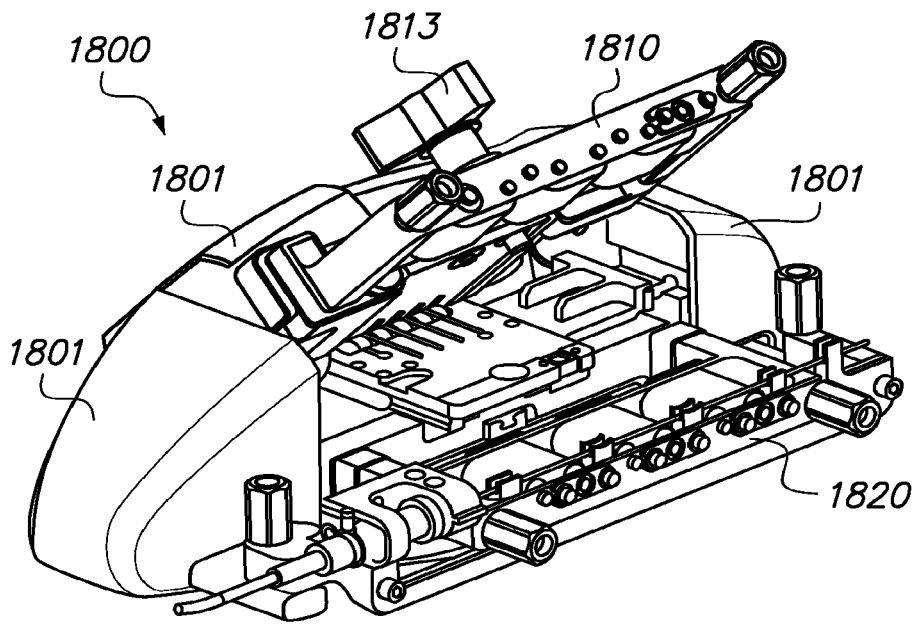
FIG. 97A2

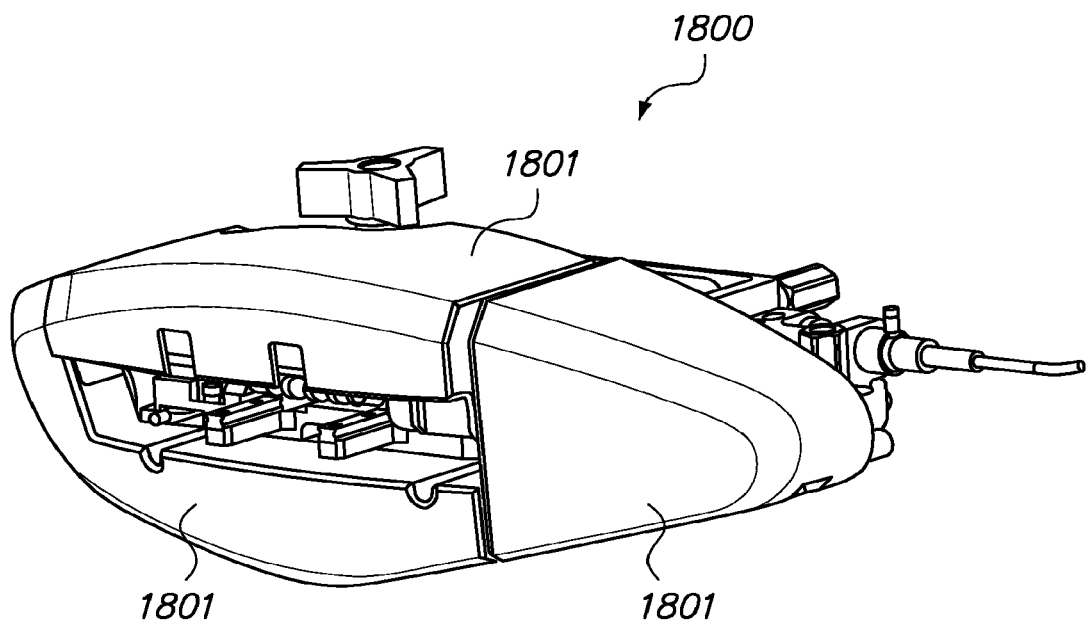
FIG. 97A3
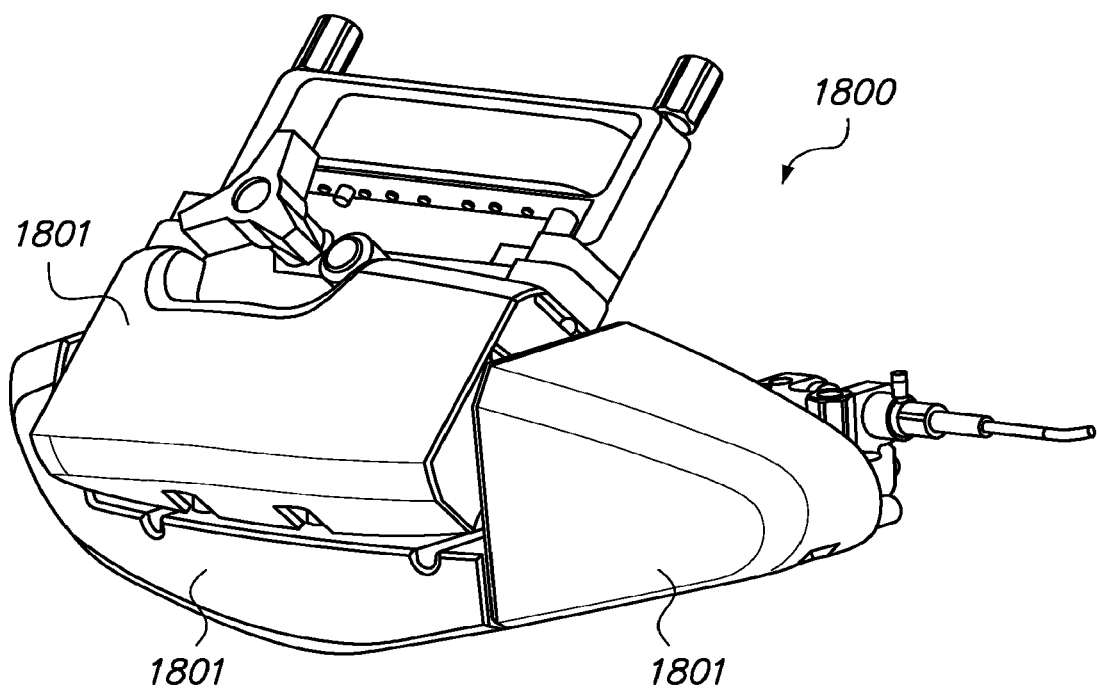
FIG. 97A4

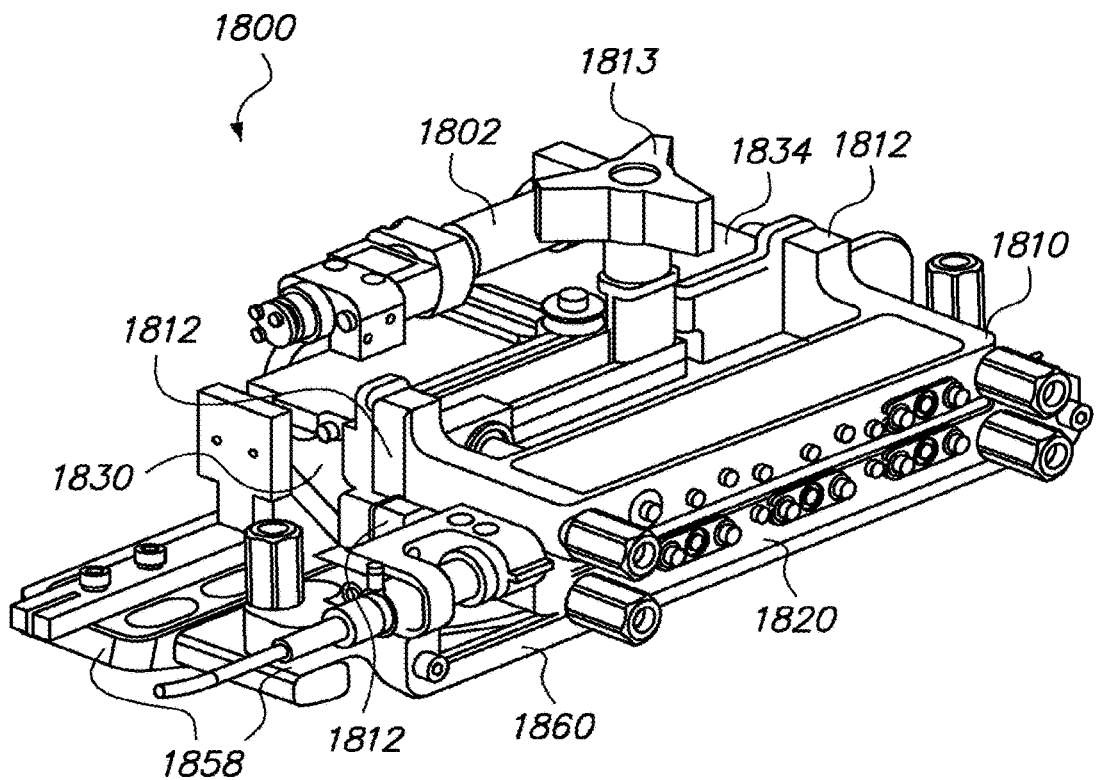
FIG. 97B1
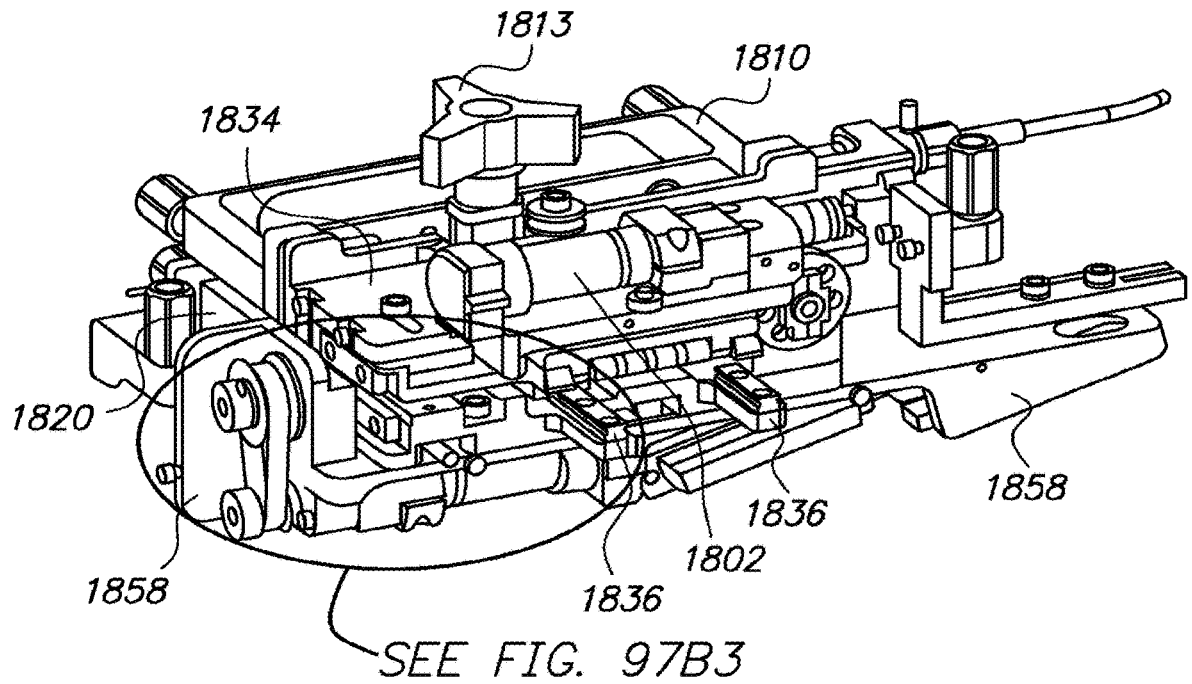
FIG. 97B2

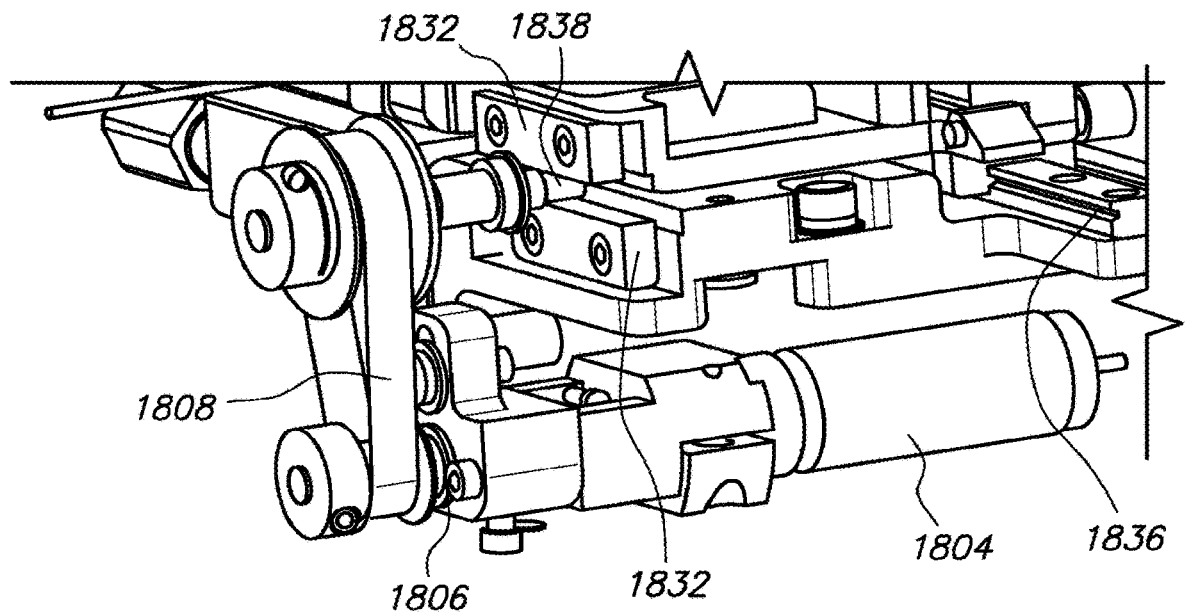
FIG. 97B3
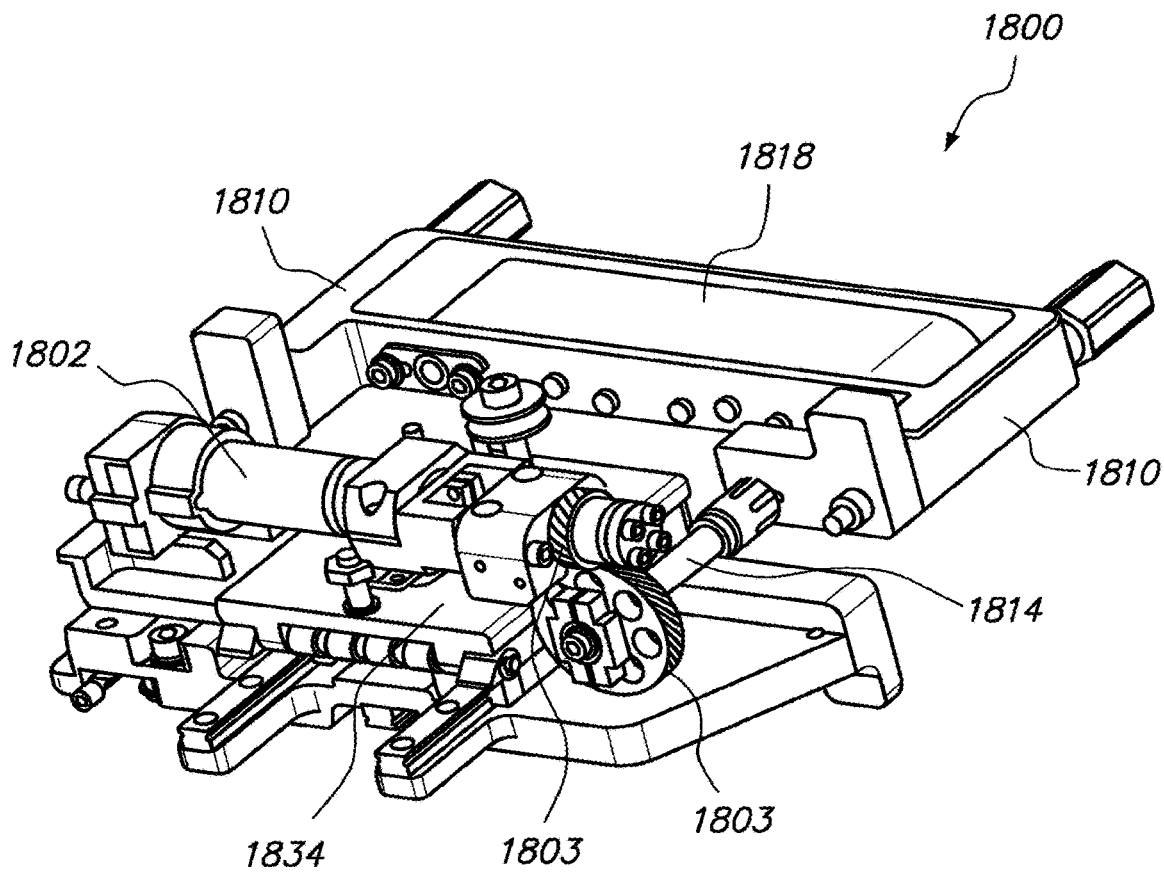
FIG. 97C

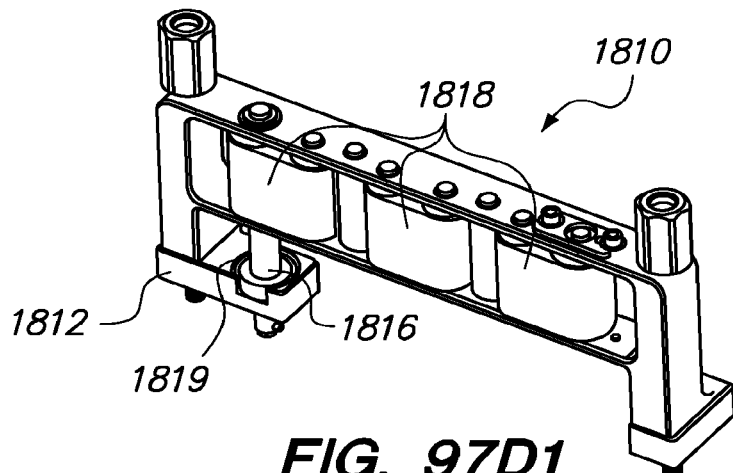
FIG. 97D1
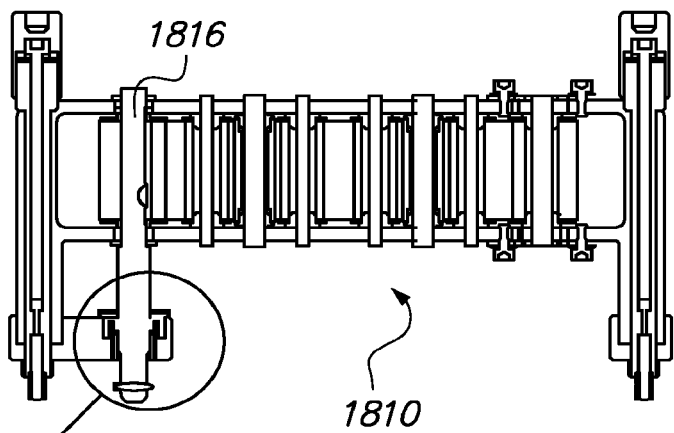
FIG. 97D2
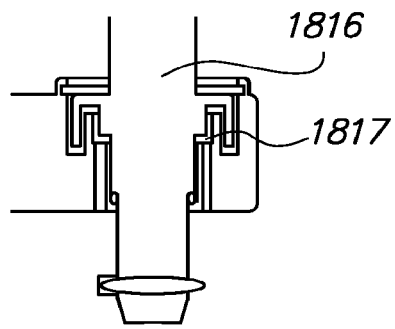
FIG. 97D3

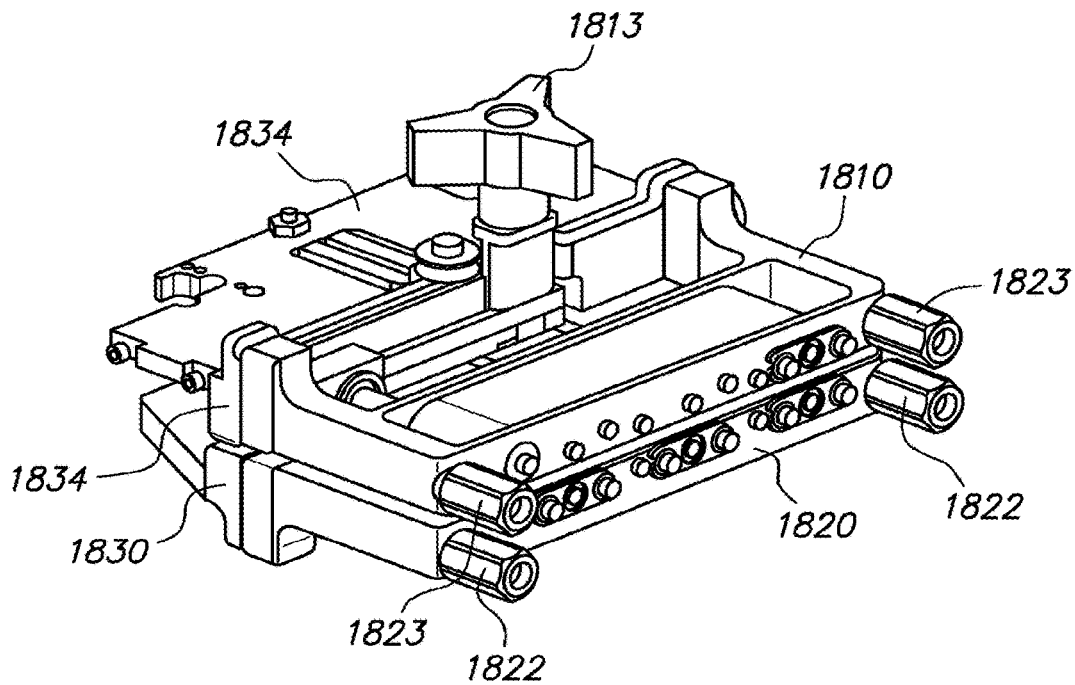
FIG. 97E1
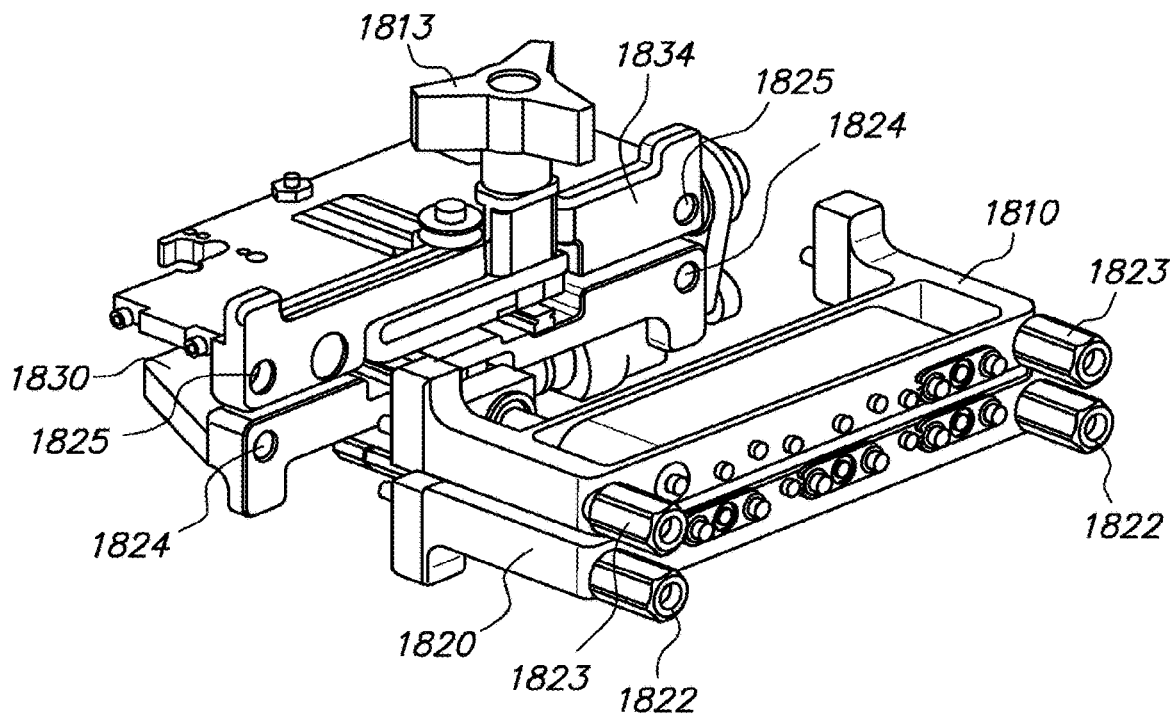
FIG. 97E2

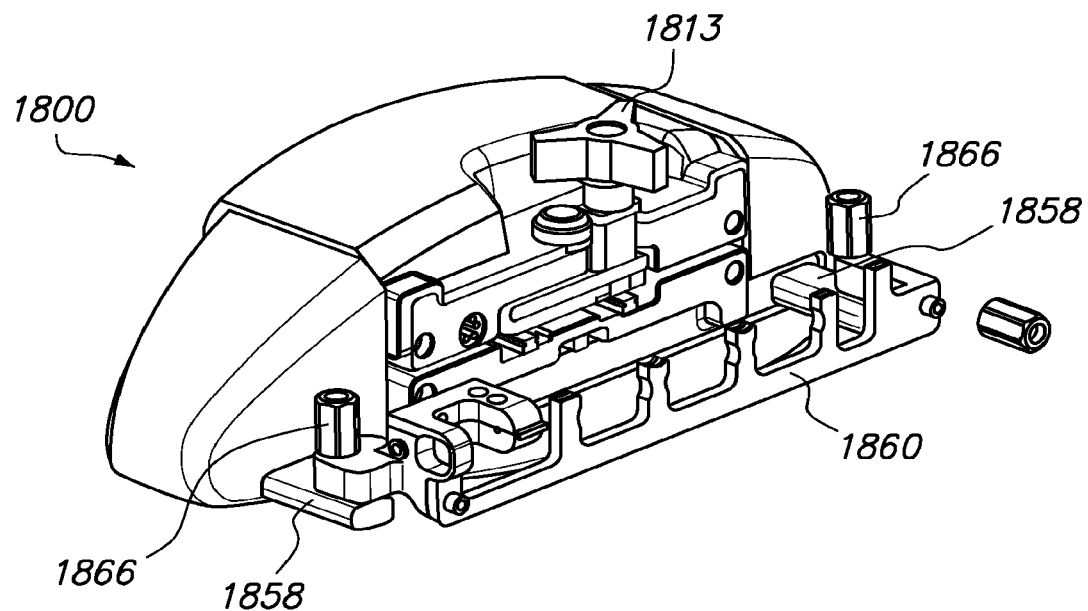
FIG. 97H1
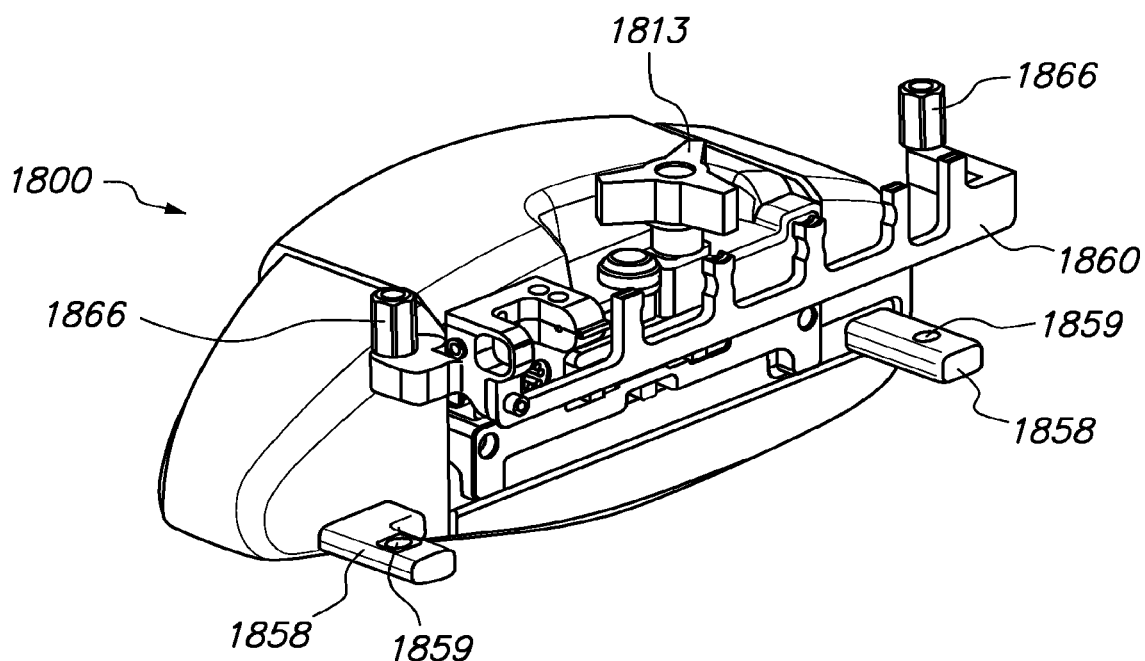
FIG. 97H2

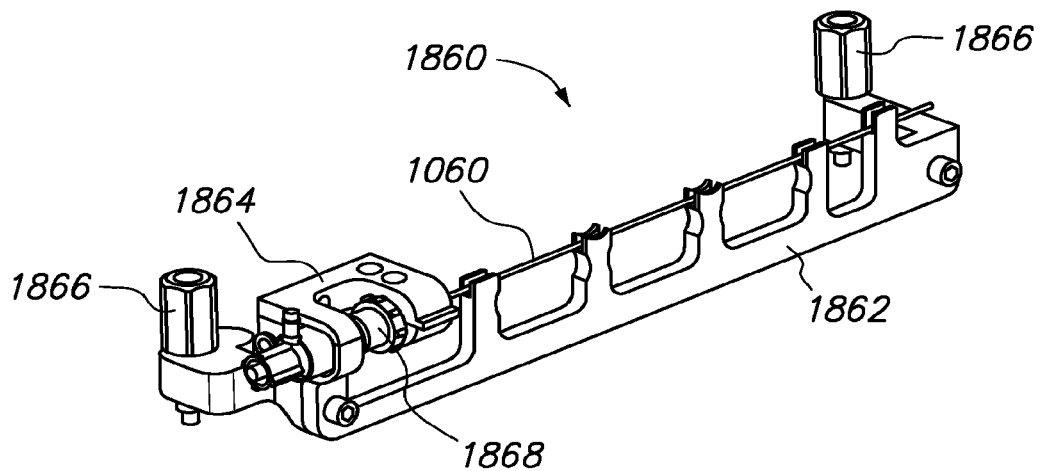
FIG. 97J1
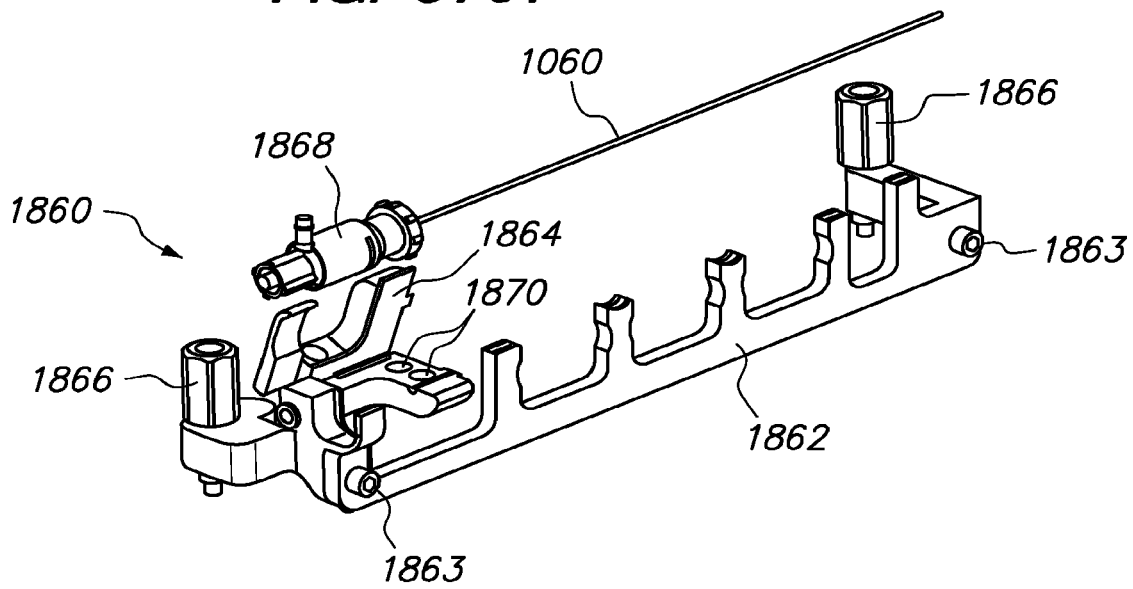
FIG. 97J2
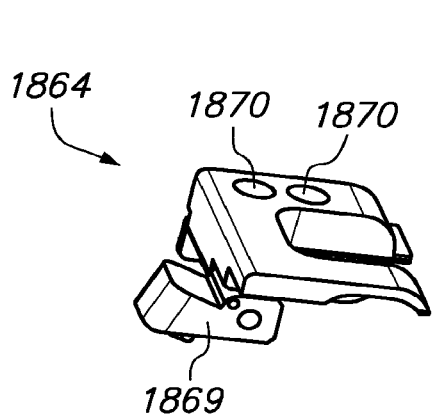
FIG. 97J3
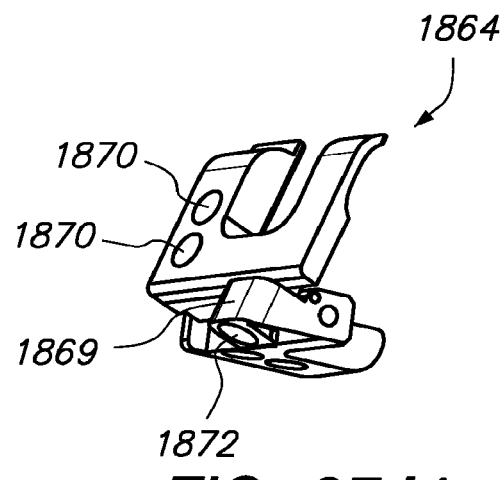
FIG. 97J4

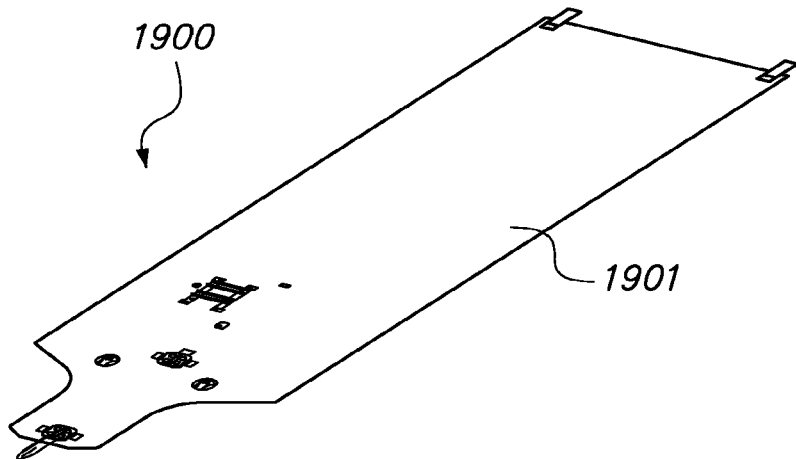
FIG. 97K1
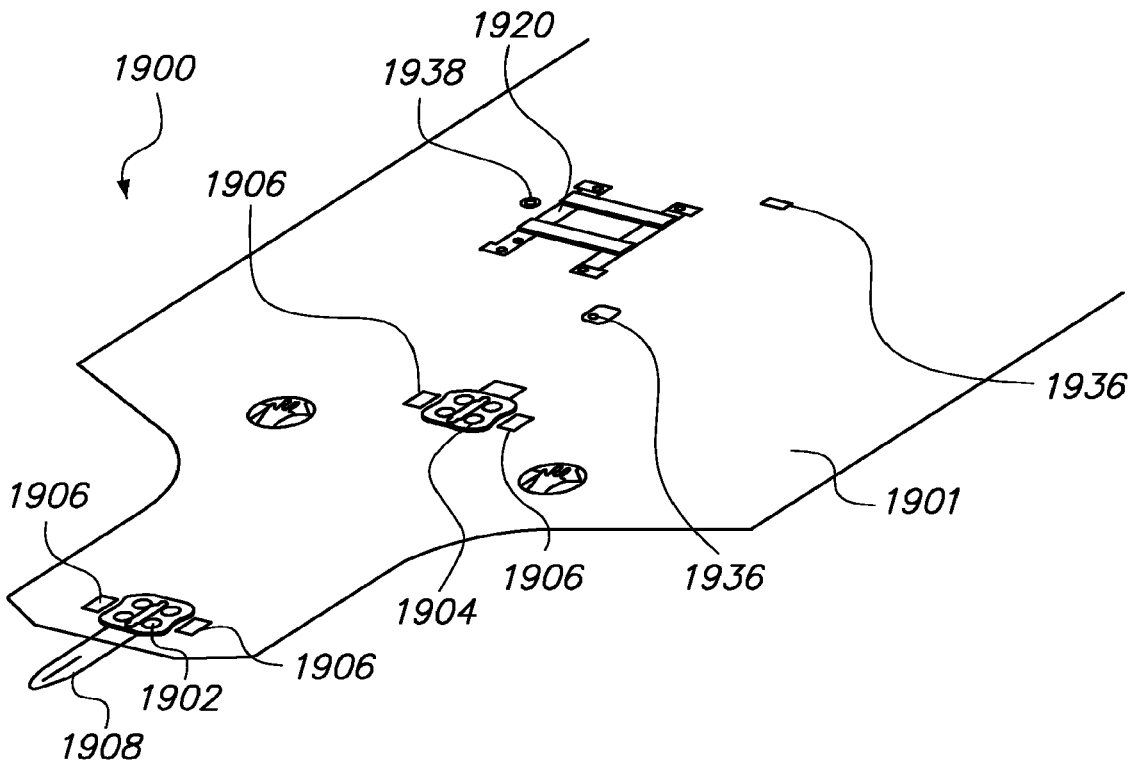
FIG. 97K2

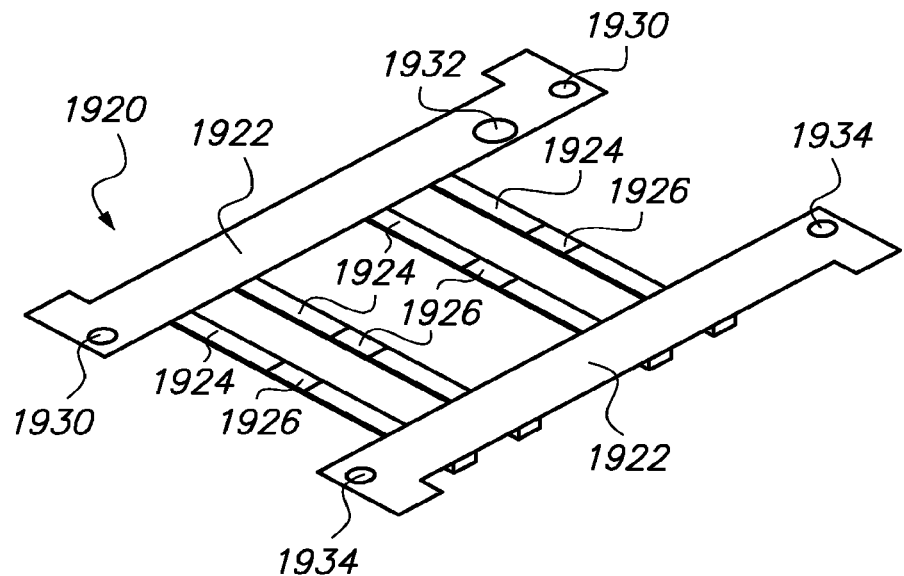
FIG. 97L1
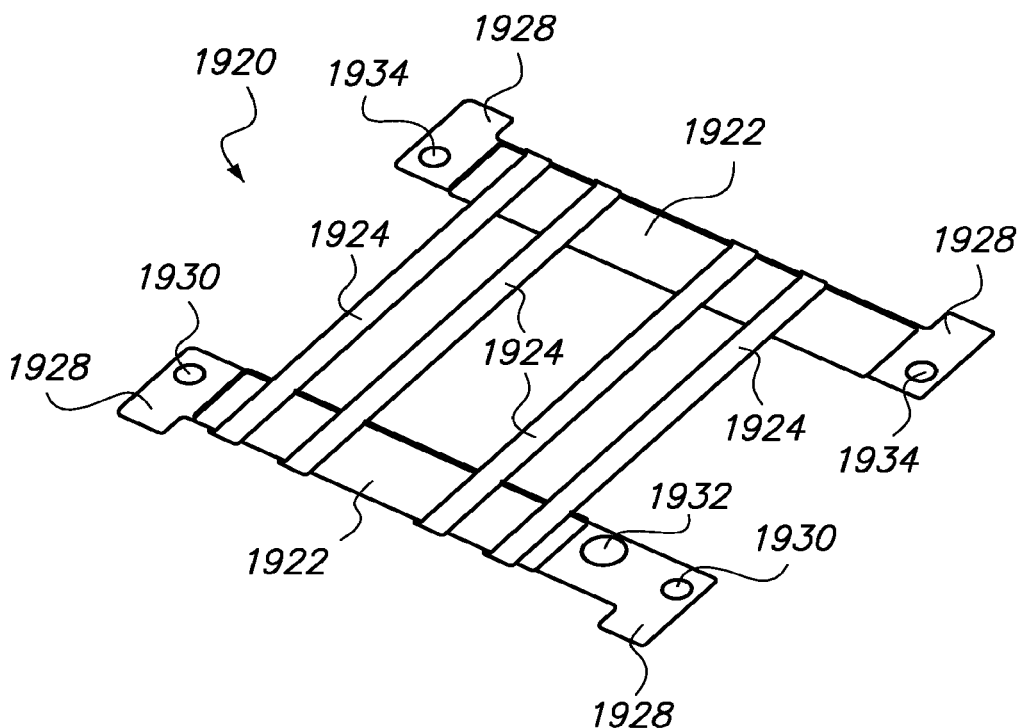
FIG. 97L2

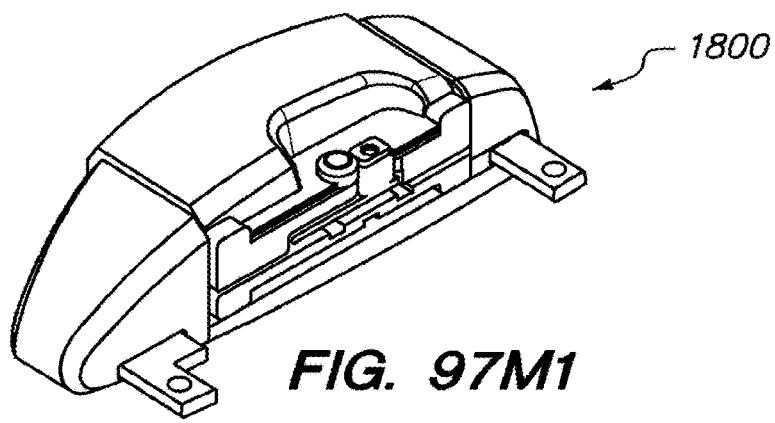
FIG. 97M1
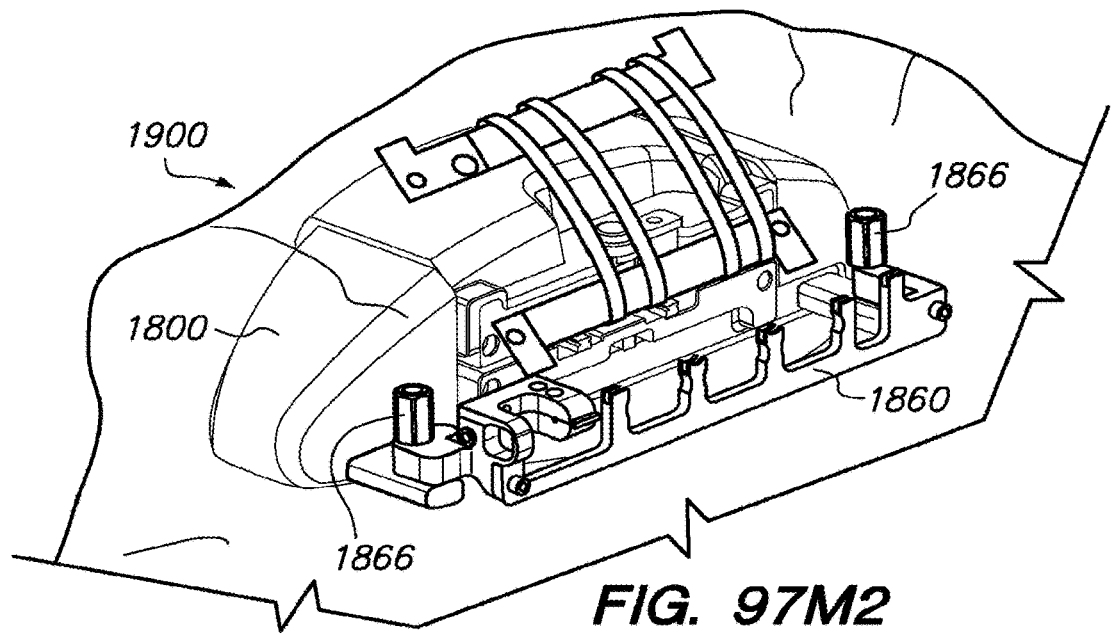
FIG. 97M2
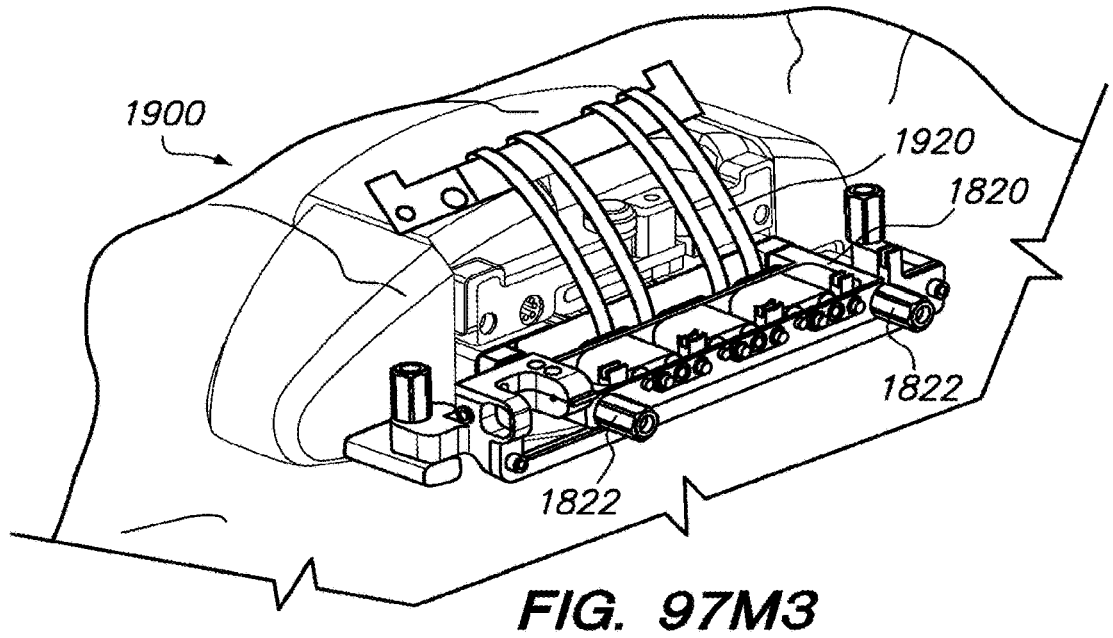
FIG. 97M3

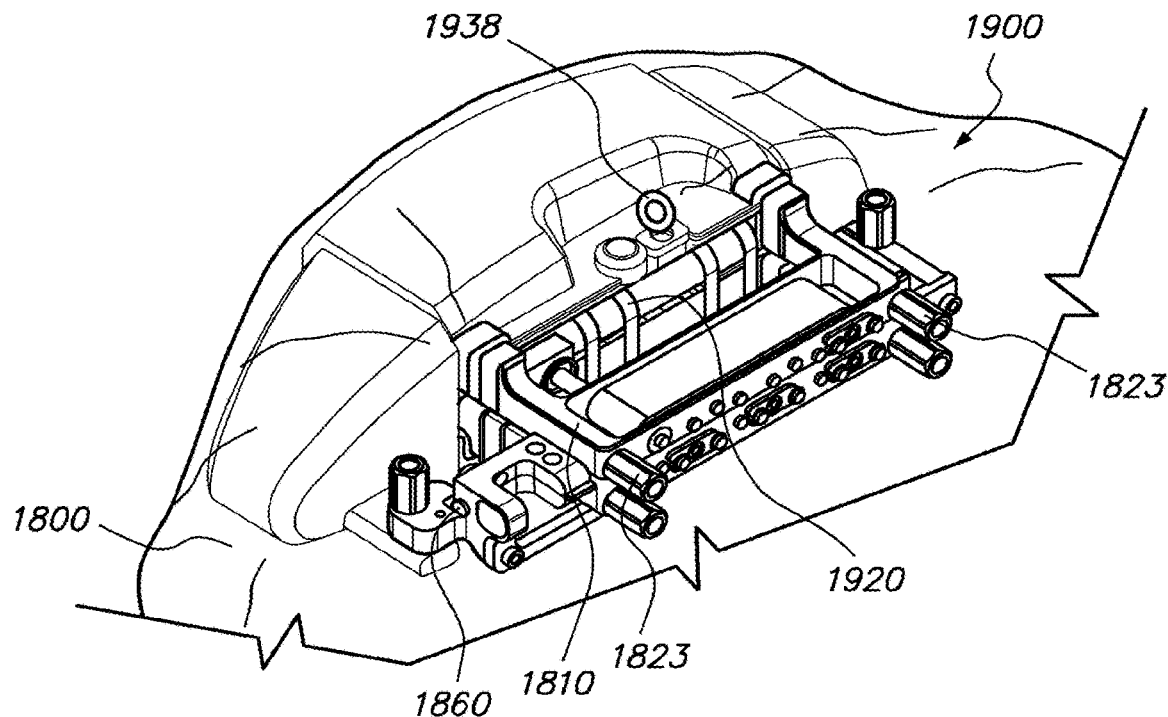
FIG. 97M4
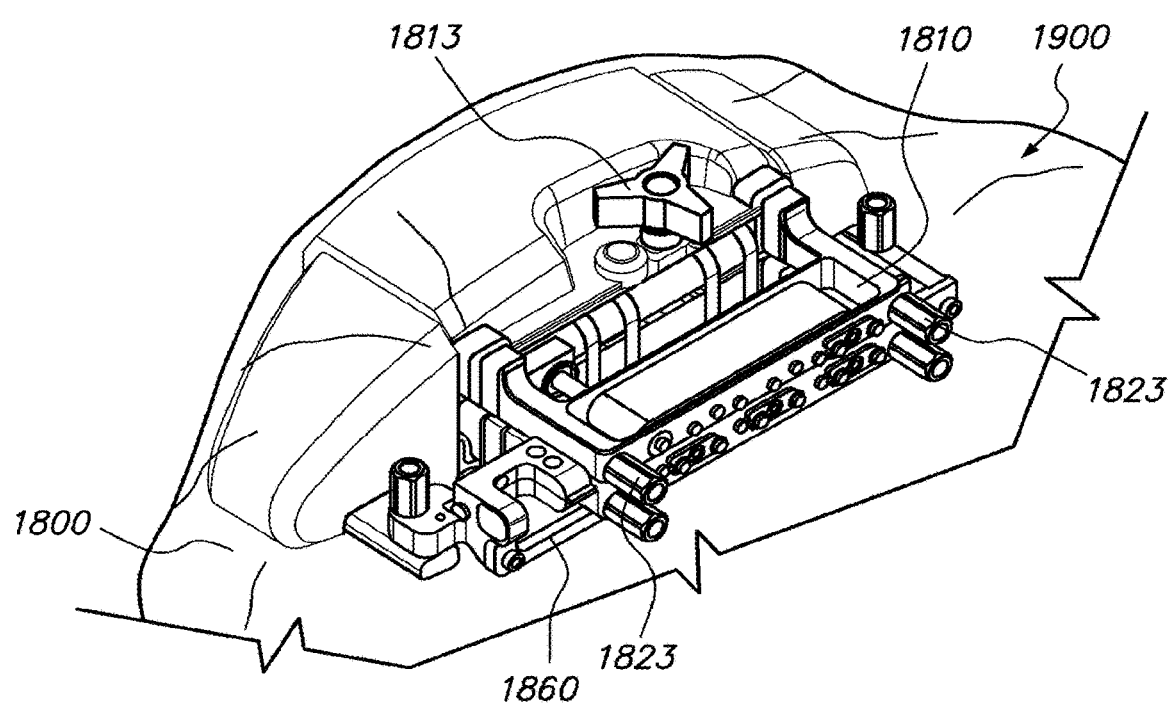
FIG. 97M5

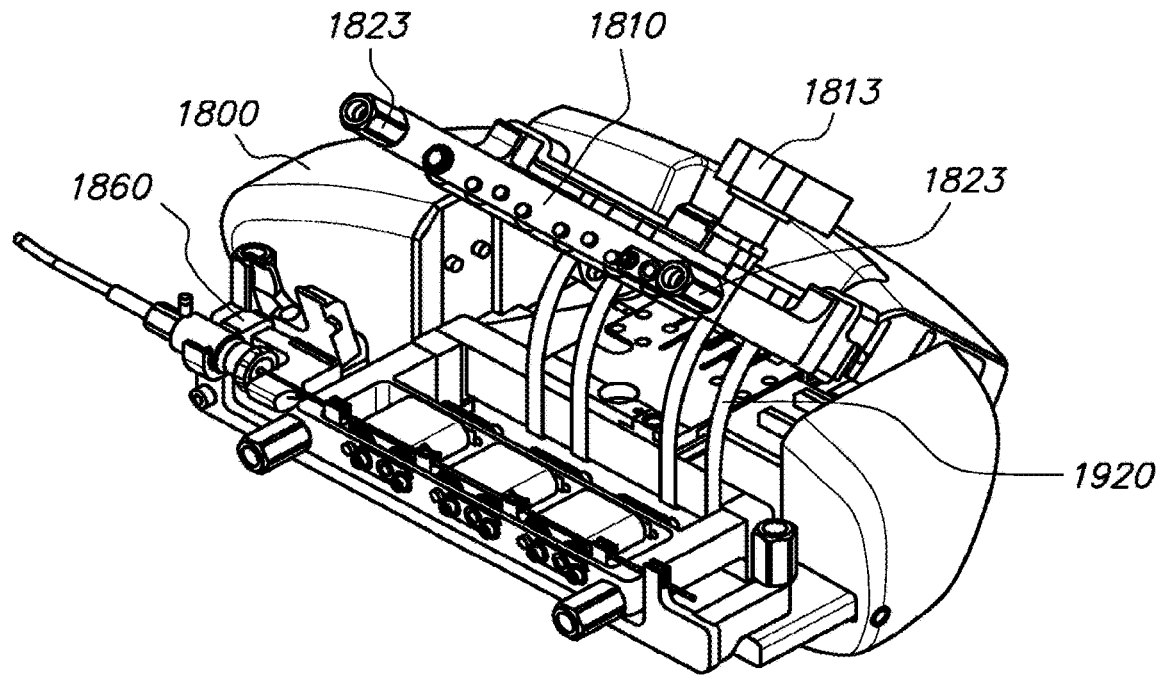
FIG. 97M6
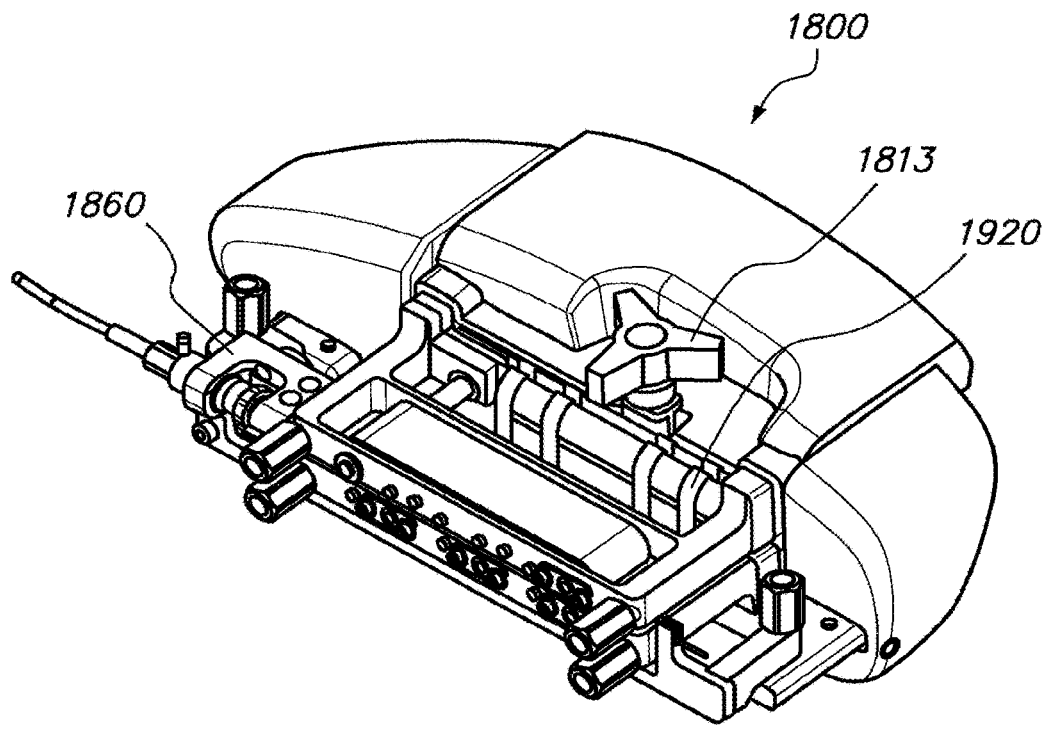
FIG. 97M7

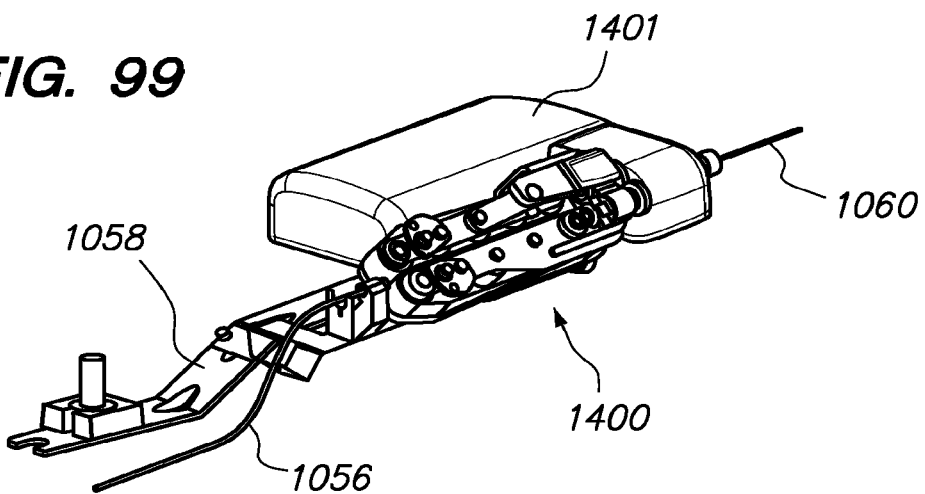
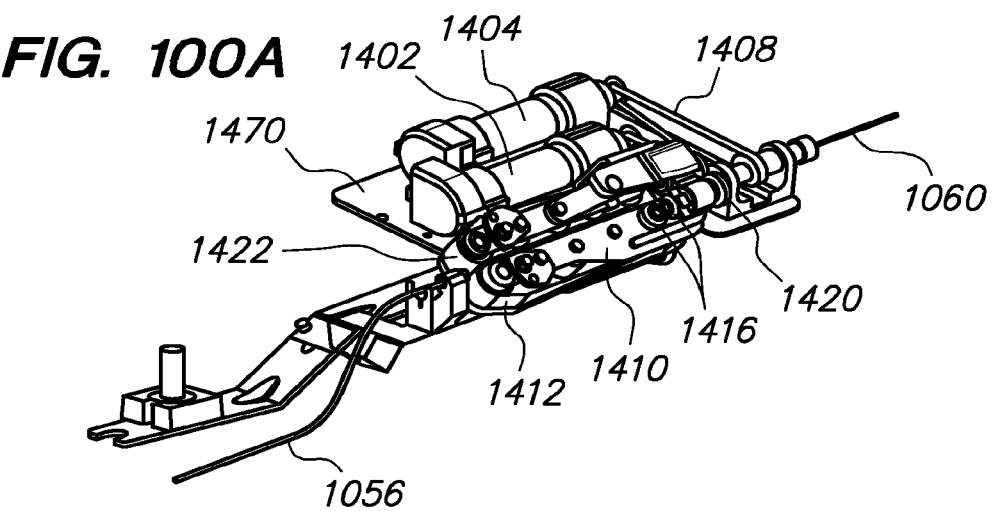
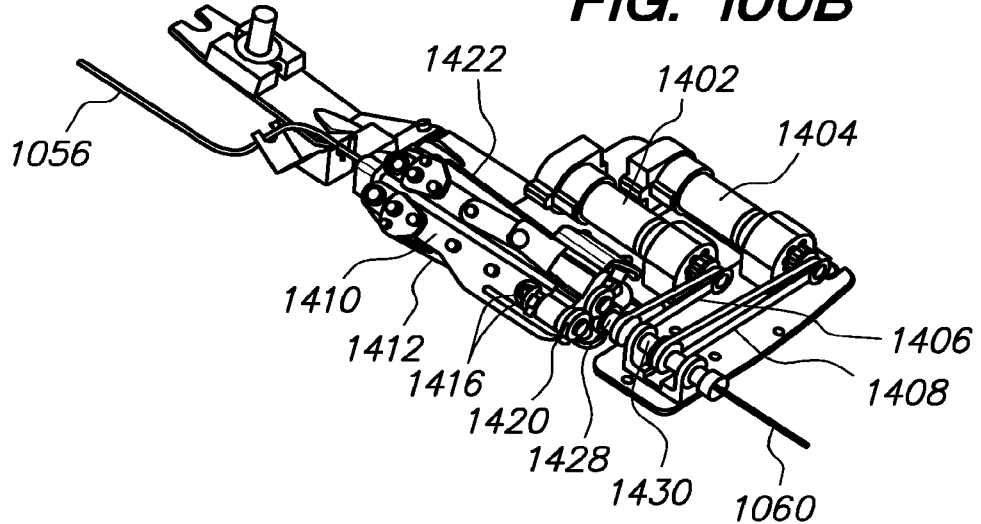

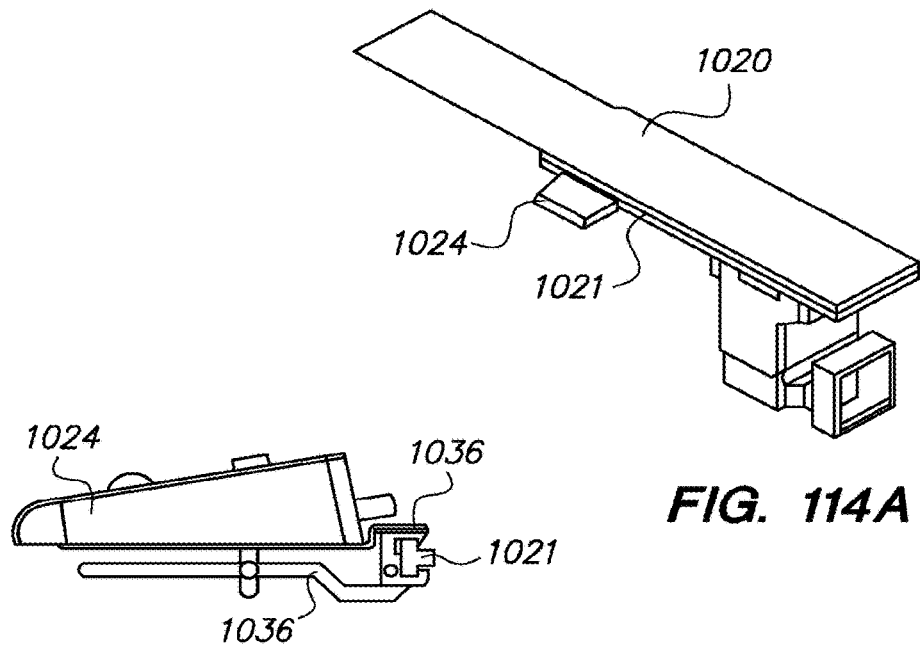
FIG. 114A
FIG. 114B
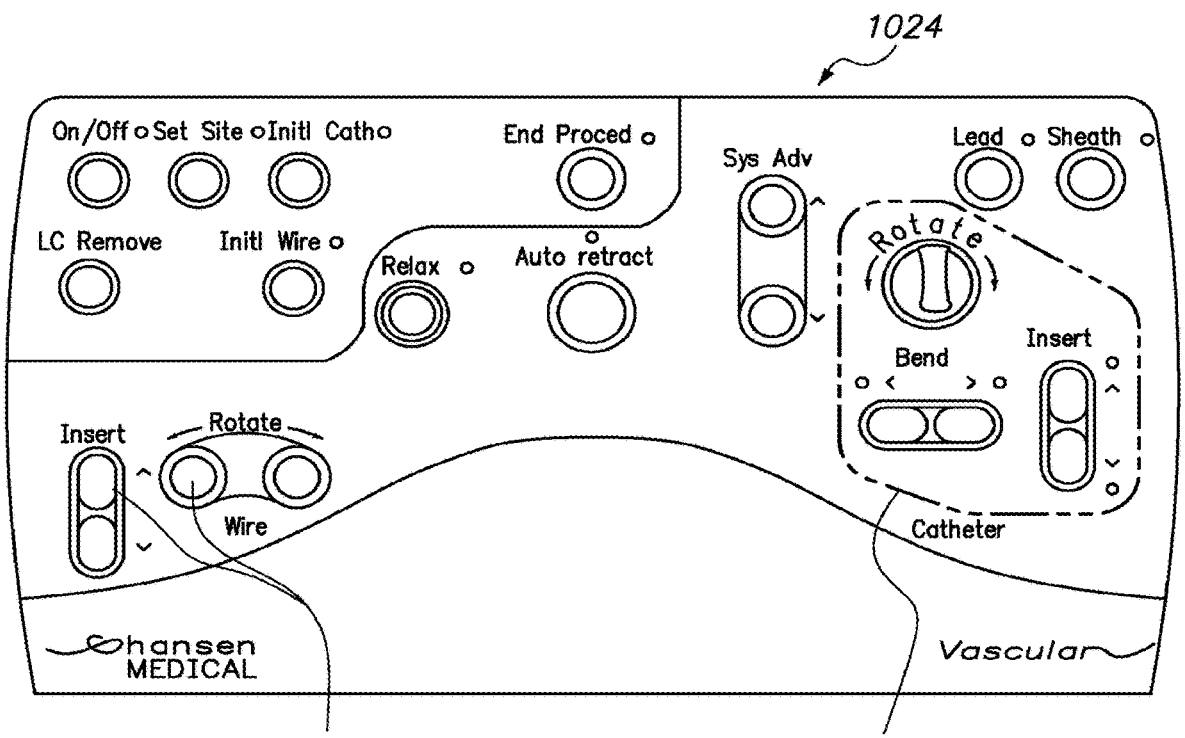
FIG. 115

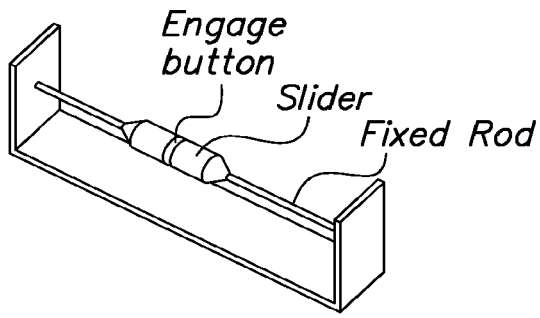
FIG. 117A
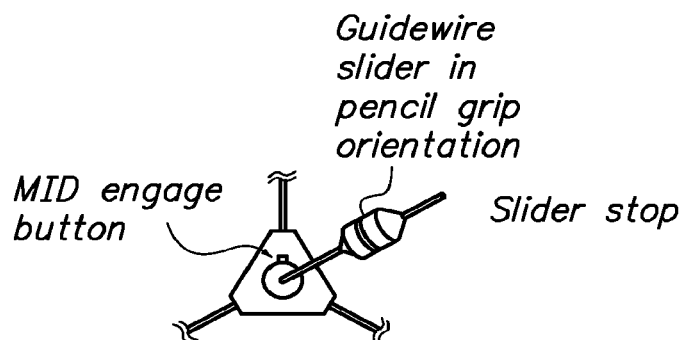
FIG. 117AA
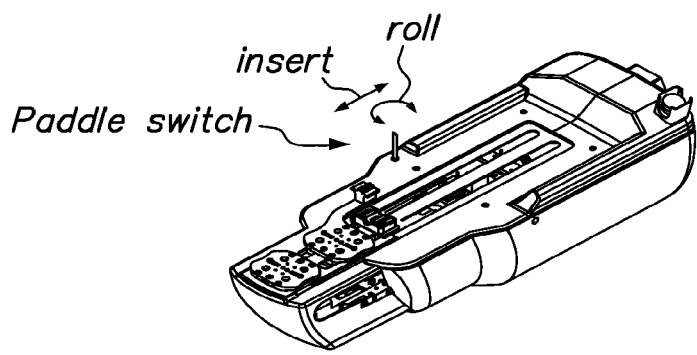
FIG. 117B
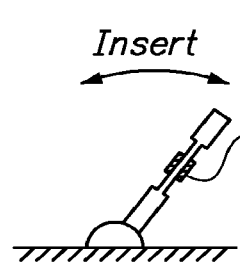
FIG. 117BB
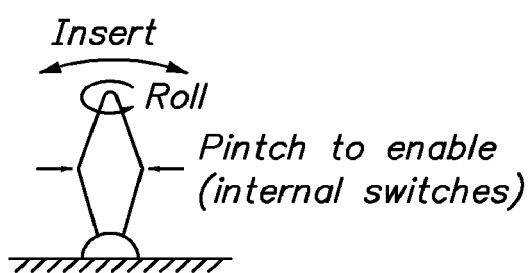
FIG. 117BBB

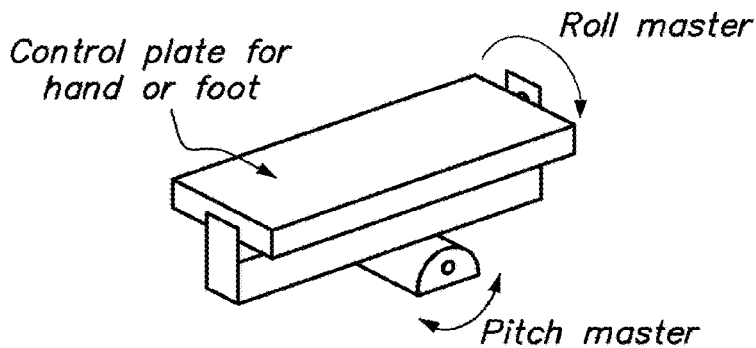
FIG. 117E
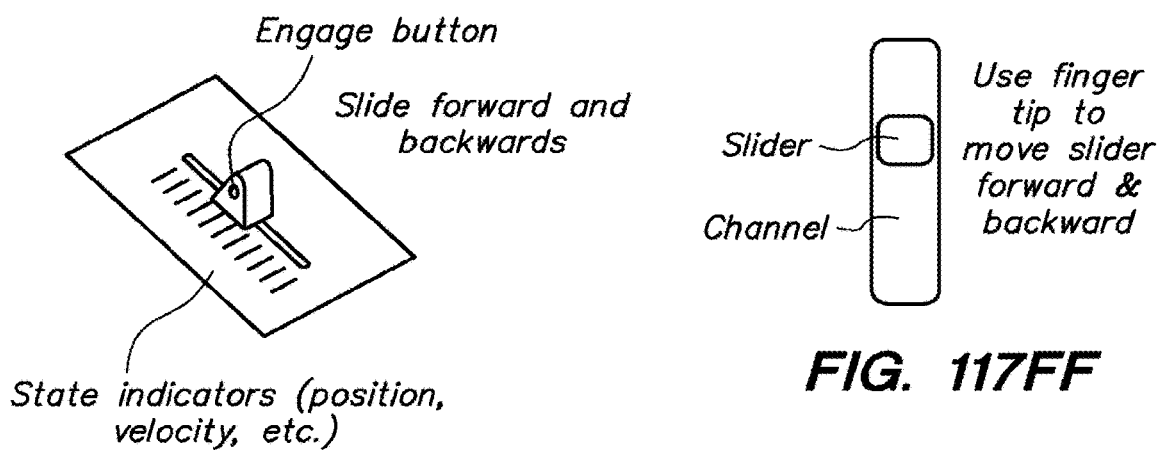
FIG. 117F
FIG. 117FF
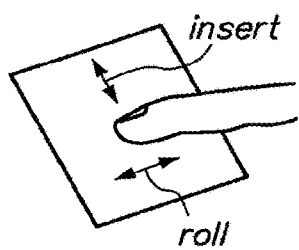
FIG. 117G
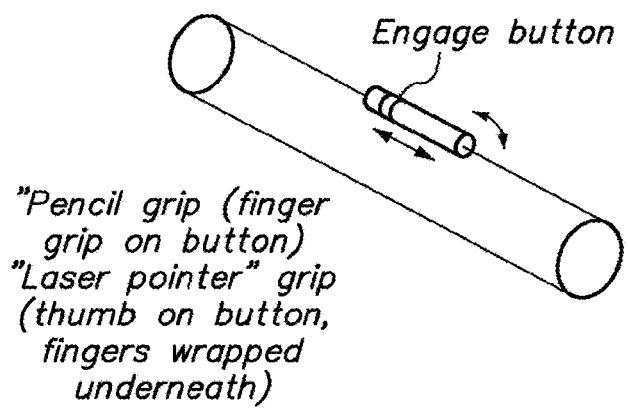
FIG. 117H

FIG. 128E  FIG. 128F
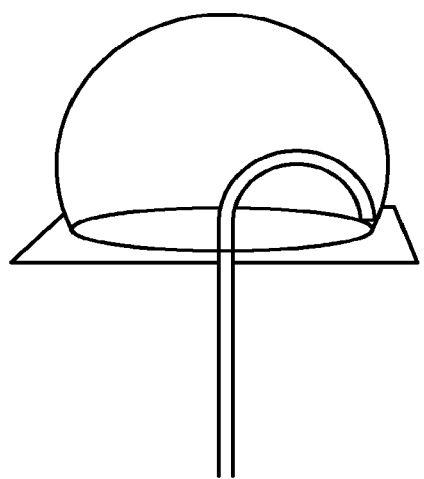
FIG. 128G

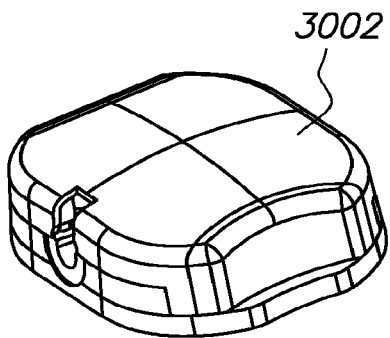
FIG. 137A
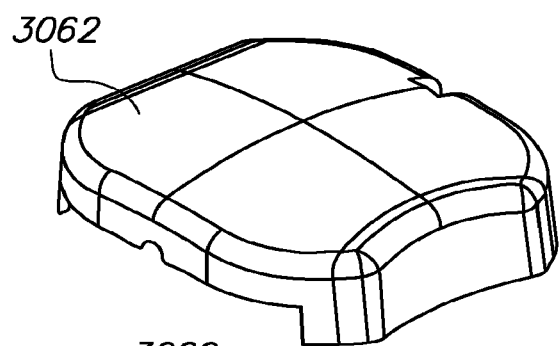
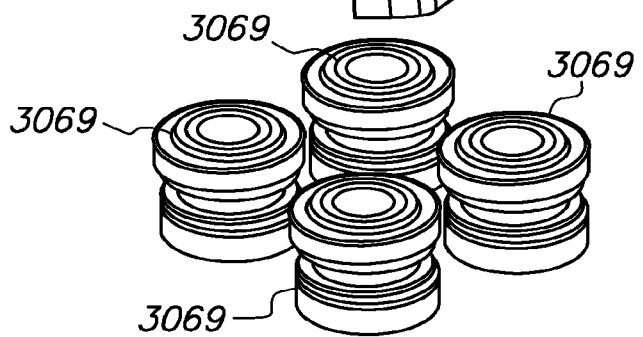
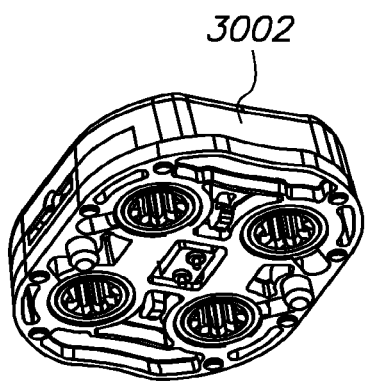
FIG. 137B
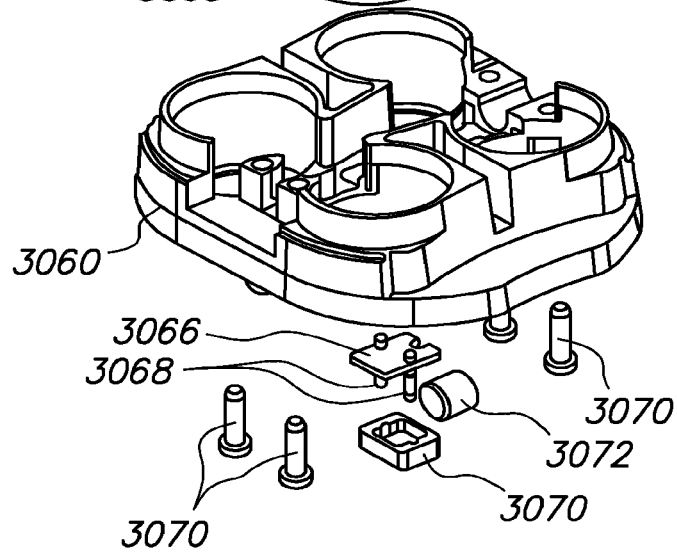
FIG. 137C

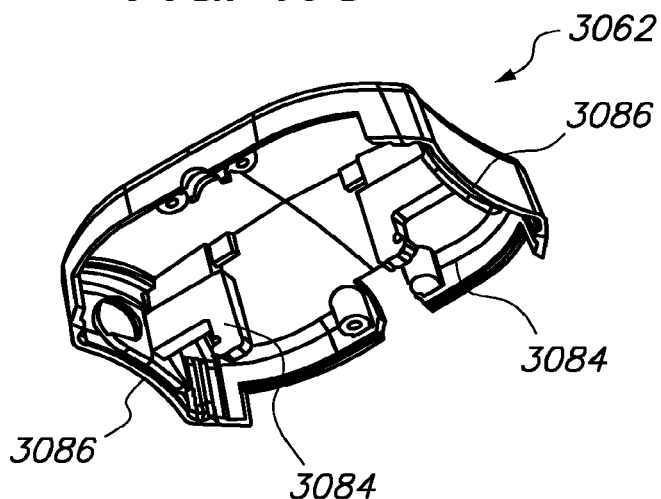
FIG. 138
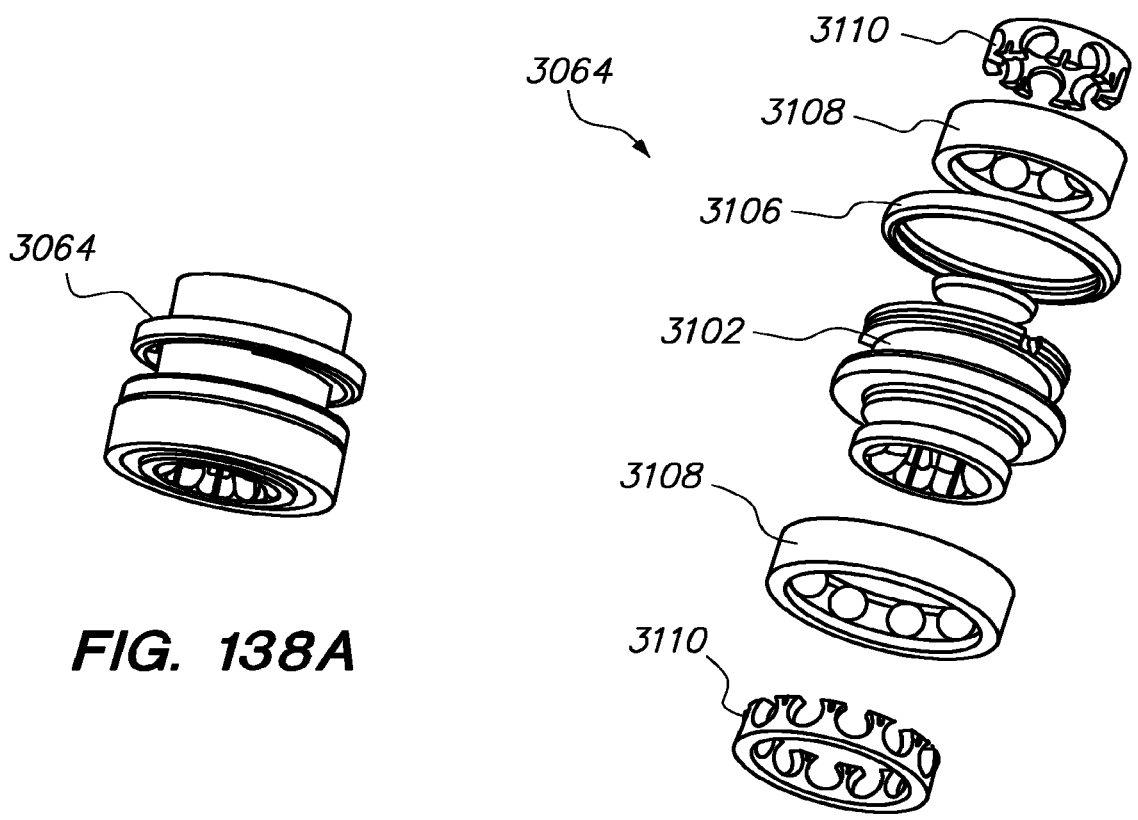
FIG. 138A
FIG. 138B

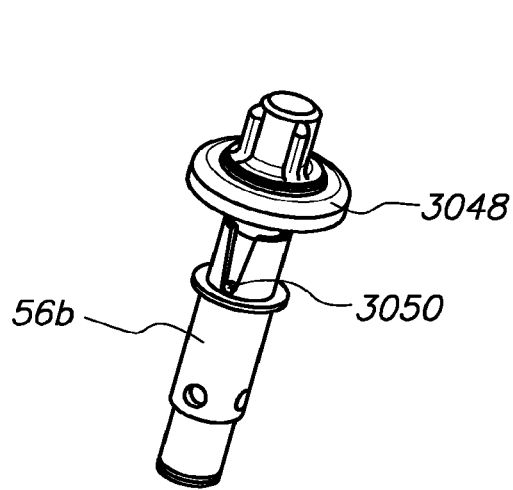
FIG. 144A
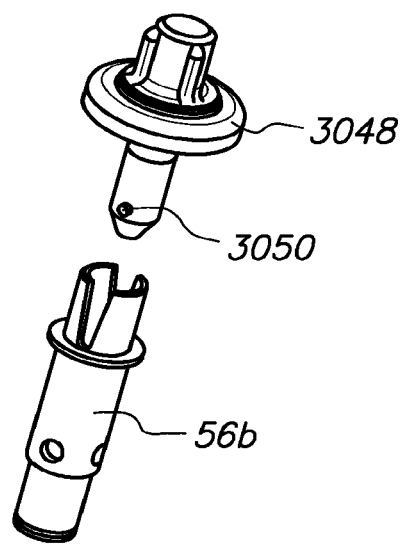
FIG. 144B
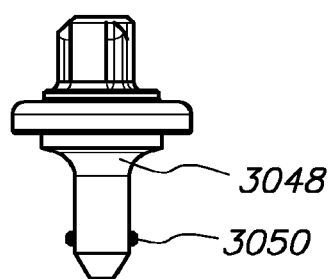
FIG. 144C
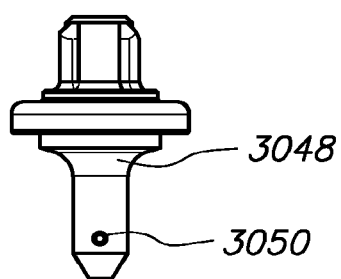
FIG. 144D
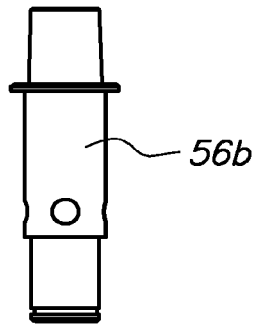
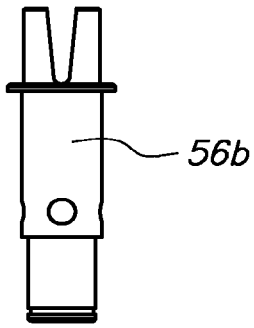

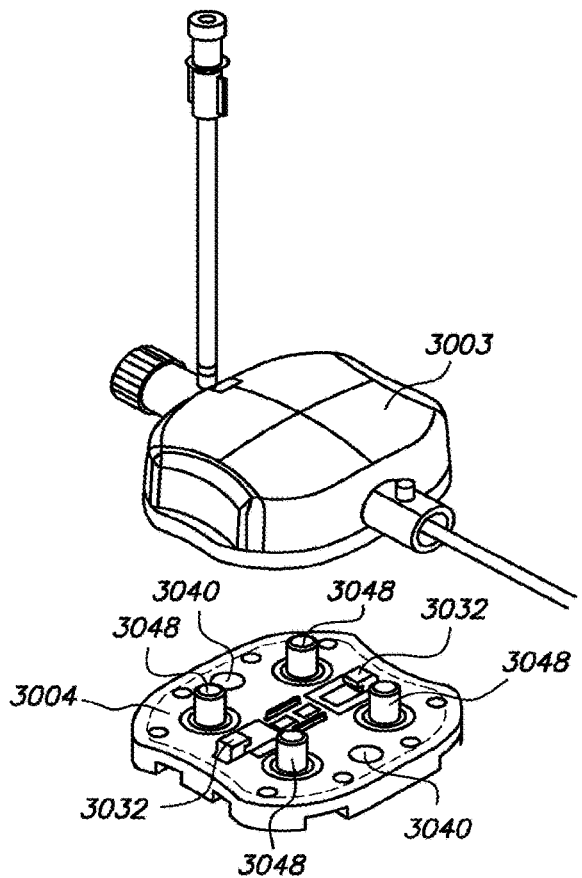
FIG. 145A
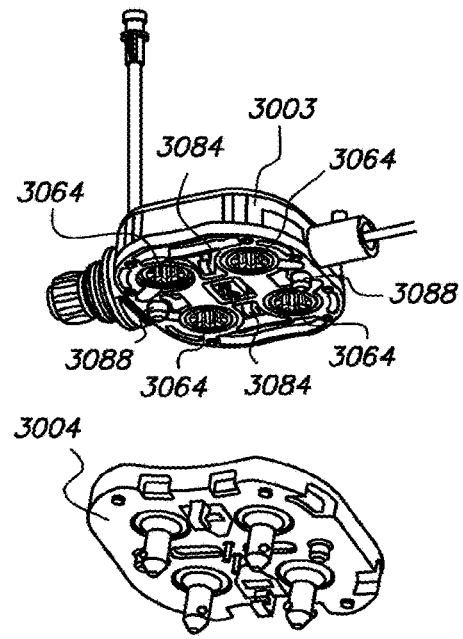
FIG. 145B
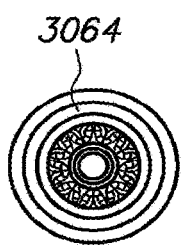
FIG. 146A
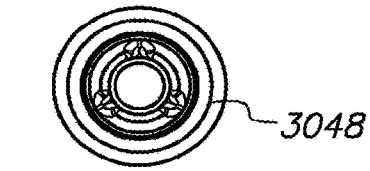
FIG. 146B
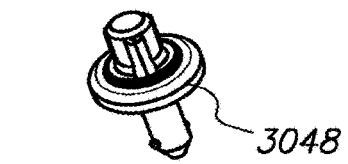
FIG. 147A
FIG. 147B

SYSTEMS AND METHODS FOR POSITIONING AN ELONGATE MEMBER INSIDE A BODY

RELATED APPLICATION DATA

This application is a continuation of U.S. patent application Ser. No. 16/165,375, filed Oct. 19, 2018, issued as U.S. Pat. No. 10,555,780 on Feb. 11, 2020, which is a continuation of Ser. No. 14/603,836, filed Jan. 23, 2015, issued as U.S. Pat. No. 10,130,427 on Nov. 20, 2018, which is a continuation of U.S. patent application Ser. No. 13/174,536, filed Jun. 30, 2011, now abandoned, entitled "SYSTEMS AND METHODS FOR POSITIONING AN ELONGATE MEMBER INSIDE A BODY," which claims priority to and the benefit of U.S. Provisional Patent Application No. 61/384,220, filed Sep. 17, 2010, and U.S. Provisional Application No. 61/482,598, filed May 4, 2011, the entire disclosures of all of which are expressly incorporated by reference herein for all purposes.

This application is related to U.S. Patent Applications entitled "Steerable catheters" having Ser. No. 13/173,994, issued as U.S. Pat. No. 8,827,948 on Sep. 9, 2014, "Robotic medical systems and methods" having Ser. No. 13/174,455, now abandoned, "Anti-buckling mechanisms and methods" having Ser. No. 13/174,563, issued as U.S. Pat. No. 8,961,533 on Feb. 24, 2015, "Systems and methods for manipulating an elongate member" having Ser. No. 13/174,605, issued as U.S. Pat. No. 9,314,306 on Apr. 19, 2016, and "User interface and method for operating a robotic medical system" having Ser. No. 13/174,638, now abandoned, all filed on Jun. 30, 2011, the entire disclosures of all of which are expressly incorporated by reference herein for all purposes.

INCORPORATION BY REFERENCE

All of the following U.S. Patent Applications are expressly incorporated by reference herein for all purposes:
U.S. patent application Ser. No. 11/179,007, filed on Jul. 6, 2005, issued as U.S. Pat. No. 7,850,642 on Dec. 14, 2010,
U.S. patent application Ser. No. 12/079,500, filed on Mar. 26, 2008, issued as U.S. Pat. No. 8,391,957 on Mar. 5, 2913,
U.S. patent application Ser. No. 11/678,001, filed on Feb. 22, 2007, issued as U.S. Pat. No. 8,092,397 on Jan. 10, 2012,
U.S. Patent Application No. 60/801,355, filed on May 17, 2006,
U.S. patent application Ser. No. 11/804,585, filed on May 17, 2007, now abandoned,
U.S. patent application Ser. No. 11/640,099, filed on Dec. 14, 2006, issued as U.S. Pat. No. 8,498,691 on Jul. 30, 2013,
U.S. patent application Ser. No. 12/507,727, filed on Jul. 22, 2009, now abandoned,
U.S. patent application Ser. No. 12/106,254, filed on Apr. 18, 2008, issued as U.S. Pat. No. 8,050,523 on Nov. 1, 2011,
U.S. patent application Ser. No. 12/192,033, filed on Aug. 14, 2008, issued as U.S. Pat. No. 9,186,046 on Nov. 17, 2015,
U.S. patent application Ser. No. 12/236,478, filed on Sep. 23, 2008, issued as U.S. Pat. No. 8,989,528 on Mar. 24, 2015,
U.S. patent application Ser. No. 12/833,935, filed on Jul. 9, 2010, now abandoned,
U.S. patent application Ser. No. 12/822,876, filed on Jun. 24, 2010, issued as U.S. Pat. No. 8,460,236 on Jun. 11, 2013, and
U.S. patent application Ser. No. 12/614,349, filed on Nov. 6, 2009, issued as U.S. Pat. No. 8,720,448 on May 13, 2014.

FIELD

The application relates generally to robotically controlled surgical systems, and more particularly to flexible instruments and instrument drivers that are responsive to a master controller for performing surgical procedures.

BACKGROUND

Robotic surgical systems and devices are well suited for use in performing minimally invasive medical procedures, as opposed to conventional techniques wherein the patient's body cavity is open to permit the surgeon's hands access to internal organs. For example, there is a need for a highly controllable yet minimally sized system to facilitate imaging, diagnosis, and treatment of tissues which may lie deep within a patient, and which may be preferably accessed only via naturally-occurring pathways such as blood vessels or the gastrointestinal tract.

SUMMARY

The subject application describes, among other things, a robotic system for controlling an elongate instrument. By means of non-limiting examples, the elongate instrument may include a catheter and a sheath surrounding at least a part of the catheter or other flexible and elongated medical instruments. In some embodiments, the sheath may be consider a catheter itself. Also, in other embodiments, the elongate instrument may optionally further include a guidewire that is at least partially surrounded by the catheter.

The elongate instrument may have different configurations in different embodiments. In accordance with some embodiments, an elongated medical device includes an elongated body having a proximal section, a distal section, and a working lumen extending through the proximal and distal sections, a first coil having a distal portion, and a proximal portion, the proximal portion of the first coil being slidable relative to the proximal section of the elongated body, and being closer to a wall of the elongated body than to an axis of the elongated body, wherein a lengthwise portion of the distal portion of the first coil is anchored to the distal section of the elongated body, and a first steering wire located within a lumen of the first coil. By means of non-limiting examples, the elongated medical device may be a catheter, a sheath, or any medical instrument having a working lumen. In one or more of the embodiments described herein, the working lumen may have a cross sectional area that is at least 30% of a cross sectional area of the elongated body. In one or more of the embodiments described herein, the lengthwise portion may be at least 10 mm. Also, in one or more of the embodiments described herein, the lengthwise portion may be at least 5% of an entire length of the first coil. In one or more of the embodiments described herein, the elongated body may have a proximal tip, and the proximal portion of the first coil may have a proximal tip that is proximal to the proximal tip of the elongated body.

The elongated medical device may have a variety of different configurations in different embodiments. In one or more of the embodiments described herein, the first coil may be anchored to the elongated body at a transition location between the proximal and distal sections of the elongated body. In one or more of the embodiments described herein, a loop at the distal portion of the first coil may be embedded into a wall of the distal section of the elongated body.

Also, in some embodiments described herein, the device may include a second coil having a distal portion anchored to the distal section of the elongated body, and a proximal portion slidable relative to the proximal section of the elongated body, and a second steering wire located within a lumen of the second coil. The steering wires allow the device to be steered in different directions during use.

The device may be mechanically driven in some embodiments. For example, in one or more of the embodiments described herein, the device may include a drivable instrument coupled to a proximal end of the elongated body and to the first and second steering wires, wherein the drivable instrument is configured to apply tension to the first and second steering wires. Also, in one or more of the embodiments described herein, the device may include a processor coupled to the drivable instrument, the processor configured to receive a user command and generate a control signal based on the user command to control the drivable instrument.

The device may also optionally include other features in different embodiments. For example, in one or more of the embodiments described herein, the device may include first and second hypotubes fixedly secured to the drivable instrument, wherein the proximal portion of the first coil is secured to the first hypotube, and the proximal portion of the second coil is secured to the second hypotube. Also, in one or more of the embodiments described herein, the device may include a liner surrounding the proximal portion of the first coil, wherein the first coil is slidable relative to the liner.

In some embodiments, the elongated body may be a body of a catheter, a guidewire, or another elongated device. In such cases, the device may include an additional elongated body that is movably disposed around at least a part of the elongated body. The additional elongated body may be another catheter, a sheath, or another elongated device.

In some embodiments, the elongated medical device may have a steerable distal section and a proximal section that remains very flexible even while the distal section is being steered. Also, one or more of the embodiments described herein, the first coil and the first steering wire may be configured to maintain a bent configuration for the distal section of the elongated body, while allowing the proximal section of the elongated body to remain flexible.

The elongate instrument may have other configurations in other embodiments. For example, in accordance with other embodiments, an elongated medical device includes an elongated body having a proximal section, a distal section, and a working lumen extending through the proximal and distal sections, a first coil, wherein at least a lengthwise portion of the first coil is anchored to the distal section of the elongated body, a second coil in the proximal section of the elongated body that is slidable relative to the proximal section of the elongated body, wherein the second coil is axially aligned with the first coil along a length of the elongated body, and a steering wire located within a lumen of the first coil and within a lumen of the second coil. In one or more of the embodiments described herein, the lengthwise portion may be at least 10 mm. Also, in one or more of the embodiments described herein, the lengthwise portion may be at least 5% of a combined length of the first coil and the second coil. In one or more of the embodiments described herein, the first coil may be embedded within a wall of the elongated body. Also, in one or more of the embodiments described herein, a distal end of the second coil may be anchored to the elongate body at a location in which there is a transition between the first and second coils. In some embodiments, each of the first coil and the second coil may have an open pitch. In other embodiments, each of the first coil and the second coil may have a closed pitch. In further embodiments, the first coil may have an open pitch, and the second coil may have a closed pitch. In some embodiments, the first coil, the second coil, and the steering wire may be configured to maintain a bent configuration for the distal section of the elongated body, while allowing the proximal section of the elongated body to remain flexible. Also, in one or more of the embodiments described herein, the elongated body may have a proximal tip, and the second coil may have a proximal tip that is proximal to the proximal tip of the elongated body.

The device may be mechanically driven in some embodiments. For example, in some embodiments, the device may include a drivable instrument coupled to a proximal end of the elongated body and to the steering wire, wherein the drivable instrument is configured to apply tension to the steering wire. Also, in some embodiments, the device may include a processor coupled to the drivable instrument, the processor configured to receive a user command and generate a control signal based on the user command to control the drivable instrument.

The device may optionally include other features in other embodiments. For example, in one or more of the embodiments described herein, the device may include a hypotube fixedly secured to the drivable instrument, wherein a proximal portion of the second coil is secured to the hypotube. Also, in one or more of the embodiments described herein, the device may include a liner surrounding the second coil, wherein the second coil is slidable relative to the liner.

In some embodiments, the elongated body may be a body of a catheter, a guidewire, or another elongated device. In such cases, the device may include an additional elongated body that is movably disposed around at least a part of the elongated body.

Embodiments of the elongated medical device described herein may be used to perform different procedures in different embodiments. In accordance with some embodiments, a method performed using an elongated medical device includes providing the elongated medical device having an elongated body having a proximal section, a distal section, and a working lumen extending through the proximal and distal sections, a first coil having a distal portion and a proximal portion, and a first steering wire located within a lumen of the first coil, and applying tension to the first steering wire, while allowing the proximal portion of the first coil to slide relative to the proximal section of the elongated body, wherein while the tension is being applied to the first steering wire, a lengthwise portion of the distal portion of the first coil is prevented from being moved relative to the distal section of the elongated body. In one or more of the embodiments described herein, the lengthwise portion may be at least 10 mm. Also, in one or more of the embodiments described herein, the lengthwise portion may be at least 5% of an entire length of the first coil. In one or more of the embodiments described herein, the elongated medical device may further include a second coil having a distal portion anchored to the distal section of the elongated body, and a proximal portion slidable relative to the proximal section of the elongated body, and a second steering wire located within a lumen of the second coil.

During the method, in some embodiments, the first coil may be prevented from being moved relative to the elongated body at a first region that is distal to a transition location between the proximal and distal sections of the elongated body, and may be allowed to slide relative to the elongated body at a second region that is proximal to the transition location. Also, in other embodiments, the lengthwise portion of the distal portion of the first coil may be prevented from being moved by embedding a loop at the distal portion of the first coil into a wall of the distal section of the elongated body.

The method may be performed using a robotic system in some embodiments. For example, in some embodiments, the tension may be applied using a drivable instrument. Also, in one or more of the embodiments described herein, the method may include generating a control signal by a processor based on a user command received by the processor, wherein the drivable instrument applies the tension to the first steering wire in response to the control signal.

In one or more of the embodiments described herein, the tension may be applied to steer the distal section of the elongated body while steering force may be isolated from the proximal section of the elongated body. Also, in some embodiments described herein, the tension may be applied to steer the distal section while a bending stiffness of the proximal section of the elongated body is not significantly affected. In still further embodiments, the tension may be applied to steer the distal section of the elongated body without creating unwanted curvature at the proximal section of the elongated body. In other embodiments described herein, the tension may be applied to steer the distal section of the elongated body while a shape of the proximal section of the elongated body is unaffected by the steering of the distal section.

The elongate instrument that may be used with the robotic system may have other configurations in other embodiments. For example, in accordance with other embodiments, an elongated medical device includes an elongated body having a proximal section, a distal section, and a working lumen extending through the proximal and distal sections, wherein the distal section has a tapered profile, a first coil having a distal portion anchored to the distal section of the elongated body, and a proximal portion slidable relative to the proximal section of the elongated body, a first steering wire located within a lumen of the first coil, a second coil having a distal portion anchored to the distal section of the elongated body, a second steering wire located within a lumen of the second coil, a control ring located at the distal section of the elongated body, and a spine located in the elongated body, wherein the first coil and the second coil are located radially away from an axis of the spine. In one or more of the embodiments described herein, the working lumen may have a tapered configuration. Also, in one or more of the embodiments described herein, the device may include a drivable instrument coupled to a proximal end of the elongated body and to the first and second steering wires, wherein the drivable instrument is configured to apply tension to the first and second steering wires. In one or more of the embodiments described herein, the device may include a processor coupled to the drivable instrument, the processor configured to receive a user command and generate a control signal based on the user command to control the drivable instrument.

The robotic system may control the elongate instrument in different configurations. In accordance with some embodiments, a robotic surgical system includes a flexible elongated member, a first member movably disposed around at least a portion of the flexible elongated member, a second member movably disposed around at least a portion of the first member, a drive assembly coupled to each of the flexible elongated member, the first member, and the second member, and a control interface for receiving an input command from a user, wherein the drive assembly is configured to automatically move one or both of the first member and the second member while maintaining the flexible elongated member at a fixed axial position in response to the received input command.

In some embodiments, the drive assembly may be configured to move the first member distally, without moving the second member, while maintaining the flexible elongated member at the fixed position, in response to the received input command. Also, in some embodiments, the drive assembly may be configured to move the first member proximally, without moving the second member, while maintaining the flexible elongated member at the fixed position, in response to the received input command. In other embodiments, the drive assembly may be configured to move the second member distally, without moving the first member, while maintaining the flexible elongated member at the fixed position, in response to the received input command. In further embodiments, the drive assembly may be configured to move the second member proximally, without moving the first member, while maintaining the flexible elongated member at the fixed position, in response to the received input command. In still further embodiments, the drive assembly may be configured to move each of the first member and the second member distally, while maintaining the flexible elongated member at the fixed position, in response to the received input command. In other embodiments, the drive assembly may be configured to move each of the first member and the second member proximally, while maintaining the flexible elongated member at the fixed position, in response to the received input command.

In one or more of the embodiments described herein, the first member may include a first pull wire, and wherein the drive assembly may be further configured to adjust a tension in the first pull wire. In some embodiments, the drive assembly may be configured to move the first member proximally relative to the second member after releasing at least some tension in the first pull wire, while maintaining the flexible elongated member at the fixed position, in response to the received input command. In other embodiments, the second member may include a second pull wire, and wherein the drive assembly may be further configured to adjust a tension in the second pull wire. In further embodiments, the drive assembly may be configured to move each of the first member and the second member proximally relative to the flexible elongated member after releasing at least some tension in the second pull wire, while maintaining the flexible elongated member at the fixed position, in response to the received input command. Also, in some embodiments, the drive assembly may be configured to translate and/or rotate the flexible elongated member.

In some embodiments, the flexible elongated member may include a guidewire. In one or more of the embodiments described herein, the guidewire may have a preformed configuration. Also, in one or more of the embodiments described herein, the system may include a mechanism for controlling and/or maintaining the preformed configuration.

In accordance with other embodiments, a robotic surgical system includes a member having a first controllable section and a second controllable section distal of the second controllable section, a drive assembly coupled to the tubular member, and a control interface for allowing a user to select one of the first and second controllable sections of the tubular member to move, wherein the drive assembly is configured to independently move the first controllable section or the second controllable section in response to an input command from the user received at the control interface. In one or more of the embodiments described herein, the first controllable section and the second controllable section may be in a telescopic configuration. In some embodiments, the drive assembly may be configured to move the first controllable section while maintaining the second controllable section in a fixed position. Also, in some embodiments, the first controllable section may have a bent configuration, and the drive assembly may be configured to move the second controllable section while maintaining the bent configuration for the first controllable section. In some embodiments, the system may include a flexible elongated member disposed inside the tubular member, wherein the drive assembly is configured to move the member while maintaining the flexible elongated member at a fixed position. Also, in other embodiments, the drive assembly may be configured to translate and/or rotate the flexible elongated member.

In some embodiments, the flexible elongated member may include a guidewire. In one or more of the embodiments described herein, the guidewire may have a preformed configuration. Also, in one or more of the embodiments described herein, the system may include a mechanism for controlling and/or maintaining the preformed configuration.

The robotic surgical system may have other configurations in other embodiments. For example, in accordance with other embodiments, a robotic surgical system includes an elongate member having a pre-shaped configuration, a member disposed over the elongate member, a drive assembly coupled to the elongate member and the member, and a control interface for receiving an input command from a user, wherein the drive assembly is configured to move the member distally relative to the elongate member along the pre-shaped configuration of the elongate member in response to the input command received at the control interface.

In some embodiments, the elongate member may include a flexible elongated member. In one or more of the embodiments described herein, the flexible elongated member may include a guidewire. Also, in some embodiments, the drive assembly may be configured to translate and/or rotate the guidewire. In other embodiments, the elongate member may have a tubular configuration. In one or more of the embodiments described herein, the tubular member may include a pull wire located in a wall thereof, and wherein the drive assembly may be configured to adjust a tension in the pull wire before moving the tubular member distally relative to the elongate member.

Also, in other embodiments, the robotic system may control two elongate members of an elongate instrument in a telescopic fashion to thereby advance the elongate instrument inside a body. For example, in accordance with some embodiments, a robotic method includes positioning a flexible elongated member that has a preformed configuration, wherein at least a part of the flexible elongated member has a first member disposed around it, and wherein the first member includes a first wire for bending the first member or for maintaining the first member in a bent configuration, releasing at least some tension in the first wire to relax the first member, and advancing the first member distally relative to the flexible elongated member while the first member is in a relaxed configuration. In some embodiments, the act of positioning the flexible elongated member may include advancing the flexible elongated member. Also, in some embodiments, the act of positioning the flexible elongated member may include using a drive mechanism. In some embodiments, the first member may include a tubular member. Also, in some embodiments, the flexible elongated member may include a guidewire. In one or more of the embodiments described herein, the guidewire may have a preformed configuration. In other embodiments, the act of positioning may include advancing and/or rotating the flexible elongated member.

In other embodiments, the method may include re-tensioning the first wire to stiffen the first member. Also, in other embodiments, the method may include repeating the acts of releasing at least some tension and advancing the first member. In still further embodiments, at least a part of the first member may have a second member disposed around it, and wherein the second member may include a second wire for bending the second member or for maintaining the second member in a bent configuration, and the method may include releasing at least some tension in the second wire to relax the second member, and advancing the second member distally relative to the flexible elongated member while the second member is in a relaxed configuration.

In some embodiments, the acts of advancing the first member and the second member may be performed simultaneously so that both the first member and the second member are advanced together. In other embodiments, the first member may be advanced before the second member. In further embodiments, the method may include re-tensioning the first wire to stiffen the first member, and re-tensioning the second wire to stiffen the second member. In still further embodiments, the first member may be advanced until a distal end of the first member has passed through an opening in a body.

The method may be performed using a drivable instrument in accordance with some embodiments. For example, in some embodiments, the first wire may be coupled to a drivable instrument, and wherein the at least some tension in the first wire may be released by the drivable instrument in response to a control signal received from a processor. Also, in some embodiments, the first member may be coupled to a drivable instrument, and wherein the first member may be advanced by the drivable instrument in response to a control signal received from a processor.

In accordance with other embodiments, a robotic method includes rolling a first member, wherein the first member is disposed around a flexible elongated member, positioning the flexible elongated member to compensate for the rolling of the first member. In one or more of the embodiments described herein, the act of rolling the first member may include rotating the first member about its longitudinal axis. In one or more of the embodiments described herein, the act of rolling the first member may include bending the first member in different radial directions to create an artificial rolling.

In accordance with other embodiments, a robotic system includes a flexible elongated member that has a preformed configuration, a first member disposed around at least a part of the flexible elongated member, wherein the first member includes a first wire, a drive assembly configured to position the flexible elongated member, a first drive mechanism configured to manipulate the first wire to bend the first member or to maintain the first member in a bent configuration, a second drive mechanism configured to move the first member relative to the flexible elongated member, and a controller coupled to the first drive mechanism and the second drive mechanism, wherein the controller is configured to transmit first control signals to operate the first drive mechanism so that the first drive mechanism releases at least some tension in the first wire to relax the first member, and to operate the second drive mechanism to advance the first member distally relative to the flexible elongated member while the first member is in a relaxed configuration. In some embodiments, the drive assembly may be configured to advance the flexible elongated member distally relative to the first member. In other embodiments, the controller may be configured to operate the first drive mechanism to re-tension the first wire to stiffen the first member after the first member is relaxed. Also, in other embodiments, the controller may be configured to operate the first and second drive mechanisms to repeat the acts of releasing at least some tension and advancing the first member.

In one or more of the embodiments described herein, the system may include a second member disposed around at least a part of the first member, wherein the second member includes a second wire, a third drive mechanism configured to manipulate the second wire to bend the second member or to maintain the second member in a bent configuration, and a fourth drive mechanism configured to move the second member, wherein the controller may be further configured to transmit second control signals to operate the third drive mechanism to release at least some tension in the second wire to relax the second member, and to operate the fourth drive mechanism to advance the second member distally relative to the flexible elongated member while the second member is in a relaxed configuration. In some embodiments, the controller may be configured to control the second drive mechanism and the fourth drive mechanism to advance the first member and the second member together and simultaneously. In other embodiments, the controller may be configured to cause the first member to be advanced before the second member. In further embodiments, the controller may be configured to operate the first drive mechanism to re-tension the first wire to stiffen the first member, and to operate the third drive mechanism to re-tension the second wire to stiffen the second member.

Embodiments of the system described herein may be used to perform various methods in different embodiments. In accordance with some embodiments, a robotic method includes inserting a first elongate member and a second elongate member into a body, wherein the second elongate member is slidably disposed around at least a portion of the first elongate member, applying tension to one or more steering wires in the first elongate member to bend a distal portion of the first elongate member, maintaining the applied tension so that the bent distal portion of the first elongate member stays stiffened, and advancing the second elongate member distally relative to the first elongate member while using the stiffened distal portion of the first elongate member as a first guide to direct the second elongate member. In some embodiments, the method may also include releasing at least some tension in one or more steering wires in the second elongate member to un-stiffen the second elongate member before the act of advancing. In some embodiments, the first elongate member may include a catheter, and the second elongate member may include a sheath. Also, in some embodiments, the second elongate member may not include any steering wire.

In one or more of the embodiments described herein, after the act of advancing, the method may include releasing at least some tension in the one or more steering wires in the first elongate member to un-stiffen the first elongate member, applying tension to one or more steering wires in the second elongate member to bend a distal portion of the second elongate member, maintaining the applied tension in the one or more steering wires in the second elongate member so that the bent distal portion of the second elongate member stays stiffened, and advancing the first elongate member distally relative to the second elongate member while using the stiffened distal portion of the second elongate member as a second guide to direct the first elongate member In some embodiments, the method may include adjusting the applied tension. In one or more of the embodiments described herein, the applied tension may be adjusted automatically. Also, in one or more of the embodiments described herein, the tension may be adjusted to maintain the distal portion of the first elongate member in a desired bent configuration.

The robotic system may also optionally include an anti-buckling device for supporting the elongate instrument as the elongate instrument is being advanced into the body in accordance with some embodiments. Such feature may prevent the elongate instrument from buckling.

One or more of the embodiments of the robotic system described herein may optionally further include a mechanism for preventing buckling of the elongate instrument. For example, in accordance with some embodiments, an anti-buckling device includes a first coupler for coupling to a first device, a second coupler for coupling to a second device that is configured to position a catheter member, a first set of support members coupled between the first coupler and the second coupler, and a plurality of holders coupled to the support members, the holders configured for supporting the catheter member, wherein the first set of support members form a support frame that can be extended by moving the first and second couplers away from each other, and can be collapsed by moving the first and second couplers towards each other. In some embodiments, the first set of support members may form a planar configuration. Also, in some embodiments, the device may further include a second set of support members that are disposed next to the first set of support members. In one or more of the embodiments described herein, the second set of support members may be configured to maintain the holders in a same orientation relative to each other, wherein the orientation may be perpendicular to a longitudinal axis of the catheter member. In further embodiments, the device may include a third set of support members that are disposed between the first and second sets of support members. In one or more of the embodiments described herein, the third set of support members may be configured to maintain the holders in a same orientation relative to each other. Also, in some embodiments, the support members may be arranged in a scissor-like configuration. In one or more of the embodiments described herein, the first set of support members may be configured to provide a variable buckling resistance for the catheter member supported by the support members in response to an advancement of the catheter member. In some embodiments, the first device may include a stabilizer that is configured to be attached to a patient. Also, in some embodiments, the first device may include a first driver and the second device comprises a second driver.

The holders in the anti-buckling device may have different features in different embodiments. For example, in one or more of the embodiments described herein, each of the holders may have an opening for accommodating a portion of the catheter member supported by the holders. Also, in one or more of the embodiments described herein, the holders may be moveable relative to a catheter member supported by the holders in a manner such that the holders are maintained at a substantially equal distance from one another as they are moved.

Other devices for supporting an elongate member are also described herein. For example, in accordance with other embodiments, a support device includes a first set of support members arranged in a scissor-like configuration to form a support frame, wherein the support frame has a first end and a second end, and can be extended by moving the first and second ends away from each other, or collapsed by moving the first and second ends towards each other, and a plurality of holders coupled to the support members, the holders configured for supporting a catheter member, wherein the holders are moveable relative to the catheter member supported by the holders, such that the holders are maintained at a substantially same distance from one another regardless of a distance between the first and second ends of the support frame. In some embodiments, the device may include a first coupler disposed at the first end of the support frame for coupling to a driver that is configured to position a catheter member. Also, in some embodiments, the device may include a second coupler disposed at the second end of the support frame for coupling to a stabilizer that is configured to be attached to a patient. In one or more of the embodiments described herein, the device may include a second coupler disposed at the second end of the support frame for coupling to a driver. Also, in one or more of the embodiments described herein, the support members may form a scissor-like configuration. In some embodiments, each of the holders may have an opening for accommodating a portion of the catheter member supported by the holders. Also, in some embodiments, the support frame may be configured to provide a variable buckling resistance for the catheter member supported by the holders in response to an advancement of the catheter member.

In some embodiments, the device may include a second set of support members disposed next to the first set of support members. In one or more of the embodiments described herein, the second set of support members may be configured to maintain the holders in a same orientation relative to each other. In further embodiments, the device may include a third set of support members disposed between the first and second sets of support members. In one or more of the embodiments described herein, the third set of support members may be configured to maintain the holders in a same orientation relative to each other.

The anti-buckling device may have different configurations in different embodiments. For example, in accordance with other embodiments, an anti-buckling device includes a first coupler for coupling to a first device, a second coupler for coupling to a second device, a first set of support members disposed between the first and second couplers, wherein the first set of support members are arranged in a scissor-like configuration, and a plurality of holders coupled to the first set of support members, the holders configured for supporting an elongated medical device. In some embodiments, the elongated medical device may include a catheter member, an endoscope, or an ablation device. Also, in some embodiments, the first set of support members may be configured to provide a variable buckling resistance for the elongated medical device being supported by the holders in response to an advancement of the elongated medical device.

Devices having other configurations that are configured to support an elongate instrument are also described herein. For example, in accordance with other embodiments, a support system includes a first elongated member with a lumen, a second elongated member slidably disposed within the lumen of the first elongated member, a first anti-buckling device configured to support the first elongated member, and a second anti-buckling device configured to support the second elongated member. In some embodiments, the first elongated member may include a sheath, and the second elongated member comprises a catheter. Also, in some embodiments, the first anti-buckling device may include support members arranged in a scissor-like configuration. In one or more of the embodiments described herein, the support members may include telescoping tubes. Also, in one or more of the embodiments described herein, the first anti-buckling device may have a first end configured to detachably couple to a first drive assembly, and a second end configured to detachably couple to a patient. In one or more of the embodiments described herein, the second anti-buckling device may have a first end configured to detachably couple to a second drive assembly, and a second end configured to detachably couple to the first drive assembly.

The support system may have different configurations in different embodiments. For example, in accordance with other embodiments, a support system includes a catheter having a first end for insertion into a patient, and a second end for coupling to a first drive assembly, and a first anti-buckling device configured to laterally support the catheter as the first end of the catheter is being advanced distally by the first drive assembly. In some embodiments, the system may include a sheath with a first end for insertion into the patient, a second end for coupling to a second drive assembly, and a lumen in which the catheter is slidably disposed, and a second anti-buckling device configured to laterally support the sheath as the sheath is being advanced by the second drive assembly. Also, in some embodiments described herein, the system may include the first drive assembly and the second drive assembly. In one or more of the embodiments described herein, the first anti-buckling device may have a first end configured to detachably couple to the first drive assembly, and a second end configured to detachably couple to the second drive assembly. Also, in one or more of the embodiments described herein, the second anti-buckling device may have a first end configured to detachably couple to the second drive assembly, and a second end configured to detachably couple to the patient. In one or more of the embodiments described herein, the first anti-buckling device may include support members arranged in a scissor-like configuration.

Embodiments of the anti-buckling/support device may be used to perform different methods in different embodiments. For example, in accordance with some embodiments, a method includes advancing a first flexible elongated member distally relative to a patient, and laterally supporting at least a part of the first flexible elongated member using a first anti-buckling device to prevent the first flexible elongated member from buckling during the act of advancing. In some embodiments, the act of laterally supporting at least a part of the first flexible elongated member may include providing a plurality of lateral supports along a length of the first flexible elongated member, and wherein the lateral supports may be slidable relative to the first flexible elongated member. Also, in some embodiments, the method may include changing a spacing of the lateral supports in response to the act of advancing. In other embodiments, the method may include advancing a second flexible elongated member distally relative to the patient, the second flexible elongated member disposed circumferentially around the first flexible elongated member, and laterally supporting at least a part of the second flexible elongated member using a second anti-buckling device to prevent the second flexible elongated member from buckling during the act of advancing the second flexible elongated member. In one or more of the embodiments described herein, the first flexible elongated member may include a catheter.

The robotic system may also optionally include a manipulator for manipulating an elongate member, such as a guidewire, in accordance with some embodiments. For example, in accordance with some embodiments, an elongate member manipulator includes an elongate member holder having first and second rotary members configured to hold an elongate member, wherein the rotary members are actuated in opposite rotational directions to generate a corresponding linear motion of the elongate member held by the rotary members along a longitudinal axis of the elongate member, and wherein the rotary members are actuated in opposite linear directions to generate a corresponding rotational motion of the elongate member held by the rotary members about the longitudinal axis of the elongate member. In some embodiments, the manipulator may include a drive assembly for actuation of the first and second rotary members, wherein the elongate member holder is releasably coupled to the drive assembly. Also, in some embodiments, the manipulator may include a sterile barrier positioned between the drive assembly and the elongate member holder, wherein the drive assembly is configured to transfer rotational motion across the sterile barrier to the rotary members to generate the corresponding linear motion of the elongate member along the longitudinal axis of the elongate member. In other embodiments, the manipulator may include a sterile barrier positioned between the drive assembly and the elongate member holder, wherein the drive assembly is configured to transfer linear motion across the sterile barrier to the rotary members to generate the corresponding rotational motion of the elongate member about the longitudinal axis of the elongate member.

In one or more of the embodiments described herein, the drive assembly may be configured to actuate the rotary members in rotational and linear directions simultaneously. Also, in one or more of the embodiments described herein, the rotary members may be actuated in the rotational and linear directions at different respective rates. Also, in one or more of the embodiments described herein, the drive assembly may be configured to provide rotational actuation and linear actuation for the rotary members separately, and wherein the rotary members may be configured to maintain engagement with the elongate member between the rotational actuation and linear actuation of the rotary members.

In some embodiments, the elongate member may include a guide wire. Also, in some embodiments, the first and second rotary members may include first and second feed rollers. In one or more of the embodiments described herein, the first feed roller may have a groove cut around an outer diameter of the first feed roller, wherein the groove may be configured for receiving an elongate member. Also, in one or more of the embodiments described herein, the first feed roller may be motor driven and the second feed roller may be idle. In addition, in some embodiments, the first rotary member may include a first flexible member with a first engagement surface, and the second rotary member may include a second flexible member with a second engagement surface. Also, in some embodiments, the first rotary member may be motor driven and the second rotary member may be idle. In further embodiments, the manipulator may include an elongate member support configured to hold the elongate member and to prevent buckling of the elongate member during rotational or linear motion of the elongate member.

Also, in some embodiments, the rotary members may include a first rotary member and a second rotary member, and the first rotary member is a first feed belt assembly comprising two or more belts with spacing between the belts to accommodate at least a portion of the elongate member support. In further embodiments, the second rotary member may include a second feed belt assembly comprising a belt wound around a plurality of pulleys to create a multiple segmented belt, the multiple segmented belt configured to contact the first feed belt assembly while providing clearance for a portion of the elongate member support extending between the belts of the first feed belt assembly. In one or more of the embodiments described herein, the first and second rotary members and the elongate member support may be arranged such that the elongate member can be held between the first and second rotary members while being supported by the elongate member support. Also, in one or more of the embodiments described herein, the elongate member support may have one or more protrusions with grooves, wherein the grooves may be configured to hold the elongate member to prevent buckling of the elongate member during rotational or linear motion of the elongate member, and the protrusions may be positioned within the spacing between the belts.

In some embodiments, the manipulator may include a roll support configured to position the elongate member so that a bend at the elongate member faces towards a first direction, and to position the elongate member so that the bend faces towards a second direction that is opposite from the first direction. In one or more of the embodiments described herein, the roll support may include a scissor jack. Also, in some embodiments, the manipulator may include a force sensor to measure force at a distal tip of the elongate member. In other embodiments, the manipulator may include one or more slip rollers for gripping the elongate member, wherein the slip rollers may be decoupled from the rotary members to detect sliding or slipping of the elongate member between the rotary members. In further embodiments, the manipulator may include a controller including a master input device, and an instrument driver in communication with the controller, the instrument driver configured to interface with a guide member and a sheath member.

In some embodiments, an elongate member manipulator may be implemented as a part of a robotic system. For example, in accordance with some embodiments, a robotic surgical system includes a controller including a master input device, an instrument driver in communication with the controller, the instrument driver configured to interface with an inner tubular member and an outer tubular member that surrounds at least a portion of the inner tubular member, and an elongate member manipulator comprising a drive assembly responsive to control signals generated, at least in part, by the master input device, and an elongate member holder releasably coupled to the drive assembly, the elongate member holder having first and second rotary members configured to hold an elongate member, wherein the drive assembly is configured to actuate the rotary members in opposite rotational directions to generate a corresponding linear motion of the elongate member along a longitudinal axis of the elongate member, wherein the drive assembly is configured to actuate said rotary members in opposite linear directions to generate a corresponding rotational motion of the elongate member about the longitudinal axis of the elongate member, and wherein the elongate member manipulator is configured to feed the elongate member into the inner tubular member. In some embodiments, the system may optionally further include a sterile barrier positioned between the drive assembly and the elongate member holder, wherein the drive assembly may be configured to transfer rotational motion across the sterile barrier to the rotary members to generate the corresponding linear motion of the elongate member along the longitudinal axis of the elongate member. Also, in some embodiments, the system may include a sterile barrier positioned between the drive assembly and the elongate member holder, wherein the drive assembly may transfer linear motion across the sterile barrier to the rotary members to generate the corresponding rotational motion of the elongate member about the longitudinal axis of the elongate member.

In some embodiments, the drive assembly may be configured to actuate the rotary members in rotational and linear directions simultaneously. Also, in some embodiments, the rotary members may be actuated in the rotational and linear directions at different respective rates. In one or more of the embodiments described herein, the drive assembly may be configured to provide rotational actuation and linear actuation for the rotary members separately, and wherein the rotary members may be configured to maintain engagement with the elongate member between the rotational actuation and linear actuation of the rotary members. In some embodiments, the elongate member may include a guide wire. Also, in some embodiments, the first and second rotary members may include first and second feed rollers. In one or more of the embodiments described herein, the first feed roller may have a groove cut around an outer diameter of the first feed roller, wherein the groove may be configured for receiving an elongate member. Also, in one or more of the embodiments described herein, the first feed roller may be motor driven and the second feed roller may be idle. In addition, in one or more of the embodiments described herein, the first rotary member may include a first flexible member with a first engagement surface, and the second rotary member may include a second flexible member with a second engagement surface. In other embodiments, the first flexible member may be motor driven and the second flexible member may be idle. In further embodiments, the system may include an elongate member support configured to hold the elongate member and to prevent buckling of the elongate member during rotational or linear motion of the elongate member. In still further embodiments, the rotary members may include a first rotary member and a second rotary member, and wherein the first rotary member comprises a first feed belt assembly comprising two or more belts with spacing between the belts to accommodate at least a portion of the elongate member support.

In some embodiments, the second rotary member may include a second feed belt assembly comprising a belt wound around a plurality of pulleys to create a multiple segmented belt, the multiple segmented belt configured to contact the first feed belt assembly while providing clearance for a portion of the elongate member support extending between the belts of the first feed belt assembly. Also, in some embodiments, the first and second rotary members and the elongate member support may be arranged such that the elongate member can be held between the first and second rotary members while being supported by the elongate member support. In one or more of the embodiments described herein, the elongate member support may have one or more protrusions with grooves, wherein the grooves are configured to hold the elongate member to prevent buckling of the elongate member during rotational or linear motion of the elongate member, and the protrusions are positioned within the spacing between the belts. In further embodiments, the system may optionally further include a roll support configured to position the elongate member so that a bend at the elongate member faces towards a first direction, and to position the elongate member so that the bend faces towards a second direction that is opposite from the first direction. In one or more of the embodiments described herein, the roll support may include a scissor jack. Also, in some embodiments, the system may include a force sensor to measure force at a distal tip of the elongate member. In further embodiments, the system may include one or more slip rollers for gripping the elongate member, wherein the slip rollers are decoupled from the rotary members to detect sliding or slipping of the elongate member between the rotary members.

Various methods for manipulating an elongate member are provided. For example, in accordance with some embodiments, a method of manipulating an elongate member in two degrees of freedom includes holding an elongate member between two rotary members, actuating the rotary members in opposite rotational directions to generate a corresponding linear motion of the elongate member along a longitudinal axis of the elongate member, and actuating the rotary members in opposite linear directions to generate a corresponding rotational motion of the elongate member about the longitudinal axis of the elongate member. In some embodiments, the rotary members may include feed belts. Also, in some embodiments, the acts of actuating may be performed simultaneously. In other embodiments, the acts of actuating may be performed at different respective rates. In still further embodiments, the acts of actuating may be performed separately, and wherein between the acts or actuating, the rotary members maintain engagement with the elongate member. In some embodiments, the method may optionally further include loading an elongate member by separating the two rotary members, and placing the elongate member on a surface of one of the two rotary members. Also, in one or more of the embodiments described herein, the method may include removing the elongate member from the first and second rotary members while maintaining the elongate member in a patient's anatomy.

Other methods for manipulating an elongate member are also provided. For example, in accordance with other embodiments, a method of manipulating an elongate member in two degrees of freedom includes transferring rotational motion across a sterile barrier to generate a corresponding linear motion of the elongate member along a longitudinal axis of the elongate member, and transferring linear motion across the sterile barrier to generate a corresponding rotational motion of the elongate member about the longitudinal axis of the elongate member. In some embodiments, the rotational motion and the linear motion may be transferred simultaneously. Also, in some embodiments, the rotational motion and linear motion may be transferred at different respective rates. In one or more of the embodiments described herein, the rotational motion and the linear motion may be transferred separately, and wherein between the acts of transferring, the elongate member may be maintained in engagement with rotary members.

In accordance with other embodiments, a method of manipulating an elongate member in two degrees of freedom includes engaging a first continuous surface with the elongate member, engaging a second continuous surface with the elongate member, actuating the first surface and second surface in opposite linear directions to generate a rotational motion of the elongate member about the longitudinal axis of the elongate member, and actuating the first surface and second surface in opposite rotational directions to generate a linear motion of the elongate member along the longitudinal axis of the elongate member. In some embodiments, the rotational motion and the linear motion may be generated simultaneously. Also, in some embodiments, the rotational motion and the linear motion may be generated at different respective rates. In one or more of the embodiments described herein, the rotational motion and the linear motion may be generated separately, and wherein the first and second continuous surfaces maintain engagement with the elongate member between the generation of the rotational motion and the linear motion.

The robotic system may also optionally include a user interface for allowing a user to operate the robotic system in accordance with some embodiments. The user interface may provide a variety of features. By means of non-limiting examples, the user interface may allow a user to align a representation of a catheter with an image of the catheter in a screen in some embodiments. In other embodiments, the user interface may provide a graphic for informing a user a constraint that is imposed by the system on manipulating the elongate instrument.

In some embodiments, the user interface may be implemented using a processor. For example, in accordance with some embodiments, a system includes a processor configured for generating a virtual representation of a catheter on a viewing screen, a first control for allowing a user to rotate the virtual representation of the catheter about a first axis, until a heading direction of the virtual representation of the catheter aligns with a heading direction of the catheter as it appears in a first fluoroscopic image, and a second control for allowing the user to rotate the virtual representation of the catheter about a second axis, until a tilt angle of the virtual representation of the catheter aligns with a tilt angle of the catheter as it appears in the first fluoroscopic image or in a second fluoroscopic image. In some embodiments, the first control may include a first slider in a touchscreen. Also, in some embodiments, the second control may include a second slider in the touchscreen. In other embodiments, the first control may include a trackball. In one or more of the embodiments described herein, the first control may be configured for rotating the virtual representation of the catheter about the first axis in a plane of the screen. In some embodiments, the system may also include an actuator coupled to the catheter and configured for bending the catheter, and a third control coupled to the actuator for allowing the user to move the bent catheter into alignment with a roll of the virtual representation of the catheter. In one or more of the embodiments described herein, the system may include a third control for allowing the user to move the virtual representation of the catheter into alignment with a roll of the catheter. Also, in one or more of the embodiments described herein, the catheter may have a bent configuration.

In some embodiments, the processor may be configured for generating the virtual representation of the catheter using kinematic information regarding the catheter. In one or more of the embodiments described herein, the processor may be configured for generating the virtual representation of the catheter based at least in part on a signal transmitted through a fiber optic that extends along a length of the catheter. In one or more of the embodiments described herein, the processor may be configured for generating the virtual representation of the catheter based at least in part on localization data obtained from electromagnetic sensors.

In some embodiments, a method may be implemented using a user interface that allows a user to align a representation of an elongate device with an image of an elongate device. For example, in accordance with some embodiments, a method includes generating a virtual representation of the catheter on a viewing screen, providing a first control for allowing a user to rotate the virtual representation of the catheter about a first axis, until a heading direction of the virtual representation of the catheter aligns with a heading direction of the catheter as it appears in a first fluoroscopic image, and providing a second control for allowing the user to rotate the virtual representation of the catheter about a second axis, until a tilt angle of the virtual representation of the catheter aligns with a tilt angle of the catheter as it appears in the first fluoroscopic image or in a second fluoroscopic image. In some embodiments, the first control may include a first slider in a touchscreen. Also, in some embodiments, the second control may include a second slider in the touchscreen. In other embodiments, the first control may include a trackball. In some embodiments, the virtual representation may be generated using kinematic information regarding the catheter. In other embodiments, the virtual representation may be generated based at least in part on a signal transmitted through a fiber optic that extends along a length of the catheter. In one or more of the embodiments described herein, the first control may be provided for rotating the virtual representation of the catheter about the first axis in a plane of the screen. Also, in one or more of the embodiments described herein, the method may include providing a third control coupled to an actuator configured for moving the catheter for allowing the user to move the catheter until the appearance of the catheter in the first or second fluoroscopic image is in alignment with a roll of the virtual representation of the catheter. In other embodiments, the method may include providing a third control for allowing the user to move the virtual representation of the catheter into alignment with a roll of the catheter as it appears in the first or second fluoroscopic image. In one or more of the embodiments described herein, the catheter may have a bent configuration.

In accordance with other embodiments, a computer product includes a non-transitory medium storing a set of instructions, an execution of which causes a method for registering an image of a catheter with a virtual representation of the catheter to be performed, the set of instructions comprising one or more instructions for generating a virtual representation of the catheter on a viewing screen, one or more instructions for allowing a user to manipulate a first control to rotate the virtual representation of the catheter about a first axis, until a heading direction of the virtual representation of the catheter aligns with a heading direction of the catheter as it appears in a first fluoroscopic image, and one or more instructions for allowing the user to manipulate a second control to rotate the virtual representation of the catheter about a second axis, until a tilt angle of the virtual representation of the catheter aligns with a tilt angle of the catheter as it appears in the first fluoroscopic image or in a second fluoroscopic image. In some embodiments, the first control may include a first slider in a touchscreen. Also, in some embodiments, the second control may include a second slider in the touchscreen. In other embodiments, the first control may include a trackball. In one or more of the embodiments described herein, manipulation of the first control may allow the user to rotate the virtual representation of the catheter about the first axis in a plane of the screen. Also, in one or more of the embodiments described herein, the set of instructions may further include one or more instructions for allowing the user to manipulate a third control for moving the catheter, until the catheter as it appears in the first or second fluoroscopic image is in alignment with a roll of the virtual representation of the catheter. In one or more of the embodiments described herein, the set of instructions may further include one or more instructions for allowing the user to manipulate a third control for moving the virtual representation of the catheter into alignment with a roll of the catheter as it appears in the first or second fluoroscopic image. In some embodiments, the one or more instructions for generating the virtual representation may include one or more instructions for using kinematic information regarding the catheter to generate the virtual representation. In other embodiments, the one or more instructions for generating the virtual representation may include one or more instructions for generating the virtual representation based at least in part on a signal transmitted through a fiber optic that extends along a length of the catheter. In one or more of the embodiments described herein, the catheter may have a bent configuration.

In accordance with other embodiments, a user interface for controlling a robotic system includes a screen displaying an image of a catheter and a dome at a distal end of the catheter, wherein the dome represents a constraint for the distal end of the catheter so that at least a part of the distal end of the catheter is required to be on an outline of the dome regardless of how the catheter is driven. By means of non-limiting examples, the dome may have a cardiod shape, a spherical shape, or any shape that is user defined/computer calculated. In some embodiments, the user interface may include a first control for allowing the user to advance or retrace the catheter, and a second control for allowing the user to steer the catheter. Also, in some embodiments, advancement or retraction of the catheter may change a size of the dome in the screen. In further embodiments, a steering of the catheter may not change a size of the dome in the screen. In one or more of the embodiments described herein, the user interface may include a user control configured to provide force feedback to a user. Also, in one or more of the embodiments described herein, the user control may be configured to provide force feedback when the user attempts to position the at least a part of the distal end of the catheter away from the outline of the dome. In some embodiments, the image of the catheter may include a computer model of the catheter.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 10 illustrates a sheath block and guide insert motor and leadscrew removed from the instrument driver shown in FIG. 5C.

FIGS. 10A and 10B illustrate different perspective views of the sheath block.

FIGS. 11A-11H illustrate side and cross-sectional views of a catheter bent in various configurations with pull wire manipulation.

FIG. 12 shows an example of an overview block diagram of a basic topology for controlling flexible devices.

FIG. 13 illustrates forward kinematics and inverse kinematics in accordance with some embodiments.

FIGS. 35A-35C illustrate the operation of a substantially flexible and steerable elongate instrument in accordance with one embodiment.

FIG. 36A and FIG. 36B illustrate curve aligned steering of a flexible and steerable elongate instrument in accordance with one embodiment.

FIGS. 37A-37E illustrate another catheter in accordance with other embodiments.

FIGS. 38-44 illustrate a sheath in accordance with some embodiments, and variations thereof.

FIGS. 45-48 illustrate methods of using a catheter and a sheath in accordance with different embodiments.

FIGS. 49-50C illustrate a valve in accordance with some embodiments.

FIGS. 53A-67C illustrate different anti-buckling devices, and components that operate with the anti-buckling devices, in accordance with different embodiments.

FIG. 96C illustrates a perspective view of a representation of an alternative elongate member manipulator with a guide wire installed.

FIGS. 96D-96E illustrate side views of the elongate member manipulator of FIG. 96C showing roll actuation of the guide wire.

FIGS. 97A1-97A2 illustrate a front view of the elongate member manipulator of FIG. 97 in an closed and open configuration respectively.

FIGS. 97A3-97A4 illustrate a back view of the elongate member manipulator of FIG. 97 in an closed and open configuration respectively.

FIGS. 97B1-97B2 illustrate front and back perspective views of the elongate member manipulator of FIG. 97A1 with the cover removed.

FIG. 97B3 illustrates a zoomed in view of a roll motor and accompanying roll mechanisms.

FIG. 97C illustrates the elongate member manipulator of FIGS. 97B1-97B2 with only insert mechanical components and a drive belt assembly displayed.

FIG. 97D1 illustrates a perspective view of the drive belt assembly of FIG. 97C.

FIG. 97D2 illustrates a cross sectional view of the drive belt assembly of FIG. 97D1.

FIG. 97D3 illustrates a zoomed in view of a drive shaft shown in FIG. 97D2.

FIGS. 97E1-E2 illustrate upper and lower slide assemblies of the elongate member manipulator of FIG. 97C with the drive belt assembly and an idler belt assembly installed and un-installed respectively.

FIG. 97H1 illustrates the elongate member manipulator of FIG. 97A1 with the drive and idler belt assemblies removed.

FIG. 97H2 illustrates a view of the elongate member manipulator of FIG. 97H1 with an elongate member holder exploded from the elongate member manipulator.

Figure 1:
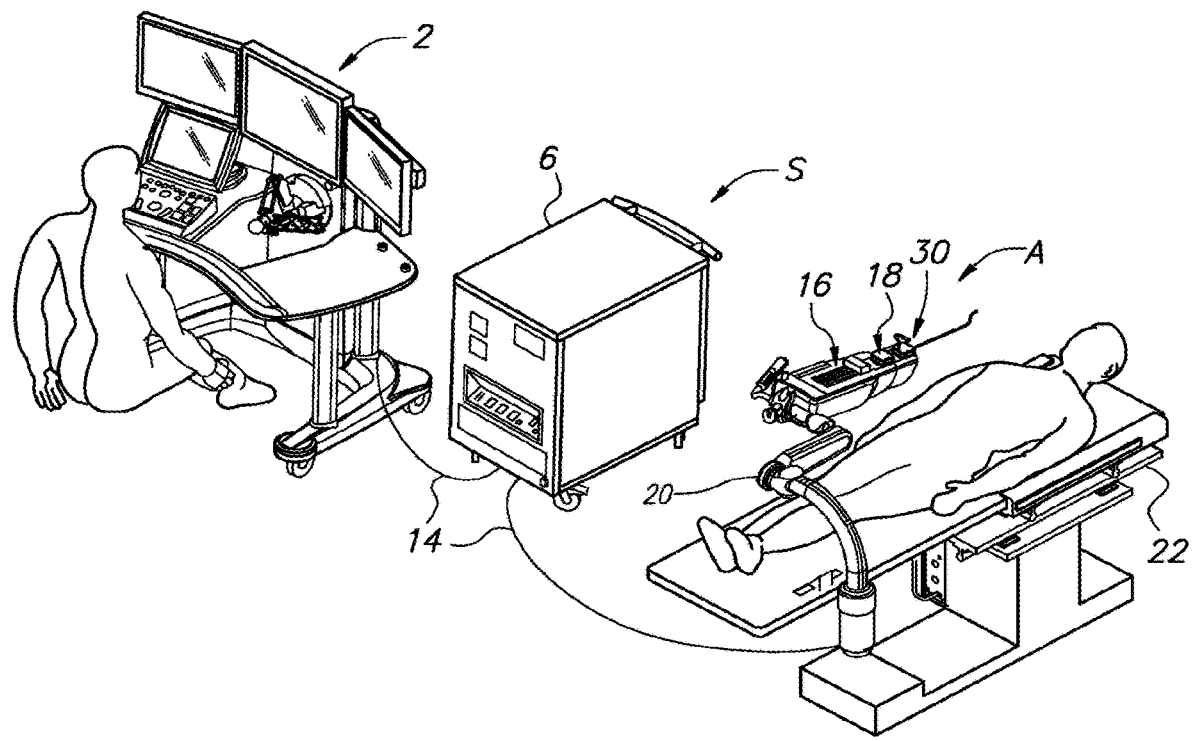
FIG. 1 illustrates a robotic surgical system in which apparatus, system and method embodiments may be implemented.
Figure 2:
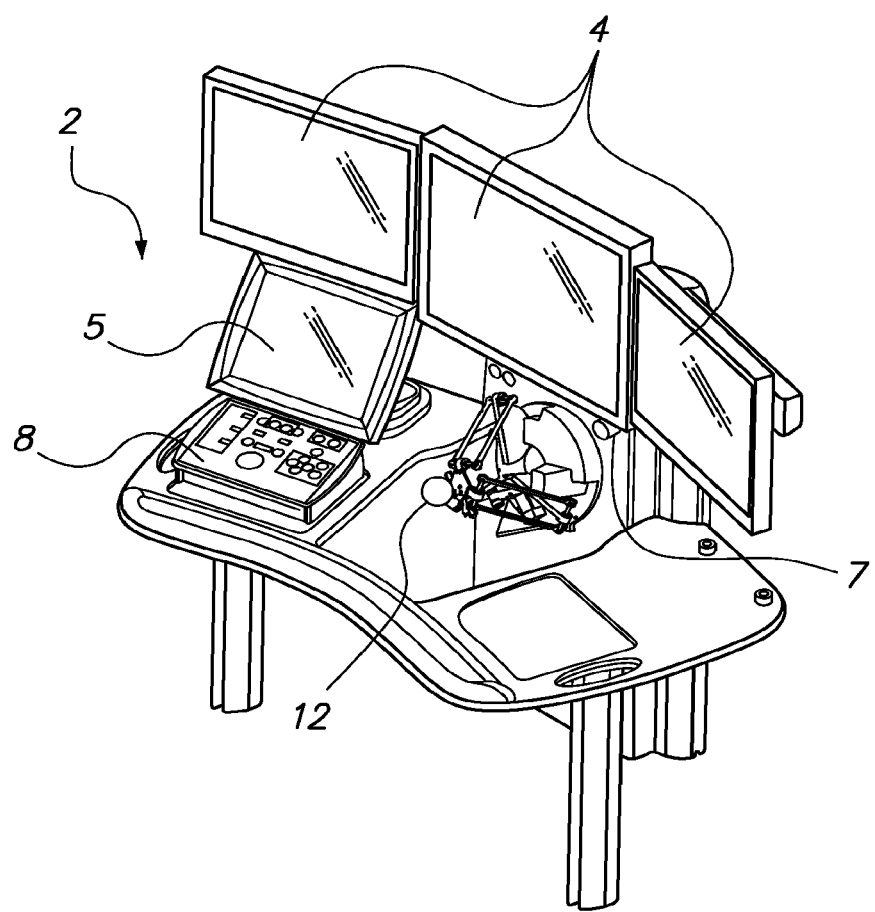
FIG. 2 illustrates an example of an operator workstation of the robotic surgical system shown in FIG. 1 with which a catheter instrument can be manipulated using different user interfaces and controls.

FIG. 97J1 illustrates the elongate member holder of FIGS. 97H1-97H2 with a guide wire and valve installed.

FIG. 97J2 illustrates the elongate member holder of FIG. 97J1 with a valve holder in an open configuration and the guide wire and valve exploded from the elongate member holder.

Figure 3A:
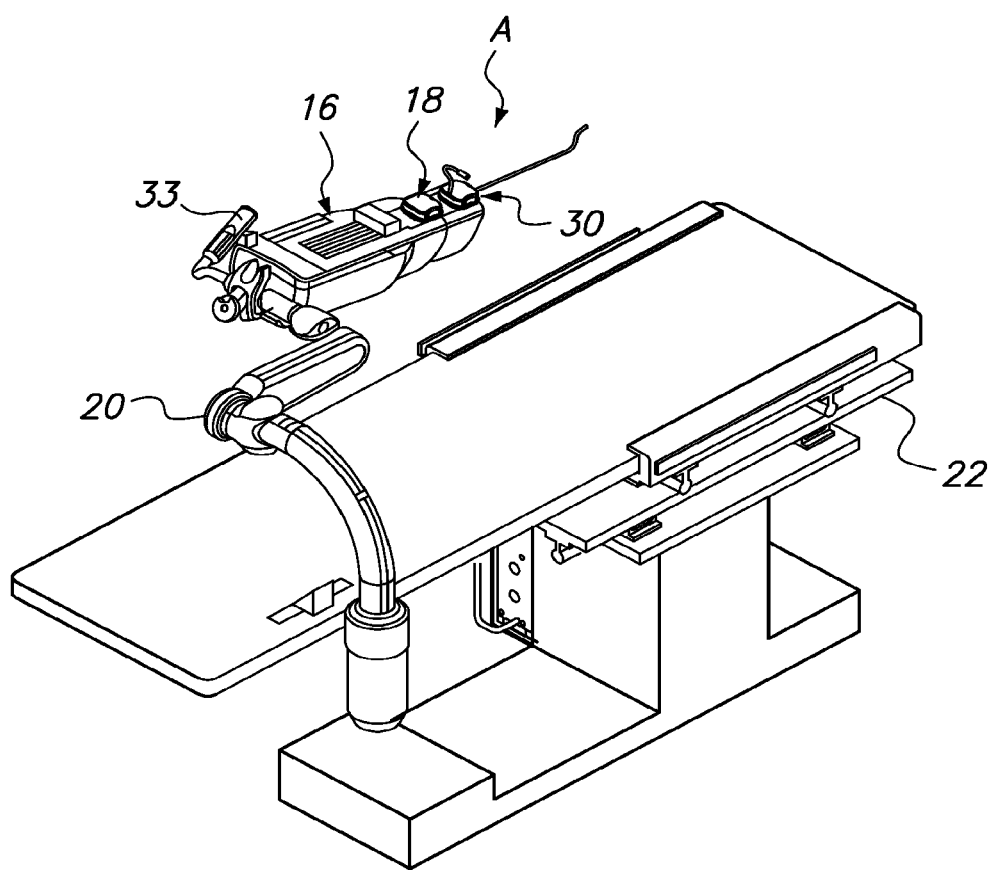
FIG. 3A illustrates a support assembly or mounting brace for a instrument driver of a robotic surgical system.
Figure 3B:
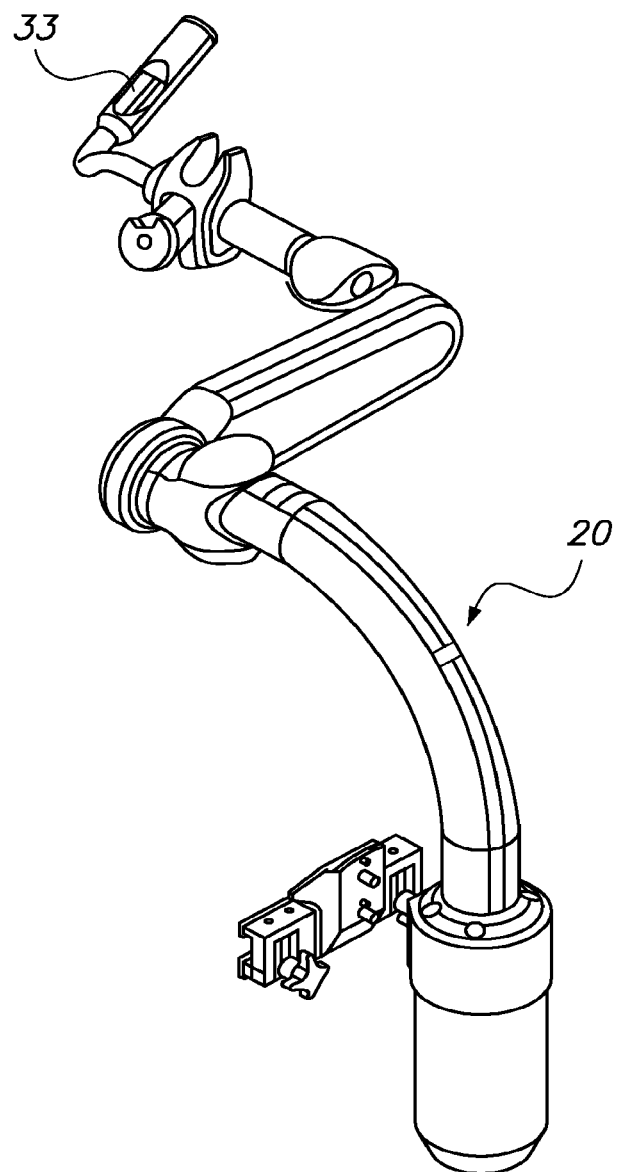
FIG. 3B further illustrates the support assembly illustrated in FIG. 3A.
Figure 3C:
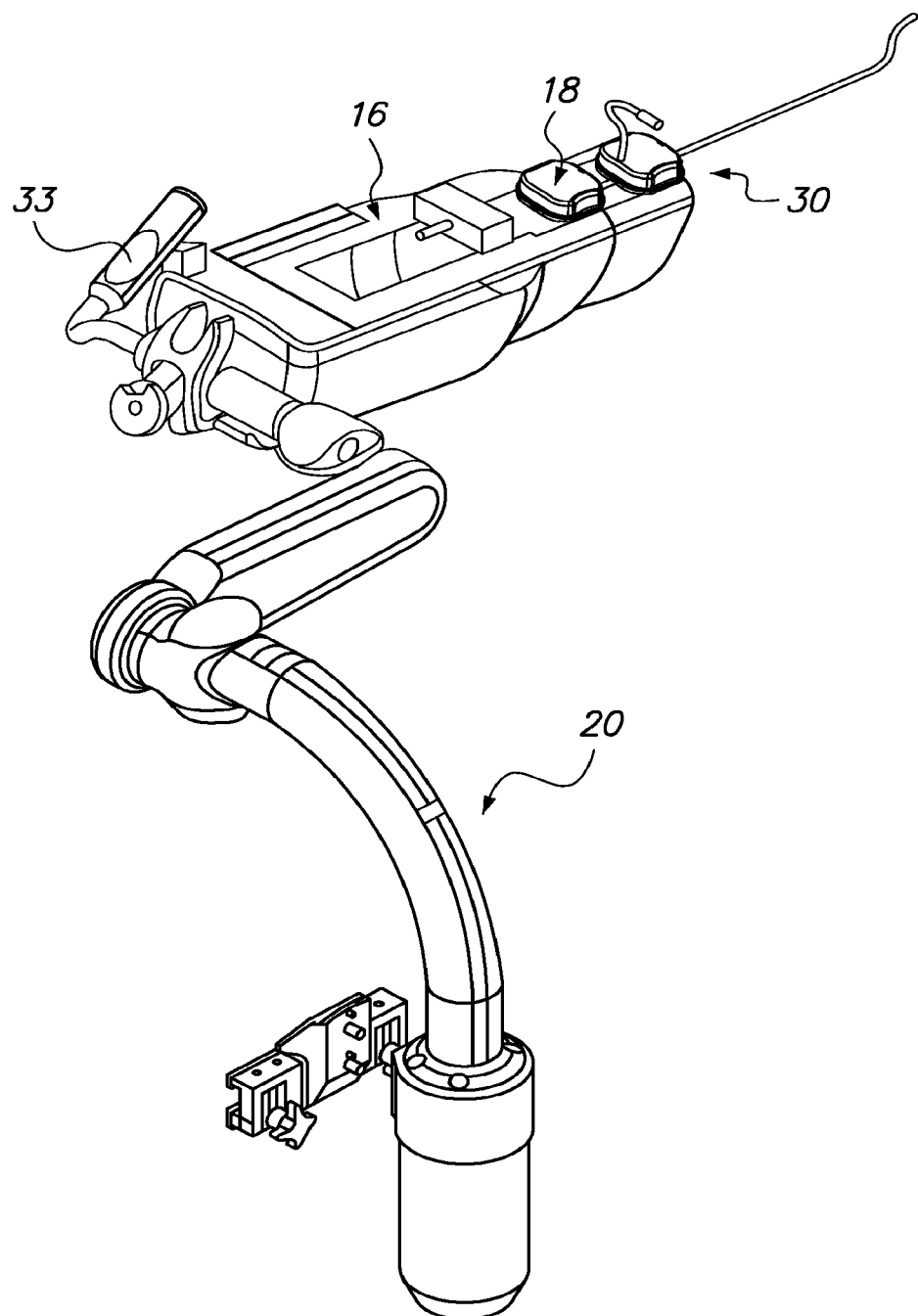
FIG. 3C is another view of the support assembly shown in FIGS. 3A-B with an attached instrument driver.
Figure 3D:
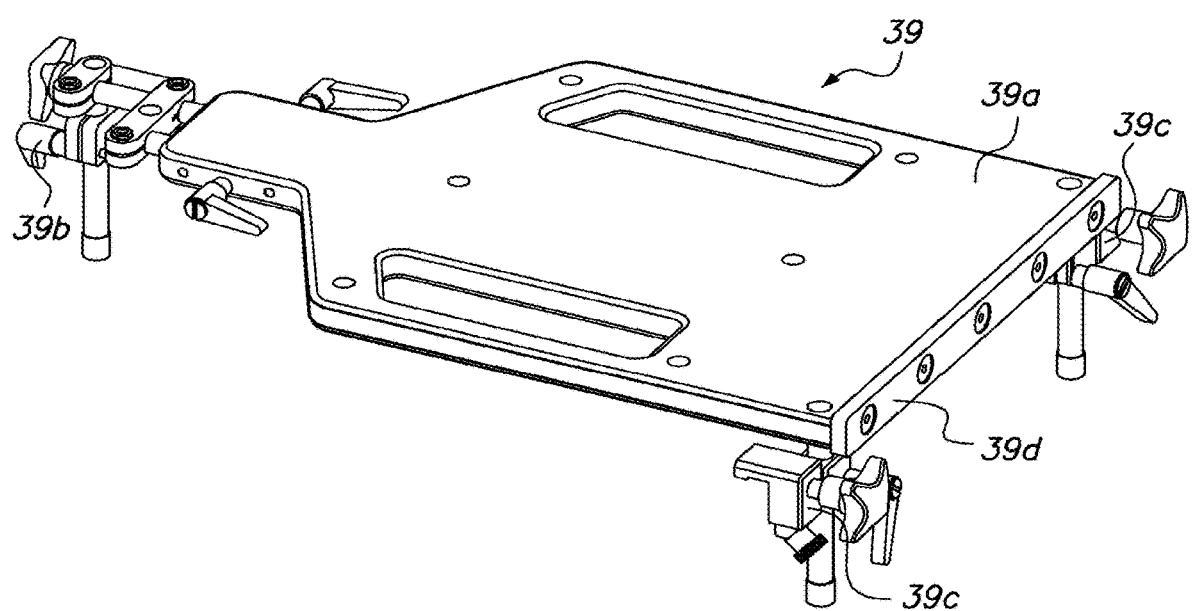
FIG. 3D is a perspective view of a support arm adapter base plate assembly configured for attaching a support assembly to an operating table or surgical bed.
Figure 3E:
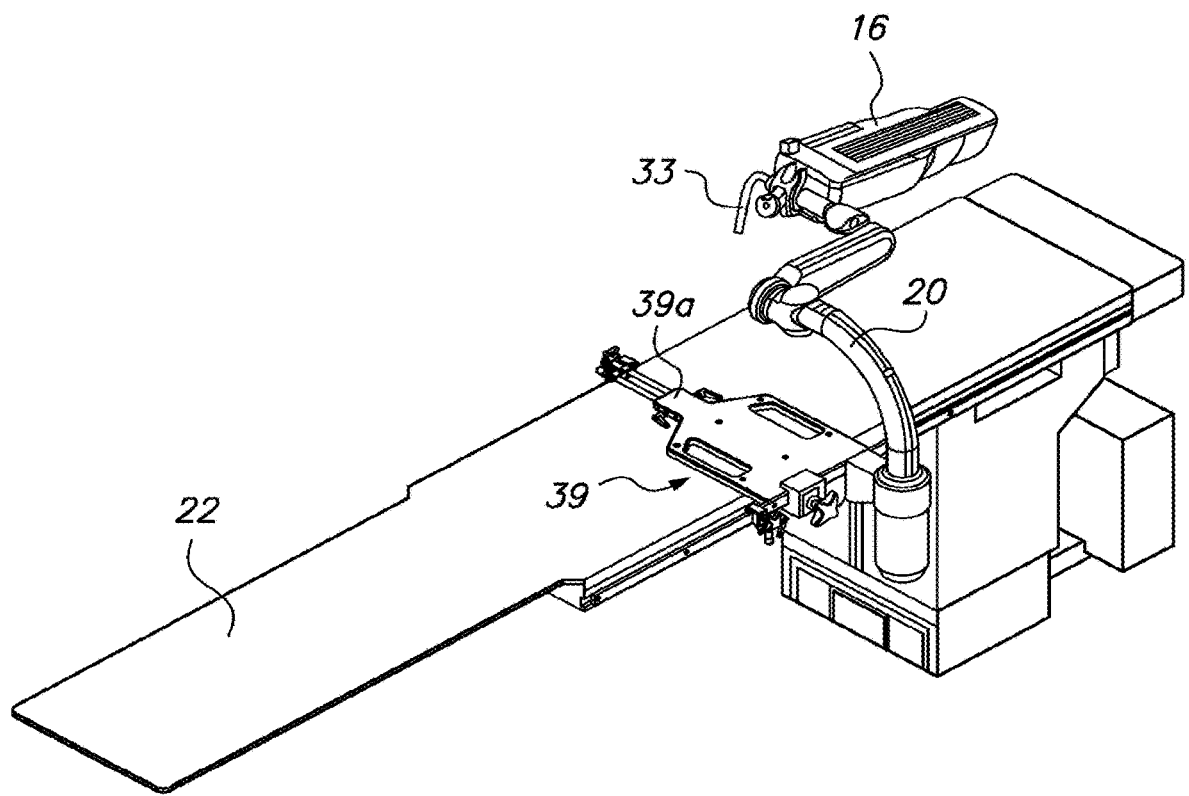
FIG. 3E further illustrates how the adapter base plate assembly is utilized to attach a support assembly and instrument driver to an operating table or surgical bed.
Figure 4:
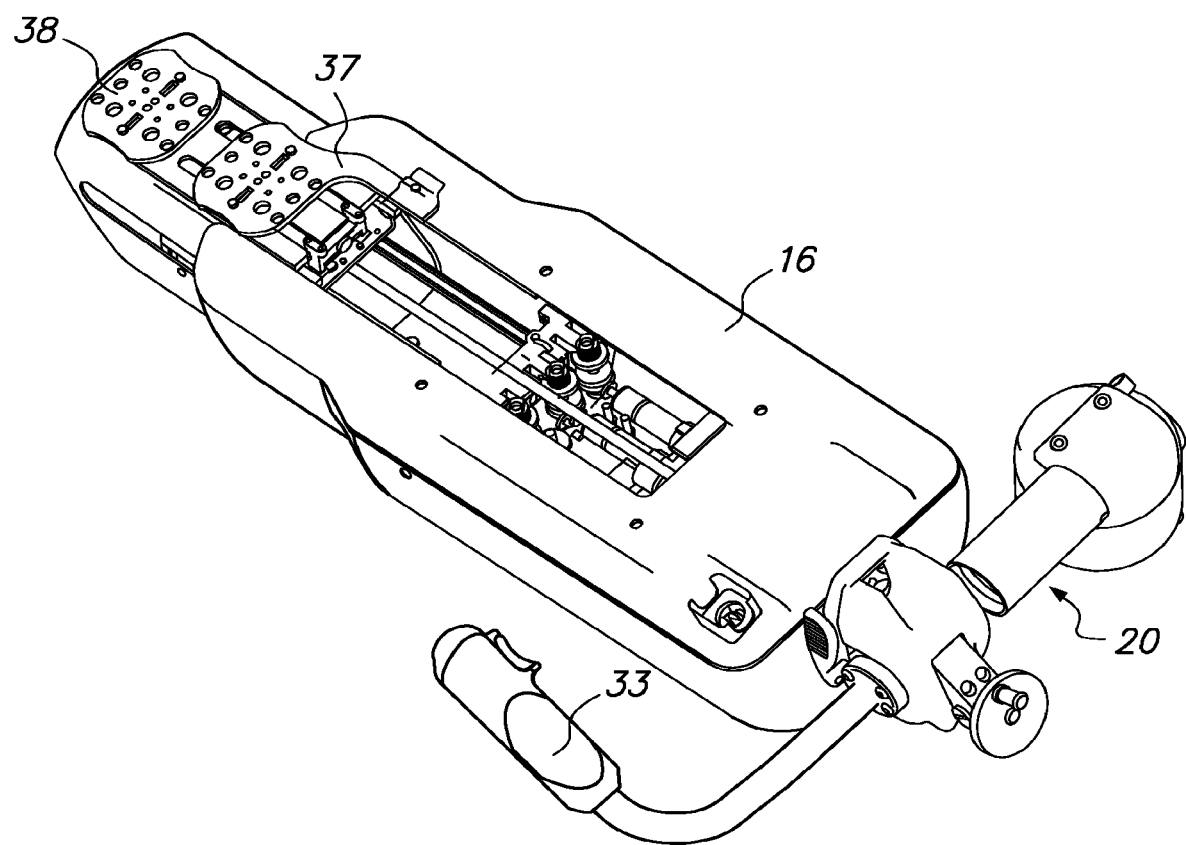
FIG. 4 illustrates an instrument driver mounted to a distal segment of a support assembly.

FIGS. 97J3-97J4 illustrate different perspective views of the valve holder of FIGS. 97J1-97J2 in closed and open configurations respectively.

FIGS. 97K1 and K2 illustrate perspective views of a drape assembly.

FIGS. 97L1-97L2 illustrate top and bottom perspective views of a tenting frame of the drape assembly shown in FIGS. 97K1-97K2.

Figure 97:
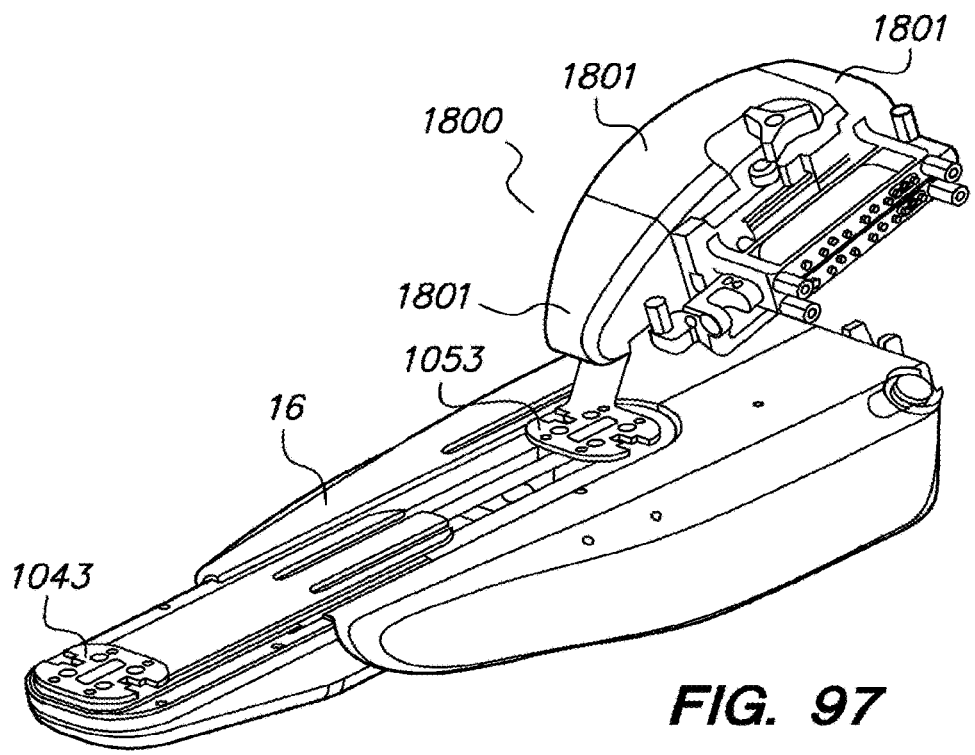
FIG. 97 illustrates a perspective view of another variation of an elongate member manipulator mounted to a variation of an instrument driver.
Figure 97A:
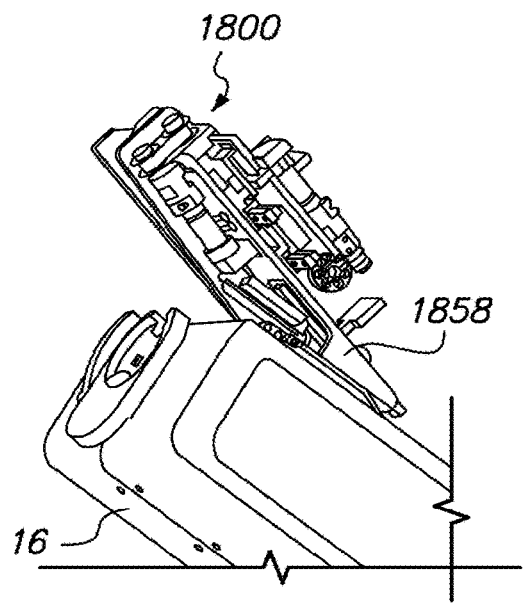
FIGS. 97aa-97ab illustrate various views of the elongate member manipulator of FIG. 97 with a cover removed.
Figure 97A:
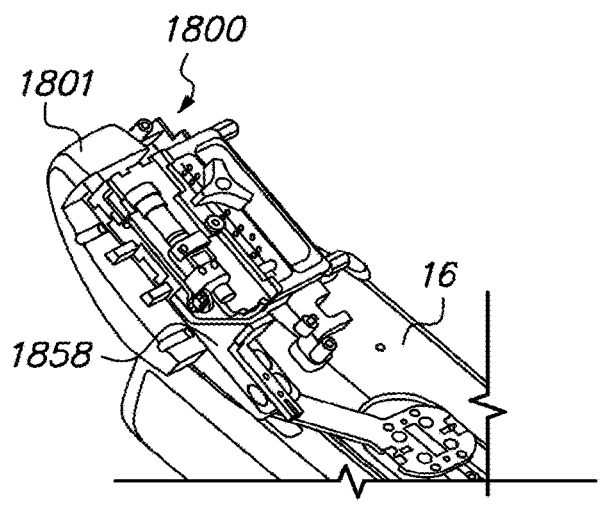

FIGS. 97M1-97M5 illustrate the drape assembly of FIG. 97K being installed on a simplified model of the elongate member manipulator of FIG. 97A1.

Figure 6A:
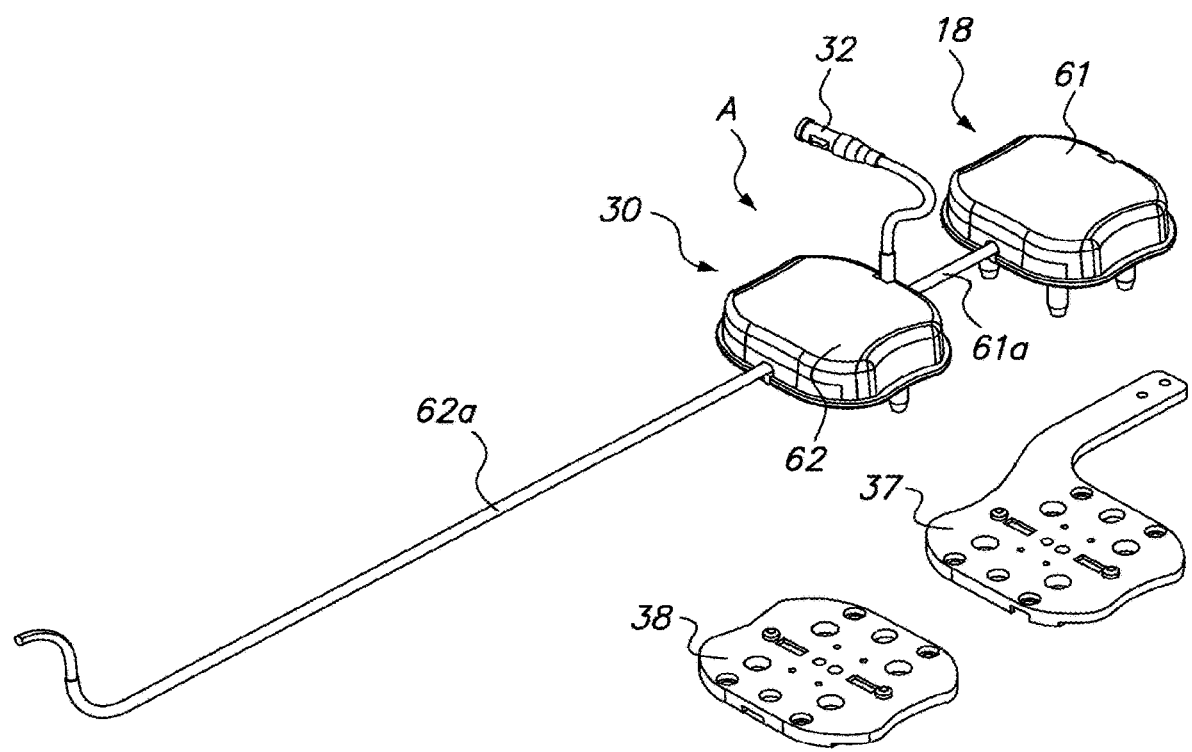
FIG. 6A illustrates a sheath and guide catheter assembly positioned over respective mounting plates.
Figure 6B:
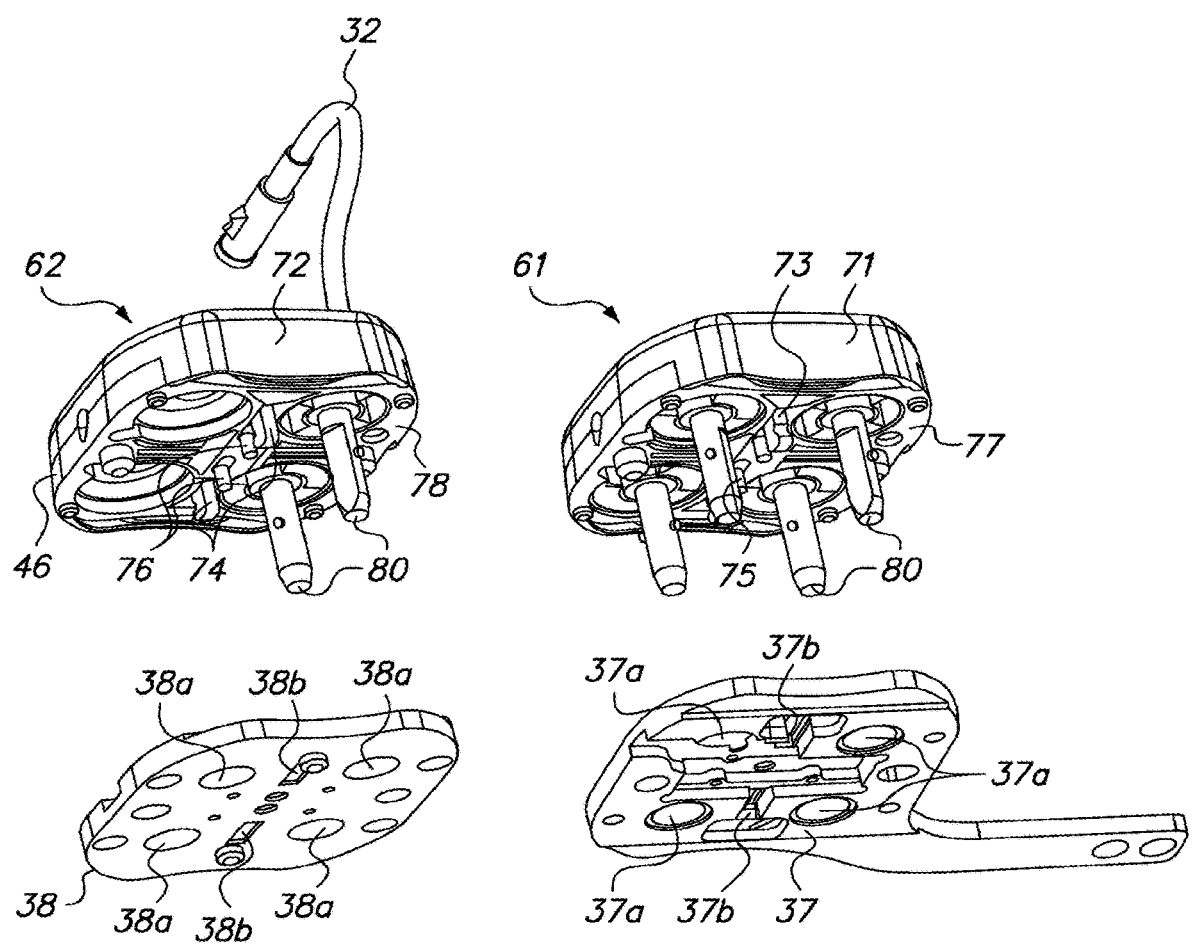
FIG. 6B further illustrates how sheath and guide splayers interface with respective mounting plates.
Figure 7:
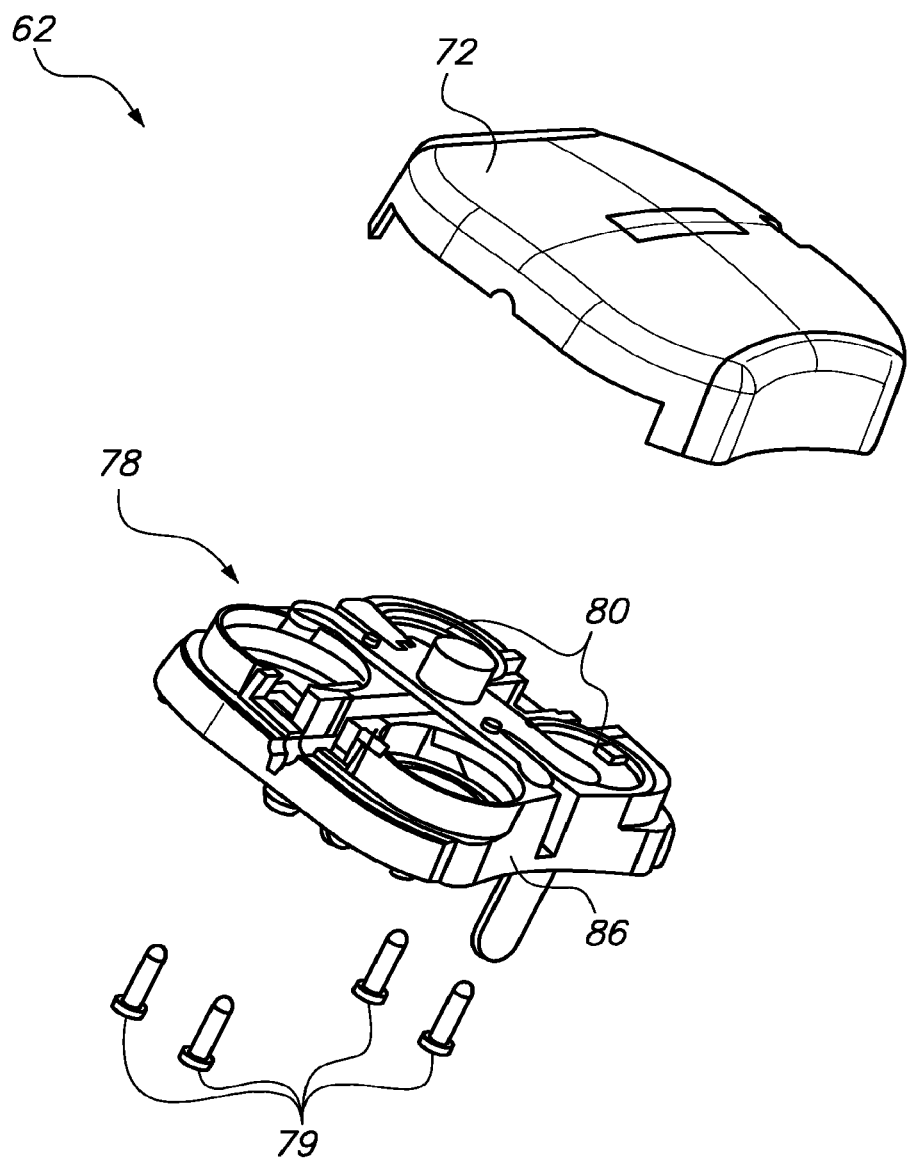
FIG. 7 illustrates an exploded view of the sheath splayer shown in FIG. 6B without a purge tube.

FIGS. 97M6-97M7 illustrate the drape installed on the elongate member manipulator of FIG. 97A1 in a closed and open configuration respectively.

Figure 98A:
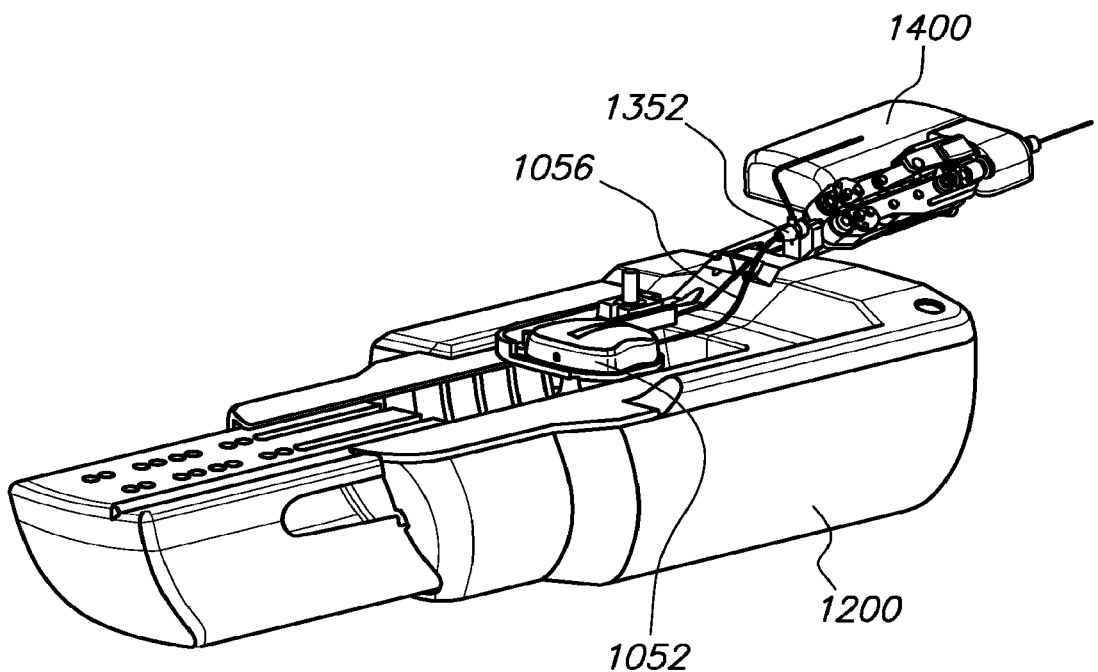

FIG. 98A illustrates a perspective view of an instrument driver with a guide splayer and another variation of an elongate member manipulator.

Figure 98B:
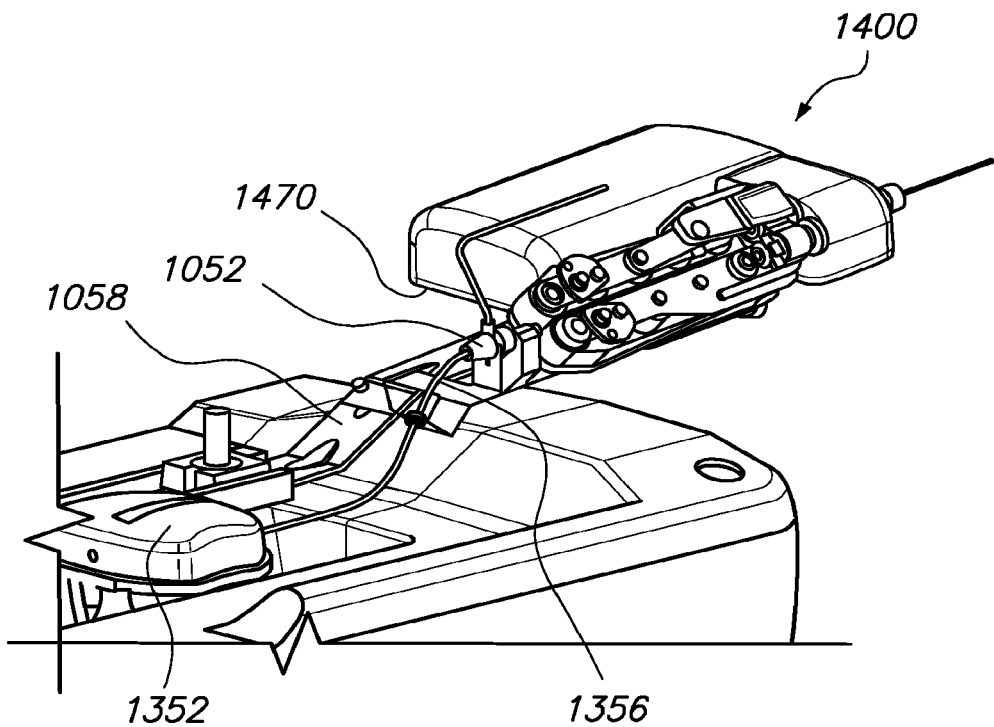

FIG. 98B illustrates a closer view of the instrument driver, guide splayer, and elongate member manipulator of FIG. 98A.

FIG. 99 illustrates a perspective view of the elongate member manipulator of FIG. 98A.

FIGS. 100A-100B illustrate perspective views of the elongate member manipulator of FIG. 99, showing a motor pack cover removed.

Figure 101A:
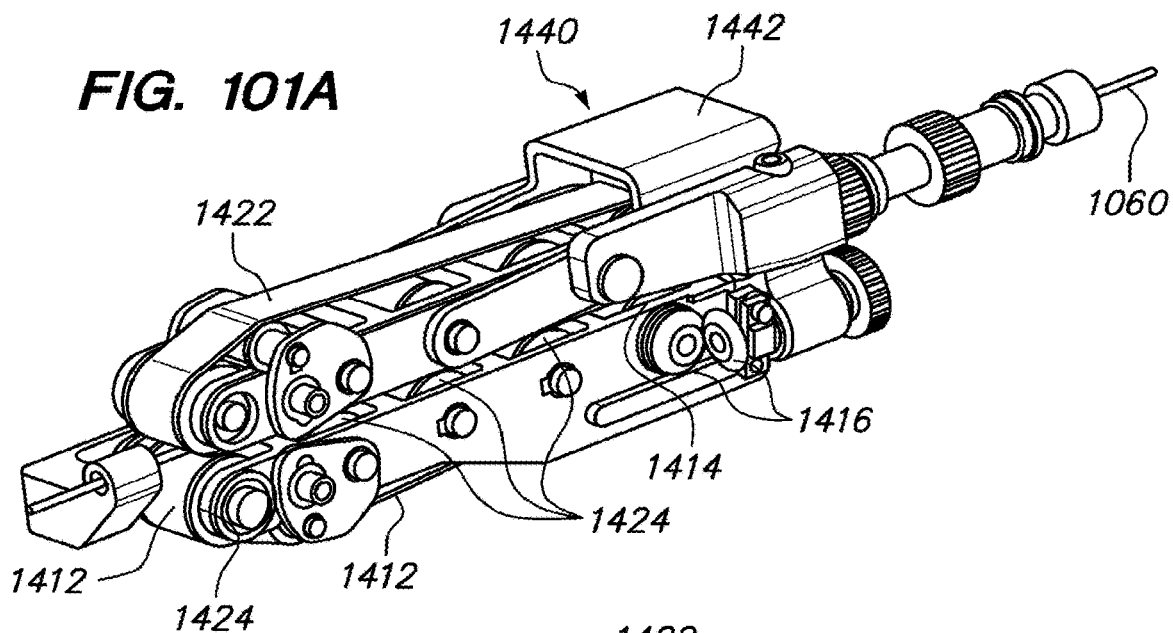
Figure 101B:
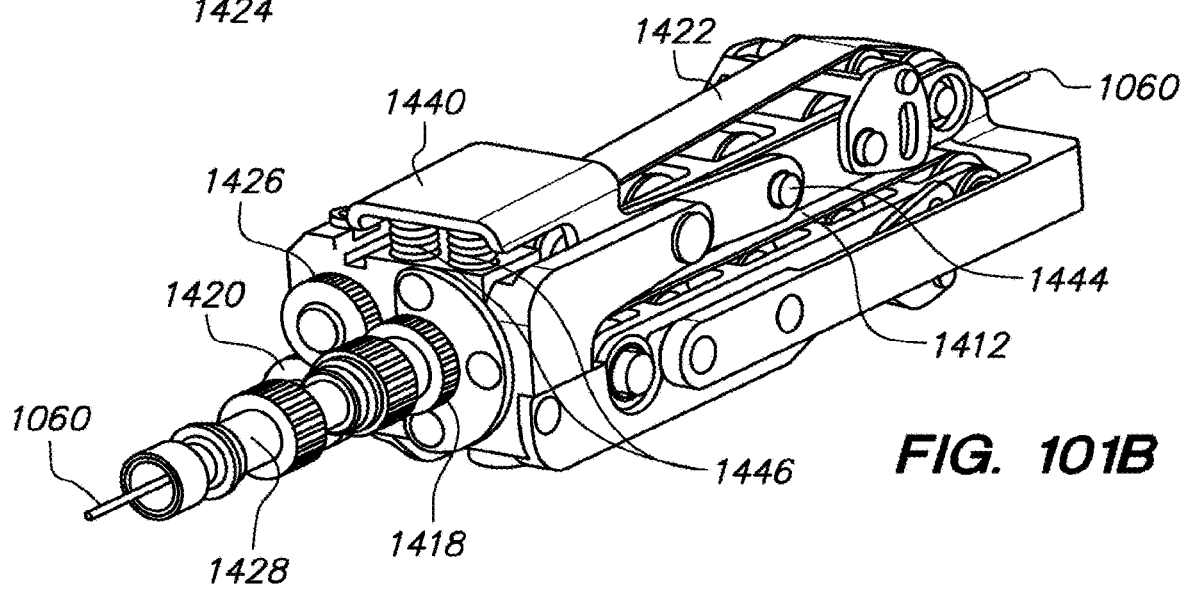

FIGS. 101A-101B illustrate front and back perspective views of a belt assembly of the elongate member manipulator of FIG. 99.

Figure 101C:
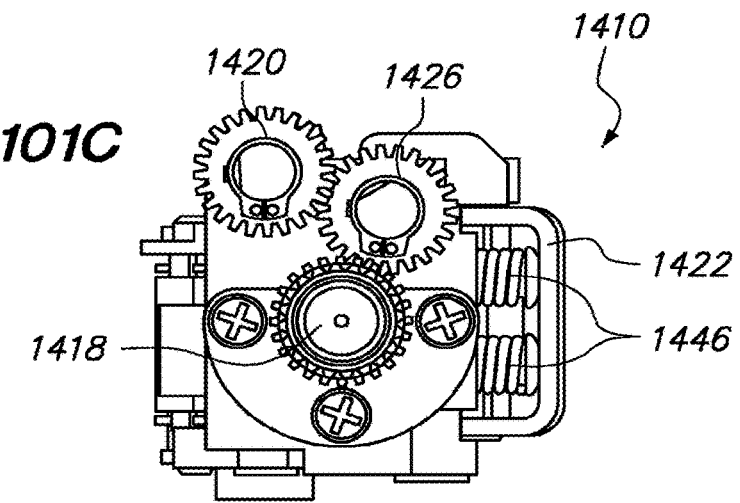

FIG. 101C illustrates a back view of the belt assembly of FIG. 101A.

Figure 102A:
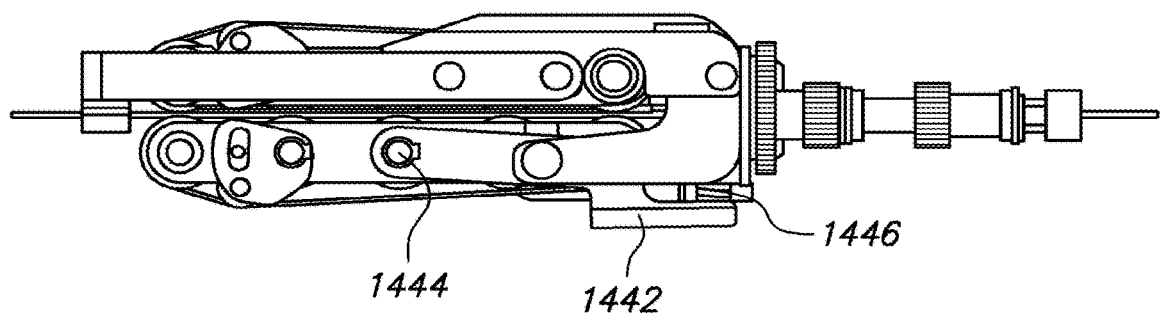

FIG. 102A illustrates a side view of the belt assembly of FIG. 101A.

Figure 102B:
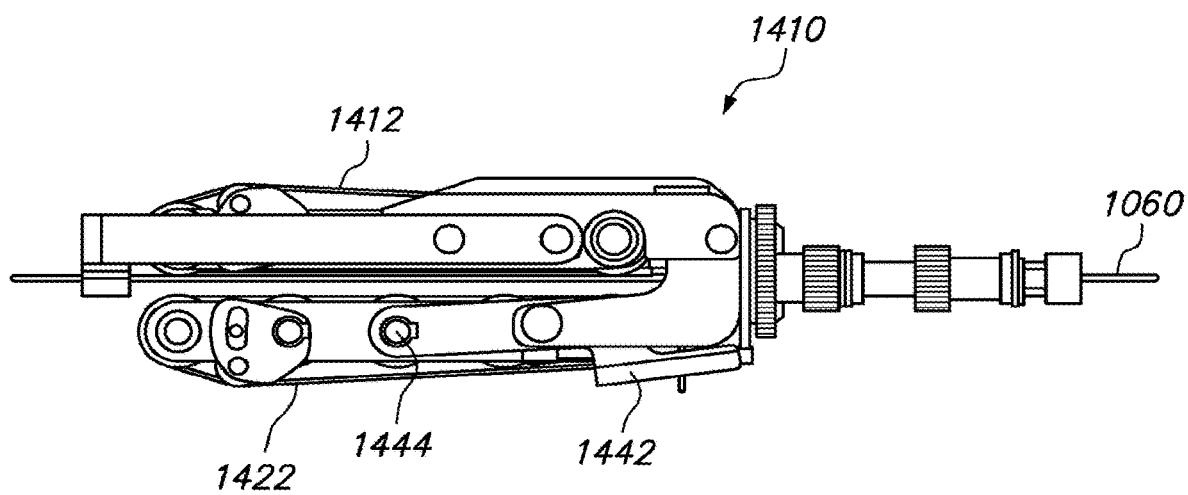

FIG. 102B illustrates the belt assembly of FIG. 102A, shown in an open configuration.

Figure 103A:
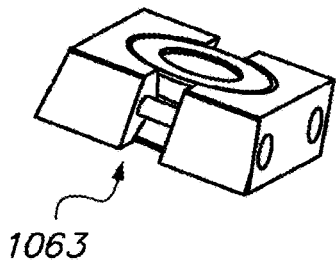
Figure 103A:
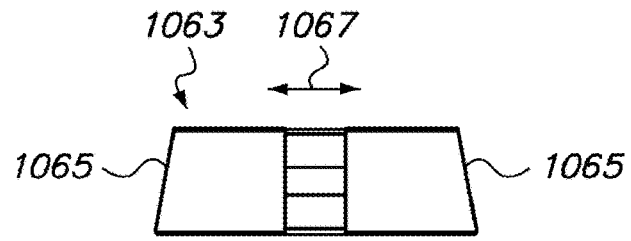
Figure 103:
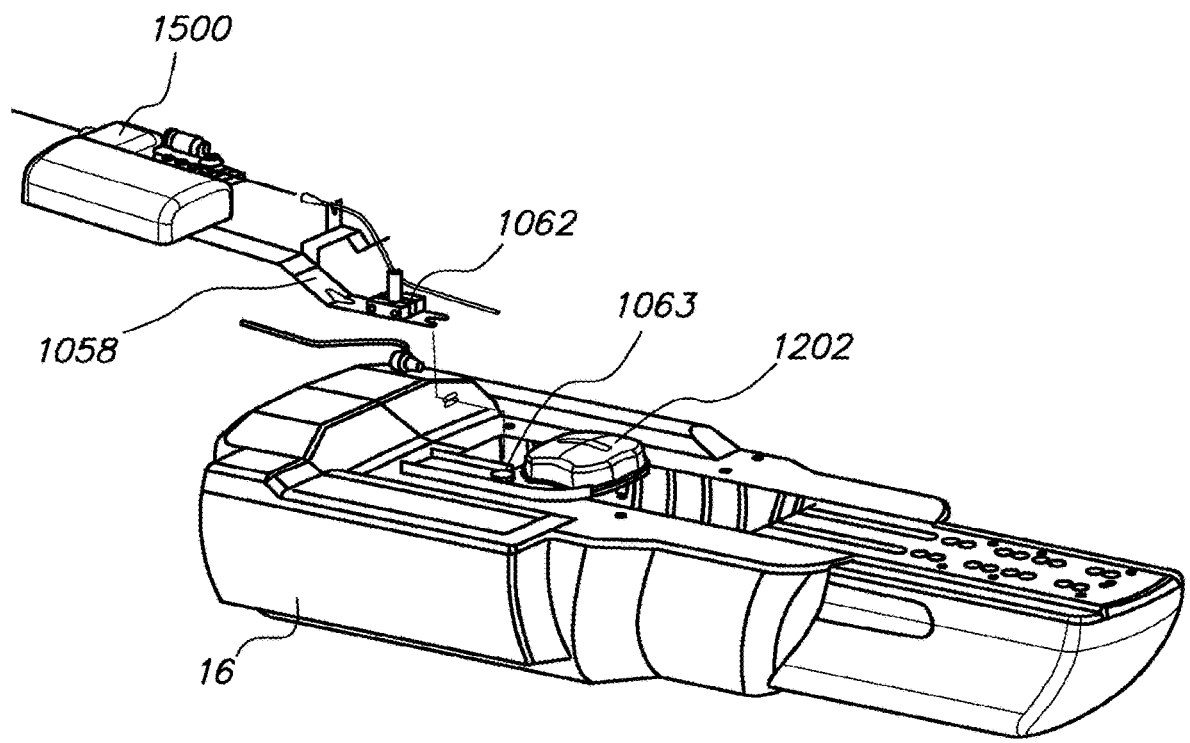
Figure 103A:
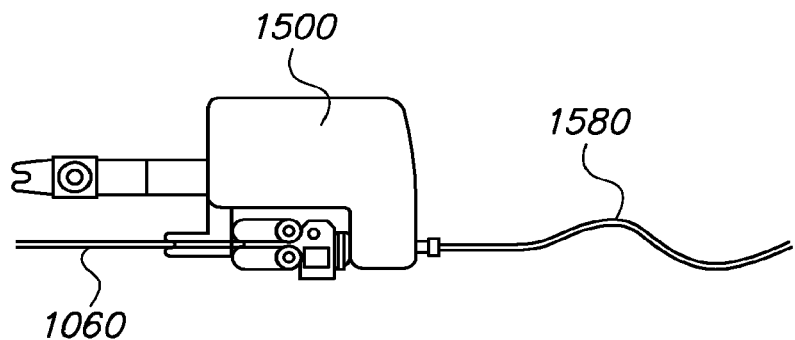

FIG. 103 illustrates a perspective view of the instrument driver, guide splayer, and an alternative variation of an elongate member manipulator, showing the manipulator un-installed.

FIGS. 103AA-103AB illustrate perspective and side views of an adapted Tiny-Vise clamp.

FIG. 103A illustrates a top view of the elongate member manipulator of FIG. 103, showing a guide wire and a roll support tube.

Figure 103B:
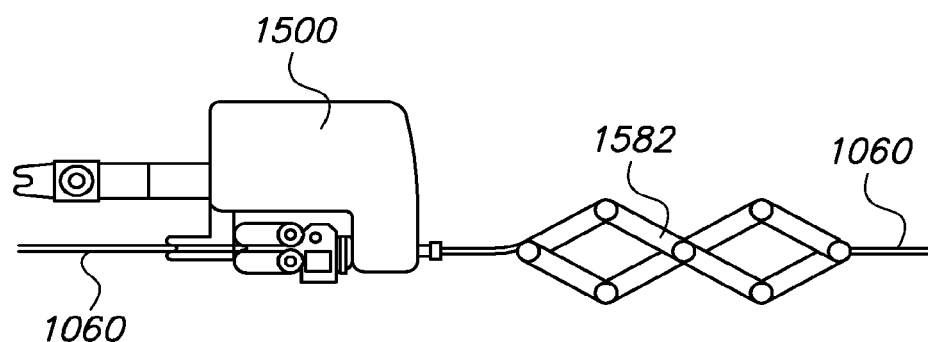

FIG. 103B illustrates a top view of the elongate member manipulator of FIG. 103, showing a guide wire and a scissor jack support.

Figure 104:
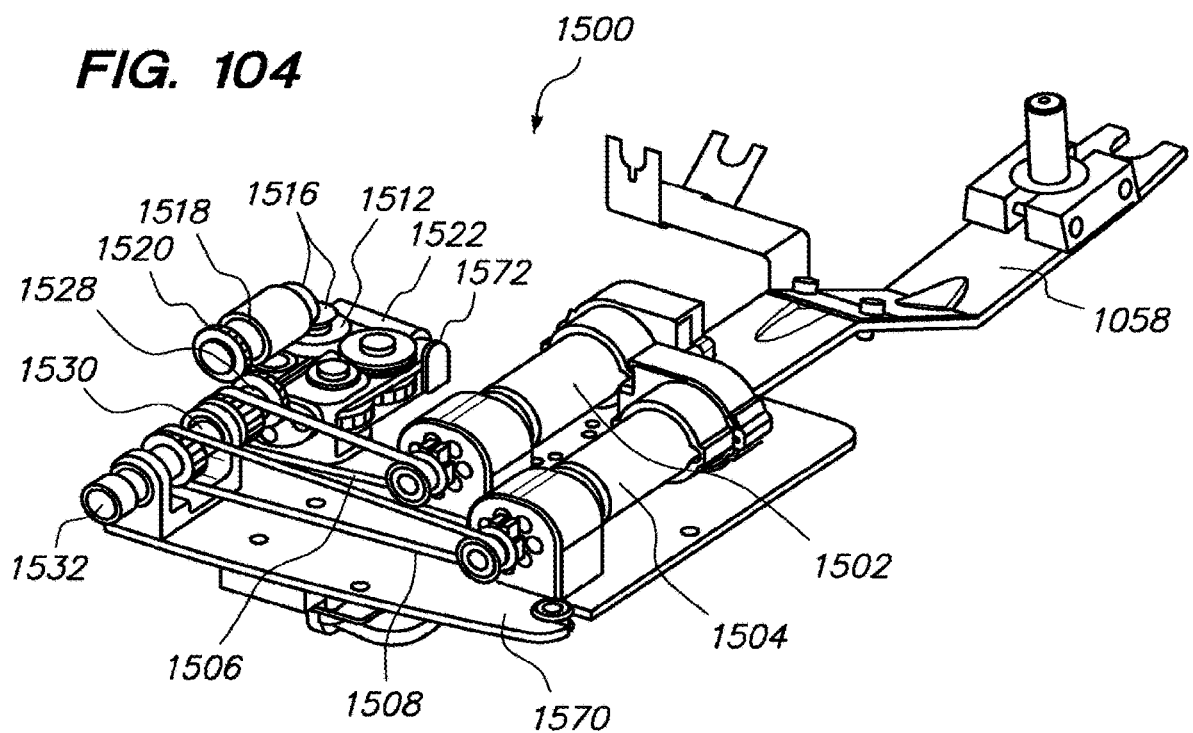

FIG. 104 illustrates a perspective view of the elongate member manipulator of FIG. 103, showing a motor pack cover removed.

Figure 105:
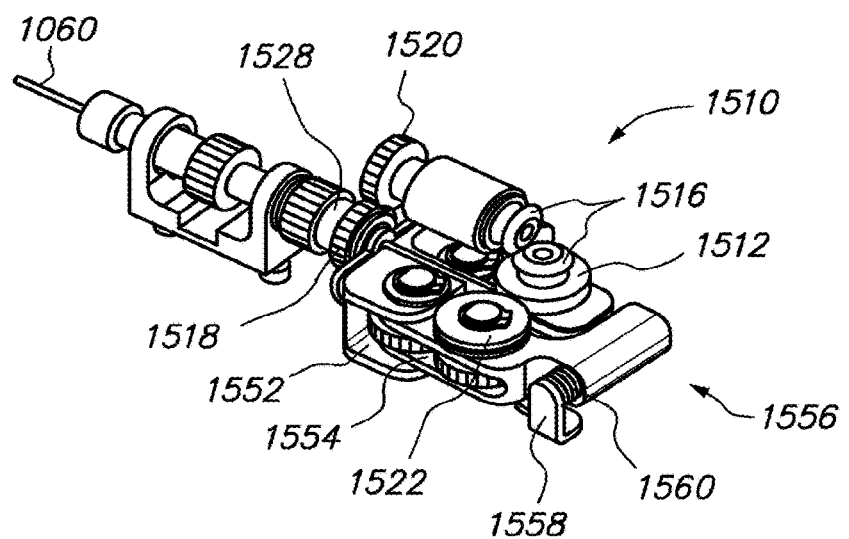

FIG. 105 illustrates a perspective view of a feed roller assembly of the elongate member manipulator of FIG. 104.

Figure 106A:
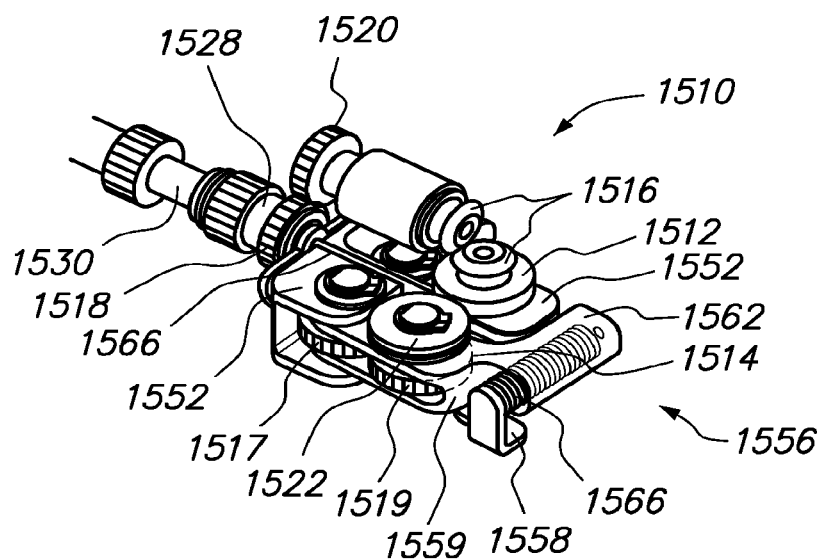

FIG. 106A illustrates a closer view of the feed roller assembly of FIG. 105.

FIGS. 106B-107A illustrate a top view of the feed roller assembly of FIG. 105.

Figure 107A:
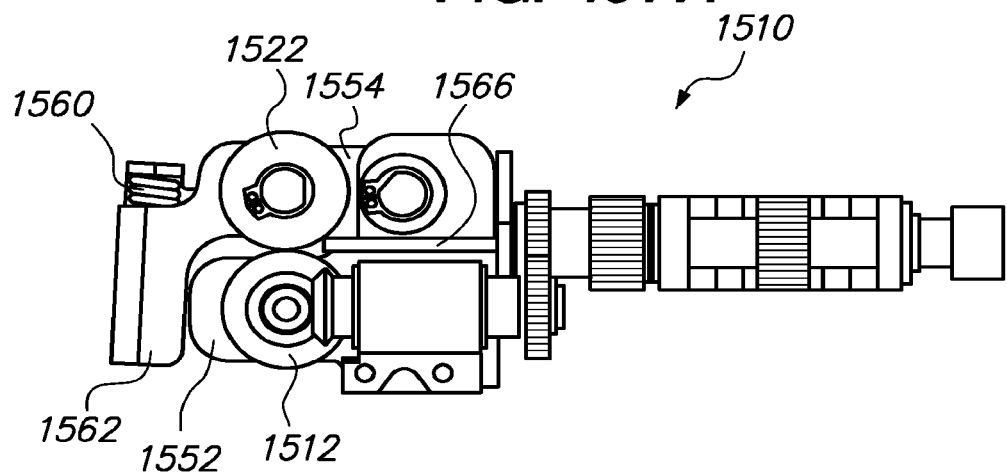
Figure 107B:
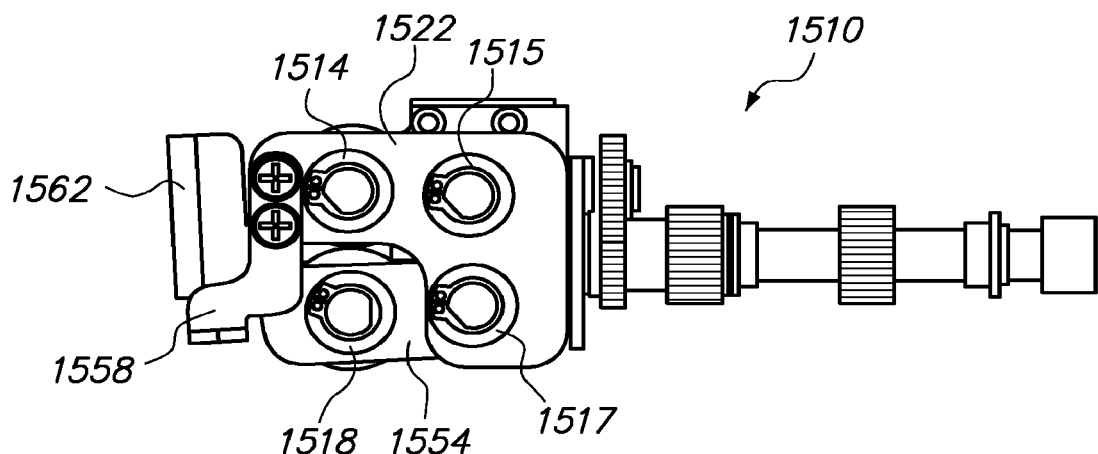

FIG. 107B illustrates a bottom view of the feed roller assembly of FIG. 105.

Figure 108A:
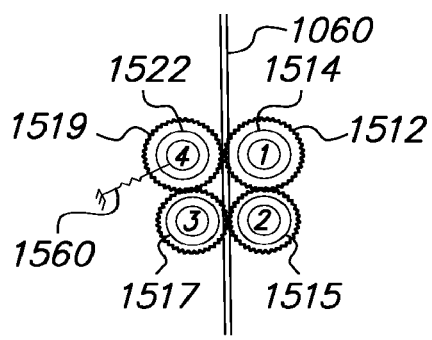

FIG. 108A illustrates a representation of the bottom view of a gear train of the feed roller assembly of FIG. 105.

Figure 108B:
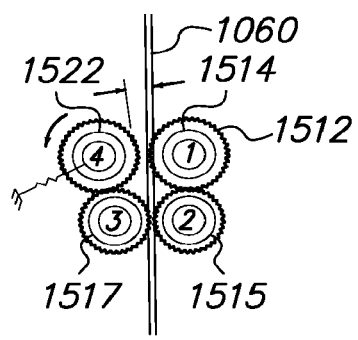

FIG. 108B illustrates the gear train representation of FIG. 108A, showing the gear train pivoted in an open configuration.

Figure 109:
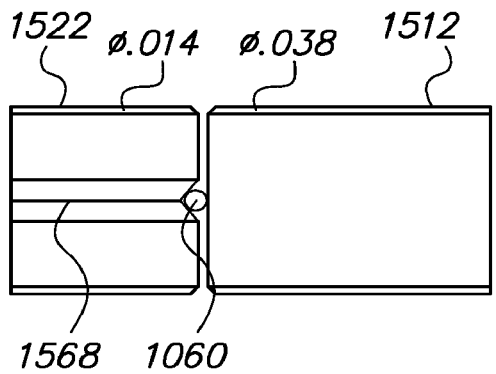

FIG. 109 illustrates a side view of a drive roller and feed roller of FIG. 105, showing a guide wire installed.

Figure 110A:
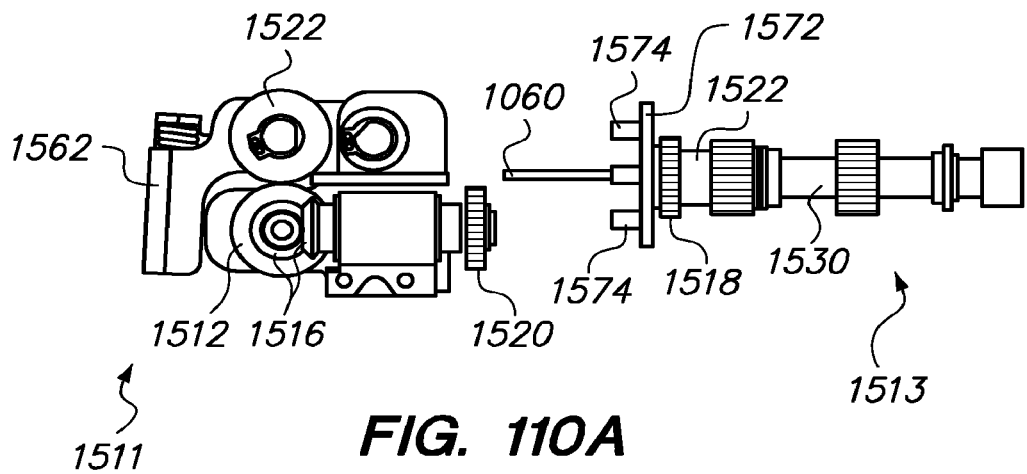

FIG. 110A illustrates a top view of the feed roller assembly of FIG. 105, showing an insert assembly removed from an actuation assembly.

Figure 110B:
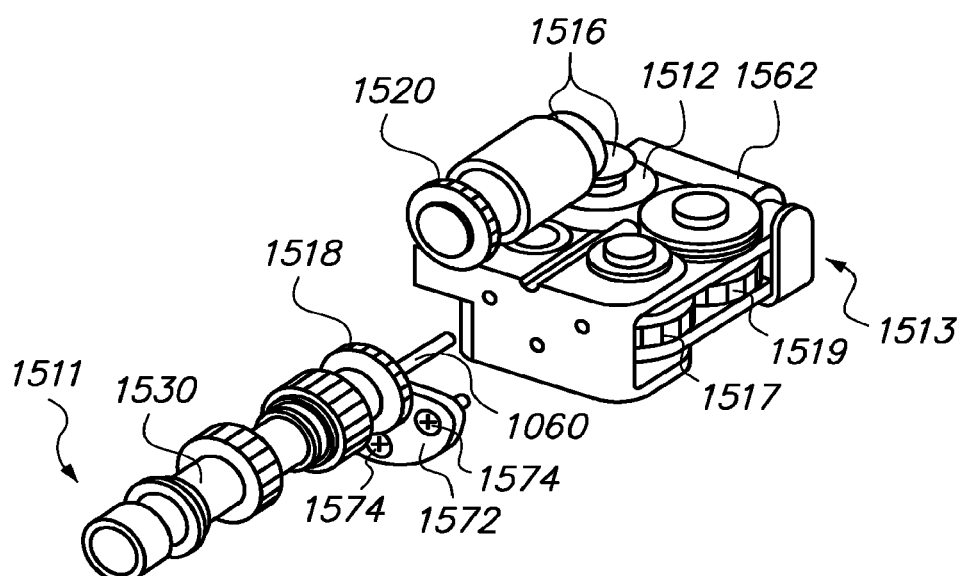

FIG. 110B illustrates a perspective view of the feed roller assembly.

FIGS. 111A-111F illustrate top views of simplified representations of various feed roller and feed belt combinations.

Figure 112A:
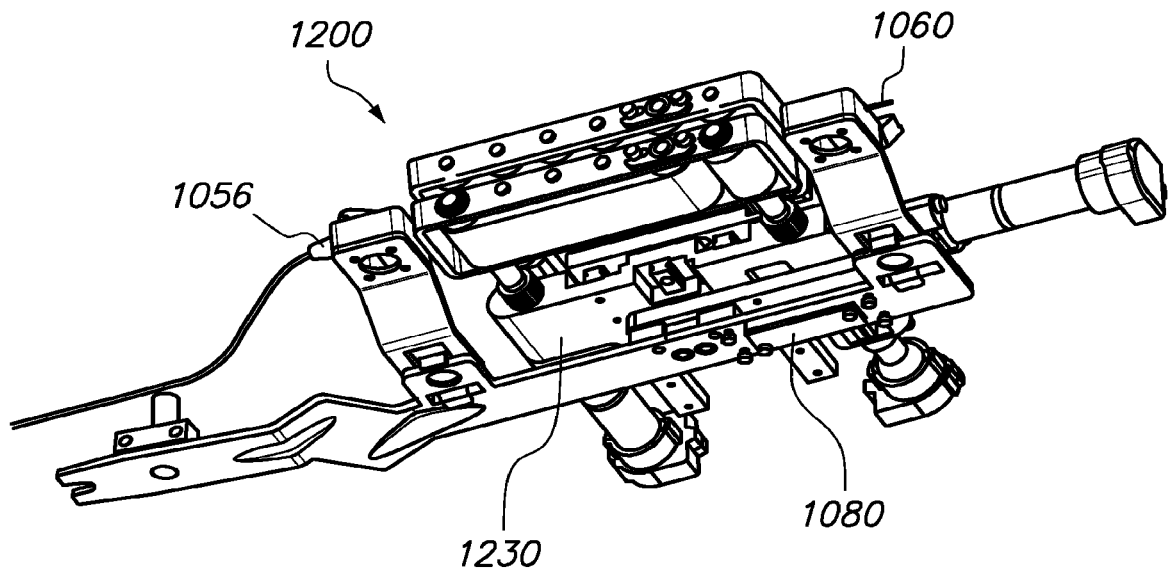

FIG. 112A illustrates a bottom perspective view of the elongate member manipulator of FIG. 85.

Figure 112B:
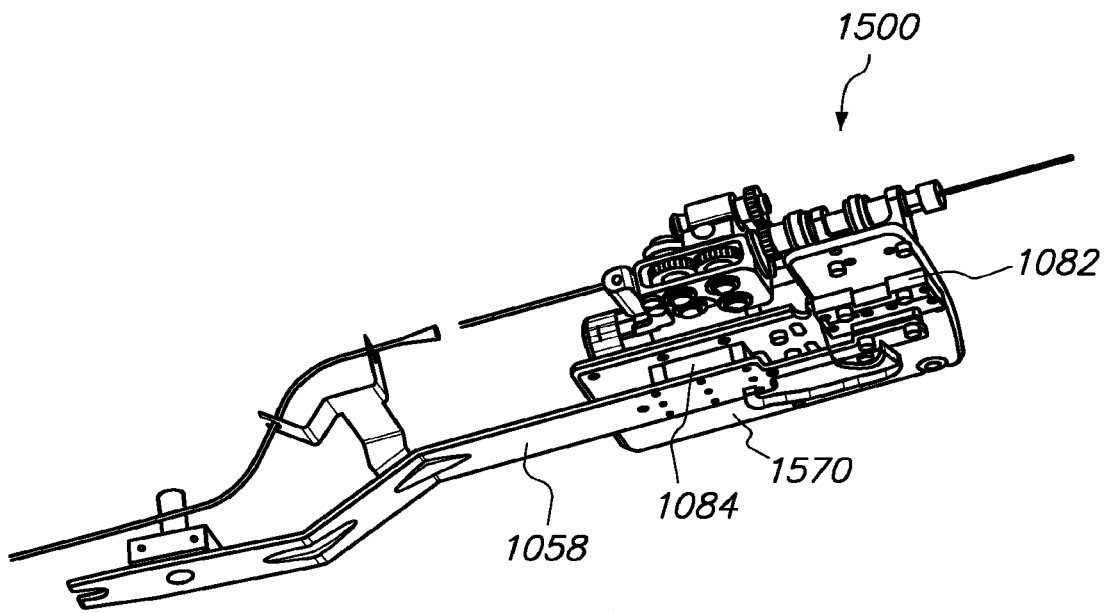

FIG. 112B illustrates a bottom perspective view of the elongate member manipulator of FIG. 104.

Figure 113:
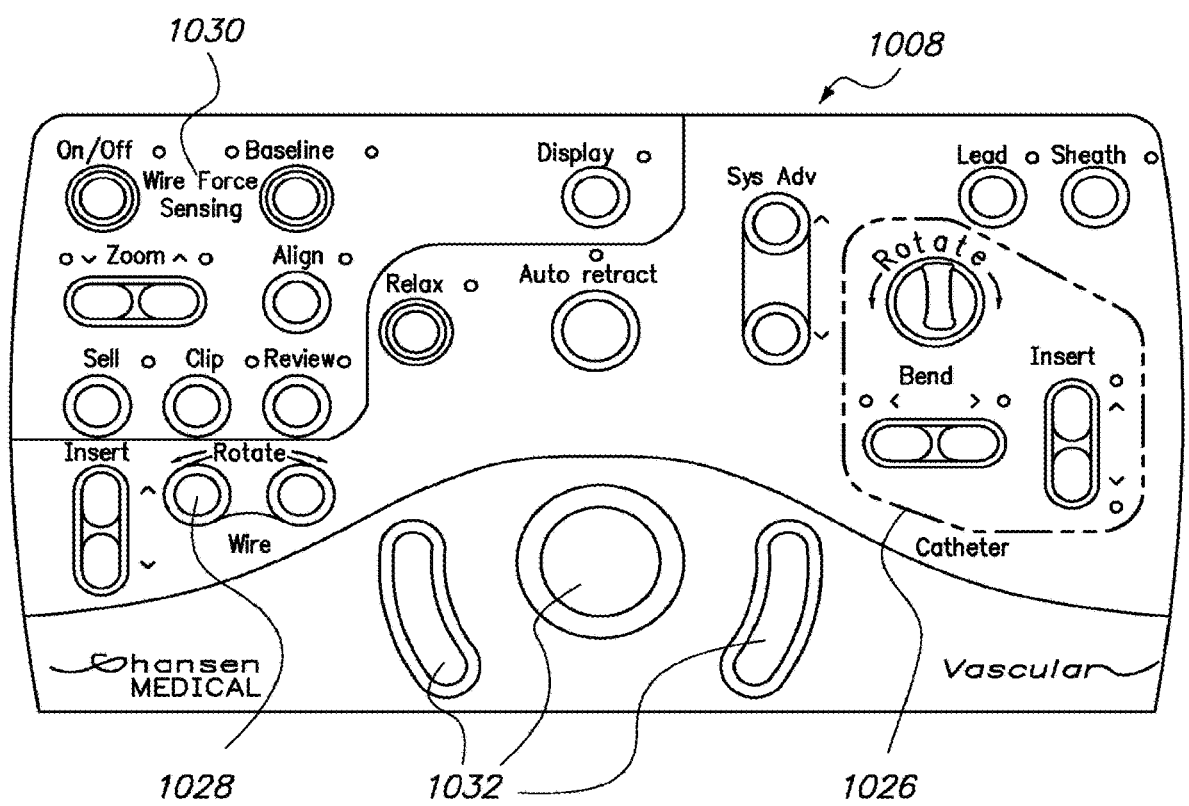

FIG. 113 illustrates a top view of a variation of a control console of the operator workstation of FIG. 1.

FIG. 114A illustrates a perspective view of a patient bed of the robotic instrument system of FIG. 1, showing a standalone console mounted to the patient bed.

FIG. 114B illustrates a side view of the standalone console of FIG. 114A, showing the standalone console mounted to a mounting bracket and a bed rail.

FIG. 115 illustrates a top view of a variation of the standalone console of FIG. 114A.

FIGS. 116 and 117A-117M illustrate variations of a master input device.

FIGS. 118A-D illustrate flow diagrams of various master-slave control options.

Figure 91A:
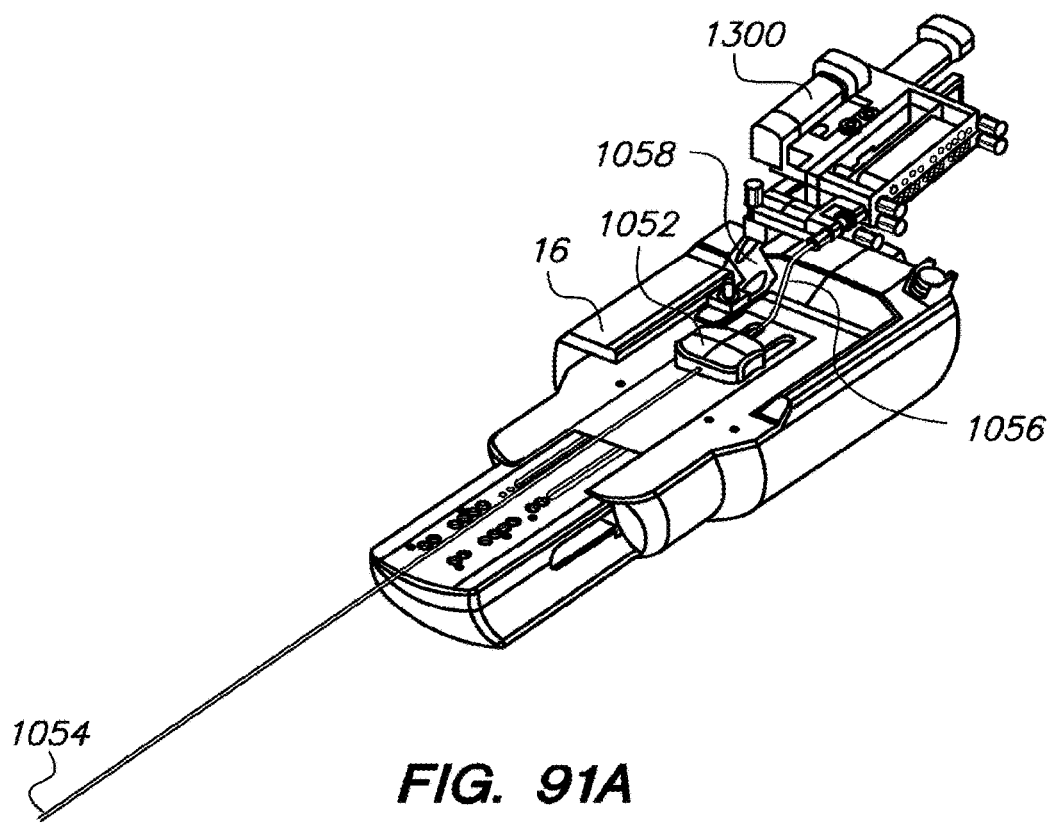
FIGS. 91A-91C illustrate perspective views of the instrument driver, the guide splayer and another alternative variation of an elongate member manipulator.
Figure 119:
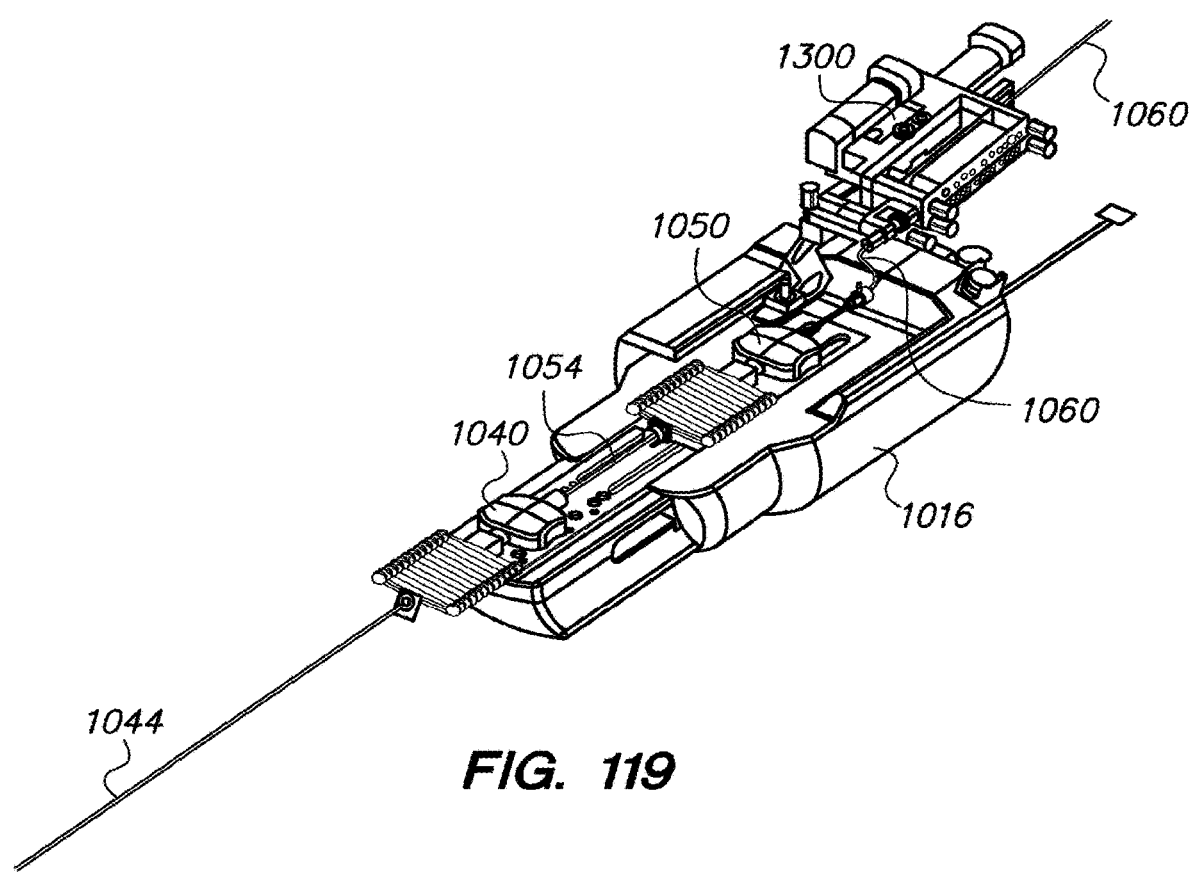

FIG. 119 illustrates a perspective view of the instrument driver and the elongate member manipulator of FIG. 91A with an anti-buckling mechanism installed.

Figure 120:
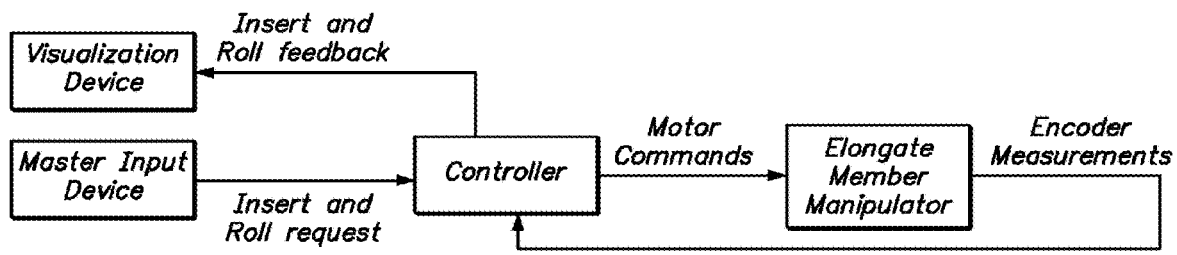

FIG. 120 illustrates a flow diagram of a variation of a control scheme for control of the elongate member manipulator of FIG. 79A, 85, 91A, 99, 103A, or 124A.

Figure 121A:
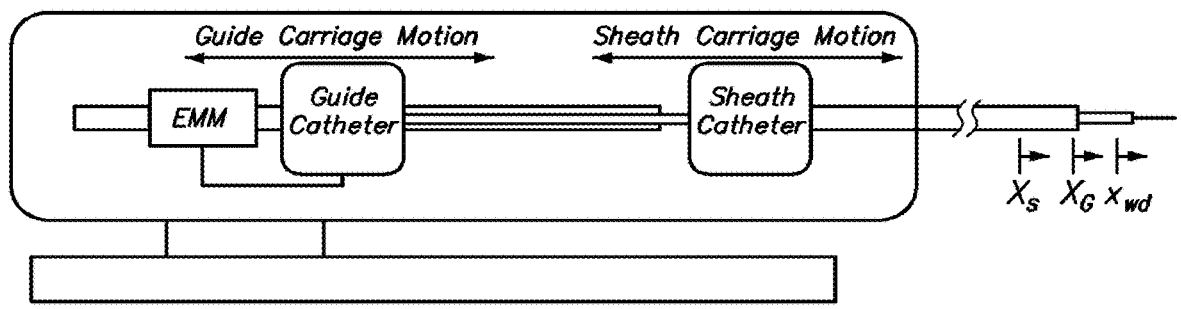
Figure 121B:
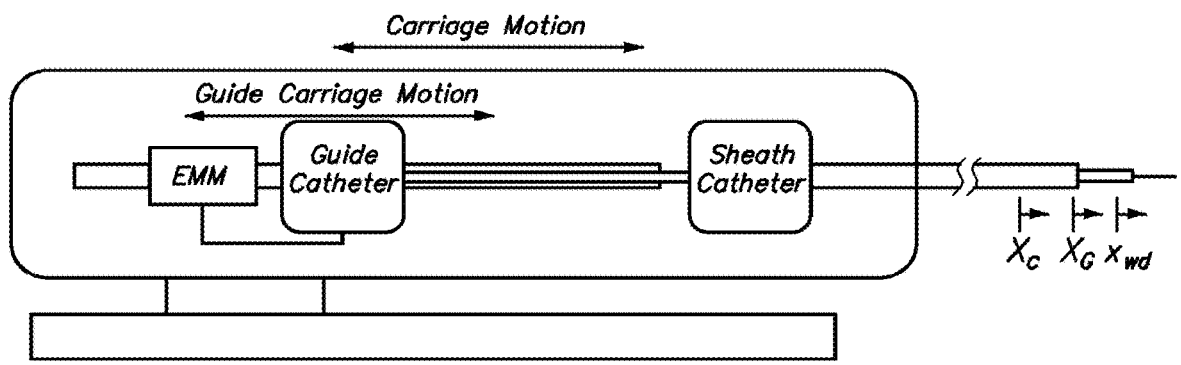

FIGS. 121A-121B illustrate block diagrams representing the instrument driver, the elongate member manipulator, the guide catheter, and the sheath catheter.

Figure 122:
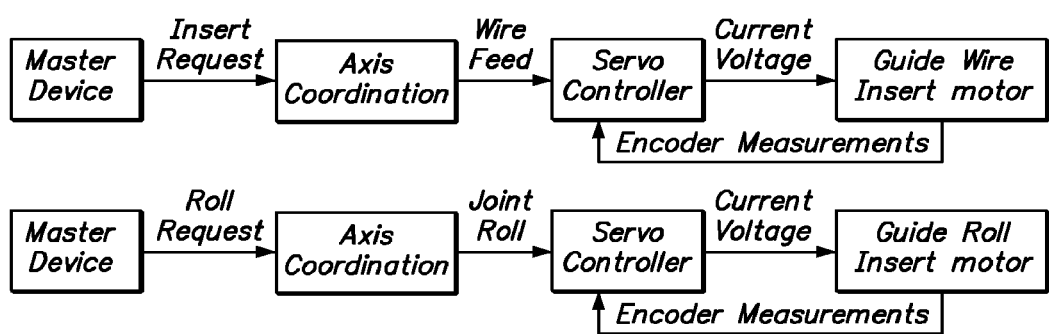

FIG. 122 illustrates a flow diagram of the controller for the configuration with a movable carriage and a coupled elongate member manipulator of FIG. 121B.

Figure 123:
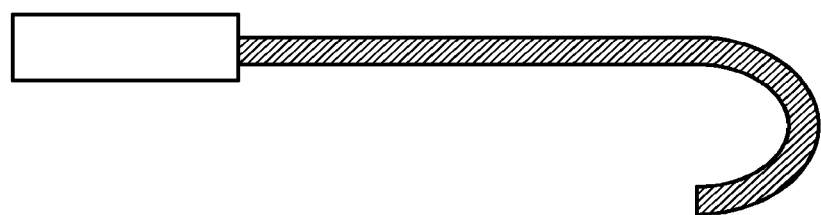

FIG. 123 illustrates a representation of a variation of a virtual guide wire.

Figure 124A:
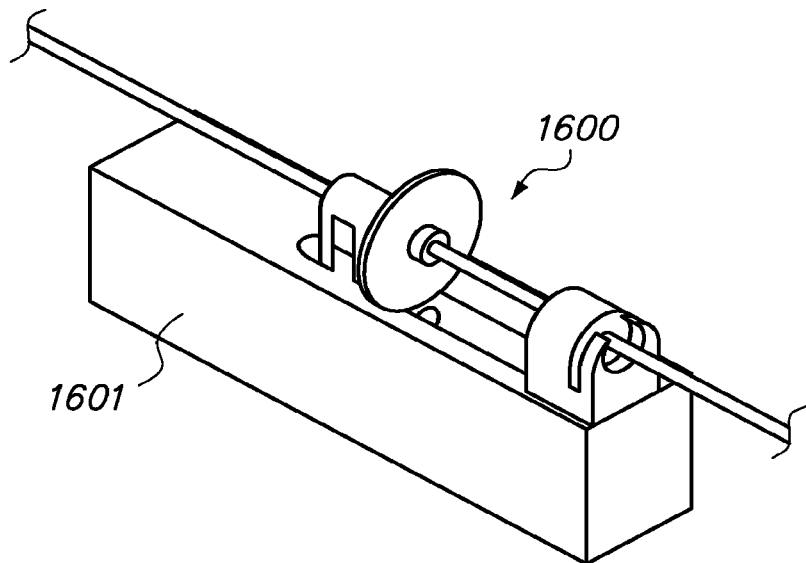

FIG. 124A illustrates a perspective view of another alternative variation of an elongate member manipulator.

Figure 124B:
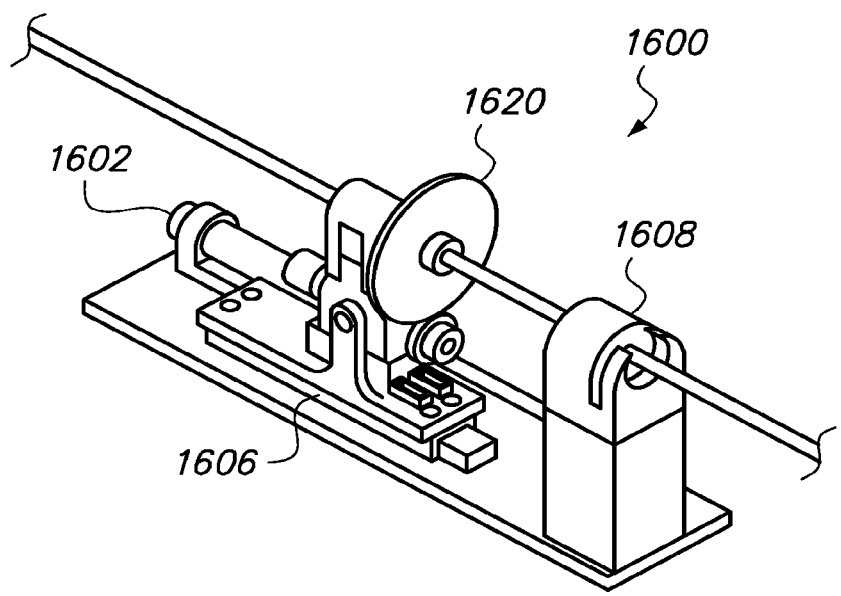
Figure 124C:
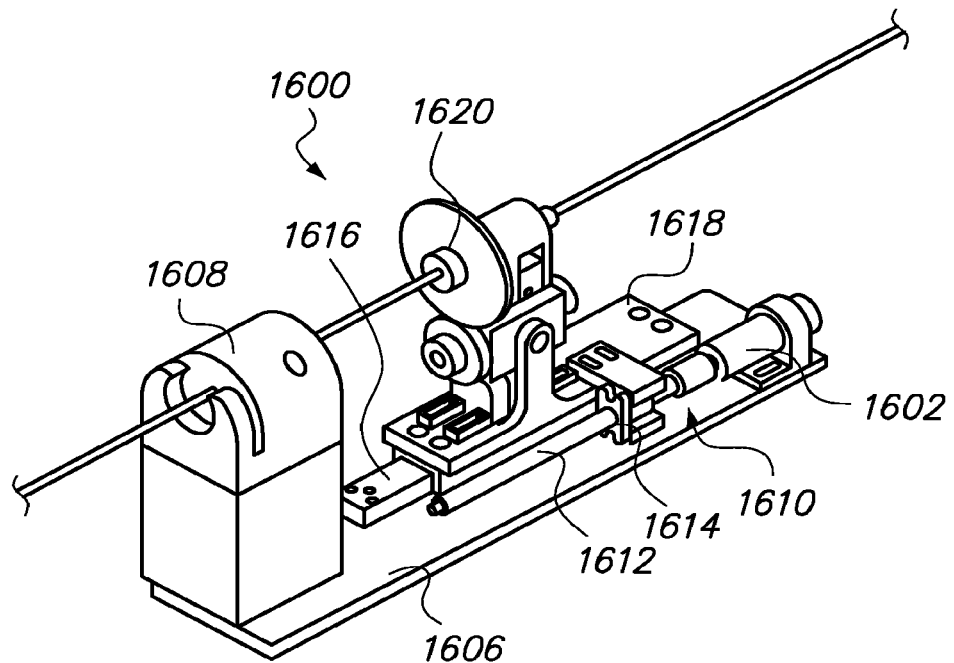

FIGS. 124B-C illustrates perspective views of the elongate member manipulator of FIG. 124A, showing the manipulator cover removed.

Figure 125A:
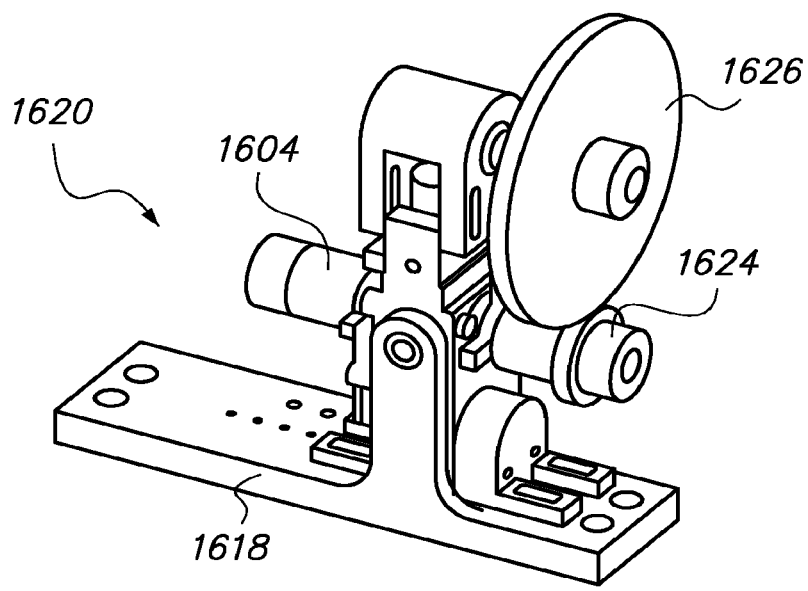
Figure 127A:
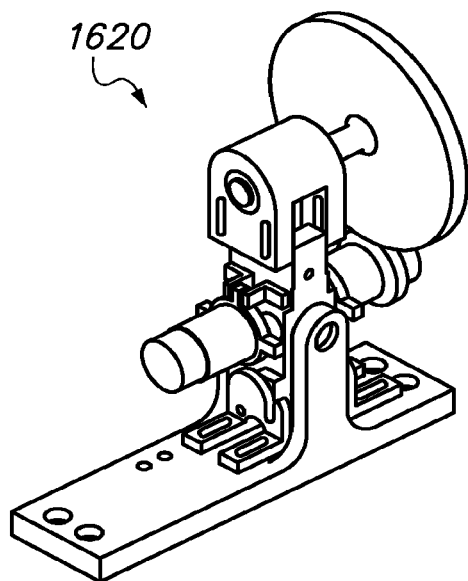

FIGS. 125A and 127A illustrate a perspective views of a rotation drive of the elongate member manipulator of FIG. 124C.

Figure 125B:
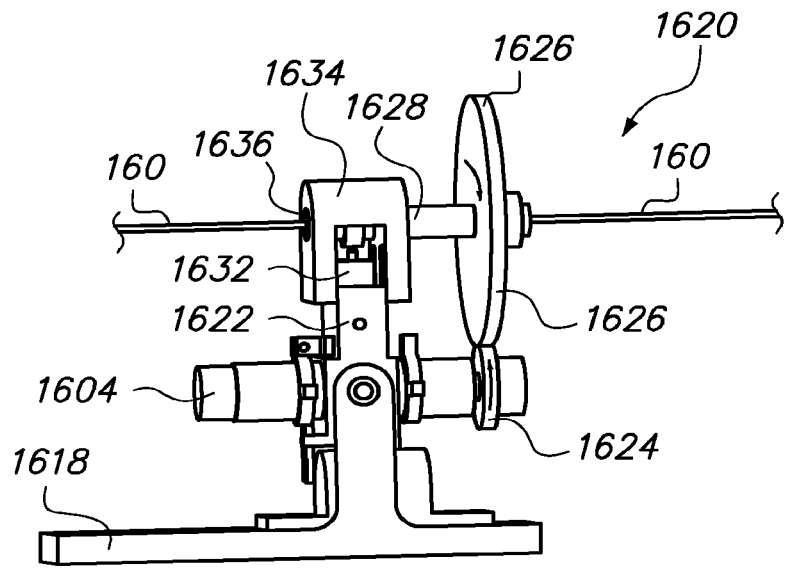

FIG. 125B illustrates a side perspective view of the rotation drive of FIG. 125A with the guide wire installed.

Figure 125C:
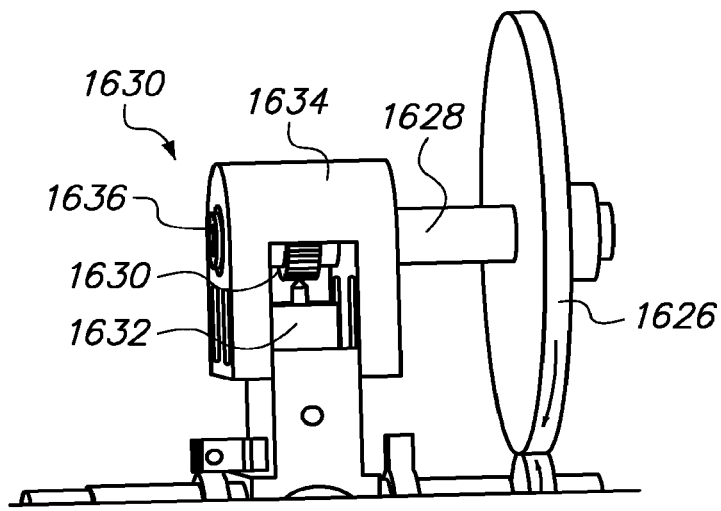

FIG. 125C illustrates a closer perspective view of the rotation drive of FIG. 125A.

Figure 126:
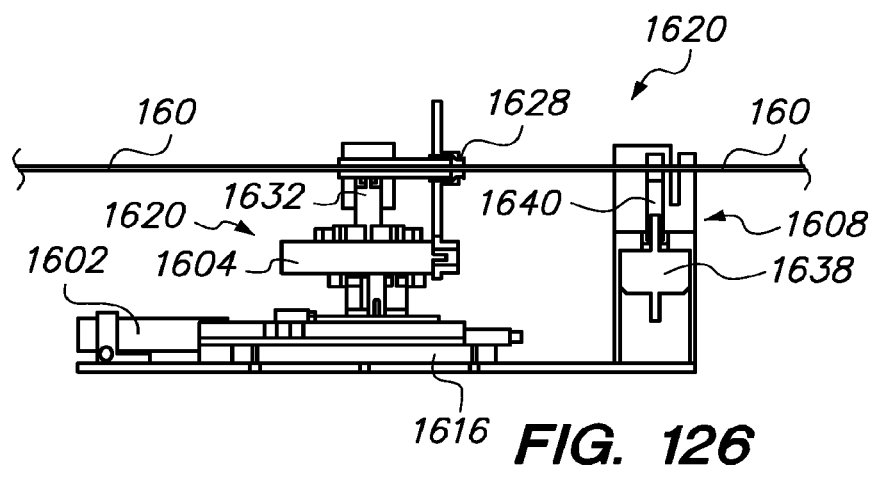

FIG. 126 illustrates a side cross sectional view of the elongate member manipulator of FIG. 124B.

Figure 127B:
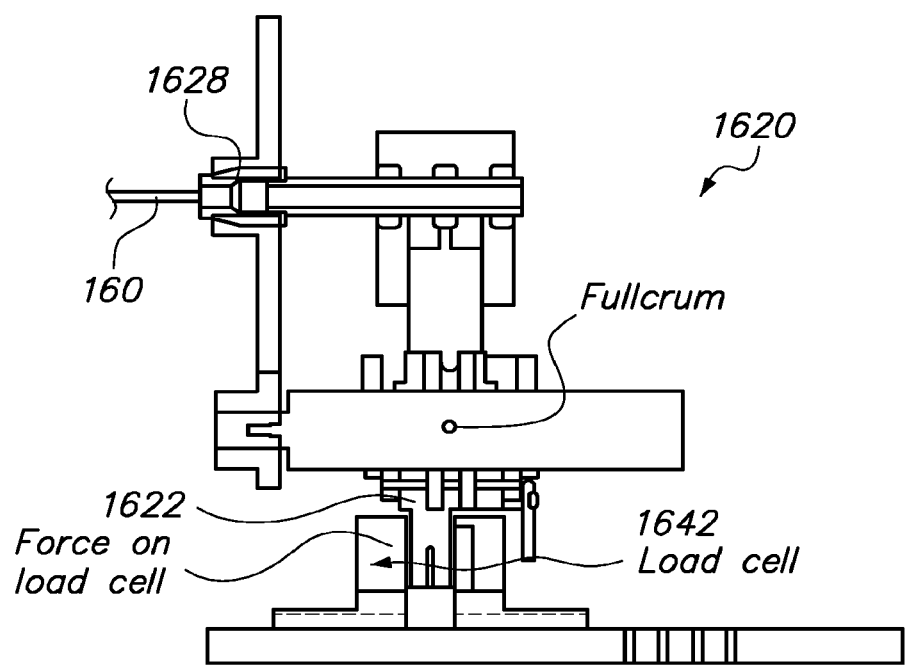

FIG. 127B illustrates a side cross sectional view of the rotation drive of FIG. 125A.

Figure 127C:
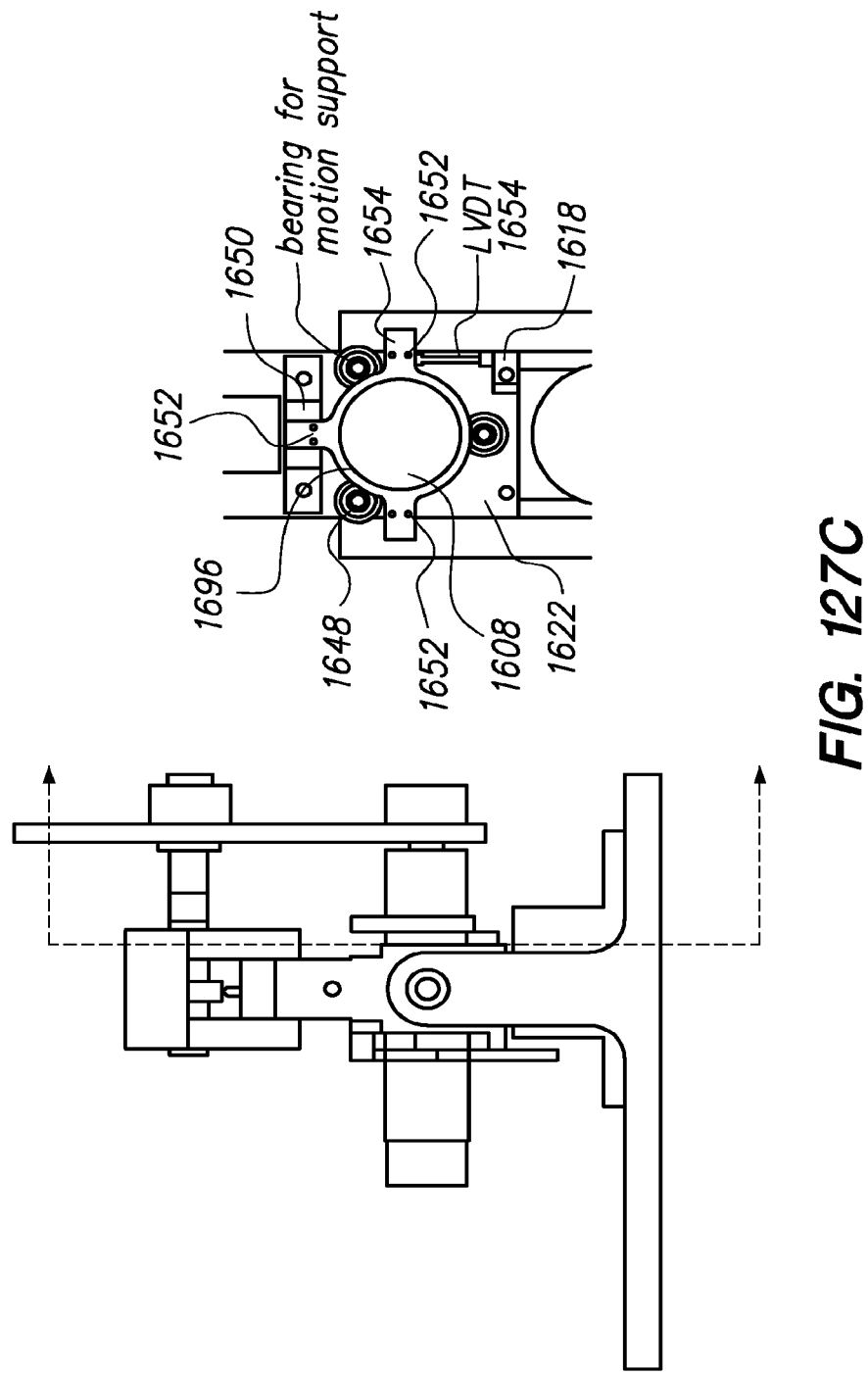

FIG. 127C illustrates a side and a cross sectional view of the rotation drive of FIG. 125A.

Figure 128A:
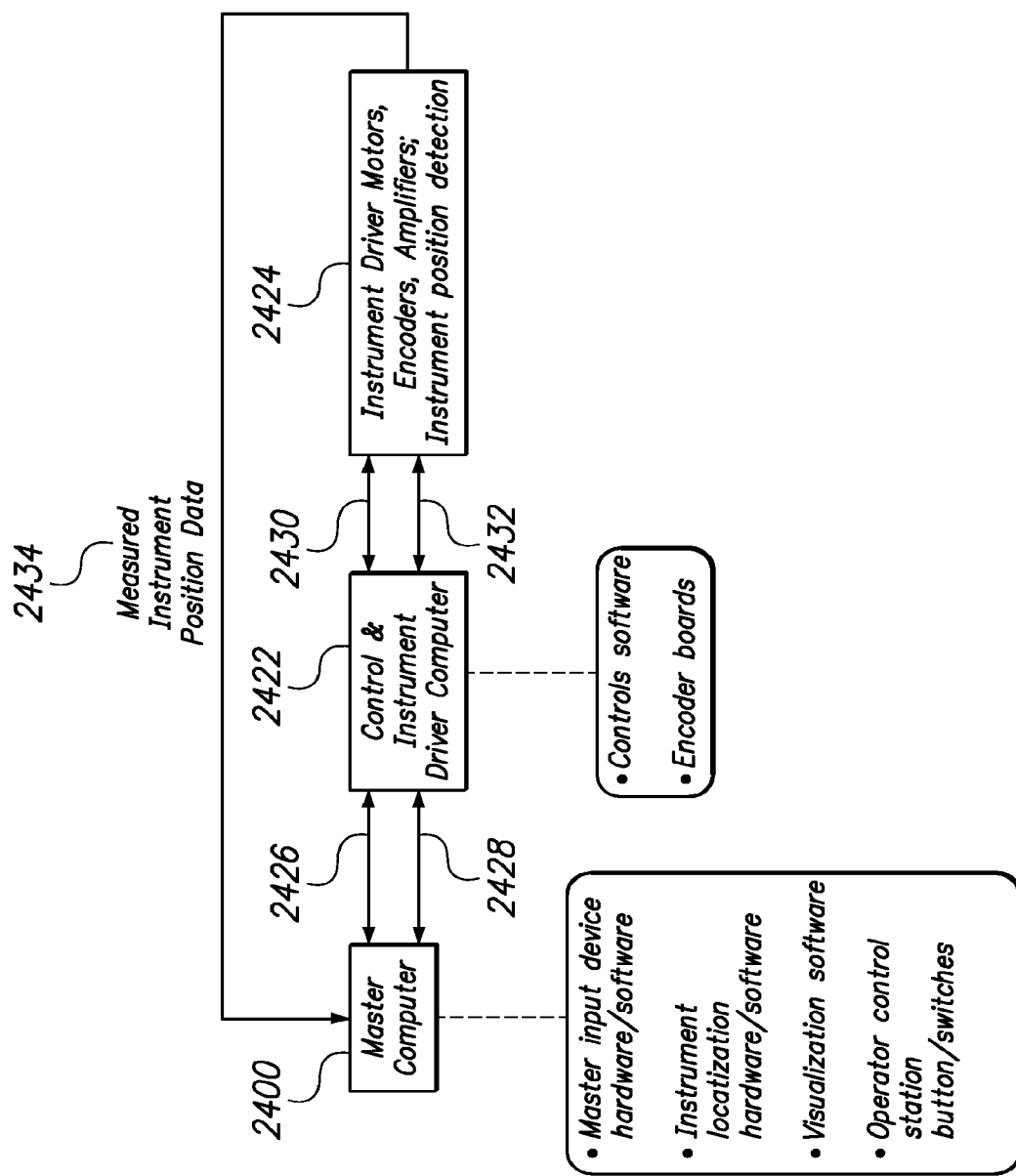

FIG. 128A illustrates a control system in accordance with some embodiments.

Figure 128B:
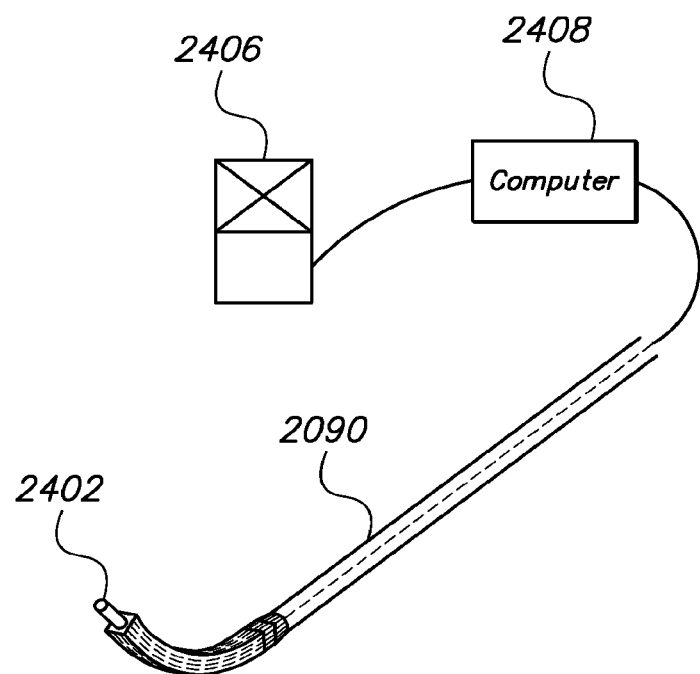

FIG. 128B illustrates a localization sensing system having an electromagnetic field receiver in accordance with some embodiments.

Figure 128C:
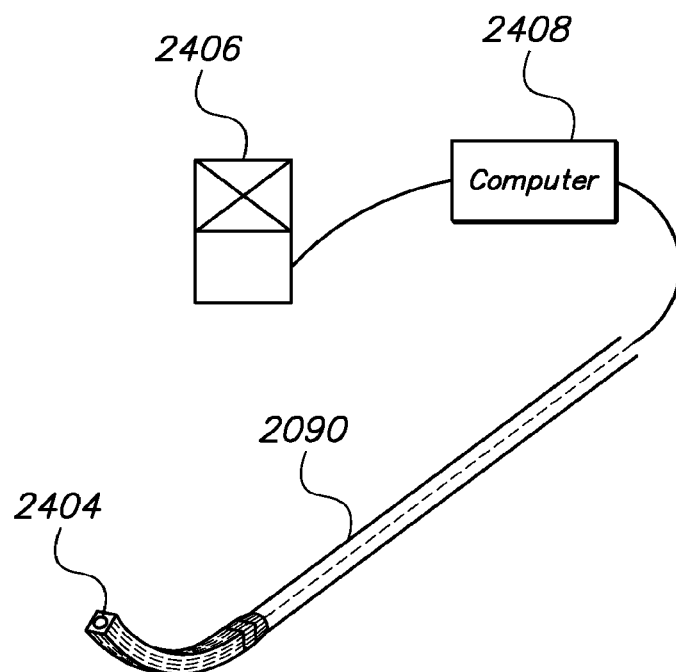

FIG. 128C illustrates a localization sensing system in accordance with other embodiments.

Figure 128D:
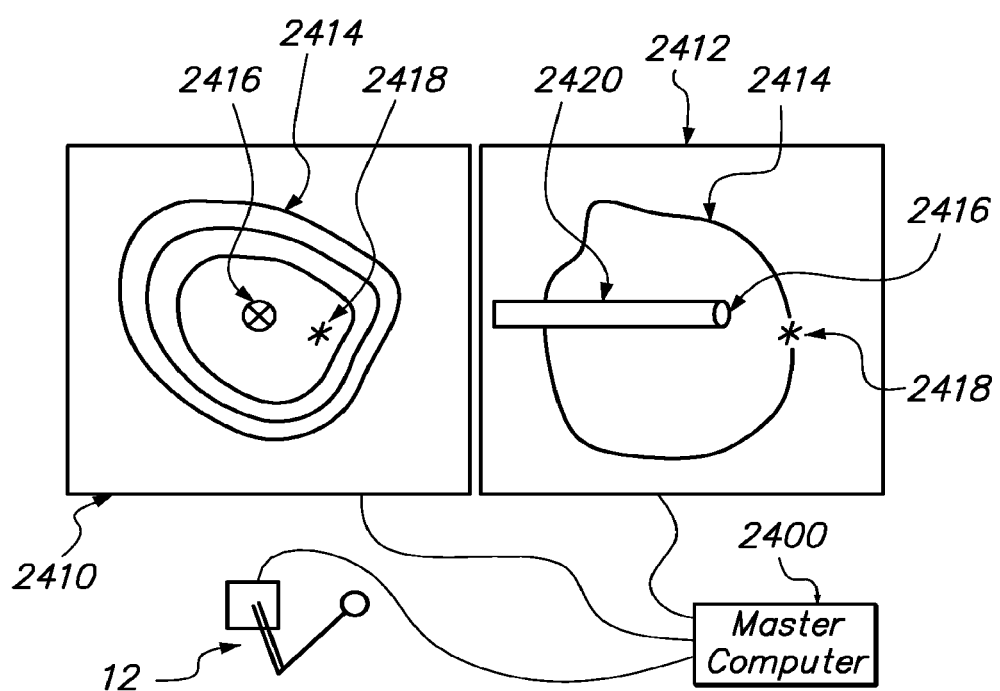

FIG. 128D illustrates a user interface for a master input device in accordance with some embodiments.

FIG. 128E illustrates a configuration of a catheter in accordance with some embodiments.

FIG. 128F illustrates another configuration of a catheter in accordance with other embodiments.

FIG. 128G illustrates a catheter that is haptically constrained to a surface of a "dome" in accordance with some embodiments.

Figure 129A:
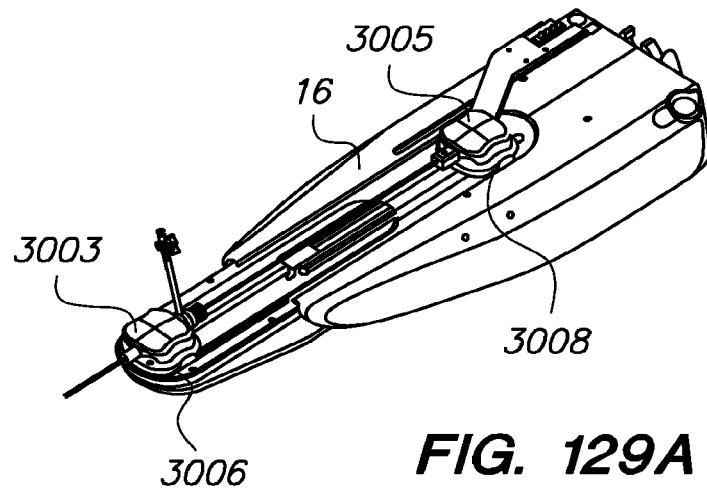

FIG. 129*a* is a perspective view of an instrument driver with a sheath and guide splayer installed.

Figure 129B:
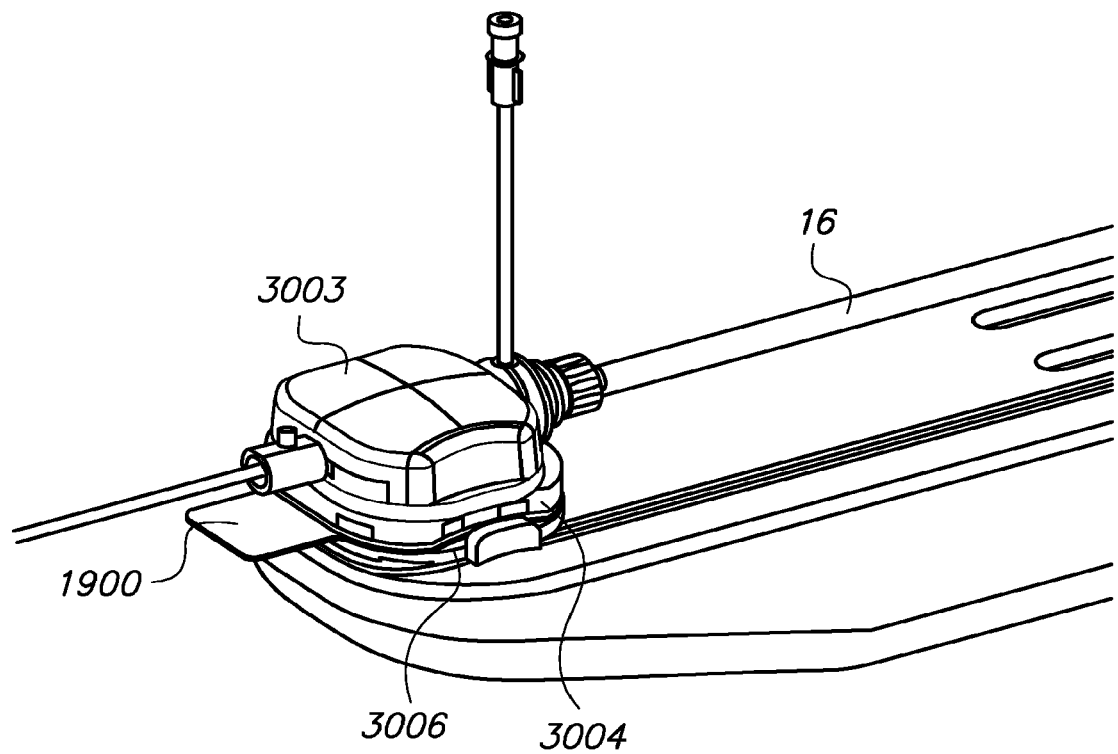

FIG. 129*b* is a zoomed in view of the sheath splayer mounted to the instrument driver of FIG. 129*a*.

Figure 129C:
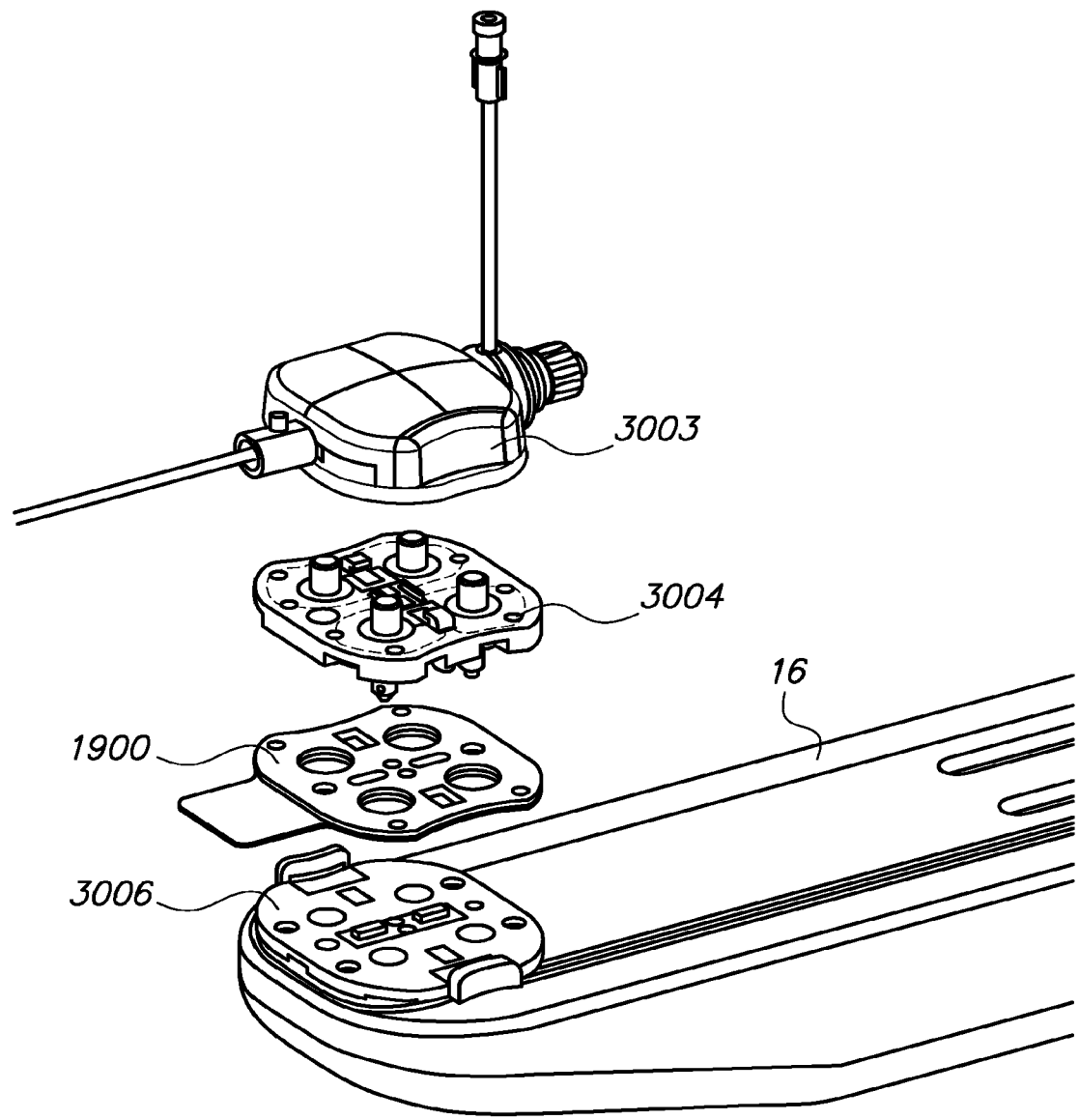

FIG. 129*c* is an exploded view of the sheath splayer and instrument driver of FIG. 129*b*.

Figure 130A:
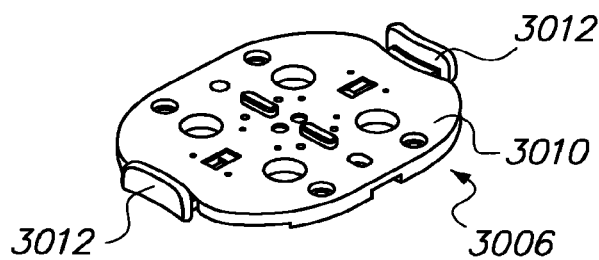
Figure 130B:
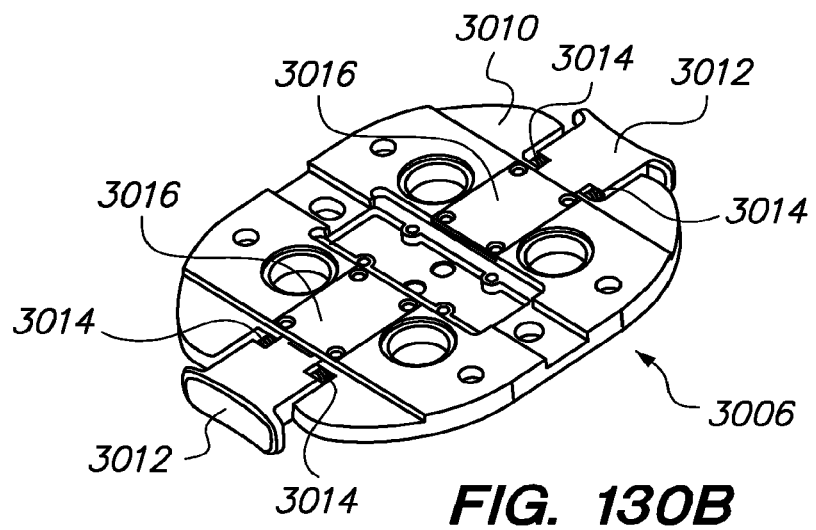

FIGS. 130*a* and 130*b* are top and bottom perspective view respectively of a sheath output plate.

Figure 130C:
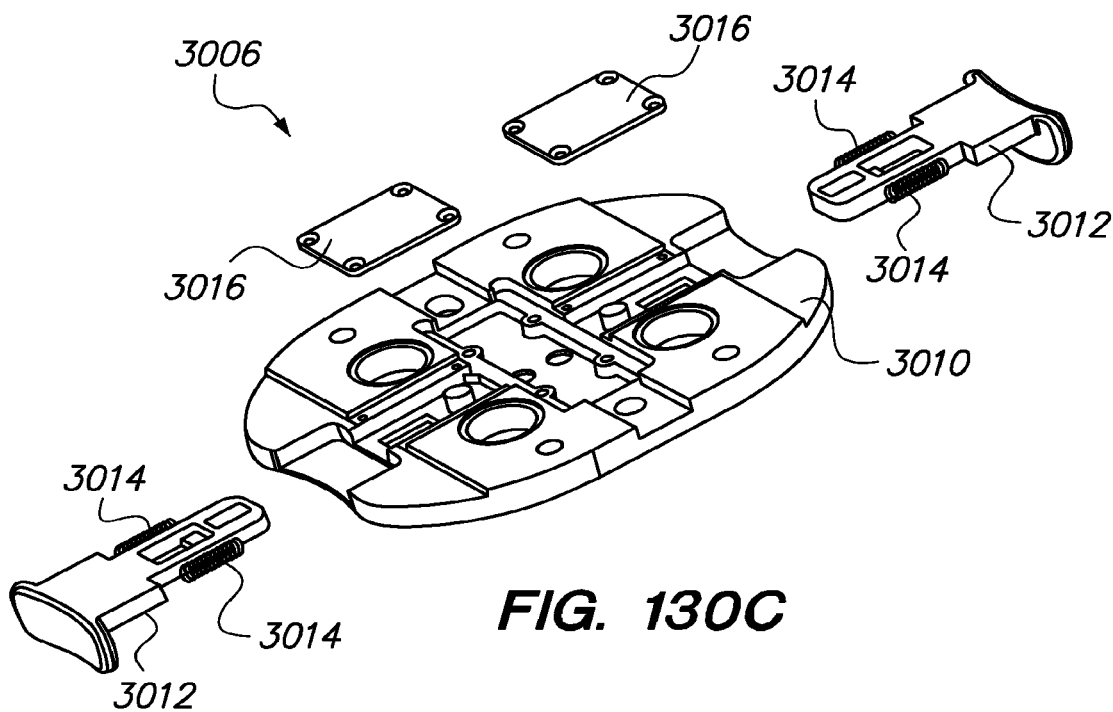

FIG. 130*c* is an exploded bottom perspective view of the sheath output plate of FIG. 130*a*.

Figure 131A:
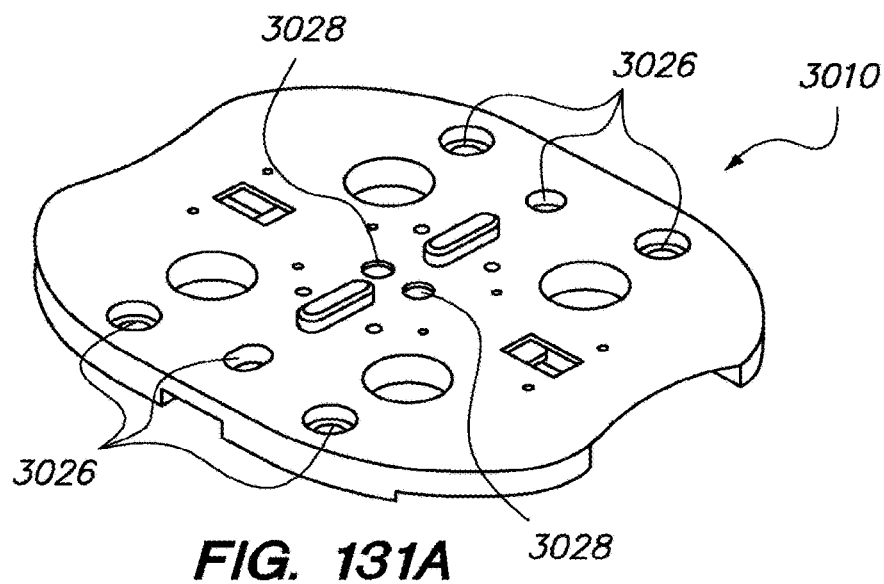
Figure 131B:
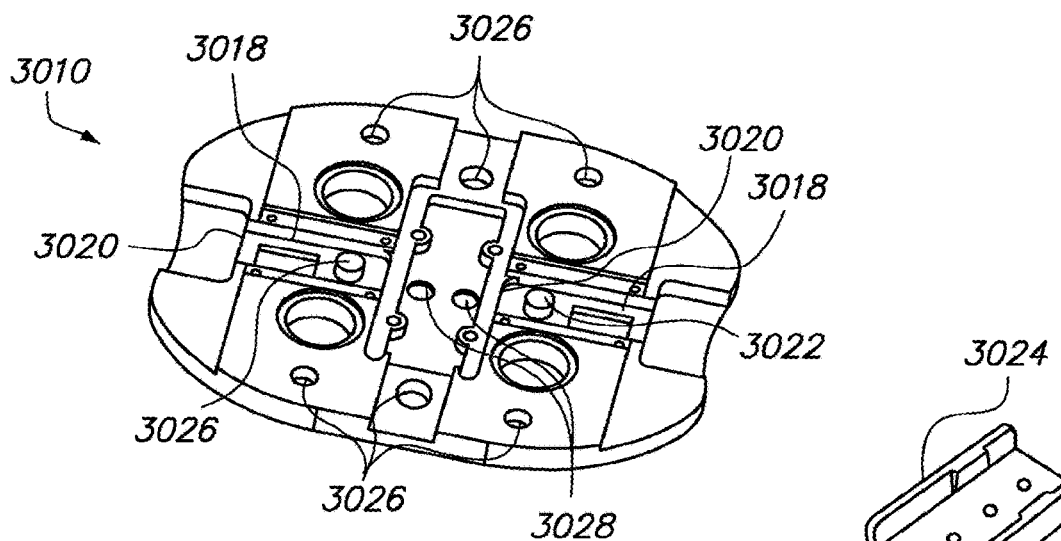

FIGS. 131*a* and 131*b* are top and bottom perspective views respectively of a base plate.

Figure 131C:
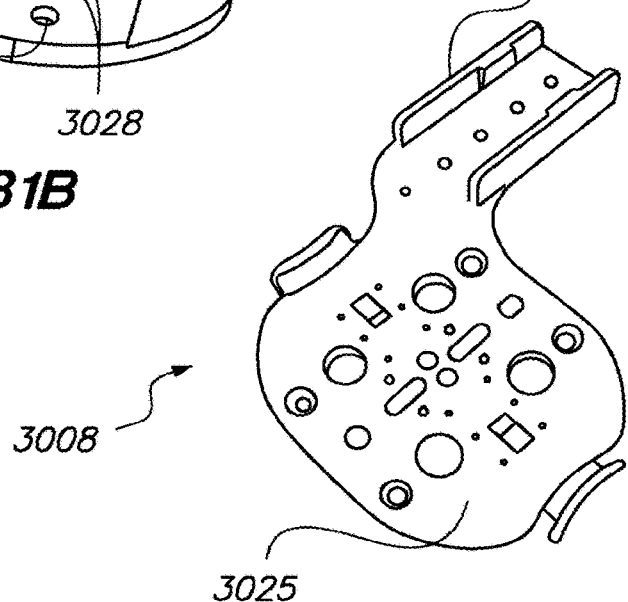

FIG. 131*c* is a perspective view of a guide output plate.

Figure 132A:
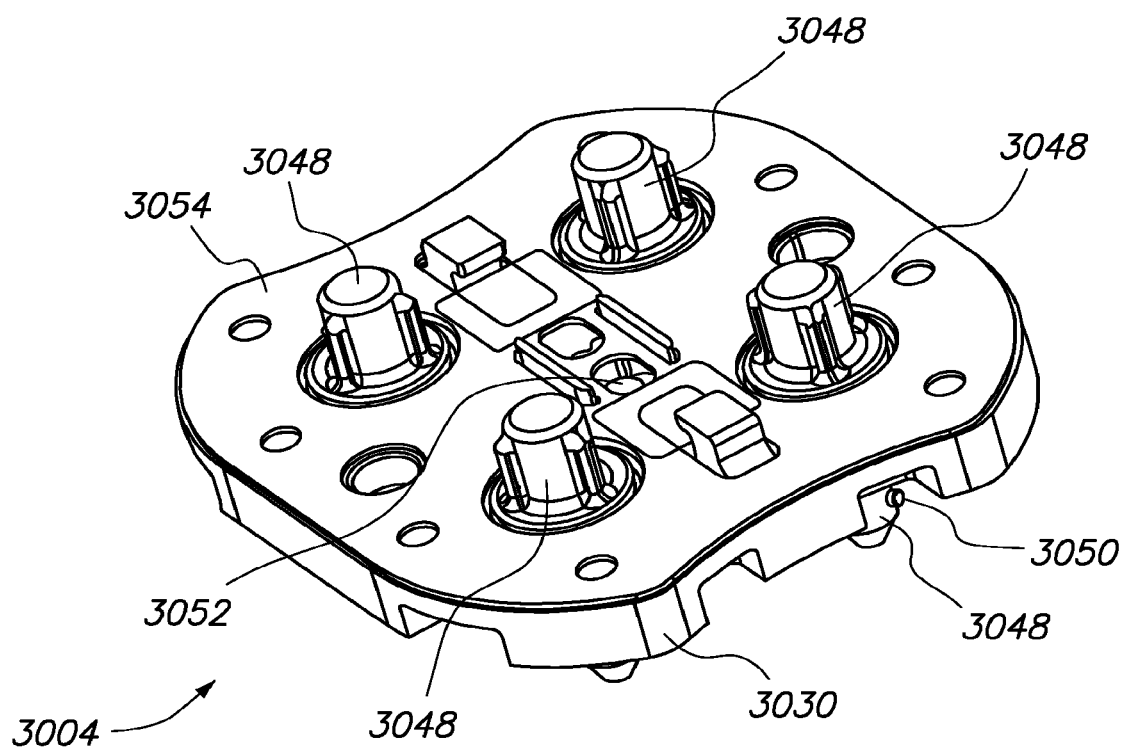
Figure 132B:
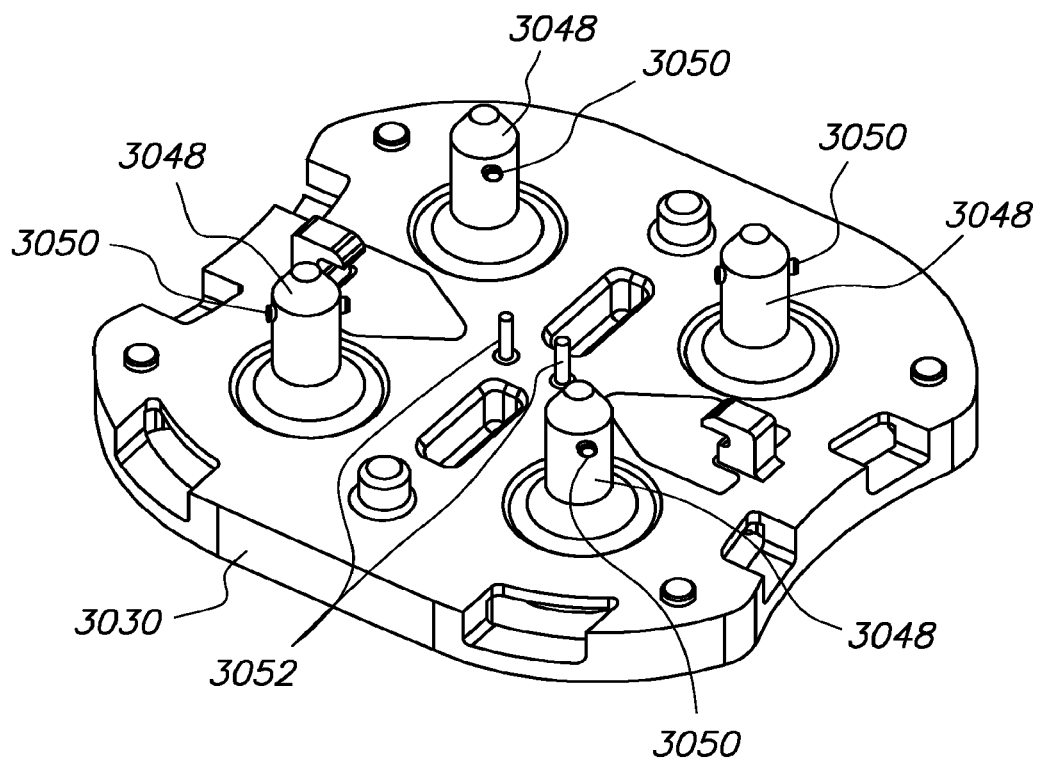

FIGS. 132*a* and 132*b* are top and bottom perspective views respectively of a drive interface apparatus.

Figure 132C:
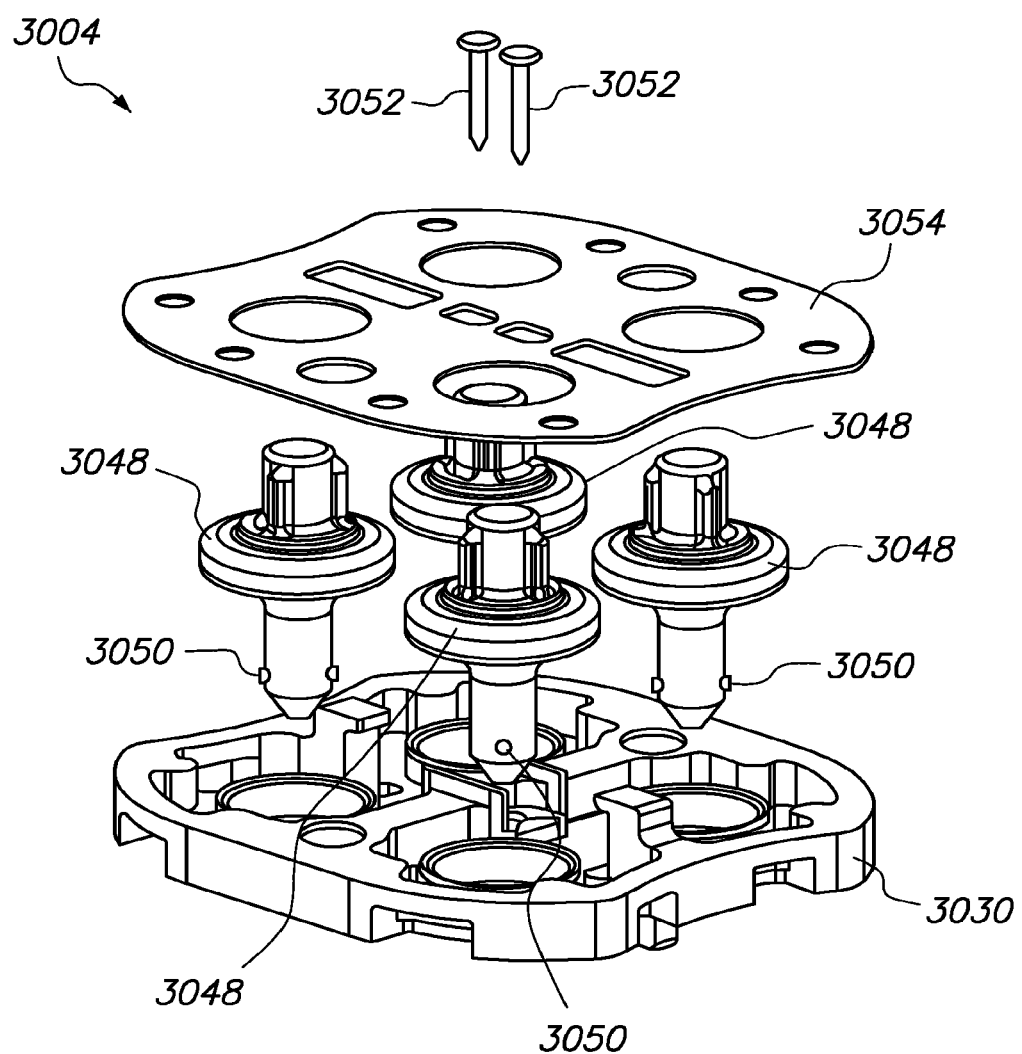

FIG. 132*c* is an exploded perspective view of the drive interface apparatus of FIG. 132*a*.

Figure 133A:
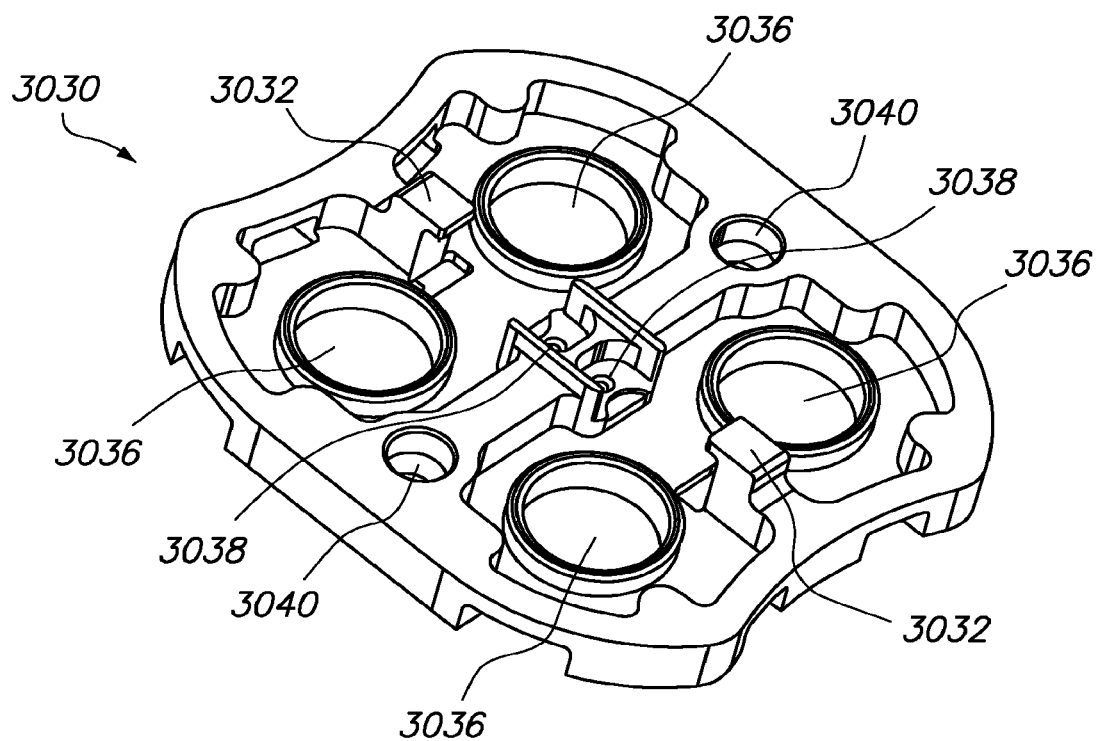
Figure 133B:
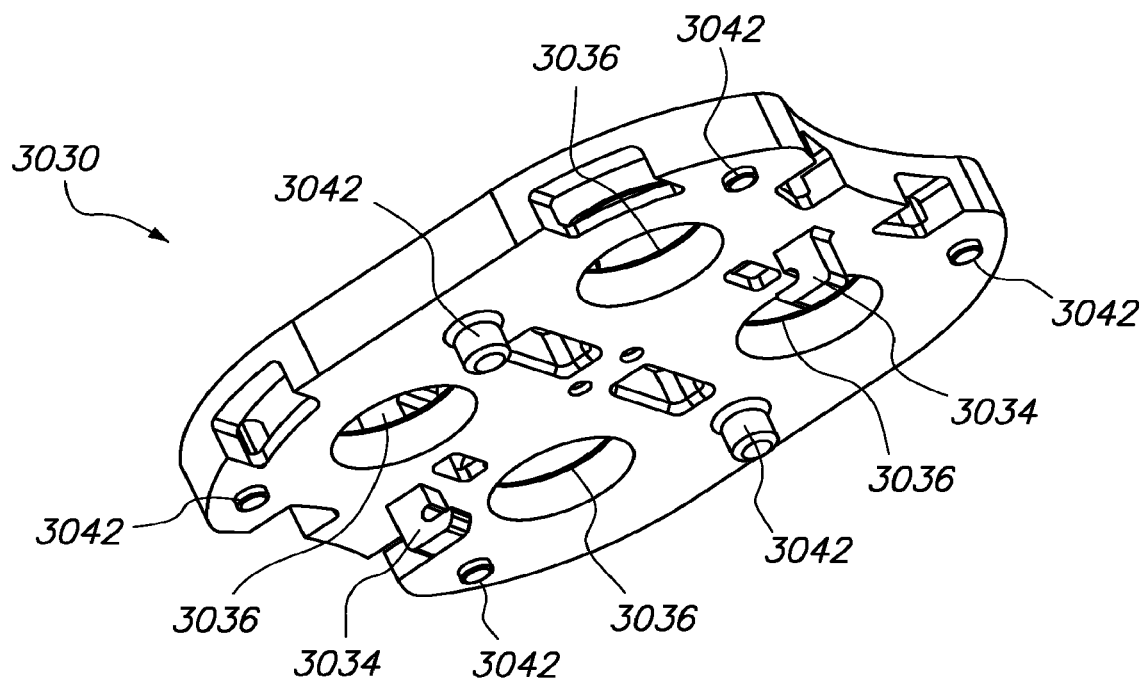

FIGS. 133*a* and 133*b* are top perspective views respectively of a drive interface base.

Figure 134A:
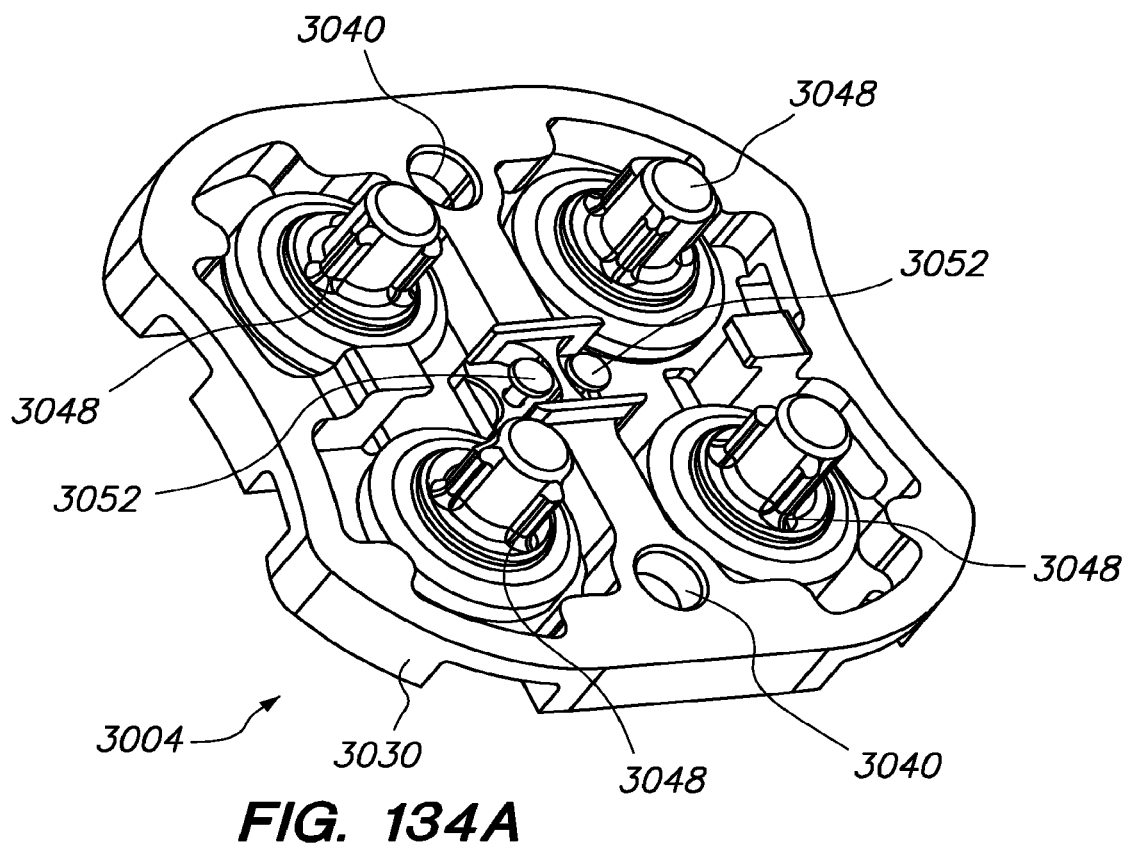
Figure 134B:
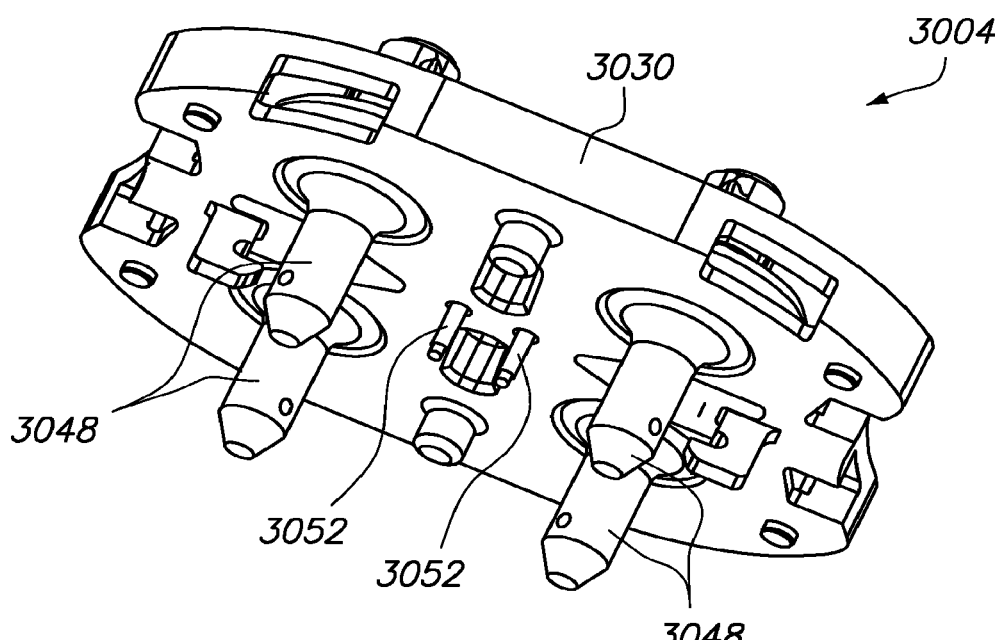

FIGS. 134*a* and 134*b* are top and bottom perspective view respectively of the drive interface base of FIG. 133*a* populated with a plurality of drive interface pulley shafts and a pair of EEPROM pins.

Figure 135A:
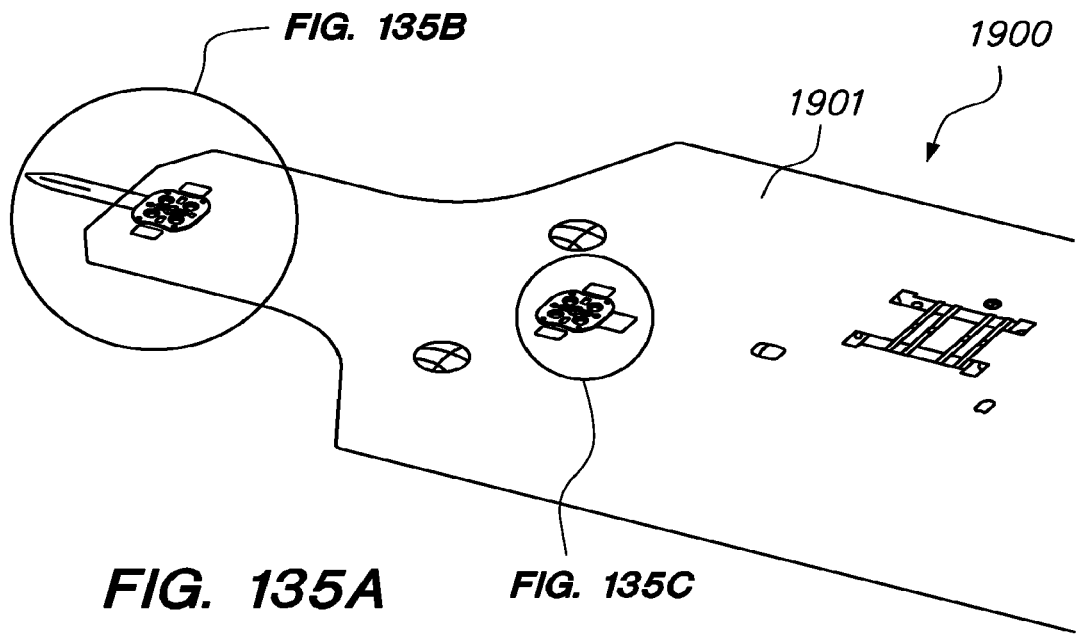

FIG. 135*a* is a perspective view of a drape assembly.

Figure 135B:
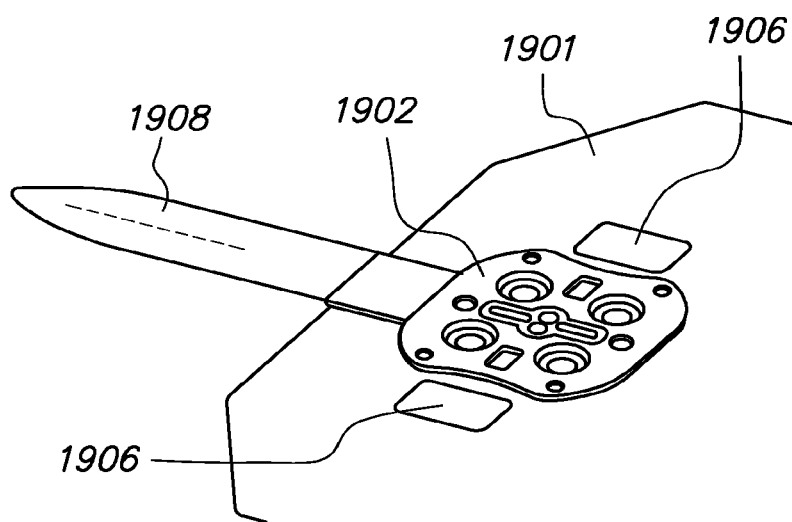

FIG. 135b is a zoomed in perspective view of a portion of the drape assembly of FIG. 135a including a sheath foam pad.

Figure 135C:
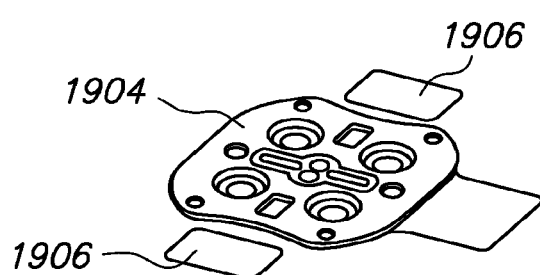

FIG. 135c is a zoomed in perspective view of a portion of the drape assembly of FIG. 135a including a guide foam pad.

Figure 136A:
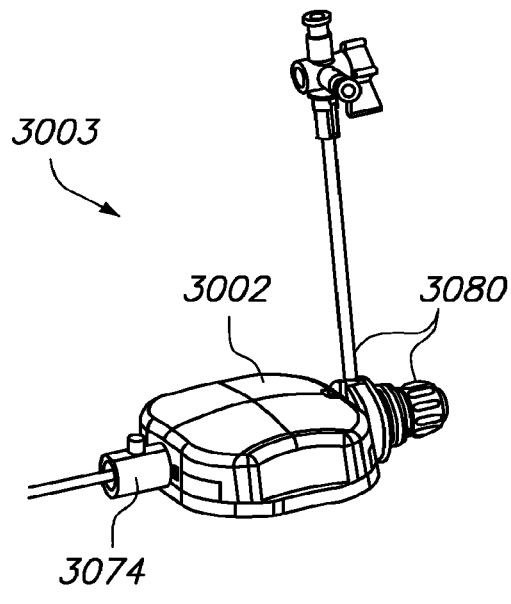

FIG. 136a is a perspective view of a sheath splayer.

Figure 136B:
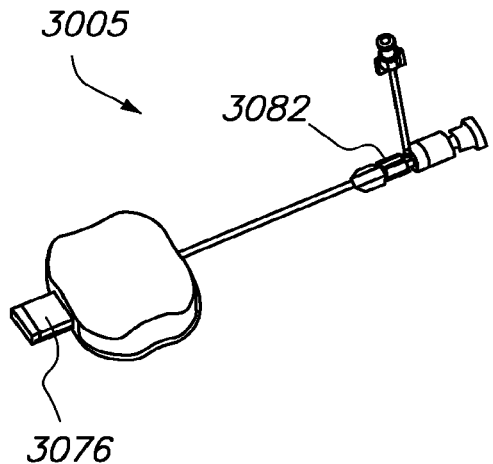

FIG. 136b is a perspective view of a guide splayer.

Figure 136C:
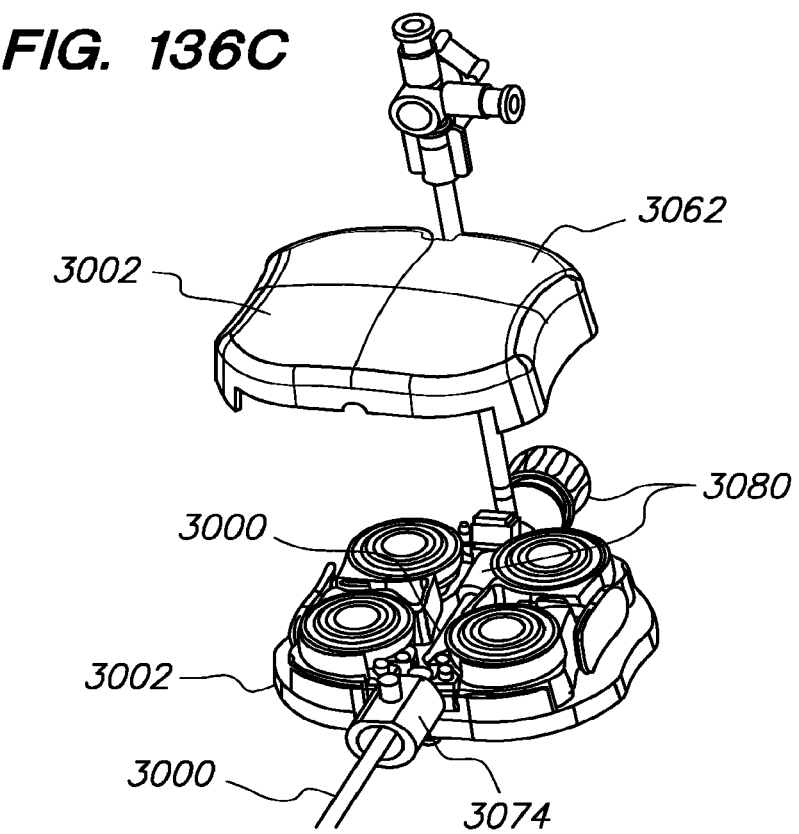

FIG. 136c is a perspective view of the sheath splayer of FIG. 136a with a splayer cover exploded from the sheath splayer.

FIGS. 137a and 137b are top and bottom perspective views respectively of a splayer body.

FIG. 137c is an exploded perspective view of the splayer body of FIG. 137a.

FIG. 138 is a bottom view of a splayer cover.

FIGS. 138a and 138b are perspective and exploded views respectively of a splayer pulley assembly.

Figure 139A:
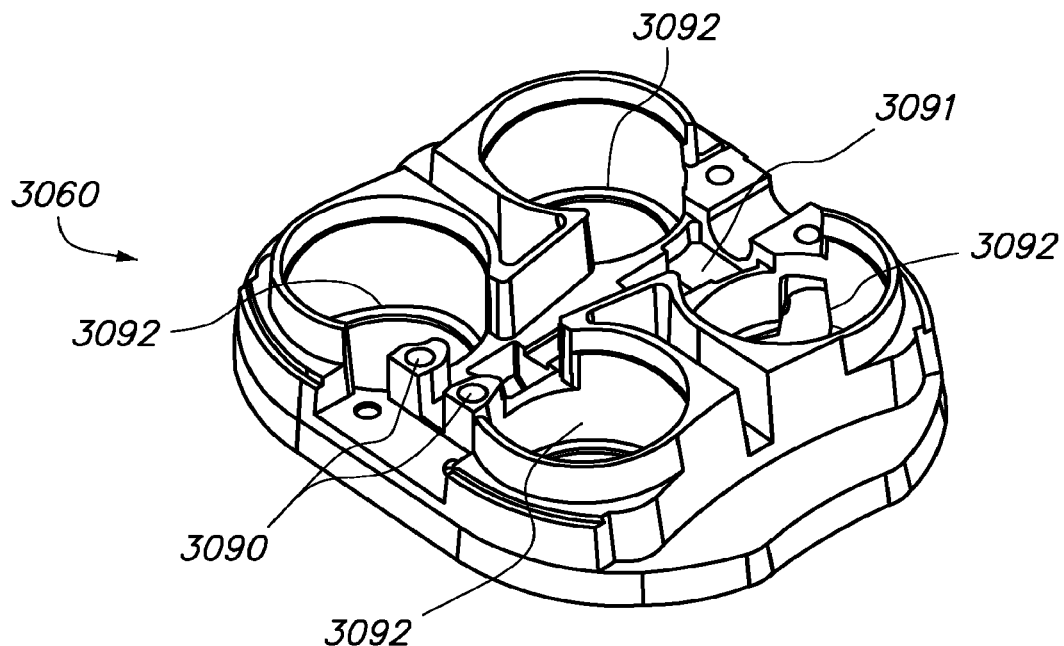
Figure 139B:
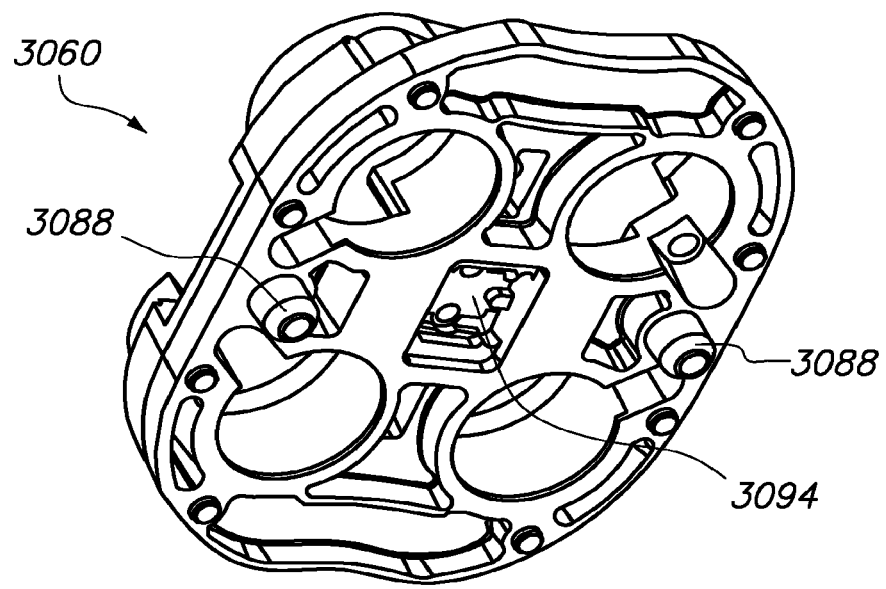

FIGS. 139a and 139b are top and bottom perspective views respectively of a splayer base.

Figure 140A:
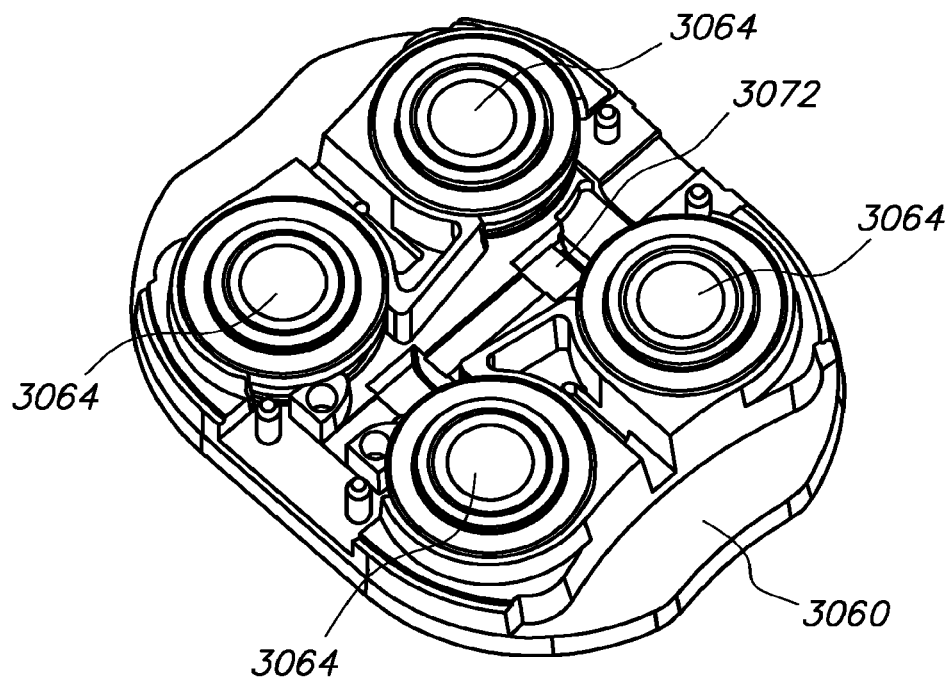
Figure 140B:
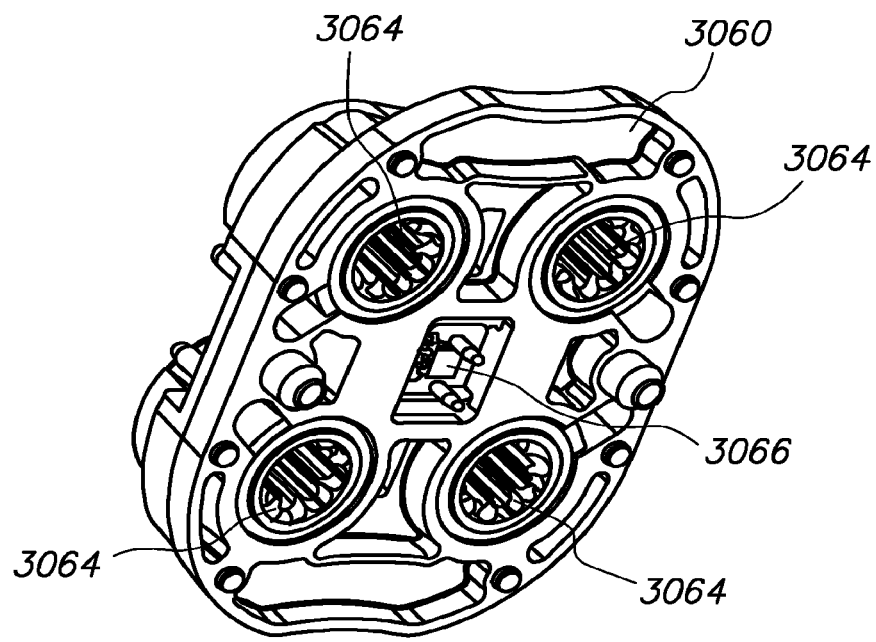

FIGS. 140a and 140b are top and bottom perspective views respectively of the splayer base of FIG. 139a populated with a plurality of splayer pulley assemblies, a splayer presence magnet, and a splayer ID chip.

Figure 141A:
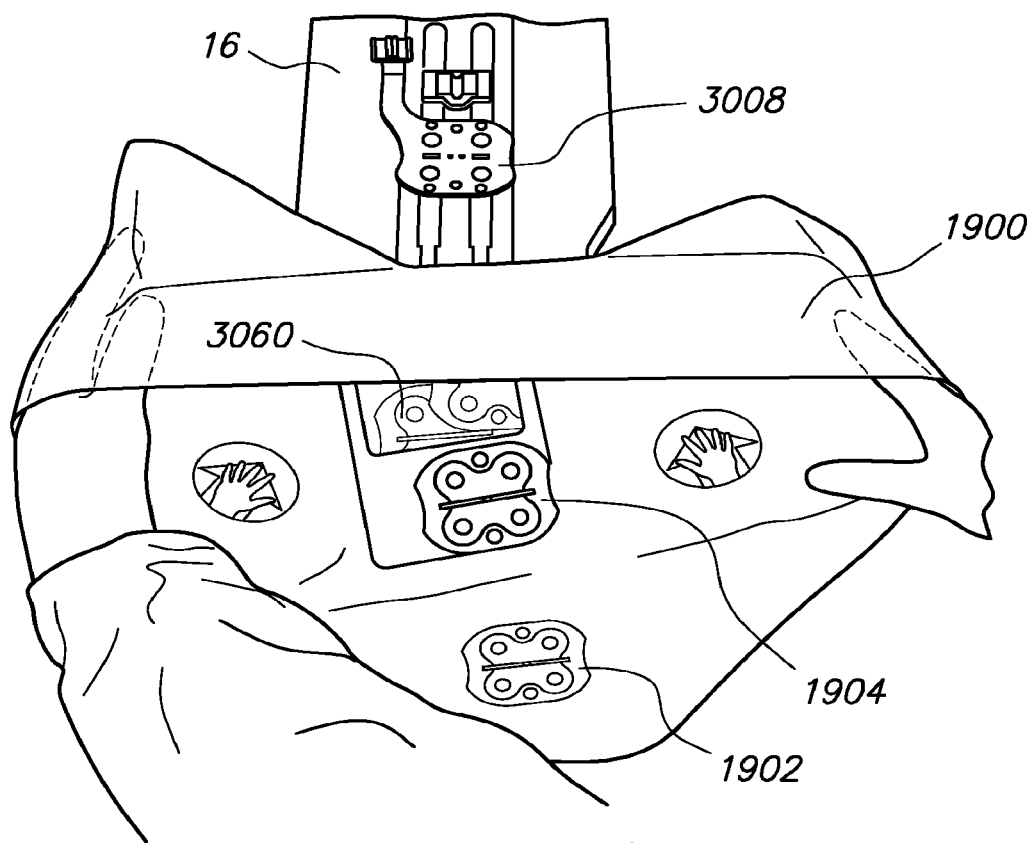
Figure 141B:
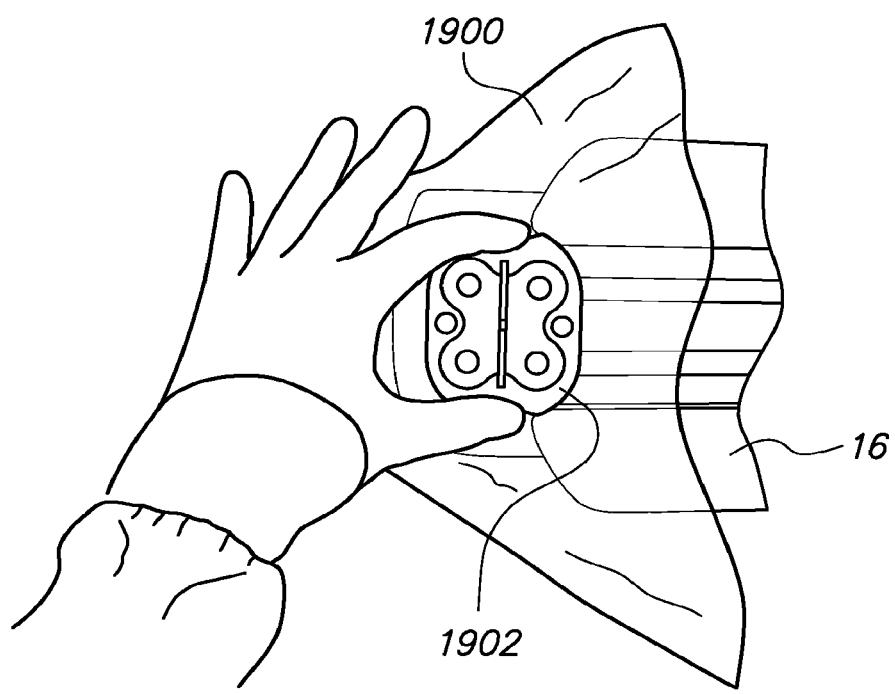

FIGS. 141a and 141b illustrate methods of installing the drape assembly of FIG. 135a over the instrument driver.

Figure 142A:
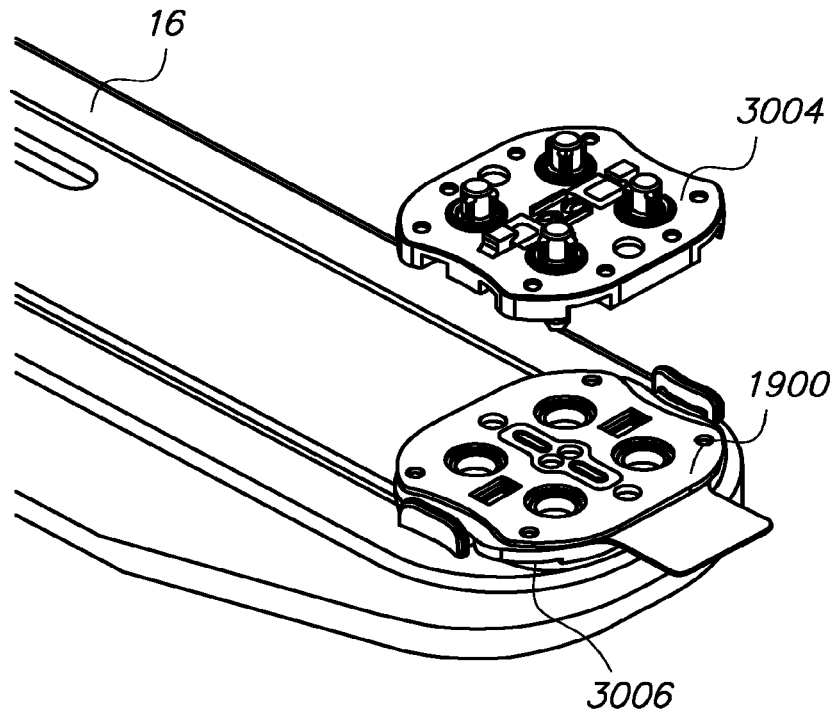

FIG. 142a is a perspective view of the instrument assembly with the drape assembly installed and the drive interface apparatus exploded from the instrument driver.

Figure 142B:
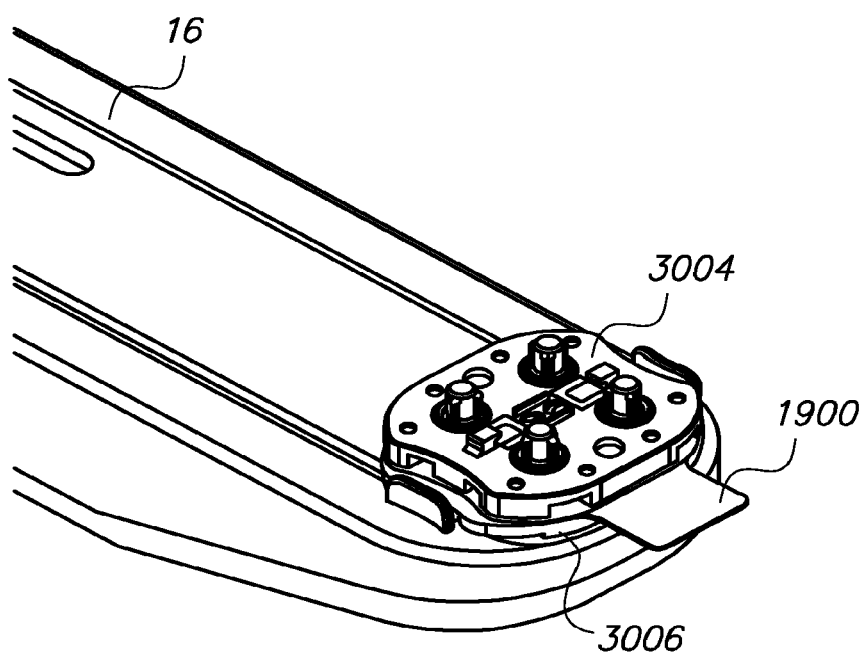

FIG. 142b is a perspective view of the instrument assembly and drape assembly of FIG. 142a with the drive interface apparatus installed.

Figure 143A:
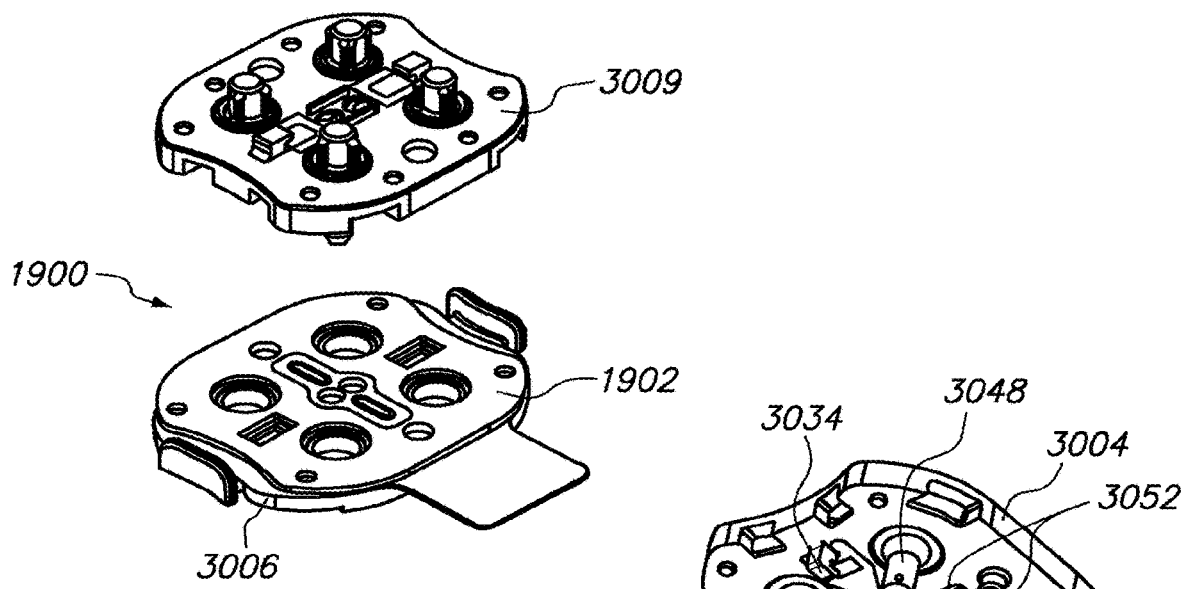

FIG. 143a is a top perspective view of the sheath output plate with the drape assembly installed and the drive interface apparatus exploded.

Figure 143B:
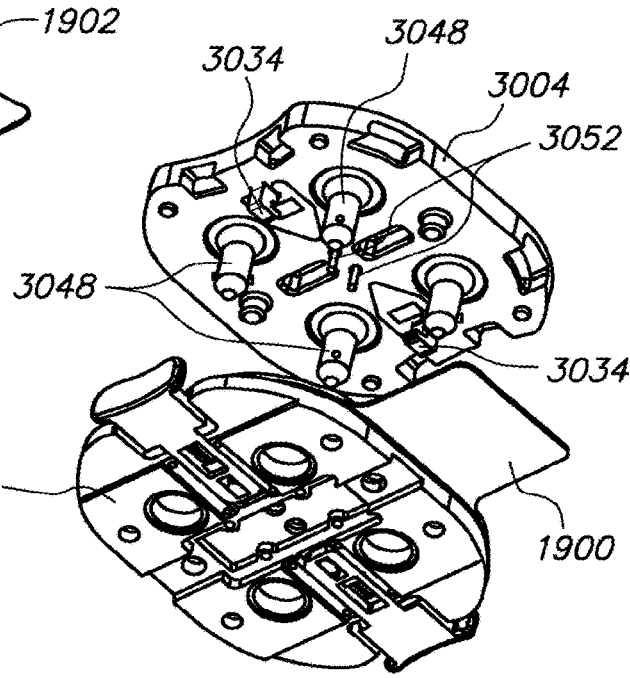

FIG. 143b is a bottom perspective view of the sheath output plate, drape assembly, and drive interface apparatus of FIG. 143a.

Figure 143C:
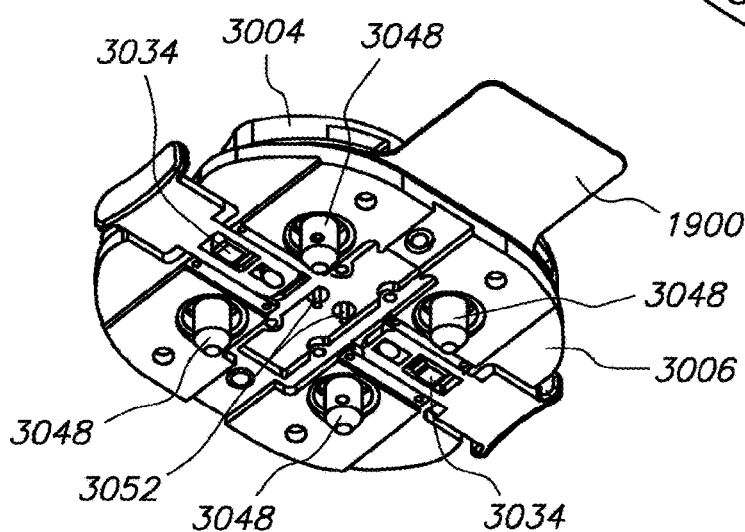

FIG. 143c is a bottom perspective view of the sheath output plate with the drape and drive interface apparatus installed.

FIGS. 144a and 144b are perspective views of a drive interface pulley shaft installed and uninstalled respectively to a sleeve receptacle.

FIGS. 144c and 144d are side and front views of the drive interface pulley and sleeve receptacle illustrated in FIG. 144b.

FIGS. 145a and 145b are top and bottom perspective view of the sheath splayer exploded from the drive interface apparatus.

FIG. 146a is a top view of the splayer pulley assembly.

FIG. 146b is a top view of the drive interface pulley shaft.

FIGS. 147a and 147b are top and bottom perspective views respectively of the splayer pulley assembly exploded from the drive interface pulley shaft.

Figure 148A:
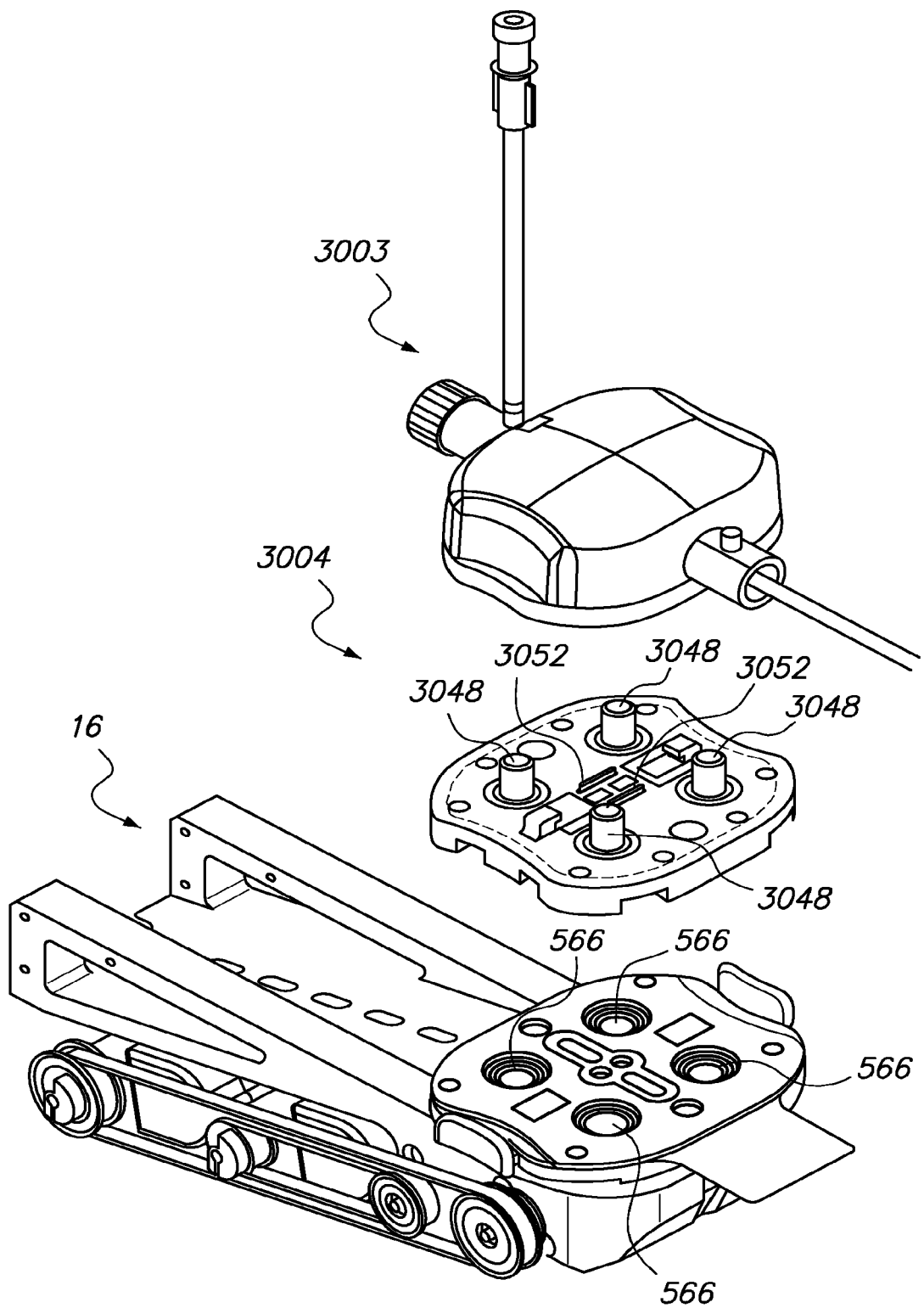
Figure 148B:
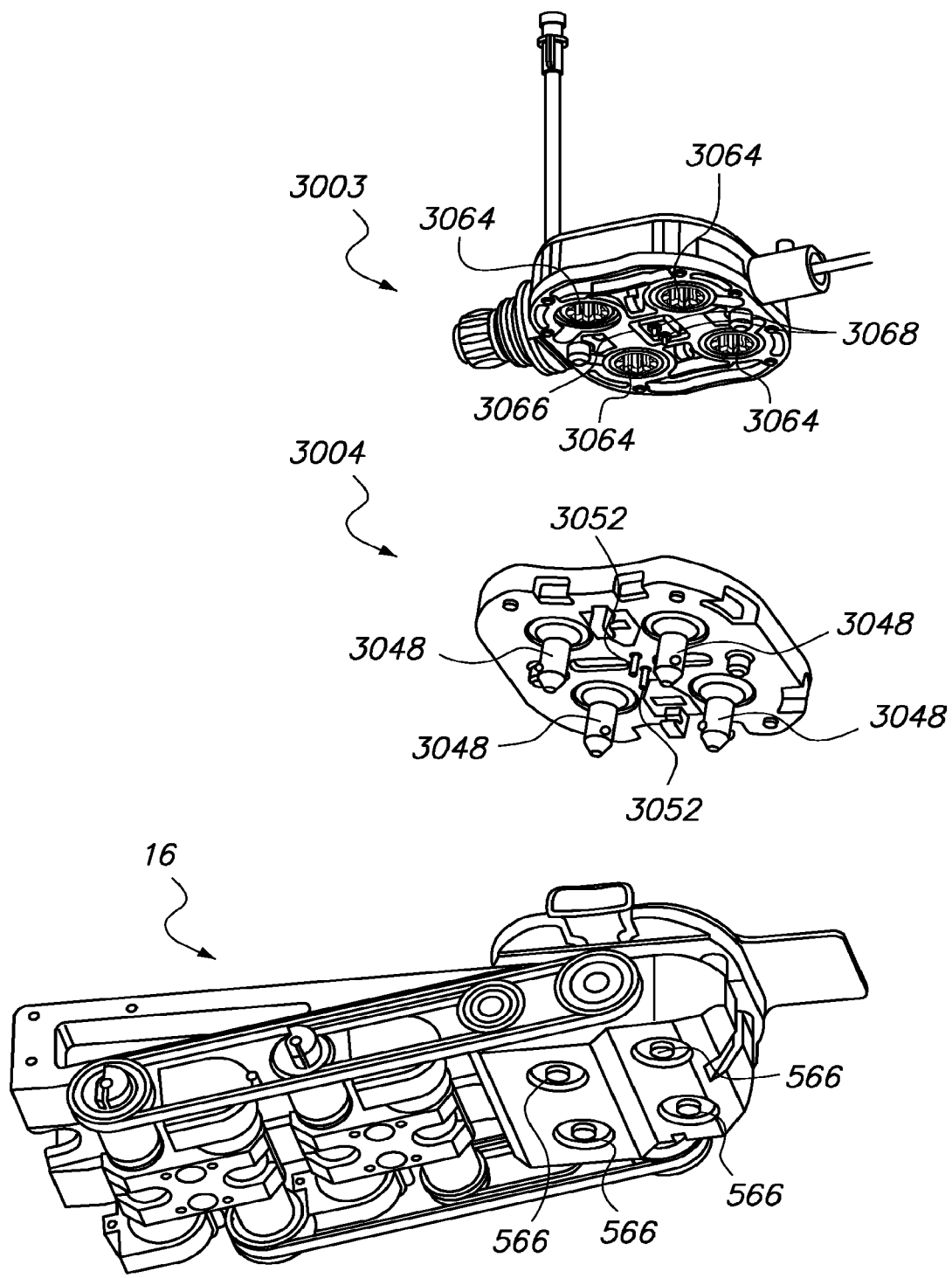

FIGS. 148a and 148b are top and bottom exploded views respectively of the instrument driver with the drape assembly installed and the drive interface apparatus and sheath splayer un-installed.

DESCRIPTION OF THE EMBODIMENTS

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

I. Robotic Surgical Systems

Embodiments described herein generally relate to apparatus, systems and methods for robotic surgical systems. A robotic surgical systems in which embodiments described herein may be implemented is described with reference to FIGS. 1-10B. Various embodiments of apparatus, system and method, including control and electronic architectures, are described with reference to FIGS. 11A-19K. Various embodiments directed to indicating catheter insertion forces as the catheter engages tissue or another object are described with reference to FIGS. 20A-B. Various embodiments directed to determining reachability of catheter instrument and viewability or fields of view at different reachable locations are described with reference to FIG. 21.

Referring to FIG. 1, a robotically controlled surgical system (S) in which embodiments of apparatus, system and method may be implemented includes a robotic catheter assembly (A) having a first or outer robotic steerable complement, otherwise referred to as a sheath instrument 30 (generally referred to as "sheath" or "sheath instrument") and/or a second or inner steerable component, otherwise referred to as a robotic catheter or guide or catheter instrument 18 (generally referred to as "catheter" or "catheter instrument"). The sheath instrument 30 and catheter instrument 18 are controllable using a robotic instrument driver 16 (generally referred to as "instrument driver"). During use, a patient is positioned on an operating table or surgical bed 22 (generally referred to as "operating table") to which a robotic catheter assembly (A) is coupled or mounted. In the illustrated example, the system (S) includes an operator workstation 2, an electronics rack 6 and associated bedside electronics box, a setup joint mounting brace 20, and an instrument driver 16. A surgeon is seated at the operator workstation 2 and can monitor the surgical procedure, patient vitals, and control one or more catheter devices.

Various system (S) components in which embodiments described herein may be implemented are illustrated in close proximity to each other in FIG. 1, but embodiments may also be implemented in systems (S) in which components are separated from each other, e.g., located in separate rooms. For example, the instrument driver 16, operating table 22, and bedside electronics box may be located in the surgical area with the patient, and the operator workstation 2 and the electronics rack 6 may be located outside of the surgical area and behind a shielded partition. System (S) components may also communicate with other system (S) components via a network to allow for remote surgical procedures during which the surgeon may be located at a different location, e.g., in a different building or at a different hospital utilizing a communication link transfers signals between the operator control station 2 and the instrument driver 16. System (S) components may also be coupled together via a plurality of cables or other suitable connectors 14 to provide for data communication, or one or more components may be equipped with wireless communication components to reduce or eliminate cables 14. In this manner, a surgeon or other operator may control a surgical instrument while being located away from or remotely from radiation sources, thereby decreasing the operator's exposure to radiation.

Referring to FIG. 2, one example of an operator workstation 2 that may be used with the system (S) shown in FIG. 1 includes three display screens 4, a touch screen user interface 5, a control button console or pendant 8, and a master input device (MID) 12. The MID 12 and pendant 8 serve as user interfaces through which the surgeon can control operation of the instrument driver 16 and attached instruments. By manipulating the pendant 8 and the MID 12, a surgeon or other operator can cause the instrument driver 16 to remotely control a catheter instrument 18 and/or a sheath instrument 30 mounted thereon. A switch 7 may be provided to disable activity of an instrument temporarily. The console 2 in the illustrated system (S) may also be configurable to meet individual user preferences. For example, in the illustrated example, the pendant 8 and the touch screen 5 are shown on the left side of the console 2, but they may also be relocated to the right side of the console 2. Further, optional keyboard may be connected to the console 2 for inputting user data. The workstation 2 may also be mounted on a set of casters or wheels to allow easy movement of the workstation 2 from one location to another, e.g., within the operating room or catheter laboratory. Further aspects of examples of suitable MID 12, and workstation 2 arrangements are described in further detail in U.S. patent application Ser. No. 11/481,433, issued as U.S. Pat. No. 8,052,636 on Nov. 8, 2011, and U.S. Provisional Patent Application No. 60/840,331, the contents of which were previously incorporated herein by reference. Additional embodiments of various MIDs and pendants will also be described later.

Referring to FIGS. 3A-C, a system (S) includes a setup joint or support assembly 20 (generally referred to as "support assembly") for supporting or carrying the instrument driver 16 over the operating table 22. One suitable support assembly 20 has an arcuate shape and is configured to position the instrument driver 16 above a patient lying on the table 22. The support assembly 20 may be configured to movably support the instrument driver 16 and to allow convenient access to a desired location relative to the patient. The support assembly 20 may also be configured to lock the instrument driver 16 into a certain position.

In the illustrated example, the support assembly 20 is mounted to an edge of the operating table 22 such that a catheter and sheath instruments 18, 30 mounted on the instrument driver 16 can be positioned for insertion into a patient. The instrument driver 16 is controllable to maneuver the catheter and/or sheath instruments 18, 30 within the patient during a surgical procedure. The distal portion of the setup joint 20 also includes a control lever 33 for maneuvering the setup joint 20. Although the figures illustrate a single guide catheter 18 and sheath assembly 30 mounted on a single instrument driver 16, embodiments may be implemented in systems (S) having other configurations. For example, embodiments may be implemented in systems (S) that include a plurality of instrument drivers 16 on which a plurality of catheter/sheath instruments 18, 30 can be controlled. Further aspects of a suitable support assembly 20 are described in U.S. patent application Ser. No. 11/481,433, issued as U.S. Pat. No. 8,052,636 on Nov. 8, 2011, and U.S. Provisional Patent Application No. 60/879,911, the contents of which are expressly incorporated herein by reference. Referring to FIG. 3D-E, the support assembly 20 may be mounted to an operating table 22 using a universal adapter base plate assembly 39, similar to those described in detail in U.S. Provisional Patent Application No. 60/899,048, incorporated by reference herein in its entirety. The adapter plate assembly 39 mounts directly to the operating table 22 using clamp assemblies 39b, 39c, and the support assembly 20 can be mounted to the adapter plate assembly 39. One suitable adapter plate assembly 39 includes a large, flat main plate 39a which is positioned on top of the operating table 22. The assembly 39 provides for various adjustments to allow it to be mounted to different types of operating tables 22. An edge of the adapter plate assembly 39 may include a rail 39d that mimics the construction of a traditional surgical bedrail. By placing this rail on the adapter plate 39a itself, a user may be assured that the component dimensions provide for proper mounting of the support assembly 20. Furthermore, the large, flat surface of the main plate 39a provides stability by distributing the weight of the support assembly 20 and instrument driver 16 over an area of the table 22, whereas a support assembly 20 mounted directly to the operating table 22 rail may cause its entire load to be placed on a limited and less supportive section of the table 22.

Figure 5A:
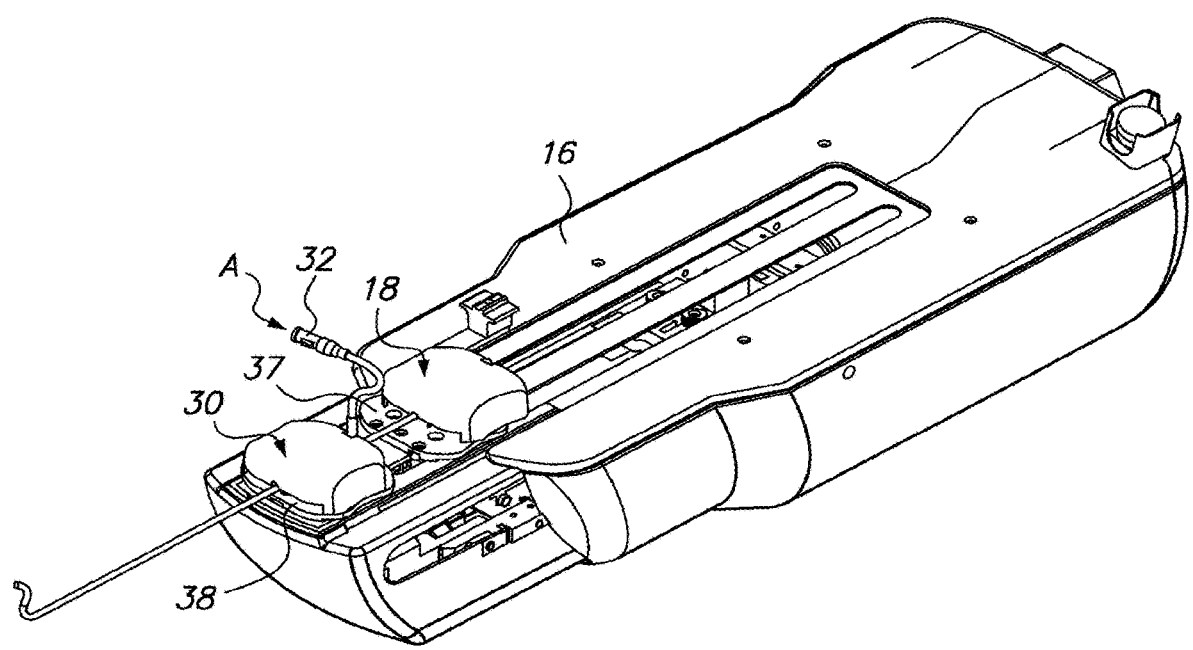
FIG. 5A illustrates a sheath and guide catheter assembly mounted on an instrument driver.
Figure 5B:
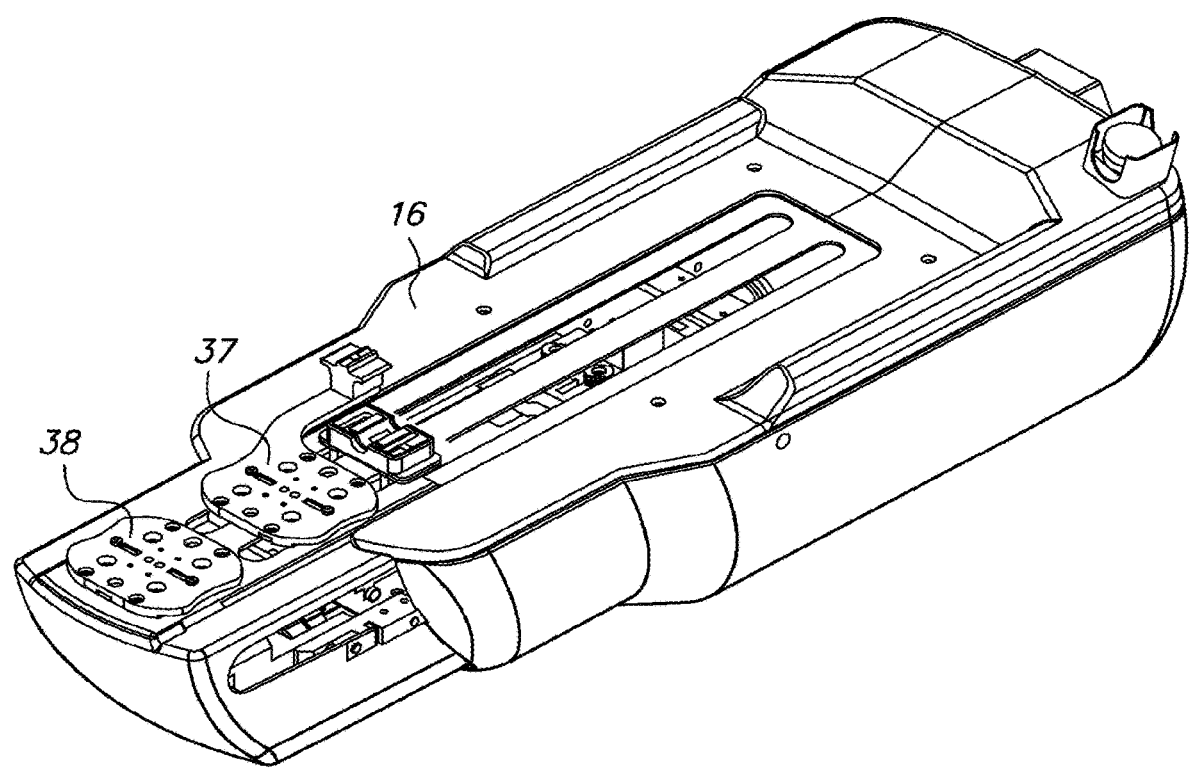
FIG. 5B further illustrates the instrument driver shown in FIG. 5A without the sheath and guide catheter assembly.
Figure 5C:
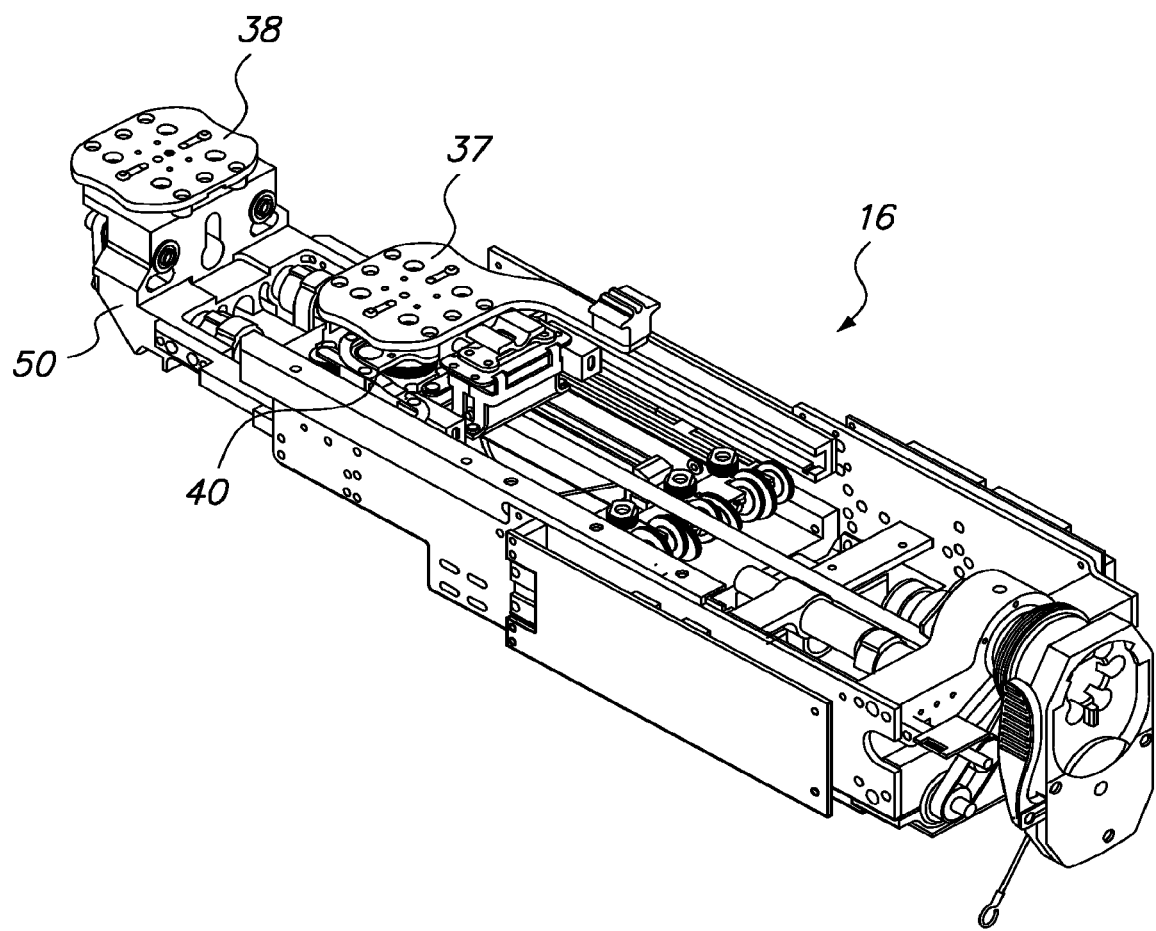
FIG. 5C further illustrates the instrument driver shown in FIG. 5B with skins removed and one of the mounting plates being moved relative to the mounting plate arrangement shown in FIG. 5B.

With further reference to FIGS. 4 and 5A, an instrument assembly (A) comprised of a sheath instrument 30 and an associated guide or catheter instrument 18 is mounted to associated mounting plates 37, 38 on a top portion of the instrument driver 16. FIG. 5B illustrates the instrument driver 16 without an attached instrument assembly (A). FIG. 5C illustrates the instrument driver 16 with skins removed to illustrate internal components which will be described in further detail. Embodiments described are similar to those described in detail in U.S. patent application Ser. No. 11/678,001, issued as U.S. Pat. No. 8,092,397 on Jan. 10, 2012; Ser. No. 11/678,016, issued as U.S. Pat. No. 8,052,621 on Nov. 8, 2011; and Ser. No. 11/804,585, now abandoned, each incorporated by reference herein in its entirety.

Referring to FIGS. 6A-B, the assembly (A) that includes a sheath instrument 30 and a guide or catheter instrument 18 positioned over their respective mounting plates 38, 37 is illustrated removed from the instrument driver 16. The guide catheter instrument member 61a is coaxially interfaced with the sheath instrument member 62a by inserting the guide catheter instrument member 61a into a working lumen of the sheath catheter member 62a. As shown in FIG. 6A, the sheath instrument 30 and the guide or catheter instrument 18 are coaxially disposed for mounting onto the instrument driver 16. However, it should be understood that a sheath instrument 16 is used without a guide or catheter instrument 18, or a guide or catheter instrument 18 is used without a sheath instrument 30 may be mounted onto the instrument driver 16 individually. With the coaxial arrangement as shown in FIG. 6A, the guide catheter splayer 61 is located proximally relative to, or behind, the sheath splayer 62 such that the guide catheter member 61a can be inserted into and removed from the sheath catheter member 61b.

Figure 7A:
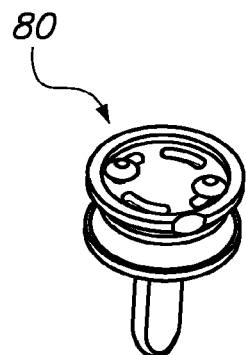
FIG. 7A illustrates a pulley assembly of the splayer shown in FIG. 7.
Figure 7B:
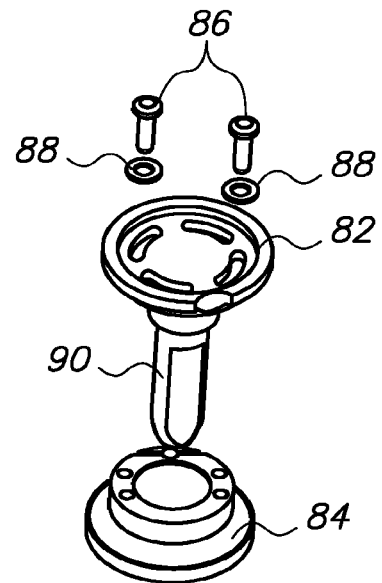
FIG. 7B illustrates an exploded view of the pulley assembly shown in FIG. 7A.
Figure 7C:
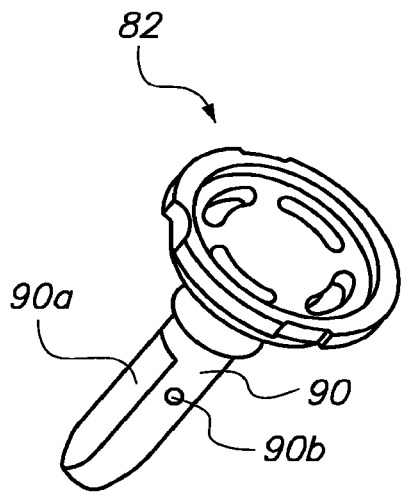
FIG. 7C illustrates the top portion of the pulley assembly shown in FIG. 7A.
Figure 7D:
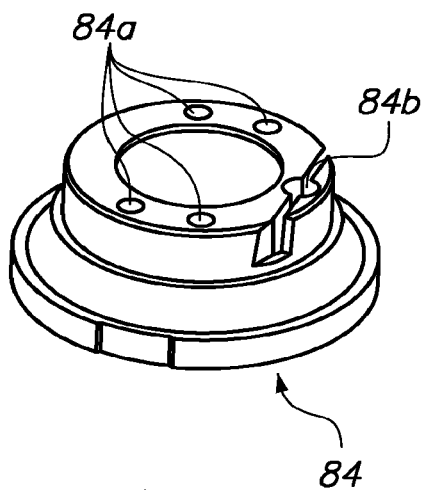
FIG. 7D illustrates the bottom portion of the pulley assembly shown in FIG. 7A.
Figure 7E:
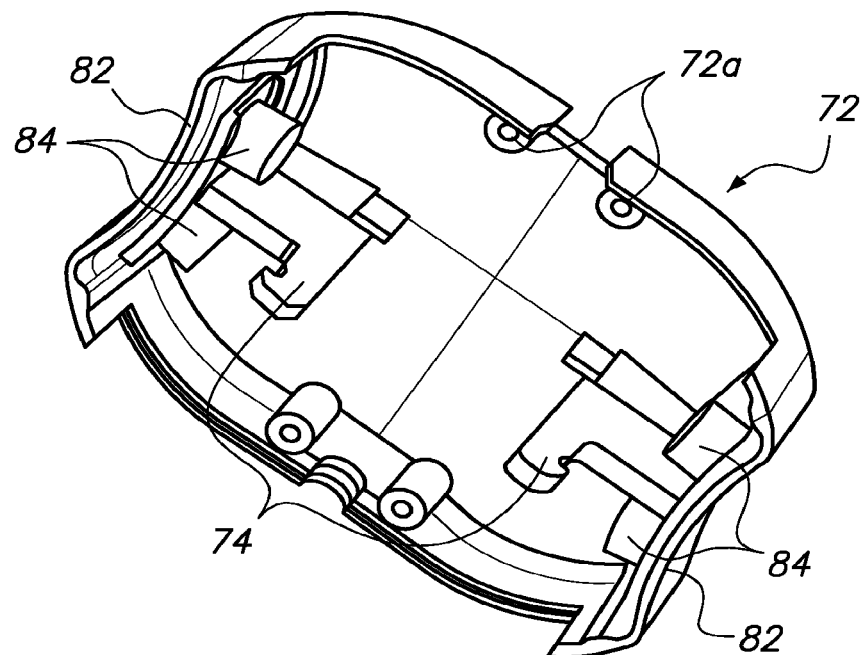
FIG. 7E illustrates a bottom perspective view of a cover of the splayer shown in FIG. 7.
Figure 7F:
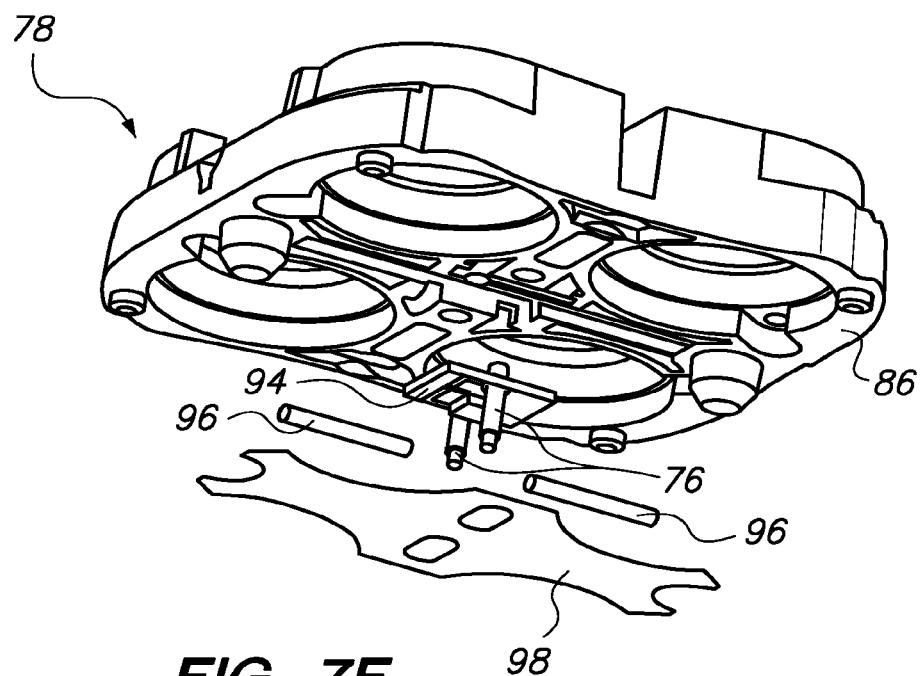
FIG. 7F illustrates an exploded view of a splayer base assembly of the splayer shown in FIG. 7.

Examples of how sheath and guide splayers 62, 61 may be structured are shown in FIGS. 7-7F. FIG. 7 illustrates the sheath splayer 62 of one embodiment illustrated without a purge tube 32. As shown in FIG. 6A, the sheath and guide splayers 62, 61, appear similar physically in construction with the exception that the guide splayer 62 includes the purge tube 32. It should be noted that the purge tube 32 may or may not be included for either the guide or sheath splayer. The sheath splayer 62 will be described herein. However it should be understood that the guide splayer 61 is of similar construction, and components of the sheath splayer 62 can be repeated for the guide splayer 61.

As illustrated in FIG. 7, the splayer 62 includes a splayer cover 72 fixably coupled to a splayer base assembly 78 using four screws 79. The splayer base 78 having four cavities to receive and house pulley assemblies 80 is used for both the guide splayer 61 and sheath splayer 62. For this embodiment of a sheath splayer 62, two cavities of the splayer base 78 are populated with pulley assemblies 80 and the remaining cavities are left open. The guide splayer 61 may have all its cavities populated with four pulley assemblies 80, as can be seen in FIG. 6B. The splayer base 78 of this implementation can be constructed from injection molded polycarbonate.

One implementation uses substantially identical pulley assemblies 80 in both the guide and sheath splayers 61,62 which are illustrated in FIGS. 7A-D. FIG. 7A illustrates the full pulley assembly 80. FIG. 7B illustrates an exploded view of the pulley assembly 80. Each pulley assembly 80 includes a top portion 82 and a bottom portion 84 held together with four screws 86 and four washers 88. Note that in FIG. 7B, only two screws 86 and two washers 88 are shown for clarity. Referring to FIG. 7C, the top portion 82 of the pulley assembly 80 includes a stainless steel insert mold or drive shaft 90 with a drive pin 90b. The drive shaft 90 includes a flat portion 90a allowing it to form a D-shaped cross section. The bottom portion 84 includes four tapped holes 84a to receive the ends of the four screws 86 and also a wire securing slot 84b. As a pulley assembly 80 is put together and mated with a catheter pull wire or control element (not shown), the pull wire can be secured to the pulley assembly 80 by inserting the pull wire into the wire securing slot 84b. The pull wire (not shown) runs down the length of a catheter from distal to proximal end then is wound about the pulley. By rotating the pulley, the pull wire bends the distal tip of the catheter controlling its bend. The kinematics of robotically controlled catheters with pull wires will be described in further detail below.

FIG. 7E illustrates the splayer cover 72 of one embodiment. The splayer cover 72 in this example includes a pair of latches 74 located on its inner surface. These latches are designed to engage with corresponding notches 38b located on the mounting plates 38 illustrated in FIG. 6B. The splayer cover 72 also includes four holes 72a to receive the mounting screws 79 used to couple the splayer cover 72 to the splayer base assembly 78. The splayer cover 72 and the latches 74 of this embodiment can be ABS molded. A pair of urethane based compliant members 82 located on the sides of the splayer cover 72 is over molded with the splayer cover 72 such that the splayer cover 72 is results as a single piece. Along opposing sides on the inside of the splayer cover 72 in this embodiment are two pairs of foam pads 84. Each pair of foam pads 84 are located adjacent to the latch 74 and serve to provide its latch 74 some spring tension wherein better engagement between the splayer cover 72 and the mounting plate 38 can be achieved. In one implementation, a user can remove a splayer 62 mounted to an RCM by squeezing at the compliant member 82, which in turn depress and disengage the latches 74 from the notches 38b of the RCM mounting plate 38.

FIG. 7F illustrates an exploded view of the splayer base assembly 78 of one embodiment which includes the splayer base 78, a printed circuit assembly 94, a set of magnets 96, and a back panel 98. During assembly of a splayer in accordance with some embodiments, the control cables of the catheter instrument are pre-tensioned by hand when the pulleys 80 are installed. Data related to individual catheter and splayer characteristics, including, but not limited to, full range of motion and critical parameters captured during the characterization process, are stored into a memory for later retrieval in the printed circuit assembly or PCA 94 which can act as a catheter identification (ID) programmable read-only memory (PROM). In alternative embodiments, other types non-volatile of memories such as flash memory or electrically programmable read-only memory (EPROM) can be used to store data. The PCA of this embodiment includes a pair of pogo pins 76 to detect contact with an RCM interface plate. The pogo pins 76 are positioned to make contact with the PCA 94 upon which the PROM is mounted as the splayer is placed onto the RCM mounting plate 38. Also located on the underside of this splayer base assembly 78 are a pair of magnets 96. In one embodiment, the magnets 96 are made of a neodymium material. As will be later described, the magnets are configured to be detected by read switches on the RCM interface to indicate splayer presence when a splayer is mounted on the RCM. The back panel 98 covers portions of the splayer base assembly 78, which is also shown in FIG. 7F. This back panel 98 includes openings for the pogo pins 76 to pass through.

Referring back to FIGS. 6A-6B, when a catheter is prepared for use with an instrument, its splayer is mounted onto its appropriate interface plate. In this case, the sheath splayer 62 is placed onto the sheath interface plate 38 and the guide splayer 61 is place onto the guide interface plate 37. In the illustrated example, each mounting plates 37, 38 has four openings 37a, 38a that are designed to receive the corresponding drive shafts 90 attached to and extending from the pulley assemblies 80 of the splayers 61, 62. In the example illustrated in FIG. 6B, two shafts 90 of the pulley assembly 80 are insertable within the right apertures or two openings 38a of the sheath interface plate 38 as the splayer 62 is mounted onto the RCM. Similarly, four shafts 90 of the guide splayer pulley assembly 80 are insertable within the four apertures or openings 37a of the guide interface plate 37.

The RCM mounting plate in accordance with some embodiments includes a flex circuit with contacts and four read switches (not shown) for detecting the presence of a splayer and to indicate that a splayer has been mounted onto the interface plate. In some embodiments, the switches are also used to read the data from the memory. In alternative embodiments, various types of contacts and switches can be implemented to detect presence and/or access the PCA 94. For this implementation, the switches are triggered by the magnets 96 of the splayer.

A user sets up the catheter by fastened it to the RCM initially. When the bottom surface of the splayer is within 180 thousandths of an inch from the interface plate, a magnetic field engages with the contact switches. The splayer 62/61 is mounted to an RCM, and the latches 73,74 are inserted through openings 38b,37b on the mounting plate to latch onto the interface plate 38,37, thus securely coupling the splayer 62/61 to the RCM. Once the splayer is engaged with the RCM, characterization parameters can be read from the PCA 94 by the RCM, allowing the RCM to set the splayer in its nominal position. In one embodiment, the data read from the PCA may include catheter length information, relative length information for zeroing up a sheath catheter and a guide catheter, and roll correction information. For example, the computer system may use the length information to initialize or configure the catheters for use by adjusting the guide catheter with respect to the guide catheter to ensure the catheters are zeroed up or that the guide catheter is located in a predefined position relative to the sheath catheter on the RCM. Similarly, the computer system may take the roll correction information, and roll off the catheter if any of the control wires are a bit offset or skewed, so that the catheter is oriented in the proper predefined direction (i.e., the 'up' direction on the catheter is really up).

The data of one embodiment is gathered through bench testing during the manufacturing process and programmed into the PROM. In alternative embodiments, the data may have originated from a different part of the process. In one implementation, the PROM may also include a unique identifier or a code to prevent the catheter from being reused. The system of one embodiment is designed to recognize whether a catheter is brand new or whether it has already been used, and is capable of rejecting a previously used catheter. For this embodiment, the catheter is pre-tensioned through load sensing so that slack is removed from the control wires. The catheters are then prepared to be driven.

The sheath interface mounting plate 38 as illustrated in FIGS. 6A and 6B is similar to the guide interface mounting plate 37, and thus, similar details are not repeated. One difference between the plates 37, 38 may be the shape of the plates. For example, the guide interface plate 37 includes a narrow, elongated segment, which may be used with, for example, a dither mechanism. Both plates 37, 38 include a plurality of openings 37*a*, 38*a* to receive drive shafts 90 and latches 73,74 from splayers 61, 62, respectively.

Figure 8A:
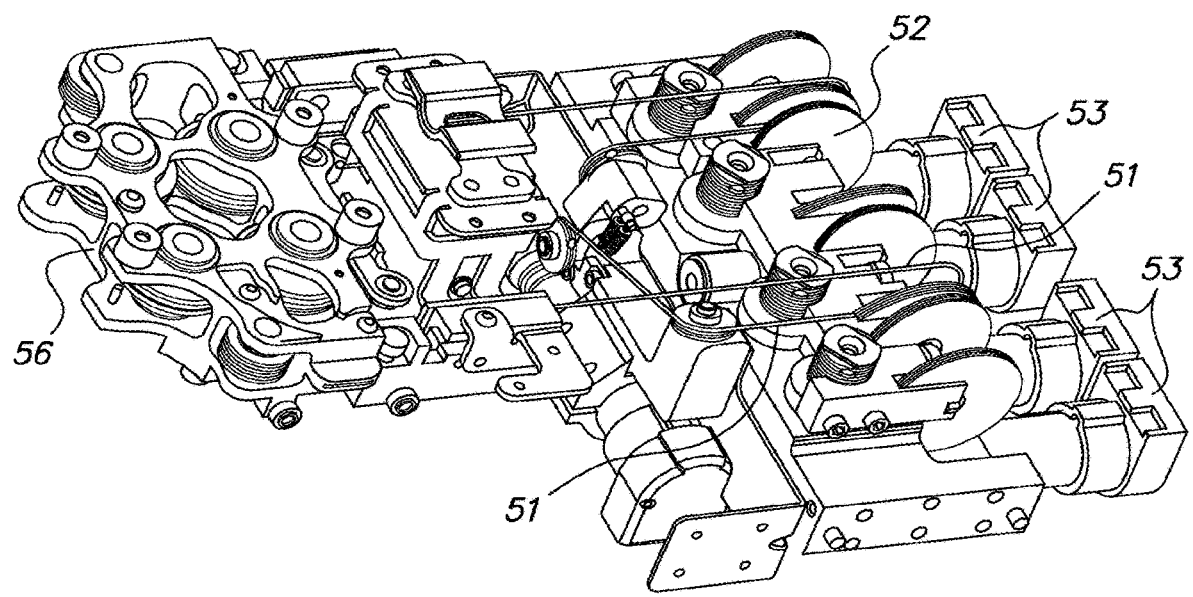
FIG. 8A illustrates a guide carriage of the instrument driver shown in FIG. 5C coupled to cabling and guide motors.
Figure 8B:
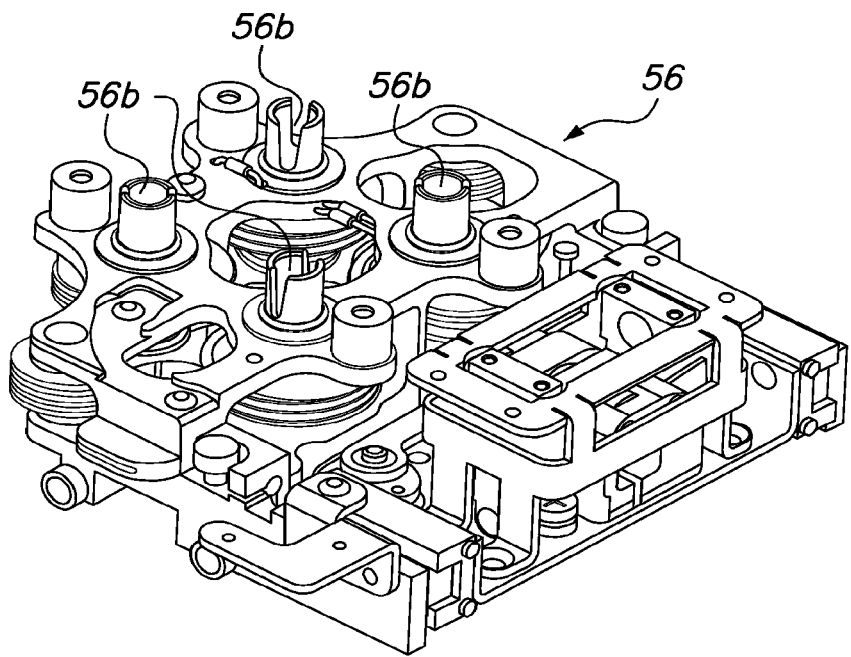
FIG. 8B is a perspective view of a slidable carriage or funicular assembly of an instrument driver and receiver slots configured to receive and engage with splayer shafts.
Figure 9A:
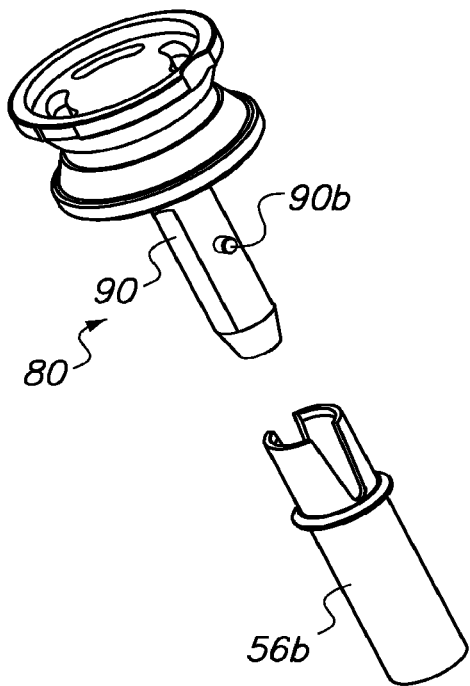
FIG. 9A is a perspective view of a drive shaft positioned for insertion into a sleeve receptacle located on an instrument driver.
Figure 9B:
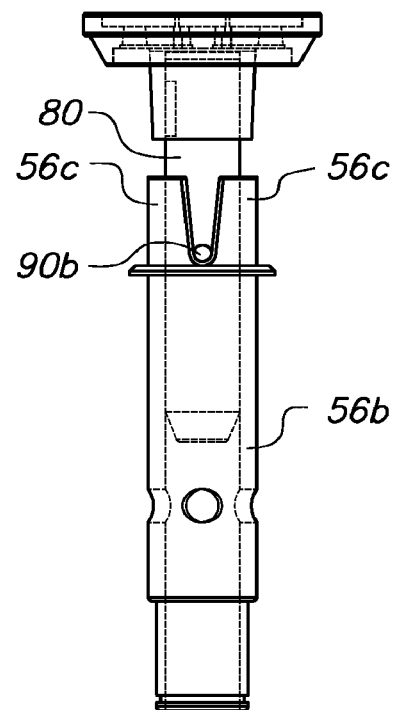
FIG. 9B of a drive shaft that is inserted into a sleeve receptacle.

Referring back to FIG. 5C the instrument driver 16 is illustrated with mounting plates 37,38 fixably coupled to a guide carriage 50, and a sheath drive block 40, respectively. FIG. 8A illustrates the guide carriage 50 removed from the instrument driver 16 coupled to cabling 51 and associated guide motors 53. The guide carriage 50 includes a funicular assembly 56 which is illustrated in FIG. 8B. The funicular assembly 56 includes four sleeve receptacles 56*b*. As previously described, the drive shafts 90 of the splayer 61 (such as that shown in FIG. 5B) first insert through the openings 37*a* in the mounting plate 37. They then engage with the sleeve receptacles 56*b*. FIGS. 9A-9B illustrate the shafts 90 of the splayer pulley assembly 61 engaging with the sleeve receptacles (56*b*) in further detail. Referring back to FIG. 7C, the drive shaft 90 has a flat edge 90*a* on one side of its cylindrical surface such that when the drive shaft 90 is viewed along its longitudinal axis, the shaft has the shape of a letter "D". It should be understood that the drive shaft 90 may include other cross-sectional shapes. The shaft 90 has an opening through which a cross pin 90*b* may be located. The drive shaft 90 may be keyed such that the shaft is designed to fit or be received within the receiving sleeve 56*b* having a certain shape. The sleeve 56*b* in the illustrated example includes a pair of V-shaped or wing shaped notches 56*c* to receive and hold the pin 90*b* of a shaft 90 as the shaft 90 is inserted into the sleeve 56*b*. In the illustrated example, the sleeve 56*b* does not employ capture pins, although such pins may be utilized.

Referring back to FIG. 8A, a set of cables 51 wound around a set of pulleys 52, are coupled on one end to a set of guide motors 53 and the other end to the sleeve receptacles 56*b*. The drive motors 53 are actuated to rotationally drive the sleeves 56*b*. A catheter assembly 30 with its splayer 61 mounted onto the instrument drive 16 would have its pulley assemblies 80 positioned inside a plurality of corresponding sleeves 56*b*. As the sleeves 56*b* are rotated, the pins 90*b* of the shafts 90 are seated in the V-shaped notches 56*c* and are engaged by the rotating sleeves 56*b*, thus causing the shafts 90 and associated pulley assemblies 80 to also rotate. The pulley assemblies 80 in turn cause the control elements (e.g., wires) coupled thereto to manipulate the distal tip of the catheter instrument 30 member in response thereto. To remove a splayer from the instrument driver in this implementation, less force is needed as the V-shaped notches 56*c* allow for quick and easy disengagement of the shafts 90 from the sleeves 56*b*.

FIGS. 10A and 10B illustrate perspective views of the sheath block 40 and motor driven interfaces 42 which are coupled to sheath articulation motors 43. The sheath articulation motors 43 are coupled the motor driven interfaces 42 which includes a set of belts, shafts, and gears which drive receptacle sleeves 56*b* (which are similar in construction and functionality to the receptacle sleeves previously described for the guide funicular assembly). When the sheath splayer drive shafts 90 are coupled to the receptacle sleeves 56*b*, the sheath articulation motors 43 drive the receptacle sleeves 56*b* causing the sheath instrument 30 to bend.

During use, the catheter instrument 18 is inserted within a central lumen of the sheath instrument 30 such that the instruments 18, 30 are arranged in a coaxial manner as previously described. Although the instruments 18, 30 are arranged coaxially, movement of each instrument 18, 30 can be controlled and manipulated independently. For this purpose, motors within the instrument driver 16 are controlled such that the drive and sheath carriages coupled to the mounting plates 37, 38 are driven forwards and backwards independently on linear bearings each with leadscrew actuation. FIG. 10 illustrates the sheath drive block 40 removed from the instrument driver coupled to two independently-actuated lead screw 45, 46 mechanisms driven by insert motors 47. Note only the guide insert motor 47 is shown. The sheath insert motor is not shown in FIG. 10. In the illustrated embodiment, the sheath insertion motor is coupled to a drive or output shaft (not shown) that is designed to move the sheath articulation assembly forwards and backwards, thus sliding a mounted sheath catheter instrument 18 forwards and backwards. The insert motion of the guide carriage can be actuated with a similar motorized leadscrew configuration.

Referring back to FIGS. 1, 2 and 6A, in order to accurately steer a robotic sheath 62*a* or guide catheter 61*a* from an operator work station 2, a control structure should be implemented which allows a user to send commands through input devices such as the pendant 8 or MID 12 that will result in desired motion of the sheath 62*a* and guide 61*a*. FIGS. 11A-11H and 12-16 illustrate examples of a control structure, which are described in further detail in the applications previously incorporated by reference.

The kinematic relationships for many catheter instrument embodiments may be modeled by applying conventional mechanics relationships. In summary, a control-element-steered catheter instrument is controlled through a set of actuated inputs. In a four-control-element catheter instrument, for example, there are two degrees of motion actuation, pitch and yaw, which both have + and −directions. Other motorized tension relationships may drive other instruments, active tensioning, or insertion or roll of the catheter instrument. The relationship between actuated inputs and the catheter's end point position as a function of the actuated inputs is referred to as the "kinematics" of the catheter.

Figures 11E, 11F:
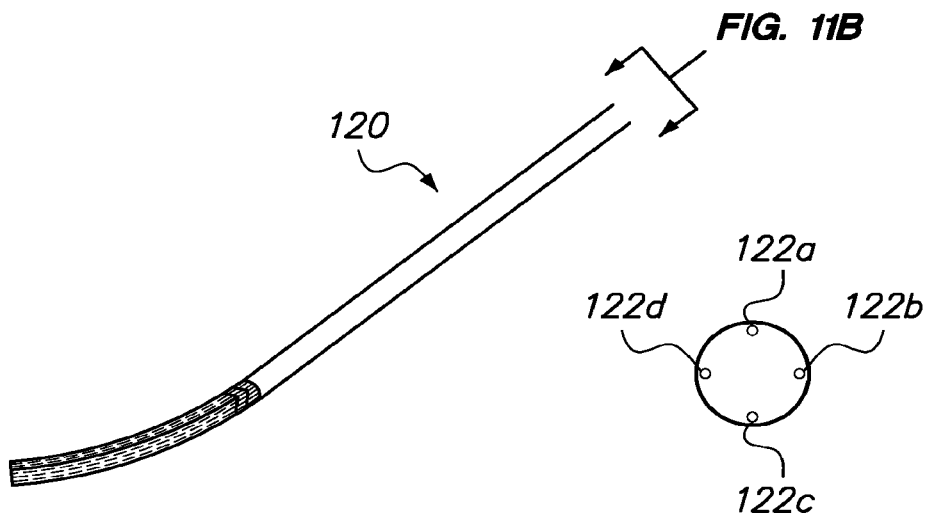
Figures 11G, 11H:
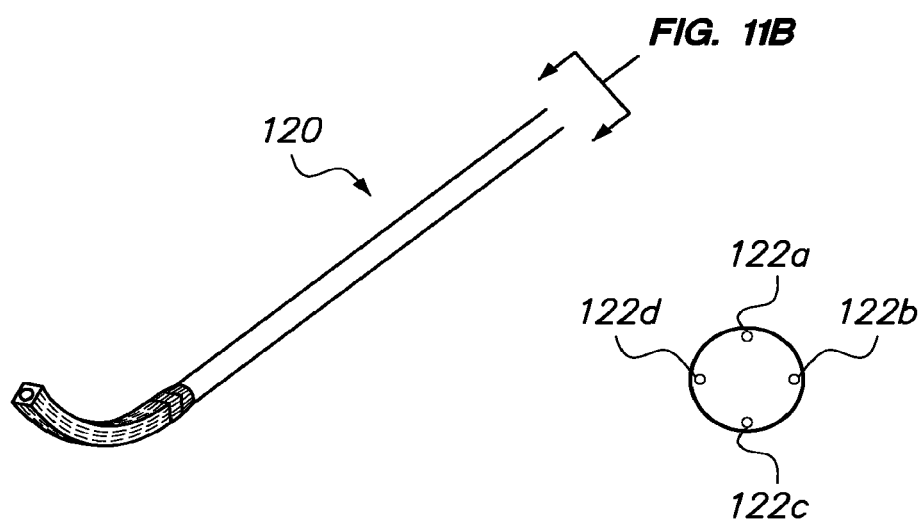

Referring to FIGS. 11A-H, the basic kinematics of a catheter 120 with four control elements 122*a*, 122*b*, 122*c*, 122*d* is reviewed. The catheter 120 may be component 61*a* or component 62*a* in some embodiments. Referring to FIGS. 11A-B, as tension is placed only upon the bottom control element 122*c*, the catheter bends downward, as shown in FIG. 11A. Similarly, pulling the left control element 122*d* in FIGS. 11C-D bends the catheter left, pulling the right control element 122*b* in FIGS. 11E-F bends the catheter right, and pulling the top control element 122*a* in FIGS. 11G-H bends the catheter up. As will be apparent to those skilled in the art, well-known combinations of applied tension about the various control elements results in a variety of bending configurations at the tip of the catheter member 120. One of the challenges in accurately controlling a catheter or similar elongate member with tension control elements is the retention of tension in control elements, which may not be the subject of the majority of the tension loading applied in a particular desired bending configuration. If a system or instrument is controlled with various levels of tension, then losing tension, or having a control element in a slack configuration, can result in an unfavorable control scenario. As previously described, each of these control elements or pull wires can be wound around a pulley which is motor actuated within the instrument driver. Maintaining adequate tension with these pulleys can be important for accurate catheter control.

FIG. 12 illustrates one example of a control flow for basic catheter control. The operator enters a command to designate a desired tip position for the device via some input mechanism (a master input device, computer software, or other user interface, etc.). Next, one or more inverse kinematic algorithms compute a desired catheter configuration in order to achieve the commanded tip position. The inverse kinematic algorithm can be varied depending on the construction of the shapeable device. The desired catheter configuration is then fed to one or more catheter mechanics algorithm to compute the positioning element displacements necessary to achieve the desired catheter configuration. These positioning element commands are then provided to the robots control algorithms (or in some cases actuators in the robot that interface with positioning elements in the shapeable element).

Based upon the applied positioning element displacements, the actual (physical) catheter mechanics including any constraints and obstructions acting on the catheter determine the real configuration or shape that the shapeable device achieves. This is illustrated on the right (slave/actual) side of FIG. 12. This real catheter configuration/shape determines the real catheter tip position. These kinematic relationships of the physical device are represented in the figure with a forward kinematics block 124. Assuming that the operator is observing the catheter tip through some sort of visualization (fluoro, endoscopy, etc), the operator can then use this visual feedback to make corrections to the commanded tip position.

Figure 14:
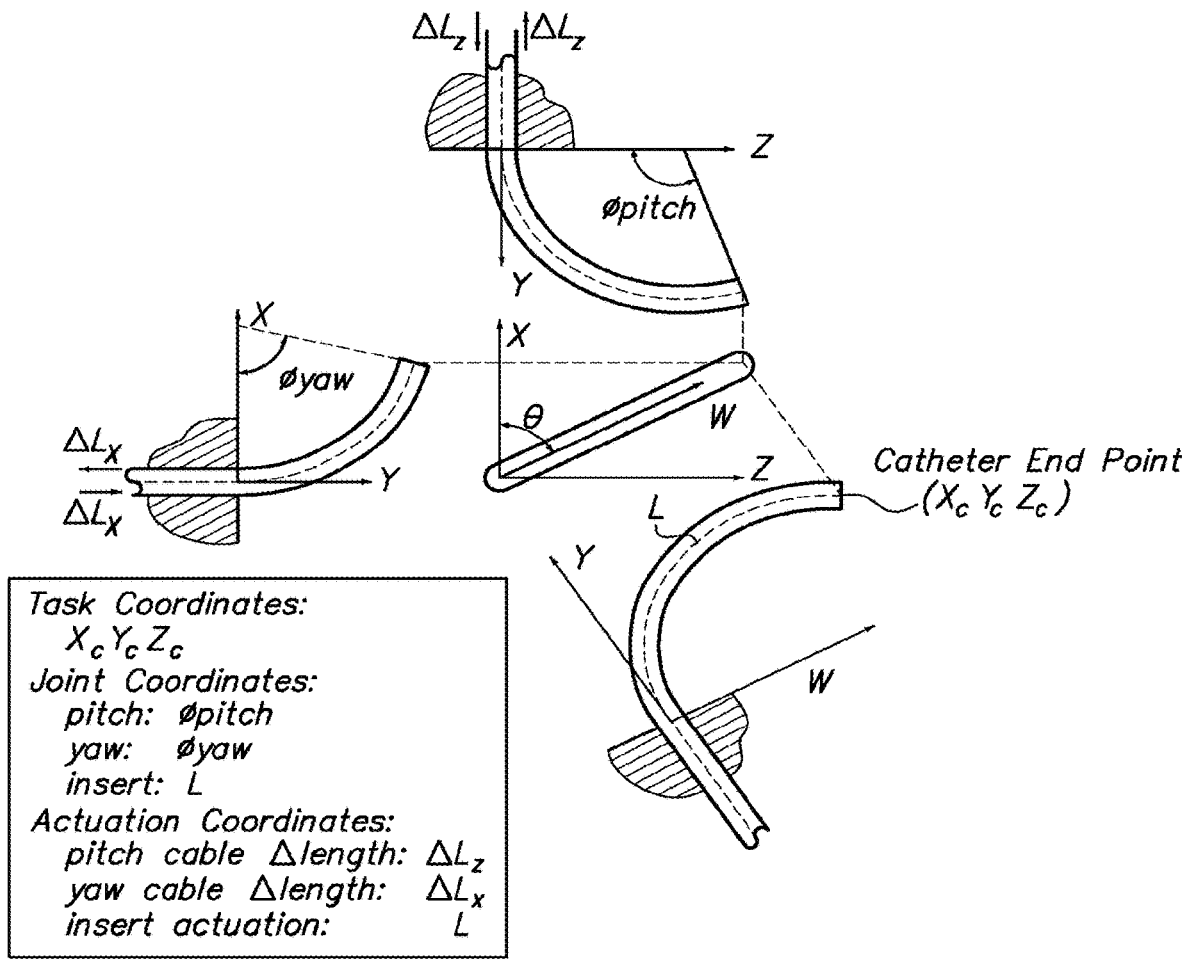
FIG. 14 illustrates task coordinates, joint coordinates, and actuation coordinates in accordance with some embodiments.

Referring to FIG. 13, the "forward kinematics" expresses the catheter's end-point position as a function of the actuated inputs while the "inverse kinematics" expresses the actuated inputs as a function of the desired end-point position. In certain embodiments, accurate mathematical models of the forward and inverse kinematics are useful for the control of a robotically controlled catheter system. For clarity, the kinematics equations are further refined to separate out common elements, as shown in FIG. 13. The basic kinematics describes the relationship between the task coordinates and the joint coordinates. In such case, the task coordinates refer to the position of the catheter end-point while the joint coordinates refer to the bending (pitch and yaw, for example) and length of the active catheter. The actuator kinematics describes the relationship between the actuation coordinates and the joint coordinates. The task, joint, and bending actuation coordinates for the robotic catheter are illustrated in FIG. 14. By describing the kinematics in this way we can separate out the kinematics associated with the catheter structure, namely the basic kinematics, from those associated with the actuation methodology.

An inverse kinematic model translates intended device motion into the commands that will adjust the actuator and/or control element to position the shapeable instrument as desired. Referring back to FIG. 12, the shapeable instrument kinematics are the mathematical relationships between the task space description of the instrument (e.g., tip position) and the configuration space description of the instrument (e.g., shape). Specifically, the inverse kinematics (task to configuration space) are used as part of the chain that translates desired tip positions into actuator commands (leading to displacements of the control elements) that move tip position of the actual device for reaching a desired tip position.

These inverse kinematic algorithms are derived based upon certain assumptions about how the shapeable instrument moves. Examples of these assumptions may include, but are not limited to: 1) Each catheter segment bends in a constant curvature arc; 2) Each catheter segment bends within a single plane; 3) Some catheter segments have fixed (constant) lengths; 4) Some catheter segments have variable (controllable) lengths.

In one variation, the development of the catheter's kinematics model is derived using a few assumptions. In one example, the included are assumptions that the catheter structure is approximated as a simple beam in bending from a mechanics perspective, and that control elements, such as thin tension wires, remain at a fixed distance from the neutral axis and thus impart a uniform moment along the length of the catheter.

Figure 15:
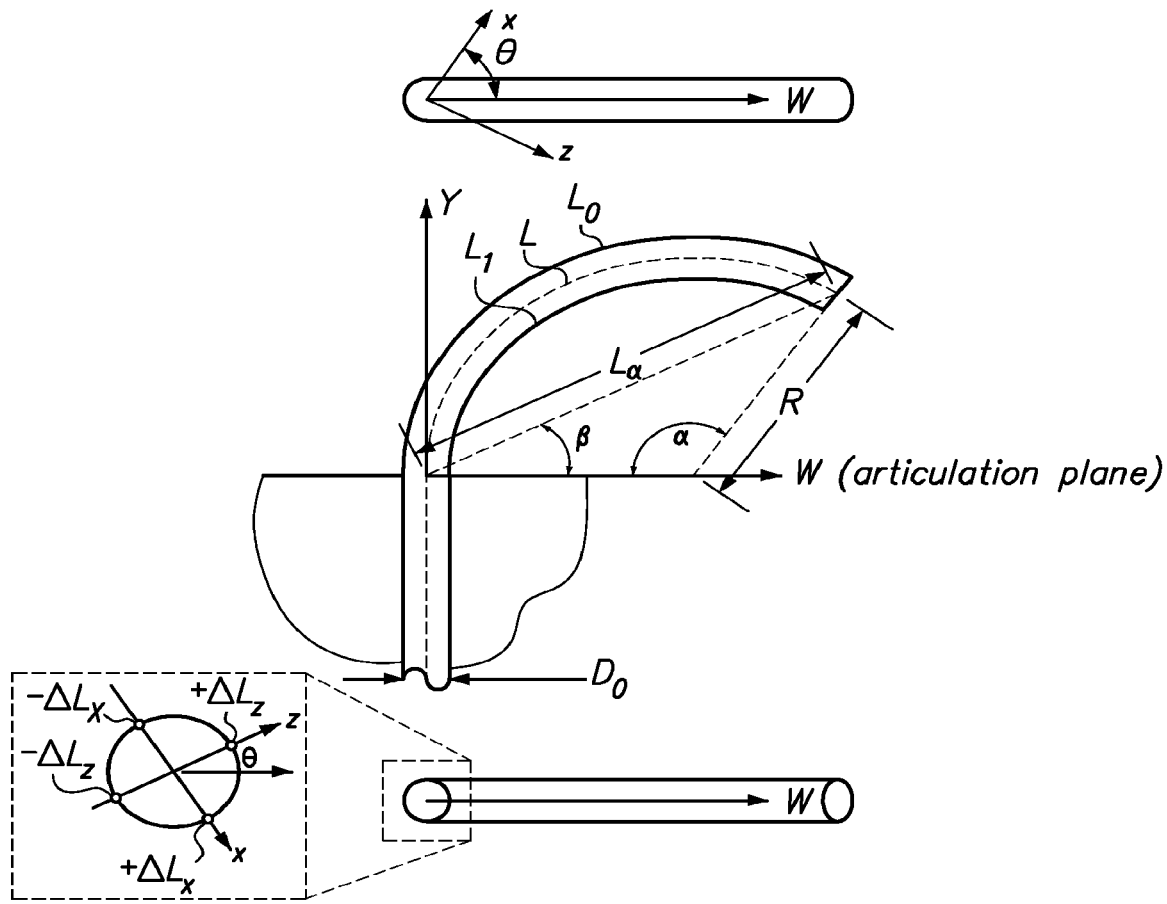
FIG. 15 illustrates variables associated with a geometry of a catheter in accordance with some embodiments.

In addition to the above assumptions, the geometry and variables shown in FIGS. 14 and 15 are used in the derivation of the forward and inverse kinematics. The basic forward kinematics, relating the catheter task coordinates ($X_c$, $Y_c$, $Z_c$) to the joint coordinates ($\Phi_{yaw}$, $\Phi_{pitch}$, L), is given as follows:

$X_c = \omega \cos(\theta)$
$Y_c = R \sin(\alpha)$
$Z_c = \omega \sin(\theta)$

Where $$w = R(1 - \cos(\alpha))$$

$$\alpha = [(\phi_{pitch})^2 + (\phi_{yaw})^2]^{1/2} \text{ (total bending)}$$

$$R = \frac{L}{\alpha} \text{ (bend radius)}$$

$$\theta = \operatorname{atan2}(\phi_{pitch}, \phi_{yaw}) \text{ (roll angle)}$$

The actuator forward kinematics, relating the joint coordinates ($\Phi_{yaw}$, $\Phi_{pitch}$, L) to the actuator coordinates ($\Delta L_x$, $\Delta L_z$, L) is given as follows:

$$\Phi_{pitch} = (2\Delta L_2)/D_c$$

$$\phi_{yaw} = \frac{2\Delta L_x}{D_c}$$

As illustrated in FIG. 13, the catheter's end-point position can be predicted given the joint or actuation coordinates by using the forward kinematics equations described above.

Calculation of the catheter's actuated inputs as a function of end-point position, referred to as the inverse kinematics, can be performed numerically, using a nonlinear equation solver such as Newton-Raphson. In another approach, shown in the illustrative embodiment, is to develop a closed-form solution which can be used to calculate the required actuated inputs directly from the desired end-point positions.

As with the forward kinematics, we separate the inverse kinematics into the basic inverse kinematics, which relates joint coordinates to the task coordinates, and the actuation inverse kinematics, which relates the actuation coordinates to the joint coordinates. The basic inverse kinematics, relating the joint coordinates ($\Phi_{yaw}$, $\Phi_{pitch}$, L), to the catheter task coordinates (Xc, Yc, Zc) is given as follows:

$$\phi_{pitch} = \alpha \sin(\theta)$$
$$\phi_{yaw} = \alpha \cos(\theta)$$

$$L = R\alpha \rightarrow \text{where} \rightarrow \rightarrow \begin{array}{ll} \overline{\theta = \text{atan2}(Z_c, X_c)} & \overline{\beta = \text{atan2}(Y_c, W_c)} \\ R = \dfrac{l \sin\beta}{\sin 2\beta} & \rightarrow W_c = (X_c^2 + Z_c^2)^{1/2} \\ \alpha = \pi - 2\beta & \overline{l = (W_c^2 + Y_c^2)^{1/2}} \end{array}$$

The actuator inverse kinematics, relating the actuator coordinates ($\Delta L_x, \Delta L_z, L$) to the joint coordinates ($\Phi_{yaw}$, $\Phi_{pitch}$, L) is given as follows:

$$\Delta L_x = \frac{D_c \phi_{yaw}}{2}$$
$$\Delta L_z = \frac{D_c \phi_{pitch}}{2}$$

Figure 16:
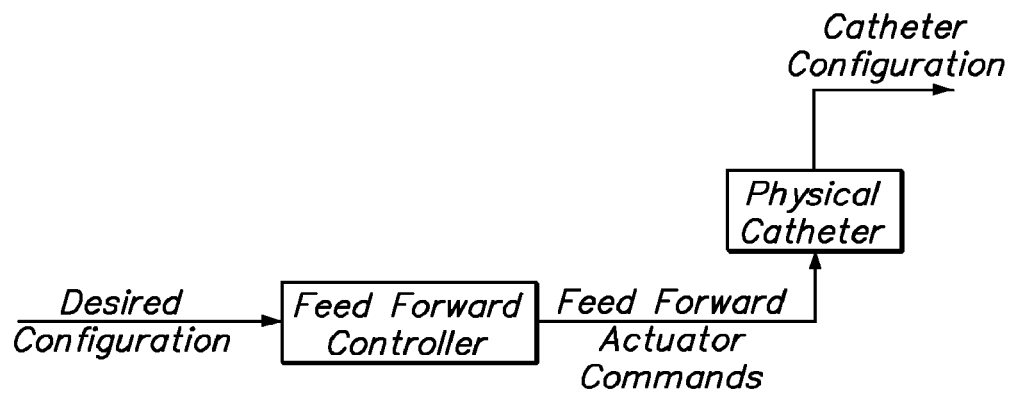
FIG. 16 illustrates a conventional open loop control model.

In one embodiment, the catheter (or other shapeable instrument) is controlled in an open-loop manner as shown in FIG. 16. In this type of open loop control model, the shape configuration command comes in to the beam mechanics, is translated to beam moments and forces, then is translated to tendon tensions given the actuator geometry, and finally into tendon displacement given the entire deformed geometry. However, there are numerous reasons why the assumed motion of the catheter may not match the actual motion of the catheter. One important factor is the presence of unanticipated or unmodeled constraints imposed by the patient's anatomy.

Accordingly, a control system that directs catheters or shapeable instruments can command joint configurations that can achieve a desired tip position. However, the presence of modeling inaccuracies and environment interaction causes a differential between the actual position from that intended. A simple tip position can quantify this error, but addressing the source of the error requires the additional information regarding the shapeable instrument. Data defining the actual or real shape of the instrument can provide much of this information.

The term "localization" is used in the art in reference to systems for determining and/or monitoring the position of objects, such as medical instruments, in a reference coordinate system. In one embodiment, the instrument localization software is a proprietary module packaged with an off-the-shelf or custom instrument position tracking system, which may be capable of providing not only real-time or near real-time positional information, such as X-Y-Z coordinates in a Cartesian coordinate system, but also orientation information relative to a given coordinate axis or system. For example, such systems can employ an electromagnetic based system (e.g., using electromagnetic coils inside a device or catheter body). Other systems utilize potential difference or voltage, as measured between a conductive sensor located on the pertinent instrument and conductive portions of sets of patches placed against the skin, to determine position and/or orientation. In another similar embodiment, one or more conductive rings may be electronically connected to a potential-difference-based localization/orientation system, along with multiple sets, preferably three sets, of conductive skin patches, to provide localization and/or orientation data. Additionally, "Fiberoptic Bragg grating" ("FBG") sensors may be used to not only determine position and orientation data but also shape data along the entire length of a catheter or shapeable instrument.

In other embodiments not comprising a localization system to determine the position of various components, kinematic and/or geometric relationships between various components of the system may be utilized to predict the position of one component relative to the position of another. Some embodiments may utilize both localization data and kinematic and/or geometric relationships to determine the positions of various components. The use of localization and shape technology is disclosed in detail in U.S. patent application Ser. No. 11/690,116, now abandoned, Ser. No. 11/176,598, now abandoned, Ser. No. 12/012,795, now abandoned, Ser. No. 12/106,254, issued as U.S. Pat. No. 8,050,523 on Nov. 1, 2011, Ser. No. 12/507,727, now abandoned, Ser. No. 12/822,876, issued as U.S. Pat. No. 8,460,236 on Jun. 11, 2013, Ser. No. 12/823,012, now abandoned, and Ser. No. 12/823,032, issued as U.S. Pat. No. 8,672,837 on Mar. 18, 2014, the entirety of all of which is incorporated by reference herein for all purposes.

To accurately coordinate and control actuations of various motors within an instrument driver from a remote operator control station such as that depicted in FIG. 1, an advanced computerized control and visualization system is preferred. The control system embodiments that follow are described in reference to a particular control systems interface, namely the SimuLink™ and XPC™ control interfaces available from The Mathworks Inc., and PC-based computerized hardware configurations. However, one of ordinary skilled in the art having the benefit of this disclosure would appreciate that many other control system configurations may be utilized, which may include various pieces of specialized hardware, in place of more flexible software controls running on one or more computer systems.

Figure 17:
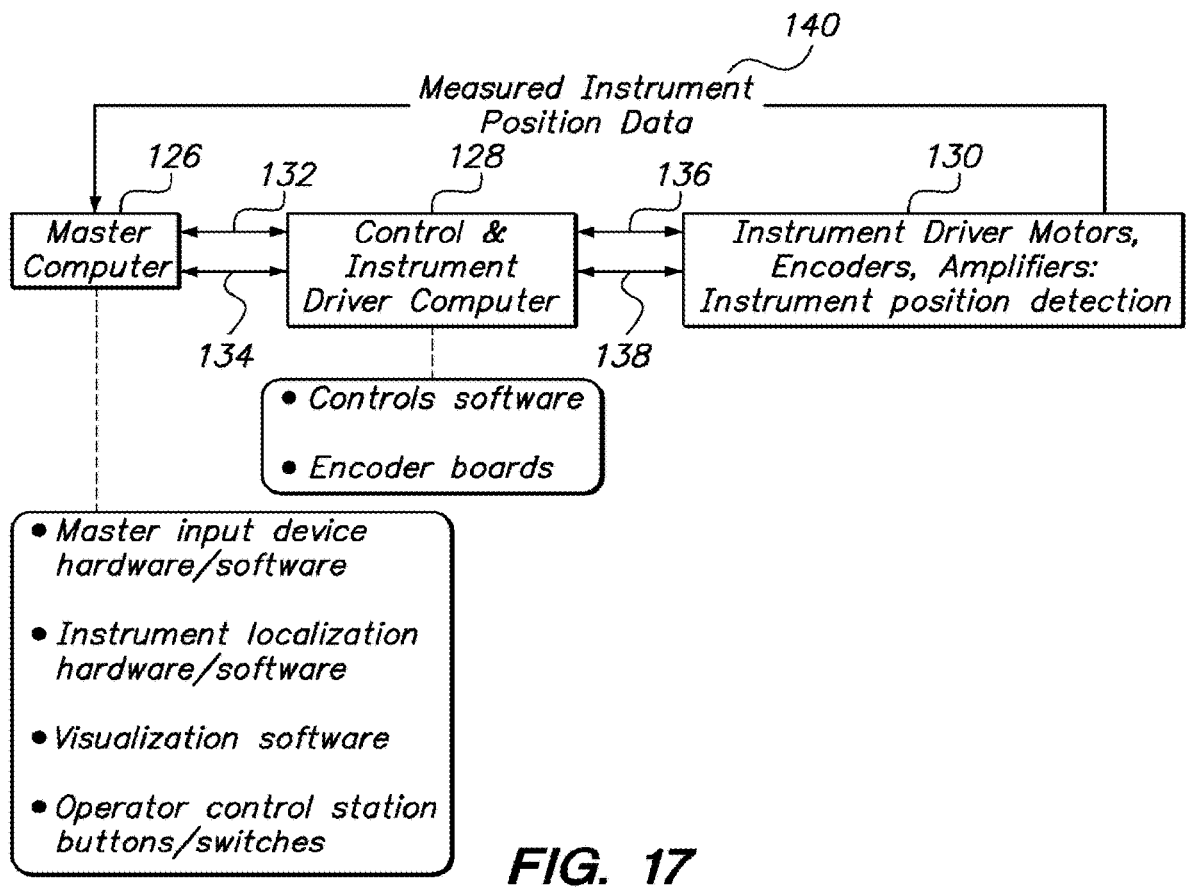
FIG. 17 illustrates a control system in accordance with some embodiments.

Referring to FIG. 17, an overview of an embodiment of a controls system flow is depicted. A master computer 400 running master input device software, visualization software, instrument localization software, and software to interface with operator control station buttons and/or switches is depicted. In one embodiment, the master input device software is a proprietary module packaged with an off-the-shelf master input device system, such as the Phantom™ from Sensible Devices Corporation, which is configured to communicate with the Phantom™ hardware at a relatively high frequency as prescribed by the manufacturer. Other suitable master input devices, such as the master input device 12 depicted in FIG. 2 are available from suppliers such as Force Dimension of Lausanne, Switzerland. The master input device 12 may also have haptics capability to facilitate feedback to the operator, and the software modules pertinent to such functionality may also be operated on the master computer 126.

Figure 18:
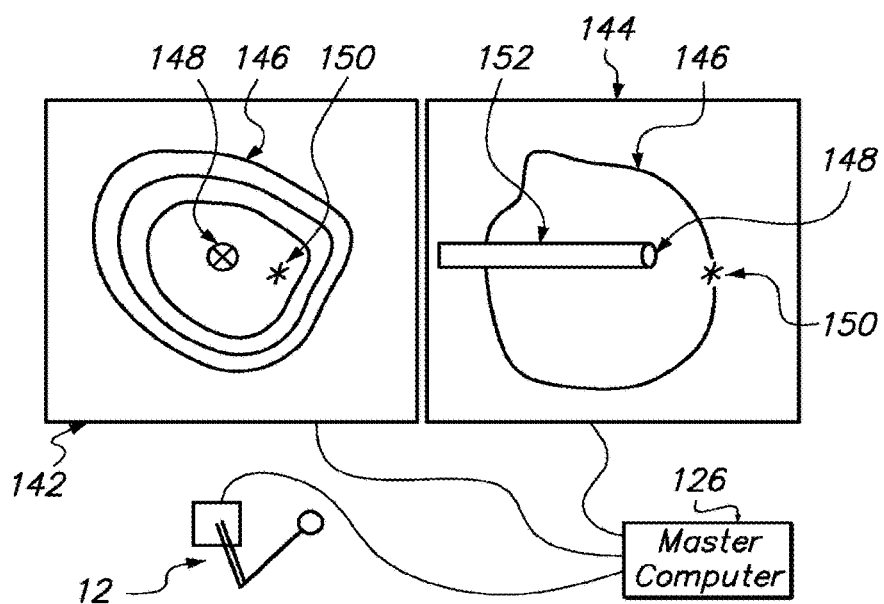
FIG. 18 illustrates a user interface for a master input device.

Referring to FIG. 17, in one embodiment, visualization software runs on the master computer 126 to facilitate real-time driving and navigation of one or more steerable instruments. In one embodiment, visualization software provides an operator at an operator control station, such as that depicted in FIG. 2, with a digitized "dashboard" or "windshield" display to enhance instinctive drivability of the pertinent instrumentation within the pertinent tissue structures. Referring to FIG. 18, a simple illustration is useful to explain one embodiment of a preferred relationship between visualization and navigation with a master input device 12. In the depicted embodiment, two display views 142, 144 are shown. One preferably represents a primary 142 navigation view, and one may represent a secondary 144 navigation view. To facilitate instinctive operation of the system, it is preferable to have the master input device coordinate system at least approximately synchronized with the coordinate system of at least one of the two views. Further, it is preferable to provide the operator with one or more secondary views which may be helpful in navigating through challenging tissue structure pathways and geometries.

Referring still to FIG. 18, if an operator is attempting to navigate a steerable catheter in order to, for example, contact a particular tissue location with the catheter's distal tip, a useful primary navigation view 142 may comprise a three dimensional digital model of the pertinent tissue structures 146 through which the operator is navigating the catheter with the master input device 12, along with a representation of the catheter distal tip location 148 as viewed along the longitudinal axis of the catheter near the distal tip. This embodiment illustrates a representation of a targeted tissue structure location 150, which may be desired in addition to the tissue digital model 146 information. A useful secondary view 144, displayed upon a different monitor, in a different window upon the same monitor, or within the same user interface window, for example, comprises an orthogonal view depicting the catheter tip representation 148, and also perhaps a catheter body representation 152, to facilitate the operator's driving of the catheter tip toward the desired targeted tissue location 150.

In one embodiment, subsequent to development and display of a digital model of pertinent tissue structures, an operator may select one primary and at least one secondary view to facilitate navigation of the instrumentation. By selecting which view is a primary view, the user can automatically toggle a master input device 12 coordinate system to synchronize with the selected primary view. In an embodiment with the leftmost depicted view 142 selected as the primary view, to navigate toward the targeted tissue site 150, the operator should manipulate the master input device 12 forward, to the right, and down. The right view will provide valued navigation information, but will not be as instinctive from a "driving" perspective.

To illustrate: if the operator wishes to insert the catheter tip toward the targeted tissue site 150 watching only the rightmost view 144 without the master input device 12 coordinate system synchronized with such view, the operator would have to remember that pushing straight ahead on the master input device will make the distal tip representation 148 move to the right on the rightmost display 144. Should the operator decide to toggle the system to use the rightmost view 144 as the primary navigation view, the coordinate system of the master input device 12 is then synchronized with that of the rightmost view 144, enabling the operator to move the catheter tip 148 closer to the desired targeted tissue location 150 by manipulating the master input device 12 down and to the right. The synchronization of coordinate systems may be conducted using fairly conventional mathematic relationships which are described in detail in the aforementioned applications incorporated by reference.

Referring back to embodiment of FIG. 17, the master computer 126 also comprises software and hardware interfaces to operator control station buttons, switches, and other input devices which may be utilized, for example, to "freeze" the system by functionally disengaging the master input device as a controls input, or provide toggling between various scaling ratios desired by the operator for manipulated inputs at the master input device 12. The master computer 126 has two separate functional connections with the control and instrument driver computer 128: one connection 132 for passing controls and visualization related commands, such as desired XYZ (in the catheter coordinate system) commands, and one connection 134 for passing safety signal commands. Similarly, the control and instrument driver computer 128 has two separate functional connections with the instrument and instrument driver hardware 130: one connection 136 for passing control and visualization related commands such as required-torque-related voltages to the amplifiers to drive the motors and encoders, and one connection 138 for passing safety signal commands.

Also shown in the signal flow overview of FIG. 17 is a pathway 140 between the physical instrument and instrument driver hardware 130 back to the master computer 126 to depict a closed loop system embodiment wherein instrument localization technology, previously described, is utilized to determine the actual position of the instrument to minimize navigation and control error, as described in further detail below.

FIGS. 19A-K depict various aspects of one embodiment of a SimuLink™ software control schema for an embodiment of the physical system, with particular attention to an embodiment of a "master following mode." In this embodiment, an instrument is driven by following instructions from a master input device, and a motor servo loop embodiment, which comprises key operational functionality for executing upon commands delivered from the master following mode to actuate the instrument.

Figure 19:
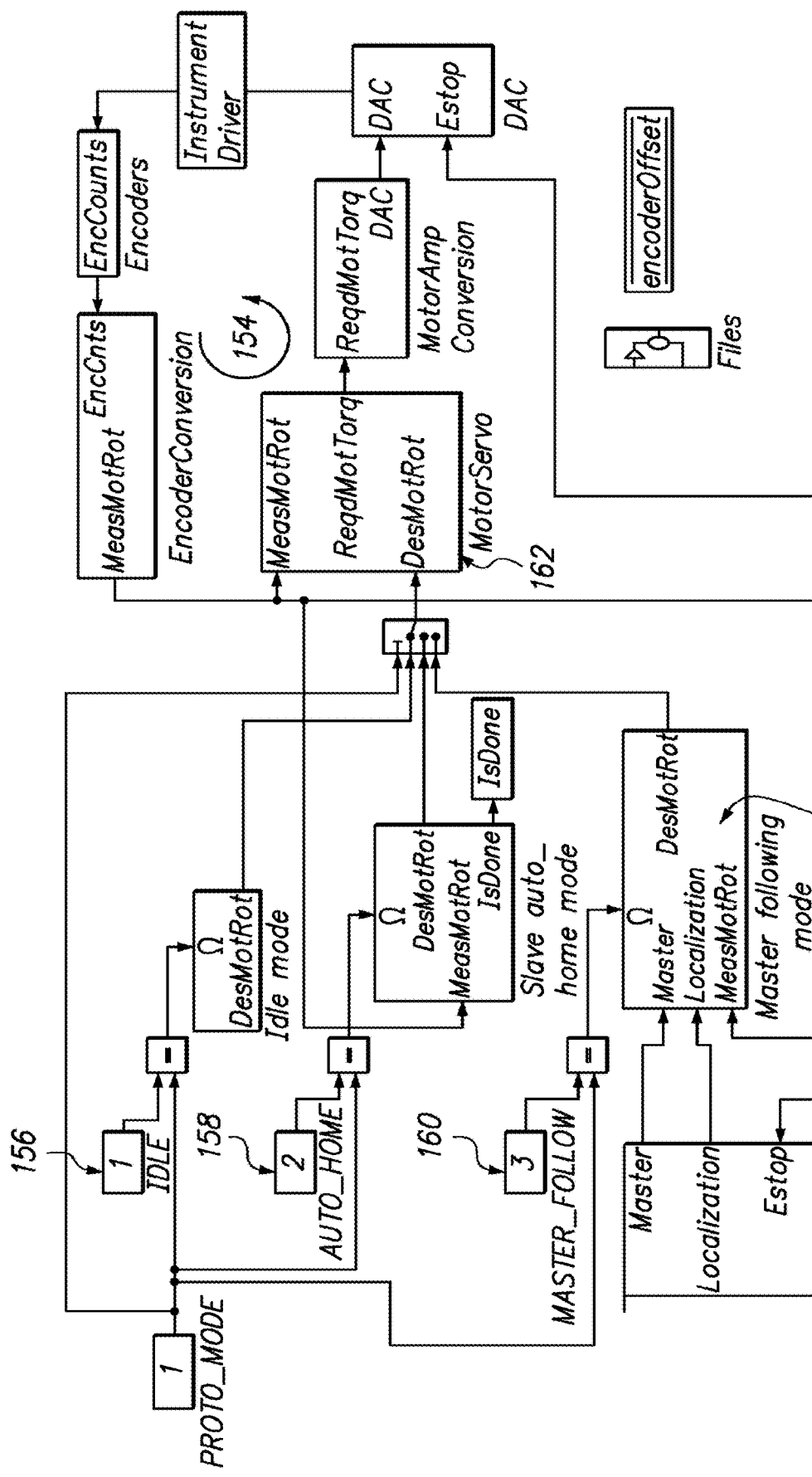
FIGS. 19-29 illustrate software control schema in accordance with various embodiments.

FIG. 19 depicts a high-level view of an embodiment wherein any one of three modes may be toggled to operate the primary servo loop 154. In idle mode 156, the default mode when the system is started up, all of the motors are commanded via the motor servo loop 154 to servo about their current positions, their positions being monitored with digital encoders associated with the motors. In other words, idle mode 156 deactivates the motors, while the remaining system stays active. Thus, when the operator leaves idle mode, the system knows the position of the relative components. In auto home mode 158, cable loops within an associated instrument driver, such as that depicted in FIG. 5A-5C, are centered within their cable loop range to ensure substantially equivalent range of motion of an associated instrument in both directions for a various degree of freedom, such as + and − directions of pitch or yaw, when loaded upon the instrument driver. This is a setup mode for preparing an instrument driver before an instrument is engaged.

In master following mode 160, the control system receives signals from the master input device, and in a closed loop embodiment from both a master input device and a localization system, and forwards drive signals to the primary servo loop 154 to actuate the instrument in accordance with the forwarded commands. Aspects of the primary servo loop and motor servo block 162 are depicted in further detail in FIGS. 20-23.

Figure 24:
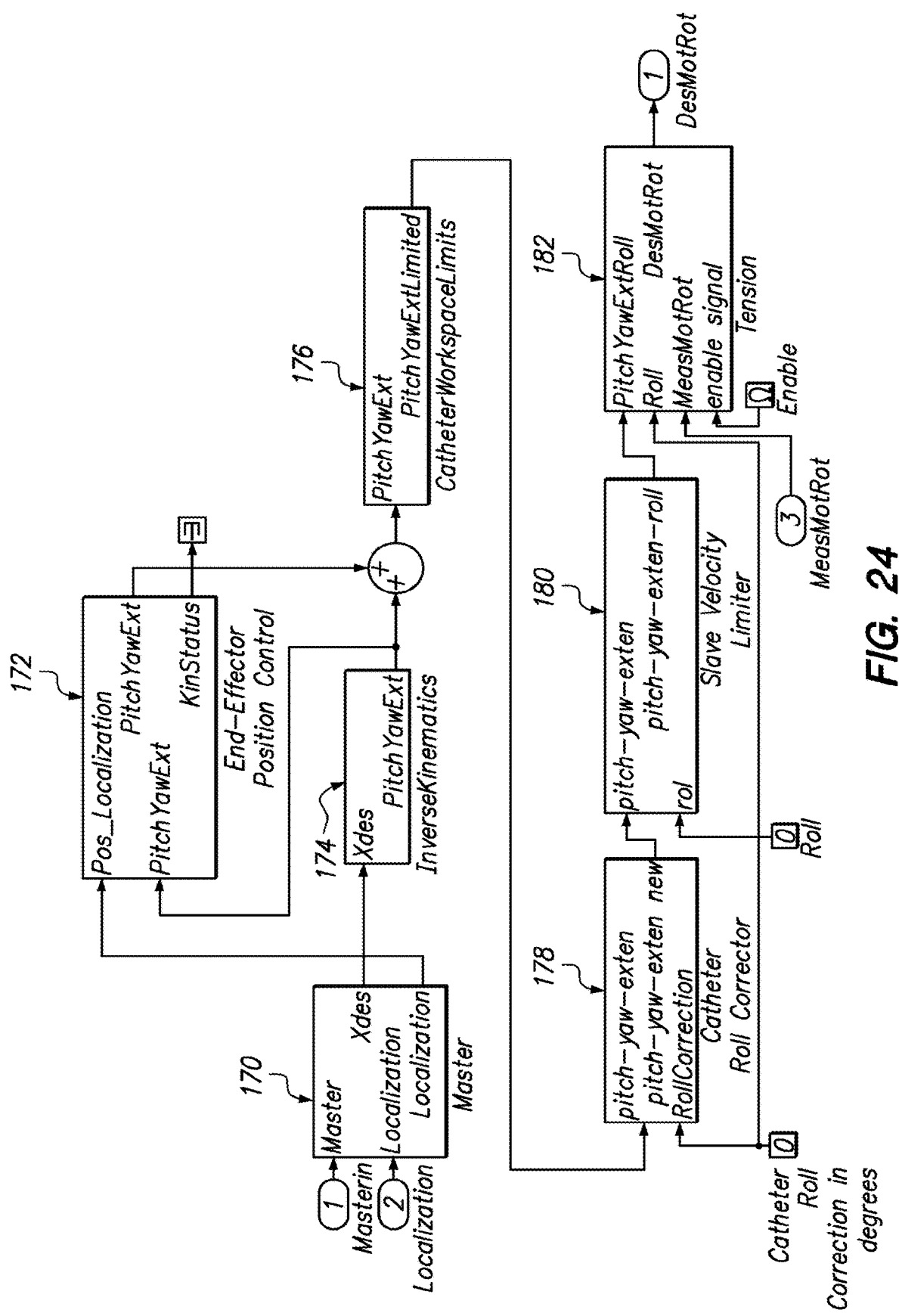
Figure 25:
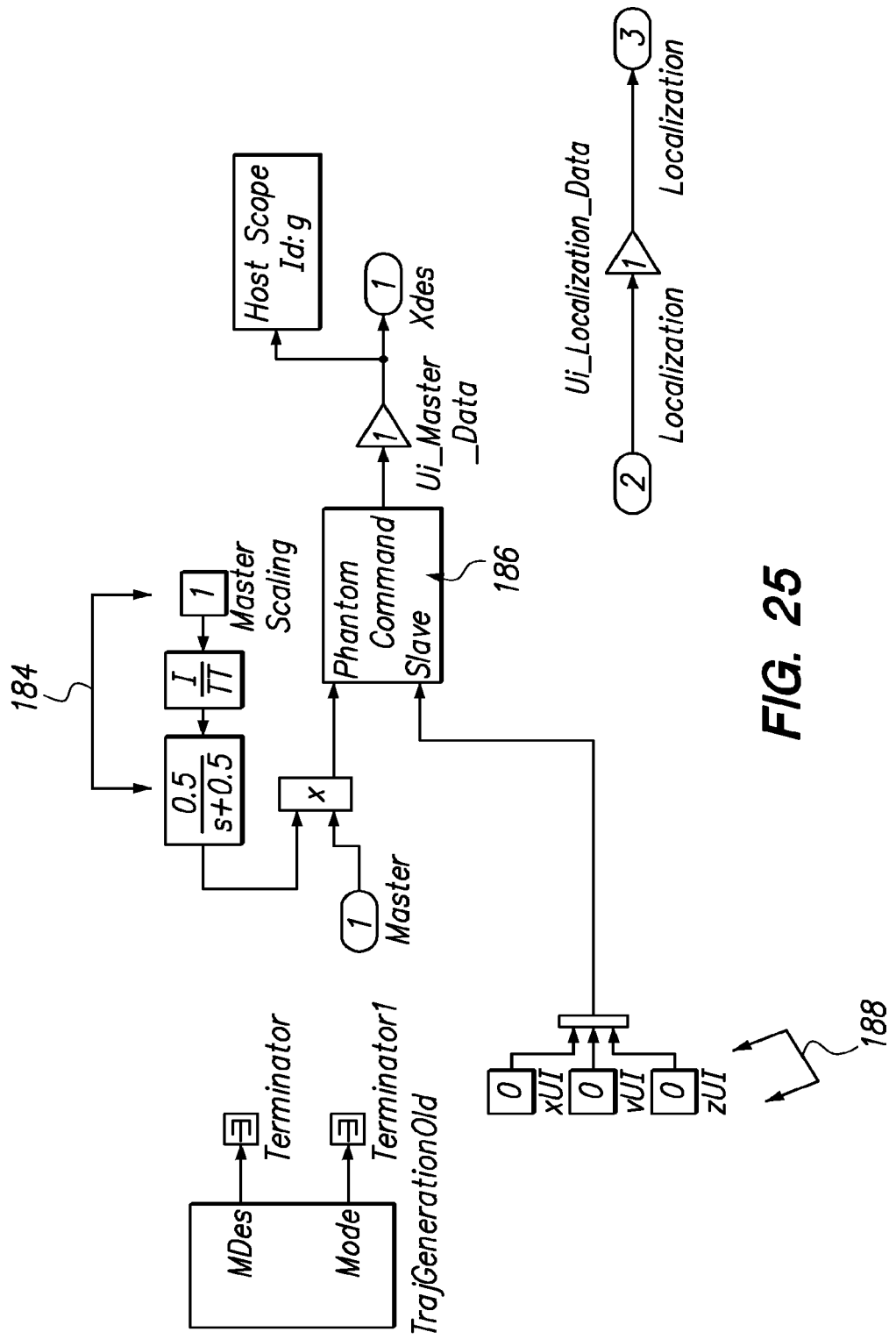

Referring to FIG. 24, a more detailed functional diagram of an embodiment of master following mode 160 is depicted. As shown in FIG. 24, the inputs to functional block 170 are XYZ position of the master input device in the coordinate system of the master input device which, per a setting in the software of the master input device may be aligned to have the same coordinate system as the catheter, and localization XYZ position of the distal tip of the instrument as measured by the localization system in the same coordinate system as the master input device and catheter. Referring to FIG. 25 for a more detailed view of functional block 170 of FIG. 24, a switch 186 is provided to allow switching between master inputs for desired catheter position, to an input interface 188 through which an operator may command that the instrument go to a particular XYZ location in space. Various controls features may also utilize this interface to provide an operator with, for example, a menu of destinations to which the system should automatically drive an instrument, etc. Also depicted in FIG. 25 is a master scaling functional block 184 which is utilized to scale the inputs coming from the master input device with a ratio selectable by the operator. The command switch 186 functionality includes a low pass filter to weight commands switching between the master input device and the input interface 188, to ensure a smooth transition between these modes.

Figure 29:
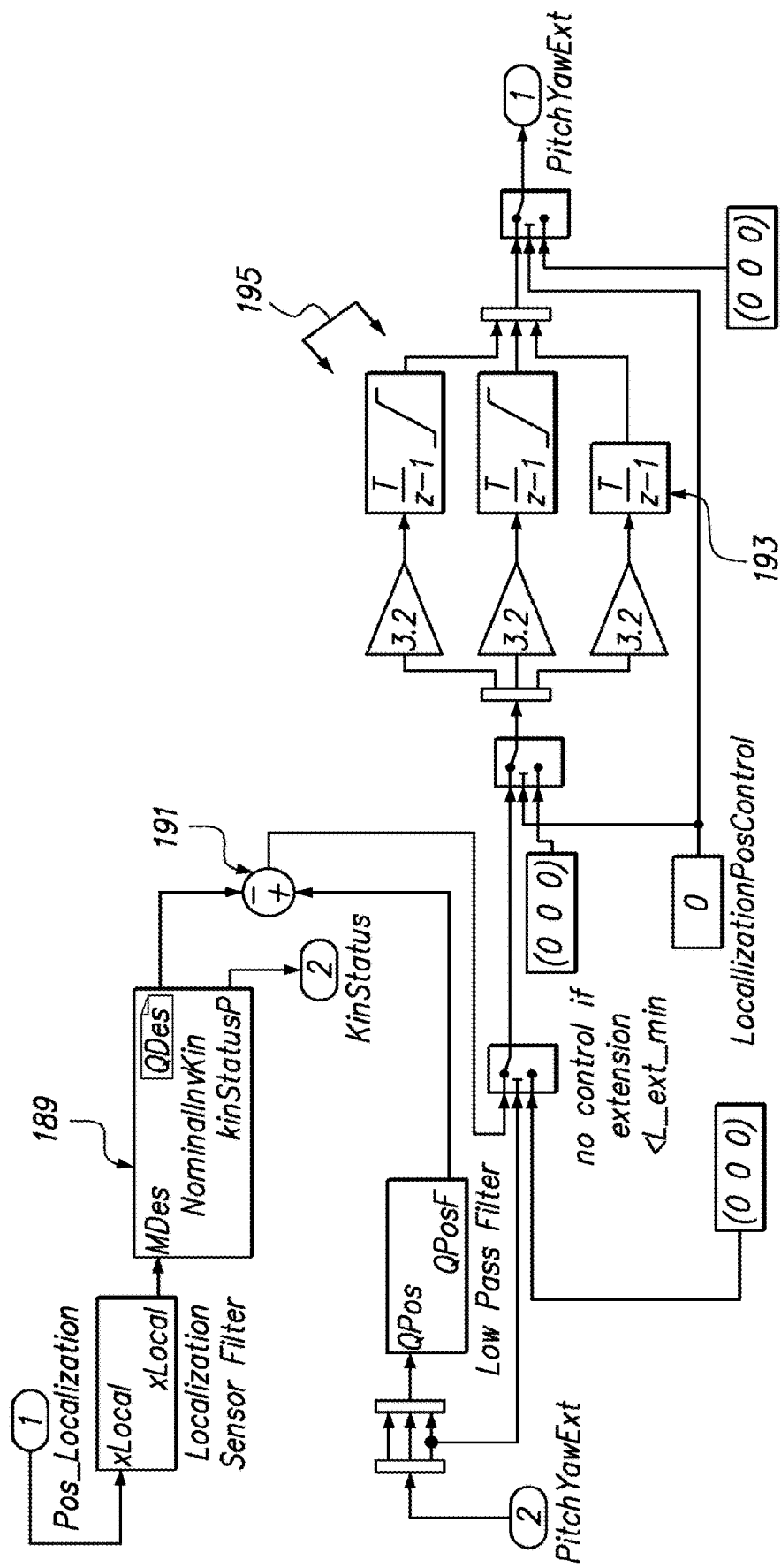

Referring back to FIG. 24, desired position data in XYZ terms is passed to the inverse kinematics block 174 for conversion to pitch, yaw, and extension (or "insertion") terms in accordance with the predicted mechanics of materials relationships inherent in the mechanical design of the instrument. The pitch, yaw, and extension commands are passed from the inverse kinematics 174 to a position control block 172 along with measured localization data. FIG. 29 provides a more detailed view of the position control block 172. After measured XYZ position data comes in from the localization system, it goes through a inverse kinematics block 189 to calculate the pitch, yaw, and extension the instrument needs to have in order to travel to where it needs to be. Comparing 191 these values with filtered desired pitch, yaw, and extension data from the master input device, integral compensation is then conducted with limits on pitch and yaw to integrate away the error. In this embodiment, the extension variable does not have the same limits 193, as do pitch and yaw 195. As will be apparent to those skilled in the art, having an integrator in a negative feedback loop forces the error to zero. Returning to FIG. 24, desired pitch, yaw, and extension commands are next passed through a catheter workspace limitation 176, which may be a function of the experimentally determined physical limits of the instrument beyond which componentry may fail, deform undesirably, or perform unpredictably or undesirably. This workspace limitation defines a volume similar to a cardioid-shaped volume about the distal end of the instrument. Desired pitch, yaw, and extension commands, limited by the workspace limitation block, are then passed to a catheter roll correction block 178.

Figure 26:
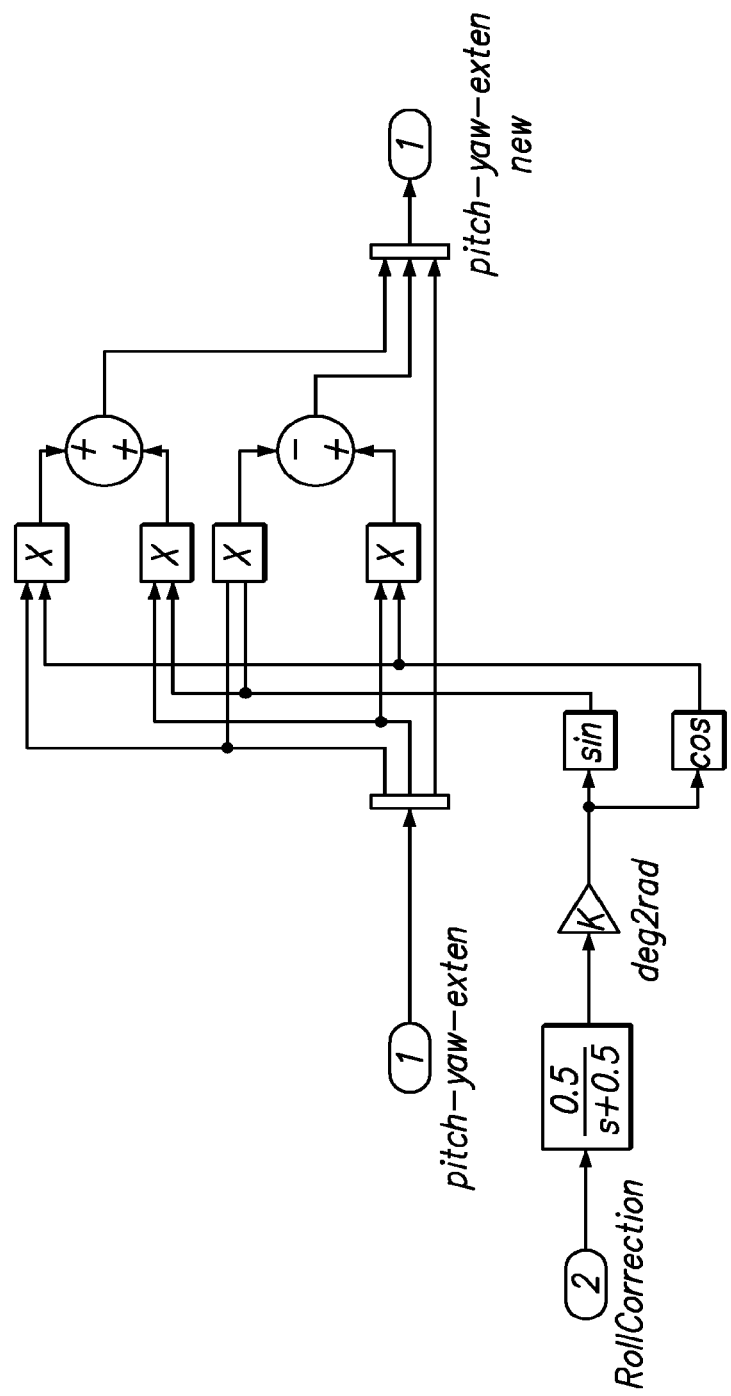

This functional block is depicted in further detail in FIG. 26, and comprises a rotation matrix for transforming the pitch, yaw, and extension commands about the longitudinal, or "roll", axis of the instrument—to calibrate the control system for rotational deflection at the distal tip of the catheter that may change the control element steering dynamics. For example, if a catheter has no rotational deflection, pulling on a control element located directly up at twelve o'clock should urge the distal tip of the instrument upward. If, however, the distal tip of the catheter has been rotationally deflected by, say, ninety degrees clockwise, to get an upward response from the catheter, it may be necessary to tension the control element that was originally positioned at a nine o'clock position. The catheter roll correction schema depicted in FIG. 26 provides a means for using a rotation matrix to make such a transformation, subject to a roll correction angle, such as the ninety degrees in the above example, which is input, passed through a low pass filter, turned to radians, and put through rotation matrix calculations.

In one embodiment, the roll correction angle is determined through experimental experience with a particular instrument and path of navigation. In another embodiment, the roll correction angle may be determined experimentally in-situ using the accurate orientation data available from the preferred localization systems. In other words, with such an embodiment, a command to, for example, bend straight up can be executed, and a localization system can be utilized to determine at which angle the defection actually went—to simply determine the in-situ roll correction angle.

Figure 27:
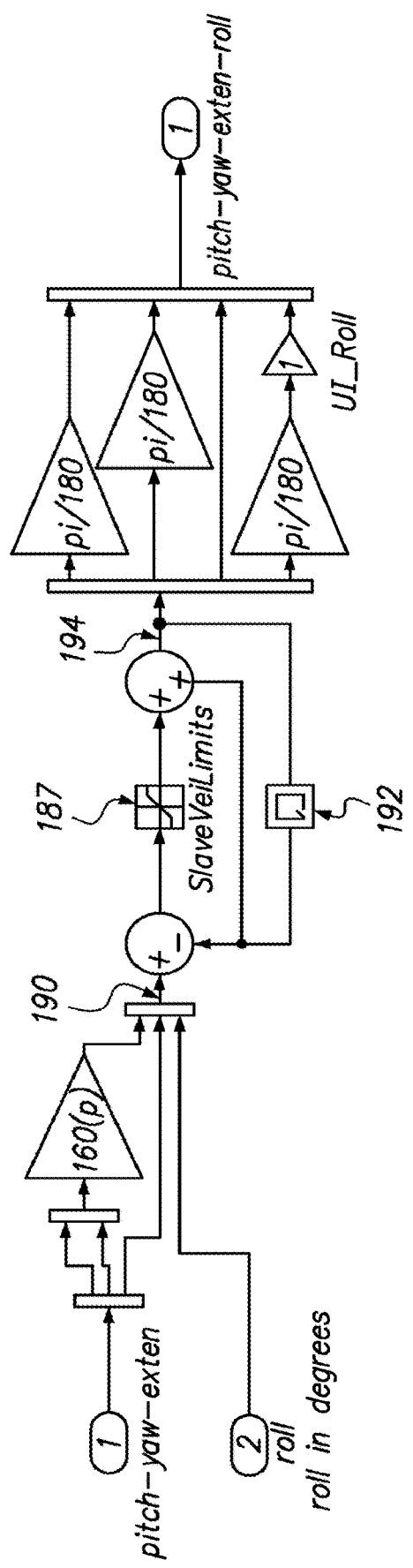

Referring briefly back to FIG. 24, roll corrected pitch and yaw commands, as well as unaffected extension commands, are output from the roll correction block 178 and may optionally be passed to a conventional velocity limitation block 180. Referring to FIG. 27, pitch and yaw commands are converted from radians to degrees, and automatically controlled roll may enter the controls picture to complete the current desired position 190 from the last servo cycle. Velocity is calculated by comparing the desired position from the previous servo cycle, as calculated with a conventional memory block (192) calculation, with that of the incoming commanded cycle. A conventional saturation block 187 keeps the calculated velocity within specified values, and the velocity-limited command 194 is converted back to radians and passed to a tension control block 182.

Figure 28:
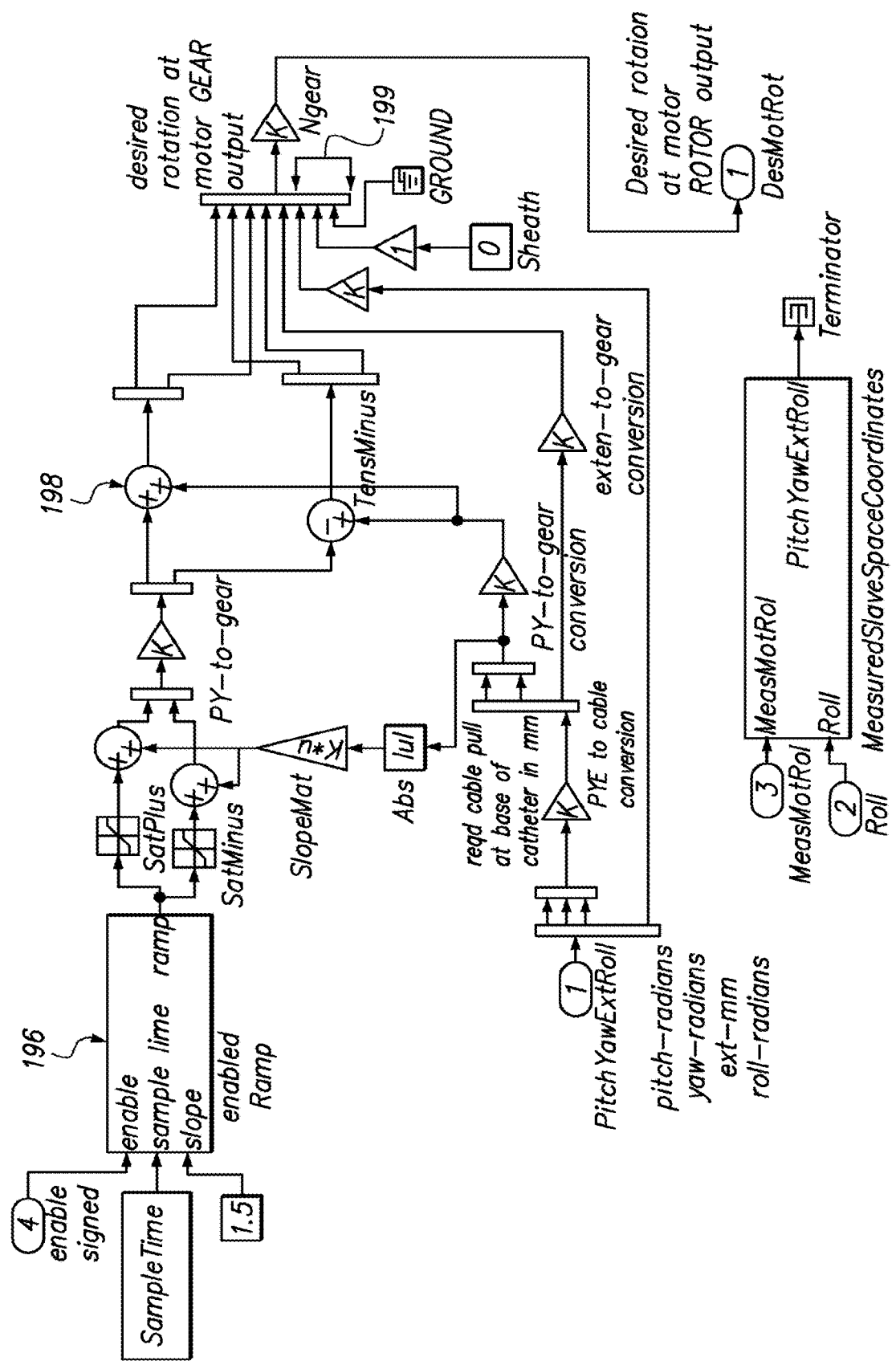

Tension within control elements may be managed depending upon the particular instrument embodiment, as described above in reference to the various instrument embodiments and tension control mechanisms. As an example, FIG. 28 depicts a pre-tensioning block 196 with which a given control element tension is ramped to a present value. An adjustment is then added to the original pre-tensioning based upon a preferably experimentally-tuned matrix pertinent to variables, such as the failure limits of the instrument construct and the incoming velocity-limited pitch, yaw, extension, and roll commands. This adjusted value is then added 198 to the original signal for output, via gear ratio adjustment, to calculate desired motor rotation commands for the various motors involved with the instrument movement. In this embodiment, extension, roll, and sheath instrument actuation 199 have no pre-tensioning algorithms associated with their control. The output is then complete from the master following mode functionality, and this output is passed to the primary servo loop 154.

Referring back to FIG. 19, incoming desired motor rotation commands from either the master following mode 160, auto home mode 158, or idle mode 156 in the depicted embodiment are fed into a motor servo block 162, which is depicted in greater detail in FIGS. 20-23.

Figure 20:
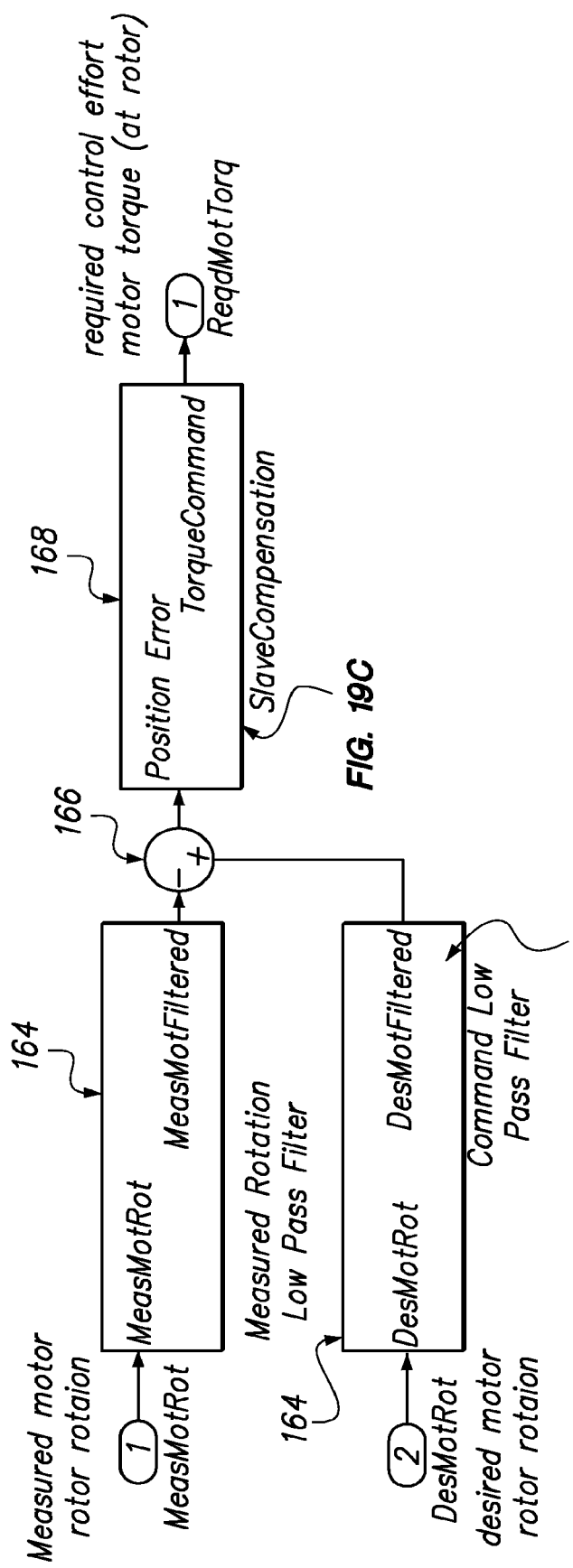
Figure 22:
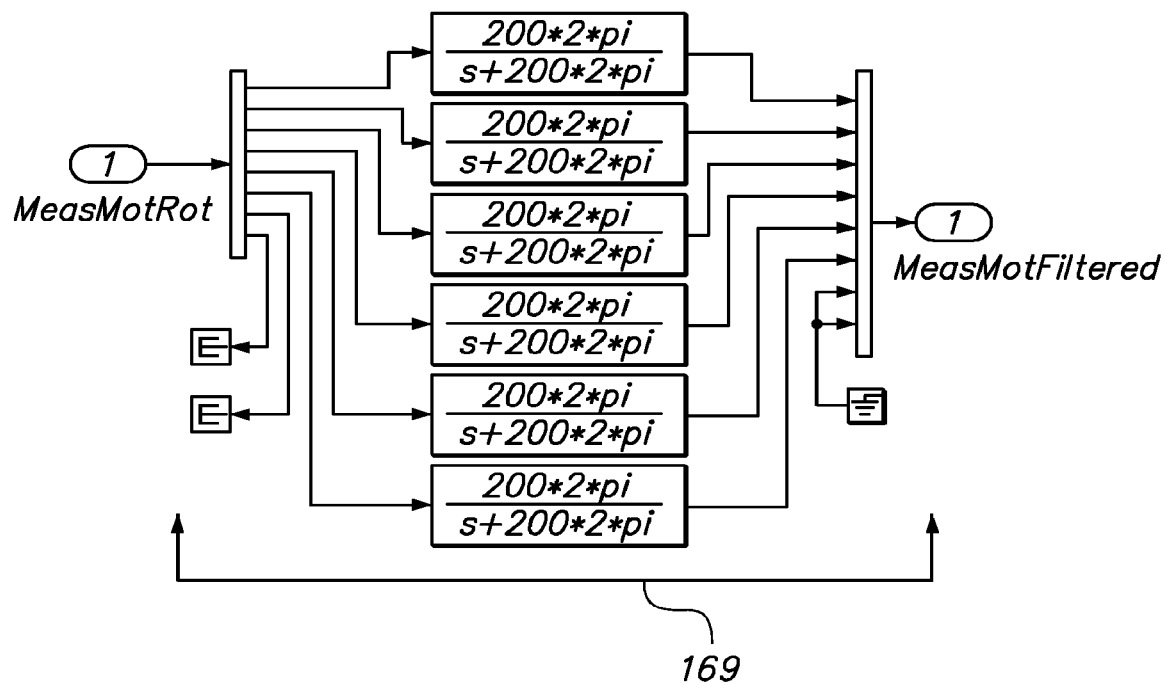
Figure 23:
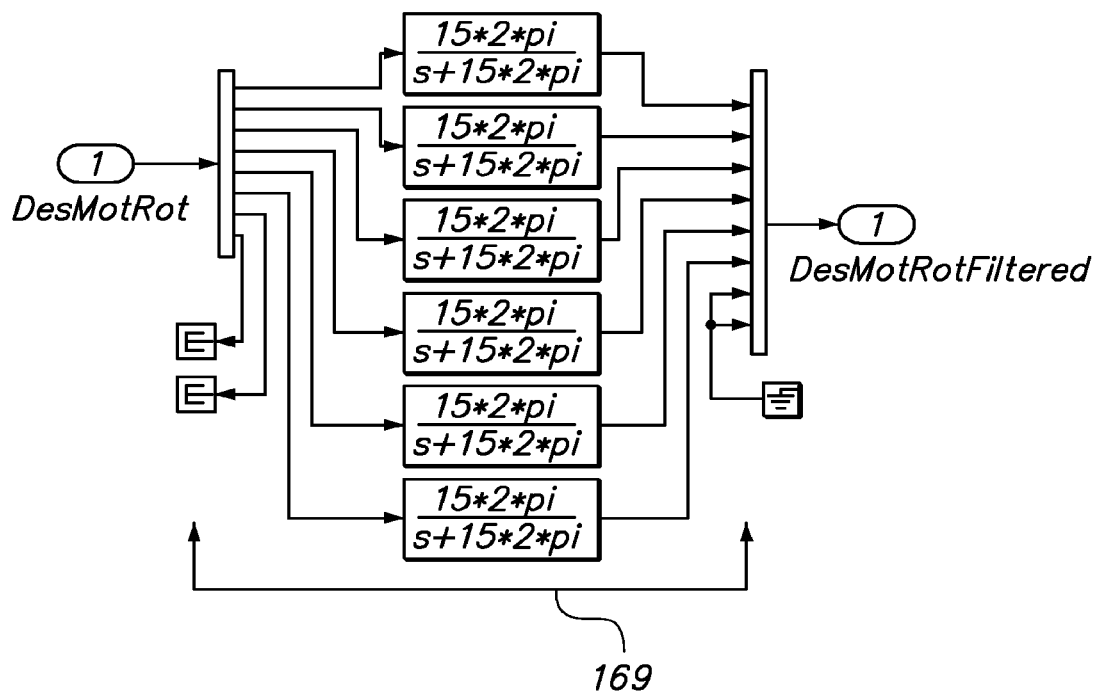

Referring to FIG. 20, incoming measured motor rotation data from digital encoders and incoming desired motor rotation commands are filtered using conventional quantization noise filtration 164 at frequencies selected for each of the incoming data streams to reduce noise while not adding undue delays which may affect the stability of the control system. As shown in FIGS. 22 and 23, conventional quantization filtration is utilized on the measured motor rotation signals at about 200 hertz in this embodiment, and on the desired motor rotation command at about 15 hertz. The difference 166 between the quantization filtered values forms the position error which may be passed through a lead filter, the functional equivalent of a proportional derivative ("PD")+low pass filter. In another embodiment, conventional PID, lead/lag, or state space representation filter may be utilized. The lead filter of the depicted embodiment is shown in further detail in FIG. 21.

Figure 21:
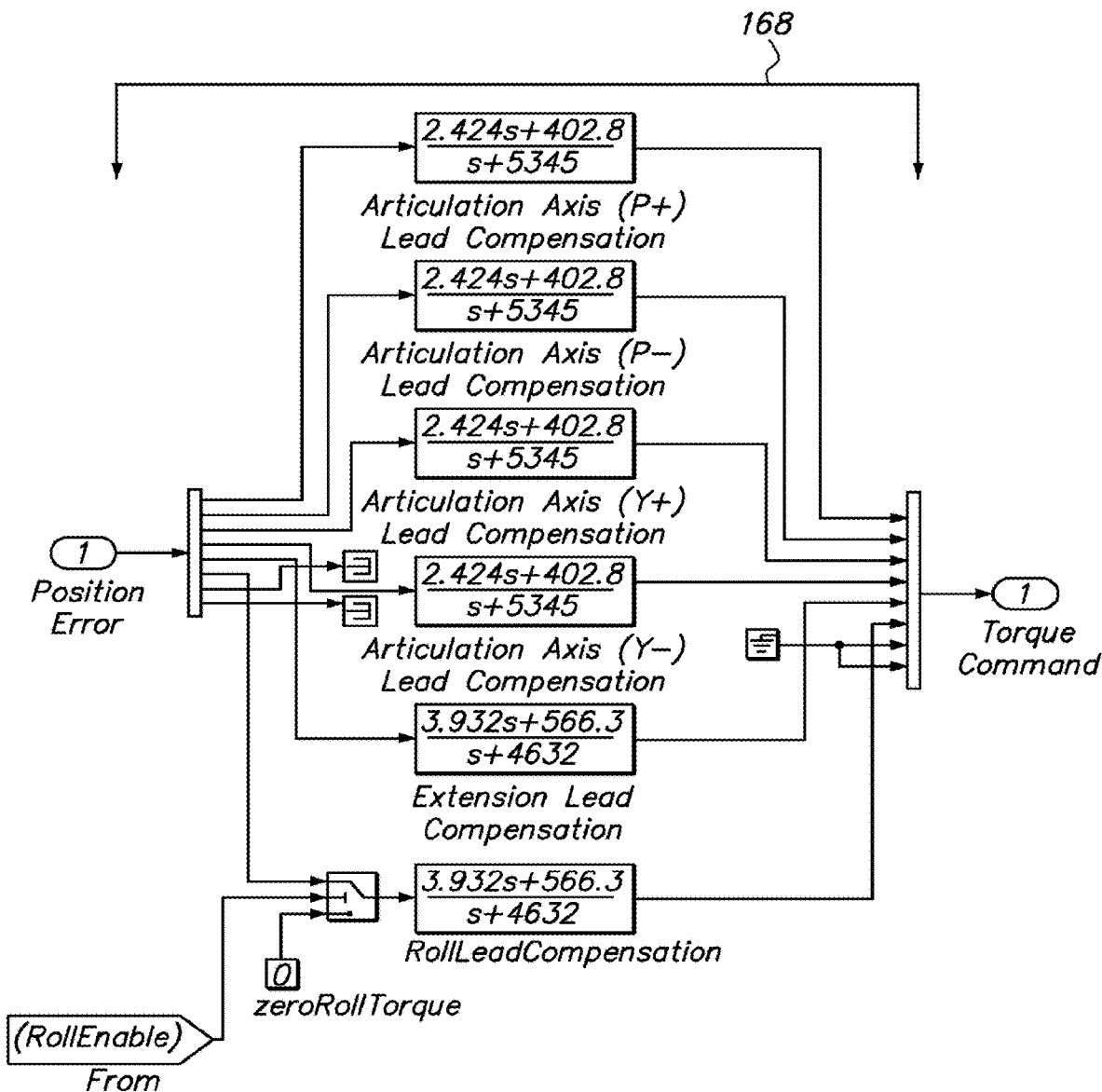

In particular, the lead filter embodiment in FIG. 21 comprises a variety of constants selected to tune the system to achieve desired performance. The depicted filter addresses the needs of one embodiment of a 4-control element guide catheter instrument with independent control of each of four control element interface assemblies for .+−.pitch and .+−.yaw, and separate roll and extension control. As demonstrated in the depicted embodiment, insertion and roll have different inertia and dynamics as opposed to pitch and yaw controls, and the constants selected to tune them is different. The filter constants may be theoretically calculated using conventional techniques and tuned by experimental techniques, or wholly determined by experimental techniques, such as setting the constants to give a sixty degree or more phase margin for stability and speed of response, a conventional phase margin value for medical control systems.

In an embodiment where a tuned master following mode is paired with a tuned primary servo loop, an instrument and instrument driver, such as those described above, may be "driven" accurately in three-dimensions with a remotely located master input device. Other preferred embodiments incorporate related functionalities, such as haptic feedback to the operator, active tensioning with a split carriage instrument driver, navigation utilizing direct visualization and/or tissue models acquired in-situ and tissue contact sensing, and enhanced navigation logic.

I-A. Insertion Force Indicator

Figure 30:
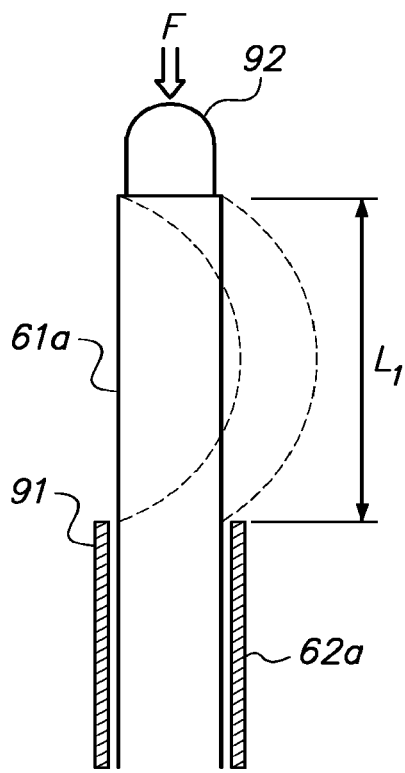
FIG. 30 illustrates a distal portion of a guide catheter extending beyond a distal end of a sheath instrument by a distance or length $L_1$ and a force F imparted on the distal tip of the guide catheter that may cause the distal portion of the guide catheter to bend or flex.
Figure 31:
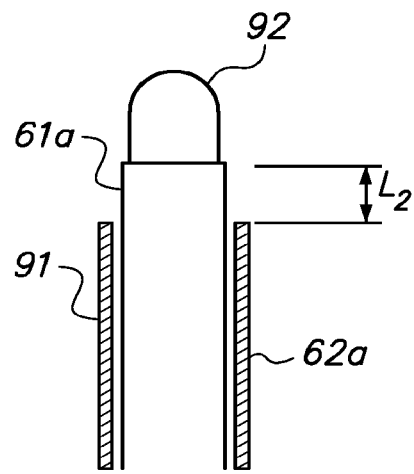
FIG. 31 illustrates a distal portion of a guide catheter extending beyond a distal end of a sheath instrument by a distance or length $L_2$ that is less than the length $L_1$ shown in FIG. 30.

Referring to FIGS. 30-31, a further embodiment is directed systems and methods for indicating catheter 61a insertion forces. When the guide catheter 61a extends from the sheath 62a and makes contact with tissue, a certain force F is imparted onto the guide catheter 61a. Depending on how far the distal tip 92 of the guide catheter 61a is extended from the sheath 62a, the force F may result in different interactions between the guide catheter 61a and tissue.

In one variation as illustrated in FIG. 30, a length $L_1$ of the guide catheter instrument 61a extends beyond the distal tip 91 of the sheath 62a. As the distal tip 92 of the guide catheter 61a makes contact with tissue with a force F, an equal and opposite force F is imparted to the guide catheter instrument 61a (represented by arrow F). Depending upon the magnitude of the force F, a portion of the guide catheter 61a, e.g., adjacent to the distal tip 92, may be caused to bend, flex or buckle under the force F, thereby reducing the force exerted on the tissue.

FIG. 31 illustrates a guide catheter 61a that extends a shorter length $L_2$ beyond the distal tip 91 of the sheath 62a. In this example, when the distal tip 92 of the guide catheter 61a makes contact with tissue with the same force F, the shorter length L2 reduces or eliminates flexing since the distal portion of the guide catheter 61a is reinforced by the distal end of the stiffer sheath 62a, resulting in a larger force F that is applied to the tissue due to less flexing.

In one system (S), motors of the instrument driver 16 are controlled to robotically control and manipulate catheter instruments 18. The amount of current supplied to the motor is proportionally related to the amount of torque generated by the motors and catheter 18 insertion force is proportional to the motor torque. Thus, the motor current is proportional to the insertion force. If the motors are driven by the same amount of current regardless of how far the guide catheter 61a extends out from the sheath 62a, the force imparted on the tissue at the contact point may differ based on length L.

For example, if a high motor current causes a high insertion force for a guide catheter 61a extending length $L_1$, the catheter 61a may dissipate a portion of that force due to flexing or bending. However, when the guide catheter 61a extends a much smaller length $L_2$, it may not yield, and the insertion force is not attenuated. In one embodiment, a kinematic model of the instrument configuration may be utilized, in concert with sensed motor torques at driveshafts within the instrument driver, to calculate, or "back out", the loads and vectors thereof that are theoretically applied to the distal end of the instrument, or other portion of the instrument in contact with an external load-applying structure.

In one embodiment, a system (S) may be configured to generate a visual or audible warning message to a user, control element or processor indicating that corrective action is required and/or to indicate a possibility of high insertion forces exerted to tissue at the distal tip 92. In one embodiment, a warning message is displayed when length L is less than a minimum length $L_{min}$ and/or the motor current I is greater than $I_{max}$. For example, the minimum length $L_{min}$ may be about 30 mm or less, and the maximum motor current $I_{max}$ may be about 250 mA or higher current levels. In cases in which the length or motor current exceeds these pre-determined values, the operator may adjust the motor current accordingly or proceed carefully to avoid causing injury. This type of force indication message may be useful for instrument driver 16 that do not have force sensing capabilities.

I-B. Reachability/Viewability

Another alternative embodiment is directed to methods and systems for assessing reachability and viewability at a particular location. More particularly, embodiments advantageously assess locations within the body that can be reached by a catheter instrument 18 of the system (S), as well as assessing the viewability or field of view at a particular location that can be reached by the catheter instrument 18. This ability is particularly significant since the field of view at a particular location may not be desirable even if it is reachable. Thus, embodiments advantageously assess field of view at reachable locations in order to provide more meaningful surgical planning and results.

For example, in the context of cardiac surgery utilizing an intracardiac (ICE) catheter. During the planning stage, an operator can determine offline before a procedure where a catheter should be driven to provide for a desired field of view that allows a region of interest to be scanned. Alternatively, a previously acquired CT model may be registered and fused with real time ultrasound data during a surgical procedure. During use, embodiments allow the ICE catheter to be driven to a position within the heart with a desired or optimum field of view for scanning of, e.g., the left atrium, or another internal tissue or segment thereof that is of interest.

Figure 32:
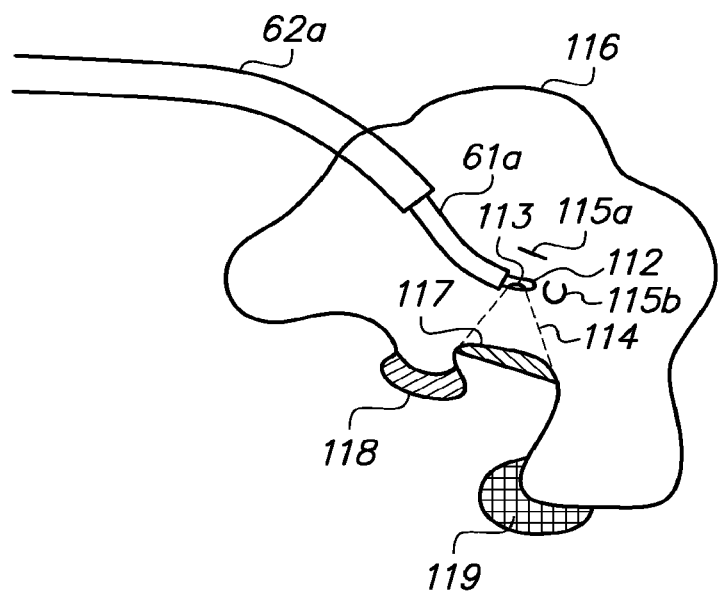
FIG. 32 illustrates assessing reachability and viewability or field of view according to one embodiment.

Referring to FIG. 32, in one embodiment, a robotic medical system includes an outer sheath 62a with a working lumen, and an inner guide catheter 61a extending through the sheath lumen, with a distal end portion of the guide catheter 61a extending out a distal end opening of the sheath 62a in an anatomic workspace 116 in a body. An intracardiac (ICE) ultrasound imaging catheter 112 is positioned in a working lumen of the guide catheter 61a, with a distal end portion of the ICE catheter 112 extending out a distal end opening of the guide catheter 61a. The ICE catheter 112 may be extended out of, and retracted into, respectively, the distal end opening in the guide catheter 61a, as indicated by arrow 115A, and may be rotated about its longitudinal axis, as indicated by arrow 115B, such that a transducer array 113 on the ICE catheter 112 is positionable within the anatomic workspace 116 to capture ultrasound images within a field of view 114 of the array 113. The depicted ICE catheter 112 comprises a substantially linear array 113 defining a field of view 114 having a substantially trapezoidal shape; ICE catheters with such configurations are available from suppliers such as the Ultrasound division of Siemens AG under the tradename AcuNav™. In other embodiments, substantially circular/disc shaped fields of view may be created utilizing an ultrasound transducer configuration which may be rotated along with a portion of the ICE catheter with a drive shaft, as in the ICE catheters available from Boston Scientific, or utilizing multiple ultrasound transducers placed circumferentially around a catheter body, as in the ultrasound imaging catheters available from Volcano Corporation. For illustrative purposes, FIG. 32 depicts a linear array, AcuNav™ type configuration—but each of the aforementioned other configurations may be similarly employed.

Depending on factors such as the anatomical boundaries and tissue structures in the anatomical workspace 116, and the relative positions and prior trajectories of the sheath 62a, guide catheter 61a, and ICE catheter 112 within the workspace 116, the system controller (not shown in FIG. 32) can model the potential relative movement the respective sheath 62a, guide 61a, and ICE catheter 112, and thus the potential movement of the field of view 114 of the transducer array 113 within the work space 116. In particular, certain tissue walls and/or structures within the anatomic workspace 116 can be readily imaged (or "viewable") by the ICE transducer 113 without requiring anything more than a relatively simple repositioning of the respective sheath 62a, guide 61a, and ICE catheter 112, respectively, such as tissue structure 117 in FIG. 21. Other tissue wall locations and/or structures may be viewable, but only by more complicated maneuvering techniques, including iterative movements of one or more of the sheath 62a, guide 61a, and/or ICE catheter 112, respectively, in order to position the transducer 113 and field of view 114, such as tissue structure 118 in FIG. 32. Still further tissue wall locations and/or structures may be difficult or impossible to capture within the field of view 114 of the ICE transducer 113 without a major repositioning of the collective instruments (sheath 62a, guide 61a, ICE catheter 112), if at all.

This "ICE viewability" analysis may be useful for both pre-operative planning, and during a procedure, wherein the robotic system controller is configured to determine a respective reach of the distal end portion of the ICE catheter 112, and thus the potential fields of view 114 that may be captured by the transducer array 113 within the anatomical workspace 116, based at least in part upon a planned or a present relative position of the respective sheath 62a, guide 61a, and ICE catheter 112 instruments. By way of non-limiting examples, the controller may determine the viewability of the various anatomic wall surfaces and/or tissue structures based at least in part on a kinematic model of one or both of the sheath and guide catheter instruments 62a and 61a. Further, the controller may display the possible field of views, viewable tissue walls and/or structures, or both, overlaying an image of the anatomic workspace on a display associated with the robotic system, wherein the image of the anatomic workspace is obtained from a model of the workspace, from an imaging system, or both.

While various embodiments haven been described herein, such disclosure is provided for purposes explanation and illustration. Further, various embodiments may be used in combination with other embodiments. Additionally, although certain embodiments are described with reference to particular dimensions or parameters, it should be understood that these dimensions and parameters are provided for purposes of explanation, and that other dimensions and parameters may also be utilized.

Embodiments and instruments of robotic systems (S) may be used in various minimally invasive surgical procedures that involve different types of tissue including heart, bladder and lung tissue, for example. Depending on the procedure, distal portions of various instruments may not be easily visible to the naked eye. Various imaging modalities including magnetic resonance (MR), ultrasound, computer tomography (CT), X-ray, fluoroscopy, etc. may be used for this purpose to visualize the surgical procedure and location of instruments. Further, it may be desirable to know the precise location of a given catheter instrument and/or working tool at any given moment to avoid undesirable contacts or movements. For this purpose, one or more localization techniques that are presently available may be applied to any of the apparatuses and methods disclosed above. For example, one or more localization coils may be built into a flexible catheter instrument. In other implementations, a localization technique using radio-opaque markers may be used with embodiments of the present invention. Similarly, a fiber optic Bragg sensing fiber may be built into the sidewall of a catheter instrument to sense position and temperature. Embodiments may also be implemented in systems that include a plurality of sensors, including those for sensing patient vitals, temperature, pressure, fluid flow, force, etc., may be combined with the various embodiments of flexible catheters and distal orientation platforms disclosed herein.

Embodiments of flexible catheters and other related instruments used in a robotic surgical system may be made of various materials, including materials and associated techniques that are the same as or similar to those described in U.S. patent application Ser. No. 11/176,598, now abandoned, the contents of which were previously incorporated by reference. For example, suitable materials may include stainless steel, copper, aluminum, nickel-titanium alloy (Nitinol), Flexinoff (available from Toki of Japan), titanium, platinum, iridium, tungsten, nickel-chromium, silver, gold, and combinations thereof, may be used to manufacture parts such as control elements, control cables, spine elements, gears, plates, ball units, wires, springs, electrodes, thermocouples, etc. Similarly, non-metallic materials including, but not limited to, polypropylene, polyurethane (Pebax™), nylon, polyethylene, polycarbonate, Delrin™, polyester, Kevlar™, carbon, ceramic, silicone, Kapton™ polyimide, Teflon™ coating, polytetrafluoroethylene (PTFE), plastic (nonporous or porous), latex, polymer, etc. may be used to make the various parts of a catheter and other system components.

Further, although embodiments are describe with reference to a catheter in the form of a guide catheter and working instruments, it is also contemplated that one or more lumens of catheters may be used to deliver fluids such as saline, water, carbon dioxide, nitrogen, helium, for example, in a gaseous or liquid state, to the distal tip. Furthermore, it is contemplated that some embodiments may be implemented with a open loop or closed loop cooling system wherein a fluid is passed through one or more lumens in the sidewall of the catheter instrument to cool the catheter or a tool at the distal tip.

Further, although various embodiments are described with reference to a sheath and/or a guide catheter having four control elements or pull wires, it may be desirable to have a guide instrument with different numbers of control elements, e.g., less than four control elements. Further, although certain embodiments are described with reference to a guide catheter in combination with a steerable sheath, other embodiments may be implemented in systems that include a guide catheter (or other catheter) in combination with a pre-bent, unsteerable sheath, or perhaps with no sheath at all. Further, embodiments described above may be utilized with manually or robotically steerable instruments, such as those described in U.S. patent application Ser. No. 11/481,433, issued as U.S. Pat. No. 8,052,636 on Nov. 8, 2011, incorporated herein by reference. The instrument driver can be configured and adapted to meet the needs of different system and instrument configurations, e.g., using different numbers of motors and gearboxes for driving control elements, or variation in the configuration for actuating a given control element interface assembly, and associated variation in the tensioning mechanism and number of control element pulleys associated with the pertinent control element interface assembly (one pulley and one cable per control element interface assembly, two pulleys and two cables per control element interface assembly, slotted, split carriage, and winged split carriage embodiments, various tensioning embodiments, etc.

II. Catheter

Figure 33A:
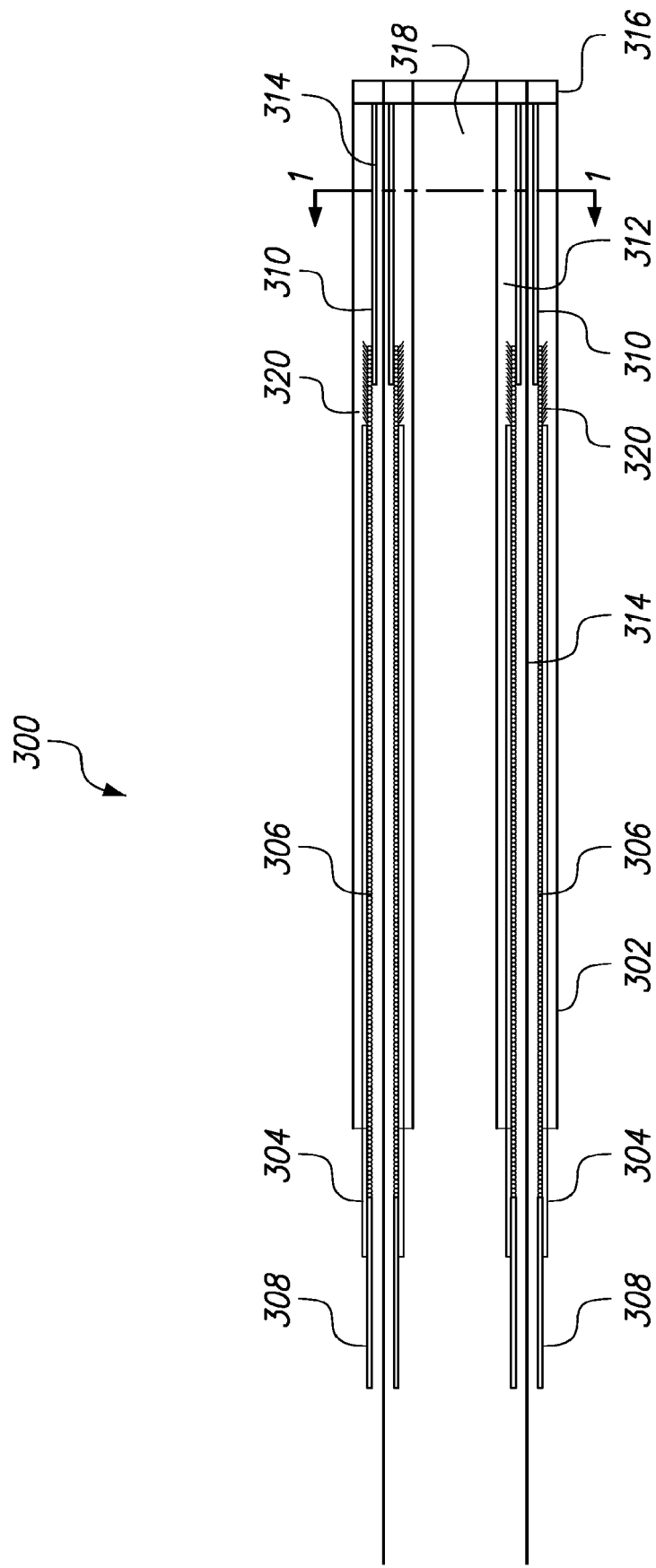
FIG. 33A illustrates a cross-sectional view of a flexible and steerable elongate instrument with variable or changeable shape control and support elements in accordance with one embodiment.

FIG. 33A illustrates a cross-sectional view of a section or portion of a flexible and steerable elongate instrument or catheter 300 of an instrument assembly in accordance with some embodiments. The catheter 300 may be coupled to the drivable assembly 182 in some embodiments. The steerable elongate instrument 300 may be substantially pliable or flexible such that when it is advanced into a patient, an operator or surgeon may easily manipulate the instrument 300 to conform, adopt, or match the shape or curvatures of the internal pathways (e.g., gastrointestinal tract, blood vessels, etc.) of the patient. As illustrated, the flexible and steerable elongate instrument or catheter 300 may be comprised of multiple layers of materials and/or multiple tube structures. For example, the elongate instrument 300 may include an outer layer or outer tube 302, a main lumen, primary lumen, or central lumen 318 defined by an inner layer or inner tube 312, and minor, secondary, or peripheral lumens incorporated in the body of the elongate instrument 300 substantially between the outer layer 302 and the inner layer 312 where operational tubes 304, flexible tubes 306, push tubes 308, and support tubes 310 are disposed or contained. The lumen 318 may be used to deliver one or more surgical instruments or tools from the proximal portion of the elongate instrument 300 to the distal portion of the elongate instrument 300 where they may be positioned and used to treat a target tissue structure inside a patient. The outer layer or outer tube 302 and the inner layer or inner tube 312 may be made of any flexible, pliable, or suitable polymer material or bio-compatible polymer material (e.g., nylon-12, Pebax®, Pellathane, Polycarbonate, etc.) or braided plastic composite structure. In some embodiments, outer layer or outer tube 302 and the inner layer or inner tube 312 may be one layer of material or one tube structure instead of separate layers of material or separate tube structures. Operational tubes 304 may not be actual tubes but may be the minor, secondary, or peripheral lumens or channels through the body of the outer layer or outer tube 302 or the operational tubes 304 may be separate operational tube structures that are disposed inside the minor, secondary, or peripheral lumens or channels in the body structure of the outer layer or outer tube 302. The operational tubes 304 may be made of any suitable polymer material, bio-compatible polymer material or metallic material (e.g., polyimide, stainless steel or spiral cut stainless steel, Nitinol, etc.). The separate operational tubes 304 may be melted and/or braided into the wall of the minor, secondary, or peripheral lumens of the outer tube 302 or inner tube 312. The operational tubes 304 may provide a substantially slidable surface and interface for the flex tubes 306, such that the flex tubes 306 may slide substantially freely about the interior of the operational tubes 304 in a substantially decoupled configuration. In some embodiments, a distal end or portion of the flex tubes 306 may be fixedly coupled to the elongate instrument. In some variations, a proximal end or portion of the flex tubes may also be fixedly coupled to the elongate instrument 300 as in a passively controlled configuration of the flex tubes 306.

For example, in a passively controlled configuration, the flex tubes 306 may passively slide along the interior of the operational tubes as the elongate instrument or catheter 300 is navigated through the anatomy, articulated or steered. As will be discussed in more detail, the slidable interface between the flex tubes 306 and the operational tubes 304 together with buffer loops of the flex tubes in the control unit substantially decouple the flex tubes 306 from the elongate instrument or catheter 300. Because of the decoupled configuration of these two structures, articulation forces supported by the flex tubes may be decoupled from at least a portion of the catheter body or structure 300. As a result of decoupling the flex tubes 306 from at least a portion the catheter body or structure, articulation forces applied to articulate or steer the distal portion of the elongate instrument or catheter 300 may not be transmitted through or along the body of the elongate instrument from the distal portion to the proximal portion of the elongate instrument, for example. Consequently, as described in this example, articulation forces may be prevented or minimized from compressing the proximal portion of the elongate instrument or catheter body; such compression if allowed to occur, may affect the stiffness or bending stiffness of the proximal portion of the catheter. In addition, this decoupling of the articulation forces for the elongate member allows that changes in the shape or length of the elongate member as it is navigated through the anatomy may not have any impact or minimal impact on the articulation performance of the distal section of the elongate instrument. As will be also discussed in more detail, in some embodiments, the flex tubes 306 may also be utilized as support or reinforcing structures to vary or change the stiffness and/or bend radius of at least a portion of the catheter. In particular, the flex tubes 306 may be very effective support or reinforcing structures when they are compressed and stiffened. In other words, an elongate instrument 300 or a section of the elongate instrument without any flex tubes 306 may be substantially flexible. With the introduction of one or more flex tubes 306 into the body of the elongate instrument or a section of the elongate instrument, the elongate instrument or the section of the elongate instrument with the flex tubes 306 may become less flexible; even though the flex tubes 306 are flexible in bending, they have axial stiffness. Several axially stiff members spread throughout the cross section of a catheter may add significant bending stiffness to the catheter. When the flex tubes 306 are compressed, such as using pull wires to apply a compressible force or load to the flex tubes, for example, they may become substantially more stiff laterally, such that the stiffened structures may affect or alter the stiffness and/or bend radius of at least a portion of the catheter where the flex tubes 306 are located. Accordingly, the flex tubes 306 may be utilized to vary or change the stiffness and/or bend radius of a portion or certain portion of the catheter by changing the positioning or placement of the flex tubes 306 in the elongate instrument 300. For example, the flex tubes 306 may be moved from one portion of the elongate instrument or catheter to another portion of the catheter. The portion from which where the flex tubes 306 were moved may become substantially more flexible or pliable without the flex tubes 306. Whereas, the portion to which where the flex tubes 306 were moved to may become substantially more stiff or less flexible or pliable. Consequently, the changes of stiffness along various portions of the elongate instrument or catheter may substantially affect the bend radius of at least a portion of the elongate instrument as pull wires are operated to articulate or steer the elongate instrument.

Referring back to the structural make up of the steerable instrument 300 as illustrated in FIG. 33A, the flex tubes 306 may be made from a coil of wire, a stack of rings, or a tube with spirally cut features. As may be appreciated by one of ordinary skilled in the art, a substantially stiff tube may become less stiff or more flexible or more pliable as a spiral cut or spirally cut feature is imparted onto a substantially stiff tube. The tube may be made from a of a high durometer plastic such as Peek™ or stainless steel or other suitable material. One of the features of the flex tube 306 is that it may provide structural support to the elongate instrument (e.g., axial and lateral support) as well as being substantially flexible (e.g., able to bend in various directions and orientations). In some embodiments, the flex tubes 306 may be constructed from one continuous coil of wire, e.g., coil tube. In other embodiments, each flex tube 306 may include a plurality of coils that are axially aligned in series. In some other embodiment, the flex tube 306 may be constructed from a stack of rings, e.g., ring tube. For a ring tube, the rings may be stacked, grouped, or maintained together in any suitable manner. In some of the embodiments, the rings may be stacked, grouped, or maintained together by a substantially flexible sleeve, sheath, membrane, or covering. The coil of wire or rings may be made from a polymer material or metallic material. For example, a coil wire or rings may be made from stainless steel, Nitinol, etc. The coil wire may be made from a round stock or a flat stock or a stock having any cross-section or profile. Similarly, the rings of the ring tube may be made from a round stock or a flat stock or a stock having any cross-section or profile. In accordance with some embodiments, the flex tubes 306 may be generally constructed from a substantially tightly wound coil of wire or a stack of rings.

Still referring to FIG. 33A, the support tubes 310 may be made of any suitable polymer material, bio-compatible polymer material, or metallic material (e.g., polyimide, stainless steel, Nitinol, etc.). The inner layer or inner tube 312 may be made of any suitable polymer material or bio-compatible polymer material (e.g., nylon-12, Pebax®, Pellathane, Polycarbonate, etc.). In addition, the elongate instrument 300 may include a control ring 316 that may be secured near a distal portion of the elongate instrument 300. In various embodiments, the proximal end or portion of one or more pull wires 314 may be operatively coupled to various mechanisms (e.g., gears, pulleys, etc.) of a control unit or splayer (such as the drivable instrument 182) of the instrument assembly. The pull wire 314 may be a metallic wire, cable or thread, or it may be a polymeric wire, cable or thread. The pull wire 314 may also be made of natural or organic materials or fibers. The pull wire 314 may be any type of suitable wire, cable or thread capable of supporting various kinds of loads without deformation, significant deformation, or breakage. The distal end or portion of one or more pull wires 314 may be anchored or mounted to the control ring 316, such that operation of the pull wires 314 by the control unit or splayer may apply force or tension to the control ring 316 which may steer or articulate (e.g., up, down, pitch, yaw, or any direction in-between) certain section or portion (e.g., distal section) of the elongate instrument 300. In other embodiments, no control ring may be used, instead the distal portion of the pull wires may be attached directly to a section or portion of the elongate instrument 300 where it may be steered, articulated, or bent. The wires may be crimped, soldered, welded or interlocked in any suitable manner to a specific location on a bending section or portion of the elongate instrument 300. The control ring 316 or the attachment point(s) may be located at any location, section, portion, or region along the length of the elongate instrument 300. Operation of the pull wires 314 may steer or articulate any of the location, section, portion, or region of the elongate instrument 300, which may in effect provide or define various bend radii for the articulated portion of the elongate instrument 300. In addition, in some embodiments there may be more than one control ring 316 mounted or installed to the elongate instrument 300 or more than one control wire attachment control locations, sections, or portions for controlling, steering, or articulating more than one section or portion of the elongate instrument 300. In some embodiments, the flexible and steerable elongate instrument 300 having more than one control rings 316 or more than one control sections may be steered, articulated, or deflected into various complex shapes or curvatures (e.g., "S" curved shapes or "J" curved shapes, etc.). For example, the steerable elongate instrument 300 may be steered, articulated, or deflected into various complex shapes or curvatures that may conform to various complex shapes or curvatures of internal pathways of a patient to reach a target tissue structure of an organ inside the patient.

In some embodiments, one or more portions of the flex tubes 306 may be incorporated or coupled to the wall of the catheter 300 and such incorporation or coupling may be used for multiple functional purposes. For example, the coupling of the flex tubes 306 to the elongate instrument 300 may be used to support articulation forces as the elongate instrument or catheter is steered or articulated. Also, in some embodiments, proximal portions of the flex tubes 306 may be slidable relative to the elongate instrument 300. As one or more of the pull wires 314 are operated by the control unit to steer or articulate the elongate instrument 300, the articulation or steering forces may be substantially transmitted along the body of the elongate instrument 300 from the portion (e.g., distal portion) of the elongate instrument 300 where the distal end or portion of the pull wires 314 may be anchored to the proximal portion of the elongate instrument 300. Since the flex tubes 306 are incorporated or coupled to the wall of the elongate instrument 300 and the flex tubes 306 are substantially configured to support axial loading, the articulation or steering loads may be decoupled from the elongate instrument 300 at the point or location where the flex tubes 306 are incorporated or coupled to the wall of the elongate instrument 300. Hence, the proximal portion of the elongate instrument may be substantially unaffected by the articulation or steering of the particular section or portion (e.g., distal section or portion) of the elongate instrument 300. The proximal portion of the elongate instrument may remain substantially flexible and pliable even when a particular portion (e.g., distal portion) of the elongate instrument is being articulated or steered. The above feature allows tension to be applied to steer the distal section of the elongate instrument 300 while steering force is isolated from the proximal section of the elongate instrument 300 (and as a result, a bending stiffness of the proximal section of the elongate instrument 300 is not significantly affected). The above feature also allows tension to be applied to steer the distal section of the elongate instrument 300 without creating unwanted curvature at the proximal section of the elongate instrument 300, and thus, a shape of the proximal section of the elongate instrument 300 is unaffected by the steering of the distal section. As such, an operator or surgeon may easily manipulate the elongate instrument 300 and urge it to conform, adopt, or match the various shape or curvatures of the internal pathways of a patient while the elongate instrument is being advanced and steered to reach various tissue structures or target sites inside a patient. In another example or application of the elongate instrument 300, the flex tubes 306 may be used as a structural support member to the catheter 300; in particular, when the flex tubes are stiffened by tensioning pull wires that may be attached to the flex tubes 306. In such application, the flex tubes 306 may support not only axial forces or loads, but also lateral forces or loads. As such, the flex tubes may increase the lateral as well as bending stiffness of at least a portion or section of the elongate instrument 300. In addition, the flex tubes 306 may also affect the bending radius of at least a portion or section of the elongate instrument 300 as the elongate instrument is steered, articulated, or manipulated.

In some embodiments, each flex tubes 306 may be located closer to a wall of the elongate instrument 300 than an axis (e.g., central axis) of the elongate instrument 300. For example, in some variations, each flex tubes 306 may be located close to a wall of the elongate instrument 300. This allows the elongate instrument 300 to have a central working lumen extending therethrough. In some cases, such central working lumen may have a cross sectional area that is at least 30% of the cross sectional area of the elongate instrument 300. Also, in one or more of the embodiments described herein, each flex tube 306 may have a proximal tip that is proximal to a proximal tip of the tubular body of the elongate instrument 300.

Figure 33B:
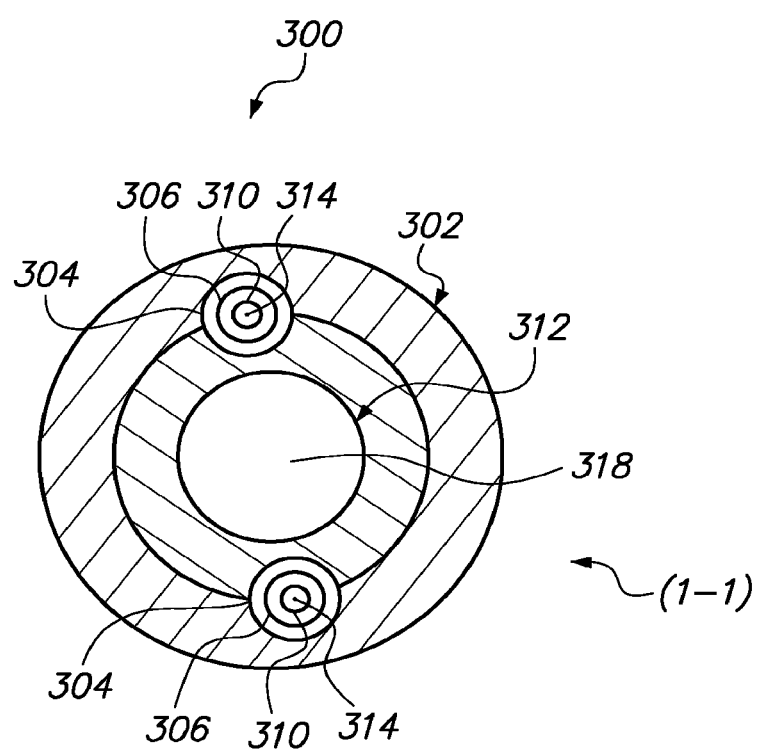
FIG. 33B illustrates another cross-sectional view (View 1-1) of a flexible and steerable elongate instrument with variable or changeable shape control and support elements in accordance with one embodiment.

FIG. 33B illustrates another cross-sectional view (View 1-1) of a section or portion of a steerable elongate instrument or catheter 300. As illustrated in FIG. 33B, the components of the elongate instrument 300 may be contained within or between the outer layer of material or outer tube 302 and the inner layer of material or inner tube 312. A primary, main, central, or working lumen 318 may be provided or defined by the inner layer of material or inner tube 312. The main lumen or central lumen 318 may be used to pass surgical instruments from the proximal end to the distal end of the elongate instrument 300 for performing various minimally invasive surgical procedures. Many of the components of the elongate instrument 300, e.g., operational tubes 304, flexible tubes 306, push tubes 308, and support tubes 310, are disposed within the minor, secondary, or peripheral lumens in the body structure of the elongate instrument, as illustrated in FIG. 33A and FIG. 33B. In some embodiments, one or more pull wires 314 may be disposed within lumens of the support tubes 310, lumens of the flex tubes 306, and lumens of the push tubes 308. As illustrated in FIG. 33A, the distal end or portion of the support tubes 310 may be secured or anchored near the distal portion of the elongate instrument 300 and the proximal end of the support tubes 310 may be slidably coupled to the distal end or portion of the flex tubes 306. In one embodiment, the distal portion of the flex tubes 306 may be secured at respective anchor points or regions 320 of the elongate instrument 300. Anchoring the flex tubes 306 to the elongate instrument 300 may provide the connections or couplings that allow force or load to be transferred from the flex tubes 306 to the elongate instrument 300 when force or load is applied to the flex tubes. For example, in some embodiments the flex tubes 306 may be actively controlled, that is one or more push tubes 308 or control members 308 may be configured to push against respective flex tubes 306. The applied force from the push tubes or control members 308 may be transmitted by way of the anchoring points 320 through the flex tubes 306 to the elongated instrument 300. In this way, at least a portion of the elongate instrument 300 may be steered or shaped by the push tubes or control members 308. Similarly, articulation or steering forces or loads may be transferred or coupled at the anchor points 320 from one portion (e.g., distal portion) of the elongate instrument 300 to the flex tubes 306, such that the flex tubes 306 may act as load bearing support elements for another portion (e.g., proximal portion) of the elongate instrument 300 where the force or load may be decoupled or not transmitted. In other words, the anchor points 320 may function as coupling points from one portion (e.g., distal portion) of the elongate instrument 300 to the flex tubes 306 where force or load may be transferred from one portion (e.g., distal portion) of the elongate instrument to the flex tubes. Similarly, the anchor points 320 may also function as decoupling points between one portion (e.g., distal portion) of the elongate instrument 300 to another portion (e.g., proximal portion) of the elongate instrument 300 where force or load may be decoupled or not transferred from one portion (e.g., distal portion) of the elongate instrument to another portion (e.g., proximal portion) of the elongate instrument.

In some embodiments, the location of the anchor points 320 may be varied to control the radius of curvature of a bending section of the elongate instrument 300 as the elongate instrument is articulated or steered. In some embodiments, the flex tubes 306 may be anchored at substantially the same points or regions of the elongated instrument 300. In some embodiments, the flex tubes 306 may be anchored at substantially different points or regions of the elongate instrument 300 to affect the bend radius of various portions of the elongate instrument 300 and/or various directions of steering or bending. The flex tubes 306 may be secured to the elongate instrument 300 in any suitable manner. In some embodiments, the distal portion of the flex tubes 306 may be fused with the material of the outer layer or outer tube 302, such as by thermal fusion. Similarly, the material of the outer layer or outer tube 302 may be fused to the flex tubes 306. For example, the flex tubes 306 may be fused to the outer layer or outer tube 302 at various places where it is not covered by the operational tubes 304, as illustrated in FIG. 33A. In some embodiments, the elongate instrument may be configured with displacement control of the flex members 306. That is, a flex tube 306 may not be fixedly coupled to the elongate instrument, instead it may be displaced along the length of the elongate instrument 300. Once the flex tube 306 is displaced to a desired location, the distal portion of the flex tube 306 may be secured or coupled to the elongate instrument 300 by a deployable and retractable anchor. The displacement of proximal portion of the flex tube 306 may be controlled by the push tube or control member 308. The deployable anchor may be deployed to couple the flex tube 306 to a particular anchor point at a particular location on the elongate instrument. The anchor may also be retracted such that the flex tube 306 may be disengaged or separated from the elongate instrument 300 such that it may be displaced to a different location along the elongate instrument 300.

Figure 34A:
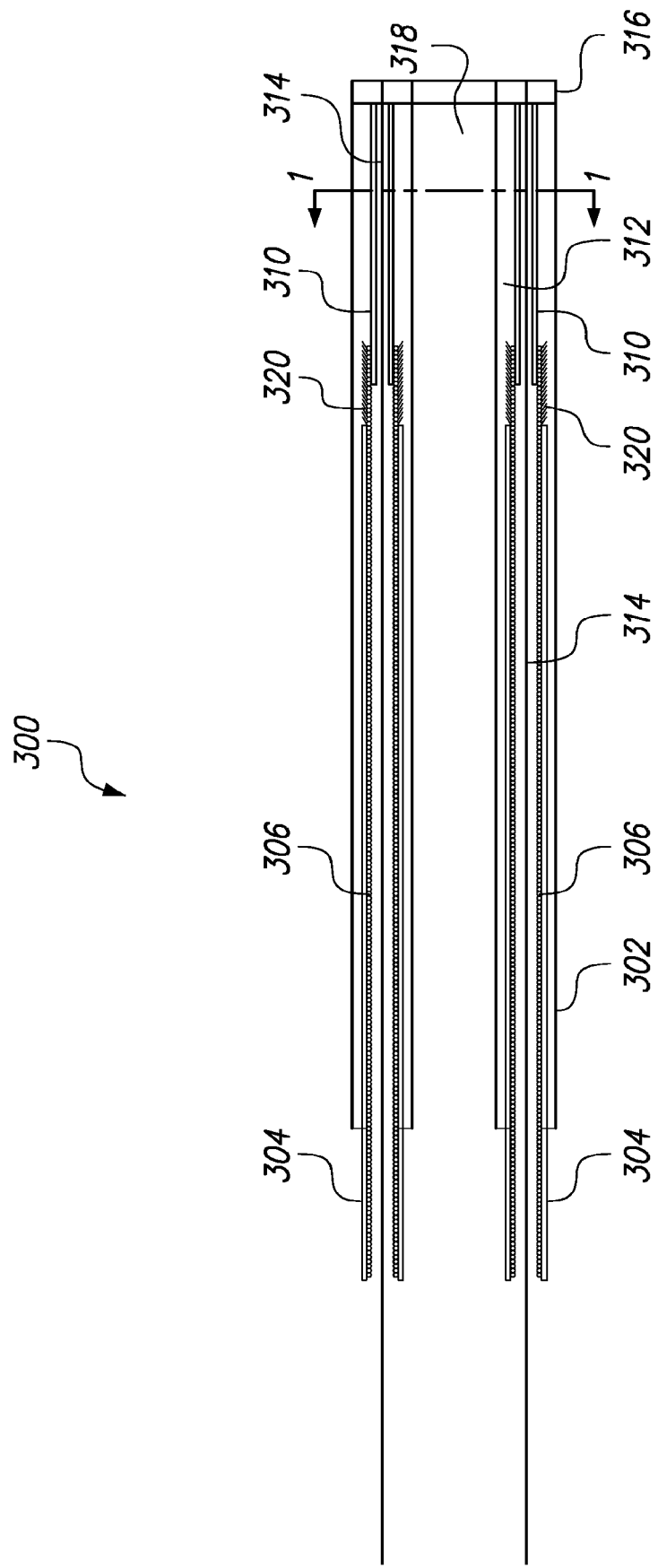
FIG. 34A illustrates an elongate instrument with passively controlled flex member in accordance with one embodiment.

As illustrated in FIG. 34A, an elongate instrument 300 with passively controlled flex members 300 may be similarly configured as the elongate instrument structure illustrated in FIG. 33A with the exception that the proximal portion of the flex members 300 may be fixedly coupled to the body of the elongate instrument, the control unit or splayer (such as the drivable instrument 182), or some other structural element or component. In some embodiments, the push tube or control member 308 may not be included as a component of the elongate instrument 300 for a passively controlled flex member. In the passively controlled configuration, the flex members 306 may include a service or buffer loop 320, as more clearly illustrated in FIG. 34B. The service loop or buffer loop 320 on the flex members 306 may provide the extra service length or buffer length needed to isolate the articulation loads as the elongate instrument 300 is pushed through the anatomy, articulated or steered.

Figure 34B:
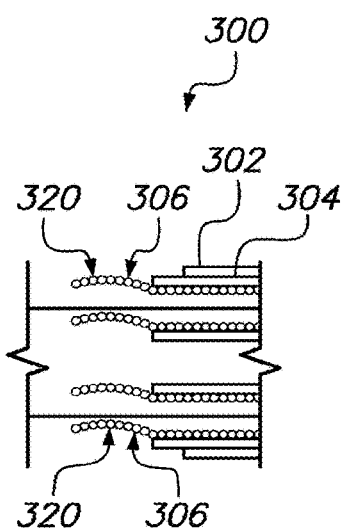
FIG. 34B illustrates a passively controlled flex member with a service or buffer loop in accordance with one embodiment.
Figure 34C:
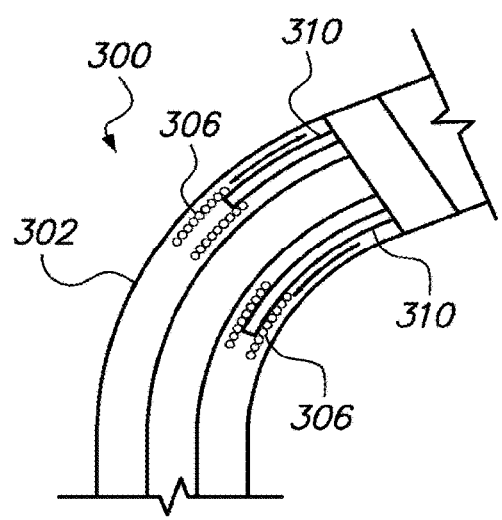
FIG. 34C illustrates support tubes or support members sliding along the flex tubes or flex members in accordance with one embodiment.

As the elongate instrument is pushed through the anatomy, steered or articulated, the support tubes 310 in the distal section may slide along the flex tubes 306 as indicated by the arrows in FIG. 34C. The support tubes 310 may provide a lumen or path for the pull wires 314 to connect to the distal section of the catheter. The support tubes 310 may also provide some amount of structural rigidity or support to the distal portion of the elongate instrument 300. In some embodiments, the elongate instrument 300 may not include any support tubes 310. In some embodiments, one or more flex tubes 306 may be extended further into the distal portion of the elongate instrument 300 to provide some structural rigidity or support to the distal portion of the elongate instrument. In some embodiments, the flex tubes 306 may be substantially more stiff or more rigid than the support tubes 310, such that when one or more flex tubes 306 are used as support structures to reinforce the distal portion of the elongate instrument 300, the distal portion of the elongate instrument may be substantially more stiff or more rigid than when it is supported by the support tubes 310. In some embodiments, the flex tube 306 may provide substantially the same or similar stiffness or structural support as the support tubes 310, such that there may not be any significant difference if the flex tubes 306 or support tubes 310 are used to provide structural support to the distal portion of the elongate instrument 300. In some embodiments, the flex tubes 306 may be substantially more flexible than the support tubes 310, such that the distal portion of the elongate instrument may be substantially more flexible or less rigid than when it is supported by the flex tubes 306.

Figure 34D:
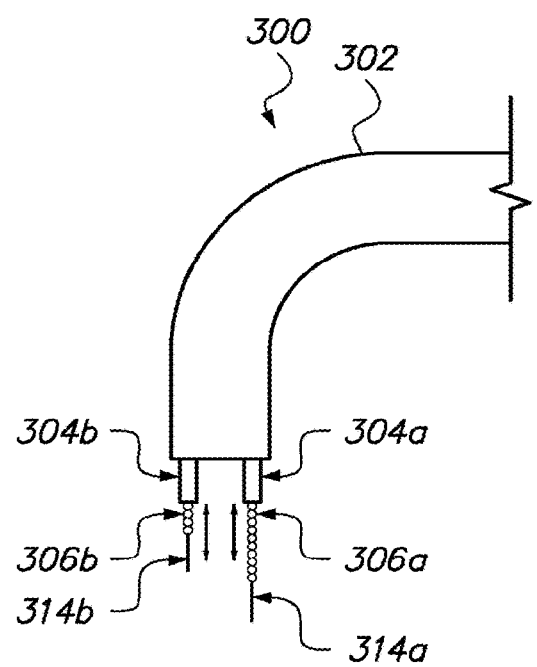
FIG. 34D illustrates slidable couplings of variable shape control and support components near the proximal section of a flexible and steerable elongate instrument in accordance with one embodiment.

Referring back to FIG. 34A, the flex tubes 306 may be slidably coupled to the operational tubes 304 while fixed at the distal end 320. As the elongate instrument 300 is steered or articulated, or as the catheter is advanced through the natural curvature of the body lumens, the flex tubes 306 may slide along the operational tubes 304 as indicated by the arrows illustrated in FIG. 34D. In one scenario, for example, the elongate instrument 300 may be steered by operating or applying tension to one of the pull wires (e.g., 314A) through operation of one or more gears and/or pulleys in the control unit or splayer. The tension on one of the pull wires (e.g., 314A) may cause the elongate instrument 300 to bend, as illustrated in FIG. 34D. The inside edge or inside region of the bend may be contracted or foreshortened, while the outside edge or outside region of the bend may be lengthened or stretched. The bend of the elongate instrument as described may cause one of the flex tubes (e.g., 306A) to slide "out" near the proximal portion of the elongate instrument 300 at the contracted or foreshorten edge or region. In this same example, another one of the flex tubes (e.g., 306B) may slide "in" near the proximal portion of the elongate instrument 300 at the lengthened or stretched edge or region, as illustrated in FIG. 34D. In order to accommodate the sliding of "in" and "out" of the flex tubes 306, the flex tubes may include a service loop or buffer loop 320 to allow for these "in" and "out" displacements or movements of the flex tubes 306. As discussed, the flex tubes 306 may be passively constrained or restrained. The flex tubes 306 may be constrained or restrained by being coupled to the elongate instrument 300, the control unit, or splayer. In addition, the flex tubes 306 may be constrained or restrained by hard-stops, tethers, etc. In some embodiments, the operational tubes 304 may be configured or allowed to float or slide substantially freely relative to the outer layer or outer tube 302. In some other embodiments, the operational tubes 304 may not be configured or allowed to float or slide substantially freely relative to the outer layer or outer tube 302.

FIG. 35A through FIG. 35C illustrate the operation of a substantially flexible and steerable elongate instrument in accordance with one embodiment. FIG. 35A illustrates an elongate instrument 300 of an instrument assembly in a substantially neutral state. In this example, the elongate instrument 300 includes an outer body 302, two sets of support tubes (not shown), operational tubes 304A, 304B, flex tubes 306A, 306B, and pull wires 308A, 308B. Each set of support tubes, operational tubes 304A, 304B, flex tubes 306A, 306B, and pull wires 308A and 308B) may be substantially axially aligned, and the pull wires 308A, 308B may be coupled to a control ring (not shown) or mounting points that are located at the distal section or portion of the elongate instrument 300. As illustrated in FIG. 35A, in the neutral state the flex tubes 306A, 306B and pull wires 308A, 308B may extend out of the operational tubes 304A, 304B at about the same amount or distance. As the substantially flexible and steerable elongate instrument 300 is advanced into the anatomy and natural pathway (e.g., blood vessel, gastrointestinal tract, etc.) of a patient, it may take on the shape of the natural pathway, as illustrated in FIG. 35B. In this example, the proximal section 338 of the elongate instrument may be bent at a curvature induced by the natural pathway (e.g., blood vessel, gastrointestinal tract, etc.), while the distal section 336 may remain relatively straight or in a substantially neutral state. Due to the bend at the proximal section 338, the flex tube 306A and pull wire 308A may slide "out" of the operational tube 304A near the inside edge or inside region of the bend as it may be contracted or foreshortened, as indicated by the arrow illustrated in FIG. 36B. At the same time, due to the bend at the proximal section 338, the flex tube 306B and pull wire 308B may slide "in" to the operational tube 304B near the outside edge or outside region of the bend as it may be lengthened or stretched, as indicated by the arrow illustrated in FIG. 35B. As may be appreciated, it may be advantageous to maintain the induced shape or curvature of the proximal section 338 of the elongate instrument 300 and at the same time articulate or steer the distal section 336 of the elongate instrument 300 to treat a target site or toward a different direction down the natural pathway.

In other embodiments of an elongate instrument where flex tube or similar control or support structure may not be used, operating or tensioning a pull wire on the outside edge of a bend may cause the elongate instrument to rotate or twist as the pull wire may tend to rotate the distal section of the elongate instrument until the pull wire is at the inside edge of the bend; this rotation or twist phenomenon or occurrence is known as curve alignment.

Figure 36C:
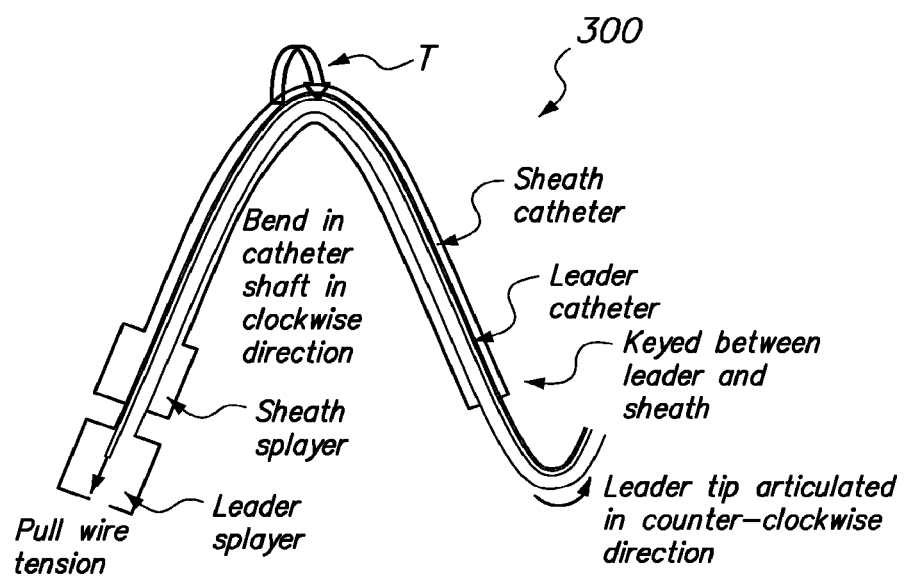
FIG. 36C illustrates an embodiment of an elongate instrument that does not have coil pipes.

FIG. 36C illustrates an embodiment of an elongate instrument or catheter 300 that does not have coil pipes in the wall of the catheter. When the proximal section of the catheter is curved (as it tracked through curved anatomy), and the catheter distal section is required to be articulated in a direction that is not aligned with the curvature in the shaft, a wire on the outside of the bend is pulled. A torsional load (T) is applied to shaft as tension increases on the pull-wire on the outside of the bend. This torsional load rotates the shaft until the wire being pulled is on the inside of the bend. This un-intentional rotation of the shaft causes instability of the catheter tip and prevents the doctor from being able to articulate the catheter tip in the direction shown. The phenomenon is known as curve alignment because the wire that is under tension is putting a compressive force on both the proximal and distal sections and so both the proximal and distal curvature will attempt to align in order to achieve lowest energy state.

Embodiments described herein may substantially eliminate this problem by providing support structures such as flex tubes that could prevent curve alignment and substantially prevent or eliminate unwanted rotation or twist of the catheter. In other words, the pull wires, flex tubes, and the distal anchor points of the pull wires at the control ring or the body of the elongate instrument may all be substantially aligned, such that operating or tensioning of the pull wires would allow the elongate instrument to bend in a substantially aligned or neutral configuration with the longitudinal axis of the pull wire and flex tube. In this configuration, there may not be any component or vector of force or load that could cause the elongate instrument to rotate or twist resulting in curve alignment as the elongate instrument is steered or bent.

Figure 36D:
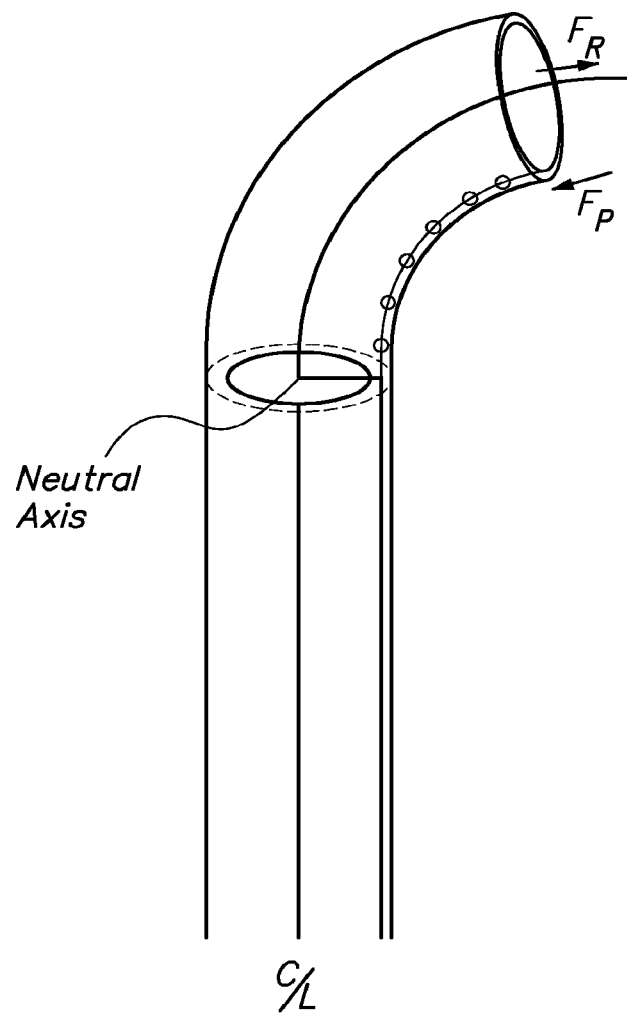
FIG. 36D illustrates a mechanics of a coil pipe in accordance with some embodiments.

The design presented in FIG. 36D and with service loops on the proximal end of the coils as per FIG. 34B substantially eliminates or prevents curve alignment and the catheter may be biased, steered, or articulated in specific planes, e.g., X-Plane, Y-Plane, Z-Plane, of articulation. By using flex tubes with service loops as support structures or "backbones" to the catheter shaft, the path length of the wire under tension does not change as the proximal shaft is curved. The flex tubes isolate the forces from the proximal section and therefore there is no tendancy to curve align the distal section with the proximal section and hence no rotation of the shaft. In FIG. 36A, as a pull wire is operated (indicated by the arrow) to steer the elongate instrument, the flex tube supports the pull wire and prevent it from moving to the inside edge of the bend, which may produce a force vector that could cause the elongate instrument to twist or rotate. In this example, the operation of the pull wire causes the distal section of the elongate instrument to be steered or articulated in a substantially upward movement, e.g., the direction or vector of articulation is in the Y-Plane. Similarly, as illustrated in FIG. 36B, as a pull wire is operated (indicated by the arrow) to steer the elongate instrument, the flex tube supports the pull wire, maintain its alignment to the longitudinal axis, and prevent it from moving to the inside edge of the bend, which may produce a force vector that could cause the elongate instrument to twist or rotate. In this example, the operation of the pull wire causes the distal section of the elongate instrument to be steered or articulated in a substantial sideway or rightward movement, e.g., the direction or vector of articulation is in the X-Plane.

It should be noted that the catheter 300 is not limited to the configuration described previously, and that the catheter 300 may have other configurations in other embodiments.

Figure 37A:
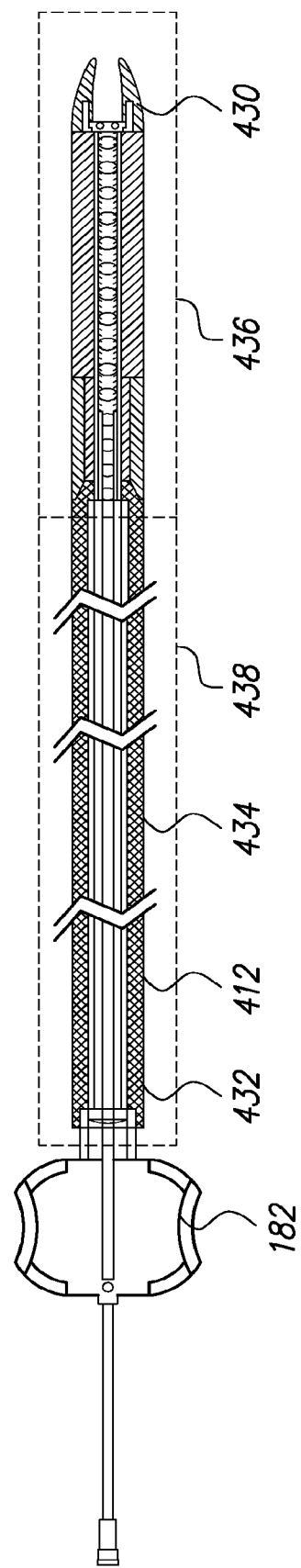

FIG. 37A illustrates a catheter 412 in accordance with other embodiments. The catheter 412 has a distal end 430, a proximal end 432 coupled to the drivable assembly 182, and a body 434 extending between the distal end 430 and the proximal end 432. In some embodiments, the proximal end 432 is fixedly secured to a hypotube that is in turn fixedly secured to the drivable assembly 182. The catheter 412 has a distal section 436 that articulates in response to control by the drivable assembly 182 and based on commands received at the workstation 2 or the bedside control 402.

FIG. 37B illustrates portion of the catheter 412 in further detail. As shown in the figure, the distal section 436 of the catheter 412 includes a spine 440 defining a lumen 441 for accommodating an instrument, such as a guidewire. The spine 440 is configured to provide support for the catheter 412, and specific bending pivot point for the catheter 412. The spine 440 may be made from a coil, or a tube with cutout slots to provide flexibility for the spine 440. As shown in the figure, the spine 440 extends partially into the proximal section 438 of the catheter 412. Alternatively, the spine 440 may extend all the way to the proximal end 432 of the catheter 412.

The catheter 412 also includes a plurality of coils 442 positioned radially relative to the spine 440. The coils 442 may be used to implement the flex tubes 306 in some embodiments. The coils 442 are configured (e.g., sized and/or shaped) to house respective control wires that are attached at their distal ends to a control ring 444, and at their proximal ends to the drivable assembly 182. In other embodiments, the each tube 306 may not be implemented using the coil 442, and may be implemented using other elongate elements, such as a continuous tube with a smooth continuous surface, a wire cage having a tubular configuration, etc.

In some embodiments, the control wire coils 442 change coil pitch from the distal section 436 to the proximal section 438. In particular, the coil loops of the coils 442 are more spaced apart at the distal section 436, but the coil loops of the coils 448 are closer together at the proximal section 438. Such configuration is advantageous in that it provides a more flexible distal section 436 so that the distal section 436 may be bent to a more tight curve. In one implementation, the coils 442 may have an open pitch while the coils 448 may have a closed pitch. In such cases, the coils 448 are wound tightly so that they are in a naturally compressed state. In such configuration, when the steering wires are pulled in tension, the shaft does not bend and the forces are transmitted to the proximal end of the catheter. Alternatively, both the coils 442, 448 may have closed pitch. In some embodiments, each distal coil 442 and its corresponding proximal coil 448 may be parts of a same coil structure, wherein the distal portion of the coil structure is constructed to have coil loops that are more spaced apart than a proximal portion of the coil structure. In other embodiments, the distal coil 442 may be a separate component that is connected to the proximal coil 448 (e.g., via a weld, adhesive, etc.).

In some embodiments, the coil 442 is anchored to the distal section 436 (e.g., the distal end), while the coil 448 is slidable relative to the proximal section 438. In other embodiments in which the coils 442, 448 are parts of a same coil, the coil may be fixed to the catheter body at the transition between the proximal section 438 and the bendable distal section 436. In some embodiments, the coil 442 is anchored to the distal section 436 by anchoring at least a lengthwise portion of a distal portion of the coil 442 to the distal section 436. The lengthwise portion may be at least 10 mm in some embodiments, and more preferably, at least 20 mm, and even more preferably, at least 30 mm. In other embodiments, the lengthwise portion may be at least 5% of a combined length of the coils 442, 448, and more preferably at least 10%, and even more preferably at least 20% of the combined length of the coils 442, 448. In other embodiments in which the coils 442, 448 are parts of a same coil, the lengthwise portion may be at least 5% of a total length of the coil, and more preferably at least 10%, and even more preferably at least 20% of the total length of the coil.

During use, the drivable assembly 182 may apply tension to one or more control wires to thereby cause a corresponding bending at the distal section 436 of the catheter 412. Although two control wire coils 442 for housing two respective control wires are shown, in other embodiments, the catheter 412 may have only one coil 442 for housing one control wire, or more than two coils 442 (e.g., four coils 442) for housing more than two control wires (e.g., four control wires). The control ring 444 is embedded within a soft tip 445, which is configured to minimize injury to tissue as the catheter 412 is advanced within the patient.

In some embodiments, the catheter 412 further includes an outer jacket 446 surrounding the coils 442. The outer jacket 446 is a low durometer material for providing flexibility for the articulating distal section 436. In some embodiments, the outer jacket 446 may be made from 35D or 25D Pebax, or from 70A or 80A Polyurethane. In other embodiments, the outer jacket 446 may be made from other materials as long as the distal section 436 is sufficiently flexible for it to be articulated.

In some embodiments, the outer jacket material 442 extends partially into the space that is between the loops of the coil 442 (FIG. 37C). Such configuration prevents the control wire from contacting the material of the outer jacket material 442, thereby allowing the control wire to be more easily slide within the lumen of the coil 442. In other embodiments, the outer jacket material 442 may not extend partially into the space that is between the loops of the coil 442. Instead, the outer jacket material 442 may be touching only the outer side of the coil 442. This may allow the coils 442 to move relative to the outer jacket 446, thereby improving the flexibility of the distal section 436. In further embodiments, the outer jacket material 442 may extend completely into the space that is between the loops of the coil 442 (FIG. 37D).

The above configurations shown in FIGS. 37C and 37D may be accomplished through a manufacturing process. For example, during a manufacturing process, a mandrel may be placed inside the coils 442 to ensure that the lumens remain unobstructed while the jacket is being laminated. The mandrel is then removed post lamination to leave a lumen (through the expanded coil encased in plastic) that the smaller diameter steering wire can slide through freely with minimum friction. In some embodiments, by varying the size of the mandrel in the lumen, the amount of encapsulation of the coils 442 with the plastic can be varied. For example, a 0.01" mandrel inside a 0.014" internal diameter coil will lead to a 0.002" of plastic inserted in through the coils 448. On the other hand, a 0.014" mandrel placed inside a 0.014" coil will ensure that no plastic encapsulates the inside surface of the coil 442. Limiting the plastic that is inserted through the coils 442 can reduce the friction when the steering wire is pulled since the wire slides more freely on the coils than on the softer plastic, as discussed. Thus, the catheter designer can trade off friction in the control wire lumen with structural integrity of the coils 442 by varying the outer diameter of the mandrel used in the manufacturing process.

Also, in some embodiments, during the design of the catheter 412, the pitch of the coil 442 and/or the size of the coil 442 may be selected to define an amount of maximum bending for the catheter 412. As shown in FIG. 37E, as the distal section 436 of the catheter 412 is being bent due to a tensioning of a control wire, the coil loops of the coil 442 that is housing the control wire will move closer to each other. As a result, the material 456 of the outer jacket 446 that is between the coil loops will undergo compression. By varying the pitch of the coil 442 during the design of the catheter 412, the amount of material 456 between the loops that would undergo compression would vary. Generally, the more material 456 that is between the loops (i.e., more spaced apart loops), the more bending will be allowed for the catheter 412, and vice versa. Also, in other embodiments in which there is no jacket material between the loops of the coil 442, the same design principle may apply. In such cases, the maximum amount of bending for the catheter 412 may be achieved when the distal section 436 is bent so much that the coil loops of the coil 442 abuts against each other. When the coils 442 abut against each other, no further articulation will be possible. Any additional force on the control wire will be transmitted directly and fully to the compressed coils 442 rather than the spine or the plastic of the articulation section. This has the benefit of preventing over-articulation that may lead to potential spine fracture, plastic deformation of the spine, or damage to the distal jacket. Thus, during the design of the catheter 412, the loops of the coil 442 may be spaced apart further if more bending is desired for the catheter 412, or spaced closer if less bending is desired. For example, a coil made of 0.003" wire with a 0.009" pitch will allow articulation of the catheter 412 to a smaller radius than a coil with a 0.006" pitch, for example.

In some embodiments, by varying the pitch of the coils 442, the bend shape at the distal section of the catheter 412 may be adjusted. A more closely-spaced section of coils (e.g., 0.006") on the proximal end will result in a larger minimum radius—i.e., that section will remain straighter than regions with a larger coil pitch (e.g., 0.009" pitch) on the distal end. This technique may be used to get small bend radii at the very distal end of the catheter 412, which can be used to reach small vessels with acute take off angles.

It should be noted that use of the coils 442 as control wire lumens in the articulating section has several additional advantages. The coils 442 have both low axial and bending stiffnesses. This lowers articulation forces since the lumens on the inside and outside of the bend will more easily contract and expand, respectively. The coils 442 also have relatively high radial strength, ensuring that they do not collapse and pinch the control wire, which would undesirably increase the wire forces. Also, the coil's 442 ability to expand and contract will decrease the resistance to bending, and will yield a more uniform bend when compared to traditional polyimide lumen constructions. In addition, the coil 442 will provide a load-bearing surface that will radially distribute the control wire load about the jacket. The use of coils 442 will also allow the jacket material to be melted around the coils 442 to thereby secure the coils 442. This will eliminate the need to braid the coils 442 onto a component of the catheter 412. The elimination of braid will in turn lower the resistance to bending (i.e., lowering the bending stiffness) because different layers may shift relative to each other with a lower force, and will also yield a lower articulation force for the catheter 412 and/or smaller bending radius for the catheter 412. However, in other embodiments, the coil 442 may still be braided to a reinforcement layer, such as a wire mesh or a spine. Alternatively, bands of higher durometer (e.g. 72D) crosslinked Pebax may be used to support the expanded coils and fix them to the spine. Cross linked Pebax has improved mechanical properties and greater dimensional stability and physical toughness compared to regular Pebax and ensures the coils are adequately fixed to the spine.

Returning to FIG. 37B, as the distal section 436 transitions to the proximal section 438, the material of the outer jacket also changes. In particular, proximal to the outer jacket 446, the catheter 412 includes another outer jacket 454 that is stiffer than the material of the distal outer jacket 446. In some embodiments, the outer jacket 454 may be made from a 40D or 55D Pebax. In other embodiments, the outer jacket 454 may be made from other materials as long as they are stiffer than that of the distal outer jacket 446. In further embodiments, the outer jacket 454 may be made from the same material as that for the outer jacket 446. In such cases, the outer jacket 446, 450 may be formed together. Thus, the designer may vary the position of the jacket transition relative to the transition in the coil pipe spacing to get a gradual change in stiffness and hence curvature between the proximal and distal sections. This reduces the likelihood of any kink points in the catheter.

As shown in the figure, the proximal section 438 of the catheter 412 includes the proximal control wire coils 448. The proximal section 438 of the catheter 412 also includes an inner jacket 452 surrounding the coils 448, and an outer jacket 454 surrounding the inner jacket 452. In some embodiments, the inner and outer jackets 452, 454 are made from different materials. In other embodiments, the inner and outer jackets 452, 454 may be made from the same materials. Also, in other embodiments, the inner jacket 452 and/or the outer jacket 454 may be made from a material that is stiffer than the material for the outer jacket 446 at the distal section 436 and/or the outer jacket at the transition section. In further embodiments, the inner jacket 452 and/or the outer jacket 454 may be made from the same material as the outer jacket at the transition section. The embodiments having the outer jacket and the inner jacket allow the designer flexibility to vary the stiffness of the catheter as desired throughout the length of the catheter, while at the same time ensuring that the steering lumens are encapsulated, that no braid is exposed, and that the structural integrity of the shaft is maintained. In addition, in one or more of the embodiments described herein the proximal section 438 of the catheter 412 may optionally further include a braid surrounding the coils 448 (e.g., embedded within the way of the jacket 452 or jacket 454) for strengthening and stiffening the proximal section 438. The braid can be stainless steel flat wire or round wire. The braid angle and pic count can be optimized to give the required stiffness and flexibility. The braid may have a constant pattern throughout the proximal section, or there may be a transition in the braid to enable higher bending stiffness at the proximal end (compared to the distal end) and higher flexibility at the distal end (compared to the proximal end).

Figure 38:
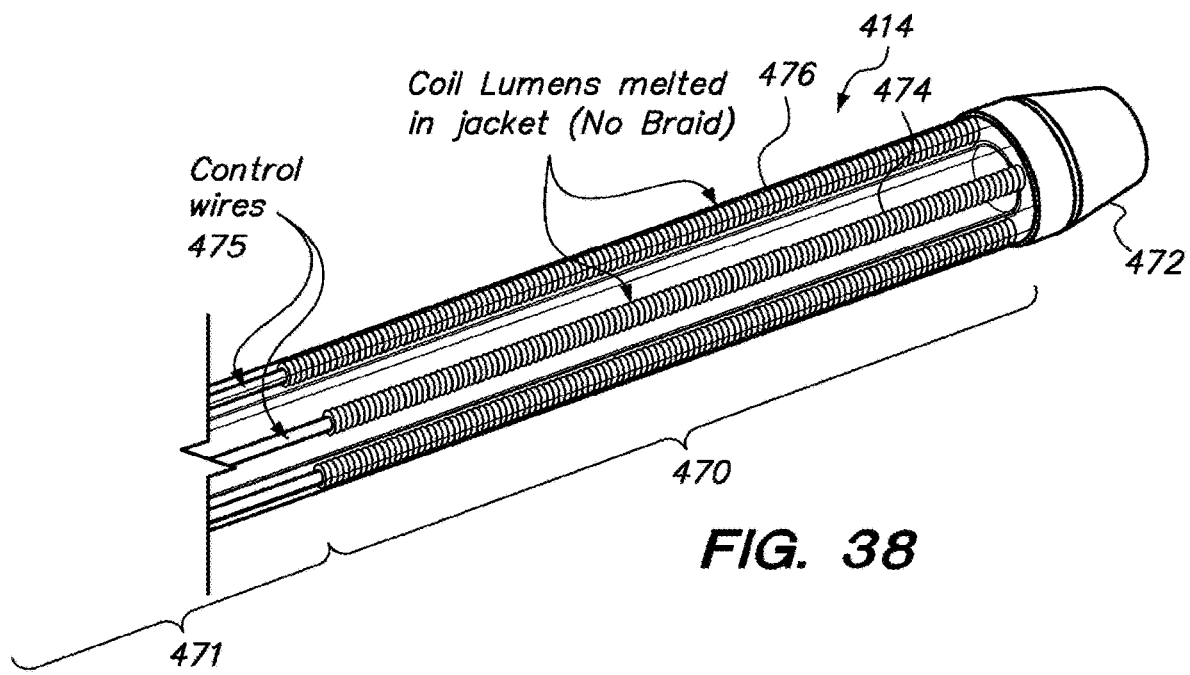

The sheath 414 will now be described. FIG. 38 illustrates the sheath 414 in accordance with some embodiments. The sheath 414 includes a bendable distal section 470, a proximal section 471, and a distal soft tip 472. The distal section 470 that is more flexible than the proximal section 471. During use, in response to control by the drivable assembly 184, the distal section 470 will bend based on commands received at the workstation 2 or the bedside control 402. In some embodiments, the proximal end 471 is fixedly secured to a hypotube that is in turn fixedly secured to the drivable assembly 184.

Figure 39:
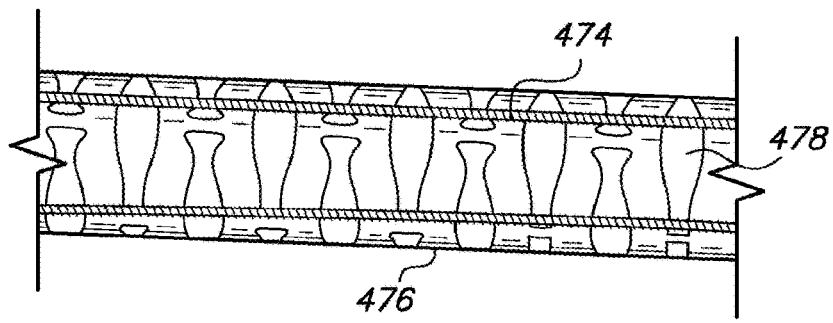
Figure 40:
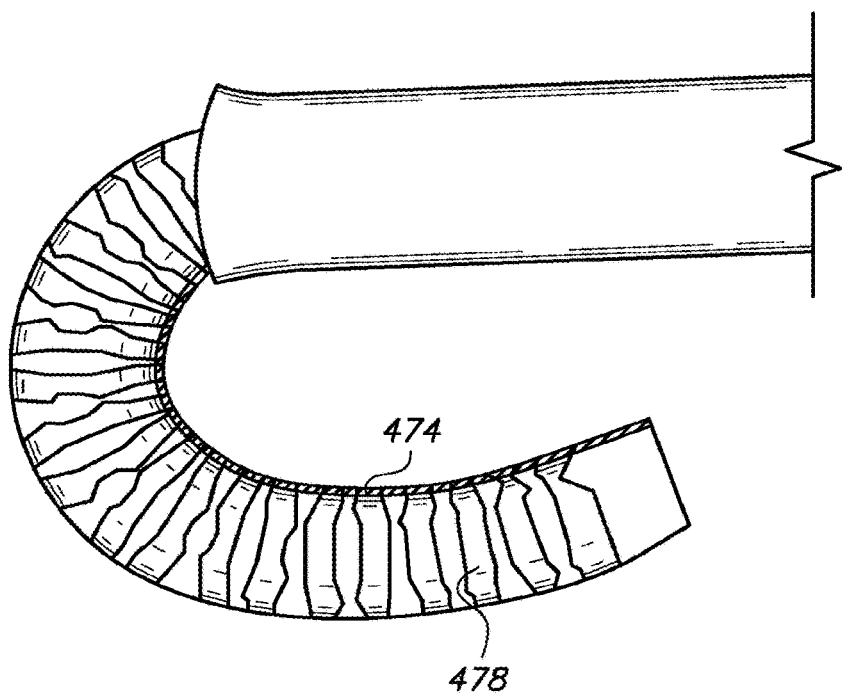

As shown in FIGS. 39 and 40, the sheath 414 may also include a spine 478 in the distal section defining a lumen 441 for accommodating an instrument, such as the catheter 412. The spine 478 is configured to provide support for the sheath 414, and specific bending pivot point for the sheath 414. The spine 478 may be made from a coil, or a tube with cutout slots to provide flexibility for the spine 478.

As shown in FIGS. 38 and 39, the sheath 414 may also include a plurality of coils 474 positioned radially relative to the spine 478. The coils 474 are configured (e.g., sized and/or shaped) to house respective control wires 475 that are attached at their distal ends to the tip 472, and at their proximal ends to the drivable assembly 184. During use, the drivable assembly 184 may apply tension to one or more control wires 475 to thereby cause a corresponding bending at the distal section 470 of the sheath 414. Although four control wire coils 474 for housing four respective control wires are shown, in other embodiments, the sheath 414 may have less than four coils 474 and control wires 475, or more than four coils 474 and control wires 475.

In the illustrated embodiments, the sheath 414 further includes an outer jacket 476 surrounding the coils 474. The outer jacket 476 is a low durometer material for providing flexibility for the articulating distal section 470. In some embodiments, the outer jacket 476 may be made from 35D or 55D Pebax, or from 70A or 80A Polyurethane. In other embodiments, the outer jacket 476 may be made from other materials as long as the distal section 470 is sufficiently flexible for it to be articulated.

In the illustrated embodiments, the control wire coils 474 have an open pitch so that the loops of the coils 474 are spaced apart. Such configuration is advantageous in that it provides a more flexible distal section 470 so that the distal section 470 may be bent to a more tight curve. In one implementation, the distal portion of the coil 474 may have an open pitch while the proximal portion of the coil 474 may have a closed pitch. In such cases, the proximal portion of the coil 474 are wound tightly so that they are in a naturally compressed state. In such configuration, when the steering wires are pulled in tension, the shaft does not bend and the forces are transmitted to the proximal end of the sheath. Alternatively, the entire length of the coil 474 may have a closed pitch. In some embodiments, each coil 474 may extend all the way to the proximal end of the sheath 414. In other embodiments, each coil 474 may transition to another coil with a closer loop spacing at the proximal section 471, as similarly discussed with reference to the catheter 412. In such cases, each distal coil 474 and its corresponding proximal coil may be parts of a same coil structure, wherein the distal portion of the coil structure is constructed to have coil loops that are more spaced apart than a proximal portion of the coil structure. In other embodiments, the distal coil 474 may be a separate component that is connected to the proximal coil (e.g., via a weld, adhesive, etc.).

In the illustrated embodiments, the distal portion of the coil 474 is anchored to the distal section (e.g., the distal end) of the sheath, while the proximal portion of the coil 474 is slidable relative to the proximal section of the sheath. In other embodiments, the coil 474 may be fixed to the sheath body at the transition between the proximal section and the bendable distal section.

In some embodiments, the outer jacket material 476 extends partially into the space that is between the loops of the coil 474 (as similarly discussed with reference to FIG. 37C). Such configuration prevents the control wire 475 from contacting the material of the outer jacket material 476, thereby allowing the control wire 475 to be more easily slide within the lumen of the coil 474. In other embodiments, the outer jacket material 476 may not extend partially into the space that is between the loops of the coil 474. Instead, the outer jacket material 476 may be touching only the outer side of the coil 474. This may allow the coils 474 to move relative to the outer jacket 476, thereby improving the flexibility of the distal section 470. In further embodiments, the outer jacket material 476 may extend completely into the space that is between the loops of the coil 474 (as similarly discussed with reference to FIG. 37D).

Also, in some embodiments, the pitch of the coil 474 and/or the size of the coil 474 may be selected to define an amount of maximum bending for the sheath 414. As similarly discussed with reference to FIG. 37E, as the distal section 470 of the sheath 414 is being bent due to a tensioning of a control wire, the loops of the coil 474 that is housing the control wire 475 will move closer to each other. As a result, the material of the outer jacket 476 that is between the coil loops will undergo compression. By varying the pitch of the coil 474 during the design of the sheath 414, the amount of material between the loops that would undergo compression would vary. Generally, the more the material that is between the loops (i.e., more spaced apart loops), the more bending will be allowed for the sheath 414, and vice versa. Also, in other embodiments in which there is no jacket material between the loops of the coil 474, the same design principle may apply. In such cases, the maximum amount of bending for the sheath 414 may be achieved when the distal section 470 is bent so much that the coil loops of the coil 474 abuts against each other. Thus, during the design of the sheath 414, the coil loops of the coil 474 may be spaced apart further if more bending is desired for the sheath 414, or spaced closer if less bending is desired.

Figure 41:
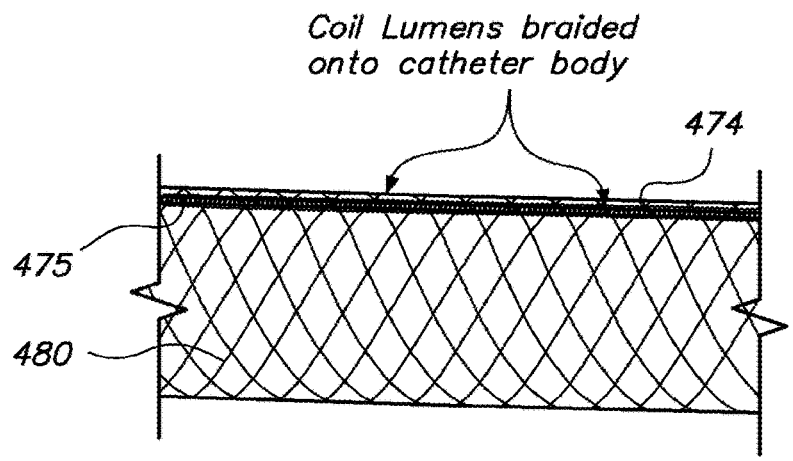
Figure 42:
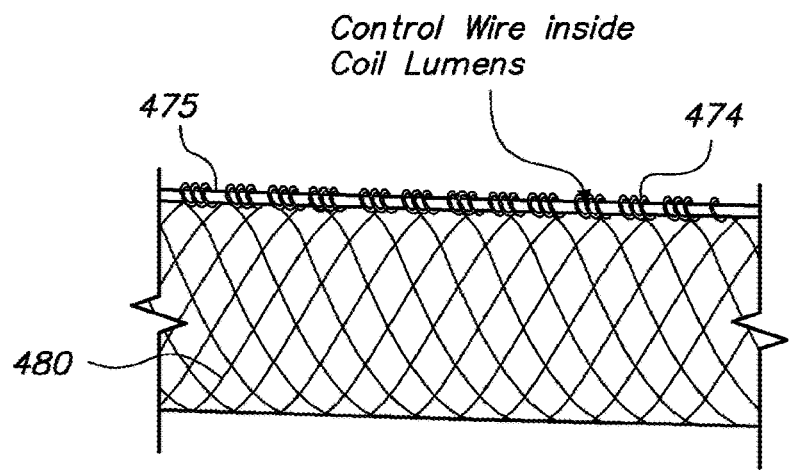

In the above embodiments, the coils 474 are surrounded by the outer jacket 476, which functions to contain the coils 474 during use. In other embodiments, the sheath 414 may further include a braided layer 480 for reinforcing the structure of the sheath 414 (FIGS. 41 and 42). In such cases, the coils 474 for housing the control wires 475 may be coupled to the braided layer. As shown in FIG. 42, in some embodiments, the coils 474 may be coupled to the outer surface of the braided layer 480, e.g., by wrapping part of the coils 474 around the braided layer 480, by attaching them using adhesive, etc. In other embodiments, the coils 474 may be coupled to the inner surface of the braided layer 480 (FIG. 41), e.g., by wrapping part of the coils 474 around the braided layer 480, by attaching them using adhesive, etc. In one approach, the coils 474 are braided by looping around the coil at the section closest to the sheath body, so that the braid will not tent over the coil. This braiding method eliminates the potential for the braid to apply loads on the control wires. This braiding approach will also minimize the coils natural tendency to peel away from the sheath 414 when high articulation forces are used, or when the jacket is made from a material with low durometer.

As shown in FIG. 43, in some embodiments, different sections along the length of the sheath 414 may have different configurations to achieve different stiffnesses. In the implementation shown, the sheath 414 includes a HDPE liner and two layers of stainless steel braid that extend all the way from the drivable assembly 184 to the distal end of the sheath 414. The liner is a coextrusion of HDPE and plexar. The plexar is a tie layer and its purpose is to ensure that the liner is properly bonded to the outer jacket extrusions. The distal 27 mm of the braid on the top layer is 100 ppi while the remainder of the top braid is at 40 ppi. In other embodiments, the pic count of the braid may also change on the bottom layer. This allows for increased stiffness in the proximal section and increased flexibility at the distal section (e.g., the distal 27 mm length) without increasing the risk of kinking. The length of the 100 ppi section can be longer or shorter than 27 mm to a give longer or shorter distal segment. In addition, the outer jacket transitions from a relatively stiff 70D pebax (not shown) in the tracking section of the sheath to 55D Pebax for a 10 cm region at the transition to the bending section. This is then followed by approximately 25 mm of articulation region. This change in durometer of the outer jacket, combined with the change in braid coverage contribute to a sharp change in stiffness in the articulation region which enables a 90° or more articulation angle to be achieved.

As shown in FIG. 44, the spine 478 and/or the braided layer 480 of the sheath 414 may have a square cross section in at least a section along the length of the sheath 414. In such cases, the coils 474 and the control wires 475 may be placed next to the straight side of the square cross section. Such configuration allows more of the jacket material 476 to be surrounding the coils 474, thereby reducing the risk that the coils 474 may cut through the jacket material 476 due to the tensioning of the control wires 475.

It should be noted that use of the coils 474 as control wire lumens in the articulating section has several additional advantages. The coils 474 have both low axial and bending stiffnesses. This lowers articulation forces since the lumens on the inside and outside of the bend will more easily contract and expand, respectively. The coils 474 also have relatively high radial strength, ensuring that they do not collapse and pinch the control wire, which would undesirably increase the wire forces. Also, the coil's 474 ability to expand and contract will decrease the resistance to bending, and will yield a more uniform bend when compared to traditional polyimide lumen constructions. In addition, the coil 474 will provide a load-bearing surface that will radially distribute the control wire load about the jacket. The use of coils 474 will also allow the jacket material to be melted around the coils 474 to thereby secure the coils 474. This will eliminate the need to braid the coils 474 onto a component of the sheath 414. The elimination of braid will in turn lower the resistance to bending (i.e., lowering the bending stiffness) because different layers may shift relative to each other with a lower force, and will also yield a lower articulation force for the sheath 414 and/or smaller bending radius for the sheath 414. However, in other embodiments, if the anchor strength of the coil 474 is desired to be improved, the coil 474 may still be braided to a reinforcement layer, such as a wire mesh or a spine.

In one or more of the embodiments of the catheter 412 and the sheath 414 described herein, the catheter 412 and/or the sheath 414 may not include any spine structure and/or any braided layer. This may have the benefit of further improving the flexibility of the catheter 412 and/or the sheath 414 at the articulating section.

To illustrate the benefits of the configurations of the catheter 412 and the sheath 414 described herein, a method of reaching a target region using a catheter and a sheath will be described. In particular, FIG. 45 shows a catheter C inserted in the right common femoral artery. The tip of the sheath C is positioned in the right common iliac artery and the catheter C is extended from the tip of the sheath to reach the iliac bifurcation. Next, the steerable distal section of the catheter C is pulled back and articulated towards the left common iliac artery and the guidewire G is advanced out from the tip of the catheter C. The guidewire G is then advanced towards the left external iliac artery. Once the guidewire G is advanced far enough to provide sufficient support for the catheter C, the control wires in the catheter C can be slacked (by removing tension in the control wires). This lowers the distal stiffness, and allows the catheter C to track more easily over the guidewire. If the catheter C is advanced distally at this point, the catheter C may sometimes follow the guidewire G over the bifurcation and into the left common iliac artery (as illustrated by the dashed path). However, in some patients with tight iliac bifurcations, the catheter C may not follow the guidewire G, but instead will prolapse up into the aorta. The force applied at the point of insertion is in the direction of the aorta, and so the catheter C may tend to move in that direction.

By providing the sheath 414 with the features described herein, the sheath 414 can be advanced forward and the distal articulation section of the sheath 414 can be articulated towards the left common iliac (FIG. 46) to support the leader. Once the sheath 414 is in this position, the shape of the sheath 414 can be locked by maintaining tension on the control wires. Next, the catheter 412 can be advanced, and the catheter 412 will deflect off the sheath 414 (rather than the artery wall), and can be advanced into the left common iliac (instead of prolapsing up into the aorta). As the catheter 412 is advanced through the deflected sheath 414, the tension on the control wire(s) of the catheter 412 is removed, and the distal steering section of the catheter 412 is allowed to straighten or to conform to whatever shape imposed by the shape of the sheath 414. As such, the shaft of the catheter 412 will follow through the articulated sheath 414. The articulated sheath 414 functions like a pre-shaped or curved lumen for the catheter 412 to be advanced therethrough. Since the sheath 414 provides the support to direct the path of the catheter 412 over the bifurcation, no tension is required on the control wires of the catheter 412 to track over the bifurcation in this example. Therefore, even if the iliac bifurcation is at a very tight angle (in some cases up to 180°), the catheter 412 can still be advanced through the sheath lumen without placing any stress or shearing forces on the wall of the artery. The insertion force may increase on the catheter 412 as the bifurcation angle gets tighter, but the loads are being applied to the inside of the sheath 414, and not to the patient anatomy. In some embodiments, the steerable sheath 414 may be adjusted to ensure that its position and/or shape can be maintained on the sheath distal section as the catheter 412 is advanced through the sheath 414. For example, the instrument driver assembly 408 may compensate for the increased load by pulling more on the control wires or slightly withdraw the sheath 414 to ensure that the sheath 414 will not damage the artery wall. In some embodiments, during the procedure, the inner surface of the sheath 414 and/or the outer surface of the catheter 412 may optionally be coated with a lubricous coating.

As illustrated in the above example, the sheath 414 or leader may be articulated to have a tight bend during a procedure. Embodiments of the sheath 414 and leader described herein allow this to happen. In particular, the control wire coils 474 in the sheath 414 or leader isolate the articulation loads from the shaft, thereby allowing the sheath 414 or leader shaft to be manufactured from low durometer flexible materials. As a result, the articulation loads are resolved via the control wire coils 474 which have a relatively high axial stiffness and low bending stiffness. These control wire coils 474 allow the distal section of the sheath 414 or leader to be articulated to a small radius, and at the same time, the proximal section of the sheath 414 or leader can be maintained very flexible.

FIGS. 47 and 48 illustrate another method for advancing the sheath 414 and the catheter 412 over the iliac bifurcation. In this technique, the catheter 412 is positioned with its distal articulation section traversing the iliac bifurcation and it is locked in this position. Embodiments of the catheter 412 described herein allows the catheter 412 to reach tight angle that may be encountered during the procedure. Next, the sheath 414 is advanced over the catheter 412, and the catheter 412 acts as a rail held in a fixed shape for the sheath 414 to glide over. As the sheath 414 is advanced further, sections with higher bending stiffness on the sheath 414 will pass over the articulated section of the catheter 412, putting an increase load on the catheter 412. The increase in load on the catheter 412 may tend to straighten the catheter 412. Embodiments of the catheter 412 described herein allows the catheter 412 to maintain its bent shape by tightening the control wire(s), which has the effect of stiffening the catheter 412. In some embodiments, the robotic system is configured to detect the increased load on the control wires (due to the placement of the sheath 414 over the catheter 412) to be detected. The operator, or the robotic system, can then apply an equal counteracting load on all the control wires of the catheter 412 to ensure that its bent shape is maintained while the sheath 414 is advanced over the iliac bifurcation.

The doctor can continue to advance the catheter 412 through the articulated sheath 414. He can continue to steer the tip of the catheter 412 to access the required points of interest in the patient's left leg (FIG. 48). In particular, FIG. 48 shows how the catheter 412 can be articulated to reach the left internal iliac artery. This articulation of the catheter 412 is carried out simultaneously with the continued insertion of the catheter 412. This requires the shaft of the catheter 412 to remain flexible at all times even when high articulation loads are being applied to bend the articulation section. Embodiments of the catheter 412 described herein allow this to happen. In particular, the control wire coils 442 in the catheter 412 isolate the articulation loads from the catheter shaft, thereby allowing the catheter 412 shaft to be manufactured from low durometer flexible materials. As a result, the articulation loads are resolved via the control wire coils 442 which have a relatively high axial stiffness and low bending stiffness. These control wire coils 442 allow the distal section of the catheter 412 to be very bendable, and at the same time, the proximal section of the catheter 412 can be maintained very flexible. Also, in some cases, the design of the catheter 412 described herein obviates the need to maintain the proximal section of the catheter 412 to be straight during use, which may be the case with some existing catheters. In particular, the embodiments of the catheter 412 described herein allow high degrees of bendability at the distal section of the catheter 412 while also allowing a flexible proximal and middle segments. This achieves consistent bending at the distal section of the catheter 412 which is independent of the shape of the proximal section of the catheter 412.

As illustrated in the above embodiments, the catheter design is advantageous over existing catheters. In steerable catheters, when the steering wire in the wall of a catheter is pulled, a pull force $F_p$ is applied through the centre line of the pullwire. A reaction force is then generated by the catheter body to resist this pull force. This reaction force $F_r$ is typically applied uniformly around the body or circumference of the catheter. The summation of the reaction force $F_R$ is applied on the center line of the catheter. The offset between the pull force and the reaction force generates a moment at the tip of the catheter. This moment is what causes the catheter to bend. In some catheters in which the entire length of a catheter is built with a uniform bending stiffness, then the entire catheter would bend uniformly. Such configuration does not result in bending of the distal section only. Some other existing catheters have attempted to address this issue by substantially increasing the bending stiffness in the proximal section of the catheter and leaving the distal section of the catheter very flexible. In this situation, when the wire is pulled, the proximal section bends only slightly (because it is stiffer) and the majority of the displacement occurs at the softer distal section. While this solution (of stiffening the proximal end) is applicable for some catheters, it will not work where the proximal section of the catheter is required to remain very flexible to traverse through tortuous anatomy such as in vascular applications. Each of the steering wires are offset from the center line of the catheter and so when the wires are tensioned to steer the catheter tip, the resulting compressive forces on a flexible catheter shaft cause unwanted stiffening of the catheter shaft, especially in the proximal section, which is undesirable. Other steerable catheters and endoscopes attempt to overcome this problem by moving the pull wires to the center of the catheter at the proximal section. By moving the pullwires to the centerline of the catheter, unwanted deflection in the shaft is eliminated, and stiffening of the catheter at the proximal section is somewhat reduced. However, this solution will not work in situation in which an open lumen down the center of the catheter is required.

Embodiments of the catheter design described herein addresses all of the above problems and is specifically applicable for catheters that require (1) significant articulation performance at the distal end, (2) a very flexible catheter shaft (especially at the proximal section), and (3) an open lumen through the middle of the catheter to deliver therapy or other devices. The design involves putting an axially stiff tube (e.g., coil) into the wall of the shaft and using this tube to isolate the steering loads from the catheter shaft. As a steering wire is pulled, the reaction load $F_r$ is applied uniformly by the wall of the coil, and the summation of the reaction force is now applied through the center of the coil pipe and not the center of the catheter. The proximal section of the coil may be tightly wound to take the reaction force. Because of this, the pull force $F_P$ of the steering wire and the reaction force $F_R$ by the coil are collinear and there is no moment generated in the proximal section of the catheter. The coil in the distal section remains loosely wound so it does not take any axial load and applies no reaction force. Therefore, the reaction force at the distal section of the catheter will continue to be applied about the centerline (or cross sectional centroid) of the catheter. This ensures that there is a moment generated at the distal section of the catheter and so the tip continues to bend when a pull force is applied to the wire. The additional benefit of placing an axially stiff member in the wall of the catheter is that it shifts the neutral axis from the catheter cross sectional centroid to the cross sectional centroid of the coil. There is significant benefit for articulation consistency when the pullwire is on the neutral axis. Therefore, this design biases the neutral axis of the catheter to make it collinear with a pullwire in the wall at the proximal section. The above design allows the catheter shaft (at least the proximal section) to be made from very flexible material. This ensures that the proximal section of the catheter can freely bend independently to fit through tortuous anatomy, regardless of how the distal section is steered.

In the above procedures, the catheter 412 and the sheath 414 work together in a telescoping motion to minimize stress on the wall of the arteries. Although the procedure is described with reference to traversing a tight iliac bifurcation, in other embodiments, the similar technique may be used to access other locations in the patient. For example, in other embodiments, similar technique may be used to access carotid arteries with tight take off angles from the aortic arch.

Figure 50A:
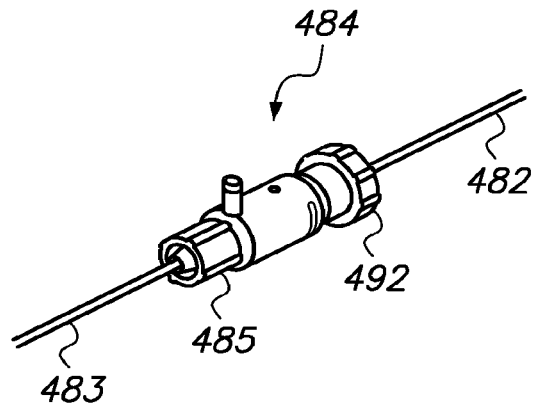
Figure 50B:
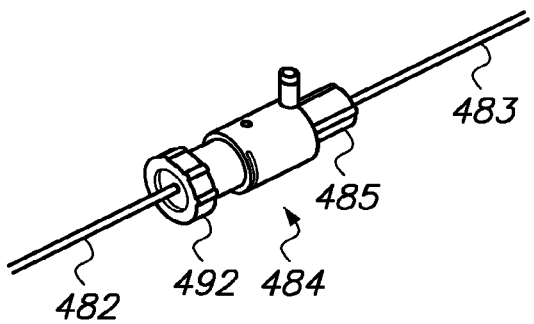
Figure 50C:
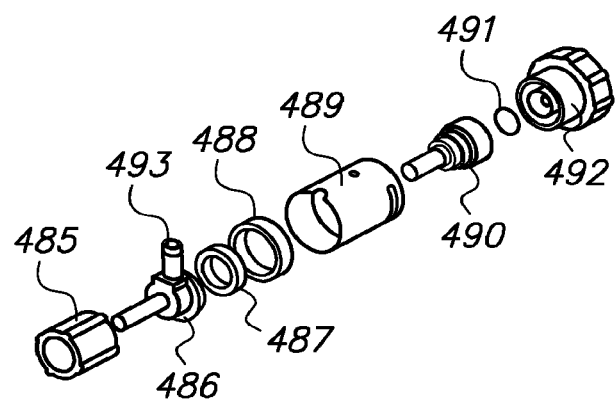

In some embodiments, after the catheter 412 has been driven to a desired location, a valve (shown in FIG. 49) on the proximal end of the catheter 412 or sheath may be tightened, and the doctor may then inject contrast through the catheter 412 or sheath to perform a selective angiogram of the region of interest. The passive hemostatic seal on the proximal end of the sheath is supported by a Touhy Borst fitting on the illustrated embodiment to ensure that it can maintain the high injection pressures. Once the contrast injection is complete, the Touhy Borst fitting is loosened and the passive valve continues to ensure hemostasis against the surface of the guidewire. FIGS. 50A-50C show the Touhy Borst valve in further details. In particular, FIGS. 50A and 50B illustrate front and back perspective views of a valve assembly 484 which is configured to be coupled at its distal end to a support tube 483 and configured to receive the guide wire 482 co-axially at its proximal end. FIG. 50C illustrates an exploded view of the valve assembly 484 including a tube nut 485, a flush joint 486, a passive valve 487, a cap 488, a valve body 489, a Touhy Borst body 490, a Touhy Borst seal 491, and a Touhy Borst nut 492. The passive valve 487 has a slit that is configured to hold hemostasis when nothing is inserted therethrough. The cap 488 has a hole that is configured to hold hemostasis when a wire or a catheter is inserted through it. The support tube 483 which can be coupled to the guide catheter (not shown) at its distal end can be inserted into the flush joint 486 and locked into position by tightening the tube nut 485. The guide wire 482 can be inserted through the proximal end of the Touhy Borst nut 492 and through the central lumen of the remainder of the valve assembly 484 eventually being fed co-axially into the support tube 483 and ultimately the guide catheter. Alternatively, the Touhy Borst can be tightened onto the leader catheter to facilitate contrast injection through the sheath. The Touhy Borst nut 492 is tightened to compress the Touhy Borst seal 491 into a sealed or completely sealed position. During operation, fluid may be introduced through a flush port 493 on the flush joint 486. The passive valve 487 acts as a one-way valve which allows the guide wire 482 to be inserted towards the distal end of the valve assembly 484 but prevents fluid from flowing towards the proximal end of the valve assembly. Thus the pressurized fluid is forced to flow through the support tube 483, and the flush of contrast is delivered to the region of the vasculature. The Touhy Borst seal 491 may be used as a secondary seal in the case where high pressure fluid is introduced which cannot be contained by the passive seal 487. In one or more of the embodiments described herein, the valve may be adjustable such that it will seal automatically as the contrast injection pressure is being applied. Also, in other embodiments, instead of using a Touhy Borst valve, other types of valve may be used.

Also, in some embodiments, once the guide wire 482 has been positioned distal of a stenosis in an artery, the catheter 412 can be withdrawn completely from the sheath 414, leaving the wire 482 and the sheath 414 in place. Next, a therapy of choice can be selected, and delivered over the wire 482 to the site of interest. By means of non-limiting examples, the therapy can range from balloon expandable stents, self expanding covered and/or uncovered stent, as well as a range of artherectomy devices that can traverse over the wire 482. As the therapy is being delivered, the user continues to have the ability to steer the distal end of the sheath 414 to help ensure that the therapy can be delivered to the desired location. For example, as the therapy is being delivered through the anatomy, the sheath 414 may tend to move away from the target location. The doctor can adjust tension on the control wires of the sheath 414 as required to compensate for this movement and ensure that the therapy will reach the required location.

III. Bedside Configuration

FIGS. 51A-51F illustrate another robotic surgical system 400 in accordance with other embodiments. The robotic surgical system 400 is similar to the embodiment described previously, except that it further has both a bed-side control 402 and a bed-side display (not shown). The bed-side control 402 is configured to provide some or all of the functions that the workstation can provide, so that the physician can perform most robotic catheter control tasks at either the workstation or the bed-side.

The system 400 also includes a setup mount (setup joint) 404 that is similar to that discussed previously. However, in the illustrated embodiments, the setup mount 404 is mounted to the patient support 22 via a rail system 406. The rail system 406 allows the setup mount 404 (and therefore, the instrument driver assembly 16) to translate along the length of the patient support 22. In some embodiments, the rail system 406 includes a motorized rail 407, that can be actuated to drive movement of the setup mount 404. In other embodiments, other mechanisms may be used, including but not limited to a lead screw, a ball screw, linear motor, belt, and/or cable drive, etc. The movement of the setup mount 404 along the rail may be caused by entering a command at the workstation, or at the bedside control 402. In other embodiments, the setup mount 404 may be allowed to move by actuating a button at the setup mount 404, thereby releasing the setup mount 404 from a locked position against the rail system 406. The setup mount 404 can then be translated manually along the axis of the patient support 22. When the setup mount 404 has reached a desired position, the button may be released to lock the setup mount 404 at the desired position. Setup mount/joint has been described in U.S. Pat. No. 7,789,874, filed on Jul. 1, 2005, the entire disclosure of which is expressly incorporated by reference herein. Alternatively, the movement of the setup mount 404 along the rail may be controlled using the workstation 2 and/or the bedside control 402. In one or more of the embodiments described herein, any of the controls, including release lever/button, may be implemented at any location, such as at the bedside control 402, at the workstation 2, on the side opposite from the side at which the bedside control 402 is located, etc. Also, in some embodiments, two release levers/buttons may be provided, with one located on the doctor's side (e.g., at the bedside control 402), and another one on the back side for ease of service and safety.

Figure 51A:
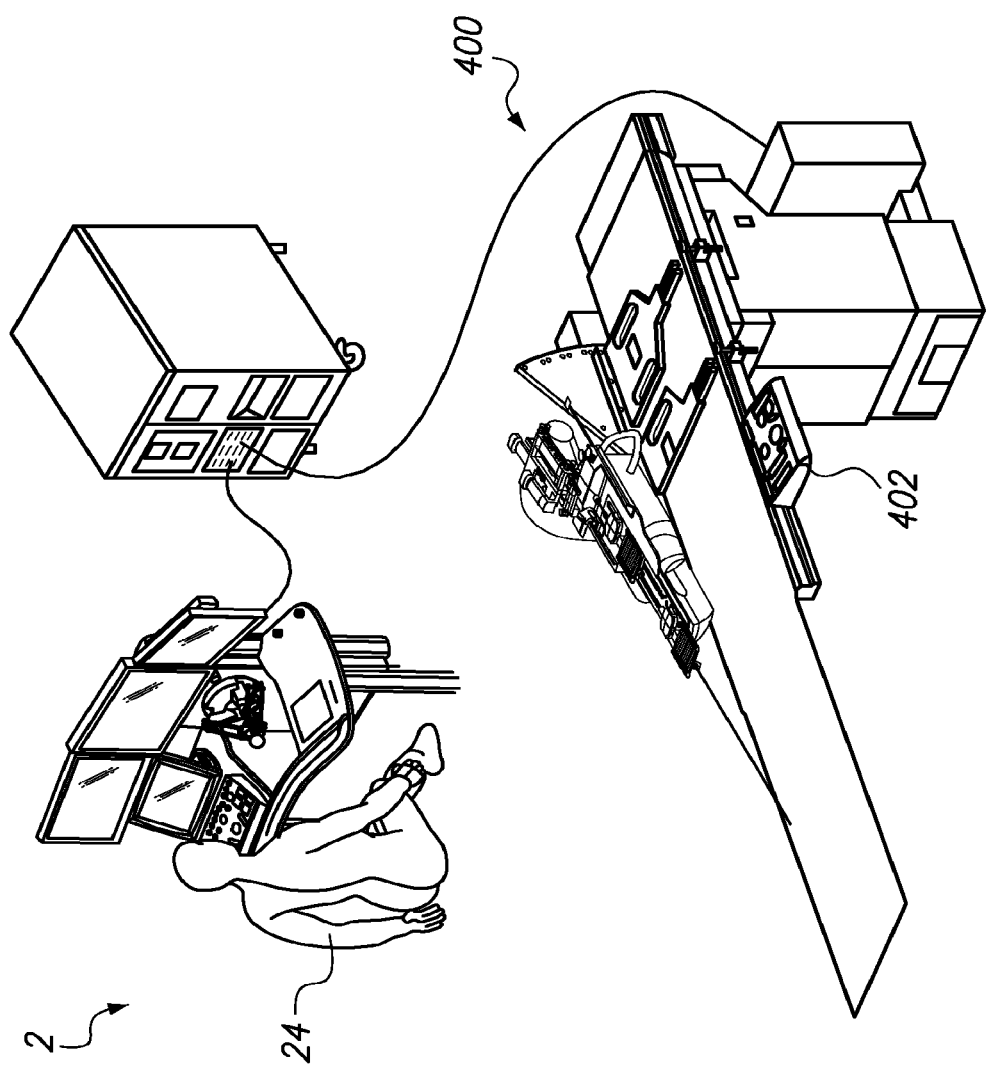
FIGS. 51A-51F illustrate another robotic surgical system 400 in accordance with other embodiments.
Figure 51B:
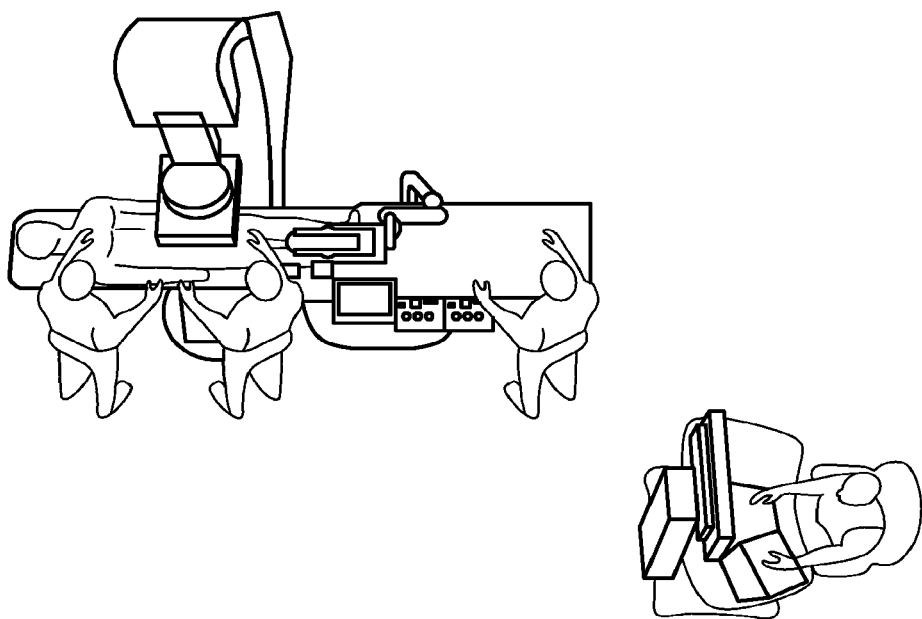
Figure 51C:
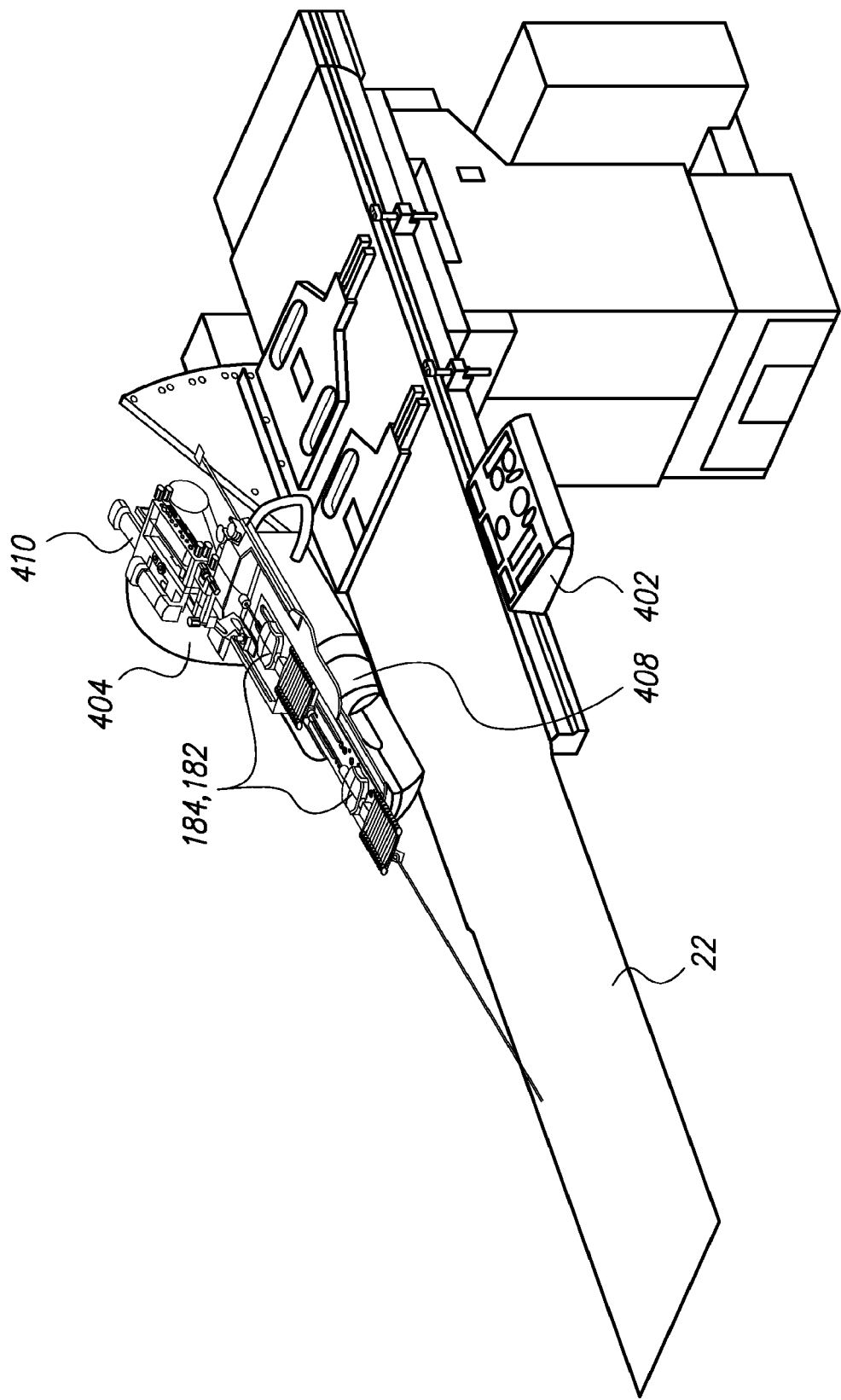
Figure 51D:
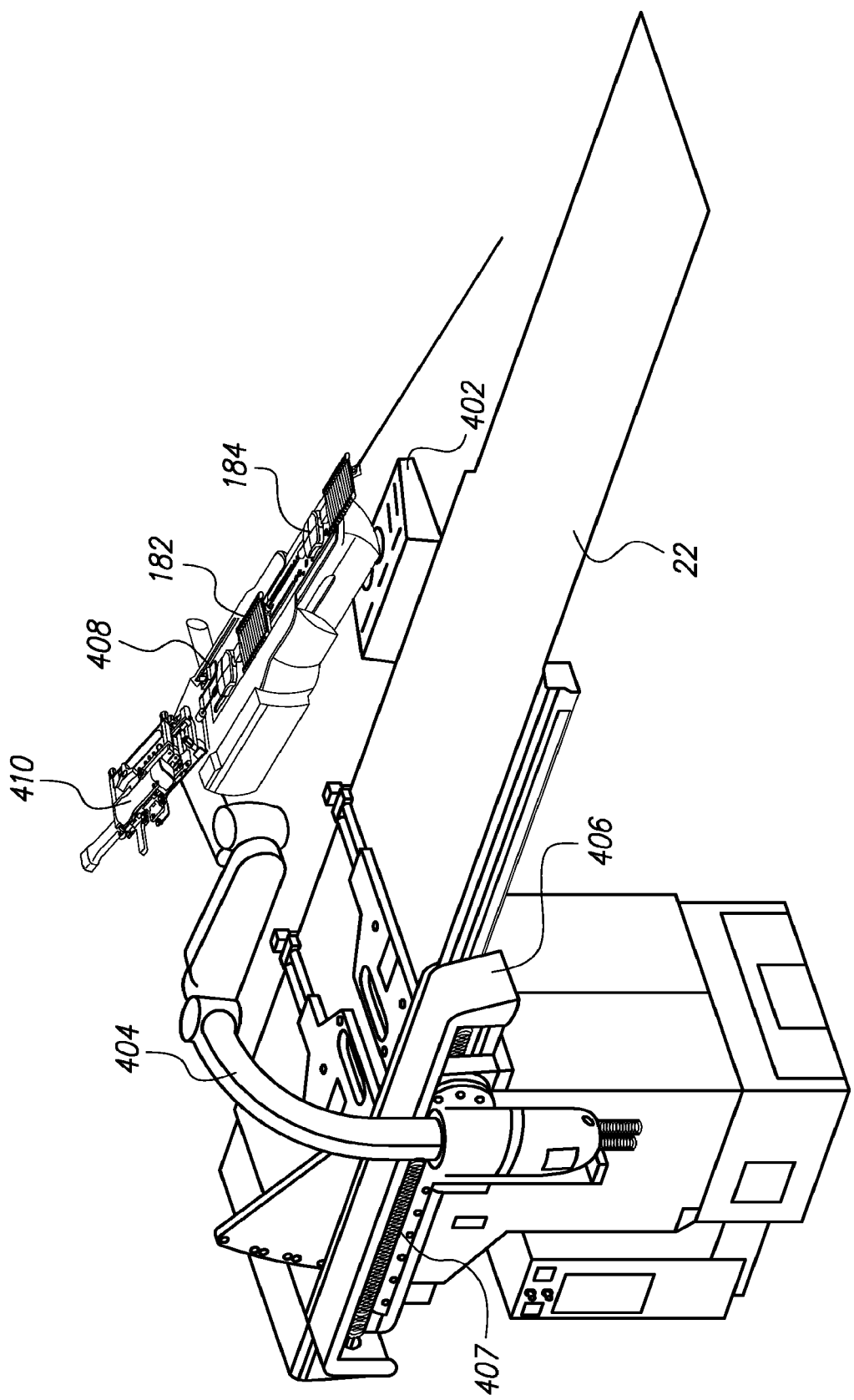
Figure 51E:
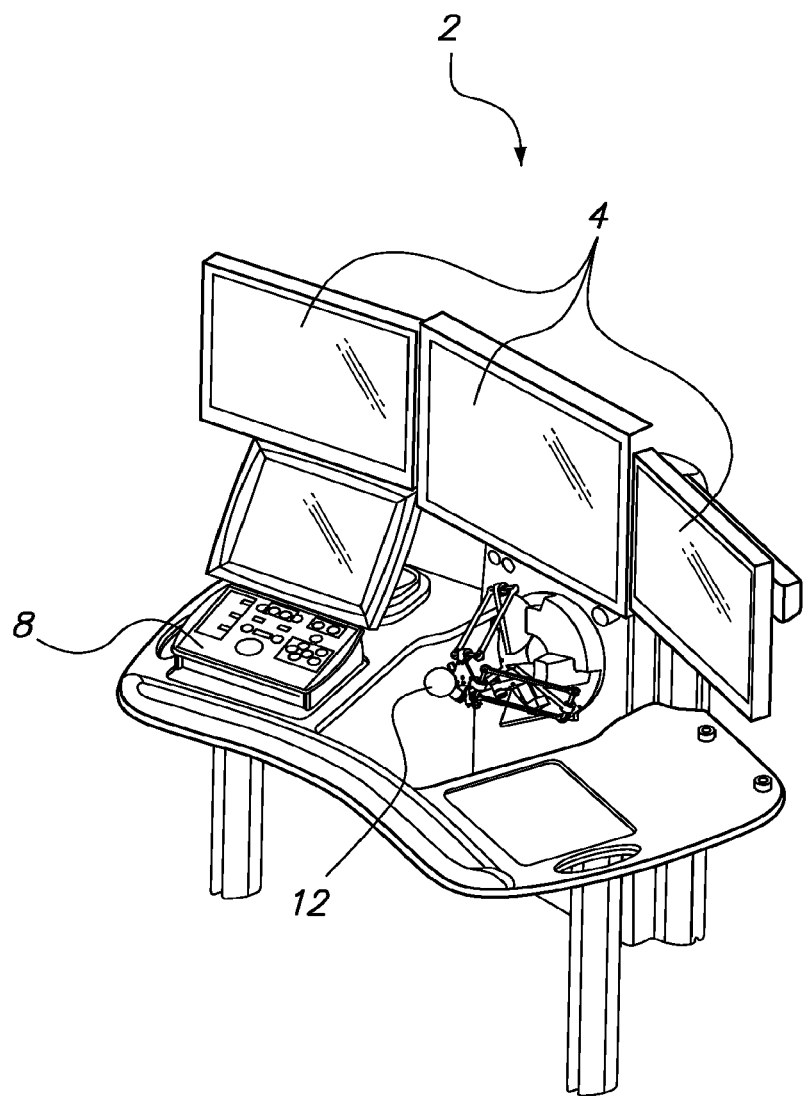
Figure 51F:
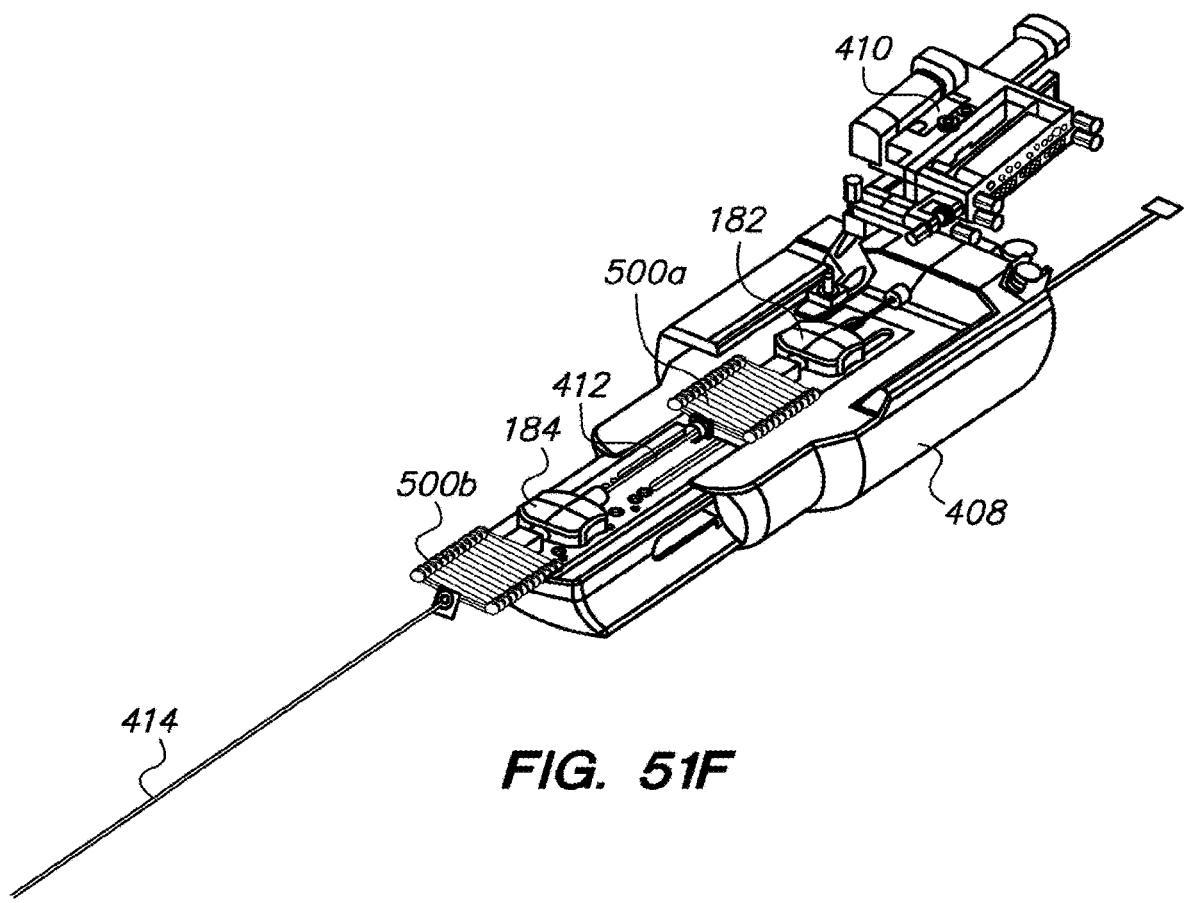
Figure 51G:
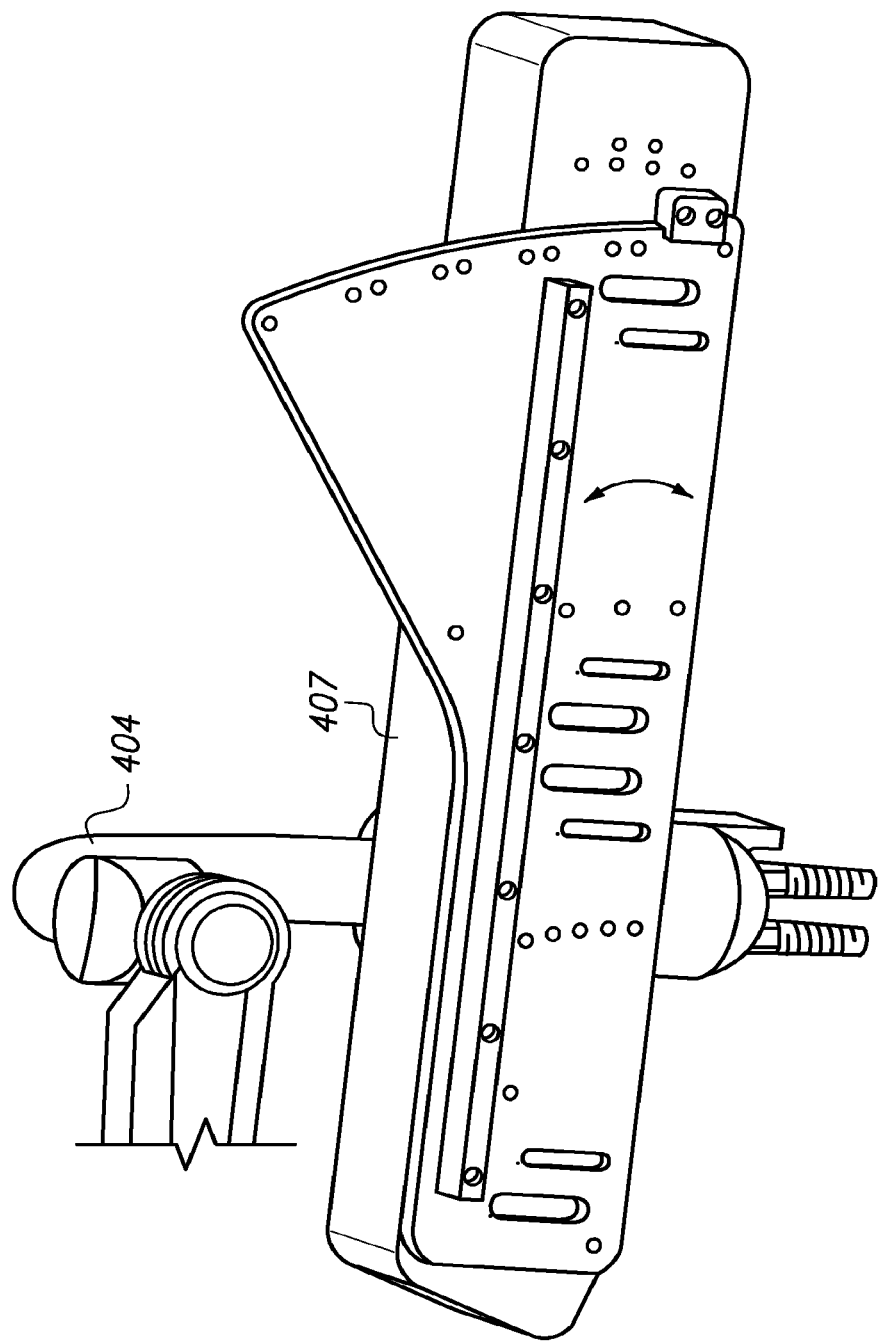
FIG. 51G illustrates a rail system configured to tilt a setup mount in accordance with some embodiments.

Also, in other embodiments, the rail system 406 may be configured to tilt the setup mount 404 (as illustrated by the arrows in FIG. 51G) in response to command entered at the workstation 2 and/or the bedside control 402. In some cases, the tilting range of the angle can be up to 20° or higher. Such configuration allows the insertion trajectory of the catheter 412 and/or the sheath 414 to be tilted (e.g., relative to the bed). In other embodiments, the rail system 406 may be configured to move in other directions in other degrees of freedom. For example, in other embodiments, the rail system 406 may move up and down to adjust the height, and/or laterally towards either side of the bed. In further embodiments, the rail system 406 may roll (e.g., tilted about its longitudinal axis). Also, in one or more of the embodiments described herein, there may be an angular motion or indexed tilt of the rail about any axis to better align with the catheter insertion, and compensate for any sagging of the catheter or an anti-buckling device (which is described herein). In further embodiments, the rail system 406 may have a 10 degree angle (or other angles) incline. In the embodiments shown in FIG. 51A, the rail shark fin (the triangular plate on one side of the bed) is configured to allow adjustment of the rail incline in 5 degree increments up to 20 degrees.

The robotic system 400 also includes an instrument driver assembly 408. The instrument driver assembly 408 includes a catheter drivable assembly 182 for positioning a catheter 412, and a sheath drivable assembly 184 for positioning a sheath 414 that is placed coaxially around the catheter 412. The instrument driver assembly 408 is similar to that discussed previously. In the illustrated embodiments, the sheath drivable assembly 184 is moveable relative to the catheter drivable assembly 182. Each of the drivers 82, 84 has four drivable elements for moving the catheter 412, and the sheath 414, respectively, in different directions. In other embodiments, the number of drivable elements in each of the drivers 82, 84 may be less than four or more than four. The instrument driver assembly 408 also includes two anti-buckling devices 500a, 500b for preventing the buckling of the catheter 412, and the buckling of the sheath 414 during use. The anti-buckling devices will be described in further detail below. The instrument driver assembly 408 further includes a guide wire manipulator 410 for positioning a guidewire (not shown) that may be placed within a lumen of the catheter 412.

IV. Driving Modes and Clinical Applications

The instrument driver assembly 408 may be configured to move the sheath 414 distally or proximally, move the catheter 412 distally or proximally, and to move the guidewire distally or proximally. In some cases, the movement of the sheath 414 may be relative to the catheter 412, while the catheter 412 remains stationary. In other cases, the movement of the catheter 412 may be relative to the sheath 414 while the sheath 414 remains stationary. Also, in other cases, the sheath 414 and the catheter 412 may be moved together as a unit. The guidewire may be moved relative to the sheath 414 and/or the catheter 412. Alternatively, the guidewire may be moved together with the sheath 414 and/or the catheter 412.

In some embodiments, each of the workstation 2 and the bedside control 402 is configured to provide some or all of the following commanded motions (driving modes) for allowing the physician to choose. In some embodiments, each of the driving modes may have a corresponding button at the workstation 2 and/or the bedside control 402.

Guidewire Insert—When this button/command is selected, the guide wire manipulator 410 inserts the guidewire at a constant velocity.

Guidewire Roll—When this button/command is selected, the guide wire manipulator 410 rolls the guidewire at a constant angular velocity.

Guidewire Size—When the size or gauge of the guidewire is inputted into through the user interface, the system will automatically alter roll and insert actuation at the proximal end of the guidewire accordingly to achieve desired commanded results. In one implementation, when a user inputs the guidewire size, the system automatically changes its kinematic model for driving that guidewire. So if the user commands a guidewire to move to a certain position, the system will calculate, based on the kinematic model, roll and insert commands, which may be different for different guidewire sizes (e.g., guidewires with different diameters).

By inputting the guidewire size, the system knows which kinematic model to use to perform the calculation. Such feature is beneficial because different sized guidewires behave differently.

Leader/Sheath Select—When this button/command is selected, it allows the user to select which device (e.g., catheter 412, sheath 414, guidewire, or any combination of the foregoing) is active.

Leader/Sheath Insert/Retract—When this button/command is selected, the instrument driver assembly 408 inserts or retracts the catheter 412/sheath 414 while holding the guidewire and any non-active device fixed relative to the patient. When this motion causes the protruding section of the catheter 412 to approach zero (due to insertion of the sheath 414 or retraction of the catheter 412), the system automatically relaxes the catheter 412 as part of the motion.

Leader/Sheath Bend—When this button/command is selected, the instrument driver assembly 408 bends the articulating portion of the catheter 412/sheath 414 within its currently commanded articulation plane.

Leader/Sheath Roll—When this button/command is selected, the instrument driver assembly 408 uses the pullwires to "sweep" the articulation plane of the device (catheter 412 and/or sheath 414) around in a circle through bending action of the device. Thus, this mode of operation does not result in a true "roll" of the device in that the shaft of the device does not roll. In other embodiments, the shaft of the device may be configured to rotate to result in a true roll. Thus, as used in this specification, the term "roll" may refer to an artificial roll created by seeping a bent section, or may refer to a true roll created by rotating the device.

Leader/Sheath Relax—When this button/command is selected, the instrument driver assembly 408 gradually releases tension off of the pullwires on the catheter 412/sheath 414. If in free space, this results in the device returning to a straight configuration. If constrained in an anatomy, this results in relaxing the device such that it can most easily conform to the anatomy.

Guide Wire Lock—When this button/command is selected, the guide wire position is locked to the leader position. As the leader is articulated or inserted, the guide wire moves with the leader as one unit.

System Advance/Retract—When this button/command is selected, the instrument driver assembly 408 advances/retracts the catheter 412 and sheath 414 together as one unit. The guidewire is controlled to remain fixed relative to the patient.

Autoretract—When this button/command is selected, the instrument driver assembly 408 starts by relaxing and retracting the catheter 412 into the sheath 414, and then continues by relaxing and retracting the sheath 414 with the catheter 412 inside it. The guidewire is controlled to remain fixed relative to the patient.

Initialize Catheter—When this button/command is selected, the system confirms that the catheter 412 and/or the sheath 414 has been properly installed on the instrument driver assembly 408, and initiates pretensioning. Pretensioning is a process used to find offsets for each pullwire to account for manufacturing tolerances and the initial shape of the shaft of the catheter 412 and/or the sheath 414.

Leader/Sheath Re-calibration—When this button/command is selected, the instrument driver assembly 408 re-pretensions the catheter 412 and/or the sheath 414 in its current position. This gives the system the opportunity to find new pretension offsets for each pullwire and can improve catheter driving in situations where the proximal shaft of the catheter 412 has been placed into a significant bend such as after crossing the illiac bifurcation. It is activated by holding a relax button down for several seconds which ensures that the device is fully de-articulated. Alternatively the re-calibration may be activated without holding down the relax button to de-articulate the device.

Leader Relax Remove—When this button/command is selected, the instrument driver assembly 408 initiates a catheter removal sequence where the catheter 412 is fully retracted into the sheath 414, all tension is released from the pullwires, and the splayer shafts (at the drivable assembly 182 and/or drivable assembly 184) are driven back to their original install positions so that the catheter 412 can be reinstalled at a later time.

Leader Yank Remove—When this button/command is selected, the instrument driver assembly 408 initiates a catheter removal sequence where the leader is removed manually.

Emergency Stop—When this button/command is selected, the instrument driver assembly 408 initiates a gradual (e.g., 3 second) relaxation of both the catheter 412 and the sheath 414. The components (e.g., amplifier) for operating the catheter 412, guidewire, or another device are placed into a "safe-idle" mode which guarantees that no power is available to the motors that drive these elements, thereby bringing them rapidly to a stop, and allowing them to be manually back-driven by the user. Upon release of the emergency stop button, the system ensures that the catheter 412 is still in its allowable workspace and then returns to a normal driving state.

Figure 52A:
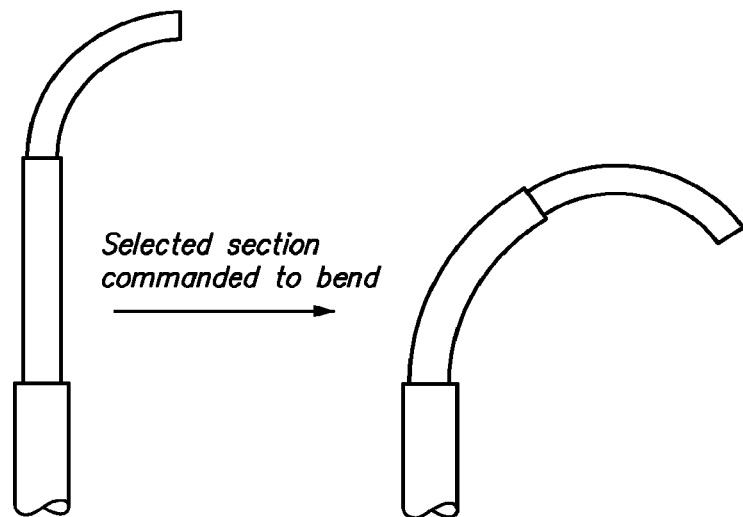
FIG. 52A illustrates driving mode(s) in accordance with some embodiments.

Segment control: In some embodiments, the workstation 2 and/or the bedside control 402 allows a user to select individual segment(s) of a multi-segment catheters (such as the combination of the catheter 412 and the sheath 414), and control each one. The advantage of controlling the catheter in this way is that it allows for many options of how to control the movement of the catheter, which may result in the most desirable catheter performance. To execute this method of catheter steering, the user selects a segment of the catheter to control. Each segment may be telescoping or non-telescoping. The user may then control the selected segment by bending and inserting it using the workstation 2 and/or the bedside control 402 to control the position of the end point of the catheter. Other segment(s) of the catheter will either maintain their previous position (if it is proximal of the selected section) or maintain its previous configuration with respect to the selected section (if it is distal of that section) (FIG. 52A).

Figure 52B:
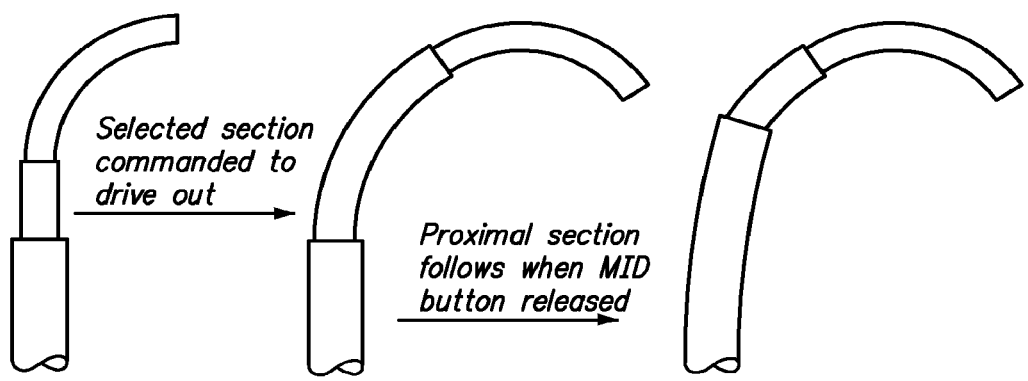
FIG. 52B illustrates driving mode(s) in accordance with other embodiments.

Follow mode: In some embodiments, the workstation 2 and/or the bedside control 402 allows the user to control any telescoping section while the more proximal section(s) follows behind automatically. This has the advantage of allowing the user to focus mostly on the movement of a section of interest while it remains supported proximally. To execute this method of catheter steering, the user first selects a telescoping section of the catheter to control. This section is then controlled using the workstation 2 and/or the bedside control 402 to prescribe a location of the endpoint of the segment. Any segment(s) distal of the section of interest will maintain their previous configuration with respect to that section. When the button on the workstation 2 or the bedside control 402 is released, any segment(s) proximal of the section of interest will follow the path of the selected section as closely as possible until a predefined amount of the selected section remains (FIG. 52B). As an alternative to this driving mode, the segment(s) of the catheter which is proximal of the section of interest could follow along as that segment is moved instead of waiting for the button to be released. Furthermore, with either of these automatic follow options, the system may optionally be configured to re-pretension the sections that have been driven out and re-align the sections that are proximal of the driven section.

Figure 52C:
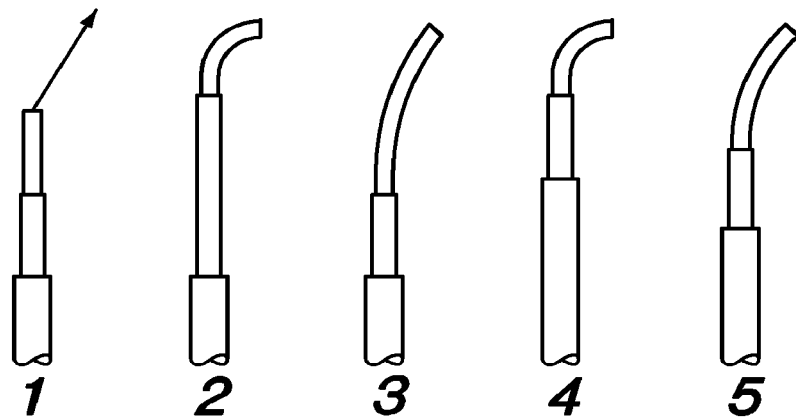
FIG. 52C illustrates driving mode(s) in accordance with other embodiments.
Figure 52D:
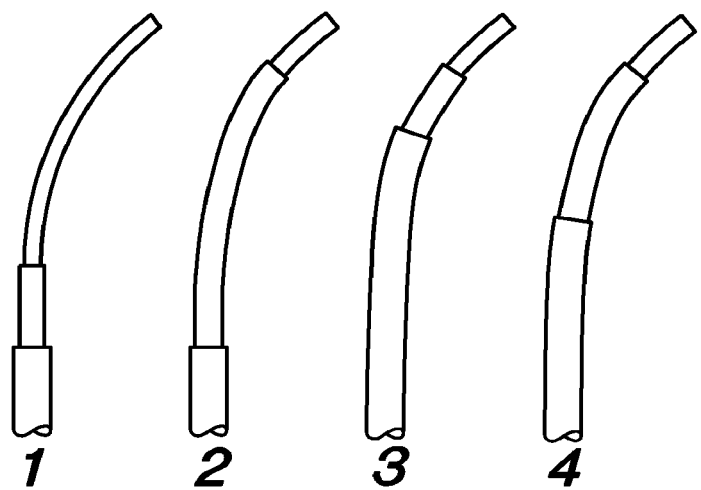
FIG. 52D illustrates driving mode(s) in accordance with other embodiments.

Follow mode may be desirable to use to bring the more proximal segments of the catheter towards the tip to provide additional support to the distal segment. In cases where there are three or more controllable sections of the catheter, there are several options for how to execute a "follow" command. Consider the example in FIG. 52D where the distal segment has been driven out as shown in frame 1. The "follow" command could be executed by articulating and/or inserting only the middle segment of the catheter as shown in frame 2. The "follow" command could be executed by articulating and/or inserting only the most proximal segment of the catheter as shown in frame 3. The "follow" command could also be executed by coordinating the articulation and/or insertion of multiple proximal segments of the catheter as shown in frame 4. Combining the motion of multiple sections has several potential advantages. First, it increases the total degrees-of-freedom available to the algorithm that tries to fit the shape of the following section(s) to the existing shape of the segment being followed. Also, in comparison to following each segment sequentially, a multi-segment follow mode simplifies and/or speeds up the workflow. In addition, multi-segment increases the distance that can be followed compared to when only one proximal segment is used to follow the distal segment.

Mix-and-match mode: In some embodiments, the workstation 2 and/or the bedside control 402 allows the user to have the option of mixing and matching between articulating and inserting various sections of a catheter. For example, consider the illustration in FIG. 52C, and assuming that the distal most section of the catheter is the "active" segment. If the user commands a motion of the tip of the catheter as indicated by the arrow in Frame 1, there are several options available for how to achieve this command: (1) Articulate and extend the "active" segment, which is illustrated in frame 3 and is likely considered the normal or expected behavior; (2) Articulate the active distal most segment and insert one of the other proximal segments, as illustrated in frames 2 and 4; (3) Articulate the active distal most segment and combine inserting motion of some or all of the segments, as illustrated in frame 5.

There are multiple potential reasons why the user might want to choose some of these options. First, by "borrowing" insert motion from other segments, some of the segments could be constructed with fixed lengths. This reduces the need for segments to telescope inside of each other, and therefore reduces the overall wall thickness. It also reduces the number of insertion degrees-of-freedom needed. Also, by combining the insert motion from several segments, the effective insert range-of-motion for an individual segment can be maximized. In a constrained space such as the vasculature, the operator may likely be interested in "steering" the most distal section while having as much effective insertion range as possible. It would simplify and speed up the workflow to not have to stop and follow with the other segments.

Locking mode: In some embodiments, the workstation 2 and/or the bedside control 402 may be configured to allow any of the section (e.g., proximal section) of a catheter to be "locked" into a given shape. Some driving modes that may take advantage of such feature include: (1) Locking the proximal segment into its current shape after each motion of the proximal segment is executed. The proximal section would then unlock whenever it is given another follow motion command. These motion commands would be either direct driving of the most proximal section or following of the more distal sections. (2) Leave the proximal section flexible for insertion by hand, then lock the proximal section once the catheter is attached to the robotic system. The proximal section could then be unlocked again for further manual insertions, either by removing the catheter from the instrument driver assembly 408 or by releasing the brake on the setup joint 404. For any of these options, the locking portion could be: (1) The proximal (actively) articulating segment, (2) some or all of the "body" of the catheter proximal of the actively articulating segments, or (3) both the proximal actively articulating segment and some portion of the non-articulating "body" of the catheter.

In other embodiments, the "follow" mode may be carried out using a robotic system that includes a flexible elongated member (e.g., a guidewire), a first member (e.g., the catheter 412) disposed around the flexible elongated member, and a second member (e.g., the sheath 414) disposed around the first member. The flexible elongated member may have a pre-formed (e.g., pre-bent) configuration. In some embodiments, the flexible elongated member may be positioned inside a body. Such may be accomplished using a drive mechanism that is configured to position (e.g., advance, retract, rotate, etc.) the flexible elongated member. In one example, the positioning of the flexible elongated member comprises advancing the flexible elongated member so that its distal end passes through an opening in the body.

Next, the first member is relaxed so that it has sufficient flexibility that will allow the first member to be guided by the flexible elongated member (that is relatively more rigid than the relaxed first member). In some embodiments, the relaxing of the first member may be accomplished by releasing tension in wires that are inside the first member, wherein the wires are configured to bend the first member or to maintain the first member in a bent configuration. After the first member is relaxed, the first member may then be advanced distally relative to the flexible elongated member. The flexible elongated member, while being flexible, has sufficient rigidity to guide the relaxed first member as the first member is advanced over it. The first member may be advanced until its distal end also passes through the opening in the body.

In some embodiments, the second member may also be relaxed so that it has sufficient flexibility that will allow the second member to be guided by the flexible elongated member (that is relatively more rigid than the relaxed second member), and/or by the first member. In some embodiments, the relaxing of the second member may be accomplished by releasing tension in wires that are inside the second member, wherein the wires are configured to bend the second member or to maintain the second member in a bent configuration. After the second member is relaxed, the second member may then be advanced distally relative to the flexible elongated member. The flexible elongated member, while being flexible, has sufficient rigidity to guide the relaxed second member as the second member is advanced over it. The second member may be advanced until its distal end also passes through the opening in the body. In other embodiments, instead of advancing the second member after the first member, both the first member and the second member may be advanced simultaneously (e.g., using a drive mechanism) so that they move together as a unit. In further embodiments, the acts of advancing the flexible elongated member, the first member, and the second member may be repeated until a distal end of the flexible elongated member, the first member, or the second member has passed through an opening in a body.

In the above embodiments, tension in pull wires in the second elongated member is released to make it more flexible than the first elongated member, and the second elongated member is then advanced over the first elongated member while allowing the first elongated member to guide the second elongated member. In other embodiments, the tension in the pull wires in the first elongated member may be released to make it more flexible than the second elongated member. In such cases, the more flexible first elongated member may then be advanced inside the more rigid second elongated member, thereby allowing the shape of the second elongated member to guide the advancement of the first elongated member. In either case, the more rigid elongated member may be locked into shape by maintaining the tension in the pull wires.

In some of the embodiments described herein, the flexible elongated member may be a guidewire, wherein the guidewire may have a circular cross section, or any of other cross-sectional shapes. Also, in other embodiments, the guidewire may have a tubular configuration. In further embodiments, the robotic system may further include a mechanism for controlling and/or maintaining the preformed configuration of the guidewire. In some embodiments, such mechanism may include one or more steering wires coupled to a distal end of the guidewire. In other embodiments, such mechanism may be the catheter 412, the sheath 414, or both. In particular, one or both of the catheter 412 and the sheath 414 may be stiffened (e.g., by applying tension to one or more wires inside the catheter 412 and/or the sheath 414). The stiffened catheter 412 and/or the sheath 414 may then be used to provide support for the guidewire.

Also, in some of the embodiments described herein, any movement of the guidewire, the catheter 412, and/or the sheath 414 may be accomplished robotically using a drive assembly. In some embodiments, the drive assembly is configured to receive a control signal from a processor, and actuate one or more driveable elements to move the guidewire, the catheter 412, and/or the sheath 414.

It should be noted that the driving modes for the system are not limited to the examples discussed, and that the system may provide other driving modes in other embodiments.

V. Clinical Applications

The different driving modes and/or different combinations of driving modes are advantageous because they allow a tubular member (catheter 412, sheath 414, or combination of both) to access any part of the vasculature. Thus, embodiments of the system described herein may have a wide variety of applications. In some embodiments, embodiments of the system described herein may be used to treat thoracic aneurysm, thoracoabdominal aortic aneurysm, abdominal aortic aneurysm, isolated common iliac aneurysm, visceral arteries aneurysm, or other types of aneurysms. In other embodiments, embodiments of the system described herein may be used to get across any occlusion inside a patient's body. In other embodiments, embodiments of the system described herein may be used to perform contralateral gait cannulation, fenestrated endograft cannulation (e.g., cannulation of an aortic branch), cannulation of internal iliac arteries, cannulation of superior mesenteric artery (SMA), cannulation of celiac, and cannulation of any vessel (artery or vein). In further embodiments, embodiments of the system described herein may be used to perform carotid artery stenting, wherein the tubular member may be controlled to navigate the aortic arch, which may involve complex arch anatomy. In still further embodiments, embodiments of the system described herein may be used to navigate complex iliac bifurcations.

In addition, in some embodiments, embodiments of the system described herein may be used to deliver a wide variety of devices within a patient's body, including but not limited to: stent (e.g., placing a stent in any part of a vasculature, such as the renal artery), balloon, vaso-occlusive coils, any device that may be delivered over a wire, an ultrasound device (e.g., for imaging and/or treatment), a laser, any energy delivery devices (e.g., RF electrode(s)), etc. In other embodiments, embodiments of the system described herein may be used to deliver any substance into a patient's body, including but not limited to contrast (e.g., for viewing under fluoroscope), drug, medication, blood, etc. In one implementation, after the catheter 412 (leader) is placed at a desired position inside the patient, the catheter 412 may be removed, leaving the sheath 414 and guidewire to provide a conduit for delivery of any device or substance.

In further embodiments, embodiments of the system described herein may be used to access renal artery for treating hypertension, to treat uterine artery fibroids, atherosclerosis, and any peripheral artery disease.

In still further embodiments, embodiments of the system described herein may be used to access any internal region of a patient that is not considered a part of the vasculature. For example, in some cases, embodiments of the system described herein may be used to access any part of a digestive system, including but not limited to the esophagus, liver, stomach, colon, urinary tract, etc. In other embodiments, embodiments of the system described herein may be used to access any part of a respiratory system, including but not limited to the bronchus, the lung, etc.

In some embodiments, embodiments of the system described herein may be used to treat a leg that is not getting enough blood. In such cases, the tubular member may access the femoral artery percutaneously, and is steered to the aorta iliac bifurcation, and to the left iliac. Alternatively, the tubular member may be used to access the right iliac. In one implementation, to access the right iliac, the drive assembly may be mounted to the opposite side of the bed (i.e., opposite from the side where the drive assembly is mounted in FIG. 1). In other embodiments, instead of accessing the inside of the patient through the leg, the system may access the inside of the patient through the arm (e.g., for accessing the heart).

In any of the clinical applications mentioned herein, the telescopic configuration of the catheter 412 and the sheath 414 (and optionally the guidewire 482) may be used to get past any curved passage way in the body, like that similarly discussed with reference to FIGS. 45-48. For example, in any of the clinical applications mentioned above, the guidewire 482 may be advanced first, and then followed by the catheter 412, and then the sheath 414, in order to advance the catheter 412 and the sheath 414 distally past a curved (e.g., a tight curved) passage way. In other embodiments, the catheter 412 may be advanced first, and then followed by the sheath 414, in order to advance the catheter 412 and the sheath 414 distally past a curved (e.g., a tight curved) passage way. In still further embodiments, the guidewire 482 may be advanced first, and then followed by the catheter 412 the sheath 414 (i.e., simultaneously), in order to advance the catheter 412 and the sheath 414 distally past a curved (e.g., a tight curved) passage way.

VI. Anti-Buckling Feature

Figure 53A:
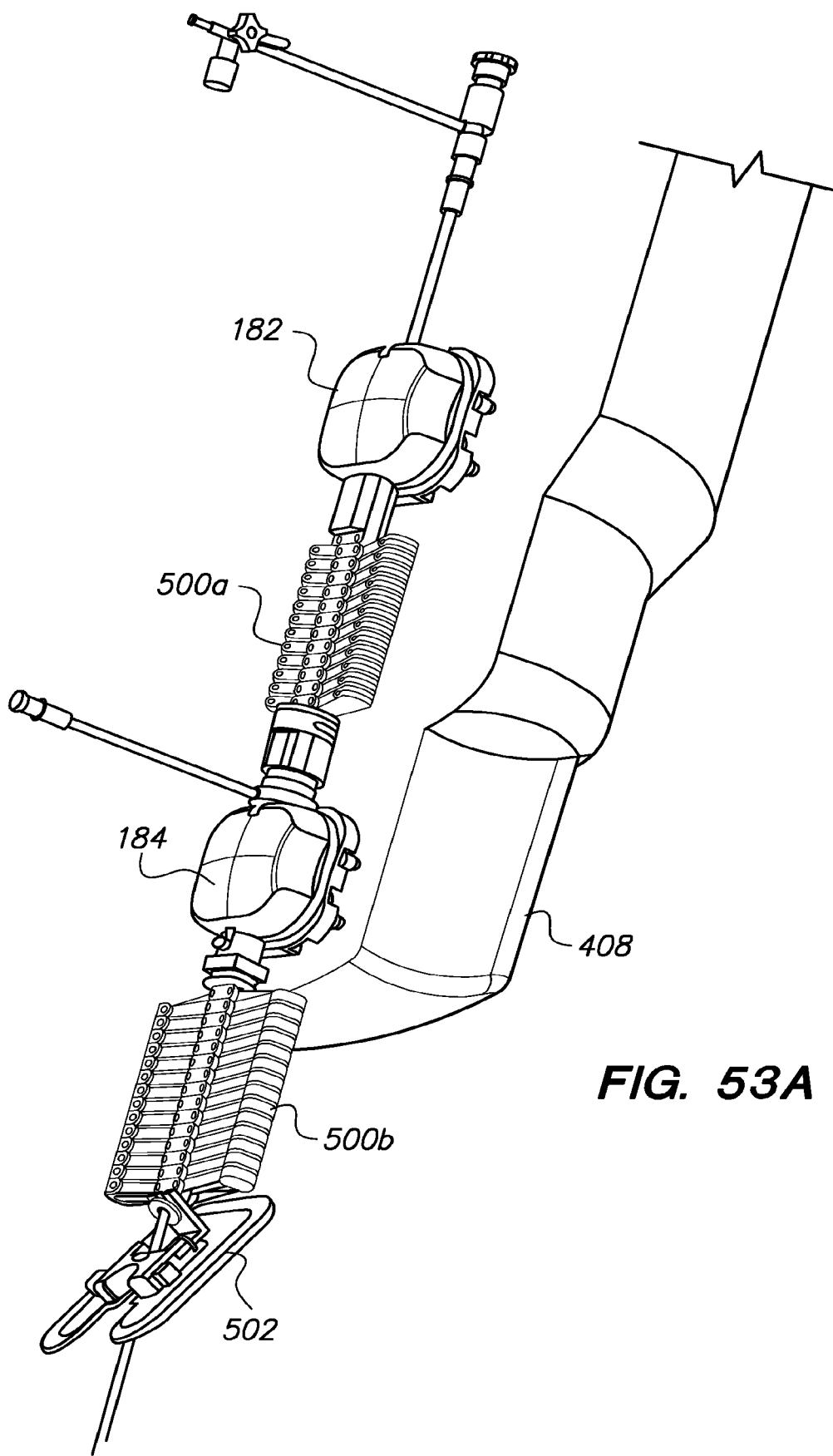

FIG. 53A illustrates an implementation of the instrument driver 408 that includes the first and second drivable assemblies 182, 184 removeably coupled to a base. The second drivable assembly 184 is slidable relative to the first drivable assembly 182. In the illustrated embodiments, the drivable assembly 184 is configured to control movement of a sheath, and the drivable assembly 182 is configured to control movement of a catheter member that is inserted into the sheath. During use, the drivable assembly 184 may be controlled to move the sheath distally towards the patient, or proximally. Also, the drivable assembly 182 may be controlled to move the catheter member towards the patient, or proximally. In another mode of operation, the drivable assembly 184 may maintain the sheath to be stationary while the drivable assembly 182 moves the catheter member distally or proximally relative to the sheath. In still another mode of operation, the drivable assembly 182 may maintain the catheter member to be stationary while the drivable assembly 184 moves the sheath distally or proximally relative to the catheter member. In another mode of operation, the drivers 182, 184 may cooperate with each other to move the catheter member and the sheath together (either distally or proximally), so that the catheter member with the sheath can translate as a unit.

As discussed, during an operation, the instrument driver assembly 408 may be configured to advance an elongate member (e.g., the sheath, the catheter member, or combination of both, any of which may be considered a medical device) distally towards the patient. In some embodiments, the elongate member may be constructed to be very flexible. In such cases, to prevent the elongate member from buckling while the elongate member is advanced towards the patient, an anti-buckling device may be coupled to the instrument driver assembly 408 to support the elongate member.

Figure 53B:
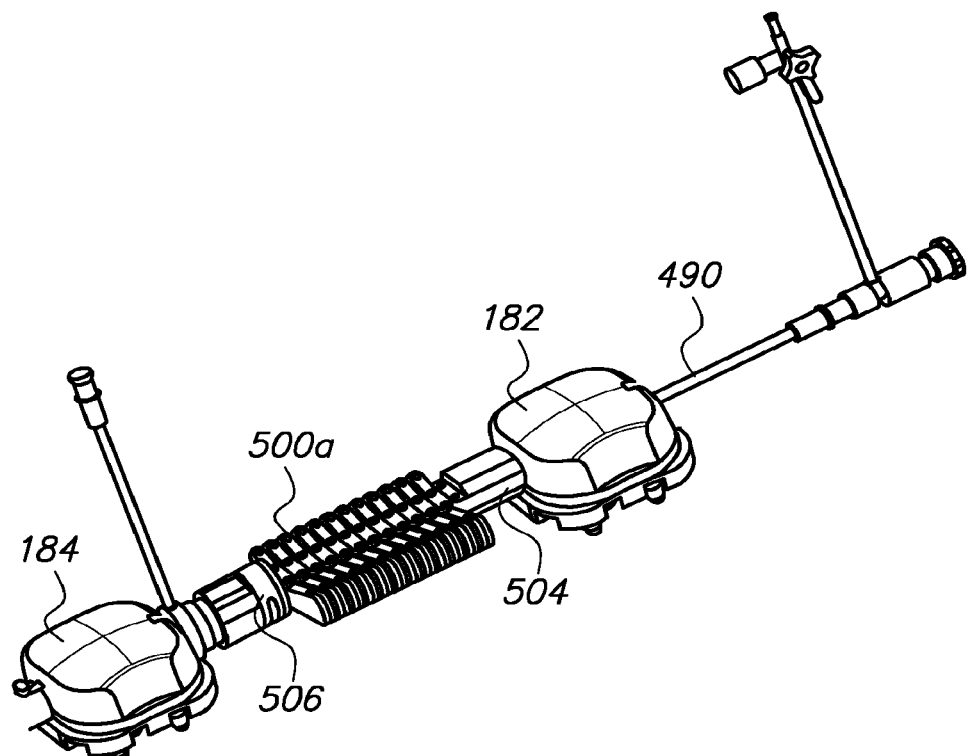

FIG. 53B illustrates an anti-buckling device 500a that is configured to detachably couple to the drivable assembly 184 and the drivable assembly 182 during use. As shown in FIG. 53B, the anti-buckling device 500a has a first end 504 for detachably coupling to the drivable assembly 182, and a second end 506 for detachably coupling to the drivable assembly 184. During use, the anti-buckling device 500a is placed around the elongate member 490 (which may be a catheter member, or another elongate medical device). The anti-buckling device 500a is then secured to the drivable assembly 182 at the first end 504, and to the drivable assembly 184 at the second end 506. The anti-buckling device 500a provides support along the length of the elongate member 490 between the drivers 82, 84, so that as the elongate member 490 is pushed towards the patient (resulting in the elongate member 490 being compressed), the catheter elongate 490 is prevented from buckling.

Figure 53G:
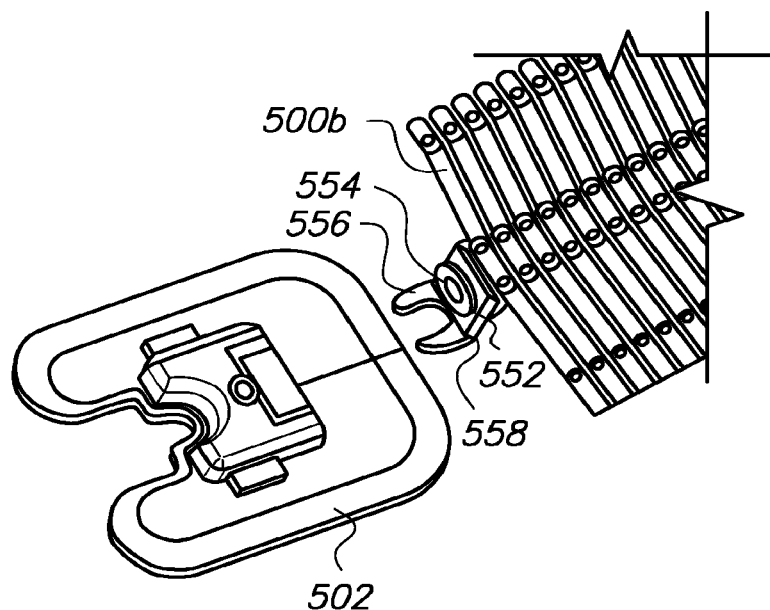
Figure 53C:
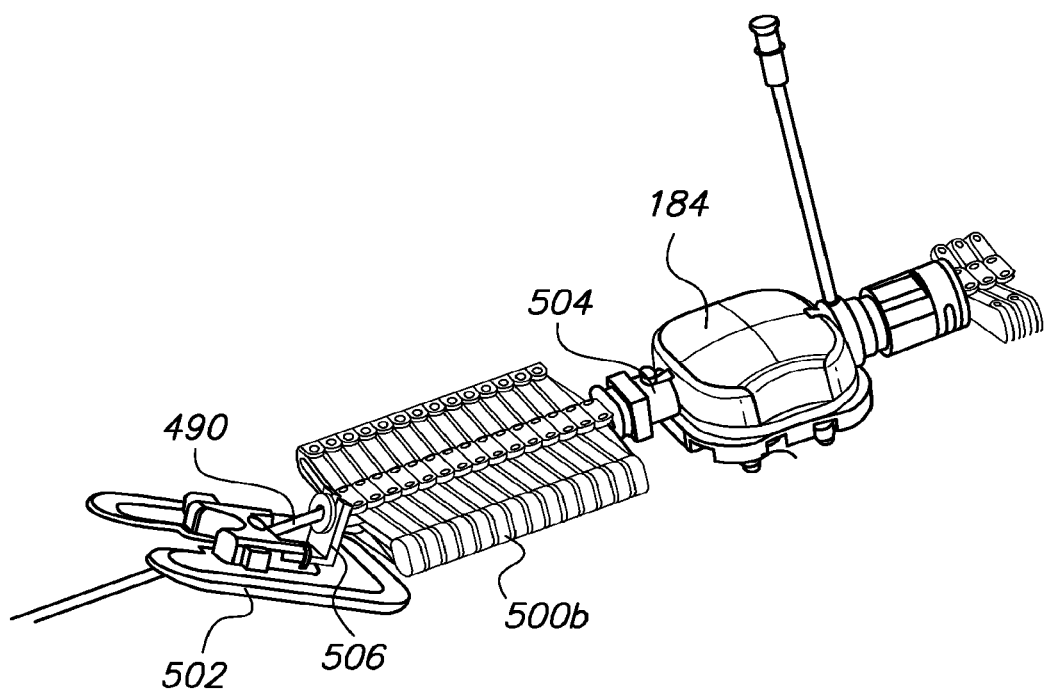

FIG. 53C illustrates another variation of an anti-buckling device 500b that is configured to detachably couple to the drivable assembly 184 and a stabilizer 502 during use. As shown in FIG. 53C, the anti-buckling device 500b has a first end 504 for detachably coupling to the drivable assembly 184, and a second end 506 for detachably coupling to the stabilizer 502. During use, the stabilizer 502 is attached to a patient's skin, and the anti-buckling device 500b is placed around the elongate member 490. The elongate member 490 may be a sheath, a catheter member, a combination of both the sheath and the catheter member, or another elongate medical device. The distal end of the elongate member 490 is then inserted into the patient through the stabilizer 502. The anti-buckling device 500b is secured to the drivable assembly 184 at the first end 504, and to the stabilizer 502 at the second end 506. The anti-buckling device 500b provides support along the length of the elongate member 490 between the stabilizer 502 and the drivable assembly 184, so that as the elongate member 490 is pushed towards the patient (resulting in the elongate member 490 being compressed), the elongate member 490 is prevented from buckling.

Figure 53D:
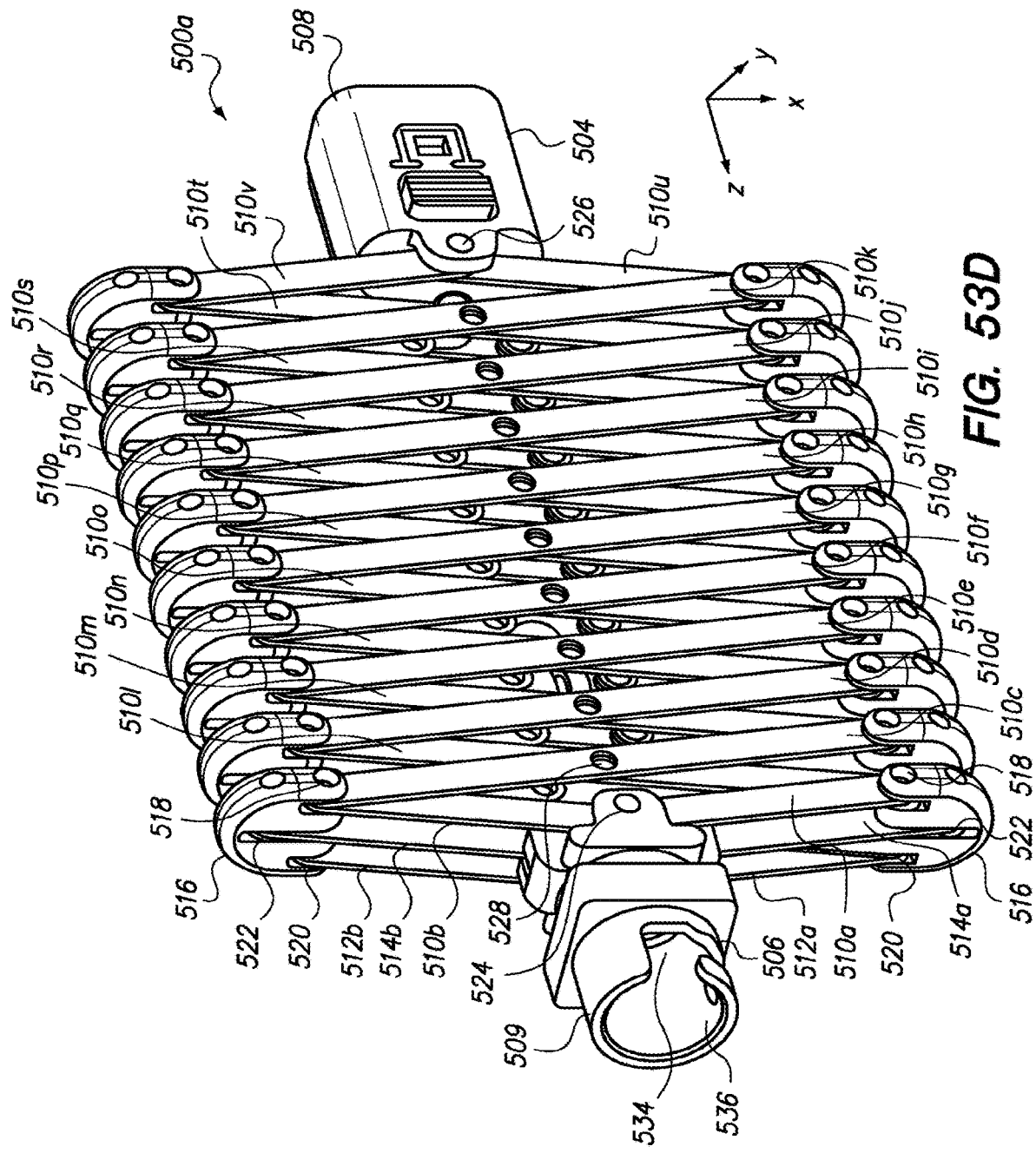
Figure 53E:
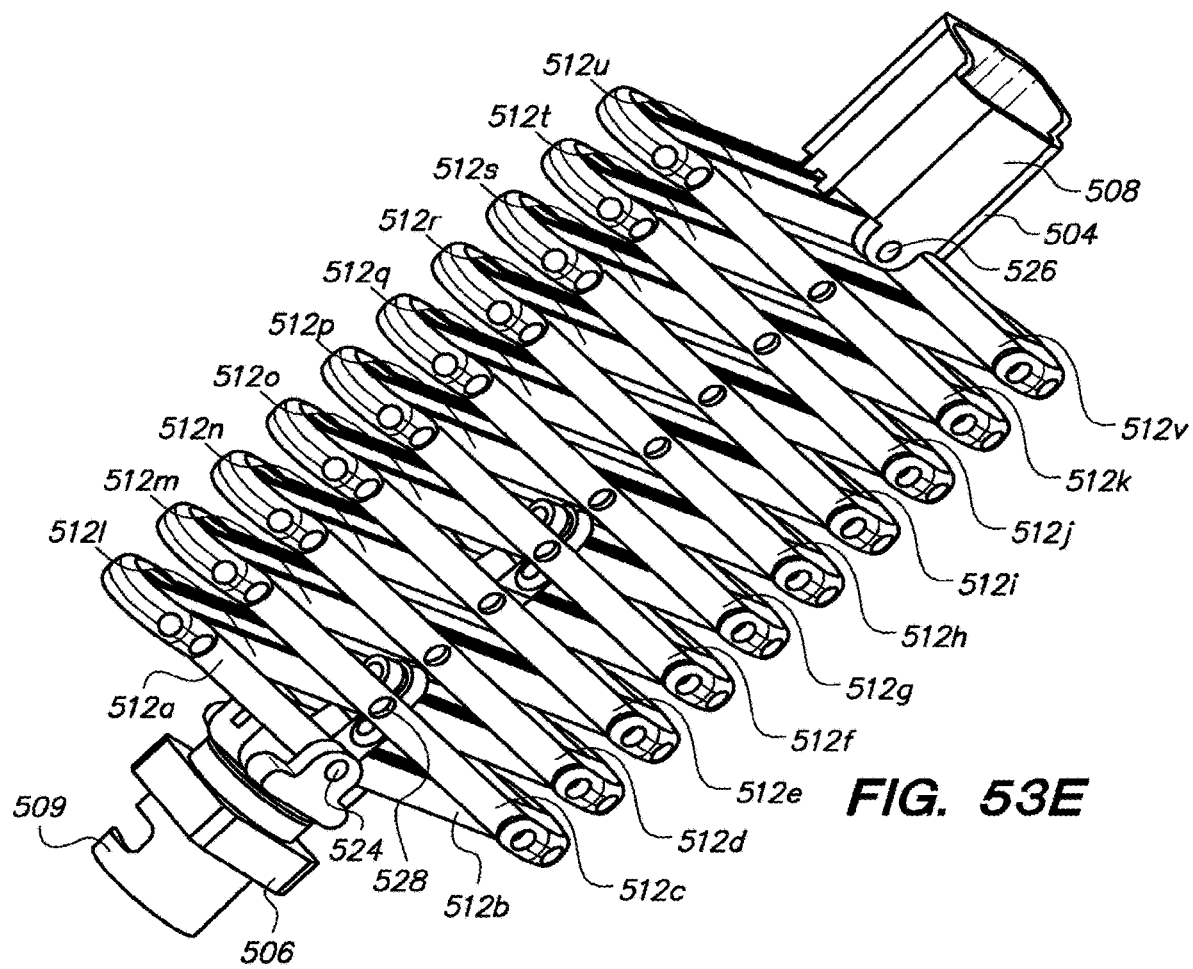
Figure 53F:
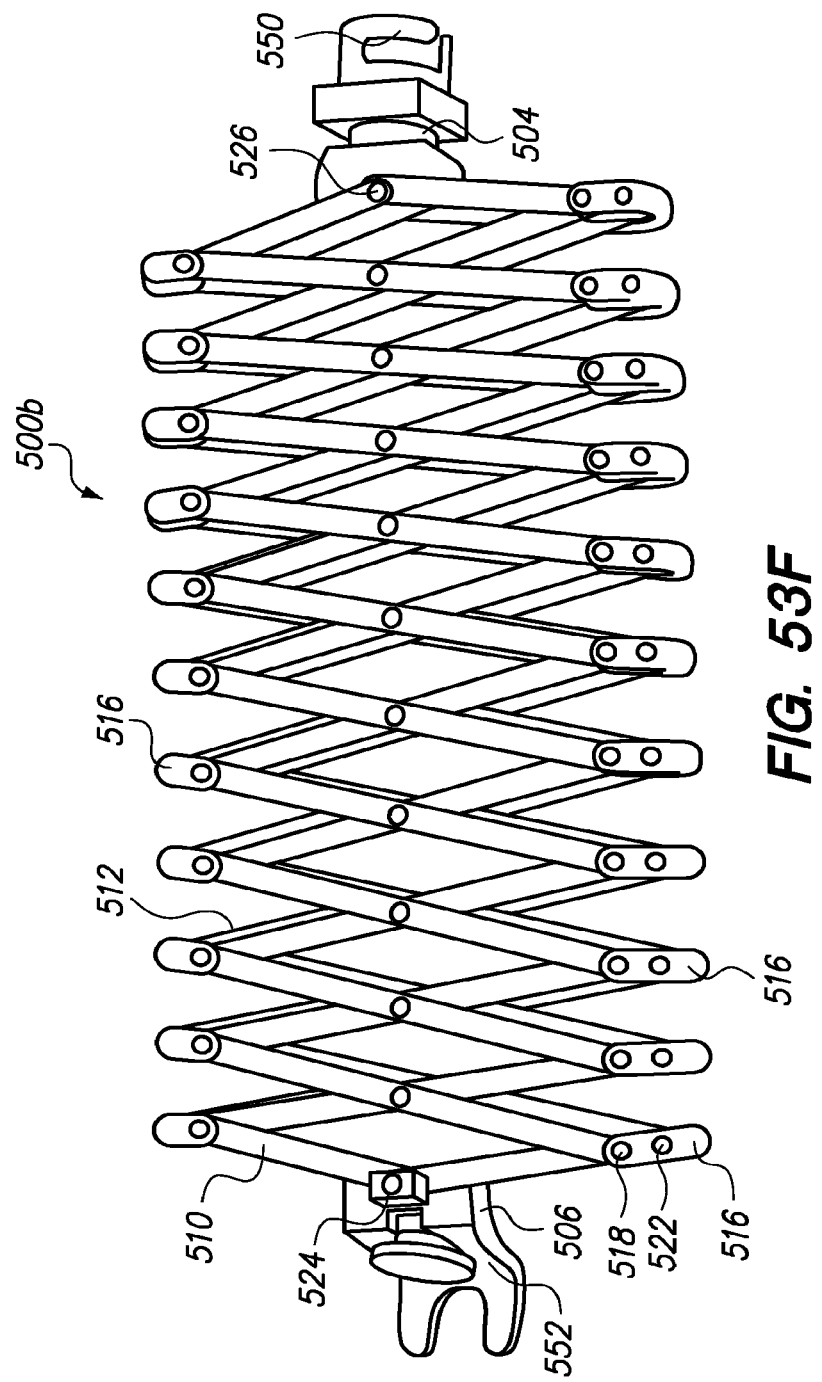
Figure 53H:
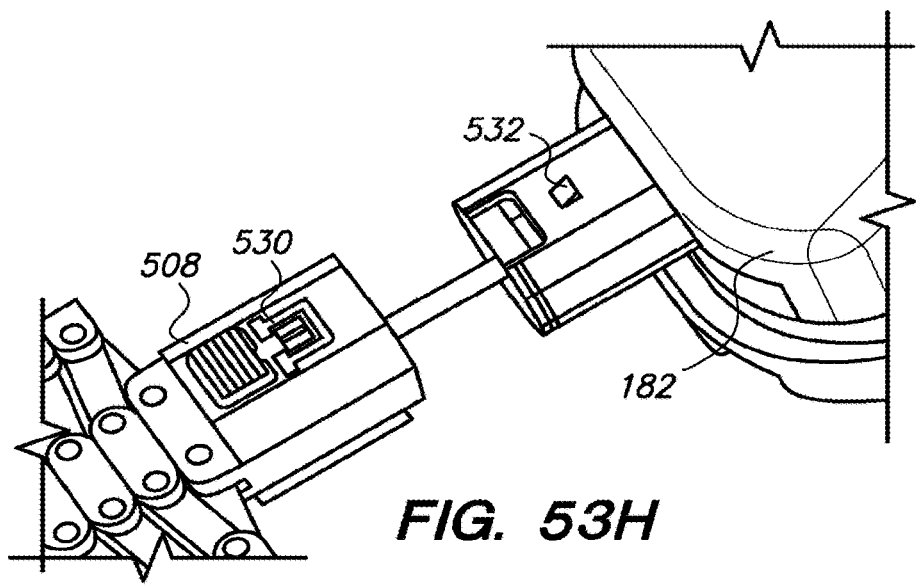
Figure 53I:
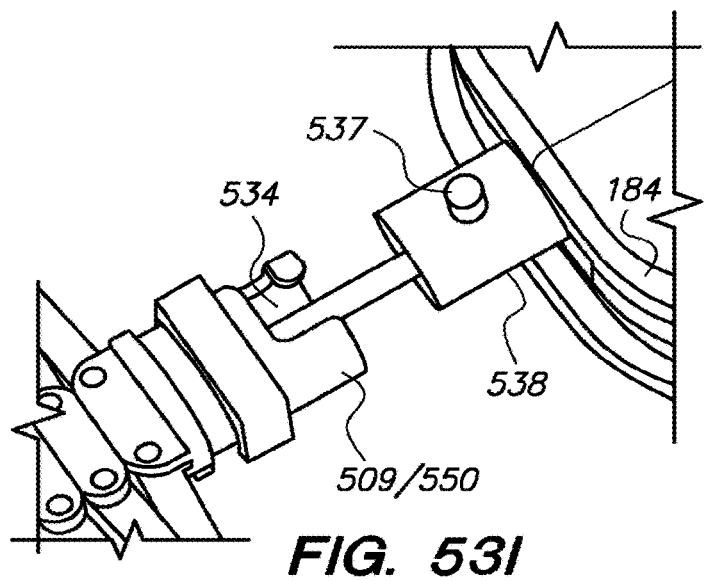
Figure 53J:
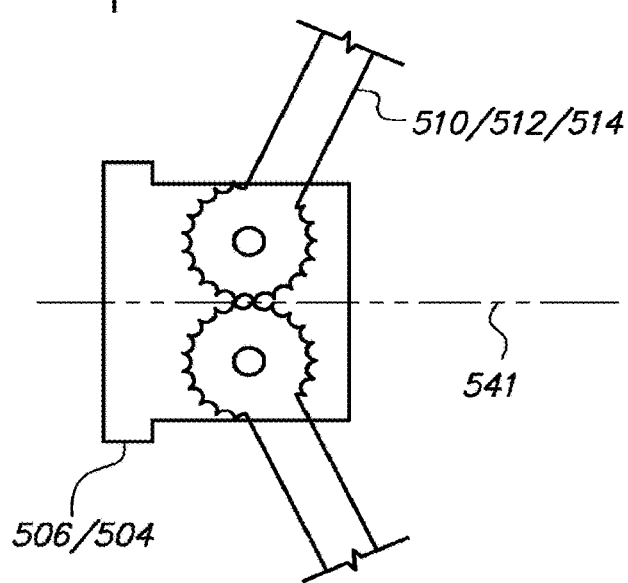

FIGS. 53D and 53E illustrate the anti-buckling device 500a in further detail. The anti-buckling device 500a includes a first coupler 508 at the first end 504, a second coupler 509 at the second end 506, and a plurality of support members 510, 512, 514 coupled between the couplers 508, 509. The first coupler 508 has a slot 530 configured (e.g., shaped and/or sized) to detachably mate with an anchor element 532 at the drivable assembly 182 (FIG. 53H). The second coupler 509 has a slot 534 for receiving a protrusion 537 at the drivable assembly 184, and an opening 536 for receiving a shaft 538 at the drivable assembly 184 (FIG. 53I). The second coupler 509 may be detachably coupled to the drivable assembly 184 by placing the second coupler 509 over the shaft 538, while allowing the protrusion 537 to pass the initial entry point at the coupler 509. The coupler 509 is then rotated to lock the protrusion 537 within the slot 534. In other embodiments, the coupler 509 may have different configurations. For example, in other embodiments, the coupler 509 may include an active valve connector hub that is configured to detachably couple to an active valve release hub (FIG. 53M). This configuration allows a user to connect the connector hub to the active valve, and rotate it in order to open or close the active valve as desired.

Returning to FIG. 53D, the support members 510 are on one side of the anti-buckling device 500a, the support members 512 are on the opposite side of the anti-buckling device 500a, and the support members 514 are located in the middle between the first and second sets of support members 510, 512. In the illustrated embodiments, support members 510m 512 create the scissor mechanism. The support members 514 create an additional set of linkages that is offset from the support members 510, 512. The purpose of the support members 514 is to hold the eyelets 540 in line. The elongate member held between two eyelets 540 will have much greater buckling resistance if the eyelets 540 are prevented from being rotated. In other embodiments, the number of support members 510, 512, 514 may be different from that shown in the figure. In particular, on one side of the anti-buckling device 500a, the support members 510a, 510b are rotatably coupled to the coupler 509 via joint 524, and support members 510u, 510v are rotatably coupled to the coupler 508 via joint 526. The rest of the support members 510c-510t are coupled together via joints 528 between the first and second ends 504, 506 in a scissor-like configuration. In other embodiments, the support members 514 are optional, and the anti-buckling device does not include the support members 514.

As shown in FIG. 53E, on the other side of the anti-buckling device 500a, the support members 512a, 512b are rotatably coupled to the coupler 509 via joint 524, and support members 512u, 512v are rotatably coupled to the coupler 508 via joint 526. The rest of the support members 512c-512t are coupled together via joints 528 between the first and second ends 504, 506 in a scissor-like configuration.

It should be noted that providing two sets of support members 510, 512 are advantageous in that they collectively provide sufficient stiffness for the anti-buckling device 500a in the Y-direction so that the anti-buckling device 500a will not sag or deflect significantly in the Y-direction between the supports at ends 506, 506. In other embodiments, the support members 510 may be made sufficiently stiff, and the joints coupling the various components of the anti-buckling device 500a may be configured to have a tight tolerance. In such cases, the anti-buckling device 500a may not require the second set of support members 512.

In the illustrated embodiments, the anti-buckling device 500a also includes a plurality of connectors 516 that connects the support members 510, 512, 514. Each connector 516 includes a first joint 518 for rotatably coupling to two of the support members 510, a second joint 520 for rotatably coupling to two of the support members 512, and a third joint 522 for rotatably coupling to two of the support members 514.

Figure 53K:
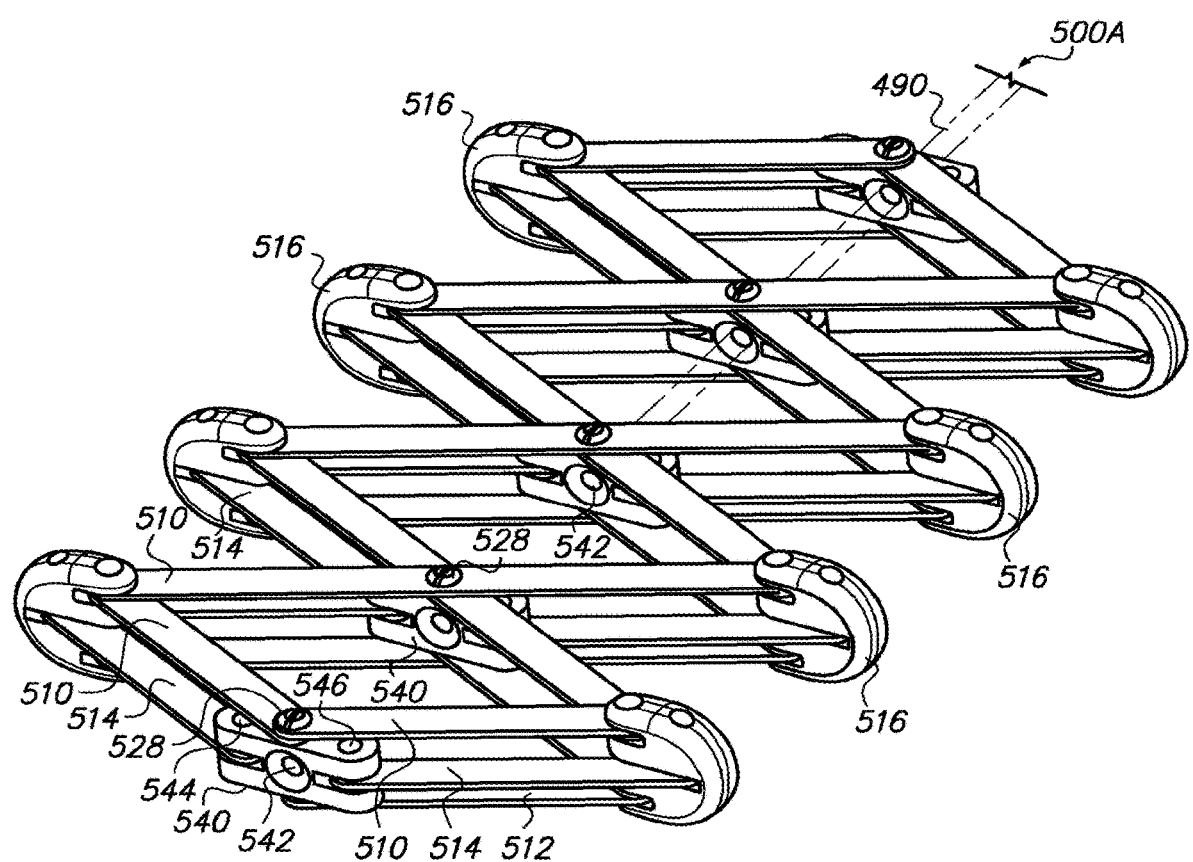

As shown in FIG. 53K, the anti-buckling device 500a also includes a plurality of holders 540 coupled between the first and second sets of support members 510, 512 at the respective joints 528. Each holder 540 has an opening 542 for accommodating the elongate member 490, a first joint 544 for rotatably coupling to one of the support members 514, and a second joint 546 for rotatably coupling to another one of the support members 514. The support members 514 together with the holders 540 are configured to support the elongate member 490 as the elongate member 490 is being inserted into the patient. In particular, as the anti-buckling device 500a is being extended (FIG. 52L) (e.g., by moving the ends 504, 506 further away from each other) or collapsed (FIG. 53D) (e.g., by moving the ends 504, 506 closer towards each other), the support members 514 are configured to move the holders 540 along the longitudinal axis of the elongate member 490 relative to the elongate member 490 so that the holders 540 are spaced substantially evenly or equally along the axis of the elongate member 490. In some embodiments, the holders 540 are considered to be spaced substantially evenly or equally when their spacing does not vary by more than 20%. The support members 514 also maintain all of the holders 540 in the same orientation relative to each other as the anti-buckling device 500a is being extended or collapsed.

In one or more of the embodiments described herein, the support members 510 (or members 512, or members 14) at one end (e.g., end 504 or 506) of the anti-buckling device 500 may optionally have mating gears (FIG. 53J). This ensures that the support members 510/512/514 on either side of the longitudinal axis 541 along the length of the anti-buckling device 500 will rotate by the same amount relative to the axis 541. This feature is also advantageous because it ensures that the holders 540 will be oriented so that the axis of the opening 542 for each of the holders 540 is substantially parallel to the longitudinal axis 541 of the anti-buckling device 500.

As shown in the illustrated embodiments, the anti-buckling device 500a provides a plurality of supports at the locations of the holders 540 that are evenly spaced along the length of the elongate member 490 regardless of how much the elongate member 490 is inserted into the patient (i.e., regardless of the distance between the first and second ends 504, 506). The plurality of supports shortens the buckling length of the elongate member 490, thereby significantly improving the buckling strength of the elongate member 490. It should be noted that the plurality of supports will prevent the elongate member 490 from buckling in a direction within the X-Z plane because the anti-buckling device 500a is very stiff in X-Z plane. Also, since the anti-buckling device 500a is relatively stiffer than the elongate member 490 in the Y-direction, the anti-buckling device 500a will also provide supports for the catheter member in all directions within the Y-Z plane to prevent the elongate member 490 from buckling in a direction that is within the Y-Z plane.

Figure 53L:
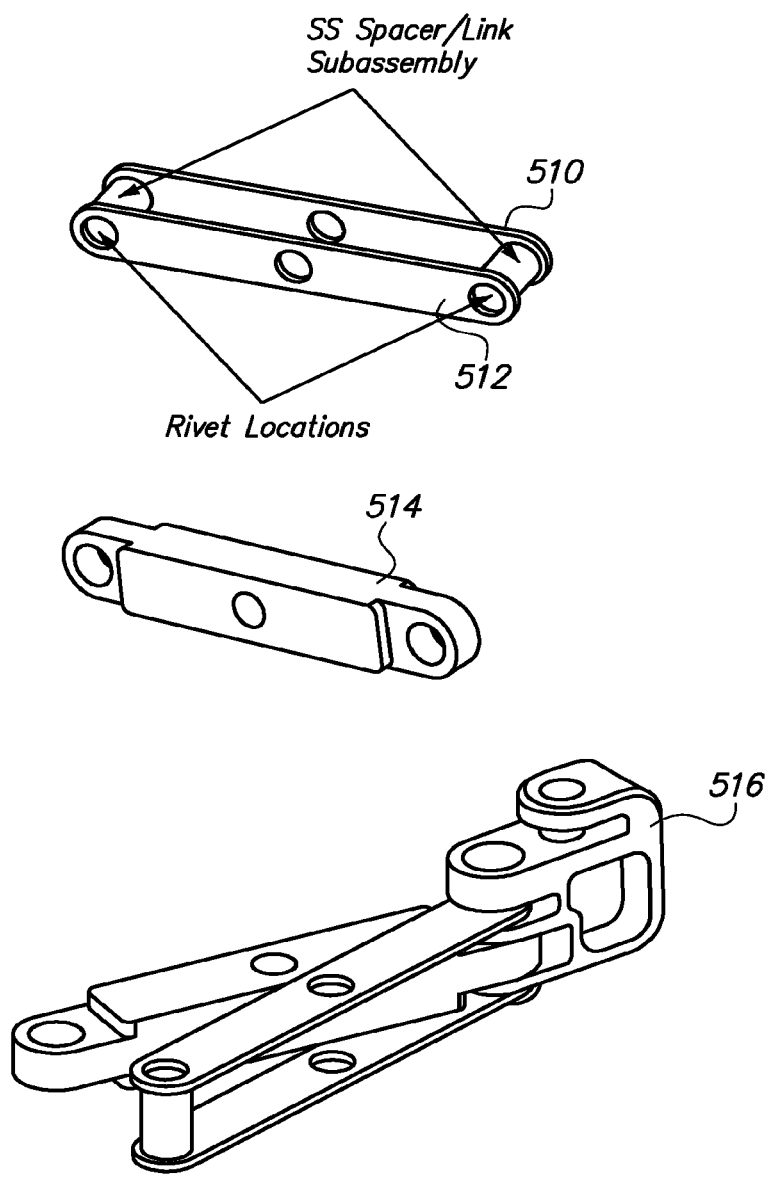
Figure 53M:
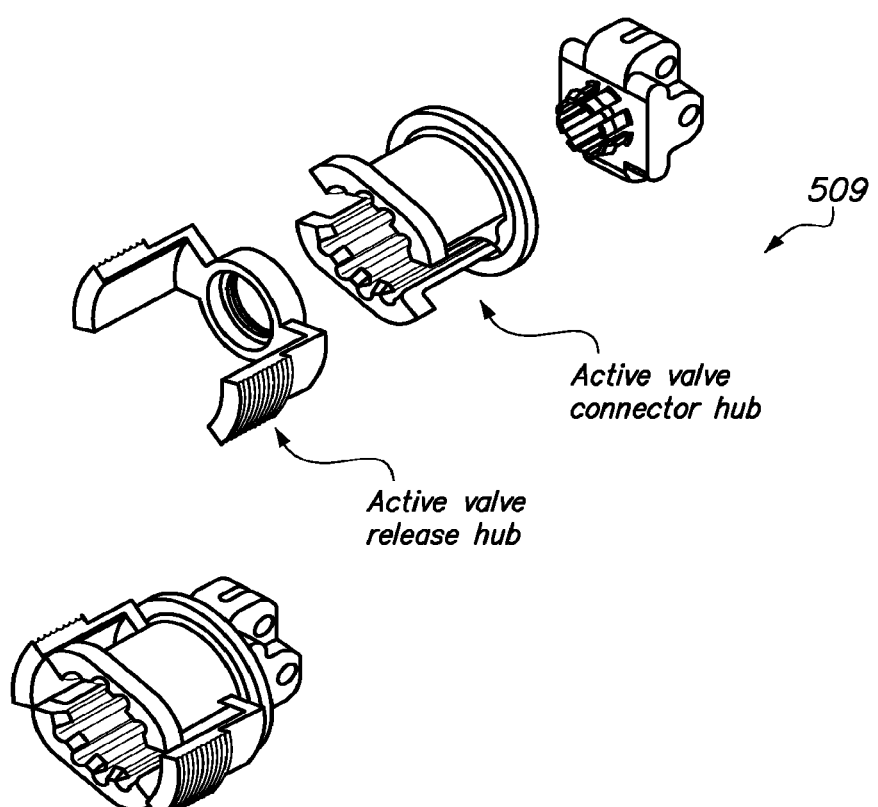

In other embodiments, to increase the rigidity of the anti-buckling device, the support members 510, 512, 514 may be implemented using a combination of a composite beam and a plastic beam (FIG. 53L). As shown in FIG. 53L, the composite beam may be formed from two stainless steel members that are spaced apart from each other with two stainless steel spacers therebetween. The plastic beam may be a PEEK beam. The composite beam and the plastic beam may be linked together to the connector 516 at one end via a hinge (e.g., rivet(s)).

The anti-buckling device 500a may be made from a variety of different materials. For example, in some embodiments, the support members 510, 512, 514 may be made from metal, alloys, plastics, polymers, etc. Also, in some embodiments, the connectors 516, and the couplers 508, 509 may be made from metal, alloys, plastics, polymers, etc. In addition, in one or more of the embodiments described herein, any moving parts in the anti-buckling device that contact each other may be made from the same material (e.g., stainless steel), or different materials (e.g., stainless steel for one, and PEEK for the other). Making two contacting parts that interact with each other with different respective materials is advantageous because it may allow the moving parts to move relatively to each other more easily without seizing. Furthermore, in one or more of the embodiments described herein, one or more components (e.g., support members 510, 512, 514) of the anti-buckling device may be made from a light weight material, such as PEEK (plastic), to reduce the overall weight of the anti-buckling device. Also, in one or more of the embodiments described herein, any of the joints (e.g., joints 520, joints 522, or joints 528) may be implemented using pins (e.g., dowel pins), rivets, or combination thereof. In one implementation, the support members 510, 512, 514 may be made from stainless steel and/or PEEK, the holders 540 may be made from PEEK, the rivets/pins may be made from stainless steel, the component housing the rivets/pins may be made from PEEK, and the end couplers 508, 509 (and similarly, couplers 550, 552 in the second anti-buckling device 500b shown in FIG. 53F) may be made from PEEK/Ultem.

The second anti-buckling device 500b is illustrated in further detail in FIG. 53F. The anti-buckling device 500b has the same configuration as the anti-buckling device 500a, except that it is used to prevent buckling between the drive assembly 184 and the insertion site or the patient. This insertion site may be at the left or right femoral artery or alternatively may be the left or right brachial artery, etc. Its proximal end 504 has a first coupler 550 for detachably coupling to the drivable assembly 184, and its distal end 506 has a second coupler 552 for detachably coupling to the stabilizer 502 (FIG. 53C). The first coupler 550 of the anti-buckling device 500b has the same configuration as the second coupler 509 of the anti-buckling device 500a, and is configured to detachably couple to a connector at the drivable assembly 184 (FIG. 53G). As shown in FIG. 53G, the second coupler 552 has an opening 554 for allowing the elongate member 490 to extend therethrough. The second coupler 552 also has a pair of protrusions 556 for inserting into a slot at the stabilizer 502, and a wall 558 for allowing the stabilizer 502 to anchor thereto. The second coupler 552 may also be directly connected to the introducer sheath at the insertion site.

Refer now to FIG. 54, the stabilizer 502 will now be described in further detail. The stabilizer 502 includes a base 560 with adhesive at its bottom side for attachment to a patient's skin, and a connector 562 for coupling with the coupler 552 of the anti-buckling device 500b. Alternatively, the base 560 or the coupler 552 may be attached to a bed or other support during use. In some embodiments, the base 560 may be a HDPE platform that includes a strain relief material underneath for providing transition from the rigid HDPE material to the patient skin. The base 560 may also include a butterfly peel-away liner (e.g., tear-resistant HDPE liner) that covers the adhesive material at the bottom side of the platform. During use, the liner may be peeled away to expose the adhesive at the bottom side of the base 560. The stabilizer 502 also includes an opening 564 formed at the base 560 for allowing the elongate member 490 to reach the patient's skin. The interface mechanism 564 includes a pair of slots 566 for receiving the respective protrusions 556 at the coupler 552, and a pair of moveable anchors 568 for anchoring against the wall 558 of the coupler 552.

Figure 55A:
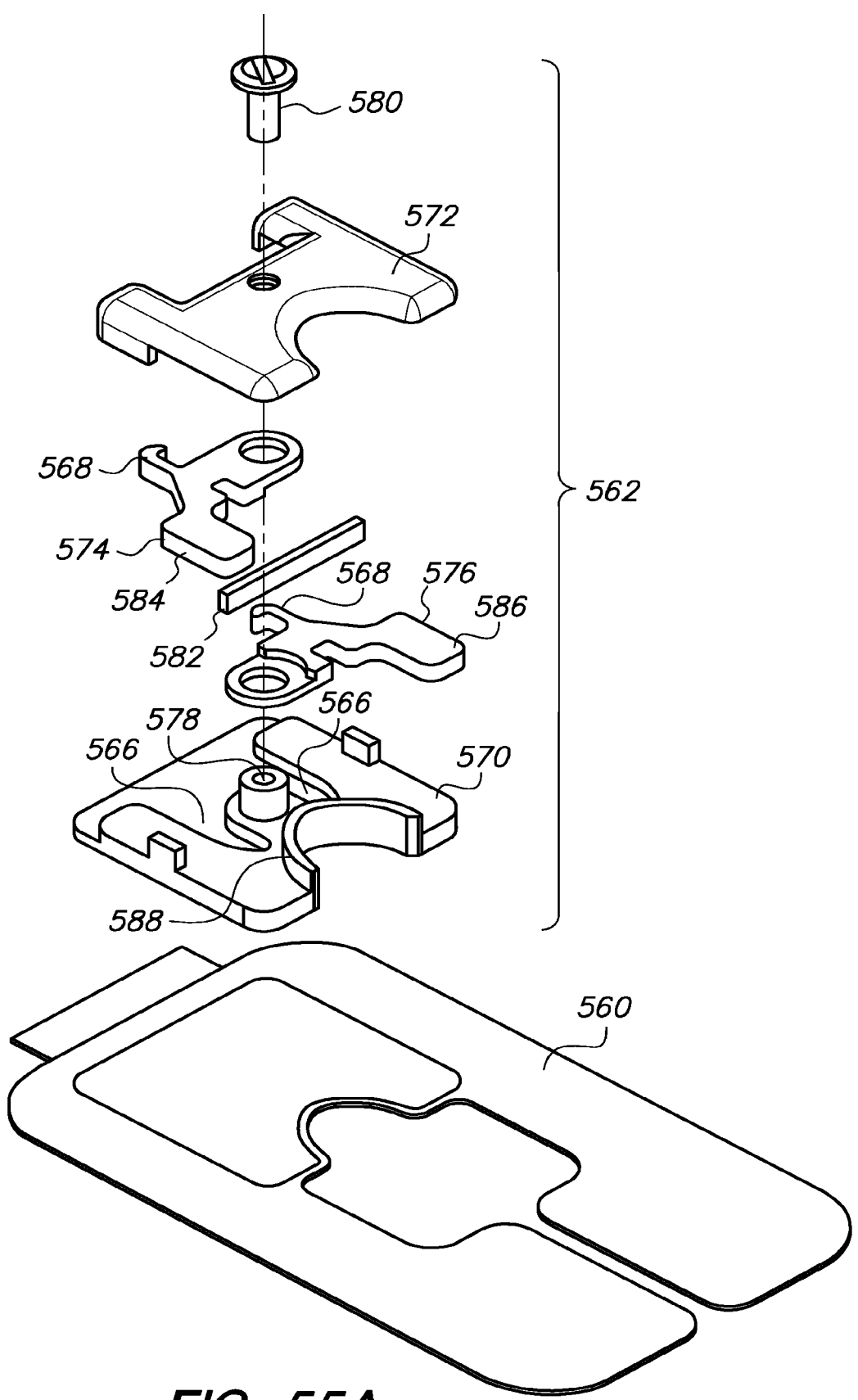
Figure 55B:

FIGS. 55A and 55B illustrate the stabilizer 502 in exploded view, particularly showing the components of the stabilizer 502. The connector 562 includes a bottom piece 570 with the two slots 562, a top piece 572, and two rotatable anchoring components 574, 576 located between the bottom piece 570 and the top piece 572. A screw 580 is provided for extending through the top piece 572, and the anchoring components 574, 576, to reach screw opening 578 at the bottom piece 572, thereby coupling the various components together. The connector 562 also includes a spring 582 (in the form of an elastic plate, e.g., formed using a metal, alloy, or plastic) for biasing the anchoring components 574, 576 so that their respective anchors 568 are urged towards each other. During use, when the coupler 552 is inserted into the slots 566, the insertion force will push wall 558 of the coupler 552 towards the anchors 568, thereby spreading the anchors 568. When the coupler 552 is further inserted into the slots 566, the wall 558 will pass the anchors 568, thereby allowing the anchors 568 to close towards each other due to the biasing force provided by the spring element 582. The anchoring components 574, 576 also include respective levers 584, 586 for allowing a user to move the anchors 568 away from each other. In particular, when the levers 584, 586 are pressed towards each other, they bend the spring 582 against the curvilinear support 588 at the bottom piece 570, thereby overcoming the biasing force that was urging the anchors 568 towards each other. This allows a user to remove the coupler 552 from the connector 562 at the stabilizer 502.

Figure 55C:
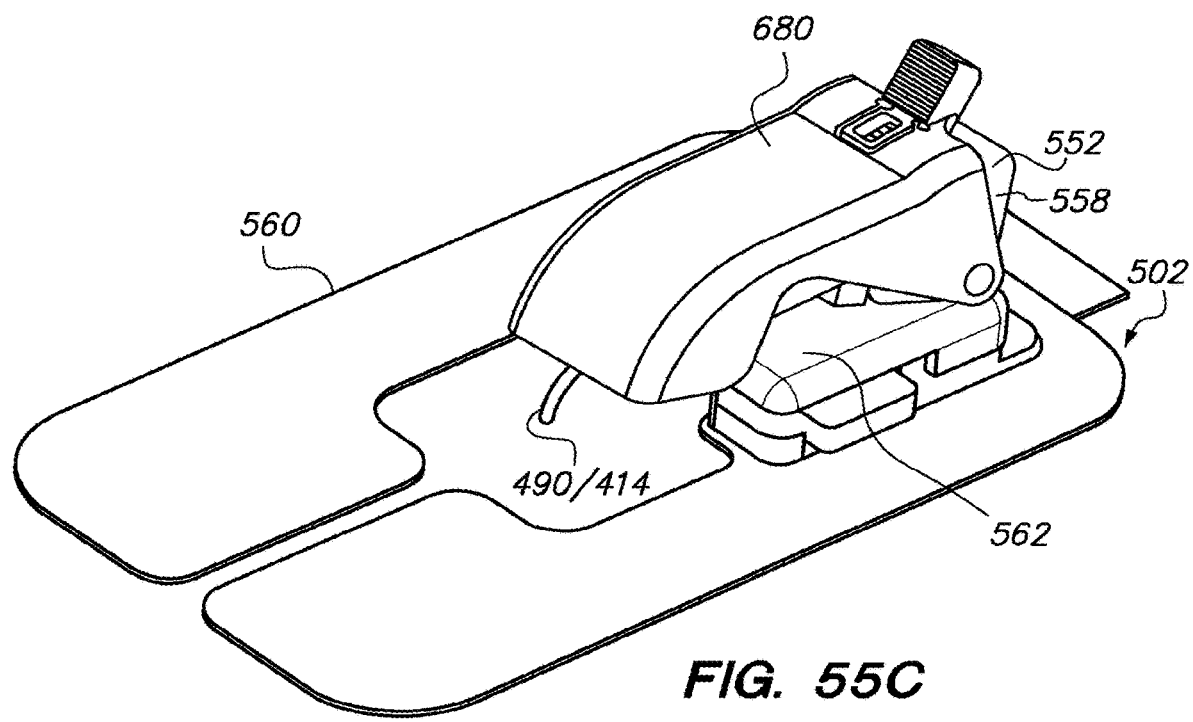
Figure 55D:
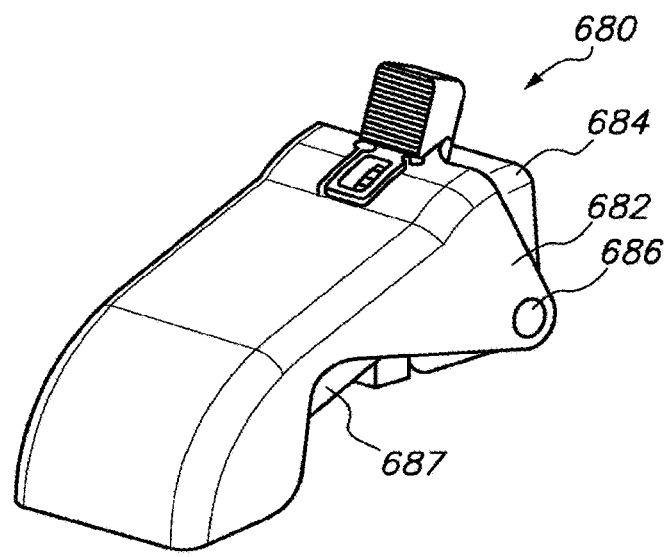
Figure 55E:
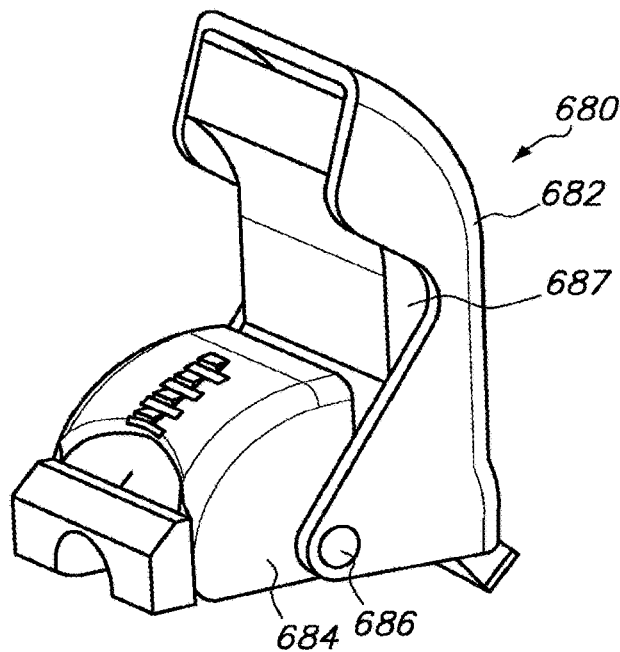
Figure 55F:
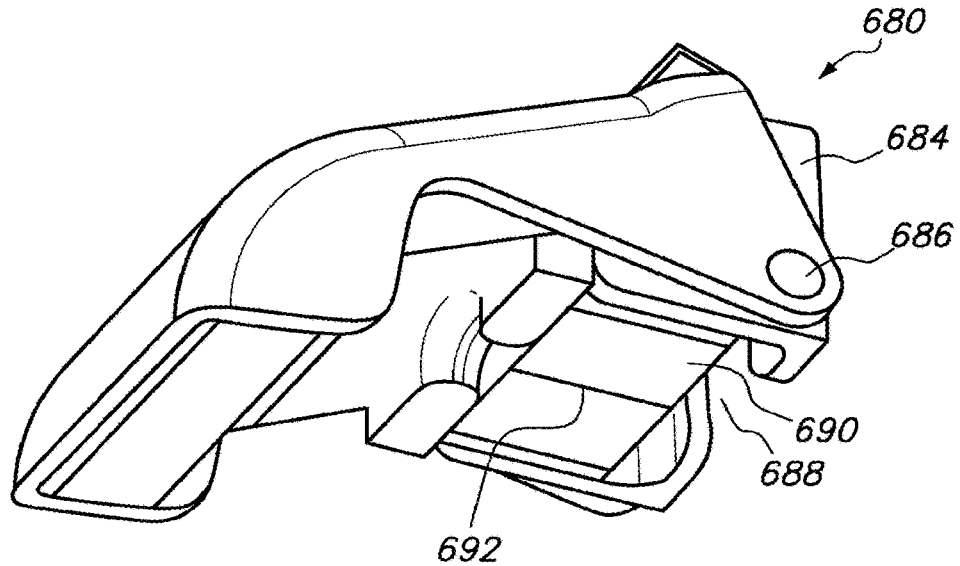

As shown in FIG. 55C, in some embodiments, the system may further include a lubricating system 680 coupled to the stabilizer 502. The lubricating system 680 is configured to apply fluid (e.g., saline, gel) onto the exterior surface of the catheter 412 as the catheter 412 is being advanced through the lubricating system 680. As shown in FIGS. 55D-55F, the lubricating system 680 includes a base 684 and a cover 682 coupled to the base 684 via a joint 686. The hinge 686 allows the cover 682 to be rotated relative to the base 684, so that the system is always in contact with the catheter irrespective of the angle of entry of the catheter into the patient. As shown in FIG. 55F, the lubricating system 680 also includes a slot 688 formed at the base 684, which is configured to mate with the ring structure formed around the opening 554 at the coupler 552 (FIG. 53G). The lubricating system 680 also includes an absorbent material 690 underneath the cover 682, wherein the material 690 has a slot or cut-portion 692 for applying fluid to the catheter 412. During use, the catheter 412 exiting from the opening 554 at the coupler 552 will go through the slot or cut-portion 692, thereby contact-ing the absorbent material 690. The absorbent material 690 will be sterile and will be soaked with saline by the user at the start of the procedure and then it automatically applies the fluid onto the surface of the catheter 412 as it passes therethrough. In some embodiments, the catheter 412 may be coated with a hydrophilic coating to reduce friction as they are pushed through the anatomy. In such cases, the lubricating system 680 may be used to hydrate the hydrophilic coating to activate it. As illustrated in the above embodiments, the lubricating system 680 provides a self lubricating or self hydration mechanism for robotically controlled catheter. This is advantageous because the doctor who is controlling the catheter remotely would be unable to manually wet the catheter with a wet gauze.

Figure 56:
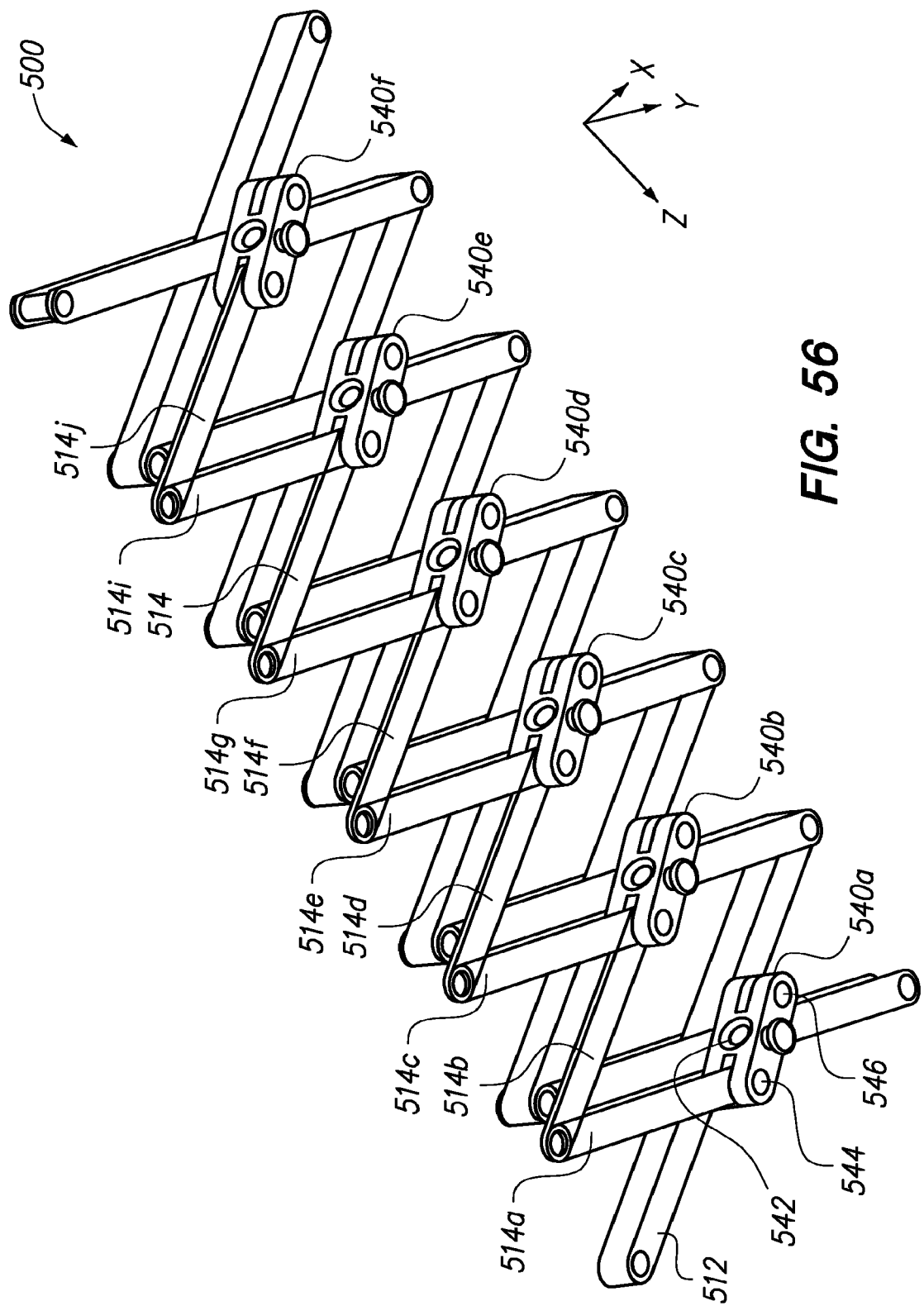

It should be noted that the anti-buckling device 500 is not limited to the above configuration, and that the anti-buckling device 500 may have other configurations in other embodiments. For example, in other embodiments, instead of having three sets of supports 510, 512, 514, the anti-buckling device 500 may include only two sets of supports. FIG. 56 illustrates another anti-buckling device 500 in accordance with other embodiments. The anti-buckling device 500 is similar to the embodiments of FIGS. 52 and 53, except that it has one set of support members 510 on one side of the anti-buckling device 500, and another set of support members 514 next to the first set of support members 510 for maintaining the holders 540 in the same orientation relative to each other. In the embodiment of FIG. 56, the anti-buckling device 500 does not include the set of support members 512 like that shown in FIG. 52. Also, unlike the embodiments of FIGS. 52 and 53, the embodiment of FIG. 56 includes support members 514 only on one side, wherein the support members 514 are coupled to the respective joints 544 on only one side of the holders 540. In other embodiments, additional support members 514 may be provided on the opposite sides, in which case, the support members 514 will be coupled to the respective joints 546 at the holders 540. The anti-buckling device 500 shown in FIG. 56 may have different connectors (not shown) at opposite ends, such as those shown in FIGS. 52 and 53, for detachably coupling to different medical devices/components.

As shown in FIG. 56, the support members 512 are relatively thicker than those in FIGS. 52 and 53. Such configuration provides sufficient stiffness for the anti-buckling device 500 in the Y-direction while obviating the need for the third set of support members 512, so that the anti-buckling device 500 will not sag or deflect significantly.

In the embodiment of FIG. 56, the support members 514 together with the holders 540 are configured to support the elongate member 490 as the elongate member 490 is being inserted into the patient. In particular, as the anti-buckling device 500 is being extended (e.g., by moving the ends 504, 506 further away from each other) or collapsed (e.g., by moving the ends 504, 506 closer towards each other), the support members 514 are configured to move the holders 540 along the longitudinal axis of the elongate member 490 so that the holders 540 are spaced evenly along the axis of the elongate member 490. The support members 514 also maintain all of the holders 540 in the same orientation relative to each other as the anti-buckling device 500 is being extended or collapsed.

As shown in the illustrated embodiments, the anti-buckling device 500 provides a plurality of supports at the locations of the holders 540 that are evenly spaced along the length of the catheter member 90 regardless of how much the elongate member 490 is inserted into the patient (i.e., regardless of the distance between the first and second ends 504, 506). The plurality of supports shortens the buckling length of the elongate member 490, thereby significantly improving the buckling strength of the elongate member 490. It should be noted that the plurality of supports will prevent the elongate member 490 from buckling in a direction within the X-Z plane because the anti-buckling device 500 is very stiff in X-Z plane. Also, since the anti-buckling device 500 is relatively stiffer than the elongate member 490 in the Y-direction, the anti-buckling device 500 will also provide supports for the elongate member 490 in the Y-direction to prevent the catheter member 90 from buckling in a direction that is within the Y-Z plane.

In any of the anti-buckling devices described herein, the buckle resistance increases as the unsupported length of the catheter gets shorter. The length of the catheter outside the patient gets shorter as the catheter is advanced further into the patient. Thus, as the catheter is being advanced into the patient, the unsupported length of the catheter becomes shorter, resulting in a higher buckling resistance provided to the catheter by the anti-buckling device. Therefore, the anti-buckling device provides a variable stiffness that allows the catheter's buckling capacity to increase as the catheter is being advanced into the patient. The further the catheter is advanced into the patient, the higher the insertion force is required to advance the catheter. In some embodiments, the buckle force of the anti-buckling device is always higher than the catheter insertion force.

Figure 57:
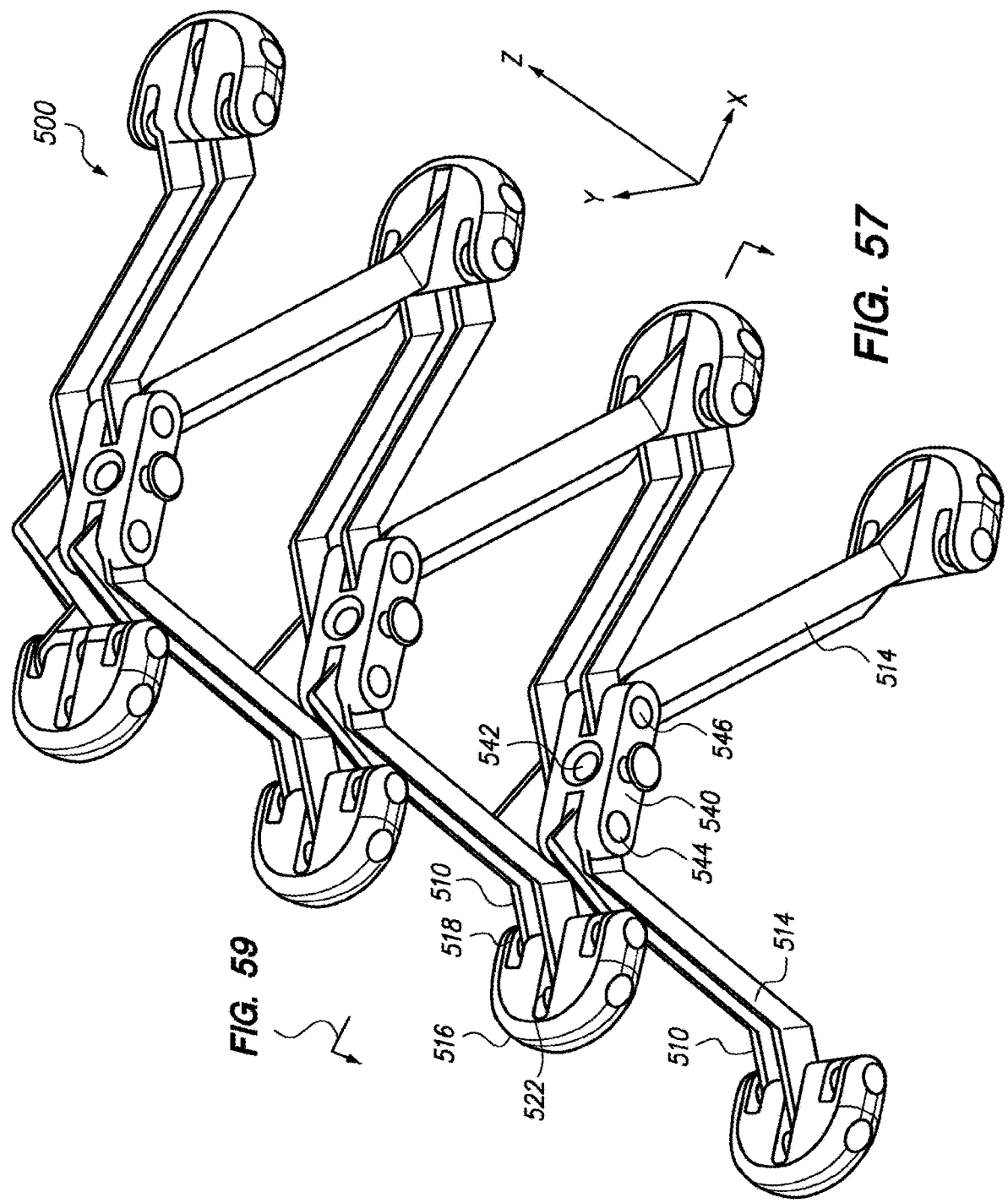
Figure 58:
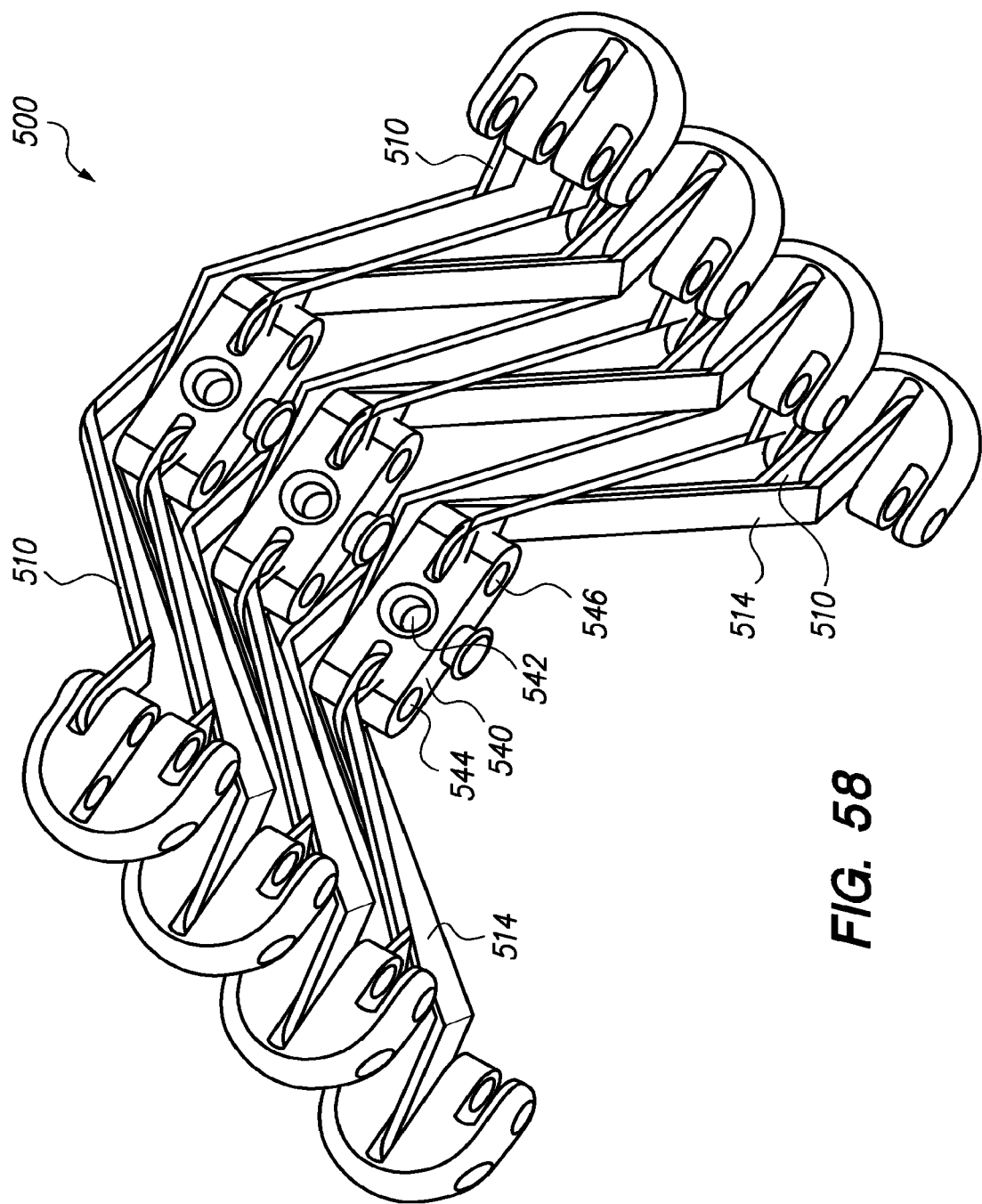
Figure 59:
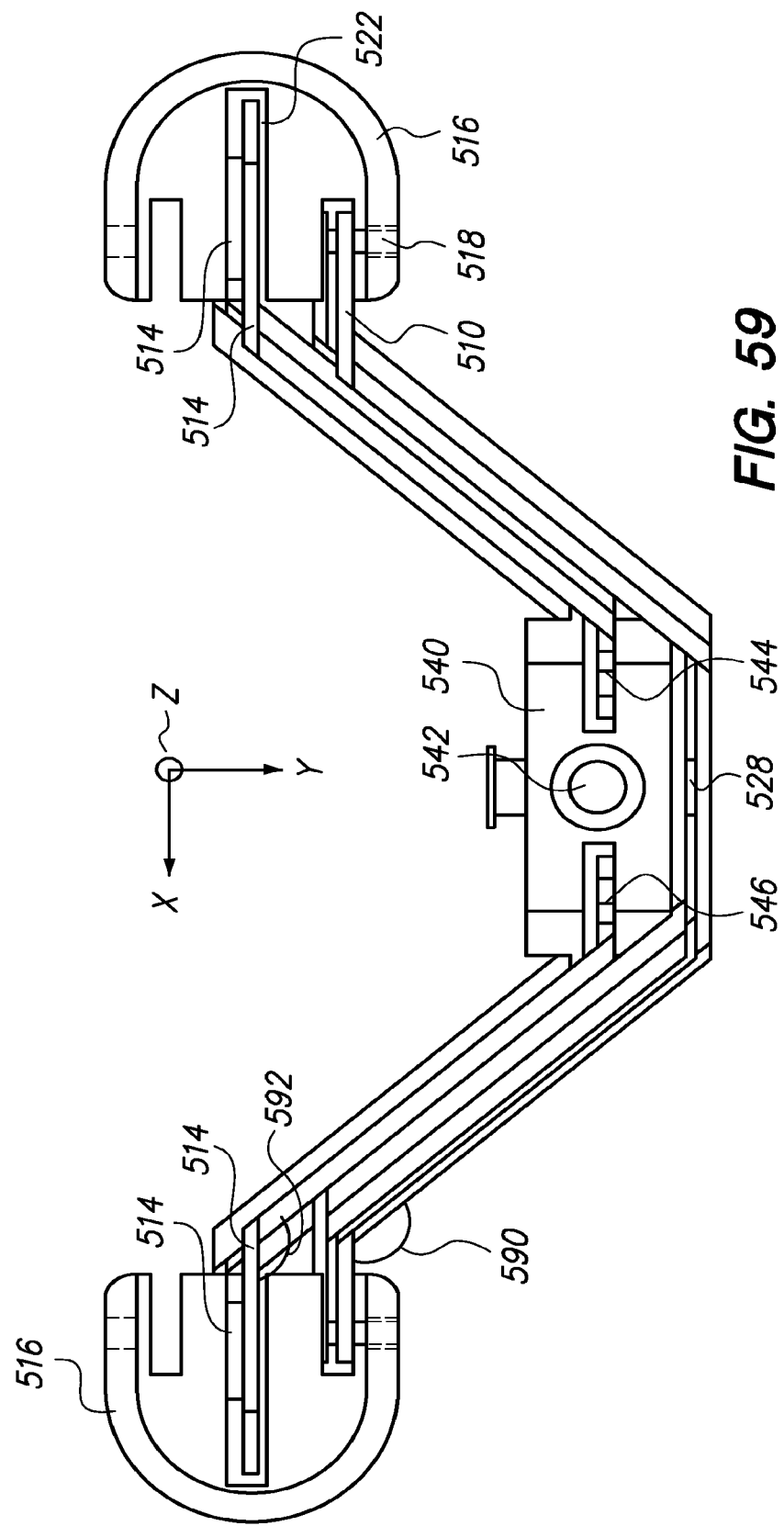

In one or more of the embodiments of the anti-buckling device 500 described herein, the anti-buckling device 500 should not be limited to the planar configuration, and the anti-buckling device 500 may have a non-planar configuration. For example, as shown in FIG. 57, the anti-buckling device 500 may have a non-planar configuration that is formed by orienting the support members 510 and the support members 514 in respective truss-configurations. FIG. 57 shows the anti-buckling device 500 in an extended configuration, and FIG. 58 shows the anti-buckling device 500 in a collapsed configuration. FIG. 59 shows a cross section of the anti-buckling device 500, particularly showing the support members 510 forming a truss configuration, and the support members 514 forming another truss configuration. In particular, each support member 510 forms an angle 590 relative to the X-Z plane, and each support member 514 forms an angle 592 relative to the X-Z plane. In the illustrated embodiments, the anti-buckling device 500 does not include the second set of support members 512. However, in other embodiments, the anti-buckling device 500 may optionally further include the second set of support members 512. In such cases, the support members 512 will be coupled to the joints 528 at the holders 540.

As shown in the illustrated embodiments of FIG. 57-59, the anti-buckling device 500 provides a plurality of supports at the locations of the holders 540 that are evenly spaced along the length of the elongate member 490 regardless of how much the elongate member 490 is inserted into the patient (i.e., regardless of the distance between the first and second ends 504, 506). The plurality of supports shortens the buckling length of the elongate member 490, thereby significantly improving the buckling strength of the elongate member 490. It should be noted that the plurality of supports will prevent the elongate member 490 from buckling in a direction within the X-Z plane because the anti-buckling device 500 is very stiff in X-Z plane. Also, due to the truss configurations of the support members 510, 514, the anti-buckling device 500 is also very stiff in the Y-direction. Thus, the anti-buckling device 500 will also provide supports for the elongate member 490 in the Y-direction to prevent the elongate member 490 from buckling in a direction that is within the Y-Z plane.

The anti-buckling device 500 shown in FIG. 57 may have different connectors (not shown) at opposite ends, such as those shown in FIGS. 52 and 53, for detachably coupling to different medical devices/components.

Figure 60:
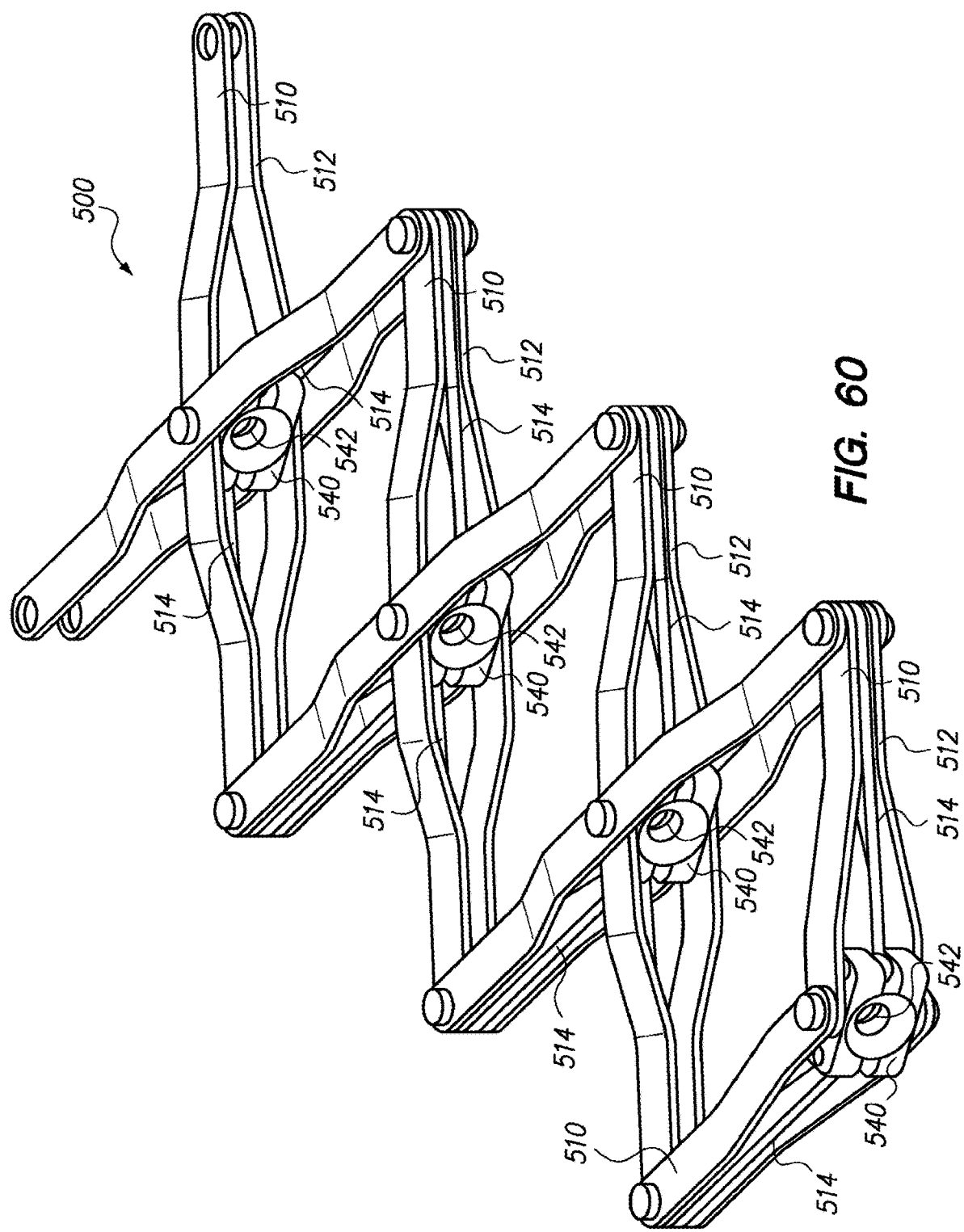

FIG. 60 illustrates another anti-buckling device 500 in accordance with other embodiments. The anti-buckling device 500 is similar to the embodiment shown in FIG. 57, except that each support members 510 has a different shape, and that the anti-buckling device 500 also includes additional support members 512 on the opposite sides. Also, the support members 514 in the anti-buckling device 500 of FIG. 60 are in the form of tension wires. During use, the support members 514 keep the holders 542 all aligned in the same orientation relative to each other.

Figure 61A:
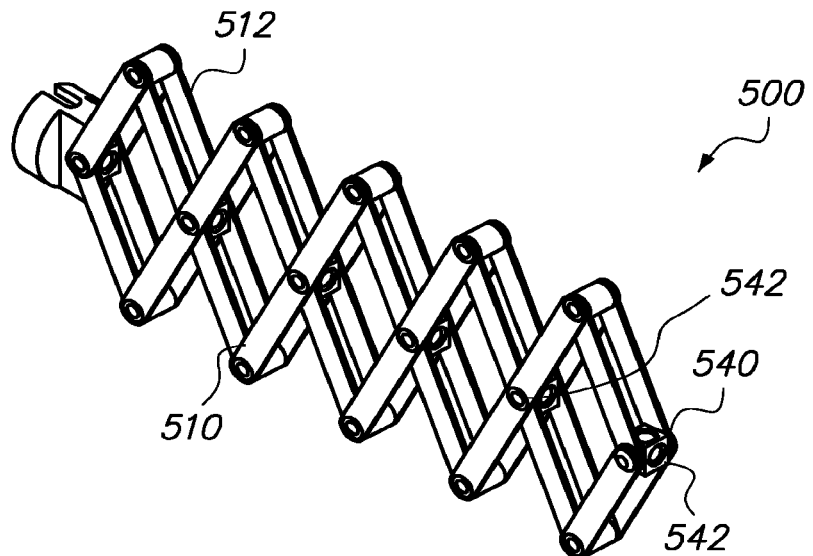
Figure 61B:
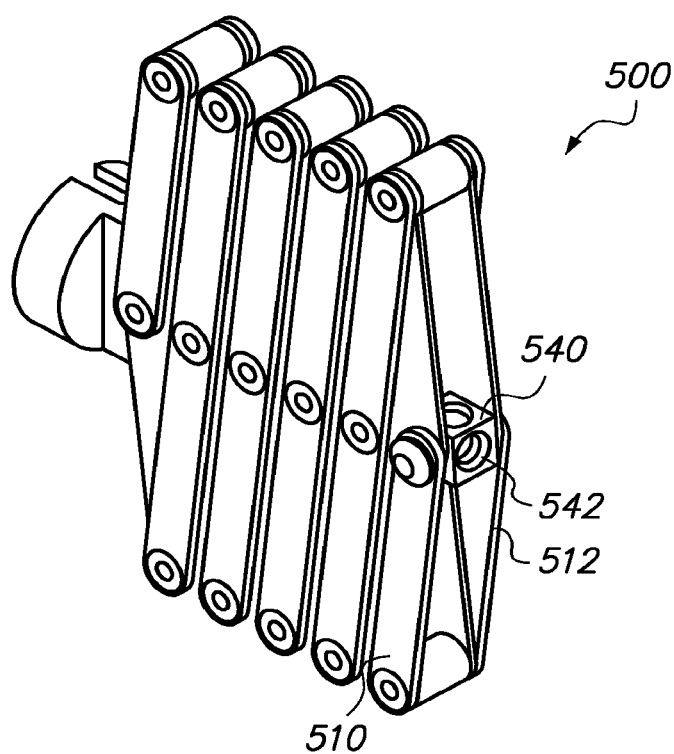
Figure 61C:
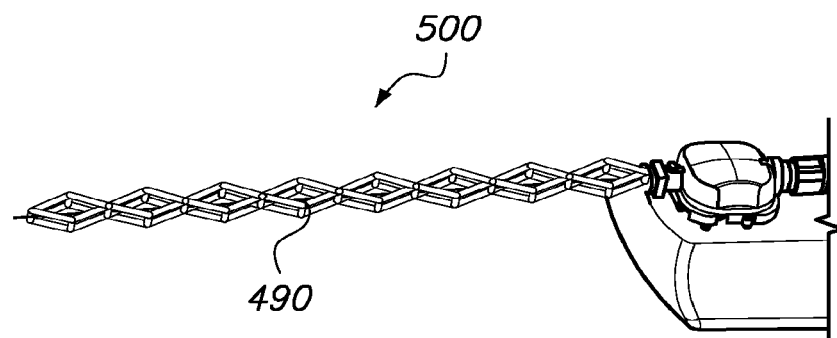
Figure 61D:
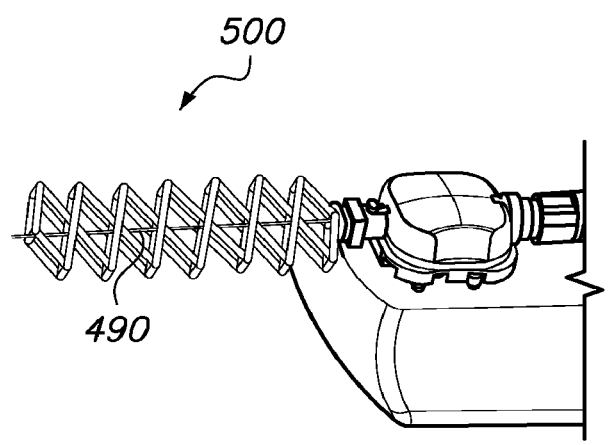

In one or more of the embodiments described herein, the anti-buckling device 500 may not include the set of support members 514 that link the holders 540 together. FIG. 61A illustrates a variation of the anti-buckling device 500 that does not include any linkage members 514 for the holders 540. In the illustrated embodiments, the holders 540 are free to rotate relative to each other. In such cases, the elongate member 490 may be made to have a sufficient bending stiffness so that the bending stiffness of the elongate member 490 will prevent each holder 540 from rotating too much relative to the longitudinal axis of the anti-buckling device 500. In such cases, while the stiffness of the elongate member 490 is sufficient to rotatably guide the holders 540, it may be insufficient to prevent buckling of the elongate member 490 (i.e., in the situation in which there is no anti-buckling mechanism). During use, the anti-buckling device 500 may have an extended configuration, like that shown in FIGS. 61A and 61C, or a collapsed configuration, like that shown in FIGS. 61B and 61D.

Figure 62:
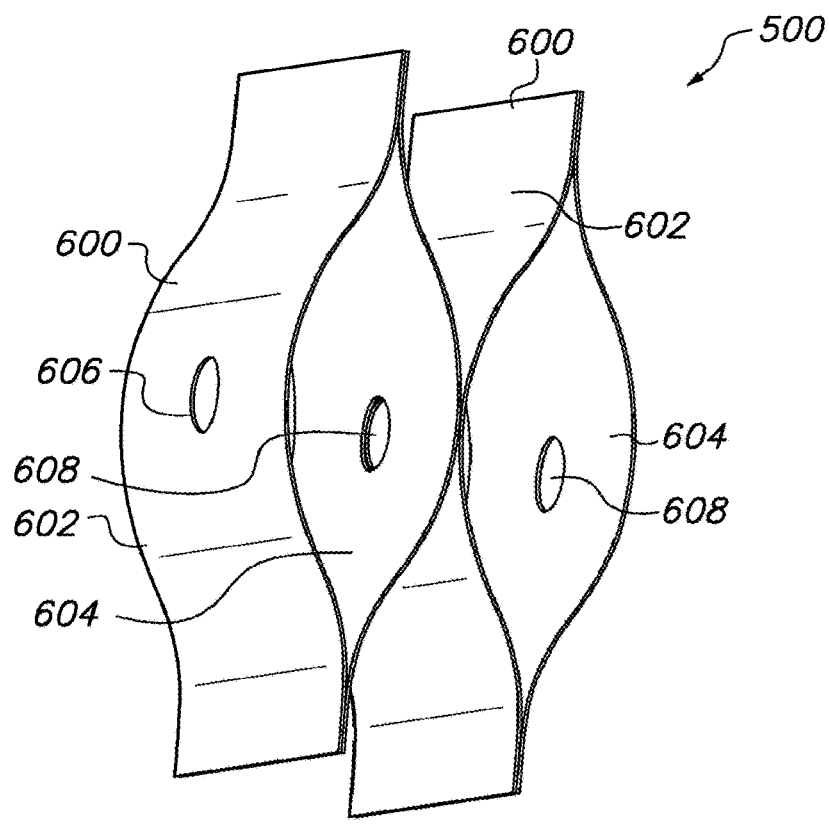

FIG. 62 illustrates another variation of the anti-buckling device 500 in accordance with other embodiments. The anti-buckling device 500 includes a plurality of support members 600. Although only two support members 600 are shown, in other embodiments, the anti-buckling device 500 may include more than two support members 600. Each support member 600 has a first portion 602 and a second portion 604 that are secured to each other at their respective ends. The first portion 602 has an opening 606 that is aligned with an opening 608 at the second portion 604. The openings 606, 608 allow the elongate member 490 to extend therethrough during use. Each of the first and second portions 602, 604 has a curvilinear profile. In one implementation, each of the portions 602, 604 may be formed by bending a plate to a desired profile, and then securing them relative to each other at their respective ends. In other embodiments, each of the portions 602, 604 may not have a curvilinear profile, and may instead have a rectilinear profile (e.g., a U or C shape with straight portions).

In the illustrated embodiments, each of the support members 600 is elastic, and can be deformed during use. In particular, the portions 602, 604 may be bent to vary the distance between the openings 606, 608. For example, during use, the drivable assembly 184 may be moved towards the stabilizer 502 to move the elongate member 490 distally. Accordingly, the anti-buckling device 500 of FIG. 62, which is placed around the elongate member 490 during use, is compressed. The compression of the anti-buckling device 500 causes the portions 602, 604 to bend towards each other, thereby shortening the unsupported length of the elongate member 490 between the supports at the respective openings 606, 608.

The configuration of the anti-buckling device 500 of FIG. 62 is advantageous in that it has significantly fewer components (compared to the embodiments of FIGS. 52 and 53). Also, the anti-buckling device 500 of FIG. 62 does not require separate holders and associated linkage for maintaining the holders in the same orientation. Instead, the openings 606, 608 at the portions 602, 604 of each support member 600 will be aligned in the same orientation as the anti-buckling device 500 is extended or collapsed. Furthermore, because each of the openings 606, 608 circumscribes completely around the elongate member 490 during use, each of the portions 602, 604 provides support against the elongate member 490 to prevent the elongate member 490 from buckling in any radial direction during use.

Figure 63:
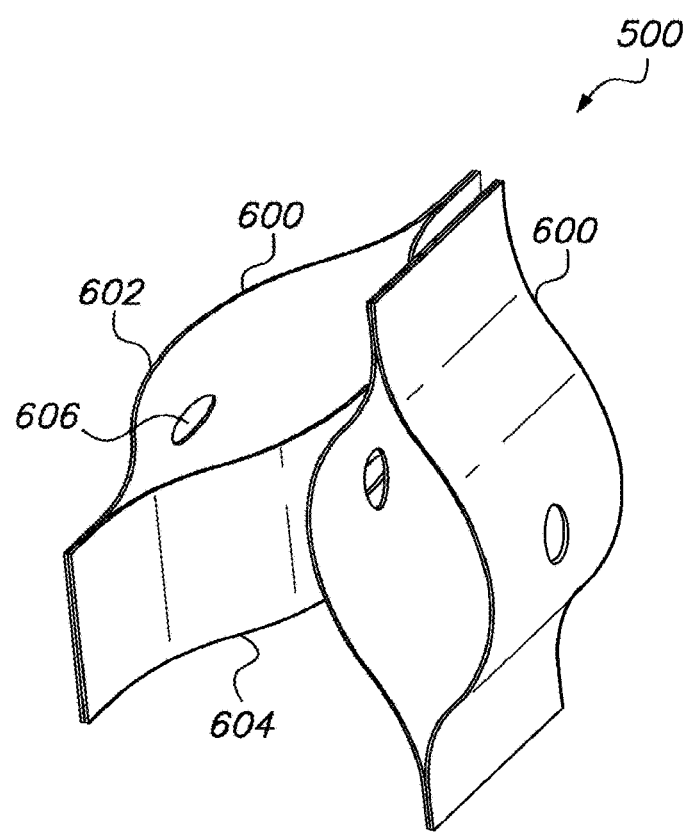

In other embodiments, the support members 600 do not need to be oriented in the same direction. Instead, a first set of every other support members 600 may be orientated in a first direction, and a second set of every other support members 600 may be oriented in a second direction that is perpendicular to the first direction (FIG. 63).

Figure 64A:
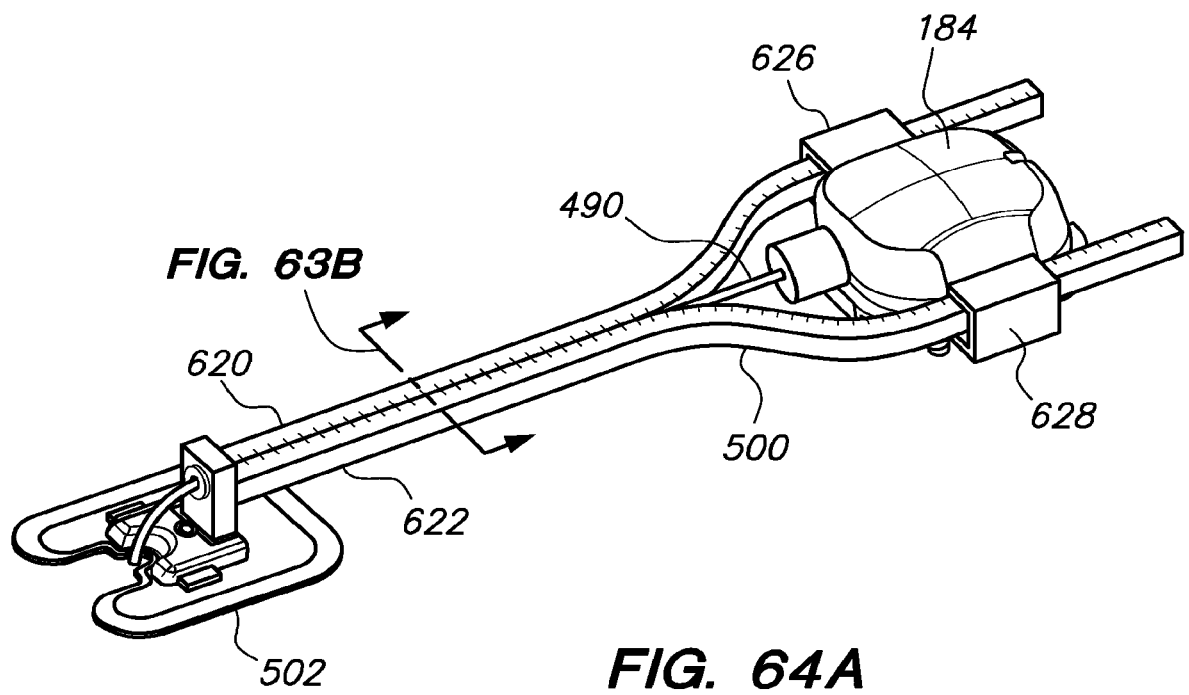
Figure 64B:
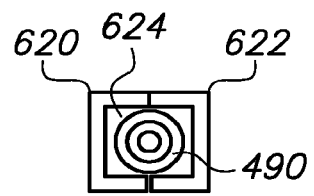

FIG. 64A illustrates another anti-buckling device 500 in accordance with other embodiments. The anti-buckling device 500 has a first portion 620 and a second portion 622 that can be detachably coupled to the first portion 620 in a zipper-like manner along the length of the elongate member 490 during use. As shown in FIG. 64B, the first portion 620 and the second portion 622 have respective C-shape cross sections, and collectively define a space 624 for housing the elongate member 490 during use. In other embodiments, each of the first portion 620 and the second portion 622 does not need to have a C-shape cross section, and may have other cross sectional shapes as long as they provide support for the elongate member 490 to prevent it from buckling. 620 and 622 do not necessarily need to have C-shaped cross sections, and may have other cross-sectional shapes in other embodiments. The design can be adjusted to add bending stiffness as shown in FIG. 64C or 64D.

During use, the portions 620, 622 of the anti-buckling device 500 is placed around the elongate member 490 (FIG. 64A). The distal end of the anti-buckling device 500 is then secured to the stabilizer 502 (e.g., using coupler 522 or another securing mechanism). The anti-buckling device 500 may further include supports 626, 628 that are proximal relative to the distal end of the anti-buckling device 500. The supports 626, 628 are configured to hold the portions 620, 622, respectively, as they are un-zipped. The drivable assembly 184 may be advanced towards the stabilizer 502 to push the elongate member 490 distally, thereby shortening the length between the stabilizer 502 and the drivable assembly 184. When this occurs, parts of the portions 620, 622 at their proximal ends unzip and translate through the supports 626, 628. Alternatively, the drivable assembly 184 may be retracted proximally to move away from the stabilizer 502, thereby increasing the length between the stabilizer 502 and the drivable assembly 184. Accordingly, parts of the portions 602, 622 will come together and zip against each other in increase the support portion for the elongate member 490. Thus, the amount of anti-buckling support provided by the anti-buckling device 500 for the elongate member 490 automatically increases in response to an increase in the unsupported length of the elongate member 490, and automatically decreases in response to a decrease in the unsupported length of the elongate member 490.

In other embodiments, the anti-buckling device 500 of FIG. 64A may be used to support other parts of the elongate member 490. For example, in other embodiments, the anti-buckling device 500 may provide anti-buckling support for the elongate member 490 that spans between the drivable assembly 182 and the drivable assembly 184 (FIG. 53A).

Figure 65A:
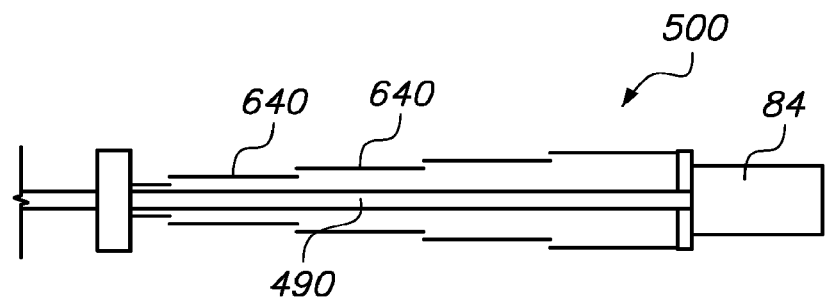

FIG. 65A illustrates another anti-buckling device 500 in accordance with other embodiments. The anti-buckling device 500 includes a plurality of tubes 640 that are arranged in a telescopic configuration. The tubes 640 may have a circular cross section, or other cross sectional shapes in other embodiments. During use, the telescopic tubes 640 are placed around the elongate member 490. As the drivable assembly 184 is advanced distally, the tubes 640 retracts relative to each other to form a shorten configuration. As the driver is moved proximally, the tubes 640 extends out of their respective neighboring tubes 640 to form a lengthen configuration. The elongate member 490 is housed within the lumen formed collectively by the tubes 640, and is prevented from buckling by the wall of the tubes 640. It should be noted that at the larger tubes 640 location, the elongate member 490 may not initially be in contact with the wall of the tubes 640. However, as the elongate member 490 is being compressed, the elongate member 490 will bend slightly due to the axial compression force applied on the elongate member 490. The bending of the elongate member 490 will bring the elongate member 490 into contact with the wall of the relatively larger tubes 640. When this happens, the tubes 640 will prevent the elongate member 490 from bending further, and will prevent the elongate member 490 from catastrophic buckling.

Figure 65B:
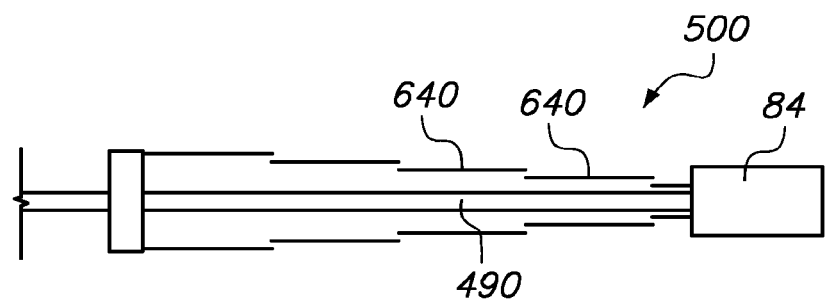
Figure 65C:
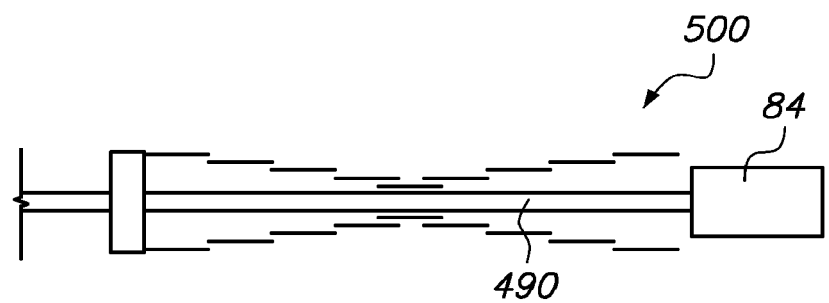
Figure 65D:
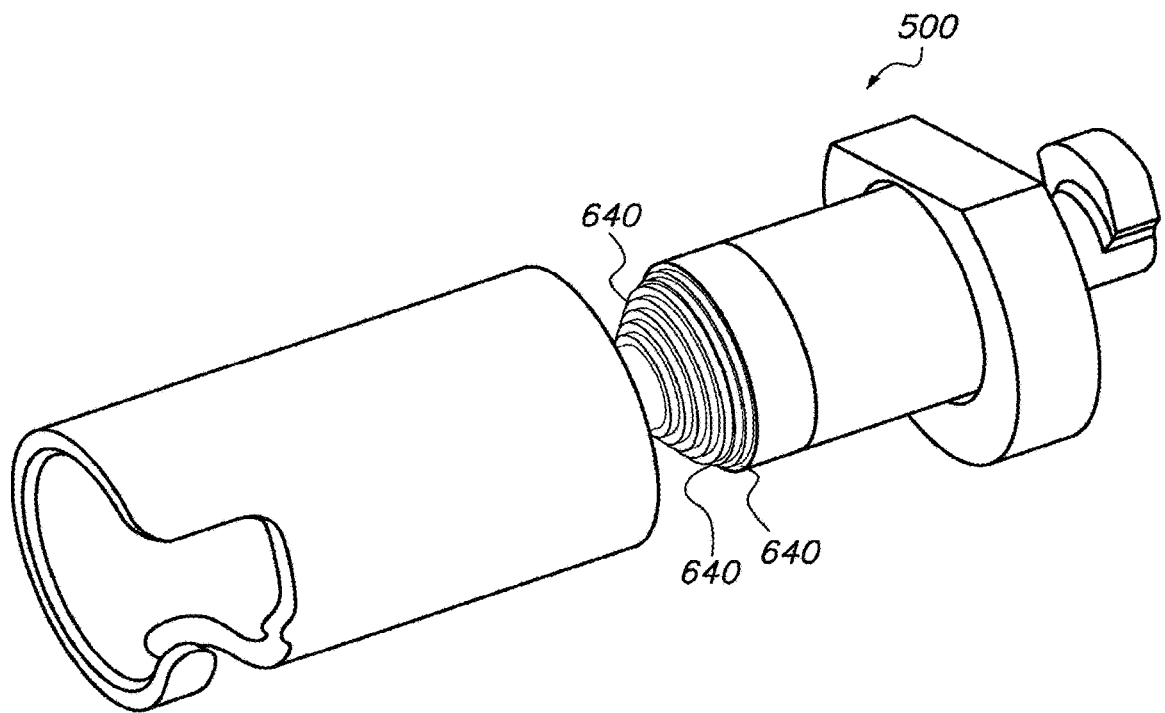
Figure 65E:
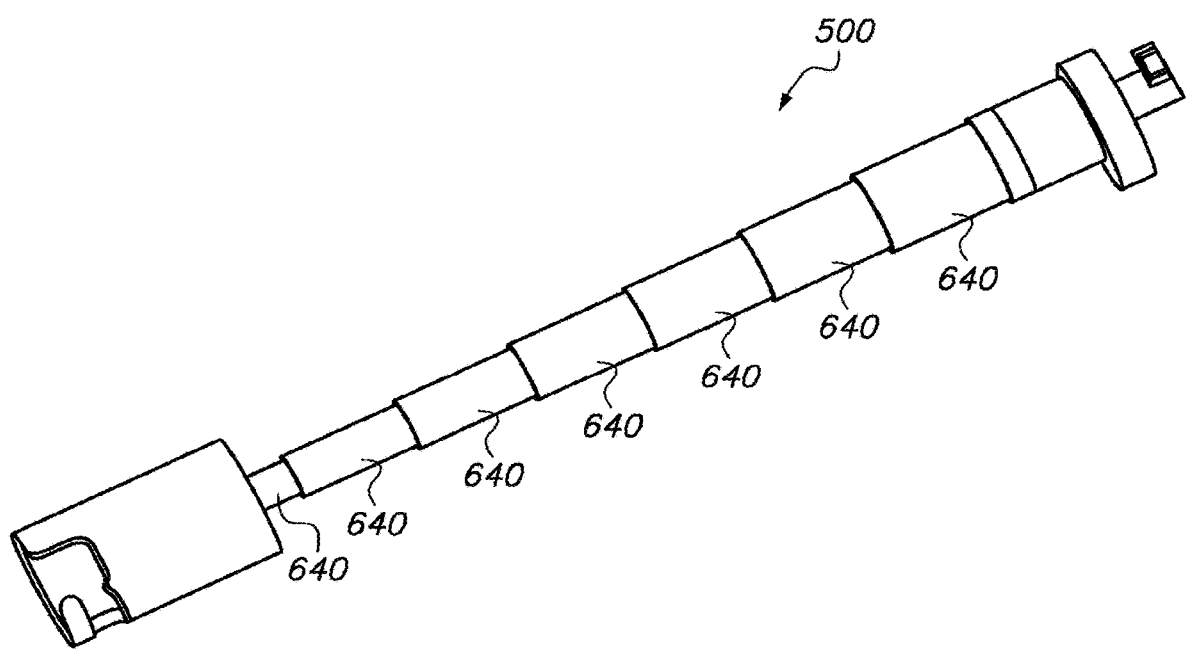
Figure 65F:
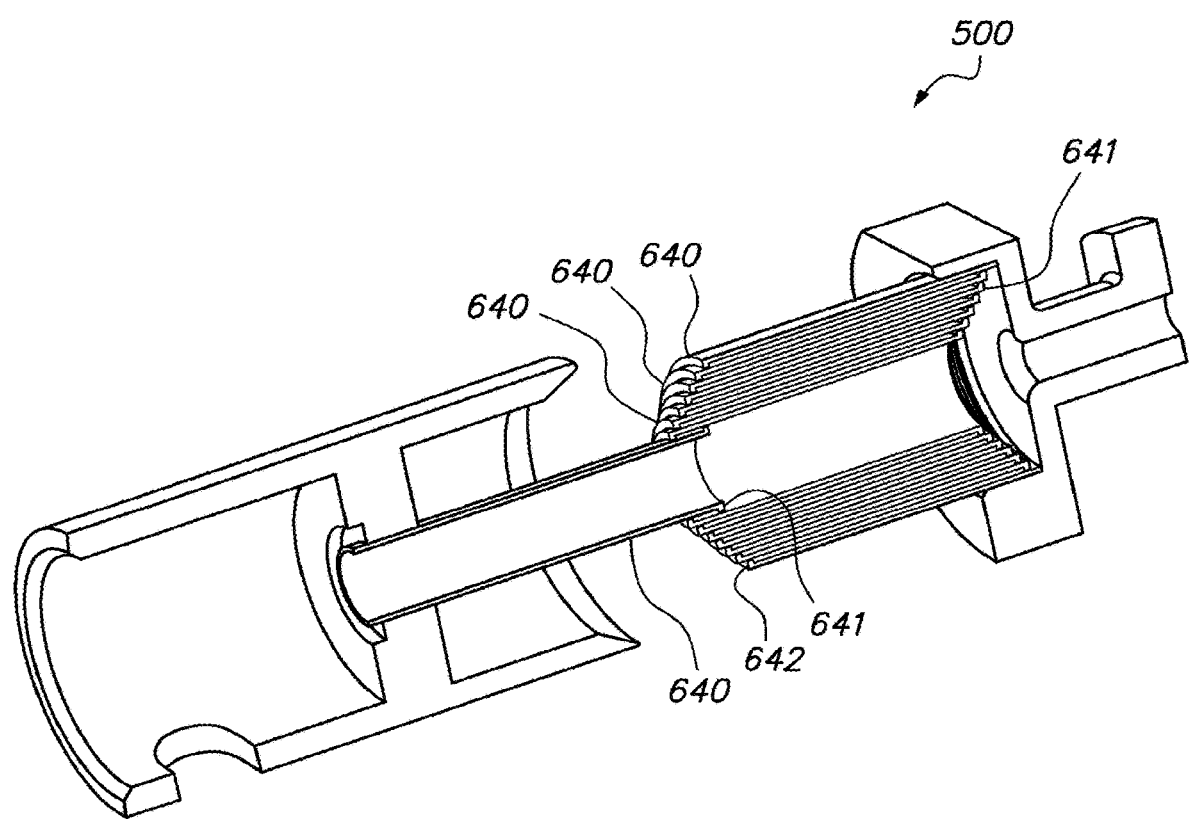
Figure 65G:
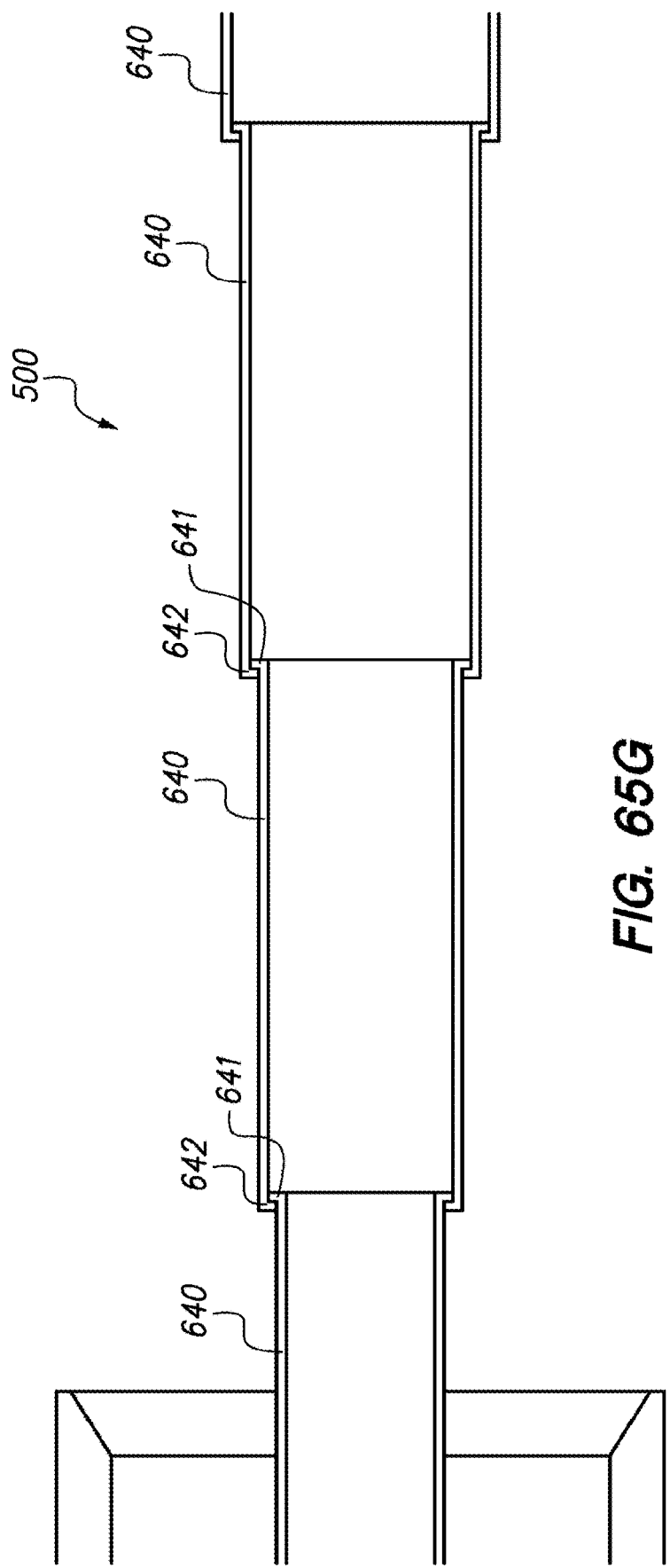

FIGS. 65D-65G illustrates an implementation of the anti-buckling device 500 of FIG. 65A in accordance with some embodiments. As shown in FIGS. 65F and 65G, each tube 640 has a stopper 641 at one end, and another stopper 642 at the opposite end. The stoppers 641, 642 are configured to couple the tubes 640 together, and prevent the tubes 640 from being detached from each other.

FIG. 65B illustrates a variation of the anti-buckling device 500 of FIG. 65A, particularly showing the tubes 640 being arranged from the smallest size to the largest size in the proximal-to-distal direction.

FIG. 65C illustrates another variation of the anti-buckling device 500 of FIG. 65A, particular showing the tubes 640 being arranged from the largest size at one end to the smallest size in the middle section, and then to the largest size again to another end.

Figure 66A:
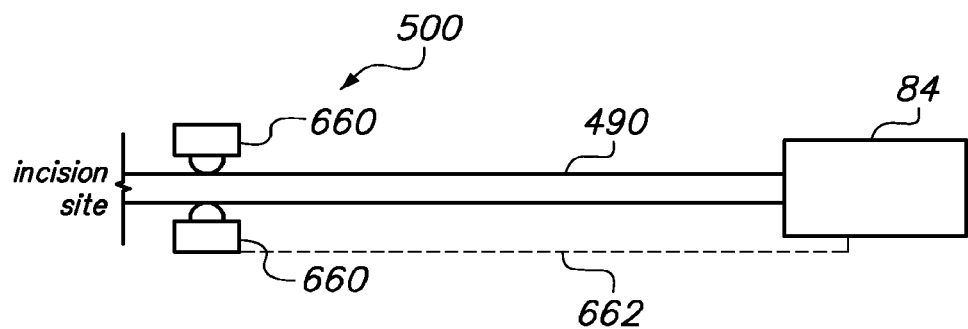

In the above embodiments, the anti-buckling device 500 may be provided on a robotic catheter when the drive assembly for the catheter is at the proximal end of the catheter. However, in other embodiments, the drive system may be provided at the distal end of the catheter for "pulling" the flexible catheter rather than "pushing" it. FIG. 66A illustrates a drive device 500 that provides an anti-buckling feature in accordance with other embodiments. The device 500 includes a pair of rollers 660 that grip against the elongate member 490 at a distal location that is close to the incision site. The device 500 also includes mechanical linkage 662 connecting the rollers 660 to the drivable assembly 184. During use, the drivable assembly 184 may be advanced distally to move the elongate member 490 into the incision site. When this occurs, the drivable assembly 184 will actuate the rollers 660 to apply tension to the elongate member 490. This will prevent the elongate member 490 from being compressed (or from being compressed excessively), and prevent the elongate member 490 from buckling.

Figure 66B:
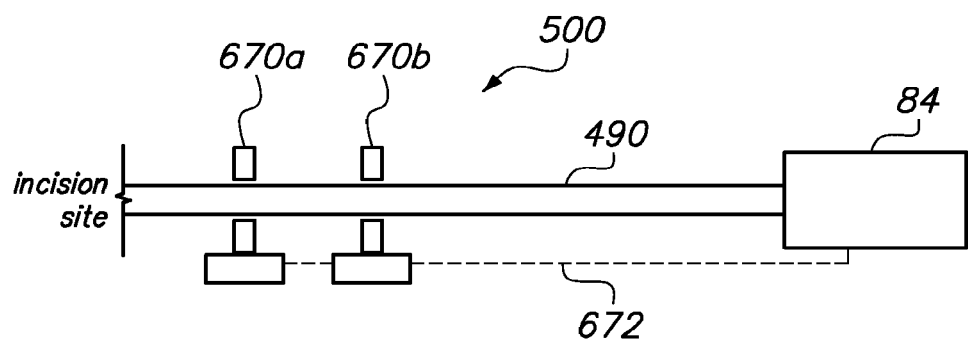

FIG. 66B illustrates another drive device 500 that provides an anti-buckling feature in accordance with other embodiments. The device 500 includes a first pair of fingers 670a for gripping against the elongate member 490 at a distal location that is close to the incision site. The device 500 also includes a second pair of fingers 670b for gripping against the elongate member 490 at a distal location that is close to the incision site. The system 500 also includes mechanical linkage 672 connecting the first and second pair of fingers 670a, 670b to the drivable assembly 184. During use, the drivable assembly 184 may be advanced distally to move the elongate member 490 into the incision site. When this occurs, the drivable assembly 184 will alternately actuate the first and second pairs of fingers 670a, 670b in accordance to a predetermined algorithm to apply tension to the elongate member 490. This will prevent the elongate member 490 from being compressed (or from being compressed excessively), and prevent the elongate member 490 from buckling.

In some embodiments, the algorithm for controlling the pairs of fingers 670a, 670b may be as follows: (1) Actuate first pair to grip the elongate member 490, (2) translate the first pair along the longitudinal axis of the elongate member 490 to pull the elongate member 490, (3) actuate the second pair to grip the elongate member 490, (4) release the first pair, (5) translate the second pair along the longitudinal axis of the elongate member 490 to pull the elongate member 490, (6) move back the first pair by some distance, (7) actuate the first pair to grip the elongate member 490, (8) translate the first pair along the longitudinal axis of the elongate member 490 to pull the elongate member 490, (9) move back the second pair by some distance, and repeat (3)-(9) to move the elongate member 490 until the elongate member 490 is desirable positioned.

Figure 67A:
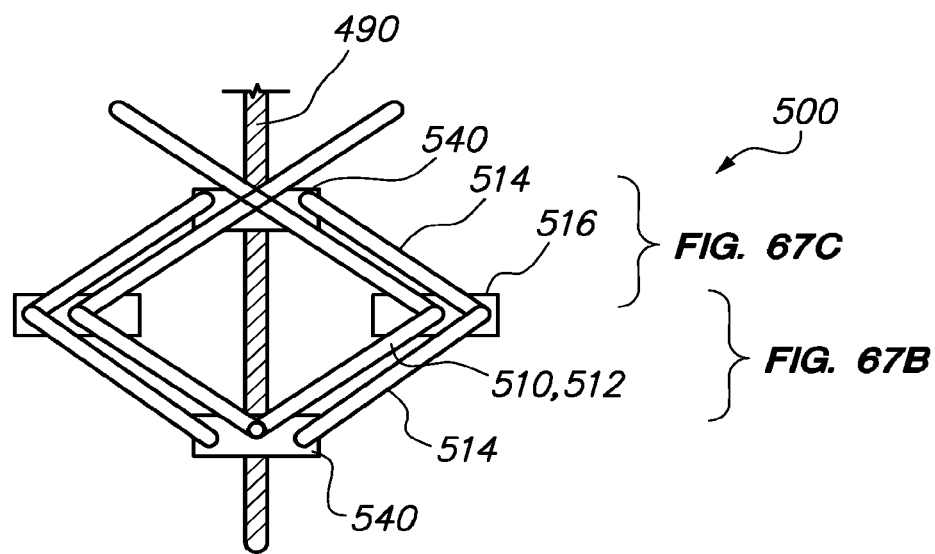
Figure 67B:
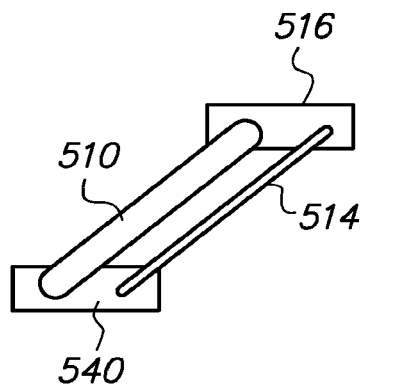
Figure 67C:
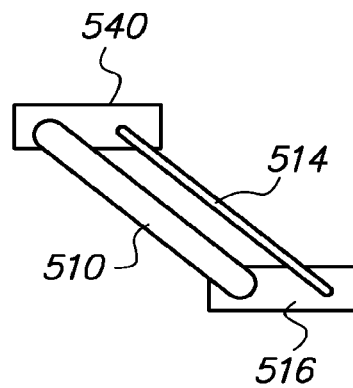

FIGS. 67A-67C illustrate another anti-buckling device 500 in accordance with other embodiments. The device 500 includes support members 510 that form into a scissor-like configuration. The device 500 may optionally include another set of support members 512 next to the support members 510, as similarly described previously. The device 500 includes a plurality of holders 540 that are coupled to the support members 510, wherein each holder 540 includes an opening for accommodating an elongated member 490 (e.g., a sheath, catheter, etc.). As shown in the figure, the device 500 further includes another set of support members 514. As illustrated in FIGS. 67B-67C, the support members 510, 514, holder 540, and coupler 516 form a parallelogram, which allows the holder 540 and coupler 516 to be maintained parallel relative to each other as the support members 510, 514 rotate. Since all of the holders 540 are maintained in parallel relative to their respective adjacent couplers 516, all of the holders 540 are also maintained in parallel relative to each other as the support members 510, 514 rotate to collapse or extend the device 500. The above configuration is advantageous because by preventing the holders 540 from rotating relative to each other, the device 500 provides a higher anti-buckling resistance for the elongated member 490 (i.e., it will be harder to buckle the elongated member 490). This is because when the holders 540 stay aligned relative to each other, the buckling load of the elongated member 490 is $4\pi^2 EI/L^2$. On the other hand, when the holders 540 are allowed to freely rotate relative to each other, the buckling load of the elongated member 490 is $\pi^2 EI/L^2$. Therefore, the elongated member 490 can undergo four times as much compressive force when the holders 540 are rotatably constrained than when the holders 540 are freely rotatable relative to each other.

As shown in the above embodiments, the device 500 is advantageous because it shortens the unsupported length of the elongate member 490, thereby preventing the elongate member 490 from buckling during use. The device 500 is also advantageous because it provides anti-buckling feature from outside the elongate member 490, and thus, obviating the need to modify the construction of the elongate member 490. Also, embodiments of the device 500 described herein provide support(s) along the length of the elongate member 490 in all circumferential directions at the location of the support(s). This has the benefit of preventing the elongate member 490 from buckling in any direction during use.

Although embodiments of the anti-buckling/drive device 500 have been described with reference to the device 500 being used at certain location of the robotic system, in other embodiments, one or more of the embodiments of the device 500 may be used to support any flexible elongate member anywhere in the robotic system, including the flexible elongate member between the stabilizer 502 and the drivable assembly 184, the flexible elongate member between the drivable assembly 184 and the drivable assembly 182, or any other member that needs support to prevent the member from buckling.

Also, although embodiments of the anti-buckling device 500 have been described with reference to a medical robotic system, it should be noted that the anti-buckling device 500 described herein may be used to provide anti-buckling feature for any medical device having an elongate and flexible configuration. For example, in other embodiments, embodiments of the anti-buckling device 500 described herein may be used to support any flexible tool in the field of medicine, such as an endoscope, a flexible grasper, laser fibers, etc.

Also, one or more of the embodiments of the anti-buckling device 500 described herein may be used as a distance measurement tool. For example, in some embodiments, a pull string attached to a spring and an encoder may be used to track the displacement of the anti-buckling device 500. In other embodiments, an encoder may be attached to any of the joints at the anti-buckling device 500 to measure the angle of a link (or links), and a processor may then calculate the overall length of the anti-buckling device 500 based on the measured angle. In other embodiments, an optical device may be configured to take an image of at least a portion of the anti-buckling device 500 (or the entire anti-buckling device 500), and the length of the anti-buckling device 500 may then be determined (e.g., by a processor) using the image. In still further embodiments, a short stroke LVDT or similar linear encoder may be used to measure a displacement between any two links, and the processor may then calculate the overall length of the anti-buckling device 500 using the measured displacement. In further embodiments, an ultrasound transducer may be used to measure a relative displacement between two links, and the processor may then calculate the overall length of the anti-buckling device 500 using the measured displacement.

In addition, in one or more of the embodiments of the anti-buckling device 500, the device 500 may further include a motor coupled to any one of the joints. In such cases, the motor may be activated to turn the joint, thereby extending or collapsing the anti-buckling device 500. In other embodiments, a linear motor may be coupled between two joints or between two support members. In such cases, the linear motor may be operated to extend or collapse the anti-buckling device 500. For example, in other embodiments, any of the joints 528 may be fixed relative to a global system. In such cases, the proximal end of the anti-buckling device 500 may be actuated (e.g., by linearly translating a support member 510/512/514, or by rotating a joint that couples to an end of a support member 510/512/514). In response to such actuation, the distal end of the anti-buckling device 500 will translate distally. The amount of distal translation by the distal end of the anti-buckling device 500 will depend on which of the joints 528 is fixed. Fixing a joint 582 that is closer to the proximal end would allow the distal end of the anti-buckling device 500 to move a relatively greater distance in response to a small translation of the proximal end of the anti-buckling device 500, but such configuration may require a relatively larger actuating force to be applied at the proximal end (and the force transmitted to the distal end is relatively small compared to the force applied at the proximal end). On the other hand, fixing a joint 582 that is closer to the distal end would allow the distal end of the anti-buckling device 500 to move a relatively small distance in response to a large translation of the proximal end of the anti-buckling device 500, but such configuration may require a relatively small actuating force to be applied at the proximal end (and the force transmitted to the distal end is relatively large compared to the force applied at the proximal end). In one or more of the embodiments described herein, the elongate member 490 may be coupled to the anti-buckling device 500, the anti-buckling device 500 may be used to move the elongate member 490 proximally and distally. For example, in some embodiments, the distal end of the elongate member 490 may be coupled to the distal end of the anti-buckling device 500.

As illustrated in the above embodiments, the anti-buckling device utilizes a scissor-like mechanism that provides a 1:1 motion for the elongate member 490. That means when the proximal end of the member 490 is advanced distally by a distance, the distal end of the member 490 will be advanced by the same distance. Also, when the proximal end of the member 490 is retracted proximally by a distance, the distal end of the member 490 will be retracted by the same distance. This is advantageous over a system that does not have any anti-buckling mechanism, in which case, advancement of the proximal end of the elongate member by a distance may not result in advancement of the distal end of the elongate member by the same distance (because the elongate member may sag or buckle). Also, due to sagging or buckling, retraction of the proximal end of the elongate member by a distance may also not result in retraction of the distal end of the elongate member by the same distance (because the sagged or buckled section needs to be straighten out before the distal end of the elongate member may be pulled proximally). Accordingly, embodiments of the anti-buckling mechanism described herein provides a support frame that has no hysteresis between insert and withdrawal of the elongate member.

Also, in some embodiments, the compressed length of the anti-buckling device may be at least 5 times shorter than its extended length. In other embodiments, the ratio between the compressed length and the extended length may have any values.

Also, as illustrated in the above embodiments, the anti-buckling device provides high lateral stiffness to support an elongate member laterally, while providing a low axis stiffness so that the anti-buckling device may be compressed in response to a decrease in length of the elongate member as the elongate member is being advanced distally. Thus, the anti-buckling device does not deflect laterally (e.g., in one plane, or in two planes that form an angle relative to each other), and can be compressed in response to axial force.

VII. Lubrication Mechanism

Figure 68:
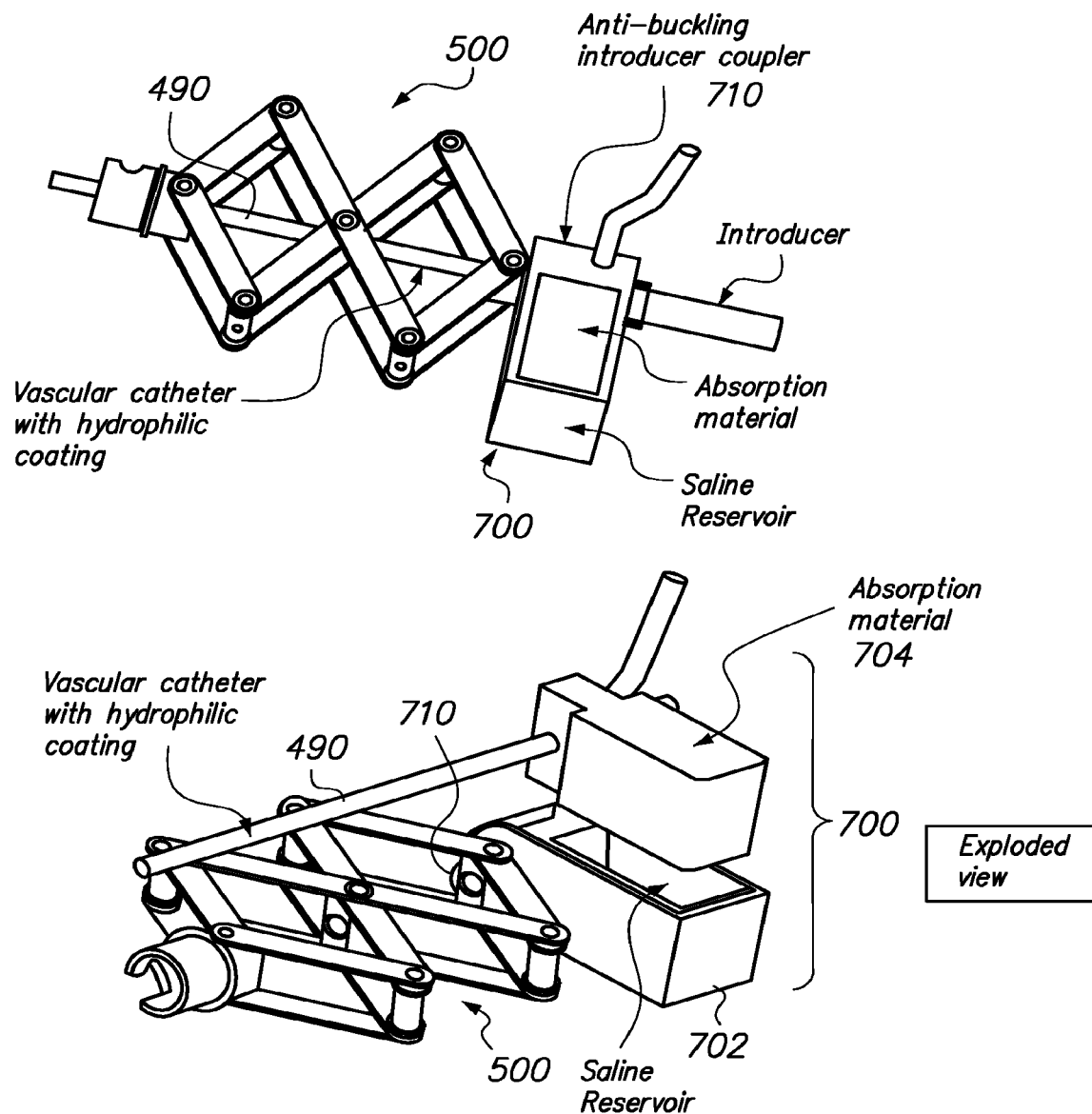
FIGS. 68-78A illustrate different lubricating mechanisms in accordance with different embodiments.

In one or more of the embodiments described herein, the anti-buckling device 500 may further include a lubrication system for lubricating at least a portion of the elongate member 490. FIG. 68 illustrates a lubricating system 700 attached to one end (e.g., the distal end) of the anti-buckling device 500. The lubricating system 700 includes a container 702 for housing fluid, such as saline, and an absorption material 704 located in the housing for absorbing the fluid and applying the fluid to the elongate member 490. The container 702 is coupled to the anti-buckling device 500 via a coupler 710. The lubricating system 700 also includes an introducer for allowing the elongate member 490 to be inserted therethrough. In the illustrated embodiments, the coupler 710 has an opening for allowing the elongate member 490 to extend therethrough. The elongate member 490, which may be a sheath, a catheter member, or a combination of both. In some embodiments, the elongate member 490 may optionally include a hydrophilic coating so that the elongate member 490 may interact (e.g., dissolve) with the saline. The dissolved coating becomes a lubricant for lubricating the elongate member 490 (which may allow the elongate member 490 to slide easily relative to object(s) that it comes in contact with—e.g., bodily tissue, supports of anti-buckling device, etc.). In other embodiments, the sterile fluid in the container 702 may itself be the lubricant, in which case, the lubricant is applied directly onto the elongate member 490 by the absorption material 704. During use, fluid (e.g., saline) is placed in the container 702, or may be applied directly to the absorption material 704. The elongate member 490 is then inserted through the anti-buckling device 500, and is advanced through the absorption material 704 that is located in the container 702. As the elongate member 490 is advanced through the absorption material 704, the absorption material 704 applies the fluid onto the surface of the elongate member 490, thereby lubricating the elongate member 490. The lubricant on the surface of the elongate member 490 allows the elongate member 490 to more easily slide relative to objects (e.g., tissue, introducer, etc.) that it comes in contact with during a medical procedure. The lubricating system 700 is advantageous in that it automatically applies lubricant onto the elongate member 490 as the elongate member 490 is advanced through the lubricating system 700.

Figure 69:
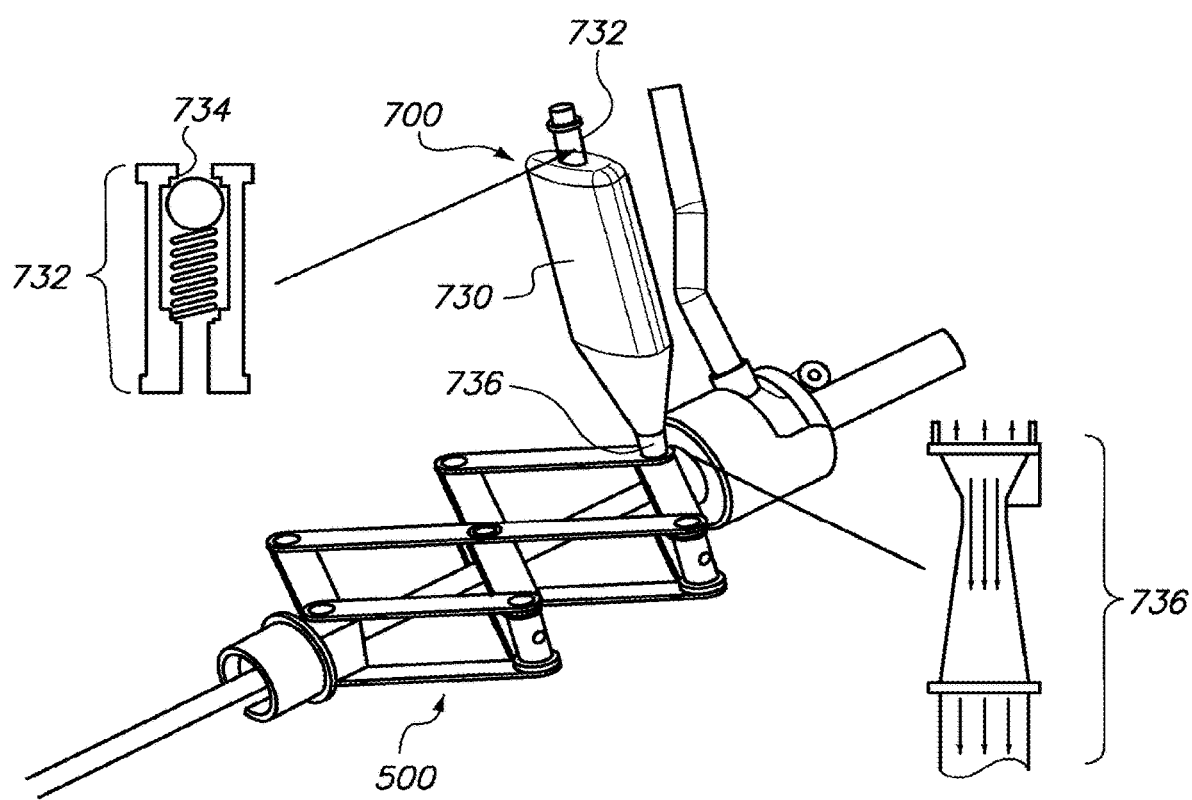

FIG. 69 illustrates another lubricating system 700 in accordance with other embodiments. The lubricating system 700 includes a bladder 730 attached to a distal end of the anti-buckling device 500. The lubricating system 700 further includes a luer lock 732 with a check valve 734, which allow a syringe to fill the bladder 730 with fluid (e.g., saline). In particular, the check valve 734 is configured so that when the syringe is not coupled to the bladder 730, fluid inside the bladder 730 is prevented from escaping out of the bladder 730 through the check valve 734. When the syringe is coupled to the bladder 730, the check valve 734 is pushed open by the syringe, thereby allowing the syringe to deliver the fluid into the bladder 730. The lubricating system 700 also includes a flow restrictor 736 at the bottom of the bladder 730 for allowing fluid to be applied onto the surface of the elongate member 490 in a controlled manner. In some embodiments, the elongate member 490 may optionally include a hydrophilic coating so that the elongate member 490 may interact (e.g., dissolve) with the saline. The dissolved coating becomes a lubricant for lubricating the elongate member 490. In other embodiments, the fluid in the bladder 730 may itself be the lubricant, in which case, the lubricant is applied directly onto the elongate member 490 by the flow restrictor 736.

Figure 70:
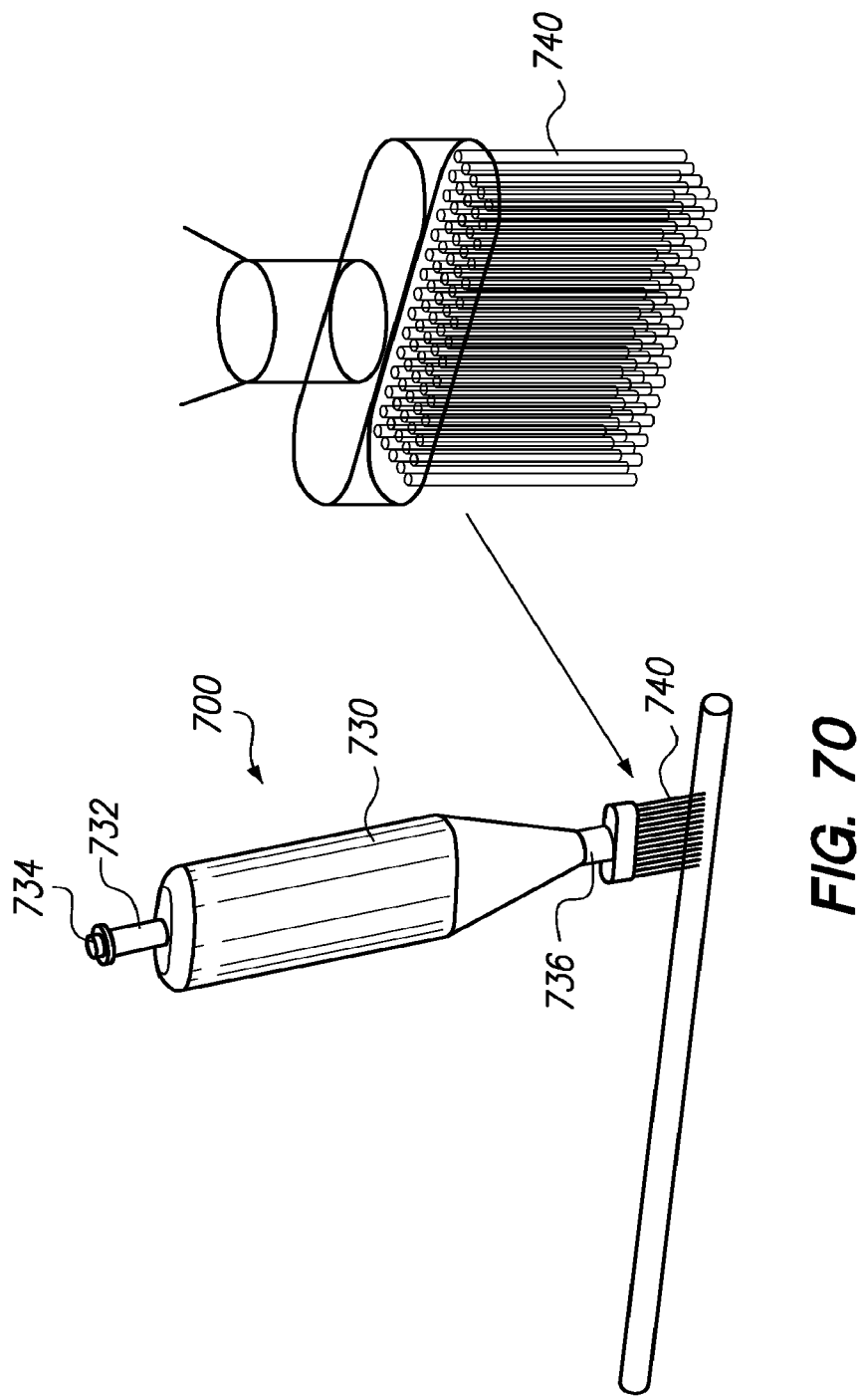

In other embodiments, the lubricating system 700 of FIG. 69 may optionally further include a brush 740 attached to the bottom of the flow restrictor 736 (FIG. 70). During use, the brush 740 applies the fluid from the bladder 730 onto the elongate member 490. In other embodiments, the device 700 itself may function as an applicator. In such cases, the user may hold the applicator 700 and may apply fluid in the bladder onto the surface of the elongate member 490 before it is inserted into a patient. The fluid may interact with a hydrophilic coating on the elongate member 490 to form lubricant. Alternatively, the fluid itself may be lubricant that is applied directly onto the elongate member 490.

Figure 71:
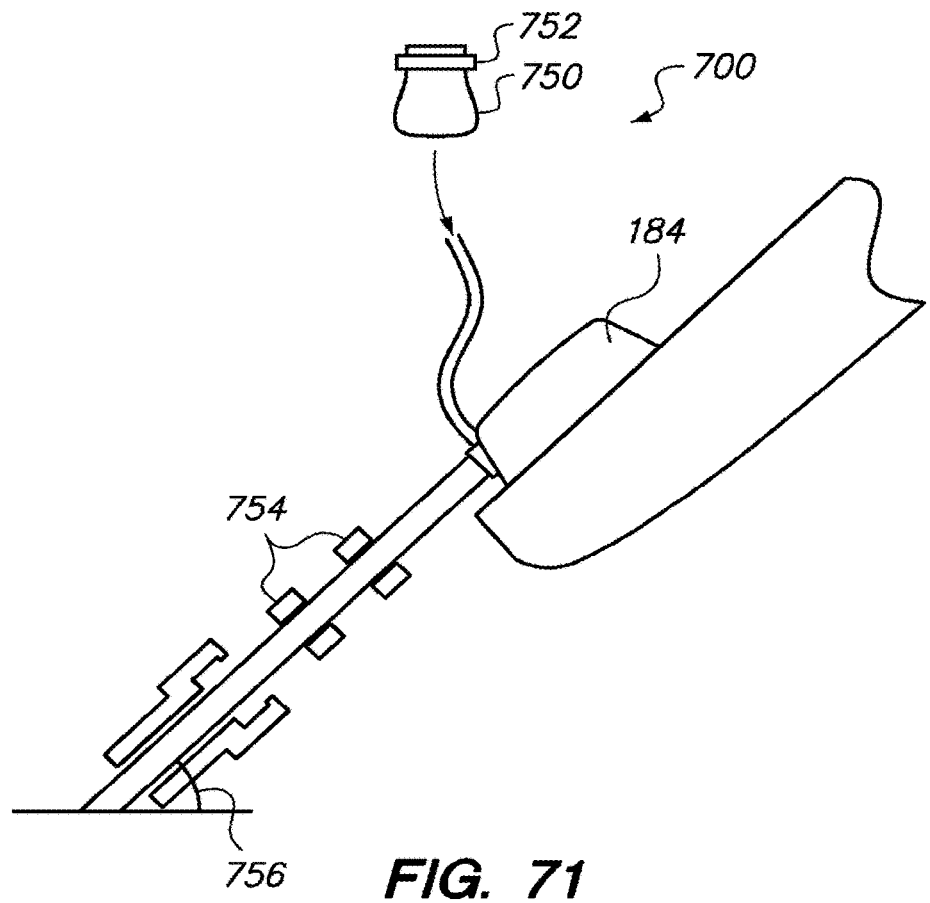

In other embodiments, the lubricating system 700 may include a container (e.g., saline bag) 750 that is compressed by a pressure cuff 752, and fluid from the container 750 is then routed to the drivable assembly 184 (FIG. 71). In the illustrated embodiments, the drivable assembly 184 has internal plumbing and a flow restricting nozzle that would allow droplets to escape. As droplets are escaped from the drivable assembly 184, they travel down the body of the elongate member 490. In some cases, the elongate member 490 may be oriented at an angle 756 that is at least 15° relative to a horizontal axis, so that the droplets may flow down the elongate member 490 more easily. The droplets travelling down the body of the elongate member 490 will reach eyelets (e.g., AB eyelets) 754 that are placed around the elongate member 490. Each eyelet 754 is configured to capture a small amount of fluid so that the elongate member 490 can absorb later. As more and more droplets leave the drivable assembly 184, all of the eyelets 754 will eventually be filled up, and the elongate member 490 will be completely hydrated. In some embodiments, each eyelet 754 has an optimized surface area (or pressure head to viscosity ratio) for capturing a desired amount of fluid. The eyelets 754 may be coupled to the anti-buckling device 500 in some embodiments, in which case, the eyelets 754 may be considered to be components of the anti-buckling device 500. For example, each eyelet 754 may be implemented at a respective holder 540 in the anti-buckling device 500. Also, in some embodiments, the holders 540 themselves may be considered to be the eyelets 754. In other embodiments, the eyelets 754 may be considered components of the lubricating system 700.

Figure 72:
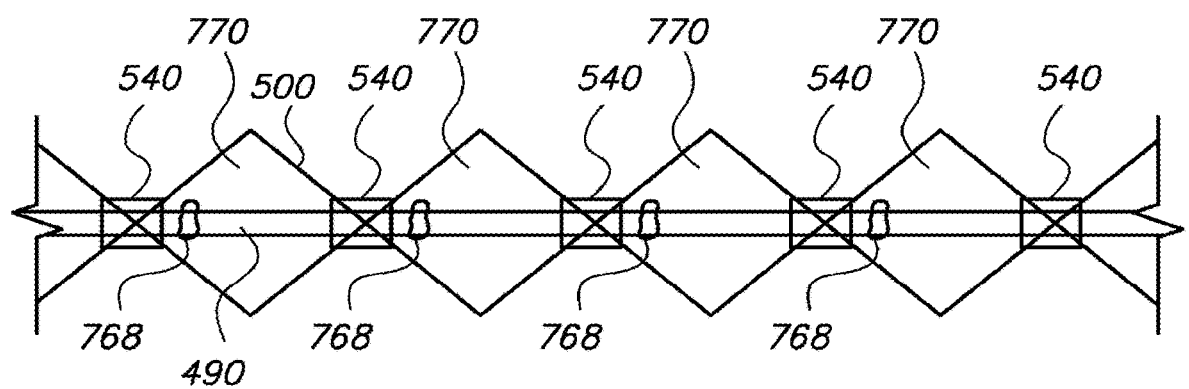

In other embodiments, a hydrogel 768 may be manually applied onto the elongate member 490 via a gauze or cotton pad at several discrete locations through openings 770 of the anti-buckling device 500 (FIG. 72). As the anti-buckling device 500 is extended or collapsed, the hydrogel 768 is spread out along the length of the elongate member 490 through the holders 540. In some embodiments, the holders 540 have eyelets that store a small amount of hydrogel for later use.

Figure 73:
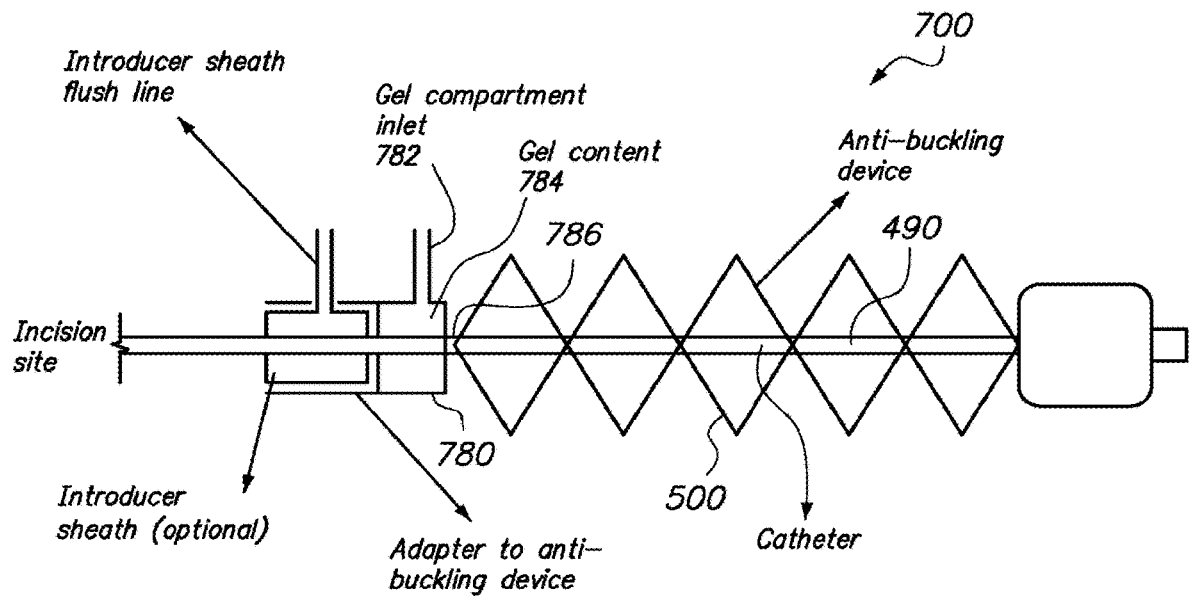

In further embodiments, the lubricating system 700 may include a gel compartment 780 proximal to an incision site for applying gel to the elongate member 490 (FIG. 73). The gel compartment 780 includes an inlet 782 for filling the compartment 780 with a gel substance 784. During use, as the elongate member 490 is inserted distally, it picks up the gel substance 784. In some embodiments, the elongate member 490 may optionally include a hydrophilic coating so that the elongate member 490 may interact (e.g., dissolve) with the gel. The dissolved coating becomes a lubricant for lubricating the elongate member 490. In other embodiments, the gel 784 may itself be the lubricant, in which case, the lubricant is applied directly onto the elongate member 490 by the gel compartment 780. In some embodiments, the gel compartment 780 may be coupled to a distal end of the anti-buckling device 500 through an adaptor 786. Also, in some embodiments, if the elongate member 490 includes a sheath surrounding a catheter member, the gel compartment 780 may be placed proximal to the introducer sheath.

Figure 74:
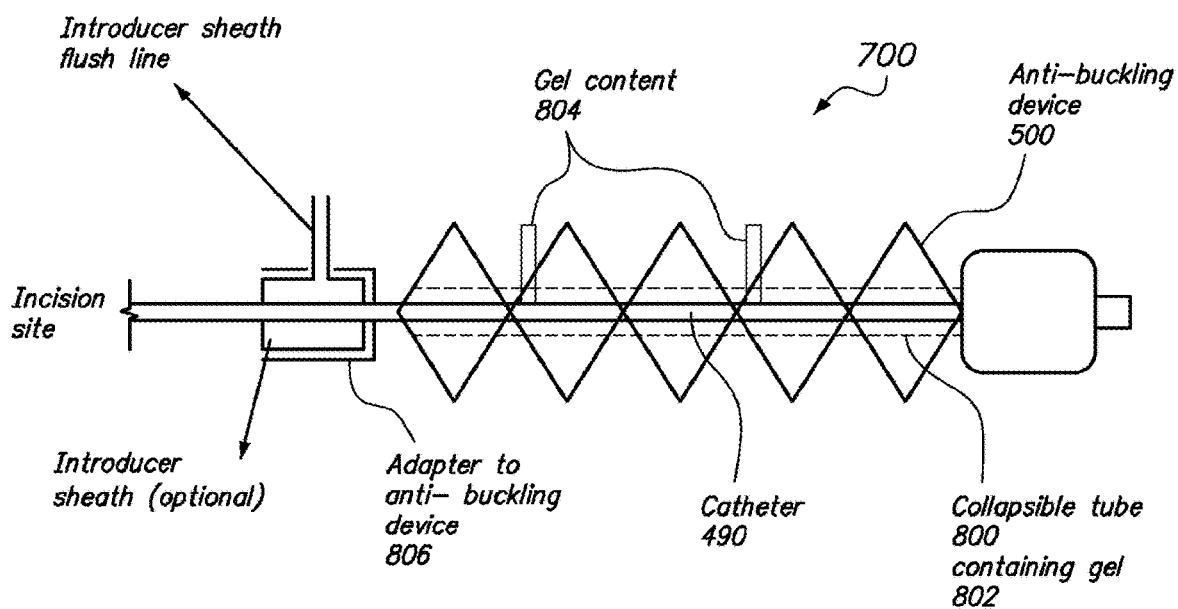

FIG. 74 illustrates another lubricating system 700 in accordance with other embodiments. The lubricating system 700 includes a collapsible tube 800 that contains gel 802. The lubricating system 700 also includes one or more inlets in fluid communication with the tube 800 for delivering the gel 802 into the tube 800. In the illustrated embodiments, the collapsible tube 800 is incorporated into the center of the anti-buckling device 500. During use, the elongate member 490 is inserted through the collapsible tube 800 at the anti-buckling device 500. The inlet(s) 804 is then used to deliver gel into the tube 800. The anti-buckling device 500 is then extended and collapsed several times to evenly spread out the gel onto the surface of the elongate member 490 before the elongate member 490 is inserted into the patient. In some embodiments, the collapsible tube 800 may be implemented using a rigid telescoping tube, a flexible accordion tube, or a bellow.

Figure 75:
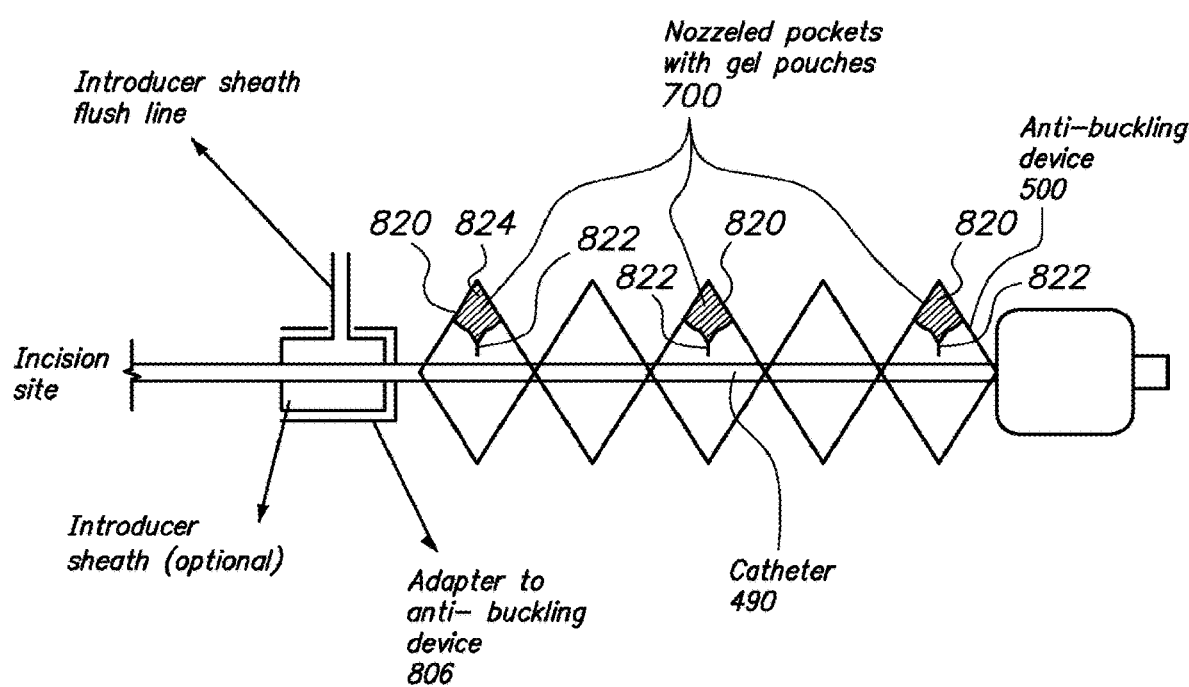

FIG. 75 illustrates another lubricating system 700 in accordance with other embodiments. The lubricating system 700 includes a plurality of pockets 820, wherein each pocket 820 has a nozzle 822 that points towards the elongate member 490. The pockets 820 may be made from a resilient material, such as polyurethane, and may be attached at several locations (e.g., at joints between two support members) at the anti-buckling device 500. In the illustrated embodiments, mini pouches of hydrogel are contained inside the pockets 820. During use, the closing action of the anti-buckling device 500 squeezes the pockets 820 down to eject the gel out of the pockets 820 and onto the surface of the elongate member 490. The anti-buckling device 500 may be extended and collapsed to distribute the gel through eyelets (e.g., holders 540) along the elongate member 490.

In other embodiments, the lubricating device 700 may be a drape made from a resilient material, such as polyurethane. Gel is applied to one side of the drape, and the drape is used to apply the gel onto the elongate member 490, the anti-buckling device 500, or both. For example, in some embodiments, the elongate member 490 together with the anti-buckling device 500 may be covered by the drape, and the drape is used to apply the gel onto the elongate member 490 and/or the anti-buckling device 500. The drape is then removed from the elongate member 490 and/or the anti-buckling device 500 before use of these devices. The anti-buckling device 500 may be extended and collapsed to distribute the gel through eyelets (e.g., holders 540) along the elongate member 490.

Figure 76:
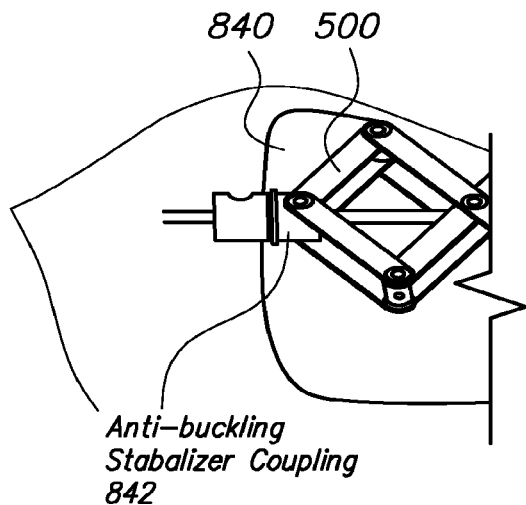
Figure 77:
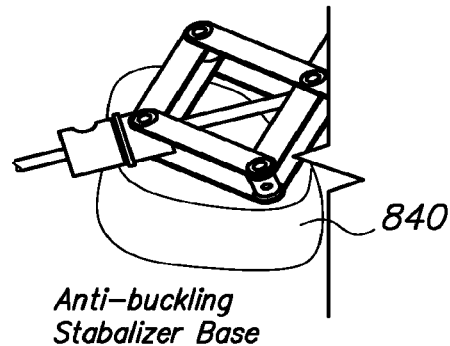

FIGS. 76-77 illustrate another lubricating device 700 in accordance with other embodiments. The lubricating device 700 includes a stabilizing device 840 with a base for attachment to the patient or a bed, and a coupling 842 that joins the anti-buckling device 500 to the stabilizing device 840. The stabilizing device 840 is configured to limit the motion of the distal end of the anti-buckling device 500 as the elongate member 490 is introduced and retracted relative to the patient. In some embodiments, as the catheter is being inserted and retracted, the stabilizer may be subjected to loads that may create a displacement in the direction of the catheter motion. In the illustrated embodiments, the lubricating device 700 includes a small membrane filled with fluid or gel at the base of the stabilizer 840, which would be actuated by the displacement of the stabilizer 840. The hydrating fluid would be delivered directly through the coupling 842, or can be delivered elsewhere by incorporating delivery conduits or a spraying mechanism.

Figure 78:
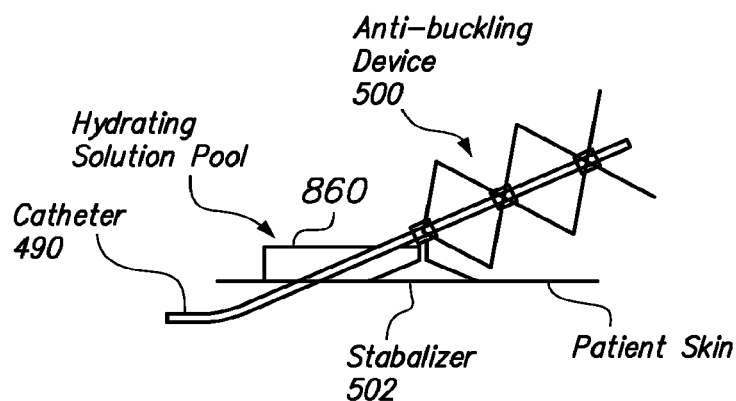

FIG. 78 illustrates another lubricating device 700 in accordance with other embodiments. The lubricating device 700 includes a container 860 containing fluid or gel. The container 860 is coupled to the stabilizer 502, which is described previously. As the elongate member 490 is being inserted into the patient's skin, the elongate member 490 is extended through the container 860, which applies the fluid or gel onto the elongate member 490. The fluid or gel may directly lubricate the surface of the elongate member 490. Alternatively, the fluid or gel may react with an optional hydrophilic coating on the elongate member 490 to form a lubricating substance.

Figure 78A:
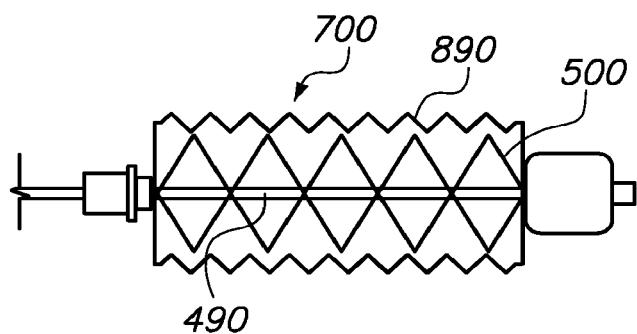

In further embodiments, the lubricating device 700 may include a membrane 890 that encapsulates the anti-buckling device 500, wherein the membrane 890 is filled with fluid or gel during use (FIG. 78A). The membrane 890 may have a bellow configuration, which allows the membrane 890 to extend and contract together with the anti-buckling device 500.

It should be noted that although the term "catheter" and the term "sheath" are used to describe some of the embodiments of the components, these terms should not be limited to the configuration shown. For example, in other embodiments, what was referred to as a "catheter" may also be called a "sheath" and vice versa. Also, in some embodiments, the term "catheter" or the term "sheath" may refer to two or more tubular structures that are arranged telescopically, or that are coupled to each other.

VIII. Guidewire Manipulator

Typical manual surgical procedures include the use of a guide wire curved at its distal tip so that the guide wire can be navigated through tortuous anatomy by hand-actuated roll and insert motion at its proximal end. Once in place, catheters can be inserted co-axially over the guide wire, the guide wire can be retracted and removed, and the catheter can remain in place providing a delivery device for other minimally invasive tools.

Guide wires or distal protection devices for certain vascular and other interventions, may be difficult to position due to their relatively minimal navigation degrees of freedom from a proximal location, and the tortuous pathways through which operators attempt to navigate them. Additionally, minimally invasive medical procedures can be time consuming and physically demanding on an operator causing not only operator fatigue but an excessive amount of exposure of the operator to radiation fields. Providing robotically and remotely precision controlled additional navigation and operational functionality options for minimally invasive interventions, would be useful.

Certain variations of systems as shown in FIG. 1 may include additional remote motorized control of other pull wire or non pull wire elongate members such as guide wires, which utilize roll and insert motions at their proximal ends to steer their distal tips. Different variations of elongate member manipulators which can provide motorized actuation of a guide wire or other elongate member are herein described. Many of the manipulator assemblies disclosed herein can be used to provide any motorized roll and insert or retraction actuation of any elongate instrument or member including but not limited to ablation probes, needles, scissors, clamps, forceps, graspers, guide wires, catheters, endoscopes, and other minimally invasive tools or surgical instruments.

FIGS. 79A-79D illustrate different views of a variation of an elongate member manipulator 1100. The elongate member manipulator 1100 includes a set of right and left motor actuated rotary members 1124, 1104. The rotary members can be used to robotically control the insertion and retraction of an elongate member, e.g., a guide wire, along a longitudinal axis of the elongate member and/or the roll or twist of the elongate member about a longitudinal axis of the elongate member. In this variation, the rotary members are in the form of cylinders or feed rollers. However, the rotary members may include any other device suitable for providing rotary motion including belts.

Figure 79A:
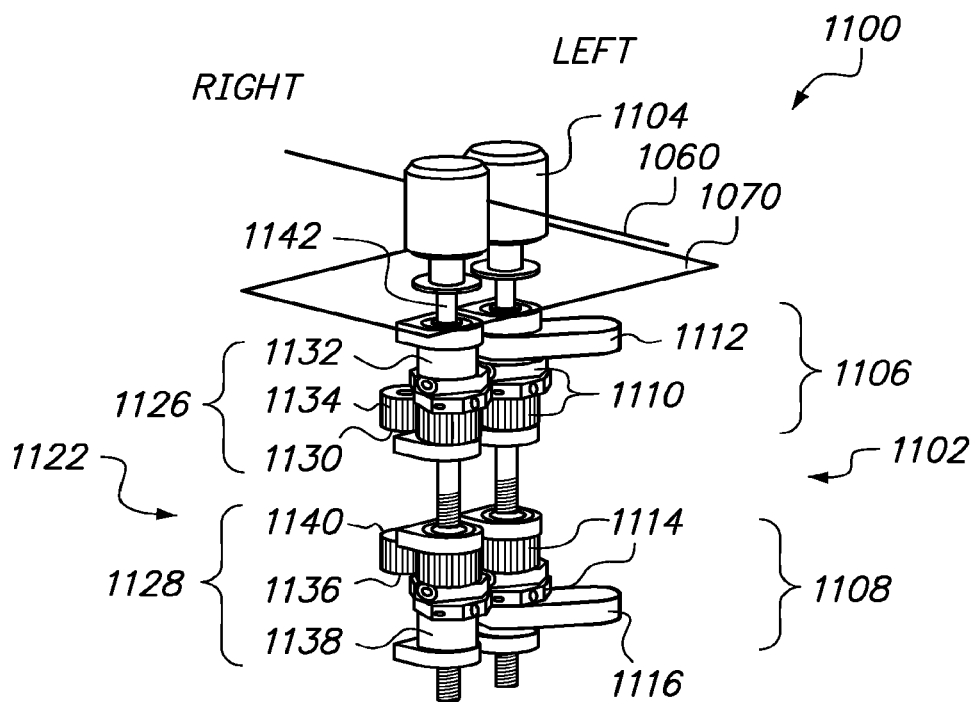
FIG. 79A illustrates a front perspective view of a variation of an elongate member manipulator.

As shown in FIG. 79A, the elongate member manipulator 1100 includes a right roller assembly 1122 and a left roller assembly 1102. Each roller assembly provides rotation and up-down or axial translation to their respective feed rollers 1124, 1104. The left roller assembly 1102 includes the left spline actuator 1106 and the left leadscrew actuator 1108. The right roller assembly 1122 includes a right spline actuator 1126 and a right leadscrew actuator 1128.

Figure 79B:
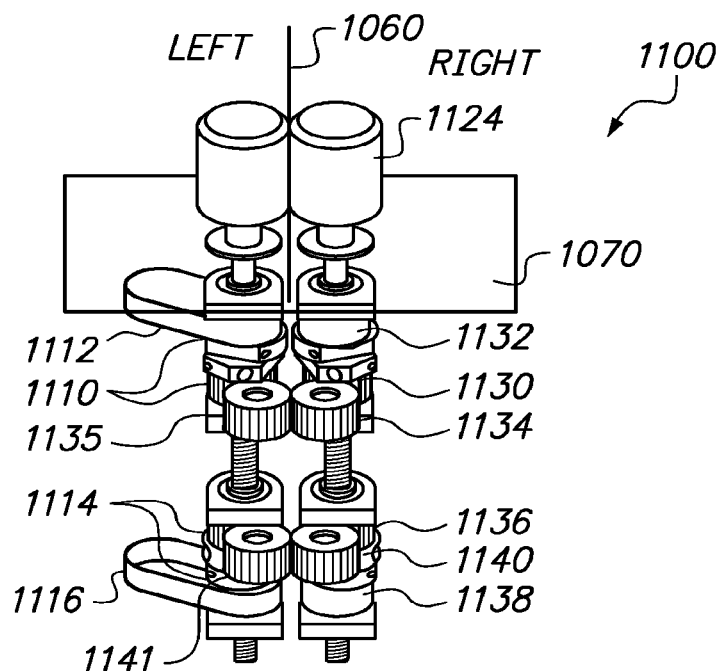
FIG. 79B illustrates an end perspective view of the elongate member manipulator of FIG. 79A.
Figure 79C:
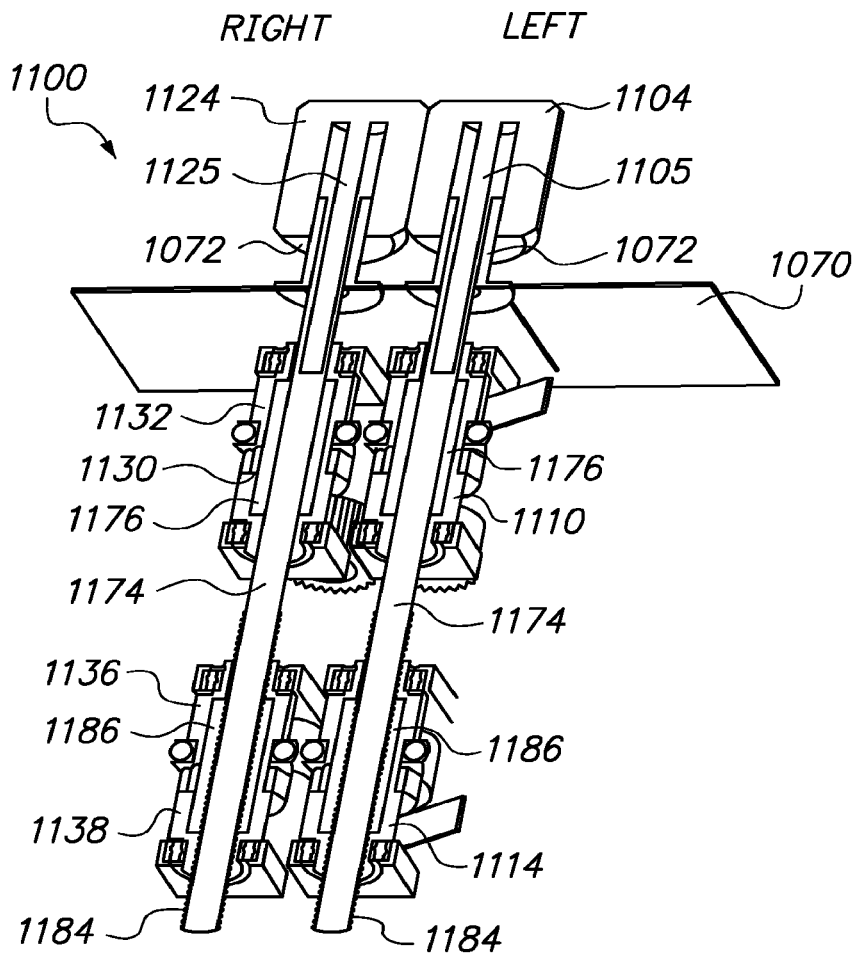
FIG. 79C illustrates a cross sectional view of the elongate member manipulator of FIG. 79A.

As illustrated in FIG. 79C, (a cross sectional view of the elongate member manipulator 1100), the internal elements of the left spline actuator 1106 may be identical to the internal elements of the right spline actuator 1126. Also, the internal components of the left leadscrew actuator 108 may be identical to the internal components of the right leadscrew actuators 1128. Thus both right and left spline actuators 1126, 1106 may include a spline shaft 1174, coupled to a spline nut 1176 which is driven by a gear train which will be described in further detail below. Similarly, the right and left leadscrew actuators 1128, 1108 may include a leadscrew shaft 1184, coupled to a leadscrew nut 1186, driven by a similar gear train.

The spline nut 1176 and leadscrew nut 1186 may be sized such that two axially adjacent gears can create a gear stack that covers the entire axial length of each nut. Thus the left spline actuator 1106 may include a left spline gear stack 1110, which acts as one gear driving the spline shaft 1174 which in turn drives the left roller 1104. The left leadscrew actuator 1108 may also have a similar left leadscrew gear stack 1114 which functions in a similar manner. In alternative variations, a smaller spline nut and smaller leadscrew nut may be utilized allowing for a single gear to be used as opposed to a gear stack.

The right roller assembly 122 may include gears that are driven (in a manner as will be described below), and instead of stacking two adjacent gears, the right spline actuator 1126 can include a smooth shaft 1132 and a right spline output gear 1130. The right leadscrew actuator 1128 can include a smooth shaft 1138 and a right leadscrew output gear 1136. The right spline output gear 1130 and right leadscrew output gear 1136 are coupled to the spline shaft 1174 and leadscrew shaft 1184 respectively and the gears drive the motion of the roller 1124.

Figure 79D:
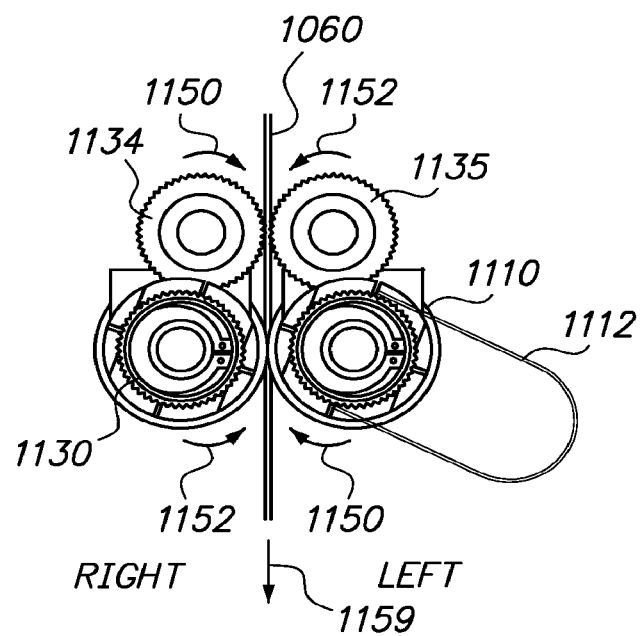
FIG. 79D illustrates a top cross sectional view of the elongate member manipulator of FIG. 79A.

In operation, the right and left rollers 1124, 1104 may rotate at substantially the same rate but in opposite directions to facilitate insertion or retraction of an elongate member, such as the guide wire 1060 (shown in FIGS. 79A-79B and 79D). Idler gears may be used to couple the motion of the right and left actuator assemblies 1122, 1102.

As shown in FIG. 79B the elongate member manipulator 1100 may include a right spline coupling gear 1134, a left spline coupling gear 1135, a right leadscrew coupling gear 1140 and a left leadscrew coupling gear 1141. To rotate the rollers 1104, 1124, the left spline gear stack 1110 is driven by a spline belt 1112, which in turn can be directly driven by a motor or driven indirectly by a series of gears, belts or pulleys (not shown). As previously described, this rotation will cause a direct rotation of the left roller 1104. Simultaneously, the left spline gear stack 1110 may use the coupling gears to drive the right roller 1124 in an opposite direction to that of the left roller 1104.

FIG. 79D, shows a top view of the elongate member manipulator 1100 (the feed rollers are not shown for clarity). In this example, the left spline gear stack 1110 is driven in the CW direction 1150, the left spline coupling gear 1135 will rotate in the CCW direction 1152, rotating the right spline coupling gear 1134 in the CW direction 1150, and the right spline output gear 1130 in the CCW direction 1152. If all the gears are sized equally, the left spline gear stack 1110 and right spline output gear 1130 will rotate at the same rate in opposite directions, rotating the rollers 1104, 1124 at equal rates in opposite directions, which would drive the guide wire 1060 in a forward propelling motion 1159. Reversing the direction of the spline belt 1112 would reverse the directions of both the left spline gear stack 1110 and right spline output gear 1130, and as a result, reverse the direction of rotation of the rollers 104, 124, thereby driving the guide wire in the reverse propelling motion.

The leadscrew actuators 1108, 1128 may function in a similar manner but alternatively cause one roller to translate upwards while the other roller translates downwards at a substantially similar rate. This motion will drive the guide wire 1060 in a roll or torque motion. The clockwise or counterclockwise directions of roll are dependent on the direction of rotation of the leadscrew belt 1116. Both insert/propelling motion and roll/torque motion can be accomplished with varying speed rates for each axis. The propelling and torque axes motions can be simultaneous, or they can be independent of each other.

Figure 81:
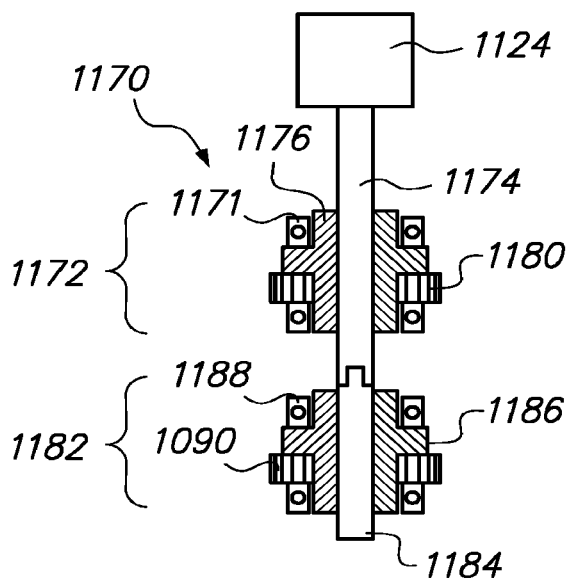
FIG. 81 illustrates a cross sectional view of one variation of a roller actuator.

FIG. 81 illustrates a cross sectional view of one variation of a roller actuator 1170 that may be utilized to provide motorized rotation and translation actuation of one or more rotary members, such as a feed roller. Such a roller actuator may be utilized to provide rotation and translation actuation of various rollers, including, for example, the rollers of elongate member manipulator 1100 described above.

The roller actuator 1170 includes a one or more spline actuators 1172 having a spline shaft 1174 coupled to a spline nut 1176 mounted on spline nut bearings 1178. The spline nut 176 is rotated by a spline gear 1180 which can either be directly motor driven or indirectly motor driven via a series of gears, belts or pulleys (not shown). The spline shaft 1174 may be fixably coupled to a rotary member such as a feed roller 1104, so that the rotation of the spline nut creates rotation of the feed roller. A single leadscrew actuator 1182 which includes a leadscrew shaft 1184, leadscrew nut 1186, leadscrew nut bearings 1188, and a leadscrew gear 1190 is provided adjacently below the spline actuator 1172 to provide up-down translation of a feed roller. The leadscrew nut 1186 is driven by the leadscrew gear 1190 which can either be directly motor driven or indirectly motor driven via a series of gears, belts or pulleys (not shown). Rotation of the leadscrew nut 1186 lifts and lowers the leadscrew shaft 1184 and spline shaft 1174, creating the up and down lift or axial translation of the feed roller.

In certain variations, the spline shaft 1174 and leadscrew shaft 1184 may be coupled so that rotation of one may cause rotation of the other. Because the spline shaft 1174 is constructed as a spline, it can be driven up and down by the leadscrew shaft 1184 without lifting the spline nut 1176, spline bearings 1178, or spline gear 1180. To actuate only rotation of the feed roller, both spline nut 1176 and leadscrew nut 1186 may be rotated at the same rate. As a result, the leadscrew shaft 1184 will rotate at the same rate as the leadscrew nut 1186 so that no lift motion will occur. To actuate only lift of a feed roller, the leadscrew nut 1186 may be rotated without movement of the spline nut 1176. Alternatively, simultaneous rotational and translational motion of a feed roller may be provided by slowing and speeding up the leadscrew nut 1186 relative to the spline nut 1176 or vice versa.

In an alternative variation, the spline shaft 1174 and the leadscrew shaft 1184 may not be coupled so that movement of the spline actuator 1172 and the leadscrew actuator 1182 are completely independent. Alternatively, the spline shaft 1174 and leadscrew shaft 1184 could be free to rotate independently by joining the two shafts in a ball and socket type configuration. Additional bearing support may be utilized in such a variation.

Figure 80A:
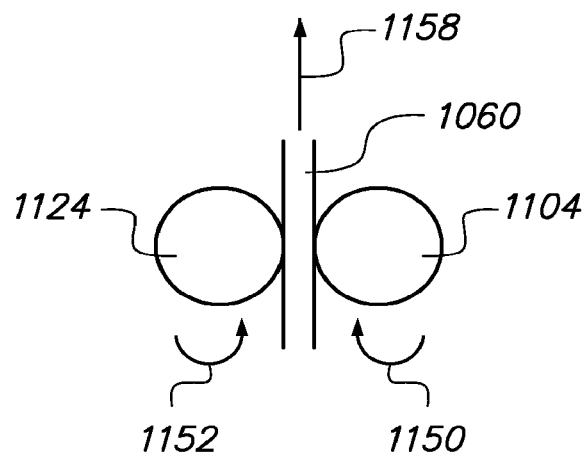
FIGS. 80A-80B are schematic illustrations showing top and front views of feed rollers actuating an elongate member.
Figure 80B:
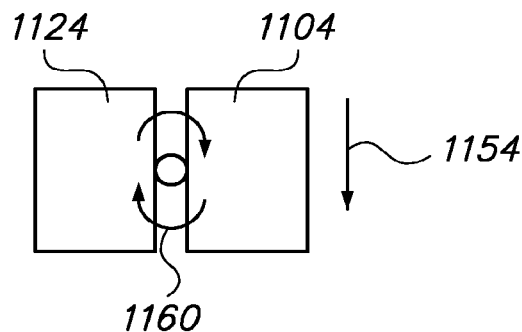

FIGS. 80A-80B illustrate examples of feed rollers in use, showing how an elongate member, e.g., a guide wire 1060, may be actuated by the feed rollers 1124, 1104. FIG. 80A illustrates a top view of a pair of feed rollers 1124, 1104 illustrating how the feed rollers can rotate about their axes in opposite directions 1152, 1150 to drive a guide wire 1060 in a backwards propelling motion or a retract motion 1158. The feed rollers can also be rotated in opposing directions to provide forward propelling or insert motion (not shown). FIG. 80B shows a front view of the feed rollers 1124, 1104 illustrating how the feed rollers can translate axially along their axes in opposite translation directions 1154 to torque or roll 1160 the guide wire 1060.

Forward or reverse insert/retract motion 1158 is dependent on the direction of rotation 1152, 1150 of the rollers 1124, 1104 while clockwise or counter-clockwise roll motion 1160 is dependent on the direction of up and down linear or axial translation 1154 of the rollers 1124, 1104. Both insert/retract motion and roll motion can be accomplished with varying speed rates for each axis. The insert and roll actuations can be independent of one another, or they may occur simultaneously. Also simultaneous roll and insert actuation can be desirable in part because traditional manual procedures are performed in that manner. Currently physicians articulate and steer manual guidewires by inserting and rolling simultaneously resulting in more of a spiraling insertion. It can be desirable for robotic systems to emulate manual procedures for physician ease of use.

In alternative variations, insert motion can be provided by feed rollers while roll motion actuation may be provided by clamping the guide wire in a clamp mechanism and rolling the clamp mechanism. In this variation roll and insert motion may be alternated between insert and roll with typical clutching mechanisms that release grip from one actuator assembly while the alternate assembly provides actuation. For example, in a feed roller variation with clutching, feed rollers used to actuate insert may release the guide wire while actuators providing rotation to roll the guide wire. The release of the guide wire from one actuator during activation of the alternate actuator in systems which use feed rollers for insert but roll the guide wire with a separate mechanism allows the guide wire to overcome friction experienced from the feed rollers during roll actuation. If insert and roll are simultaneously actuated the wire may be gripped in the insert feed rollers which could result in the stripping or winding up the wire.

Systems which clutch between insert and roll actuators typically release grip of the guide wire by one actuator to allow the alternate actuator to grip the guide wire. By releasing the wire, any tracking of guide wire position using encoders may be lost which could decrease the accuracy of position tracking. Also, additional actuators may result in a more complex or more costly system.

In certain variations, a guide wire 1060 may be loaded into the elongate member manipulator 1100 by being back or front loaded or fed into the feed rollers 1104, 1124 while rotating the feed rollers 1104, 1124 in an insert or retract motion.

In certain variations, the elongate member manipulator 1100 may be designed such that at least a portion of the elongate member manipulator 1100 remains in a sterile field. For example, the motors and drive mechanisms or drive components of the elongate member manipulator may be situated in a non-sterile field and a sterile drape could be placed in-between the drive components and the feed rollers. Thus, the elongate member, e.g., a guide wire, held by the feed rollers will remain sterile for insertion into a patient's anatomy. In certain variations, components of an elongate member manipulator which are meant to remain sterile may be disposable and/or the complexity of such components may be minimized in order to minimize or reduce overall costs of such disposable components or the elongate member manipulator.

Referring back to FIGS. 79A-79C, one variation of a sterile drape 1070 used to create a sterile field that includes the feed rollers 1104, 1124 and guide wire 1060 is illustrated. All other components could be positioned in a non-sterile field.

Figure 82:
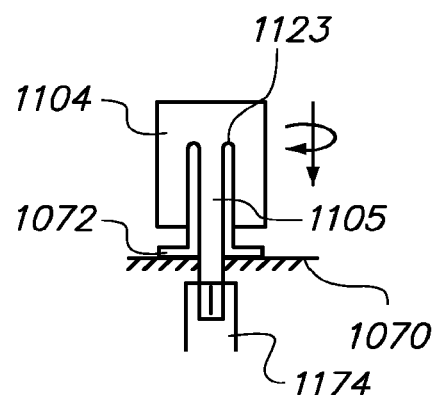
FIG. 82 illustrates a cross sectional view of one variation of a feed roller with a drape.

FIG. 82 shows an example of the sterile drape 1070 installed between the left feed roller 1104 and the spline shaft 1174. The sterile drape 1070 may be designed such that the roller 1104 can be removeably replaceable where the drape 1070 could be placed over the spline shaft 1174 and the rollers could be installed over the drape in the sterile field. The sterile drape 1070 could have a sterile drape bushing 1072 that is fixably attached to the drape 1070. The roller 1104 could be coupled to the bushing 1072 via a roller shaft 1105 extending through the bushing 1072 which is coupled to the spline shaft 1074 in the non-sterile field. The roller shaft 1105 and spline shaft 1074 could be coupled by keying each shaft to mate, thus allowing rotation of the spline shaft 1074 to cause a one to one rotation of the roller shaft 1105. The key can be shaped as a hexagon, triangle, star, cross or any other shape. The roller 1104 may rotate relative to the bushing and may translate up and down like a piston. A fastener may be provided to secure the roller 1104 in place to prevent slippage in the axial direction. Alternatively, the roller shaft 1105 may be threaded and coupled to a threaded hole in the spline shaft 1174. As the roller 1104 moves up and down, a left roller groove 1123 on the roller may create a labyrinth seal and maintain a sterile boundary between the bushing 1072 and roller 1104. Optionally, an o-ring or lip seal can be placed between the bushing 1072 and roller 1104 to prevent fluid ingress and create an improved sterile boundary. The sterile drape 1070 could provide for a sterile interface for the right feed roller 1124 in the same manner.

Figure 83:
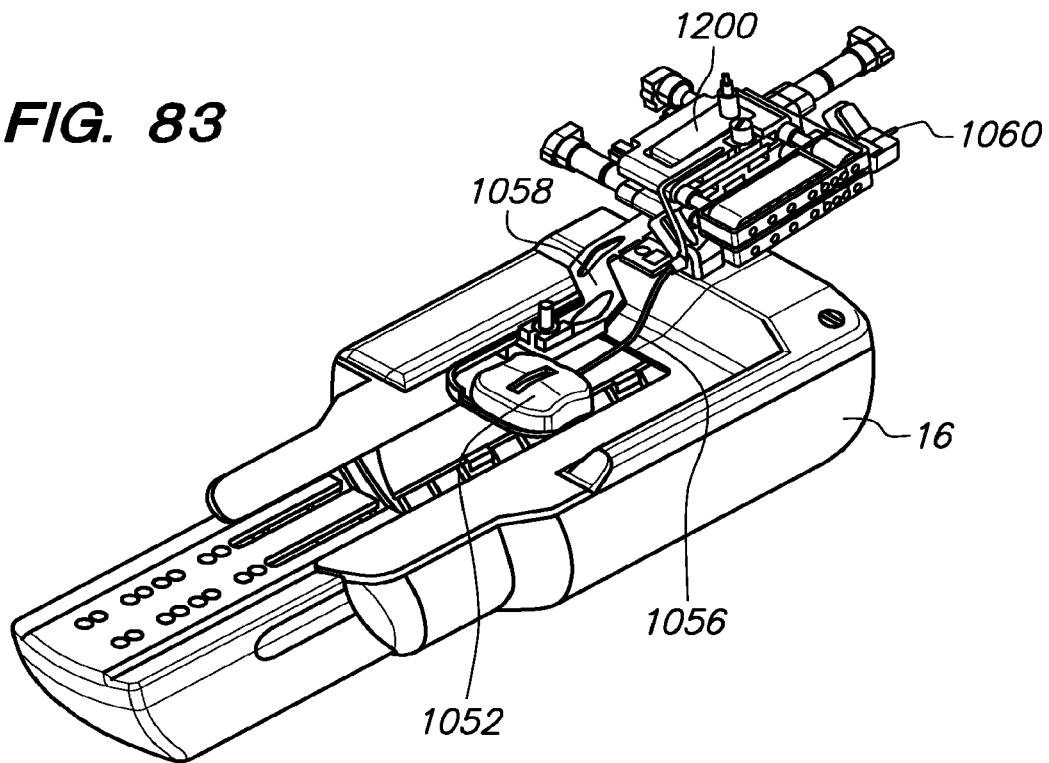
FIG. 83 illustrates a perspective view of the instrument driver, the guide splayer and a variation of an elongate member manipulator.
Figure 83A:
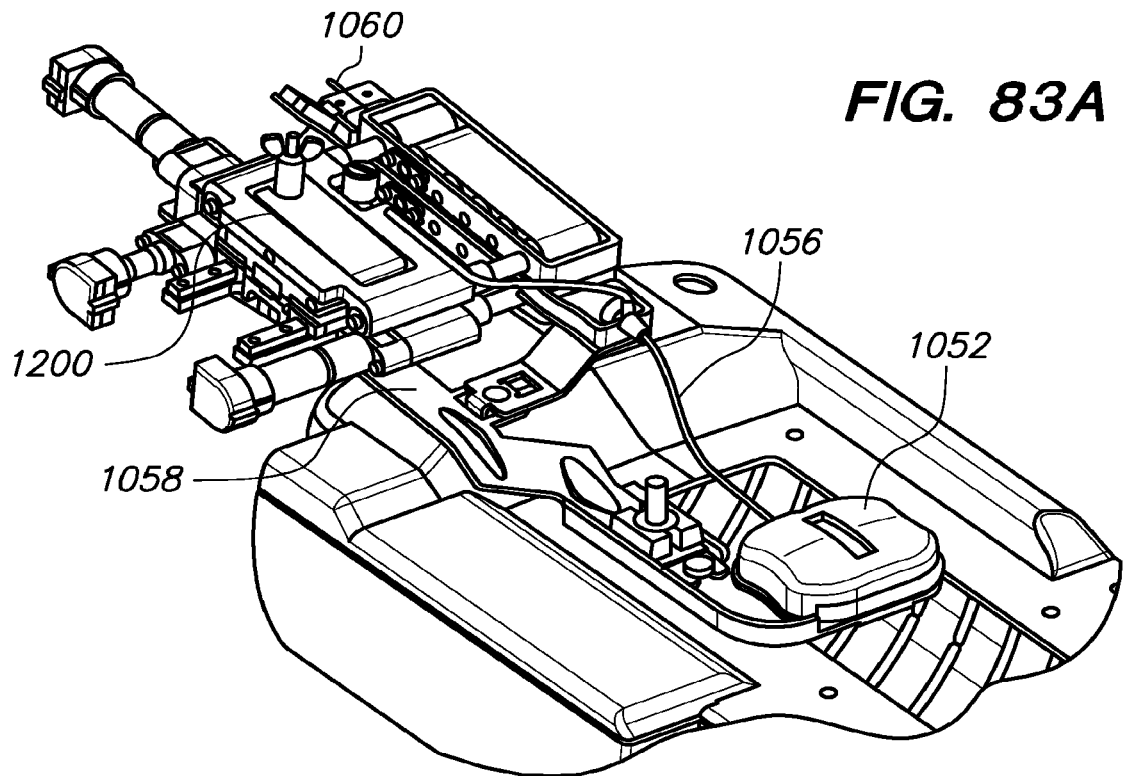
FIG. 83A illustrates a closer view of the instrument driver, the elongate member manipulator, and the guide splayer of FIG. 83.

FIGS. 83-83A illustrate another variation of an elongate member manipulator 1200 which includes rotary members in the form of belts. The elongate member manipulator 1200 is shown mounted on an instrument driver 16. The elongate member manipulator 200 may by utilized to feed an elongate member, such as guide wire 60, co-axially into a guide catheter splayer 1052. The guide wire 1060 may be fed into a support tube 1056 which subsequently feeds into the guide catheter splayer 1052, and ultimately into a guide catheter (not shown). In certain variations, the elongate member manipulator may be mounted on the instrument driver along with a guide and/or a sheath splayer/catheter or the elongate member manipulator may be mounted alone. Optionally, the elongate member manipulator may be utilized to feed an elongate member, such as guide wire, co-axially into a sheath and or catheter. Optionally, the elongate member manipulator may be utilized to feed an elongate member, such as guide wire, directly into a patient's body or anatomy.

Figure 84:
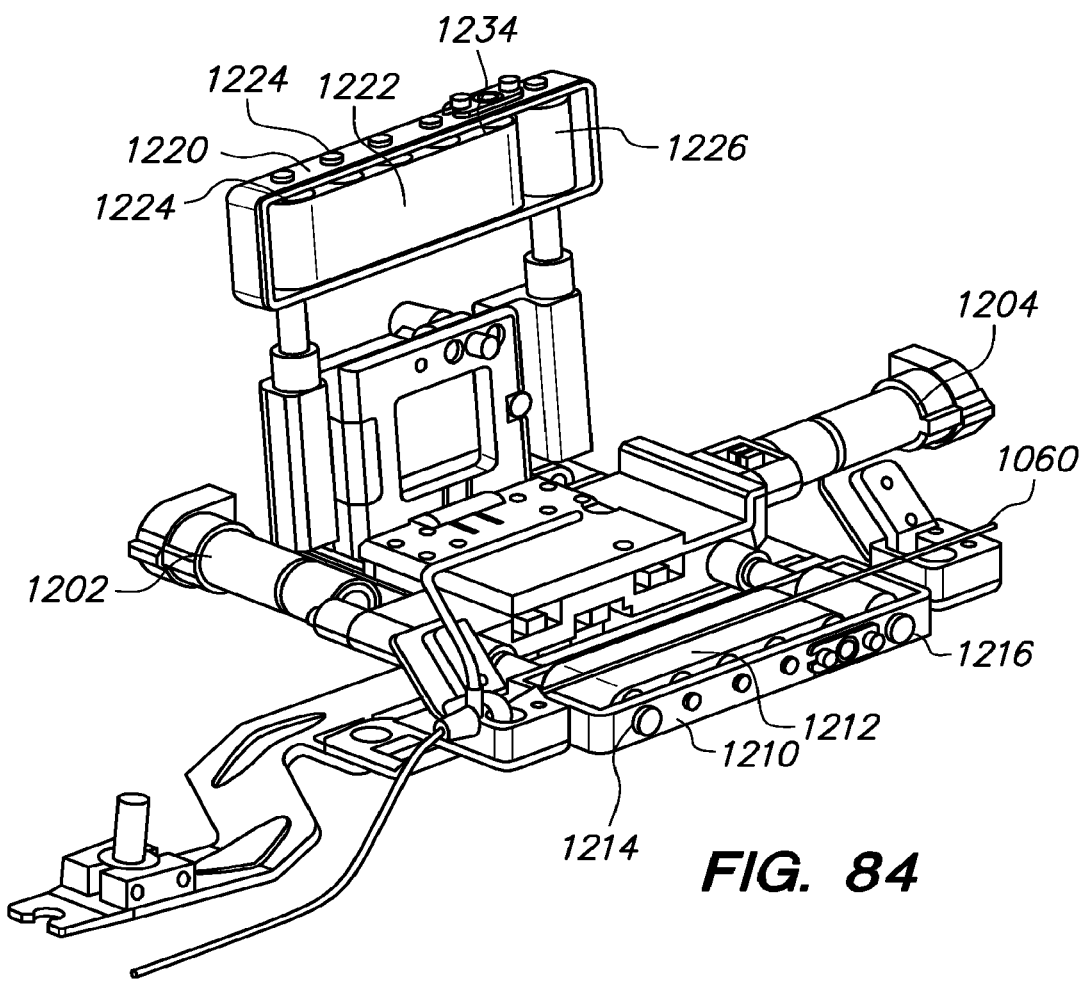
FIG. 84 illustrates a perspective view of the elongate member manipulator of FIG. 83, showing the manipulator in an open configuration and mounted to a manipulator mounting bracket.

FIG. 84 illustrates the elongate member manipulator 1200 in an open hinged configuration. The elongate member manipulator can include a drive assembly and an elongate member holder. The components of the elongate member holder include a drive belt assembly 1210 and an idler belt assembly 1220. Both belt assemblies include belts 1212, 1222 with pulleys 1214, 1224. The drive pulley 1084 may be directly driven by an insert servo motor 1102 or other mechanism to turn the drive belt 1212. The idler belt 1222 is free to rotate about the idler pulley 1224. The belts may be constructed from various materials known to person having ordinary skill in the art. The belts may have various dimensions. For example, about 1" wide Texin® or silicon rubber, durometer 90A profiled timing belts may be utilized covering a length of about 4.5" from opposite outer diameter edges of the belt. Other variations may use alternative widths, other dimensions, and materials with alternative durometers for the belts. In one variation the belts can be constructed from any gamma sterilizable material which is well known in the art including but not limited to thermoplastics such as ABS or PET, fluoropolymers such as polyvinyl fluoride, polymides, polystyrenes, polyurethanes, polyesters, or polyesters. Optionally, bands or feed rollers could be used in place of belts.

Figure 85A:
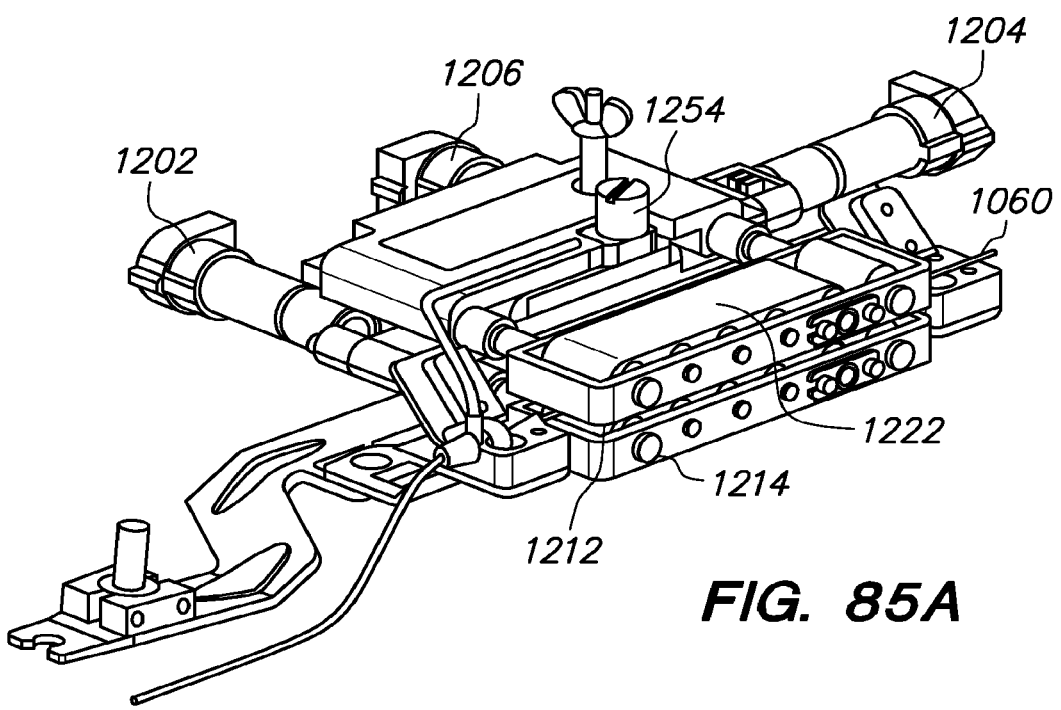
FIG. 85A illustrates the elongate member manipulator of FIG. 84, showing the manipulator in a closed configuration.
Figure 85B:
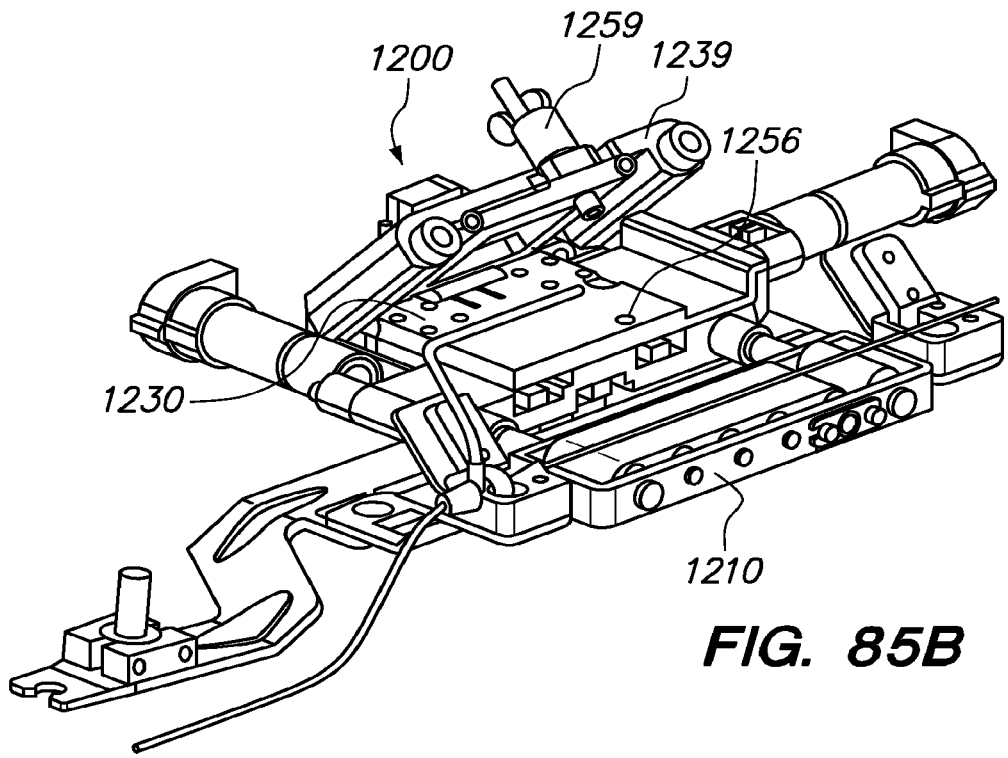
FIGS. 85B-85C illustrate the elongate member manipulator of FIG. 84 with an idler belt assembly removed, showing the manipulator open by varying degrees.
Figure 85C:
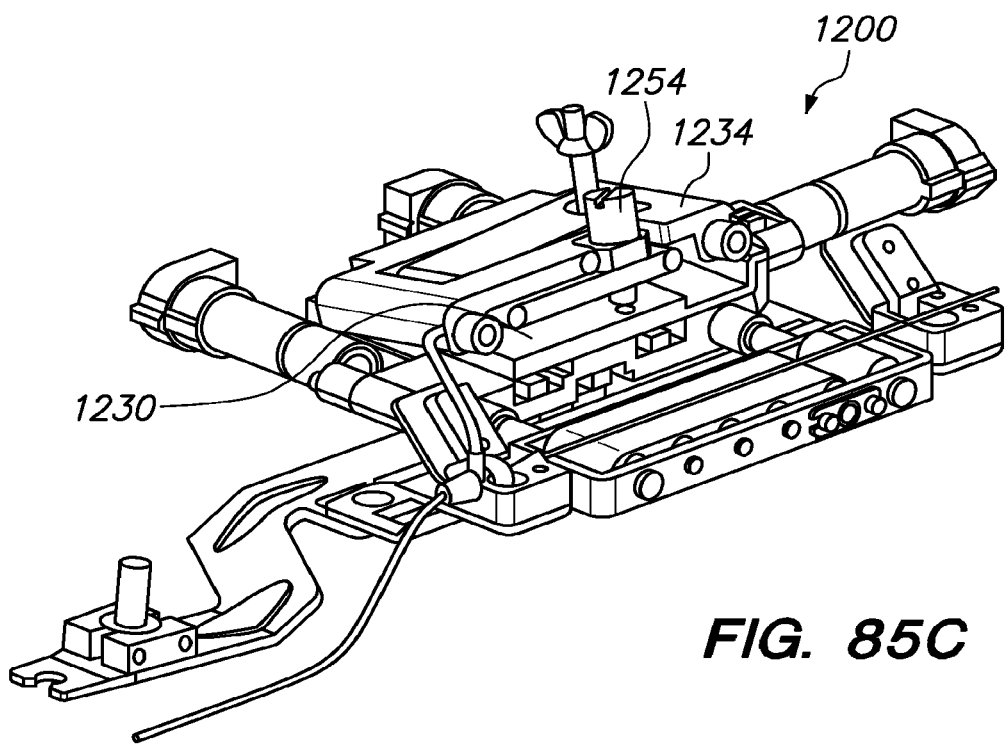

As shown in FIGS. 85A, 85B and 85C, the drive assembly can include an upper slide assembly 1234, a lower slide assembly 1230, an insert motor 1202, and a roll motor 1204, as well as a set of rails, a rack and a pinion (not shown here but described in detail below). In use, as illustrated in FIGS. 84 and 85A, the upper slide assembly 1234 can hinge open a plurality of degrees for workflow clearance, the guide wire 1060 can be placed on the drive belt 1212, and the elongate member manipulator 1200 or system can be closed so that the guide wire 1060 is held between the drive belt 1212 and the idler belt 1222. This allows a guide wire to be loaded into the elongate member manipulator 1200 anywhere along the length of the guide wire 1060, which may expedite the loading procedure instead of being restricted to load the wire by feeding the wire from the back of the system. Also the guide wire can be loaded when the belts are in any position. For example, the drive belt 1212 may be at an arbitrary position such that the drive motor 1202 does not require any type of initialization or homing before installation of the guide wire 1060. Additionally a guide wire can be removed from the elongate member manipulator 1200 or system mid procedure if the operator desires to switch from using the robotic manipulator to manual control of the guide wire.

Figure 85D:
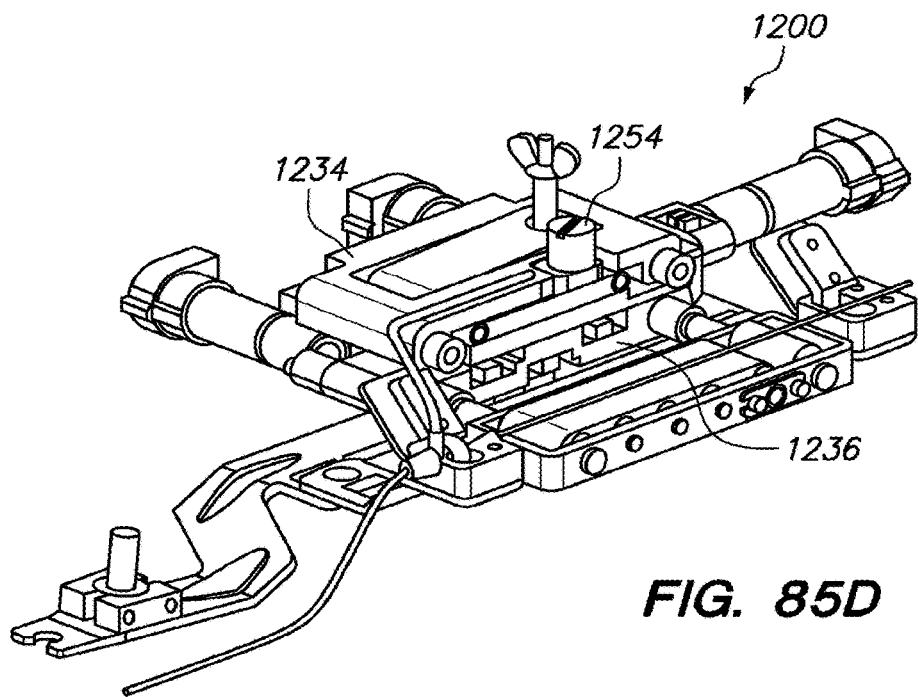
FIG. 85D illustrates the elongate member manipulator of FIG. 85B in a closed configuration.
Figure 85E:
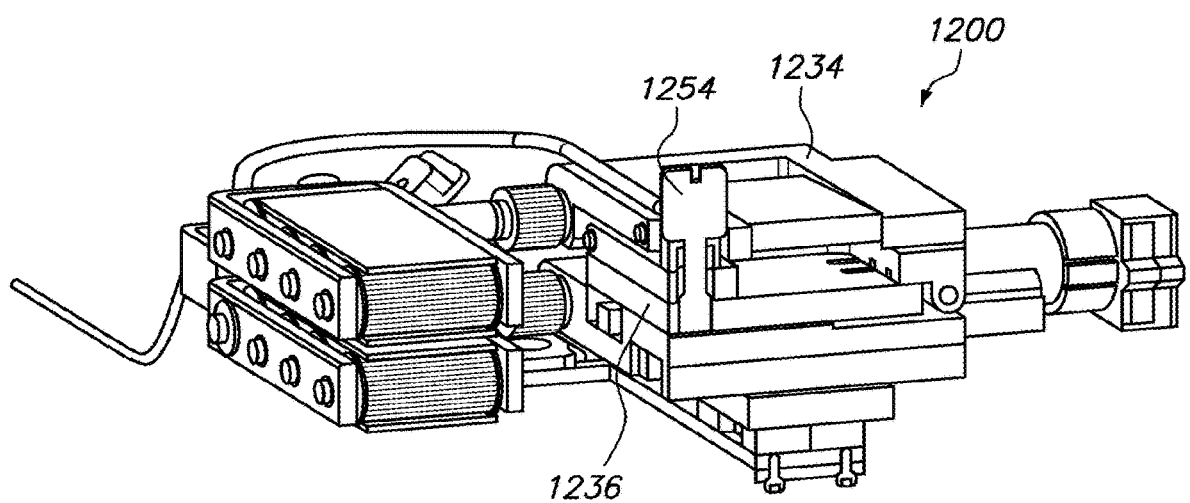
FIG. 85E illustrates a cross-sectional view of the elongate member manipulator of FIG. 85A.

In alternative variations a guide wire can be backloaded into a manipulator. A back loaded guide wire would be retracted or pulled out of a patient's body before removing the guide wire from the manipulator to switch to manual control To ensure that the upper slide assembly 1234 and lower slide assembly 1230 stay closed during operation, a captive screw 1254 can be used. A variation including a captive screw 1254 is shown in FIGS. 85B-E which illustrate an isometric view of the elongate member manipulator 1200 with only the drive belt assembly 1210 shown (idler belt assembly not shown for clarity). FIG. 85B illustrates the elongate member manipulator 1200 in an open position, FIG. 85C illustrates the elongate member manipulator 1200 as it is partially closed, and FIG. 85D shows the elongate member manipulator 1200 closed and locked. The captive screw 1254 remains captive with the upper slide assembly 1234 and locks into a threaded hole 1256 in the lower slide assembly 1230. FIG. 85E illustrates a cross section of the elongate member manipulator illustrating the operation of the captive screw 1254. In alternative variations, a latch, fastener or other type of locking, fastening or latching mechanism may be used instead of a captive screw.

As illustrated in FIG. 85A, once the guide wire 1060 is loaded and held between the drive belt 1212 and the idler belt 1222, the insert motor 1202 drives the drive pulley 1214, turning the drive belt 1212 and propelling the guide wire 1060 forward or backwards (insert or retract) depending on the rotational direction of the motor and pulley. With sufficient frictional pinching, gripping, pressing, or holding force holding the guide wire 1060 between the drive belt 1212 and idler belt 1222, the idler belt 1222 will turn at the same rate as the drive belt 1212, and the belts will hold the guide wire 1060 such that lateral linear movement or displacement of the guide wire relative to the belts may be eliminated, minimized or reduced.

Figure 86A:
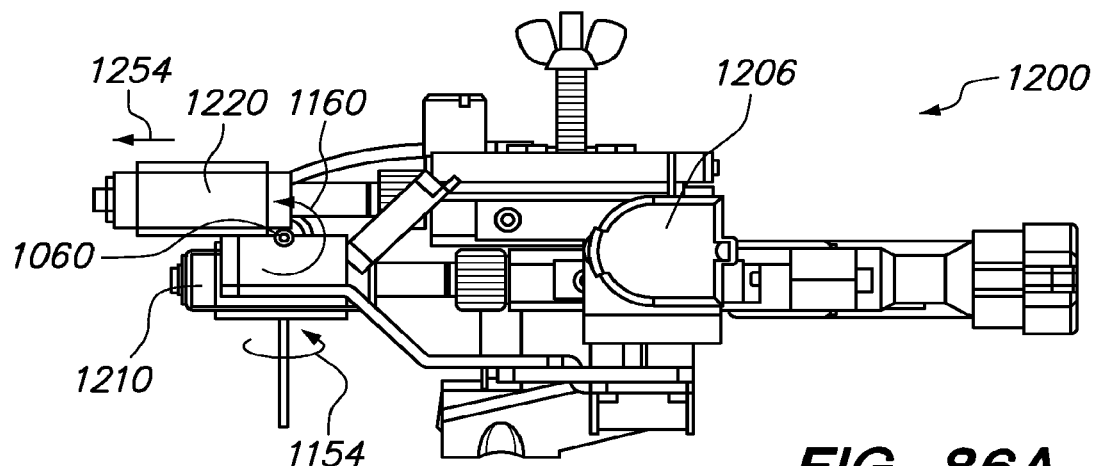
FIG. 86A illustrates a back view of the elongate member manipulator of FIG. 84.
Figure 86B:
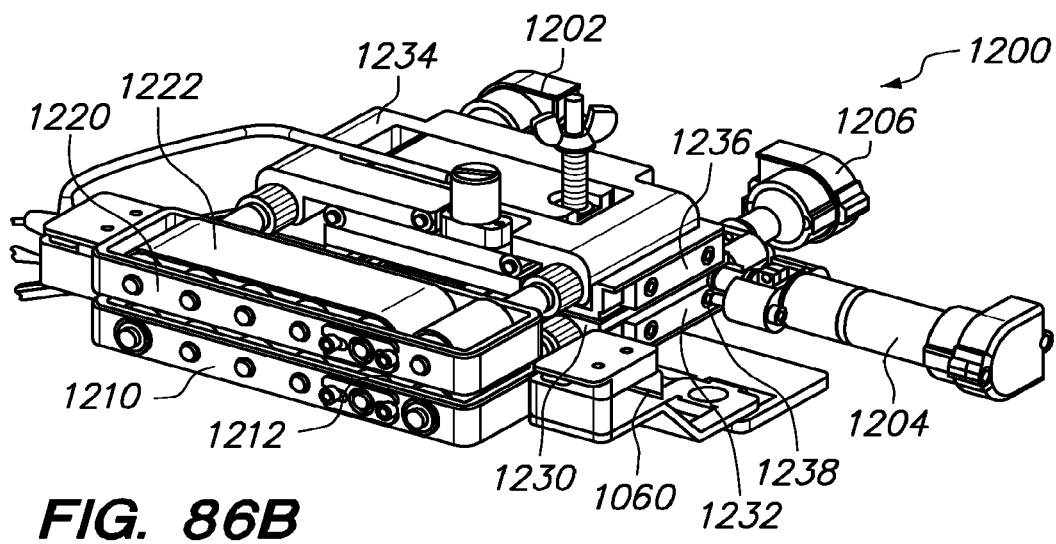
FIGS. 86B-86C illustrates various perspective views of the elongate member manipulator of FIG. 85.
Figure 86C:
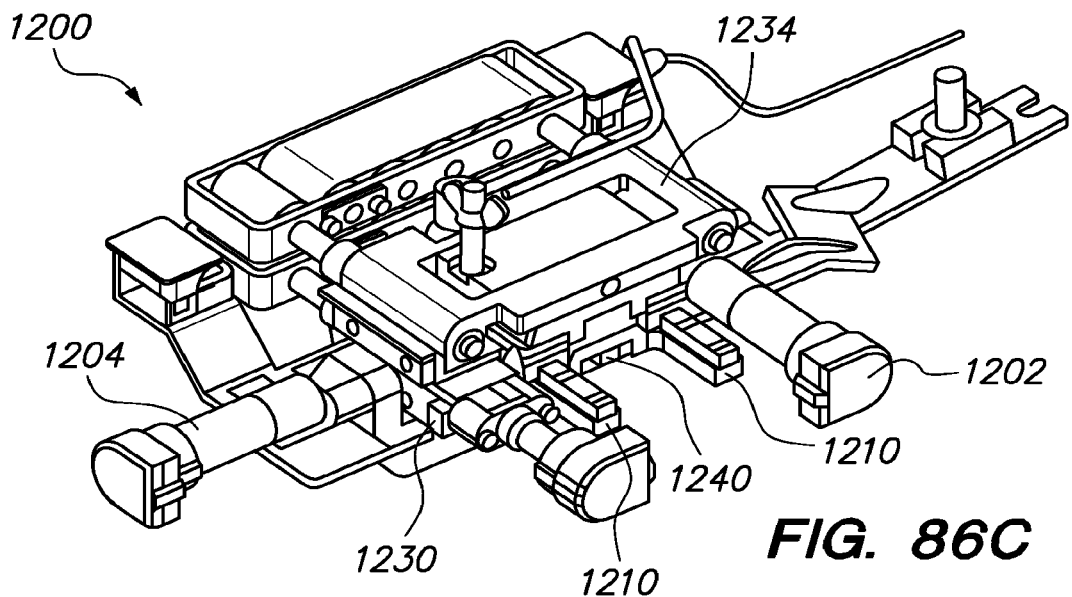

FIGS. 86A-86C illustrate various views of the elongate member manipulator 1200 showing various components of the elongate member manipulator that function to provide roll actuation of the guide wire 1060. (Some components of the elongate member manipulator 1200 are hidden for clarity.)

FIG. 86A illustrates an end view of the elongate member manipulator 1200. FIGS. 86B-86C illustrate perspective views of the elongate member manipulator 1200 providing different angles showing the lower slide assembly 1230 and the upper slide assembly 1234. The lower slide assembly 1230 and upper slide assembly 1234 may each be attached to linear rails 1240. The lower slide assembly 1230 includes the insert motor 1202 and a slip detection encoder 1204. The drive belt assembly 1210 attaches to the lower slide assembly 1230 while the idler belt assembly 1220 attaches to the upper slide assembly 1234. Both lower and upper assemblies 1230, 1234 have a rack 1232, 1236 that is coupled to a pinion 1238 driven by a roll motor 1206. The roll motor 1204 is mounted stationary relative to the instrument driver so that when the pinion 1238 is turned, the slide assemblies 1230, 1234 move or translate in opposing directions, driving both the drive belt assembly 1210 and the idler belt assembly 1220 in opposing translational directions 1154. This motion will roll, rotate or torque the guide wire 1060 as shown by the arrow 1160. Translation of the drive belt assembly 1210 and idler belt assembly 1220 in directions opposite those shown in FIG. 86A would result in roll of the guide wire in the direction opposite that of arrow 1160.

In an alternative variation (not depicted), either the upper or lower slide assemblies could be coupled to a leadscrew so that motorized rotation of the leadscrew would result in translation of one slide assembly relative to the other. Roll and insert can be independently actuated or actuated simultaneously as described previously.

When the elongate member manipulator 1200 is in a closed configuration holding the guide wire 1060, a sufficient pinching force between the drive belt 1212 and idler belt 1222 may be necessary to provide adequate frictional force to actuate insert, or retraction, and/or roll of the guide wire 1060. As various guide wires 1060 with varying wire diameters may be loaded into the elongate member manipulator 1200, it may be desirable to adjust the pinching force such that the applied pinching force is high enough to provide for insert and roll actuation while low enough to prevent damage or buckling of the guide wire 1060.

Figure 87A:
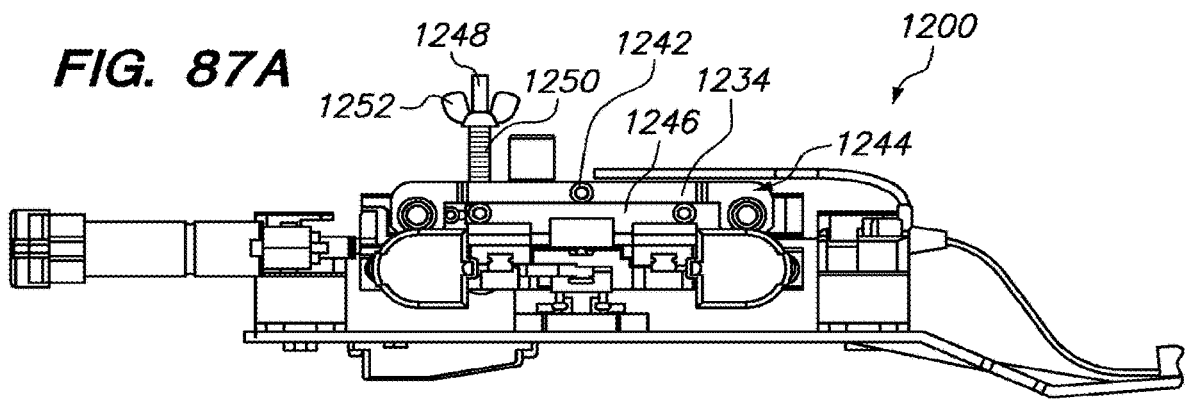
FIG. 87A illustrates a side view of the elongate member manipulator of FIG. 85, showing a hinge mechanism in a closed configuration.
Figure 87B:
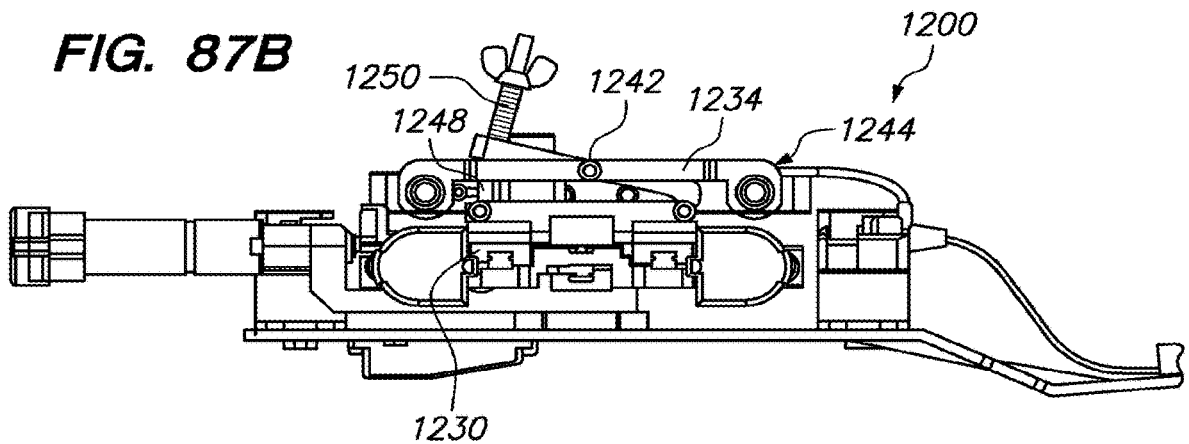
FIG. 87B illustrates the elongate member manipulator of FIG. 87A, showing the hinge mechanism in an open configuration.
Figure 87C:
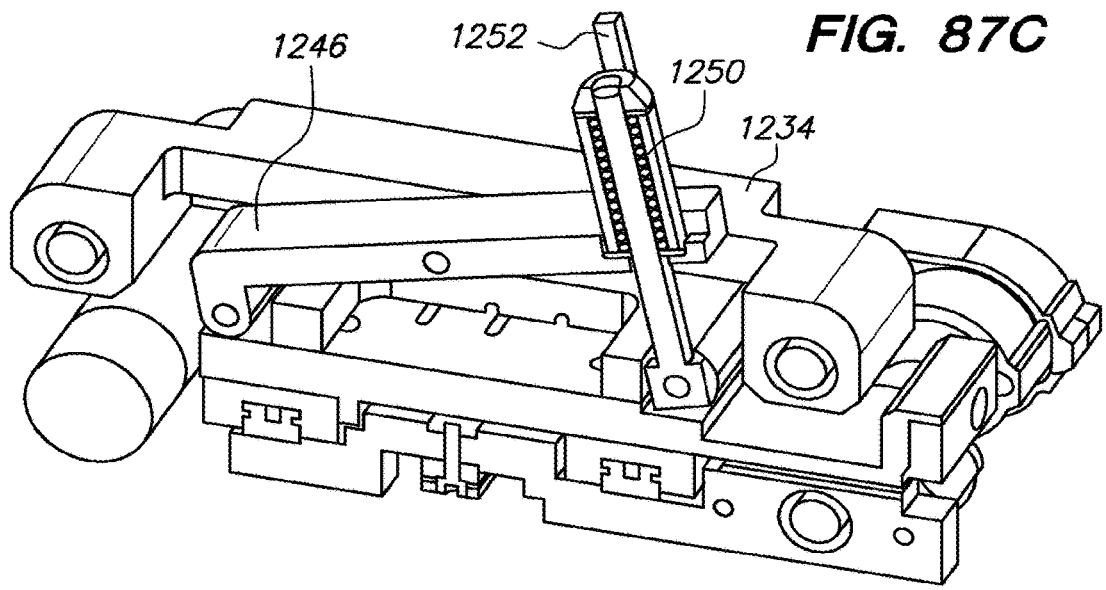
FIG. 87C illustrates a cross sectional perspective view of the elongate member manipulator of FIG. 84.

Thus, in certain variations, the upper slide assembly 1234 of an elongate member manipulator can include a hinge 1242 and a suspension mechanism 1244. FIGS. 87A-87B show a left side view of an elongate member manipulator 1200 with the suspension mechanism 1244 in an open and closed configuration respectively, while FIG. 87C shows a cross section of the assembly 1234 with the suspension mechanism 1244. The suspension mechanism 1244 may include a lever arm 1246, a lever shaft 1248, a lever spring 1250 and a tightening nut 1252. The suspension mechanism 1244 may provide a mechanism by which the force applied by the lever spring 1250 to hold the guide wire between the idler belt assembly 1220 and the drive belt assembly 1210 may be adjusted in order to accommodate a variety of guide wire diameters while providing sufficient pinching force for a variety of guide wire diameters.

As illustrated in FIG. 87B, the tightening nut 1252 may be used to control the swing of the lever arm 1246 to adjust the grip force between the upper slide assembly 1234 and the lower slide assembly 1230 to apply the necessary grip force for various wire diameters and to provide an increased force ratio for wire compression. By way of example but not limitation, if a 2 to 1 force ratio could be applied where a 20 lb wire load was required, a 10 lb spring would be applied to the lever. The range of guide wire diameters that could be accommodated for this example may range from about 0.014"-0.038".

Figure 88:
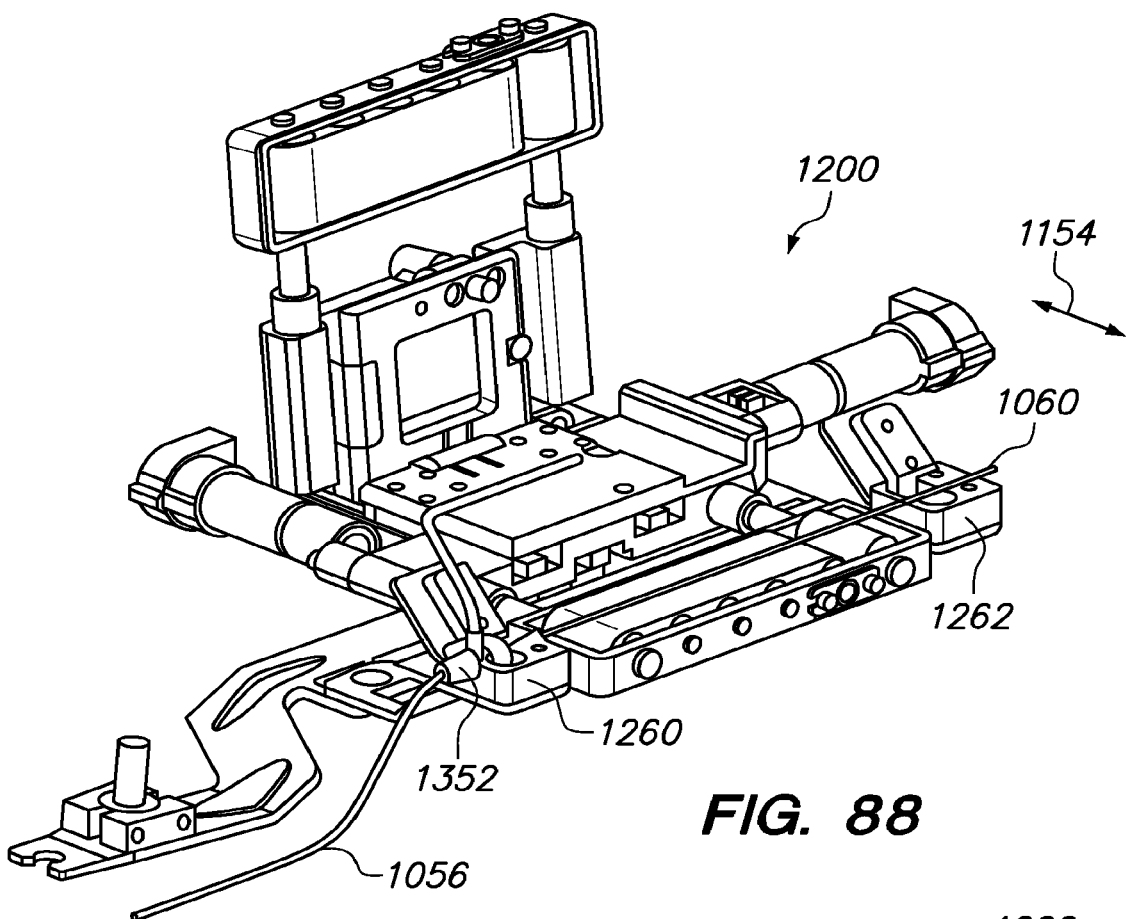
FIG. 88 illustrates a perspective view of the elongate member manipulator of FIG. 84 with wire holders installed, showing both the manipulator and wire holders in open configurations.
Figure 89:
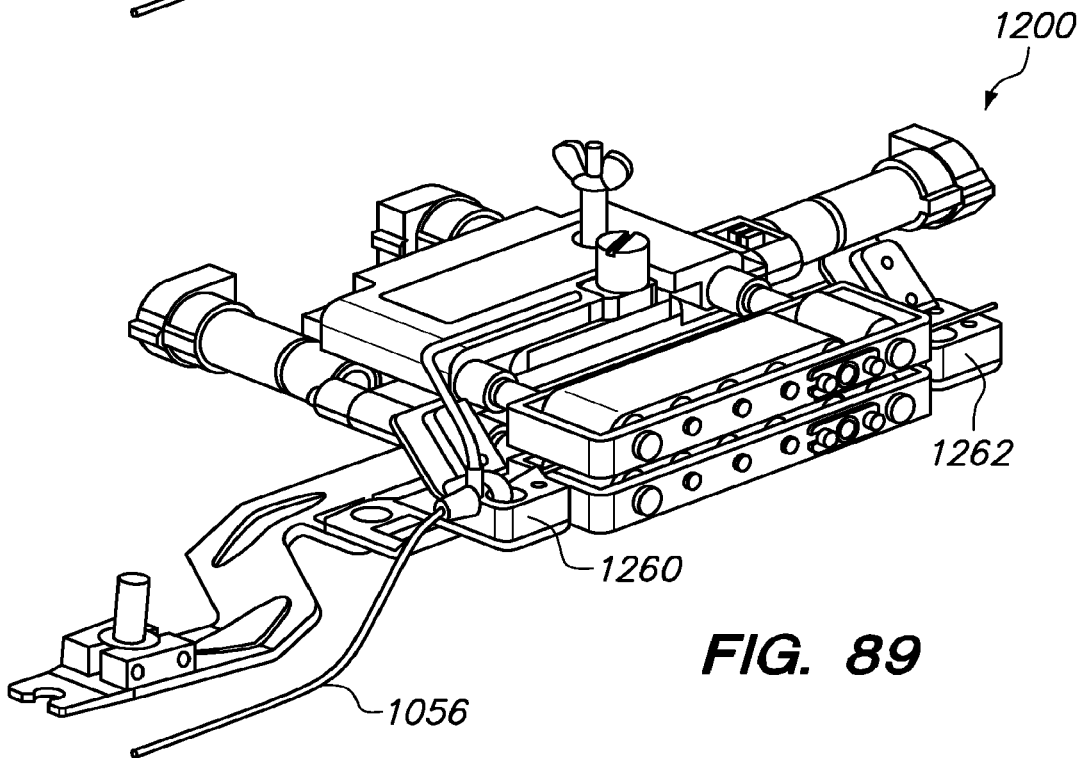
FIG. 89 illustrates the elongate member manipulator of FIG. 88, showing the manipulator and wire holders in closed configurations.

FIGS. 88 and 89 illustrate a pair of elongate member brackets or wire holders 1260, 1262 that can be used to prevent a guide wire 1060 or other elongate member from sliding or slipping laterally or in the direction of slide assembly or belt assembly translation while the guide wire or elongate member is being rolled or twisted. Such wire holders may hold or grip a guide wire in addition to or in place of the frictional pinching force provided by the rotary member, rollers or belts. FIG. 88 illustrates the elongate member manipulator 1200 with a pair of wire holders 1260, 1262 where both the elongate member manipulator and the wire holders are in an open configuration. FIG. 89 illustrates the manipulator 1200 and wire holders 1260, 1262 in a closed configuration.

The wire holders 1260, 1262 may be in the form of simple clamps or other configurations that can open and close to load and hold the guide wire 1060 and/or the guide wire support tube 1056. Cut outs in the holders may be sized to allow for the guide wire 1060 and/or the valve assembly 1352 to be held in place along a longitudinal axis of a belt assembly while also allowing the guide wire to move in a propelling motion or a roll motion without excess friction. In order to prevent or minimize any undesired slippage in the translation direction 1154 (See FIG. 86A) during roll of the guide wire, which may result from the tolerance provided by such cut outs, dimensions of the wire holders can be varied. The wire holders may be designed to minimize or prevent such slippage in the translation direction while also minimizing or preventing propelling and/or roll friction. Additionally, lubricants could be used to minimize or prevent propelling and/or roll friction while still minimizing or preventing slippage in the translation direction.

Alternatively, some situations may require minimizing lubrication of the guide wire in order to provide adequate gripping of the wire. In one variation, as the guide wire is retracted or de-inserted from the patient, sections of the guide wire may become coated with blood or fluid. When the sections are retracted between the drive belt assembly 1210 and idler belt assembly 1220, the guide wire 1060 may become slippery preventing the guide wire manipulator 1200 from adequately rolling and de-inserting the guide wire 1060. Thus, an absorbent material (not shown) may be integrated or included into the wire holder 1260 to remove blood or fluid from the guide wire 1060 as it is retracted into the guide wire manipulator 1200. In certain variations, the absorbent material could be integrated only in the distal wire holder 1260 and not the proximal wire holder 1262 since the length of guide wire proximal to the drive and idler assembly belts 1210, 1220 is no longer engaged in the guide wire manipulator 1200. In alternative embodiments the absorbent material can be integrated into both wire holders 1260, 1262 or only the wire holder 1262 preventing any outside fluids from coating the guide wire during the insert forward propelling actuation motion as well or to provide additional fluid removal of the guide wire during retraction. The absorbent material can included but is not limited to any type of sponge, wicking cloth, or polymer. Alternatively, a wiper mechanism can be integrated into the wire holders 1260, 1262.

In addition to the slippage that may occur during roll motions, a guide wire 1060 or other elongate members may also be susceptible to slippage between the drive belt 1212 and idler belt 1222 in the direction of insertion or retraction motion while the guide wire is being propelled forward or backward, despite maximizing pinching force and optimizing belt materials. Roll and/or insert motors 1202, 1204 can be provided with encoders to measure the commanded insert and roll of a guide wire. To help improve the accuracy of this measurement, a mechanism for slippage detection during insert or retraction may be provided.

Referring back to FIG. 84, in certain variations, the elongate member manipulator 1200 may include a drive side slip roller 1216 and idler side slip roller 1226 for guide wire insertion or retraction tracking. One or more fo the drive and idler slip rollers 1216, 1226 may be decoupled from motion of the drive and idler belts 1212, 1222. The drive roller 1216 is shown directly coupled to an encoder 1206 (illustrated in FIG. 85) for guide wire slip detection. The drive side slip roller 1216 can be constructed from a harder material, e.g., PET, and the idler side slip roller 1226 can be constructed from a softer material, e.g., an open celled rubber. The harder PET will not deform from contact with the guide wire 1060 preventing the outside diameter of the drive side slip roller 1216 from varying. Since the insertion or retraction distance may be calculated from encoder counts (where encoders are used) and roller diameter, it is important that the roller coupled to the encoder be non-deformable material such as PET. Conversely, the softer material, e.g. the open celled rubber could allow for compression compliance which will assist with guide wire grip. The combination of materials allows for a tight grip on the guide wire 1060 during insertion/retraction, but provides for a smooth slip during roll. Alternative materials could be used to allow for this smooth slip while still providing adequate gripping of the wire during insertion and retraction. Any type of gamma sterileizable material can be used which can be chosen based on durometer. Alternatively, the drive side slip roller 1216 may be constructed form a softer material and the idler side slip roller 1226 may be constructed from a harder material and the encoder may be should be coupled to the idler slip roller 1226.

In order to maximize workflow while keeping the guide wire 1060 and belt assemblies 1210, 1220 in the sterile field, a mechanism that allows for easy removal and replacement of the sterile components, including the guide wire and belt assemblies, may be provided. The belt assemblies may be detachable or removable from the slide assemblies and/or remaining components of the elongate member manipulator such that a drape or other sterile barrier may be installed or inserted between the sterile components, e.g., the belt assemblies, and the non-sterile components, e.g. the slide assemblies. Additionally, the sterile components may be disposable. Accordingly, the complexity of the sterile components or assembly of the elongate member manipulator may be minimized to reduce cost, and many components of the elongate member manipulator, such as certain motors, gears, capstans, etc., may be designed or configured such that they remain in the non-sterile field.

Figure 90A:
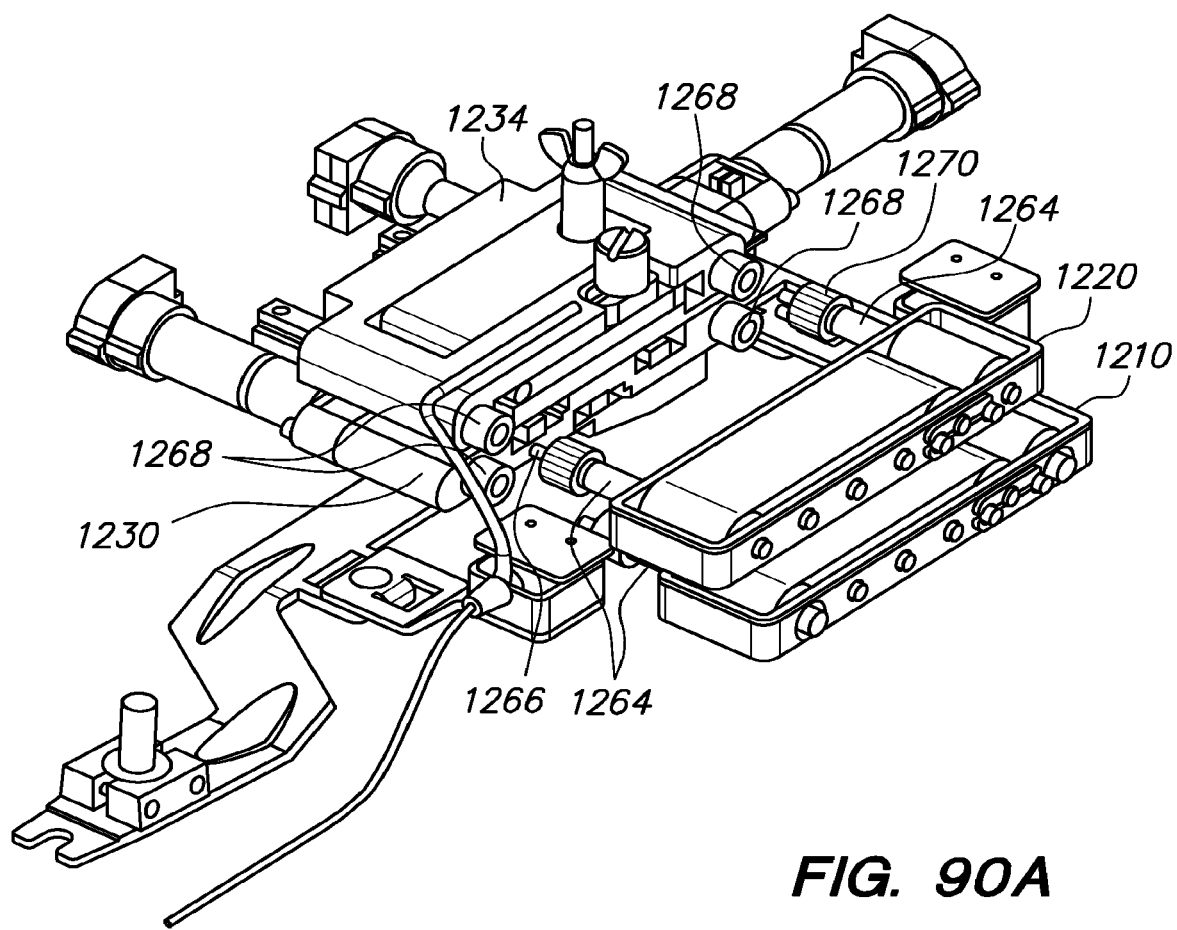
FIG. 90A illustrates an exploded perspective view of the elongate member manipulator of FIG. 84, showing the idler belt assembly and a drive belt assembly partially removed.
Figure 90B:
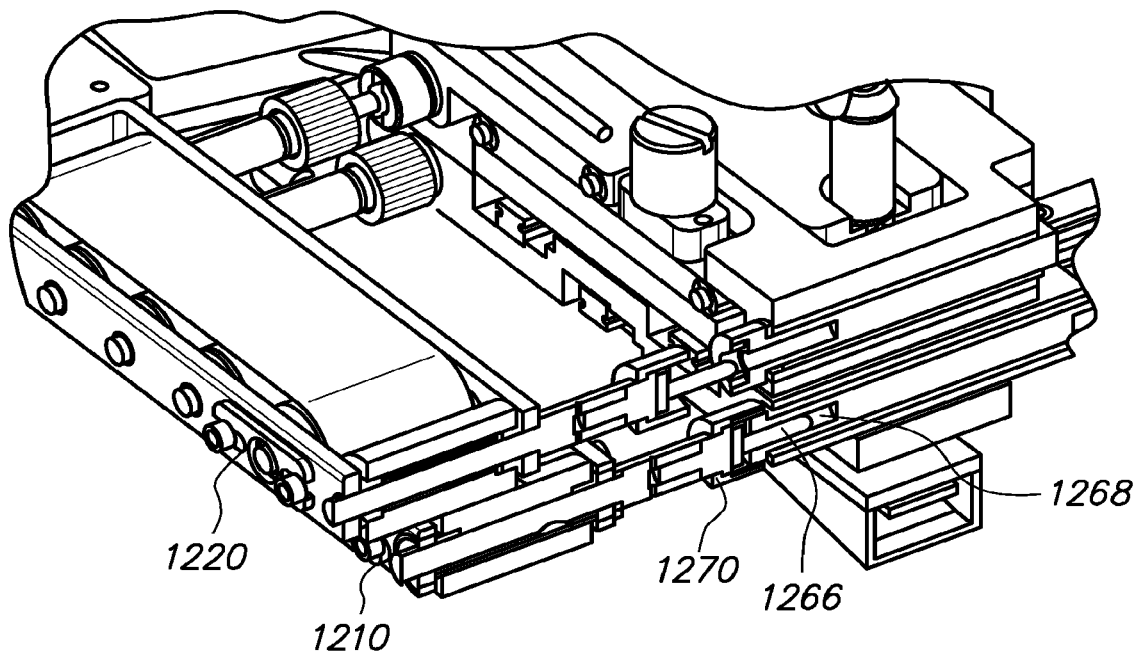
FIG. 90B illustrates a cross sectional view of the elongate member manipulator of FIG. 84, showing the idler belt assembly and the drive belt assembly partially un-installed.
Figure 90C:
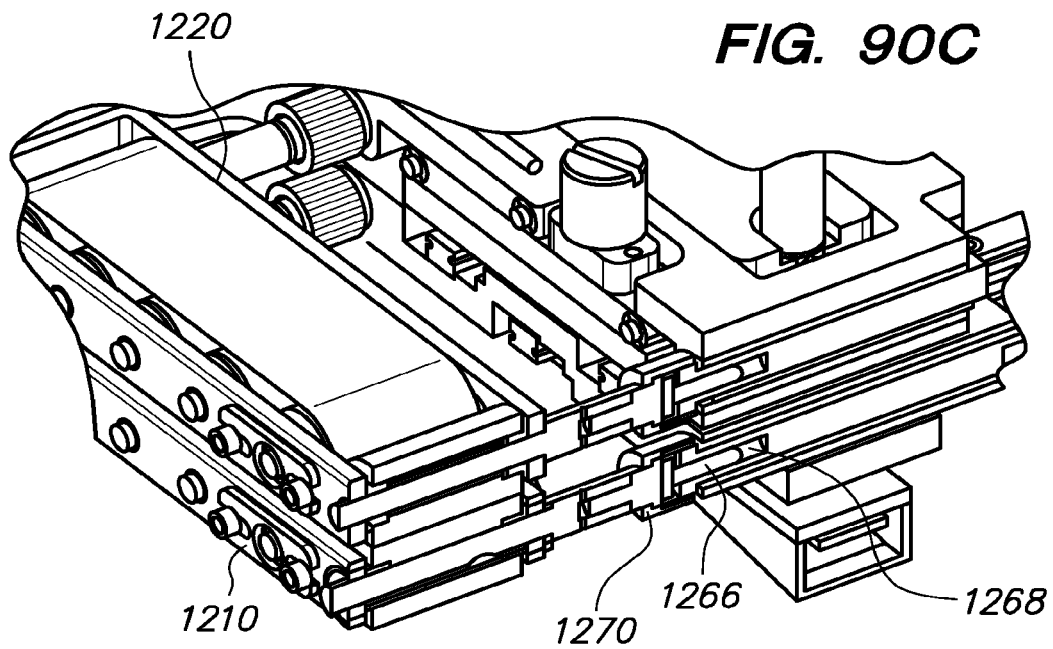
FIG. 90C illustrates a cross sectional view of the elongate member manipulator of FIG. 84, showing the idler belt assembly and the drive belt assembly fully installed.

FIGS. 90A-90C illustrate the drive belt assembly 1210 and the idler belt assembly 1220 as sterile assemblies of minimal complexity having pulleys and belts, where the assemblies can be removed and replaced easily. FIG. 90A illustrates the elongate member manipulator 1200 with the drive belt assembly 1210 and the idler belt assembly 1220 removed or detached from the slide assemblies 1230, 1234. The belt assemblies may include a drive shaft 1264 having a cross pin 1266 to key into socket 1268 provided in the slide assemblies 1230, 1234. Alternatively a spline or taper element could be used. A captive nut 1270 may be attached to the disposable drive and idler belt assemblies 1210, 1220 and remain in the sterile environment. FIG. 14B shows a cross section of the elongate member manipulator where the drive belt assembly 1210 is fully installed and the idler belt assembly 1220 partially installed in the slide assemblies while FIG. 90C shows the same cross section with both belt assemblies 1210, 1220 fully installed in the slide assemblies.

Figure 91B:
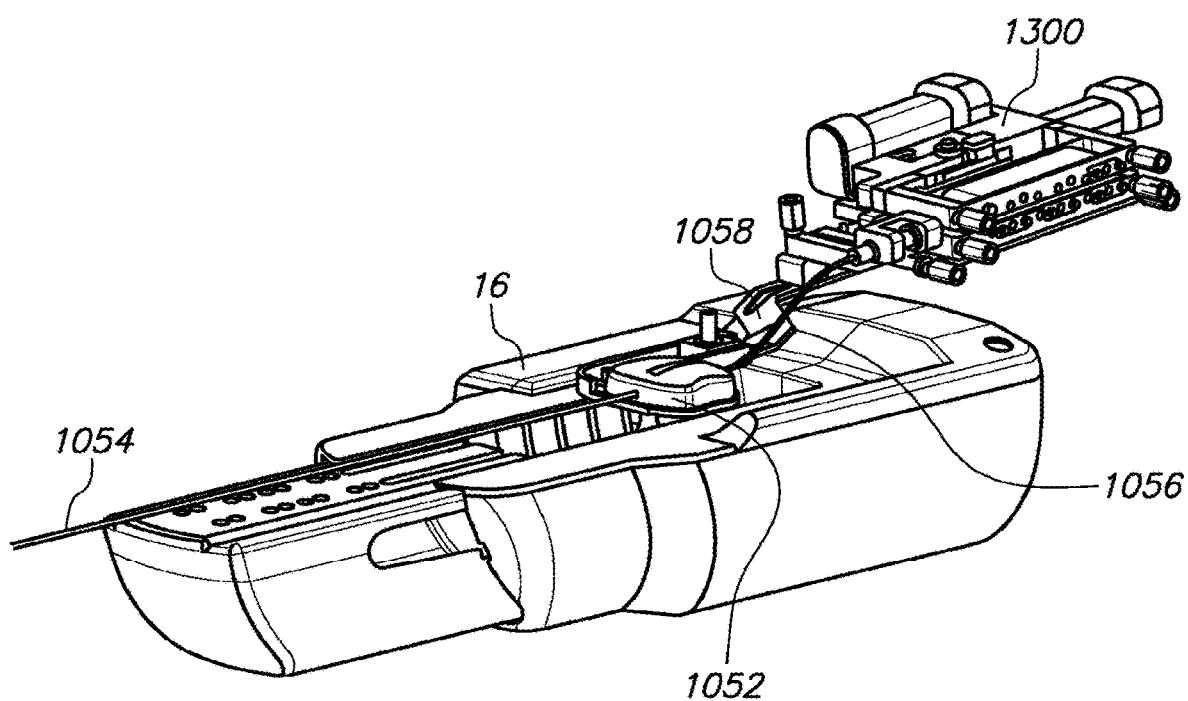
Figure 91C:
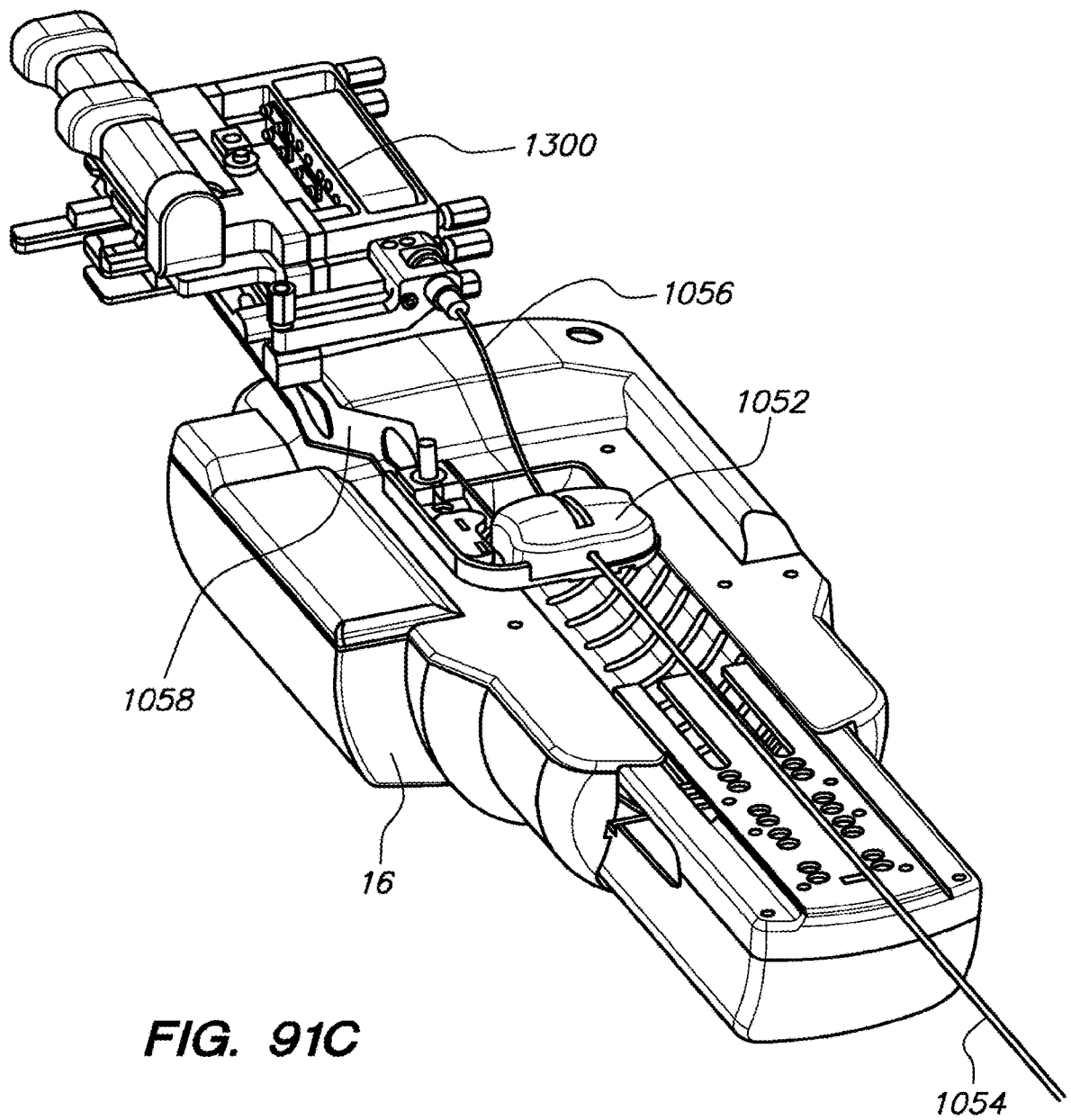

FIGS. 91A-C illustrate another variation of an elongate member manipulator 1300. The elongate member manipulator 1300 may be mounted to a manipulator mounting bracket 1058 which is mounted to the instrument driver 1016. The elongate member manipulator 1300 may be utilized to feed an elongate member, such as guide wire (not shown), co-axially into a support tube 1056 which subsequently feeds into the guide catheter splayer 1052, and ultimately into a guide catheter 1054. In certain variations, the elongate member manipulator 1300 may be mounted on the instrument driver 1016 along with a guide and/or a sheath splayer/catheter or the elongate member manipulator 1300 may be mounted alone.

Figure 91D:
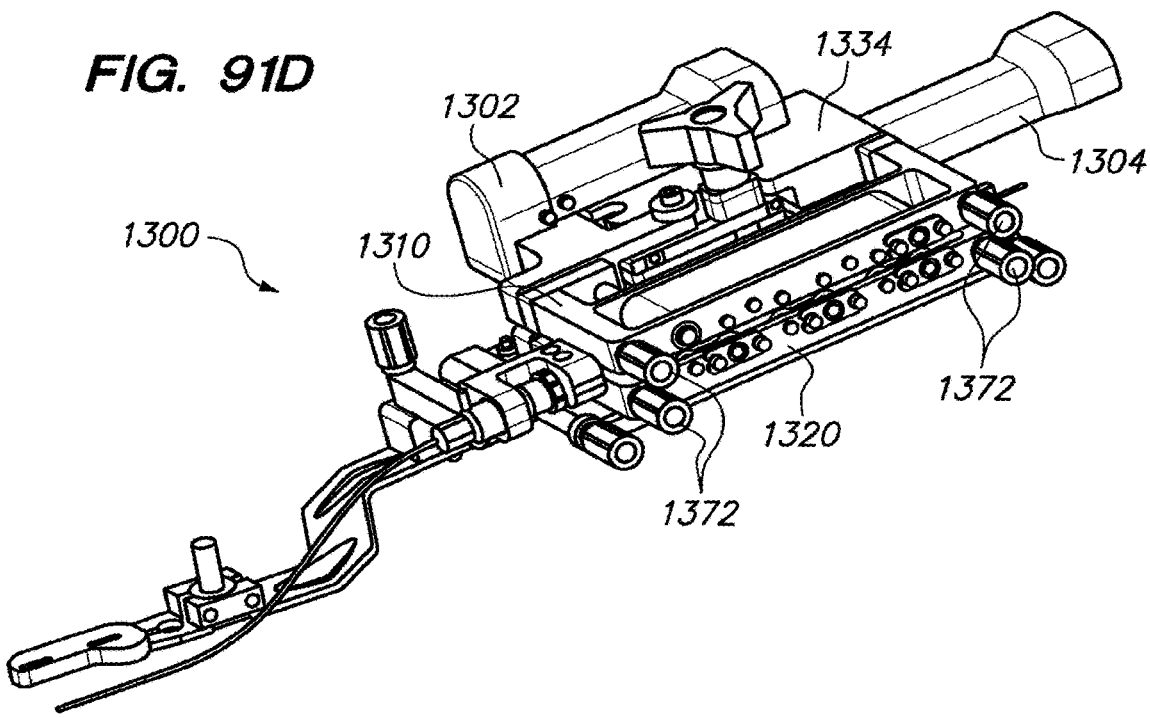
FIGS. 91D-91E illustrate perspective views of the elongate member manipulator of FIG. 91A.
Figure 91E:
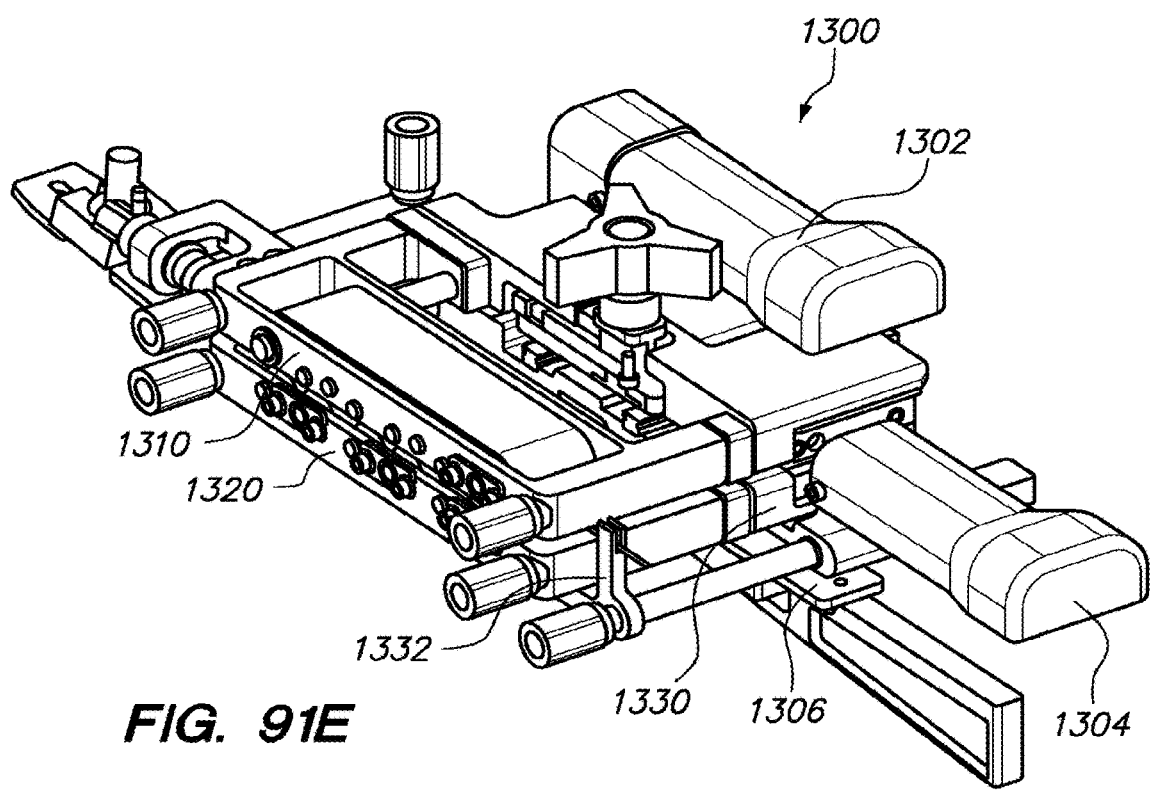
Figure 91F:
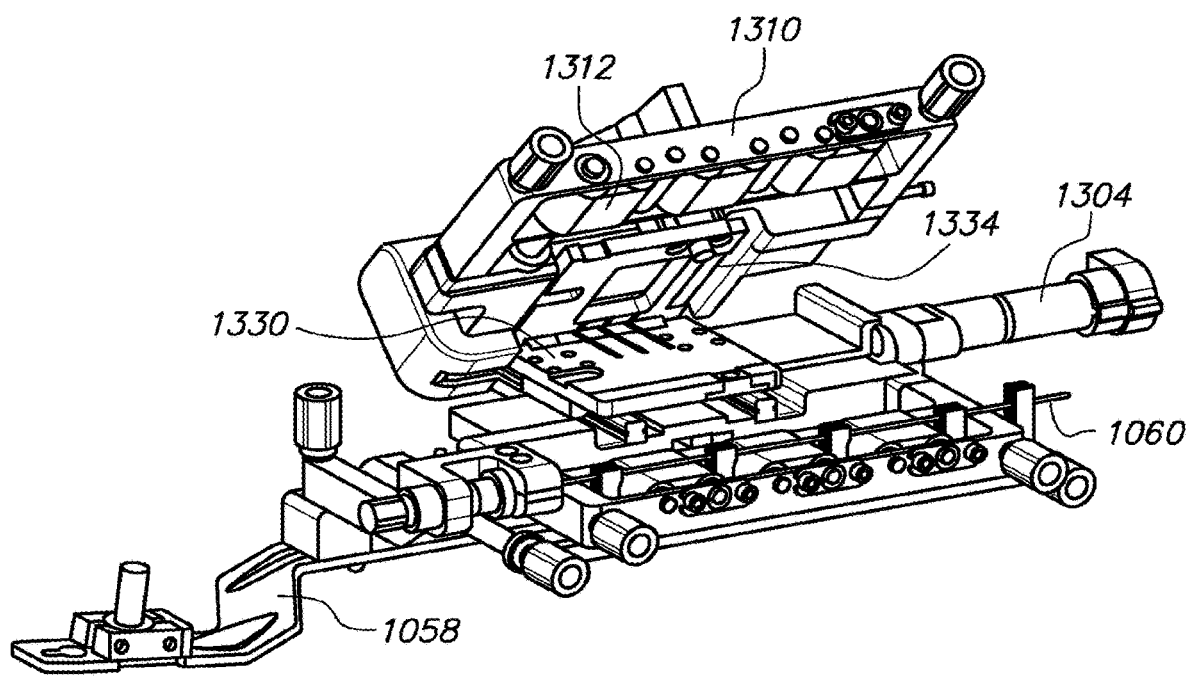
FIG. 91F illustrates a perspective view of the elongate member manipulator of FIG. 91A, showing the elongate member manipulator in an open configuration.
Figure 91G:
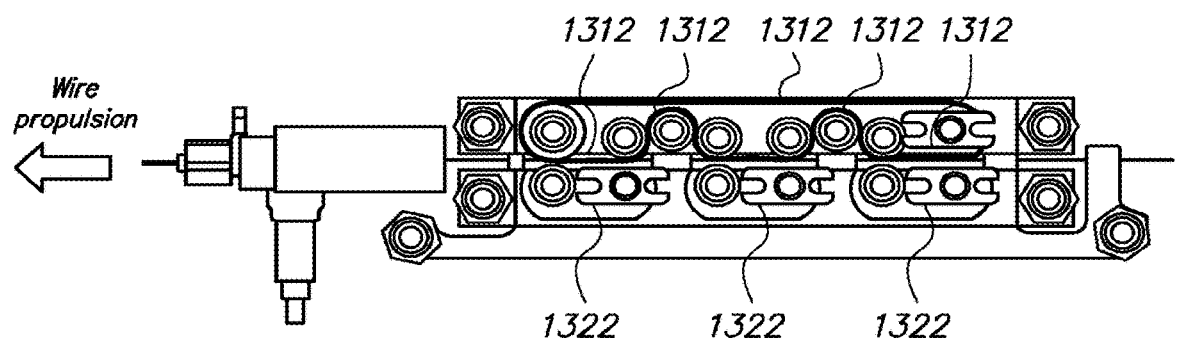
FIG. 91G illustrates a side view of the elongate member manipulator of FIG. 91A, showing the manipulator mounting bracket, a roll motor, and an insert motor all removed.
Figure 91H:
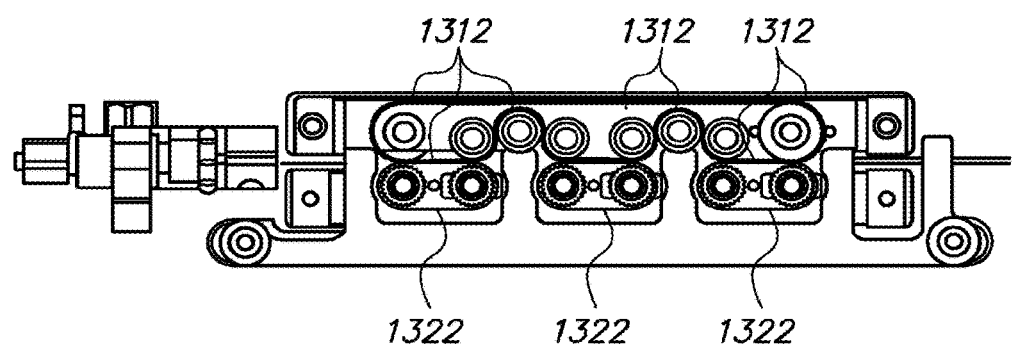
FIG. 91H illustrates a cross sectional side view of the elongate member FIG. 91A, showing the manipulator mounting bracket, the roll motor, and the insert motor all removed.

FIGS. 91D-H illustrate various views of the elongate member manipulator 1300. FIGS. 91D-E show perspective views of the elongate member manipulator 1300 in a closed configuration, FIG. 91F shows a perspective view of the elongate member manipulator 1300 in an open configuration, and FIGS. 91G-H show right and left side views of the elongate member manipulator 1300 in a closed configuration.

The elongate member manipulator 1300 may include an upper slide assembly 1334, a lower slide assembly 1330, a drive belt assembly 1310, an idler belt assembly 1320, an insert motor 1302, a roll motor 1304, and an elongate member support 1332. The insert motor 1302 may be fixably mounted to the upper slide assembly 1334 while the roll motor 1304 may be fixably mounted to a manipulator base 1306 or to the lower slide assembly 1330. The elongate member support 1332 may also be mounted to the manipulator base 1306 or lower slide assembly 1330 using one or more screws 1336 or other attachment mechanisms. The drive belt assembly 1310 may be removeably coupled to the upper slide assembly 1334 while the idler belt assembly 1320 may be removeably coupled to the lower slide assembly 1330 both using one or more screw assemblies 1372 or other attachment mechanisms.

Figure 92A:
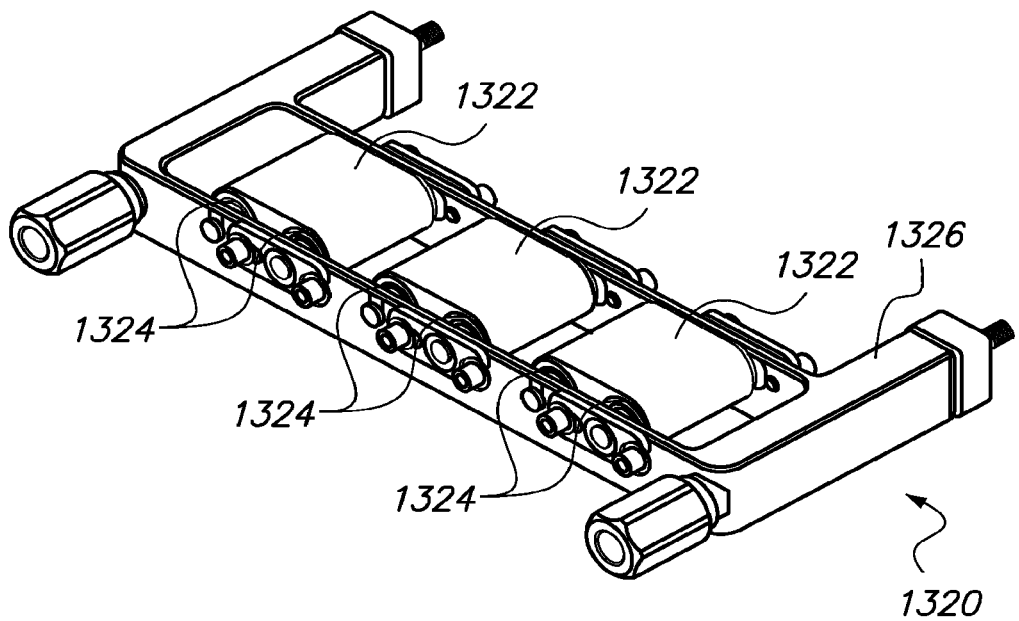
FIGS. 92A-92B illustrate perspective views of an idler belt assembly of the elongate member manipulator of FIG. 91A.
Figure 92B:
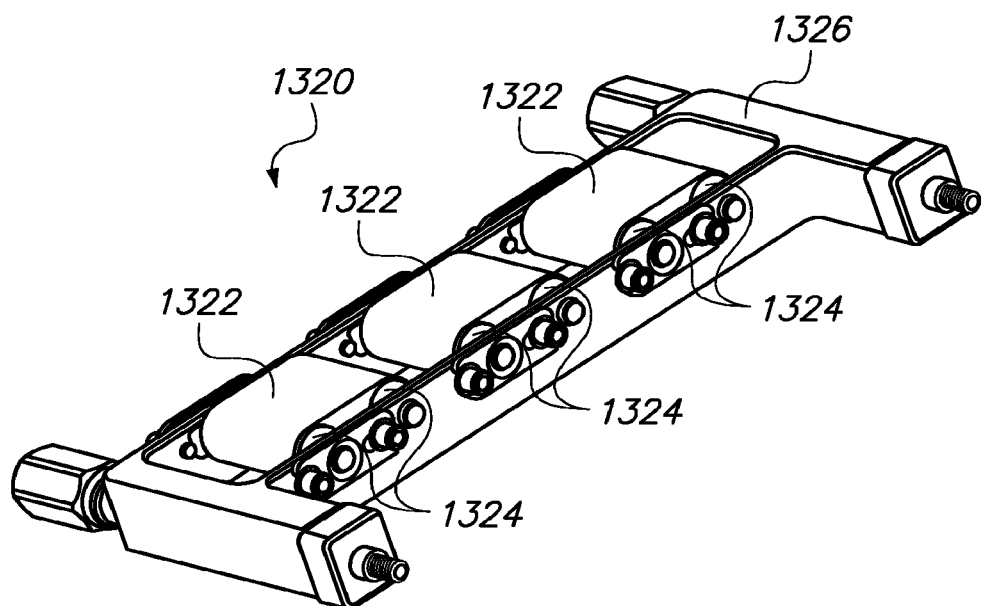
Figure 93A:
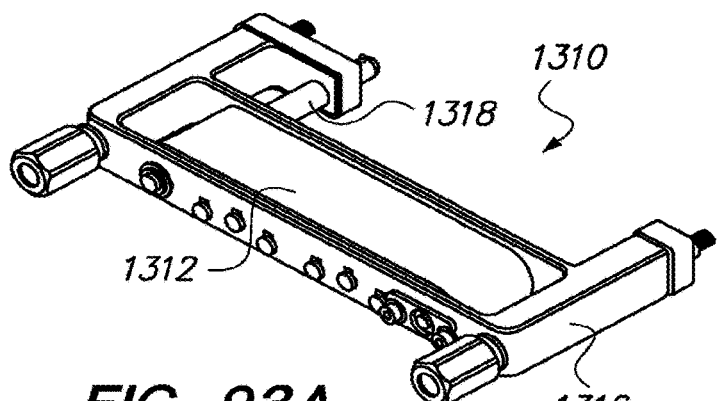
FIGS. 93A-93D illustrate various perspective views of a drive belt assembly of the elongate member manipulator of FIG. 91A.
Figure 93B:
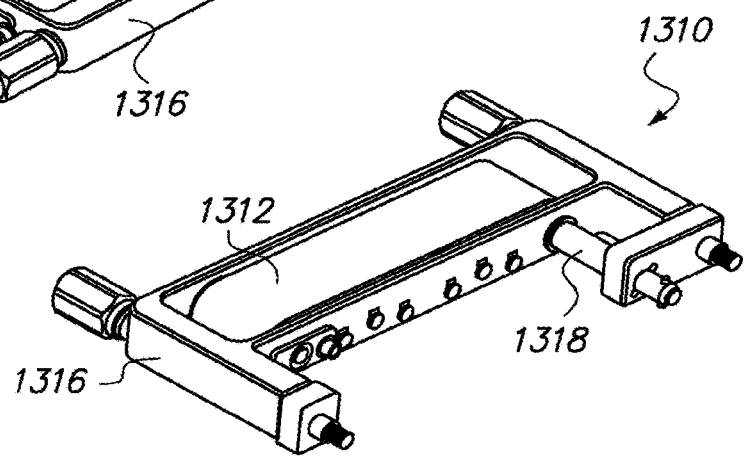
Figure 93C:
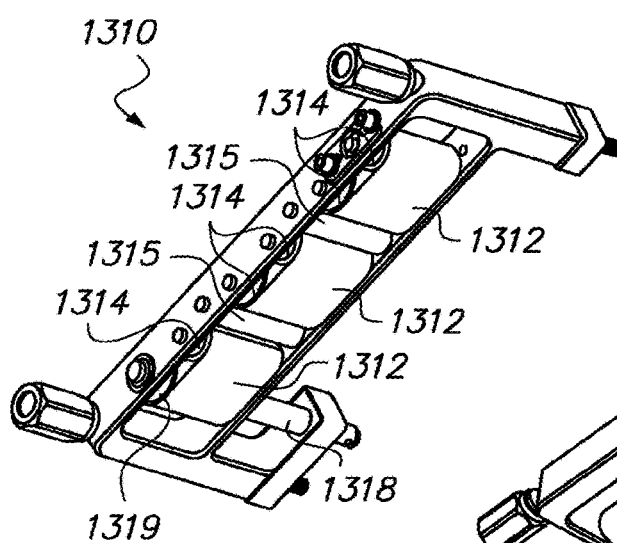
Figure 93D:
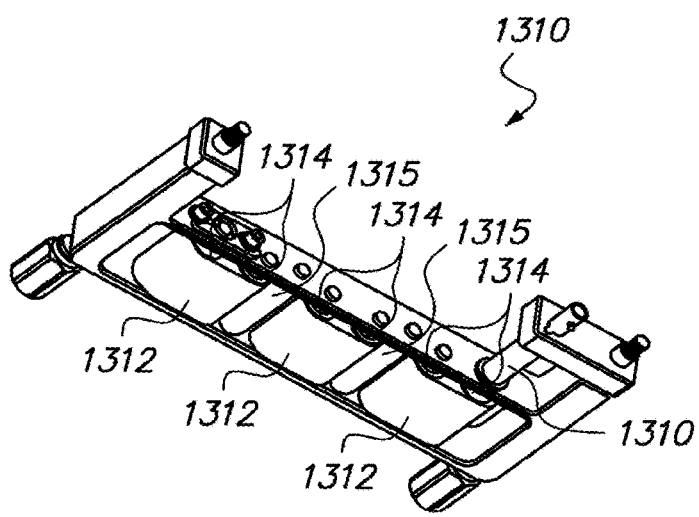

FIGS. 92A-B illustrate perspective views of a variation of an idler belt assembly 1320. In this variation, three small, separate idler belts 1322 are free to rotate about passive idler pulleys 1324 rotatably mounted to an idler frame 1326. The multiple small idler belts 1322 may be spaced apart allowing the elongate member support 1332 to be inserted, positioned or to extend between two or more of the belts 1322 as shown in FIG. 91F. In certain variations, two or more idler belts may be utilized in an idler belt assembly.

FIGS. 93A-93D illustrate perspective top and bottom views of a variation of a drive belt assembly 1310. In this variation, the serpentine belt 1312 is snaked in a "serpentine" like or weaving manner around one or more of the drive pulley 1319, the serpentine idler pulleys 1314 and the reverse idlers 1315, which are each rotateably mounted to the drive frame 1316. This provides a mating, multiple segmented belt that may make contact with the multiple small idler belts 1322 while still providing clearance for the elongate member support 1332. The drive pulley 1319 may be fixably coupled to a drive shaft 1318. Materials for various components for both the idler belt assembly 1320 and drive belt assembly 1310 could include but are not limited to Polyurethane 90A for the belts 1212, 1322, and anodized Al 6061-T6 for the frames 1316, 1326 and pulleys (1315, 1315, 1319, 1324). Other similar materials may be utilized.

Figure 94A:
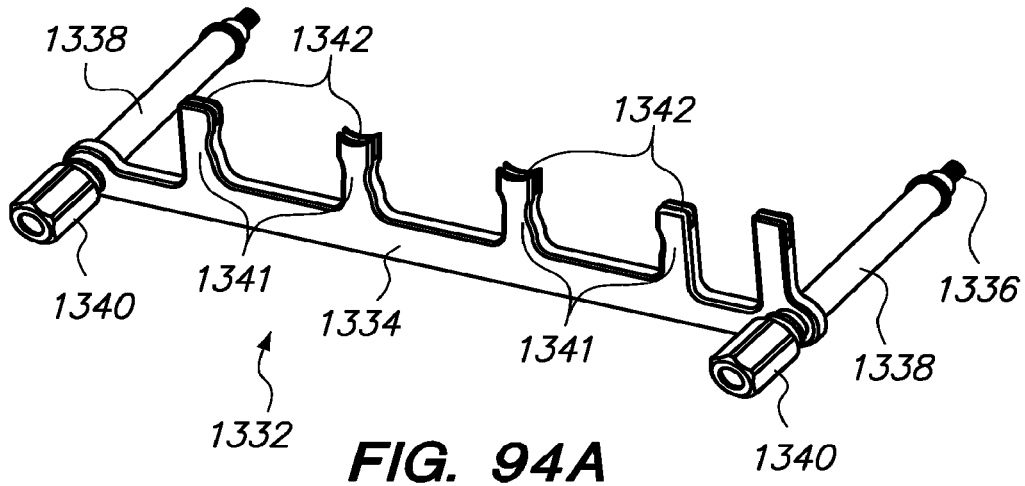
FIG. 94A illustrates a perspective view of an elongate member support of the elongate member manipulator of FIG. 91A.
Figure 94B:
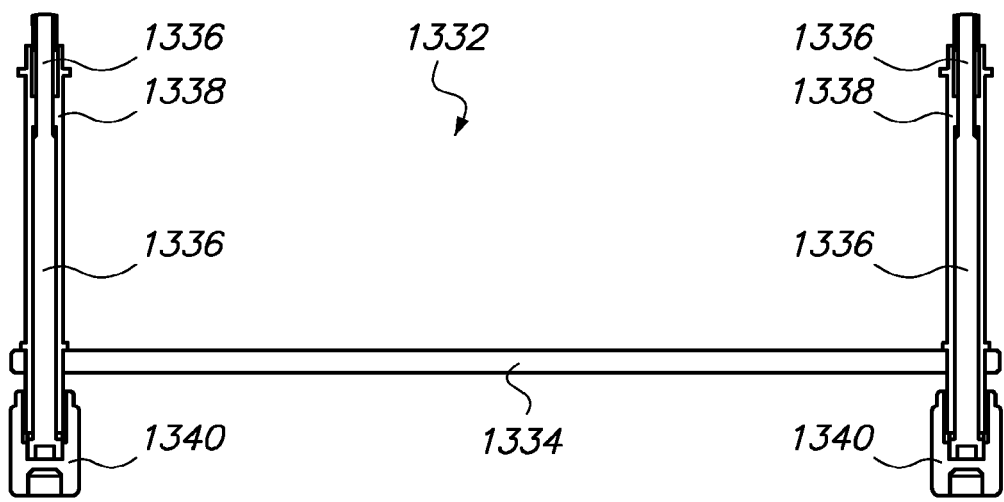
FIG. 94B illustrates a cross sectional top view of the elongate member support of FIG. 94A.

FIGS. 94A-94B show another variation of an elongate member support 1332 that may be used in the elongate member manipulator 1300. FIG. 94B illustrates a cross-sectional top view of the elongate member support 1332. Certain portions of the support 1332 or the entire support 1332 may be sterilizable. The support 1332 may include a support body 1334 and one or more screws 1336 embedded in support rods 1338 which are controlled by screw knobs 1340 may also be provided on the support 1332. The support body 1334 may have arms or protrusions 1341 and/or grooves 1342 for holding an elongate member. In one variation, the elongate member support 1332, the support rods 1338 and/or the screw knobs 1340 may be made of a softer material such as a PET (poly ethylene terephthalate) thermoplastic, while the screws 1336 may be made of stainless steel. In alternative variations, the above components may be made from a variety of materials and the materials could vary based on desired hardness of materials as well as costs.

During operation, the upper slide assembly 1334 may hinge or rotate open as shown back in FIG. 91F to allow for the guide wire 1060 to be installed onto the elongate member support 1332. The elongate member support 1332 provides a holder for the guide wire 1060 while centering the guide wire 1060 in a desirable position. The multiple belt configuration provided by the idler belts 1322 allows for positioning and clearance of the elongate member support 1332 in between the idler belts 1322. The positioning of the elongate member support 1332 may be such that the guide wire 1060 is supported while still being adequately held between the multiple small idler belts 1322. Also various elongate member supports could be provided each with different sized grooves to allow for use of varying sized guide wires. The elongate member supports may also be sterile and/or disposable or they may be non-sterile. For example, the elongate member support 1332 could be provided as a sterile disposable and be removed and replaced with an alternatively sized elongate member support if a different sized guide wire was necessary mid-procedure.

Figure 94C:
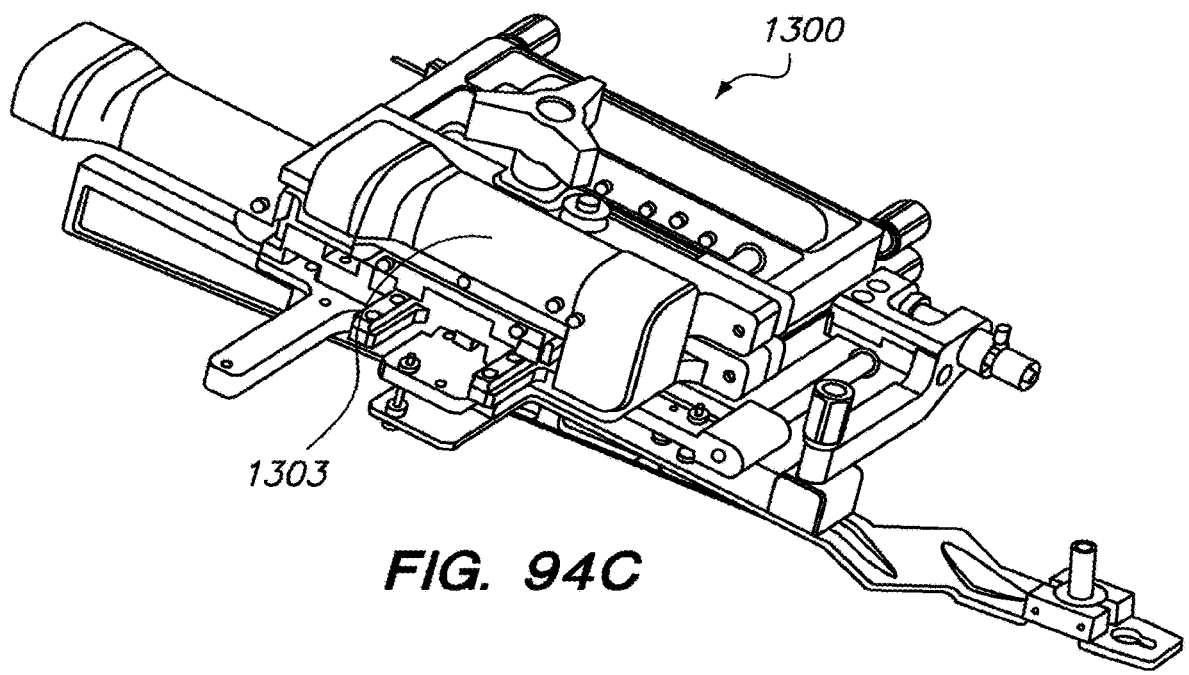
FIG. 94C illustrates an alternative perspective view of the elongate member manipulator of FIG. 91A, showing the manipulator mounted to a manipulator mounting bracket.
Figure 94D:
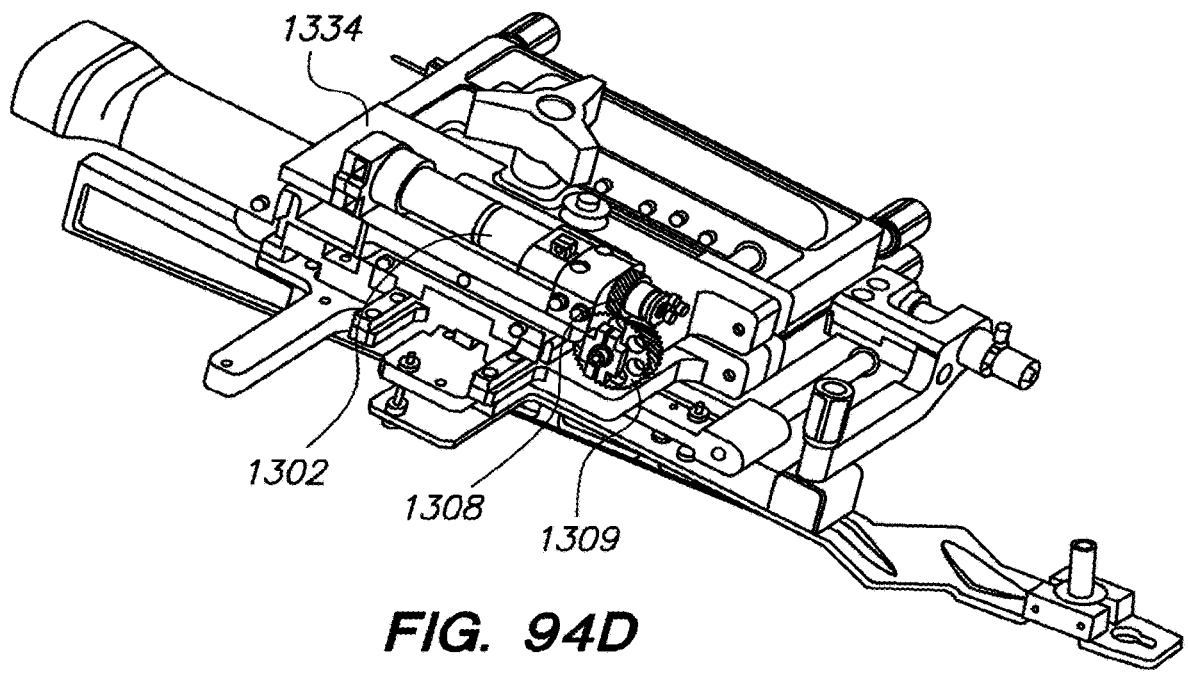
FIG. 94D illustrates the elongate member manipulator of FIG. 94C, showing an insert motor cover removed.
Figure 94E:
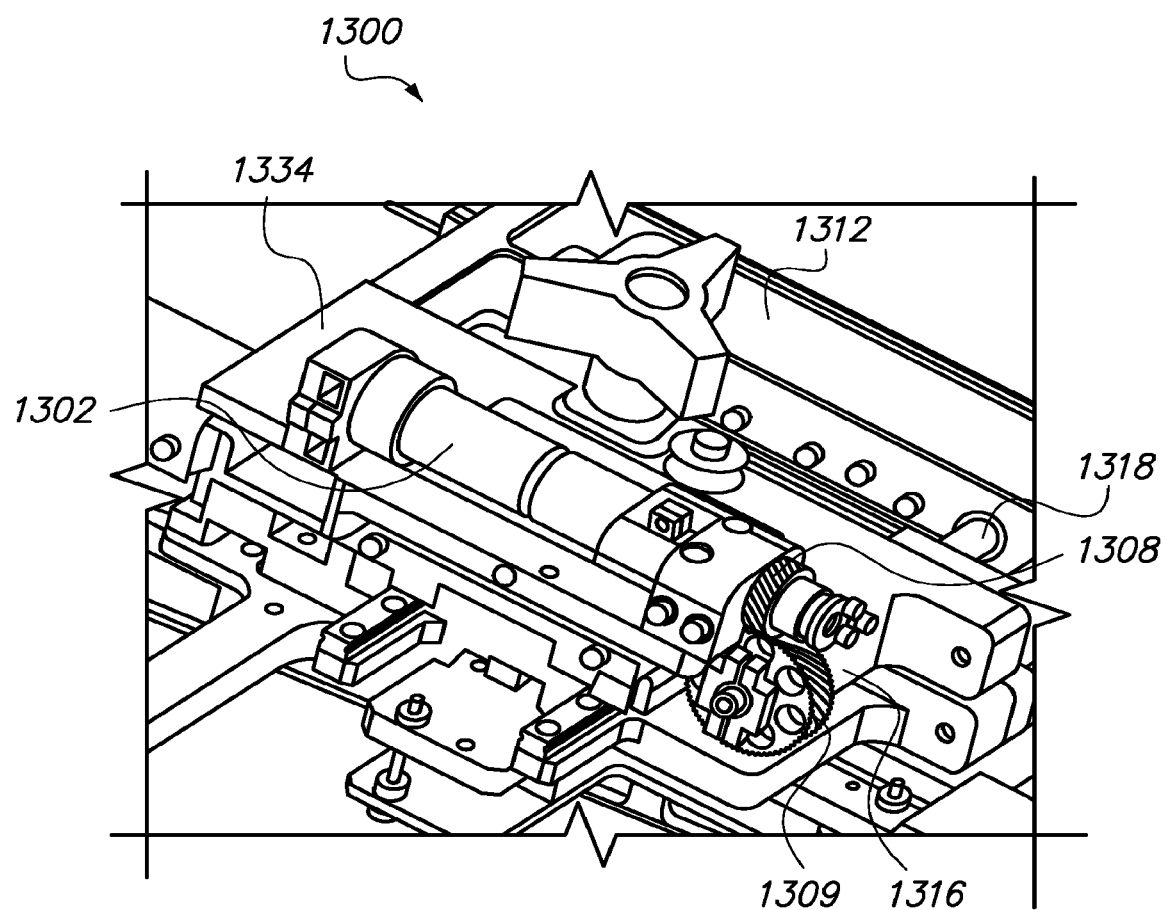
FIG. 94E illustrates a zoomed in view of the insert motor of the elongate member manipulator of FIG. 94D.

FIG. 94C illustrates an alternative perspective view of the elongate member manipulator 1300 with an insert motor cover 1303 mounted thereon, FIG. 94D illustrates the same perspective view with the insert motor cover removed, and FIG. 94E illustrates a zoomed in view of the elongate member manipulator 1300 with the motor cover 1303 removed displaying the insert motor 1302 mounted to the upper slide assembly 1334. The insert motor 1302 has a shaft (not shown) which is coupled to helical gear1 1308, which drives bevel gear2 1309, which is directly coupled to the drive shaft 1318. The drive shaft 1318 is rotatably mounted to a drive frame 1316. The drive shaft 1318 may be driven by the insert motor 1302, thereby turning the drive pulley (not shown), to actuate the serpentine belt 1312 in a forwards or reverse direction.

In the closed configuration of the elongate member manipulator 1300, as shown in FIGS. 91D and 91E, the idler belt assembly 1320 and the drive belt assembly 1310 may hold the guide wire 1060 with enough frictional force to propel the guide wire 1060 in the insert or retract directions when the insert motor 1302 is actuating the serpentine belt 1312. The multiple small idler belts 1322 will passively roll in the opposite rotational direction as the serpentine drive belt 1312.

The upper slide assembly 1334 may be actuated by a roll motor 1304 which causes the upper slide assembly 1334 to translate relative to the lower slide assembly 1330 to roll the guide wire 1060 held between the belt assemblies. The roll motor can drive a pinion which is coupled to racks on both the upper and lower slide assemblies 1334, 1330 to actuate the translational movement the slide assemblies as previously described Alternatively, any equivalent type of mechanism such as a leadscrew configuration could be used to actuate translation of the upper and lower slide assemblies. The elongate member support 1332 not only positions or holds the guide wire 1060 or other elongate member in the elongate member manipulator 1300 as previously described, but it also prevents the guide wire 1060 from buckling during guide wire insertion, retraction or roll actuation.

Other variations of the idler belt assembly 1320 could include any number of idler belts and pulleys, spaced apart by various distances which may allow for installation or positioning of the elongate member support 1332 between the belts. Accordingly the elongate member support 1332 could be provided with any number of support protrusions, spaced at any distance, and the drive belt assembly 1310 could be provided with any number of pulleys spaced apart at varying distances to provide for a plurality of windings. The idler belt assembly 1320 and drive belt assemblies 1310 can be configured to have mating belt segments such that the distances between each small idler belt 1322 is minimized to maximize belt contact with the guide wire 1060. The number of protrusions provided by the elongate member support 1332 could vary based on the diameter of the elongate member. For example, a greater number of protrusions and/or grooves may be provided for an elongate member having a smaller sized diameter which may require more support to prevent buckling of the elongate member.

Figure 95A:
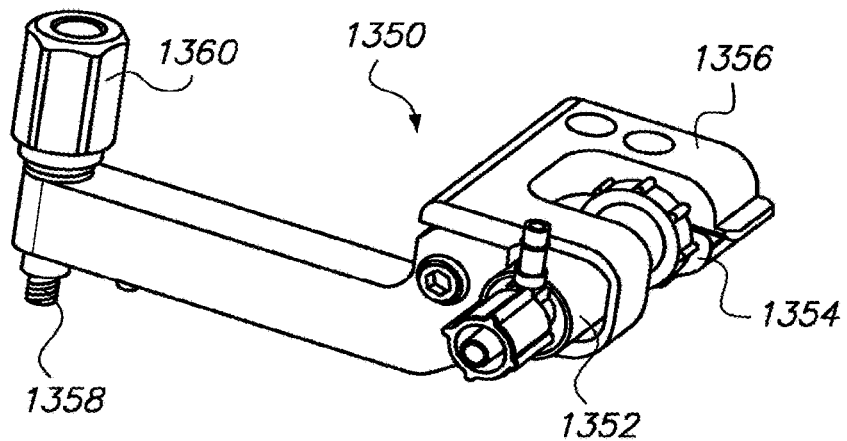
FIG. 95A illustrates a perspective view of a valve holder of the elongate member manipulator of FIG. 91A, showing the valve holder in a closed configuration.
Figure 95B:
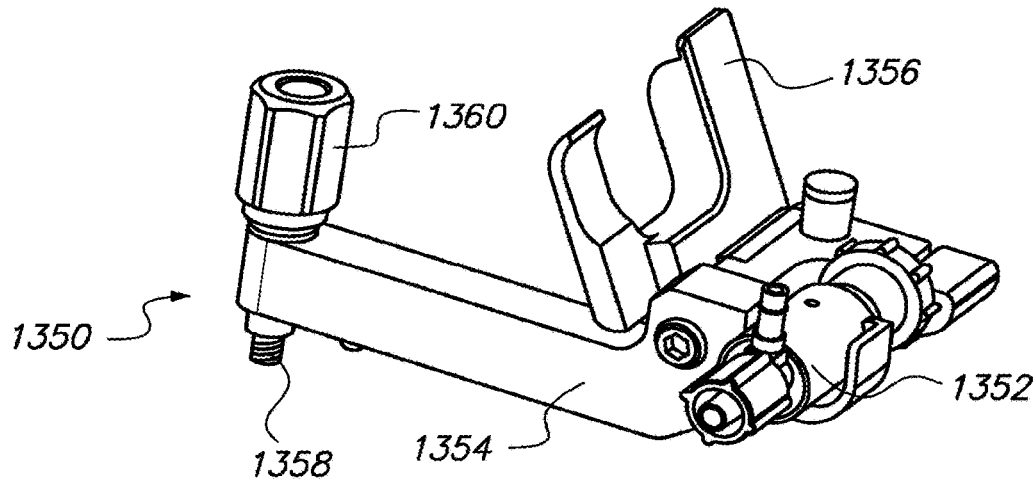
FIGS. 95B-95C illustrate various perspective views of the valve holder of FIG. 95A in an open configuration.
Figure 95C:
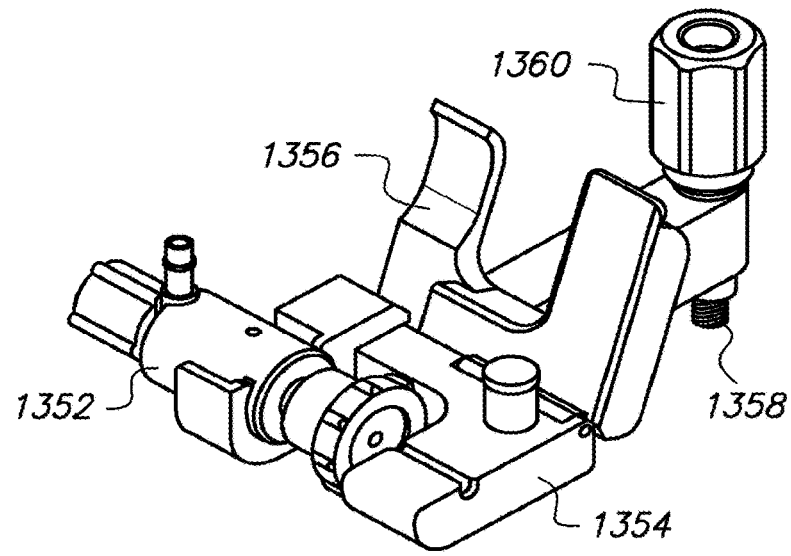
Figure 95D:
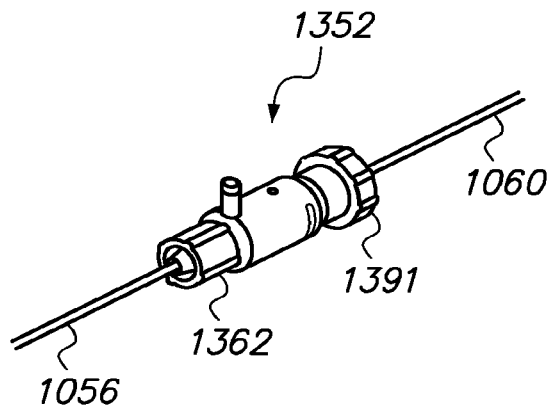
FIGS. 95D-95E illustrate front and back perspective views of a valve assembly of the elongate member manipulator of FIG. 91A, showing a support tube and guide wire installed.
Figure 95E:
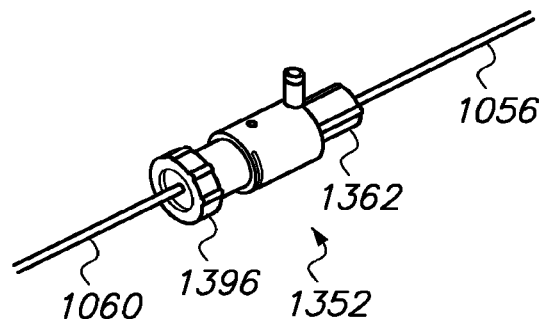
Figure 95F:
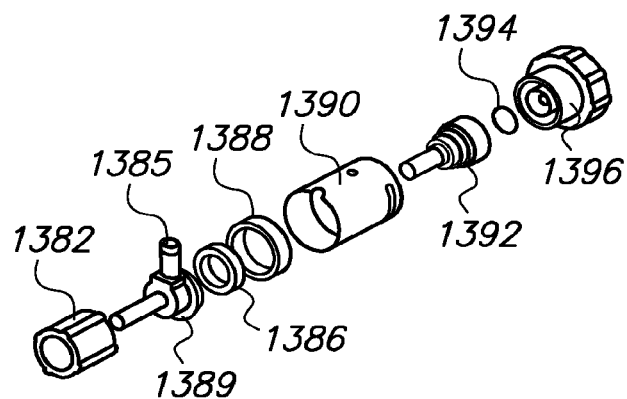
FIG. 95F illustrates an exploded perspective view of the valve assembly of FIG. 95D, showing the support tube and guide wire removed.

Referring to FIGS. 95A-95C, an elongate member manipulator (not shown) can also include a valve holder 1350 which provides a mount for a valve assembly 1352 that encapsulates the elongate member (not shown). The valve holder 1350 may include an elongate member holder 1354 and a cover 1356. The valve holder 1350 can be mounted to an elongate member manipulator mounting bracket (not shown) with a screw 1358 and a knob 1360. A set of magnets (not shown) may be embedded in the cover 1356 and/or in the elongate member holder 1354 to provide a locking mechanism which holds the valve holder 1350 in a closed configuration. In other variations, different types of locking mechanisms such as, but not limited to clamps, latches, screws, etc., may alternatively be used. In one variation, the cover 1356, the elongate member holder 1354, and the knob 1360 could be made of a softer material such as a PET (poly ethylene terephthalate) thermoplastic while the screw 1358 could be made of stainless steel and the magnets could be made of neodymium. In alternative variations the materials could vary based on desired hardness of materials as well as costs.

If an operator desires to manually control the guide wire 1060 and decouple it from a robotic elongate member manipulator, such as manipulator 1300, the drive belt assembly 1310 can be pivoted open as illustrated in FIG. 15F, the valve holder 1350 can be opened, and the guide wire can be removed from the system along with the valve assembly 1352 and support tube 1056. The guide wire 1060 can then be rolled and inserted by hand in a manual manner which is well known in the art. The guide wire 1060 and valve assembly 1352 at any time can be quickly re-installed in the elongate member manipulator 1300 and robotic operation can continue seamlessly.

Figure 96:
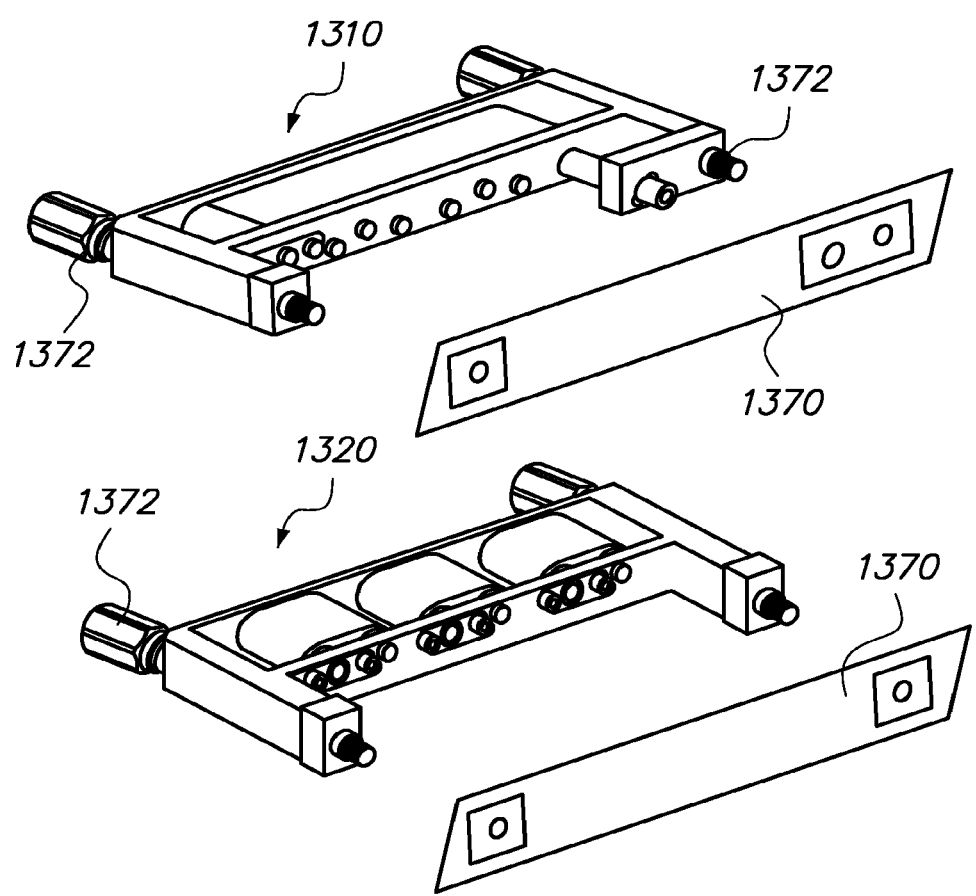
FIG. 96 illustrates the drive belt assembly and idler belt assembly of FIG. 91A, showing a portion of the drape.

As shown in FIG. 96, both the drive belt assembly 1310 and idler belt assembly 1320 can be removeably replaceable to allow for installation of a sterile drape 1370 separating the sterile field portion of the elongate member manipulator from the non-sterile field portion of the elongate member manipulator (not shown). FIG. 96 illustrates the drive belt assembly 1310 and idler belt assembly 1320 being mounted using screw assemblies 1372. While similar captive screw mechanisms as previously described in reference to FIGS. 90A-C can be used, FIG. 96 illustrates an alternative variation. It should be understood that either variation shown in FIGS. 90A-C and the variation shown in FIG. 96 can be used for any elongate member manipulators described herein along with any other comparable type of mechanism which is well known in the art.

Figure 96A:
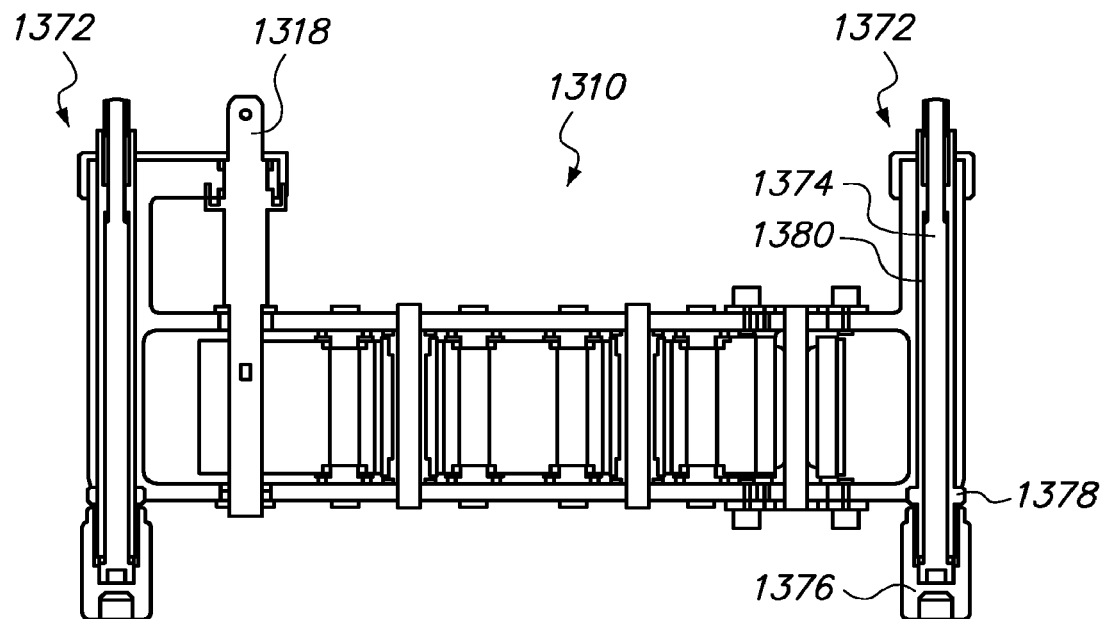
FIG. 96A illustrates a cross sectional bottom view of the drive belt assembly of FIG. 94A.
Figure 96B:
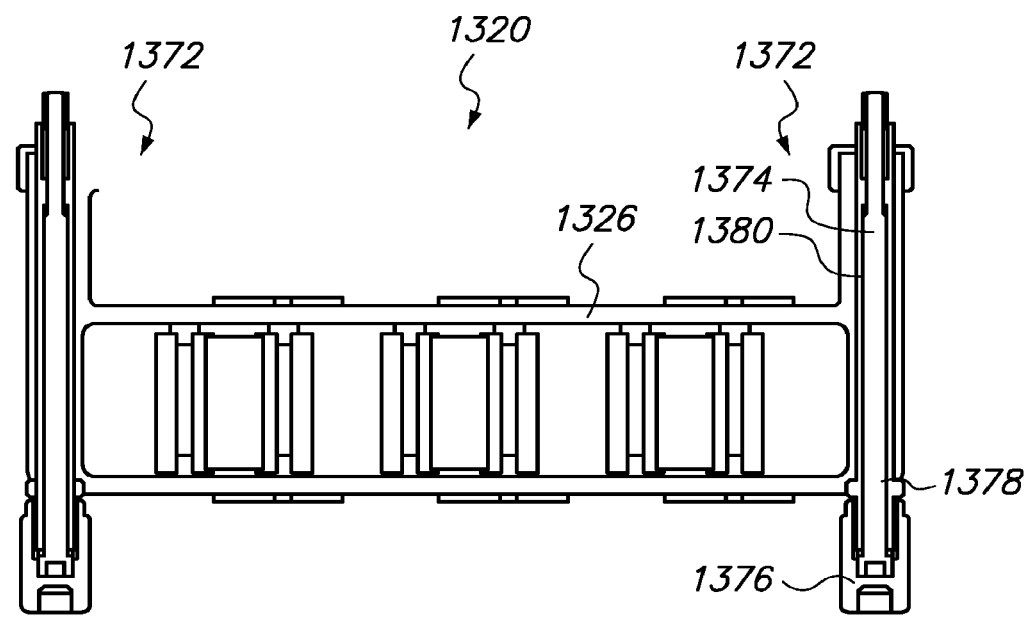
FIG. 96B illustrates a cross sectional bottom view of the idler belt assembly of FIG. 92A.

FIGS. 96A and 96B illustrate cross sectional top views of the drive belt assembly 1310 and idler belt assembly 1320. In one variation, the screw assemblies 1372 can be identical for the idler and drive belt assemblies or can vary in materials and dimensions if necessary to support different weights of each idler and drive belt assembly.

In an alternative variation, the drive belt assembly 1310 and idler belt assembly 1320 may need to be electrically isolated. Accordingly, the screw assembly 1372 can include a screw 1374, a knob 1376, an isolation cap 1378, and an isolation sleeve 1380. The screw 1374 can be made of stainless steel while the knob 1376 and isolation sleeve can be made of a thermoplastic, such as PET, and the isolation cap can be made of a thermoplastic, such as Ultem, providing for electric isolation. Alternatively, any other non-conductive material or thermoplastic can be used to manufacture the knob 1376, isolation sleeve 1380, and isolation cap 1378 or the drive frame 1316 and idler frame 1326 can be manufactured from a plastic or any other non-conductive material allowing for the screw assembly to be simplified and manufactured from stainless steel or any other type of metal.

The variation of elongate member manipulator 1300 shown in FIGS. 91A-91F provides the idler belt assembly 1320 and elongate member support 1332 on the lower half of the manipulator 1300 while the drive belt assembly 1310 is provided on the upper half of the manipulator 1300 such that the drive belt assembly 1310 may pivot open to allow loading of a guide wire 1060. In this variation, the insert motor 1302 may be mounted to the upper slide assembly 1334. In an alternative variation, the drive belt assembly 1310 may be provided on the lower stationary half of the manipulator 1300 so the idler belt assembly 1320 with elongate member support 1332 could pivot for guide wire 1060 loading. In the latter variation, optionally, the insert motor 1302 may remain mounted to the stationary half of the manipulator 1300 which could be desirable.

FIGS. 96C-96E illustrates a representation of an alternative elongate member manipulator 1700 which provides insert actuation using linear slide motion as opposed to feed rollers or feed belts as described in previous variations (see e.g., FIGS. 84, 91D, 99, and 104). FIG. 96C illustrates a perspective view of the guide wire manipulator 1700 which can include a pad assembly 1702 mounted on a linear slide 1704 which The guide wire 1060 can be held between two pads of the pad assembly 1702. To insert or retract the guide wire 1060, the pad assembly 1702 can driven by a motorized leadscrew or motorized belt and pulley configuration (not shown) in the same manner which the guide splayer or sheath splayer is inserted as described in detail in the aforementioned incorporated references. FIGS. 96D and E illustrate side views of the elongate member manipulator 1700 during roll actuation where the two pads of the pad assembly 1702 could be translated relative to one another to actuate roll of the guide wire 1060. Sizing of the pads can vary as can pad material to provide the optimum frictional hold on the guide wire 1060 during roll and also during insert. Wire holders (not shown) can also be used to prevent slippage during roll. Insert and roll actuations can be completely independent motions actuated simultaneously or individually.

FIG. 97 illustrates another variation of an elongate member manipulator 1800 mounted to a variation of an instrument driver 1016. The instrument driver includes a guide output plate 1053, a sheath output plate 1043. FIGS. 97aa-ab illustrate different perspective views of the elongate member manipulator 1800 shown without a cover 1801 for clarity. The elongate member manipulator 1800 can be fixably mounted to a manipulator mounting bracket 1858 which in turn can be fixably mounted to the guide output plate 1053.

FIGS. 97A1 and 97A3 illustrate different perspective views of the elongate member manipulator 1800 in a closed configuration while FIGS. 97A2 and 97A4 illustrate the elongate member manipulator in an open configuration. The elongate member manipulator 1800 includes the cover 1801, a drive belt assembly 1810, an idler belt assembly 1820, and an elongate member support 1860. The cover 1801 is configured in three sections such that a middle section may hinge open to allow the elongate member manipulator to open for loading and unloading of a guide wire 1060 and valve assembly 1352 into and out of the elongate member support 1860. The elongate member manipulator 1800 can be locked in a closed configuration by securing a locking knob 1813 into a locking knob threaded hole 1815.

FIGS. 97B1-B2 illustrate different perspective views of the elongate member manipulator 1800 with the cover 1801 removed. Several components including but not limited to the drive belt assembly 1810, the idler belt assembly 1820, an upper slide assembly 1834, a lower slide assembly 1830, an insert motor 1802, a roll motor 1804, and the elongate member support 1860 are structurally and functionally similar to corresponding components of the elongate member manipulators 1200, 1300 of FIGS. 9B and 15D-F previously described. Referring to FIG. 97B2 both the roll and insert mechanism can be seen. FIG. 97B3 illustrates a zoomed in view of the roll motor and accompanying mechanisms with the manipulator mounting bracket (1858 shown in FIG. 97B2) hidden for clarity. The roll motor 1804 directly drives a roll drive shaft 1806 which is coupled to a roll belt 1808 which in turn drives a pinion 1838. As previously described in detail, the pinion 1838 drives a rack which controls linear movement of the upper slide assembly 1834 relative to the lower slide assembly 1830 along linear bearings 1836. The belt drive assembly provides increased torque when actuating the upper slide assembly 1834. The drive belt assembly 1810 can be fixably coupled to the upper drive assembly 1834 while the idler belt assembly 1820 can be fixably coupled to the lower drive assembly 1830. Thus linear movement between the drive and idler belt assemblies 1810, 1820 provide for roll of a guide wire held between the belt assemblies 1834, 1820. Foot supports 1812 may be provided to provide cantilever support of the belt assemblies 1810, 1820 as they are mounted to the upper and lower slide assemblies respectively 1834, 1830. The upper slide assembly 1834 may then be locked to the lower slide assembly 1830 in a closed configuration using the locking knob 1813 which threads into the lower slide assembly 1830.

FIG. 97C illustrates the insert motor 1802 mounted to the upper slide assembly 1834 with the drive belt assembly 1810 installed. Other components of the guide wire manipulator 1800 are hidden for clarity. The insert motor 1802 drives a set of helical gears 1803 that actuate an insert shaft 1814. When the drive belt assembly 1810 is coupled to the upper slide assembly 1834, a drive shaft (not shown) is engaged with the insert shaft 1814. As the insert shaft 1814 is actuated by the insert motor 1802, the drive shaft actuates a drive belt 1818 in a manner previously described in detail for the elongate member manipulator 1300 shown in FIGS. 15A-D. The drive shaft 1816 can be seen in FIGS. 97D1-D3. FIG. 97D1 illustrates a perspective view of the drive belt assembly 1810, FIG. 97D2 illustrates a cross sectional bottom view of the drive belt assembly 1810, and FIG. 97D3 illustrates a zoomed in view of the end of the drive shaft 1816 which is coupled to the upper slide assembly 1834. A drape which will be described in detail below can be installed between the drive and idler belt assemblies 1810, 1820 and the upper and lower slide assemblies 1834, 1830 respectively. The drape will provide a sterile barrier between the mechanisms of the elongate member manipulator 1800 and the belt assemblies 1810, 1820. In some situations fluids, for example blood, saline, or water may flow onto the drape. In order to prevent fluid ingress into the mechanisms of the elongate member manipulator through particularly the insert shaft 1814 shown in FIG. 97C,21C, a labyrinth seal 1817 may be provided. The labyrinth shape of the drive shaft 1816 as shown in FIG. 97D3 in conjunction with the labyrinth seal creates a winding path which fluid would need to pass through before leaking into the insert shaft 1814. Additionally, the drive shaft 1816 rests within a hole 1819 in the foot support 1812 which may be configured with a ring groove 1819 which can direct fluid away or downwards prior to entering the labyrinth seal 1817.

In one variation, to accurately grip the guide wire between the belt assemblies 1810, 1820, the belt assemblies are configured such that they are predominantly parallel with respect to one another. An adjustment mechanism that provides for alignment of the drive belt assembly to the idler belt assembly is described with reference to FIGS. 97E1-G. FIGS. 97E1-E2 illustrates the elongate member manipulator 1800 with several components hidden for clarity showing the upper and lower slide assemblies 1834, 1830 fixably coupled to the drive and idler belt assemblies (1810,1810, 1820) respectively. The drive belt assembly 1810 can be fixably coupled to the upper drive assembly 1834 while the idler belt assembly 1820 can be fixably coupled to the lower drive assembly 1830 using screw assemblies 1822 which are configured to thread into belt assembly mounting holes 1824. Thus adjustment of the upper slide assembly 1834 relative to the lower slide assembly 1830 will result in corresponding adjustment of the drive belt assembly 1810 with respect to the idler belt assembly 1820. While the lower slide assembly 1830 can be mounted stationary to the manipulator mounting bracket 1858 without adjustments, the upper slide assembly may be configured with adjustment mechanisms which will now be described.

Figure 97F:
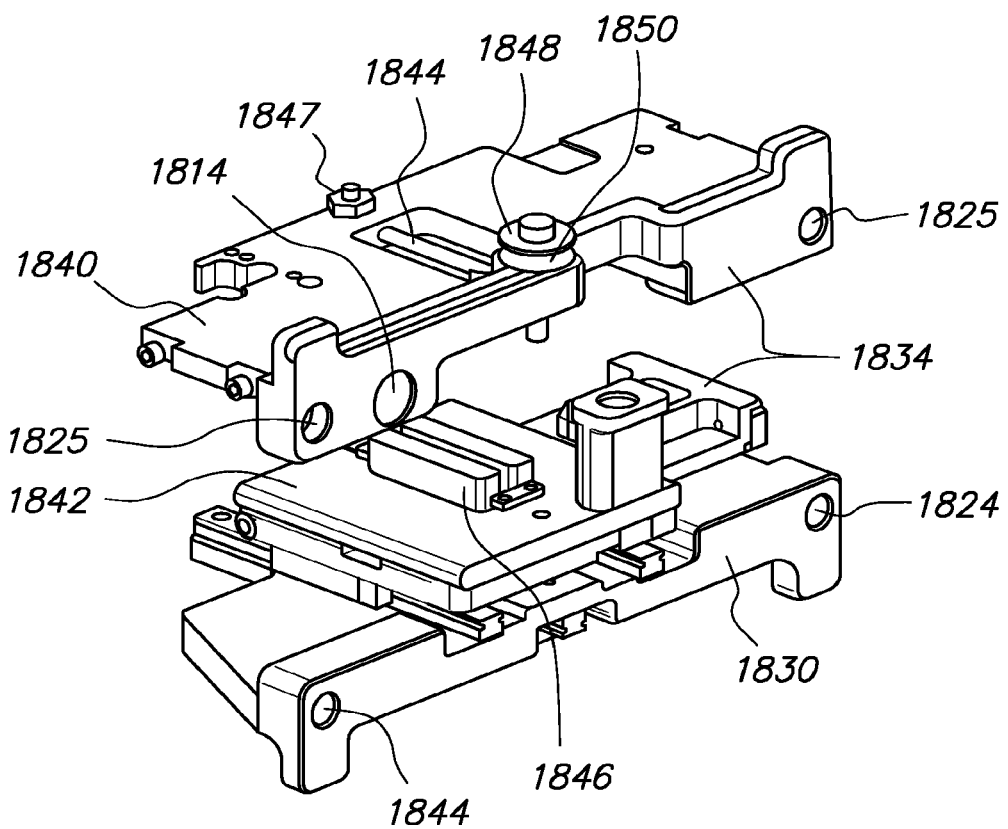
FIG. 97F illustrates an exploded view of the upper slide assembly of FIGS. 97E1-97E2.
Figure 97G:
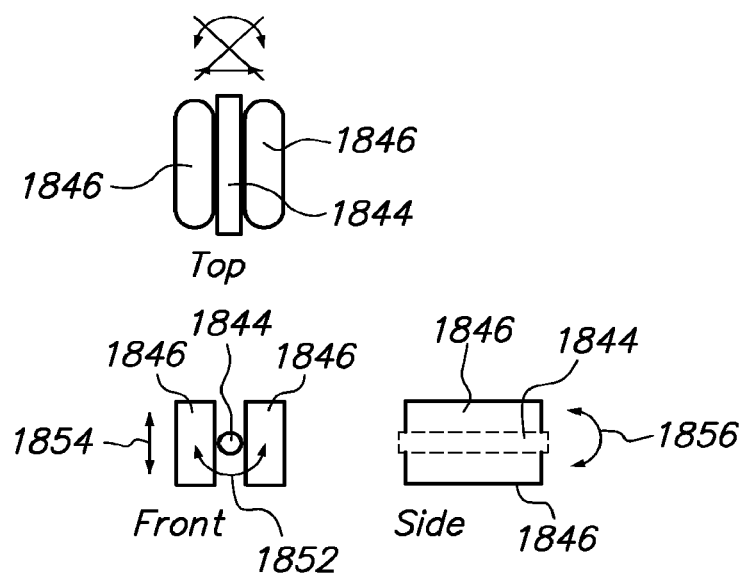
FIG. 97G illustrates a top, front and side view of a simplified representation of an alignment bar and cradle of the upper slide assembly shown in FIG. 97F.

FIG. 97F illustrates a partially exploded view of the elongate member manipulator (800)1800 of FIG. 97E with the drive and idler belt assemblies hidden for clarity. The upper slide assembly 1834 can include a top plate 1840 and a bottom plate 1842. The top plate 1840 which includes an alignment bar 1844 centered in a top plate opening 1841, an adjustment set screw 1847, an adjustment nut screw 1848 and an adjustment spring 1850 is illustrated exploded from the bottom plate 1842 which includes a cradle 1846. When assembled, the cradle is configured to hold the alignment bar 1844 in a manner that allows the alignment bar 1844 to float in three separate axes of motion. FIG. 97G illustrates a simplified representation of the alignment bar 1844 held within the cradle 1846 showing top, front and side views. The alignment bar 1844 can rotate about its own axis as shown with roll arrow 1852, translate up and down as shown with vertical arrow 1854, and also rotate in a rocking motion as shown with pitch arrow 1856. The alignment bar 1844 is constrained in this configuration from rotating in a yaw motion or translating in a side to side direction. It is also constrained by the fit of the cradle 1846 to the top slide plate opening 1841.

In this configuration, because the drive belt assembly 1810 is fixably mounted to the top plate 1840, as the top plate 1840 floats in a roll, vertical, or pitch direction, the drive belt assembly 1810 and top plate 1840 float as a single component. The adjustment set screw 1847 can be tightened or loosened to set the overall height of the top plate 1840 and drive belt assembly 1810 relative to the idler belt assembly 1820. The adjustment not screw 1848 is tightened down increasing the downward force provided by the adjustment spring 1850 which presses the belt assemblies together. The adjustment set screw 1847 acts as a reaction or pivot point allowing the top plate 1840 to gimble about the roll and pitch axes of the alignment bar 1844. As the drive belt assembly 1810 comes in contact with the idler belt assembly 1820, the latter of which is stationary, the alignment bar 1844 provides the capability of self parallel alignment between the two belt assemblies. The alignment nut is tightened completely to secure the top plate 1840 to the bottom plate 1842 such that the position of the drive belt assembly 1810 is securely set.

FIGS. 97H1-H2 illustrate the elongate member manipulator 1800 with the drive belt assembly and idler belt assembly removed showing the elongate member support 1860 mounted to the manipulator mounting bracket 1858 using a pair of mounting set screws 1866 which thread into member support mounting holes 1859. FIG. 97J1 illustrates the elongate member support 1860 with the valve assembly 1352 and guide wire 1060 installed. The elongate member support 1860 includes a support body 1862 and a valve holder 1864 which can be securably fixed to the support body 1862 using screws 1863. FIG. 97J2 illustrates the elongate member support 1860 in an open configuration allowing the valve assembly 1352 and guide wire 1060 to be removed. The valve assembly 1352 and guide wire 1060 can be coupled as an assembly and can be removed and replaced into the elongate member manipulator 1800 with opening of the valve holder 1864 and the opening of the drive belt assembly 1810 which hinges open as previously described. FIG. 97J3 illustrates the valve holder 1864 in a closed configuration including a set of magnets 1870 are in the top and bottom portions of the valve holder 1864 which lock the valve holder 1864 in a closed position. A stop 1869 can be provided to prevent the valve holder 1864 from opening beyond a set rotation to prevent collision with any other components of the elongate member manipulator 1800 or any other tools or instruments used during a surgical procedure. Magnets 1872 embedded in the stop and top portion of the valve holder 1864 lock the valve holder 1864 in an open position as shown in FIG. 97J4.

FIG. 97K1 illustrates a variation of a drape assembly 1900 that may be used to cover the elongate member manipulator and instrument driver. As previously described, the drape assembly can be used to create a sterile barrier between the instrument driver and non-sterile portions of the elongate member manipulator with the drive belt assembly, idler belt assembly, and guide wire. The drape assembly allows transfer of mechanical motion from the instrument driver to each splayer as well as from the motors of the elongate member manipulator to the drive and idler belt assemblies. FIG. 97K2 illustrates a zoomed in view of the drape assembly 1900 which can include a drape body 1901, sheath foam pad 1902, a leader foam pad 1904, a tenting frame 1920, drape member support holes 1936, and a locking knob hole 1938. The drape member support holes 1936 and locking knob hole 1938 can be reinforced with frames that will provide additional strength to prevent tearing of the drape when screws are installed through the holes. The sheath and leader foam pads 1902, 1902 were described previously in detail.

Referring to FIGS. 97L1-L2, the tenting frame 1920 is illustrated from top and bottom perspective views respectively showing flexure bases 1922, flexures 1924, adhesive portions 1926, and reinforcement members 1928. Each flexure base 1922 of the tenting frame 1920 can be fixable attached to the drape body 1901 with adhesive. The flexures 1924 of the tenting frame 1920 can adhere to the drape body 1901 along adhesive portions 1926 of each flexure 1924 positioned along the centerline of the tenting frame 1920. The remaining length of each flexure 1924 can be free to move relative to the drape body 1901. The reinforcement members 1928 can include drape idler belt mounting holes 1934, drape drive belt mounting holes 1930 and a drape drive shaft hole 1932. The reinforcement members 1928 are provided to reinforce the mounting holes 1930, 1934. The reinforcement members 1928 can be made from a material which is tough enough to provide some strength where high forces will be imposed while also providing flexibility. Also it can be desirable for the reinforcement members 1928 to remain as thin as possible. If the reinforcement member 1928 are thick and compressible, as mounting screws are tightened down the material is compressed. As the material settles in the screws may require re-tightening which can be undesirable for mid-procedure work flow. The reinforcement members 1928 can be made from polycarbonate or any other type of plastic which fulfills the stiffness, thickness, and material strength requirements. Materials for other components can include but not be limited to polyethelene for the drape body 1901 and high-density polyethylene (HDPE) for the tenting frame flexure base 1922, flexures 1924, and reinforcement frames for the drape drive shaft holes 1932, drape idler mounting holes 1934, drape member support holes 1936, and drape locking knob hole 1938.

FIG. 97M1 illustrates a simplified model of the elongate member manipulator 1800. For clarity, only the model of the elongate member manipulator 1800 and drape assembly 1900 are being shown. It should be understood that the elongate member manipulator 1800 may be installed on the previously described instrument driver (1016 of FIG. 15A) and the drape assembly 1900 can be configured to surround both the instrument driver and elongate member manipulator 1800. In order to install the drape assembly 1900 to the elongate member manipulator 1800, the sterile components including the drive and idler belt assemblies, the elongate member support (1810, 1820, and 1860 respectively), and the locking knob 1813 are removed from the elongate member manipulator 1800 as shown in FIG. 97M1.

Referring back to FIGS. 97A2, 97H2, 97K2, 97L1, 97E2 and to FIGS. 97M2-M5, one variation of a method of installing a drape onto an elongate member manipulator 1800 can be seen. In this variation, the drape member support holes 1936 are aligned with the member support mounting holes 1859 and the elongate member support 1860 can be installed by securing the mounting set screws 1866 into the member support mounting holes 1859 as shown in FIG. 97M2. The drape idler belt mounting holes 1934 are aligned with the idler belt mounting holes 1824 and the idler belt assembly 1820 is installed to the lower slide assembly 1830 by securing the idler screw assemblies 1822 into the idler belt mounting holes 1824 as shown in FIG. 97M3. The tenting frame 1920 is folded over such that the drape drive belt mounting holes 1930 can be similarly aligned with the drive belt assembly mounting holes 1825 and the drive belt assembly 1810 can be installed by securing the drive screw assemblies 1823 into the drive belt assembly mounting holes 1825 in the upper slide assembly 1834 as shown in FIG. 97M4. The locking knob 1813 is then fit through the drape locking knob hole 1938 and secured into the locking knob thread hole 1815. The drape is held securely in place between the sterile components including the elongate member support 1860, the idler and drive belt assemblies 1820, 1810, and locking knob 1813 providing a sterile barrier between the sterile components and the non-sterile components of the elongate member manipulator 1800 and instrument driver.

During use, the locking knob 1813 can be loosened while being held captive such that the elongate member manipulator 1800 can be opened in order to load a guide wire 1060 as shown in FIG. 97A1-A2.21A1-A2. The tenting frame 1920 is unfolded and stretched allowing the elongate member manipulator to open while continuing to cover the non-sterile components of the elongate member manipulator 1800. The guide wire 1060 and valve assembly 1352 can then be loaded and the elongate member manipulator 1800 can be closed for use including the rolling of the guide wire 1060 by translation of the upper and lower slide assemblies 1834, 1830 as previously described. The tenting frame 1920 can serve multiple functions. It pushes the drape body 1901 in an outward direction so that the drape body 1901 is not pinched between the upper and lower slide assemblies 1834, 1830 as they are opened and closed. Also because the upper and lower slide assemblies 1834, 1830 translate relative to each other during use, excess drape material must be provided so that the drape body 1901 doesn't tear with this movement. Because the tenting frame 1920 is secured to the drape body 1901 only along its centerline along the adhesive portions 1926, the tenting frame 1920 shapes the drape body 1901 to manage the excess drape material.

FIGS. 98A-98B illustrate a different variation of an elongate member manipulator 1400 mounted on the instrument driver 1016 using a manipulator mounting bracket 1058 such that a guide wire (not shown) can be fed into the valve assembly 1352, then into the support tube 1056 which subsequently feeds into a guide splayer 1052 or sheath splayer. In alternative variations, the elongate member manipulator 1400 could be mounted on the instrument driver 1016 with a guide and/or a sheath splayer assembly (e.g., the assembly 50/40 in FIG. 2), the elongate member manipulator could be mounted with just a sheath assembly 1040 or the elongate member manipulator 1400 could be mounted alone.

FIG. 99 illustrates the elongate member manipulator 1400 mounted to the manipulator mounting bracket 1058 with a guide wire 1060 loaded therein. FIGS. 100A-100B illustrates the elongate member manipulator 1400 without a motor pack cover 1401 showing an insert motor 1402, a roll motor 1404 and a belt assembly 1410. FIGS. 101A-101C illustrate a front and rear perspective view as well as a end view of the belt assembly 1410 which includes a drive belt 1412, an idler belt 1422, a drive pulley 1414, idler pulleys 1424, bevel gears 1416, a driving gear 1418, an idler gear 1426, a driven gear 1420, and a clamp assembly 1440. The belt assembly 1410 can be removably replaceable such that a sterile drape can be inserted between the belt assembly 1410 and the remaining drive components, such that the belt assembly 1410 may be positioned in a sterile field with the guide wire 1060.

To aid in loading the guide wire 1060 into the belt assembly 1410, the clamp assembly 1440 may be provided to open and close the belt assembly 1410 as shown in FIGS. 102A and 102B. FIGS. 102A-102B each illustrate a side view of the drive assembly 1410 where FIG. 102A shows the belt drive assembly in a closed configuration while FIG. 102B shows the belt drive assembly in an open configuration. As seen best in FIGS. 101B-101C, the clamp assembly 1326 includes a clamp 1442 that levers about a pivot 1444 to open and close the idler belt 1412 portion of the belt drive assembly in a clamping motion. A pair of clamp springs 1446 can be used to provide the clamping force for closing the clamp assembly in a nominally closed position. The clamp springs 1446 can be sized to provide for enough clamp force to hold the drive and idler belts 1412, 1422 together and effectively pinch the guide wire 1060 so it can be secured between the drive and idler belts 1412, 1422 while preventing damage to the guide wire 1060. To load the guide wire 1060, the clamp 1442 can be manually opened by compressing the springs 1446 while the guide wire may be back loaded through the belt drive assembly.

In order to actuate the belt assembly 1410, FIG. 100B and to FIG. 101B show the insert motor 1402 driving an insert belt 1406, turning an insert shaft 1428, turning the driving gear 1418, the idler gear 1426 and ultimately the driven gear 1420 which is coupled to a shaft driving the bevel gears 1416. The idler belt 1422 is free to rotate around the passive idler pulleys 1424. As seen in FIG. 101A, the bevel gears drive the drive pulley 1414 which turns the drive belt 1412 over idler pulleys 1424. The drive belt 1412 and the idler belt 1422 are pressed together causing the idler belt 1422 to rotate in the opposite direction as the drive belt 1412 and thus driving the guide wire 1060 pinched between both belts in the insert or retract direction depending on the direction of the drive belt actuation. Referring back to FIG. 100B, roll actuation of the guide wire 1060 is illustrated. In order to roll the guide wire 1060 the entire belt assembly 1410 is rolled on a roll shaft 1430. The roll shaft 1430 is coupled to a roll belt 1408 driven by the roll motor 1404.

FIG. 103 illustrates another variation of an elongate member manipulator 1500 coupled to the instrument driver 1016 via a mounting bracket 1058 positioned such that a guide wire (not shown) could feed through the elongate member manipulator 1500 and into a guide catheter splayer 1202 and/or sheath splayer. In alternative variations, the elongate member manipulator 1500 could be mounted on the instrument driver 1016 with a guide and/or a sheath splayer assembly (e.g., assembly 50/40 in FIG. 2), the elongate member manipulator could be mounted with just a sheath assembly 1040, or the elongate member manipulator 1400 could be mounted alone.

FIG. 104 shows the elongate member manipulator 1500 with its cover removed, mounted to a manipulator base 1570 which in turn is mounted to the manipulator mounting bracket 1058. The elongate member manipulator 1500 includes an insert motor 1502, insert belt 1506, feed roller assembly 1510, roll motor 1504, and roll belt 1508. The insert motor 1502 and roll motor 1504 are each fixably mounted to the manipulator base 1570 and are coupled to an insert shaft 1528 and roll shaft 1530 respectively.

FIG. 105 illustrates the feed roller assembly 1510 which includes the roll shaft 1530 and the insert shaft 1528. The insert motor 1502 drives the insert belt 1506, which rotates the insert shaft 1528 coupled to a drive gear 1518, which drives a driven gear 1520 which is coupled to bevel gears 1516, ultimately rotating a drive feed roller 1512, which can be positioned adjacent to an insert feed roller 1522. In one variation, the insert feed roller 1522 could be passive such that when the drive feed roller 1512 is actuated in one rotational direction, the frictional force between the drive feed roller 1512 and insert feed roller 1522 causes the insert feed roller to rotate in the opposite rotational direction. A guide wire (not shown) can be positioned between the drive feed roller 1512 and insert feed roller 1522 such that rotation of the feed rollers would result in a propelling actuation of the guide wire in the insert or retract directions depending on the rotational direction of the feed rollers.

Figure 106B:
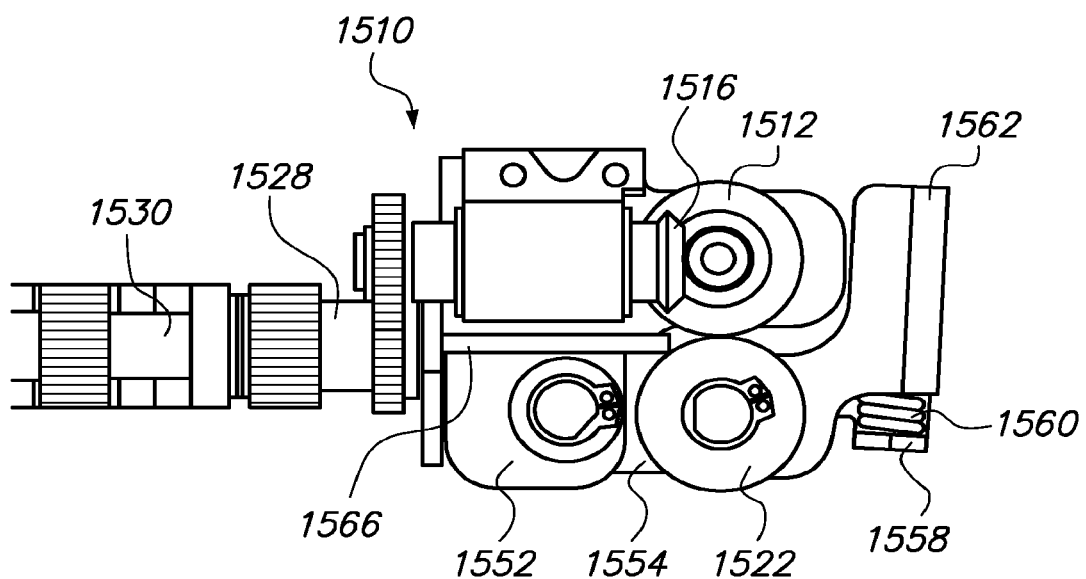

An alternative variation for actuation of the feed rollers is illustrated in FIG. 106A which is a zoomed in view of the feed roller assembly 1510 with certain components hidden or shown as transparent for clarity. FIG. 106B is a top view of FIG. 106A. In this variation, the insert feed roller 1522 is not passive but is driven at the same rate as drive feed roller 1512 in an opposite rotational direction thereby inserting or retracting the guide wire 1060 held between the feed rollers.

FIG. 107A illustrates a top view of the feed roller assembly 1510 while FIG. 107B illustrates a bottom view where certain components are shown as transparent for clarity. In this figure a feed roller gear train can be seen which includes four gears with identical gear ratios including a drive gear 1514, a first idler gear 1515, a second idler gear 1517 and a driven gear 1519. By way of example but not limitation, each gear could be sized with a 48 pitch and 27 tooth count which could be coupled to feed rollers that are ⅝" in diameter. In alternative variations, the gears could be sized with varying pitch and tooth count and the feed roller may have varying diameters.

Drive gear 1514 is coupled to drive feed roller 1512 such that rotary motion of drive feed roller 1512 actuates drive gear 1514 in a one-to-one rotary motion. Drive gear 1514 rotates first idler gear 1515 which rotates second idler gear 1517, rotating driven gear 1519 which is coupled to driven feed roller 1522 such that rotation of driven gear 1519 actuates insert feed roller 1522 in a one-to-one rotary motion. Thus rotation of the drive feed roller 1512 via the gears, belts and motors previously described rotates insert feed roller 1522 at the same rate in an opposite rotational direction. By way of example, when drive feed roller 1512 is rotated in the clockwise direction, drive gear 1514 is also rotated at the same rate in the clockwise direction. Drive gear 1514 then drives first idler gear 1515 in the counterclockwise direction, which drives second idler gear 1517 in the clockwise direction, which drives driven gear 1519 in the counterclockwise direction all at the same rotational rate if all gears have identical gear ratios. Driven gear 1519 coupled to the idler feed roller 1414 rotates idler feed roller in the counterclockwise direction resulting in opposite rotation of the drive feed roller 1512 and the driven feed roller 1522.

Roll of the guide wire may be actuated by rolling the feed roller assembly 1510. Referring back to FIG. 104, the roll motor 1504 is illustrated actuating the roll belt 1508 which in turn rotates the roll shaft 1530 rolling a feed roller assembly 1510 and ultimately rolling the guide wire (not shown) being held tightly between the feed rollers 1512, 1522.

With elongate member manipulators 1400 and 1500, the insert belt 1406, 1506 and roll belt 1408, 1508 are coupled to shafts 1428, 1528, 1430, 1530 which are rotatably coupled to bearings so they are free to rotate independently about the same axis of rotation. However, if either the belt assembly 1410 or feed roller assembly 1510 is actuated to roll but the insert belt 1406, 1506 remains stationary, the drive belt 1412 or drive feed rollers 1512 will not remain stationary. Using the elongate member manipulator 1400 from FIG. 100B as an example, if the belt assembly 1410 rolls by actuating the roll motor 1404 and the insert motor 1402 remains off, the driving gear 1418 remains stationary while the idler gear 1426 circumvents the driving gear 1418 with the motion of the roll assembly 1402. Thus, the rotation of the idler gear 1426 results in rotation of the driven gear 1420 and subsequent rotation of the bevel gears 1416 causing rotation of the drive belt 1412 and undesired insert of the guide wire 1060. The actuation of the insert motor may match the actuation of the roll motor such that as the idler gear 1426 circumvents driving gear 1418 without rotating about its own axis. The rotation of the insert motor 1402 and roll motor 1404 may be coordinated to achieve the desired actuation.

In order to actuate the guide wire in the feed/insert/retract direction only, the insert motor would be actuated while the roll motor would remain off. In order to roll the guide wire only without insertion/retraction, the roll motor is turned and the insert motor is turned at an identical rate. In order to feed and roll the guide wire simultaneously, the insert and roll motors may be actuated at different rates. Because the current variation actuates roll by rolling the entire structure, roll and insert of the guide wire can be simultaneously actuated without the effect of stripping or winding up the guide wire. The guide wire does not have to overcome any frictional holding effects at the feed belts when being actuated in a roll direction since the feed belts themselves are being rolled.

FIGS. 106A-107B show an example of a spring mechanism 1556 that can provide for a constant force applied to the guide wire (not shown) by the feed rollers 1512, 1522. The spring mechanism 1556 can provide for the ability to grip variously sized guide wire diameters, and it can also allow for top loading of the guide wire into the feed roller assembly 1510. The spring mechanism 1556 can include a frame 1552, a pivot frame 1554, a spring mount 1558, and a spring 1560. The frame 1552 is shown in FIG. 106A as a solid case surrounding second idler gear 1517, first idler gear 1515, and drive gear 1514. The frame 1552 remains stationary relative to the insert shaft 1528 such that the only movement experienced by the frame 1552 is rotation during roll of the feed roller assembly 1510. The pivot frame 1554 is shown as a transparent case fit into the frame 1552 but surrounding driven gear 1519, second idler gear 1517 and the spring 1560 in a cup 1562. The spring mount 1558 is shown as a solid flange which holds one end of the spring 1560 in place constraining it within the cup 1562. The spring mount 1558 may be attached to the main plate 1452 using a pair of screws 1564, so that it is stationary to the frame 1552 (as best shown in FIG. 31B). The pivot frame 1554 is mounted such that it can rotate about second idler gear 1517 but due to the spring force the pivot ram 1554 is held in a nominally closed position pinching the feed rollers 1512, 1522 together. The spring 1560 can be sized to optimize the force necessary to hold a guide wire with enough friction to actuate it in the insert and roll directions while not damaging the guide wire. By way of example but not limitation, the pivot plate can be sized so that a swing arm allows a 2 to 1 pinch advantage between feed rollers such that a 2.5 lb spring would result in a 5 lb pinch force at the feed rollers. With a 2.5 lb spring, the range of guide wire diameters could be between about 0.014" and 0.038." In this example, a wire diameter smaller than about 0.014" may not be gripped adequately to provide insert and roll motion without slipping and a wire diameter above about 0.038" may be damaged by the pinch force.

In one variation, the guide wire 1060 can be back loaded into the elongate member manipulator by manually loading the guide wire 1060 into the proximal end of the feed roller assembly 1510, loading it into the proximal end of the roll shaft 1532 which could be provided with a thru lumen, and actuating the insert motor 1502 to actuate the feed rollers 512, 522 in the insert direction until the desired length guide wire 1060 is fed through the elongate member manipulator 1500. In an alternative variation, the guide wire 1060 can be back loaded into the roll shaft 1530 as described above but then top loaded into the feed roller assembly 1510. To top load the guide wire 1060 the spring 1560 could be compressed by manually squeezing the pivot frame 1554 towards the cup 1562 on the frame plate 1552, pivoting both the pivot plate 1554 and idler feed roller 1522. FIGS. 108A and 108B show a representation of the bottom view of the gear train and feed rollers, and illustrate the spacing between the drive feed roller 1512 and the idler feed roller 1522 created by squeezing the spring 1560 and pivot frame 1554. The guide wire can then be loaded from above into a groove 1566 shown in FIGS. 106A, 106B, and 107A which helps center the guide wire between the feed rollers 1512, 1522.

FIG. 109 illustrates a variation of a feed roller configuration that may prevent or reduce slippage of the guide wire 1060 between the drive feed roller 1512 and the insert feed roller 1522 when insert or roll motion is actuated. In this variation, the drive feed roller 1512 is configured with a V-groove 1568 cut around its diameter. The guide wire 1060 may fit in the V-groove 1568 and be held in position by the insert feed roller 1522. The guide wire 1060 may be held by three points of contact, two within the V-groove 1568 and one with the drive feed roller 1512 without a groove thus constraining the guide wire 1060 vertically and rotationally. In alternative variations, a similar groove may be cut into the drive feed roller 1512 or it may be cut in the drive feed roller 1512 and not the insert feed roller 1522. The groove may be of various dimensions depending on the range of wire diameter sizes and the necessary contact between the groove and the guide wire. The groove may also be of various shapes including but not limited to semi-circular, square, or any polygon shape which could provide for necessary contact with the guide wire.

Referring back to FIG. 107A, a guide wire groove 1566 is provided to help align the guide wire (not shown) vertically with the V-groove 1568 in the drive feed roller 1412 as well as center the guide wire in between both feed rollers 1512, 1522.

As previously described, it can be desirable to maintain the guide wire 1060 and a minimal number of disposable components in a sterile field and the remaining components in a non-sterile field. As shown in FIGS. 110A-110B, in one variation, the feed roller assembly 1510 could be separated into two sub-assemblies, an insert assembly 1511 which is maintained in the sterile field and an actuation assembly 1513 positioned in the non sterile field. The insert assembly 1511 could include the gears and rollers provided for insertion of the guide wire including but not limited to the spring mechanism 1556, gears (1514, 1515, 1517, 1519), rollers 1512, 1522, driven gear 1520, and bevel gears 1516. The actuation assembly 1513 could include the driving gear 1518, insert shaft 1528, and roll shaft 1530. While the actuation assembly 1513 still includes a number of gears and pulleys, a number of expensive components including gears, the insert and roll motors 1502, 1504, insert and roll belts 1506, 1508, and instrument driver 1016 would remain in the non-sterile field.

FIGS. 109-110 also show one way to mount the insert assembly 1511 to the actuation assembly 1513 allowing for separation of sterile versus non-sterile components where the insert assembly 1511 could be removeably coupled to the actuation assembly 1513 which is fixably mounted to the other components of the elongate member manipulator 1500. A sterile drape (not shown) could be positioned between the insert assembly 1511 and the non-sterile components. Referring to FIG. 110 as well as back to FIG. 108, the insert assembly 1511 could be mounted to a mounting plate 1572 using mounting screws 1574. The mounting plate 1570 could be fixably mounted to a manipulator base 1570 which provides the base structure for the insert motor 1502, the roll motor 1504 and the feed roller assembly 1510. In alternative variations, an interface that allows for quick removal and replacement of the insert assembly 1511 without the use of tools could be used. Additionally the interface could include mating components on the sterile drape.

Figure 111A:
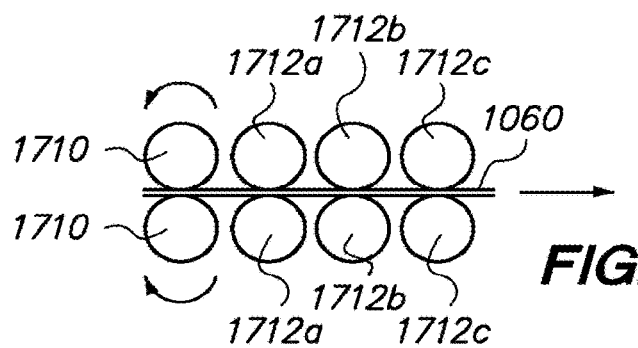
Figure 111B:
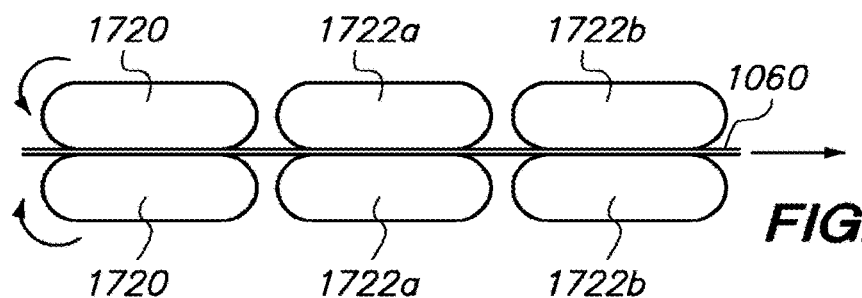
Figure 111C:
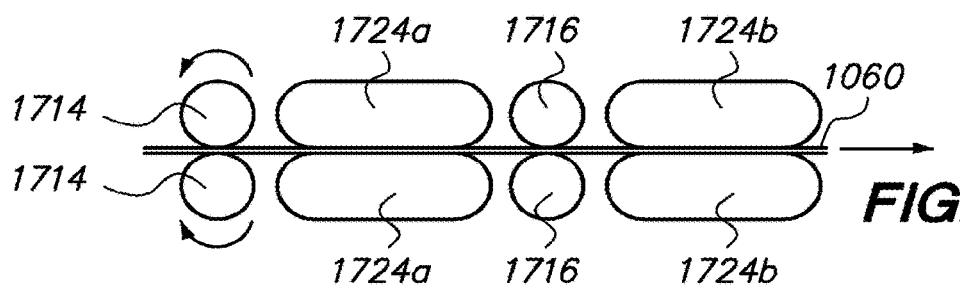
Figure 111D:
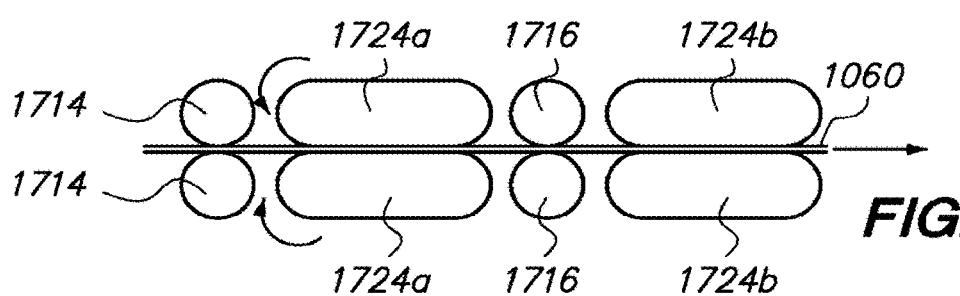
Figure 111E:
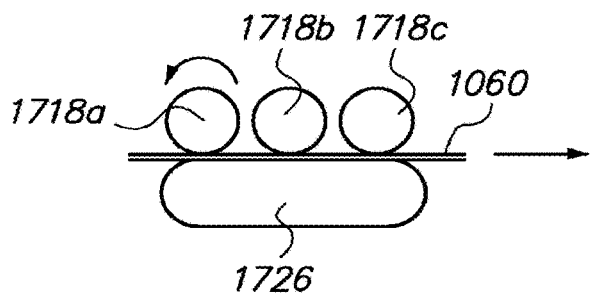
Figure 111F:
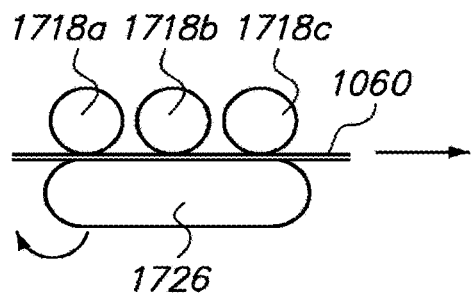

It should be understood that any of the previously described elongate member manipulators could include multiple variations of feed roller and/or feed belt combinations. FIGS. 111A-111D illustrate examples of such combinations. FIG. 111A illustrates a variation using multiple feed roller pairs 1710, 1712a, 1712b, 1712c for actuating the guide wire 1060 where motor driven feed roller pair 1710 drives the guide wire 1060 in an insert motion while feed roller pairs 1712a, 1712b, 1712c can be idler rollers which are free to rotate. FIG. 111B illustrates a variation using multiple feed belt pairs 1720, 1722a, 1722b for actuating the guide wire 1060 in an insert motion where feed belt pair 1720 is motor driven and feed belt pairs 1722a, 1722b are idler belts which are free to rotate. FIG. 111C illustrates a variation that uses a combination of feed roller pairs and feed belt pairs where feed roller pair 1714 is motor driven while feed roller pair 1716 and feed belt pairs 1724a, 1724b are idle and free to rotate. Alternatively feed belt pair 1724a can be motor actuated while feed belt pair 1724b and feed roller pairs 1714, 1716 are idle as shown in FIG. 111D. FIGS. 111E and 111F illustrate alternative variations which feed rollers and feed belts are not used in pairs but a single set of feed rollers 1718a, 1718b, 1718c and a feed belt 1726 are used to grip the guide wire 1060. FIG. 111E illustrates a variation in which the feed roller 1718a is motor driven to actuate the guide wire 1060 while FIG. 111F illustrates the feed belt 1726 as motor driven.

It should be understood that alternatively any of the idle roller pairs and idle belt pairs could be motor driven, any motor driven feed roller pairs and feed belt pairs could be idle, and while a specific number of pairs of rollers and/or belts are illustrated, any number can be used. Additionally in any pair of feed rollers or feed belts, one feed roller or feed belt could be motor driven while the other could be idle. In the configuration illustrated in FIGS. 111C and 111D, any combination of feed roller pairs and feed belt pairs could be used in any order and furthermore any combination of feed rollers, feed roller pairs, feed belts and feed belt pairs from any of the variations previously described may be used. Motor driven actuation can be provided in the manner previously described and roll actuation of the guide wire can be provided with the translation of the feed rollers/feed belts along their own axes of rotation also previously described.

FIGS. 124A-C illustrate another alternative variation of an elongate member manipulator 1600. FIG. 124A illustrates the elongate member manipulator 1600 with a manipulator cover 1601 installed while FIG. 124B illustrates the manipulator cover 1601 removed. The elongate member manipulator 1600 includes a member holder 1608, an insertion drive 1610, and a rotation drive 1620 each of which can be directly or indirectly mounted to a manipulator base 1606. FIG. 124C shows the insertion drive 1610 which includes an insert motor 1602, a leadscrew 1612, a leadscrew nut 1614, and/or a linear slide 1616.

FIGS. 125A-C illustrate a perspective, side, and zoomed in views of the rotation drive 1620 respectively which includes a rotation base 1618, a rotation drive bracket 1622, roll motor 1604, a drive gear 1624, a rotation gear 1626, a collet 1628, a collet solenoid 1632, and/or a collet mount 1634. The collet 1628 can be coupled to the collet mount 1634 using collet bearings 1636 such that the collet 1628 can be free to rotate within the collet mount 1634. The collet 1628 may also be coupled or fixably coupled to the rotation gear 1626 such that actuation of the rotation gear 1626 would drive rotation of the collet 1628.

FIG. 125B illustrates the rotational drive 1620 with the guide wire 1060 loaded. It should be understood as described previously that the guide wire 1060 is shown for illustrative purposes and any type of elongate member may be loaded into the manipulator 1600. In order to load the guide wire 1060 into the system, the collet 1628 can be opened, the guide wire 1060 can be backloaded into the system, and the collet 1628 can then be closed gripping the guide wire 1060. The collet 1628 functions as a typical chuck or collet chuck as is well known in the art such that in order to loosen or tighten the collet 1628, one end of the collet 1628 would be held stationary while the other end is rotated. Depending on the direction of rotation, the collet is either tightened around the guide wire 1060 or loosened from the guide wire 1060. In this variation, the opening and closing of the collet 1628 can be automatically or remotely controlled. The collet 1628 can be geared such that collet teeth 1630 can mate with the collet solenoid 1632. When the collet solenoid 1632 is activated to engage one end of the collet 1628 is held stationary, the roll motor 1604 can turn the drive gear 1624, which will rotate the rotation gear 1626, rotating the other end of the collet 1628 which will loosen or tighten the collet 1628 depending on the direction of rotation.

Once the collet 1628 is closed adequately holding the guide wire 1060, the collet solenoid 1632 can be disengaged from the collet teeth 1630. In this configuration, rotation of the rotation gear 1626 which is indirectly driven by the roll motor 1604 will not cause the collet 1628 to loosen or tighten. Instead, the entire collet 1628 will rotate with the rotation gear 1626 thus rolling the guide wire 1060 which is held securely in the collet 1628.

In order to actuate the guide wire 1060 in the propelling motion, inserting or retracting it axially, the rotation drive 1620 can be mounted to linear slide 1616 as shown in FIG. 124C. The leadscrew nut 1614 can be fixably mounted to the rotation base 1618 and coupled to the leadscrew 1612 such that when the insert motor 1602 drives the leadscrew 1612, rotation drive 1620 is controllably driven linearly and the guide wire 1060 can be controllably propelled in the insert or retract direction depending on the rotational direction of the insert motor 1602.

In one variation, the insert/retract stroke can be limited by the physical travel of the linear slide 1616. In an alternative variation, an infinite insert or retract distance may be achieved.

FIG. 126 shows a side cross sectional view of the elongate member manipulator 1600 illustrating the member holder 1608 which can include a holder solenoid 1638. The holder solenoid 1638 can include a holder tip 1640 that is actuated to hold or release the guide wire 1060. When the guide wire 1060 is being actuated in the roll or propelling directions, the holder solenoid 1638 can be actuated to release the guide wire 1060 to move freely through the member holder 1608. When the linear slide 1616 has reached its forward limit in the propelling direction, the holder solenoid 1638 can be actuated to hold the guide wire 1060 in the member holder 1608, the collet 1628 can be actuated to open, releasing its grip on the guide wire 1060, and the rotational drive 1620 can be translated back to the reverse limit of the linear slide 1616. The collet 1628 can then be actuated to tighten around the guide wire 1060, the holder solenoid 1638 can be actuated to release the guide wire 1060 within the holder member 1608, and the guide wire 1060 can again be actuated in the propelling and roll directions in the manner previously described. The same method can be used in the retract direction.

In one variation, algorithms for control of the elongate member manipulator 1600 can be applied such that the sequence of collet and holder solenoids 1632, 1638 as well as insert and roll motors 1602, 1604 are coordinated to create rapid and seamless actuation of the elongate member manipulator 1600. Additionally algorithms can be implemented that will control the opening and closing of the collet 1628 based on the size of the guide wire 1060, catheter or any other type of elongate member that would be loaded into the elongate member manipulator 1600. A lookup table of rotations based on type of guide wire or elongate member could be programmed into the system controller and the user could input the information regarding the type of elongate member into the system before use. The look up table could be created using empirical data or calculations based on known mechanical properties of the elongate member. Alternatively, closing and opening of the collet could be based on sensed force during of rotation of the rotation gear 1626. When the collet solenoid 1632 is actuated to hold the collet teeth 1630 and the collet 1626 is being actuated to close using the rotation gear 1626, sensing the force imparted on the gear during rotation could be an indicator of when to cease rotation as the collet 1626 closes around the guide wire 1060. Mechanisms for sensing force will be described in further detail below.

For certain variations of the elongate member manipulator, it can be desirable to provide the capability of measuring the external force applied to the distal end of the elongate member, e.g., a guide wire. Thus, if the distal tip of the guide wire makes contact with tissue, the user could be aware of the force being applied to the tissue. The elongate member manipulator 1600 illustrated in FIGS. 124A-C can include a variation of force sensing that provides for force sensing during insert/retract and roll actuation of the guide wire 1060.

FIG. 127A illustrates the rotation drive 1620 for the elongate member manipulator 1600 and FIG. 127B illustrates a side cross sectional side view of rotation drive 1620 displaying a load cell 1642 mounted stationary relative to the rotation base 1618 and a fulcrum 1644 which allows the lower portion of the rotation drive bracket 1622 to pivot towards or away from the load cell 1642. Thus any forces experienced by the guide wire 1060 which is held securely in the collet 1628, will cause the rotation drive bracket 1622 to transmit forces to the load cell 1642. With known kinematics and base-lining of initial load cell readings, force applied to the distal tip of the guide wire may be calculated.

FIG. 127C illustrates a side view of the rotation drive 1620 with a back cross sectional view of the rotation drive 1620. In this variation, the roll motor 1604 is mounted to a motor bracket 1646 which is supported on a set of bearings 1648 which constrain the bracket 1646 in a fixed vertical and horizontal position yet allow the bracket 1646 to rotate about the roll motor rotational axis as illustrated by the arrows 1652. The bracket 1646 can include a lever 1654 which can be positioned against an LVDT sensor 1656 that can be fixably mounted to the rotation drive bracket 1622. Thus a reactive torque imparted on the motor 1604 in the rotational direction would be transmitted to the LVDT 1654 and could be read as resistive force experienced by the guide wire 1060 during a roll actuation. In order to prevent damage to the LVDT 1654, hard stops 1650 could be mounted to the rotation drive bracket 1622.

FIG. 112A illustrates a variation of an apparatus that provides force measurement of a guide wire distal tip during insert. FIG. 112A shows a bottom perspective view of the elongate member manipulator 1200. It should be understood that the elongate member manipulator 1200 is shown by way of example, and this force sensing apparatus could be used for any of the elongate member manipulators described herein. The lower slide assembly 1230 is mounted to the manipulator mounting bracket 1058 to which a strain gauge 1080 is also mounted. When force is applied to the distal tip of the guide wire 1060, the lower slide assembly 1230 mounted to the manipulator mounting bracket 1058 is displaced causing a reading in the strain gauge 1080. The strain reading can be used to calculate a guide wire distal tip force.

An alternative variation of a force measurement apparatus is illustrated in FIG. 112B. In this variation, the elongate member manipulator 1500 is shown with a strain gauge load cell 1082 fixably mounted to the manipulator base 1570. The manipulator base 1570 is mounted to the manipulator mounting bracket 1058 using a pair of linear slides 1084 which allow movement of the manipulator base 1570 and thus the elongate member manipulator 1500 in the insert/retract direction or the direction along the axis of the guide wire (not shown in FIG. 112B). A force sensing block 1086 is fixably mounted to the manipulator mounting bracket 1058 but is positioned so that it fits between the arms of the load cell 1082. When an external force is applied to the distal tip of the guide wire (not shown), the elongate member manipulator 1500 is moved back in the retract direction along with the manipulator base 1570 via the linear slides 1084. The load cell 1082 is also pushed in the retract direction making contact with the force sensing block 1086 resulting in a force reading from the load cell 1082.

Strain gauges or load cells mounted to the manipulator base 1470, 1570 or bottom of the elongate member manipulator 1200, 1300 may be used to sense distal tip force for any of the variations of elongate member manipulators described previously in a manner described above. However, other types of sensors mounted to either the distal tip of the elongate member or on the proximal end of the elongate member on the elongate member manipulator may be used to detect distal tip force including but not limited to strain gauges, piezoelectric sensors, tactile sensors, and quartz force sensors. Alternatively, sensors can be used to detect a change in length of the elongate member which measurement can be used in combination with known mechanical properties to calculate force. Examples of such sensors include but are not limited to a fibers, optical sensors, electromagnetic sensors, inductive sensors, capacitive sensors, vision systems etc.

The elongate member manipulators described herein may be mounted to any type of structure depending on the desired use and any environmental constraints. In one variation, the elongate member manipulator may be mounted to a stationary arm mounted to a bedside rail of a patient bed. In alternative variations, the elongate member manipulator could be mounted to a bedside cart. In the variation shown back in FIG. 83A, the elongate member manipulator 1200 is mounted directly to the manipulator mounting bracket 1058, which is fixably mounted to the instrument driver 1016. The elongate member manipulator 1300 could be mounted in a similar fashion. FIGS. 98B and 103 show the elongate member manipulator (1400 and 1500 respectively) each including a manipulator base 1470, 1570 which is fixably mounted to the manipulator mounting bracket 1058, which is fixably mounted to the instrument driver 1016. The various mounting mechanisms for mounting the instrument driver to a bedside rail or cart were described previously.

One example of a mechanism for mounting the manipulator mounting bracket 1058 to the instrument driver 1200 is best shown in FIG. 103. Though the elongate member manipulator 1500 is shown in this figure, it should be understood that any of the elongate member manipulators described herein can be mounted in the same manner using the same apparatus. In this variation, a vise clamp 1062, such as one found from CarrLane Tiny Vise™, which provides a clamp as well as a captured hex screw, can be used to fixably attach the manipulator mounting bracket 1058 to a tapped hole 1064 on the instrument driver 1200. The vise clamp 1062 provides enough clamping force as well as thrust force to securely attach the mounting bracket 1058 to the instrument driver 1200 while preventing the mounting bracket 1058 from lifting away from the instrument driver 1200 due to the weight of the elongate member manipulator 1500. In an alternative variation an adapted vise clamp 1063 may be altered to chamfer the edges 1065 of the vise clamp as shown in FIGS. 103AA and 103AB. The adapted vise clamp 1063 can be coupled with a mating bracket (not shown) so that as the adapted vice clamp 1063 is tightened, it expands within the bracket locking it into place as shown with the arrows 1067. In one variation, a sterile drape (not shown) may be placed between the adapted vise clamp 1063 and the mating bracket (not shown) allowing a separation between sterile and non-sterile components without puncturing the sterile drape, preventing any breakage of the sterile barrier.

In alternative variations, a plurality of different types of mounting screws, bolts, or any fastener sized properly to obtain the desired clamping force could be used in place of the vice clamp 1062 while the mounting bracket 1058 can be dimensioned at a thickness that could prevent lifting due to elongate member manipulator 1400 weight or due to the weight of any of the various elongate manipulators described herein.

FIGS. 103A-B illustrate variations of a roll support 1580, 1582. Depending on the size and type of elongate member or guide wire being used, it may be difficult to provide enough torque at the proximal end of a guide wire or elongate member to accurately roll the distal section. The roll support tube 1580,1582 can provide any number of opposing bends necessary, creating a wave with varying pitch and amplitude between successive bends. In one variation, the roll support may be adjustable such that the number of bends can be altered depending on required torque.

Referring to FIG. 103A, the elongate member manipulator 1500 is shown with the roll support tube 1580. The roll support tube 1580 may be configured to receive the guide wire 1060 or various sizes and types of guide wires coaxially, and can be provided proximally adjacent to the elongate member manipulator 1500. The roll support tube 1580 provides rigid curves which place the guide wire 1060 in several bends. As the guide wire 1060 is actuated in roll, the roll support tube 1580 remains in the curved configuration but rotates about the longitudinal axis of the guide wire 1060. The bends prevent the wire from rolling within the roll support tube, minimizing or eliminating uncontrolled wind up of the guide wire within the support tube or guide catheter. Thus the roll support tube 1580 assists in providing the torque necessary to gain accurate roll control of the wire through the guide catheter (not shown) or support tube (not shown) provided at the distal end of the elongate member manipulator 1500. In alternative variations, the roll support tube 1580 could be manufactured from a semi-flexible material which provides rigid support during roll actuation. The roll support tube 1580 can be hand molded to provide the necessary bend configuration.

FIG. 103B illustrates an alternative variation of a roll support tube 1582 which provides bends of variable pitch and amplitude. Because the roll controllability of the guide wire is dependent on the size and material of the wire itself, different wires may require sharper bends in order to gain accurate controllability while bends that are too sharp for some types of wires may cause damage to the wire. Thus a scissor jack support 1582 can be used to provide the bends necessary to provide torque control in an adjustable manner for various types of wire. The scissor jack support 1582 may provide torqueability support in the same manner as the roll support tube 1582 and provides for an adjustability of curve amplitude and pitch.

Referring back to FIG. 1, an operator 12 is shown at an operator workstation 22 which provides remote control of a guide catheter 1054, sheath catheter 1044, and elongate member manipulator. Details regarding the control of the sheath catheter, guide catheter, and instrument driver are provided in the aforementioned incorporated references. Control of an elongate member manipulator can be approached in a manner similar to the way any remotely controlled robotic master slave system would be controlled according to the references incorporated herein or as is well known in the art. The elongate member manipulator systems of any of the previously described variations will be described herein where the master would be an input device such as the operator workstation 22 and the slave would be any of the elongate member manipulators (1100, 1200, 1300, 1400 or 1500). The elongate member manipulator fundamentally has two degrees of freedom, roll and insert, that could be controlled with a single master with two degrees of freedom, or by two separate master devices that each control one degree of freedom. The following provides various masters that provide input for these degrees of freedom. In other variations, the manipulator can provide one or more degrees of freedom controlled by one or more masters.

Referring back to FIG. 2, an example of an operator workstation 22 providing for inputs for control of the guide catheter, sheath catheter and elongate member manipulator is illustrated. As previously described the operator workstation 22 includes the master input device 1212 acting as a joystick type controller along with the pendant 8 acting as a keyboard type input device. In one variation, the guide catheter is controlled using the master input device 1212 allowing for steering of the distal tip of the guide catheter as viewed on the display monitors 44 while the sheath catheter and the guide wire are controlled using the pendant 8. As previously described in detail, the master input device 1212 includes several sensors which detect the position of the master input device 1212 shown in this variation as a joystick. Those sensors send signals to the controller that are interpreted as commands.

FIG. 113 illustrates a variation of the pendant 8 of FIG. 2 which would include controls for the sheath catheter and elongate member manipulator. In order to steer the sheath catheter, the bend, insert and rotate controls 1026 located on the right side of the pendant 8 could be used while the rotate and insert controls 1028 located on the lower left side of the pendant 8 could be used to control the elongate member manipulator. In alternative variations, the distal tip of the guide wire could be controlled using the master input device 6 while the guide and sheath catheters are controlled by the control console 8 or the sheath catheter could be controlled by the master input device 6. In fact any combination of controls could be implemented using either or both the control console 8 and/or the master input device 6.

The display and force sensing controls 1030 located on the upper left of the control console 8 could be used to control the views on the monitors and activate and control force sensing capabilities respectively and the trackball controls 1032 could be used to control cursors on the display. As described in detail in the aforementioned incorporated references, the display could show images of patient anatomy in the form of models or fluoroscopic images. Cartoon images of the guide, sheath, and guide wire within the patient anatomy can be displayed showing commanded positions. Actual images of the guide, sheath, and guide wire can be shown from fluoroscopic data. Additionally the display can also show force feedback readings In an alternative variation, it could be desirable for the controls to be located closer to the patient bed. Referring to FIG. 114A, a variation of the patient bed 1020 is shown with a standalone console 1024 mounted to the bedside rail 1021 such that the operator could control the system from beside the bed. FIG. 114B illustrates a side view of the standalone console 1024 mounted to the bedside rail 1021 where the patient bed 1020 is not shown for clarity. The standalone console 1024 can rest on a mounting tray 1036 that is fixably attached to the bedside rail 1021 via a clamp 1038. FIG. 115 illustrates one example of standalone console 1024 which eliminates some components from the control console 1008 and retains the controls for the sheath catheter 1026 and the elongate member manipulator 1028. In alternative variations, the standalone console 1024 could be used in conjunction with the control console 1008 with two operators working together in which case one console could override controls if conflicting commands are sent from each console of another depending on configuration.

Alternatively, several other types of input devices could be used to provide the signals for the one or more degrees of freedom necessary to control the elongate member manipulator. In the case where either the elongate member manipulator is mounted to a setup structure alone or mounted on the instrument driver, but control of only the elongate member manipulator is necessary, other types of input devices may be used.

Figure 116:
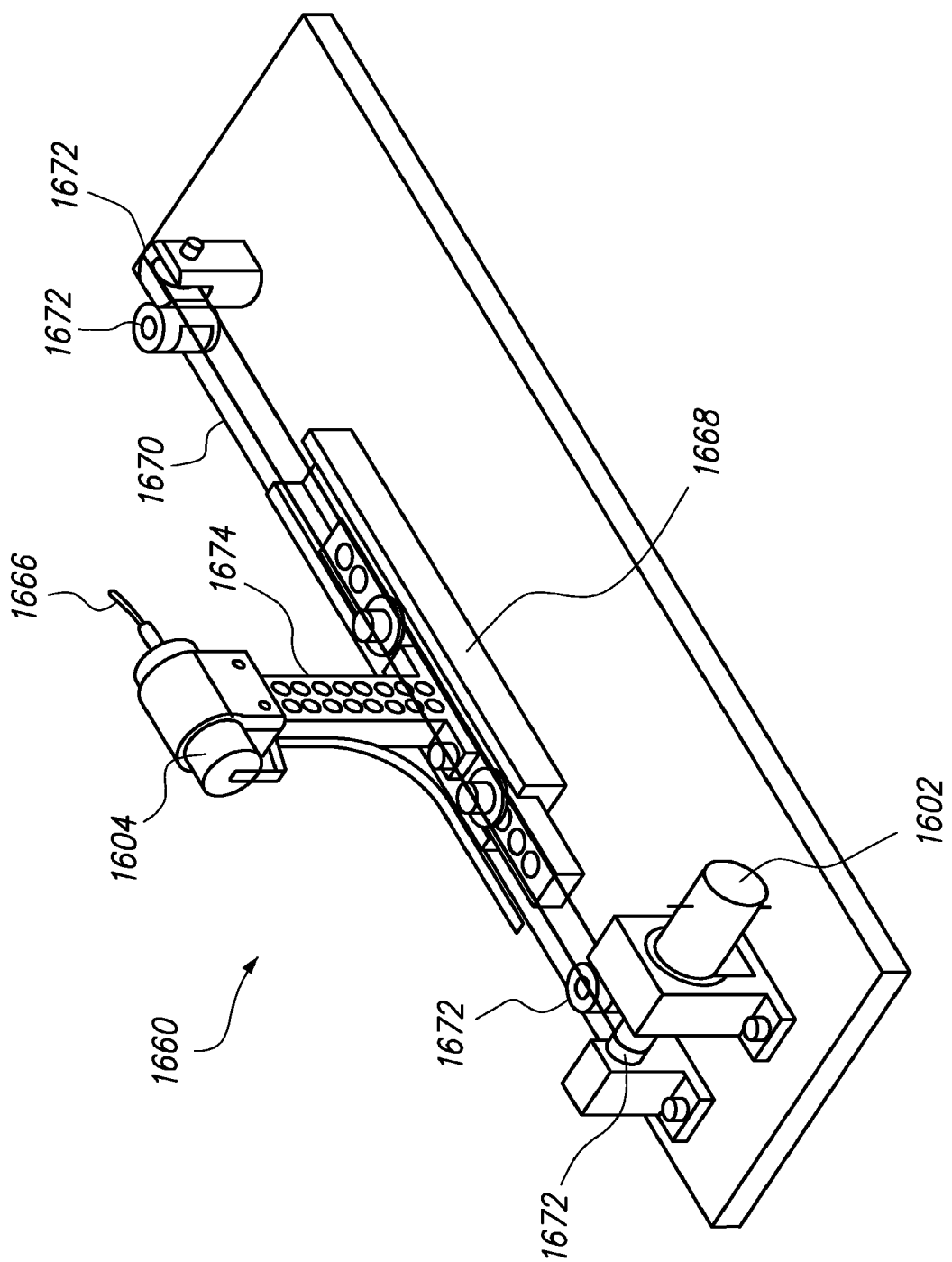

FIGS. 116-116N illustrate various master input devices that could be used in place of a joystick controller and/or console.

FIG. 116 illustrates an alternative variation of a master input device. As is well known the art, manual control of guide wires typically includes a two handed sequence to propel a guide wire in the insert or retract directions. Typically the guide wire is coupled to an introducer that can be used as a handle for an operator. The operator will advance the guide wire, by using a front hand to support the introducer and the rear hand to grip the guide wire pushing it through the introducer. This only accounts for advancement of the guide wire a short distance so the front hand may release the introducer, grip the guide wire, allowing the rear hand to release the guide wire in order to grip it a short distance further back along the guide wire. The front hand can now release the guide wire to allow the rear hand to advance the wire. This is repeated until the guide wire is advanced to the desired position typically advancing the wire 1" to 2" at a time. In many cases, the total insert distance can be as far as 2 meters. The wire can be rotated manually using one or both hands to rotate the wire while inserting it.

The master input device shown in FIG. 116 stimulates the motion physicians are accustomed to during manual procedures while eliminating the need for multiple two handed iterations necessary for manual insert. The master input device 1660 can include an insert motor 1662, a roll motor 1664, a flexible member 1666, a handle (not shown), a linear slide 1668, actuation cables 1670, pulleys 1672, and/or a support 1674. The handle (not shown) is coupled to the flexible member 1666, which in turn is coupled to the roll motor 1604, which is fixably mounted to the support 1674, mounted to the linear slide 1668. Using the pulleys 1672 and actuation cables 1670 the linear slide 1668 is coupled to the insert motor 1602. A variety of motors may be utilized, e.g., the motors can be 13 mm DC brush servo motors and the handle can include a grasper button (not shown). The support 1674 can be made from a lightweight material, such as a lightweight plastic and the linear slide 1668 can also be lightweight and low friction.

During operation, the user depresses the grasper button and rotates the handle (not shown). The roll motor 1604 which is equipped with an encoder reads the rotation of the handle and transmits this data to the controller which will control the roll of the elongate member manipulator. In order to control insert, the user depresses the grasper button, moves the handle forwards or backwards along the linear slide 1668, while the insert motor 1602 encoder reads the rotation of the motor 1602 and thus the linear movement of the handle. This data is again transmitted to the controller. When the user has reached the physical limit of the linear slide 1668, the grasper button is released and the user may slide the handle to a nominal linear position without sending a signal to the controller indicating desired propelling actuation of the elongate member manipulator.

FIG. 117A illustrates a master input device based on a slider that can be moved on a fixed rod. When the engage button is pressed the translation and rotation of the slider are measured by sensors and used to command the insert and rotation of the guide wire. When the engage button is released, the slider can be moved freely or alternatively can be spring loaded to return to a fixed position. The slider can be mounted to a handle as shown in FIG. 117AA.

Figure 117C:
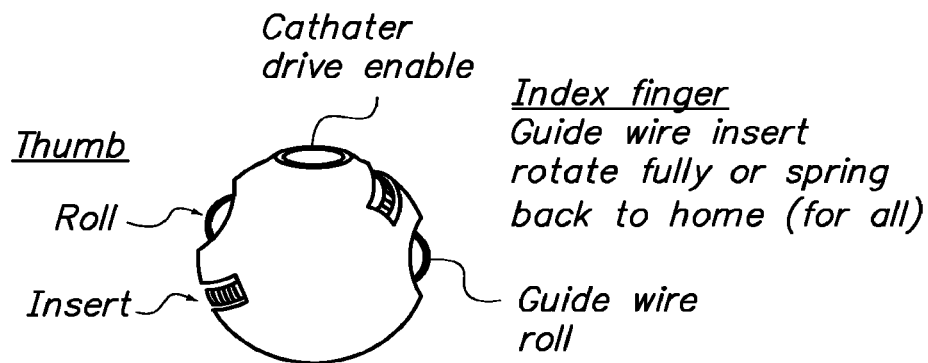
Figure 117C:
Figure 117D:
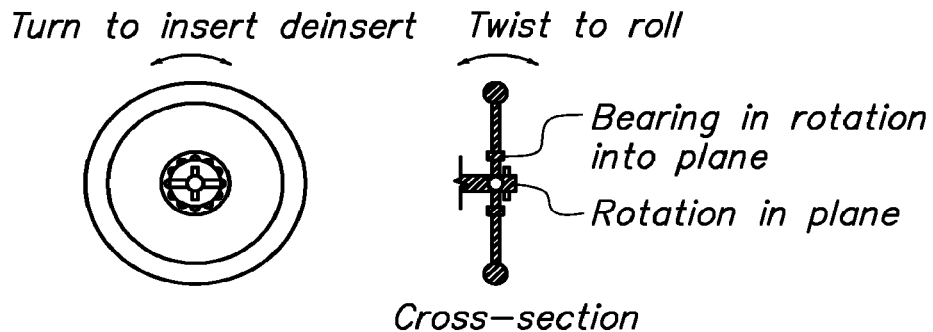
Figure 117D:
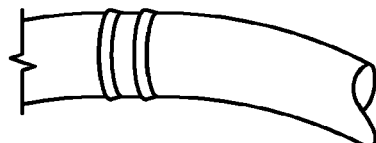

FIG. 117B illustrates a paddle switch that could be mounted to the instrument driver 1016 which could control insert, or retract, and/or roll of the guide wire. The paddle switch can be provided with recessed contact switches as shown in FIG. 117BB that may be pressed to enable the paddle switch. Alternatively the paddle switch can be pinched from both sides as shown in FIG. 117BBB to activate it. FIG. 117C illustrates scroll-wheels that can be incorporated into the handle of a master input device. Each scroll-wheel could be used to control a different degree of freedom on the elongate member manipulator. Alternatively FIG. 117CC shows buttons incorporated on the master input device handle that could control different degrees of freedom on the elongate member manipulator measuring force applied to each button to determine control of the manipulator. FIG. 117D shows a wheel with a circular cross-sectioned rim. By hiding most of the wheel inside of a housing or below the table surface, the user is presented with a rail that can be moved in a quasi-linear fashion by rolling the wheel. This gives an infinite range of travel device that could be used to control insert of the guide wire. The wheel could be tilted to either side to control roll of the guide wire.

Figure 117I:
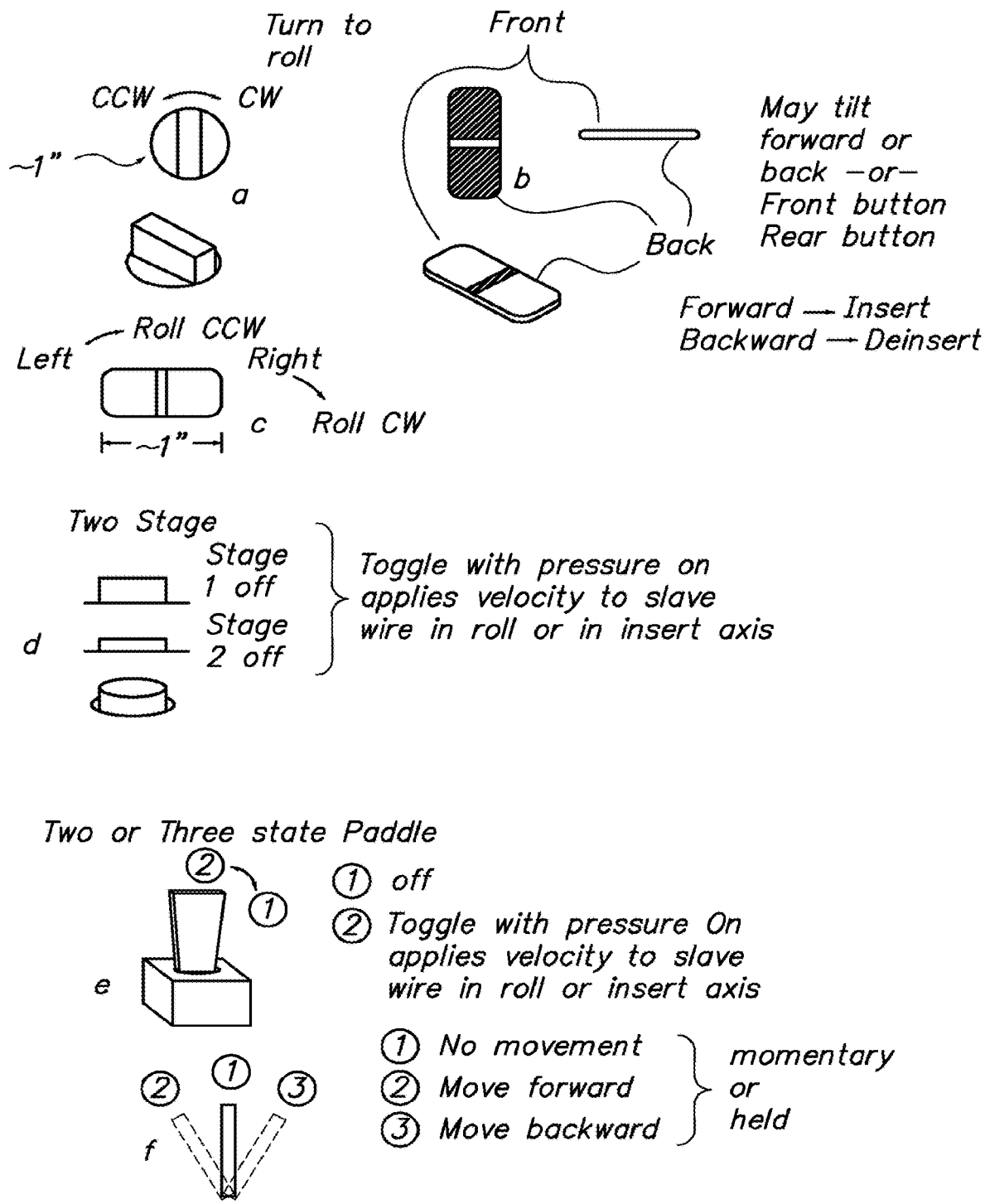
Figure 117J:
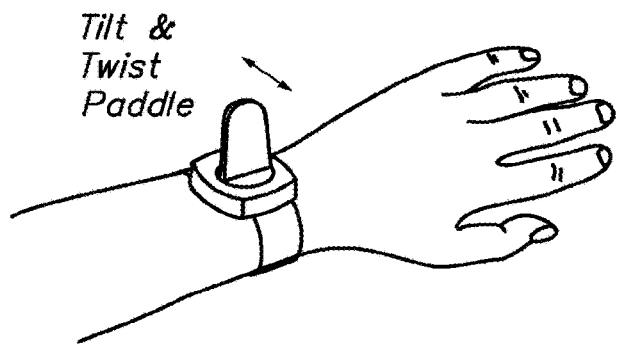
Figure 117K:
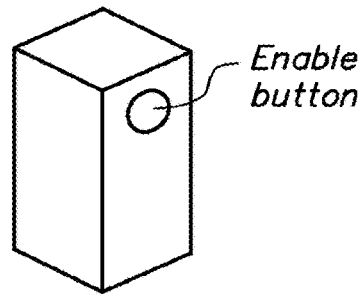
Figure 117L:
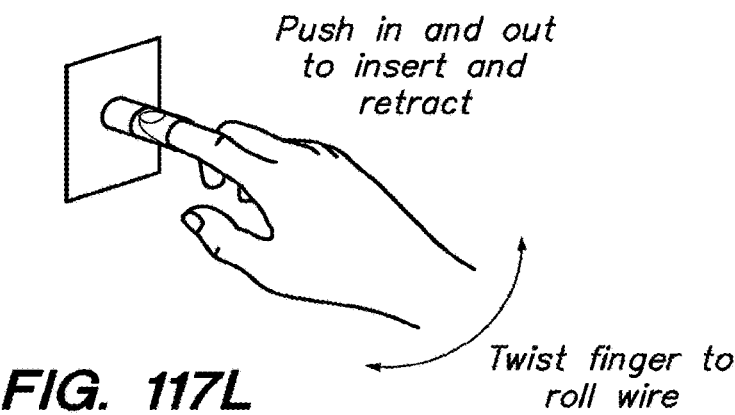
Figure 117M:
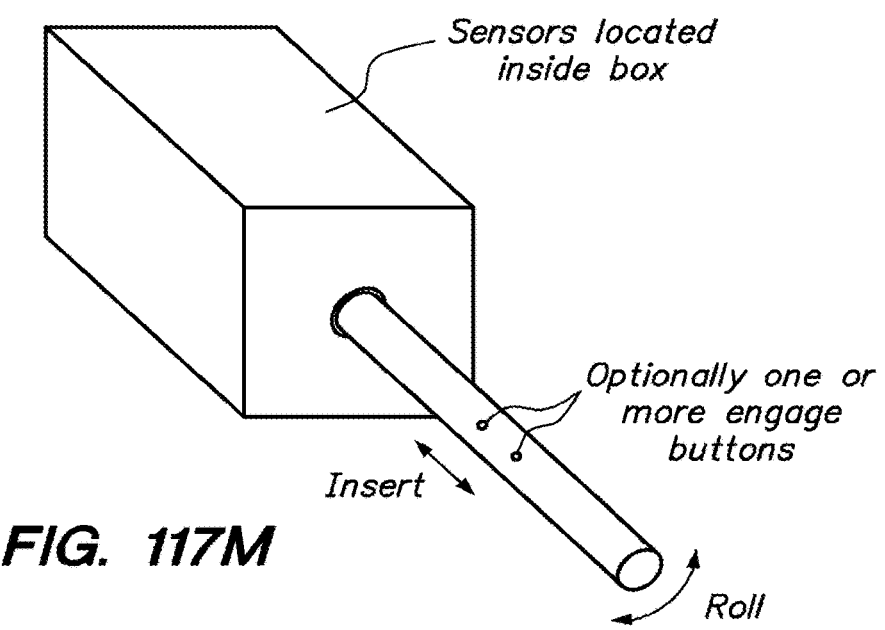
Figure 118A:
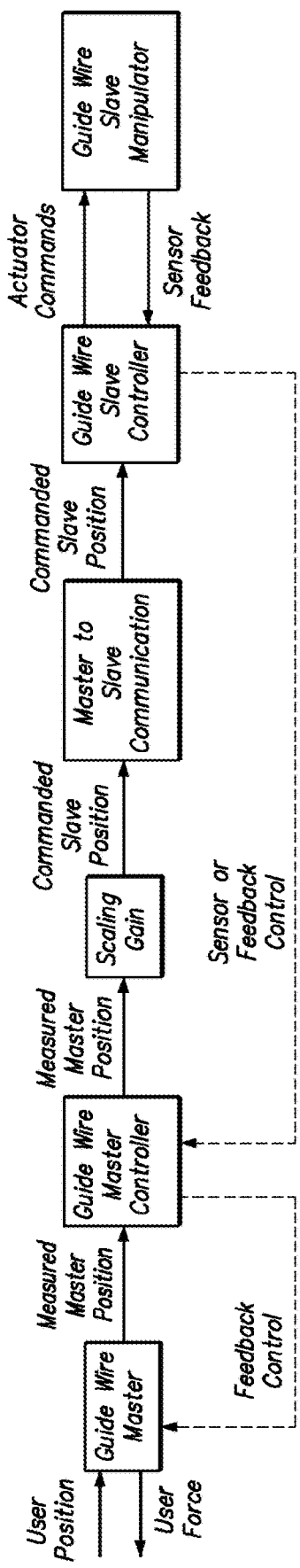
Figure 118B:
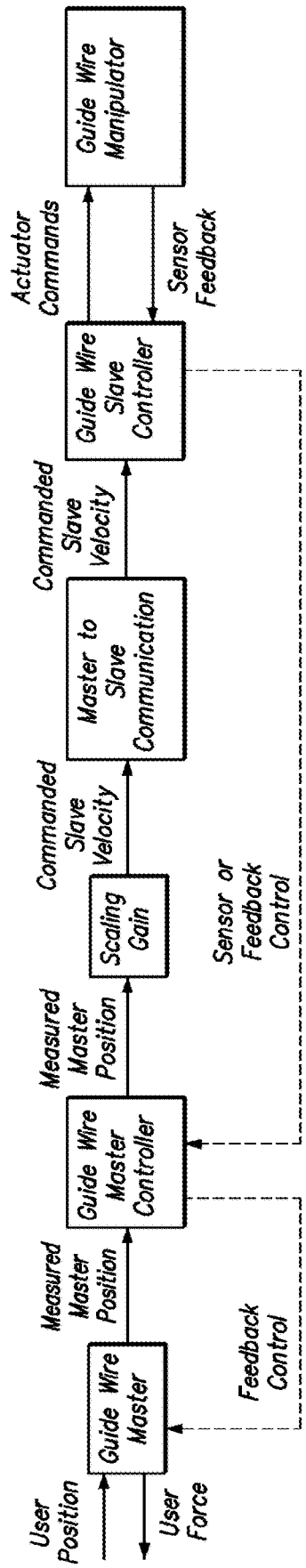
Figure 118C:
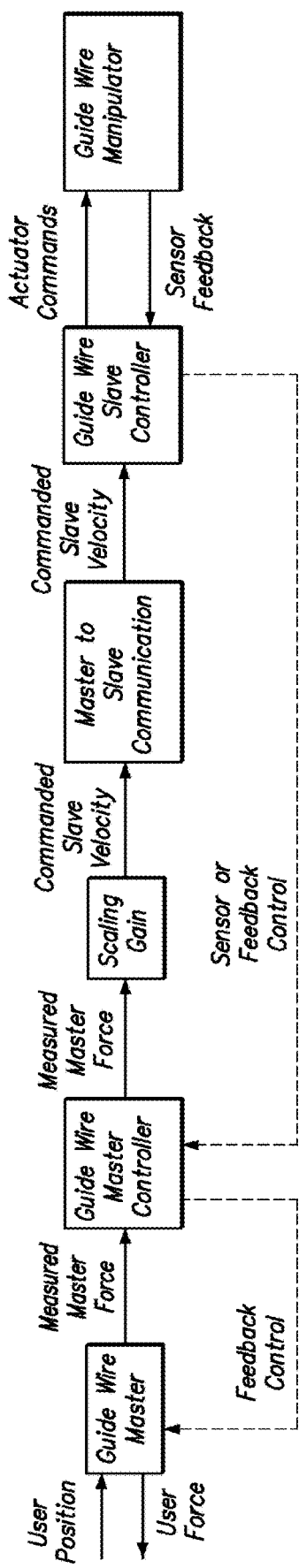
Figure 118D:
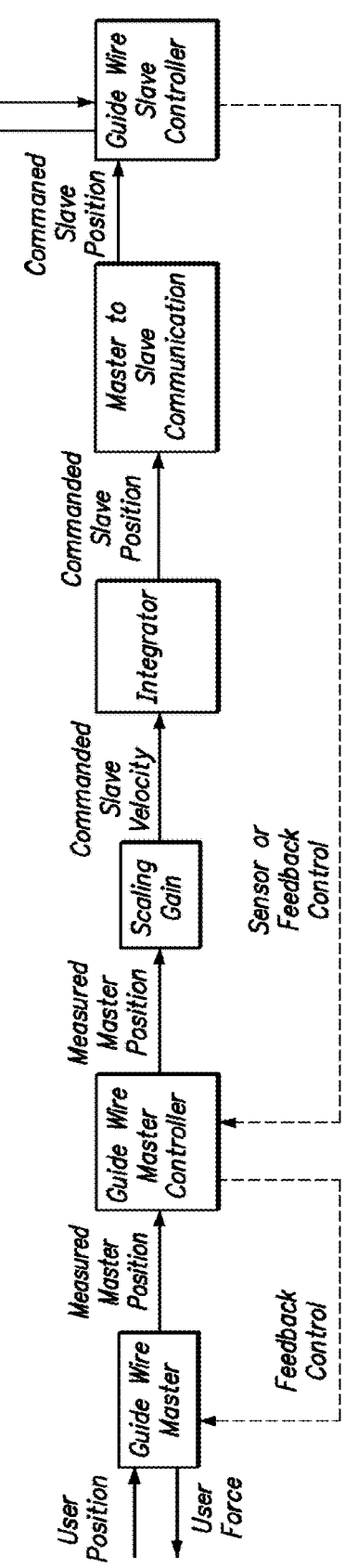

FIG. 117DD shows another variation where the rail itself is constructed out a series of rollers so that it can be spun to control the roll of the guide wire. FIG. 117E shows a control plate mounted to a 2-DOF (pitch-roll) rotation platform. This control plate could be manipulated by the physician with either their hand or foot providing pitch motion to control insert or retraction and rolling motion to control guide wire roll. FIGS. 117F and 117FF show linear sliders (with an optional engage button) that can be used to control one DOF of the elongate member manipulator. FIG. 117G shows a touchpad device that could be used to control the guide wire manipulator. Moving the user's finger forwards/backwards would control insertion of the guide wire and moving the user's finger side-to-side would control roll of the guide wire manipulator. Alternatively a trackball could be used in a similar fashion (not shown). FIG. 117H shows a "clothes-line" type configuration of a wire or cable looped around several pulleys. The user could directly insert, retract and/or roll this wire by hand or through the use of an optional wire torque device to allow for easier gripping of the wire. FIG. 117I shows a wide variety of buttons that could be used alone or in combination to control the guide wire manipulation device. Various methods of use of such buttons will be described in detail later. FIG. 117J shows a wrist-mounted master input device. FIG. 117K shows a hand-held inertial master input device. FIG. 117L shows a master input device that is manipulated by inserting, retractiong and/or rolling the operator's finger. FIG. 117M shows a haptic feedback master. The user manipulates the master by inserting, retracting and/or rolling it. The master is mounted to a compartment that contains sensors and motors. The master could be free to slide, spring loaded, or fixed. The active master may sense input and provide feedback to the user via motors under servo control.

The input devices may measure a signal from the operator and map this signal into a command to the slave such as the elongate member manipulator. Input devices on the master side may measure various different types of signals including but not limited to force, position, velocity, acceleration, or discrete events such as buttons presses. These measured signals could be converted into commands in the form of force, position, velocity, acceleration, or a higher level task. A few combinations of various input signals to commands will be discussed further using the elongate member manipulator as the slave however it should be understood that these variations will be presented by way of example and not limitation. Any combination of the aforementioned signals and commands could be implemented including types of comparable signals and commands that are not explicitly mentioned but are well known in the art. Additionally, any slave mechanism could be commanded including but not limited to the mechanisms actuating the guide catheter, sheath catheter, and instrument driver.

FIG. 118$a$-$d$ illustrates flow diagrams of the various master-slave control mapping options. FIG. 118$a$ illustrates one variation where a position signal is measured from the input master device and a position command is sent to the slave. Motions of the master are translated into motion commands and sent to the slave in a one to one motion in one variation while in an alternative variation the motion command could be subject to a scaling factor or more complex mapping function in a manner described in detail in the aforementioned incorporated references. In some instances the elongate member manipulator has a very large range of motion which may require either the input device to have a comparably large workspace or the input device to have clutching capability allowing it to clutch to different portions of the of the slave workspace. In an alternative variation shown in FIGS. 118$b$ and 118$d$, a position signal is measured from the input master device and a velocity command is sent to the slave. This typically involves a master device that is spring-loaded to return to its zero position such that when the user releases, the master returns to zero and the slave stops moving. This approach has the advantage of using a master with a relatively small range of motion to control a very large (up to infinite) range of motion on the slave. In FIG. 118$b$ the slave is controlled using velocity commands while in FIG. 118$d$ the slave is controlled using position commands. FIG. 118$d$ further illustrates a variation where position sensors on the guide wire manipulator itself are used for closed loop iterative control of the guide wire manipulator in order to more accurately position the guide wire manipulator. In yet another variation shown in FIG. 118$c$, a force signal is measured from the input master device and a velocity command is sent to the slave such that a higher force measurement will result in an increased velocity of the slave. Using a device such as the buttons on the MID handle as illustrated in FIG. 117CC for example, the harder the operator pushes on the button, the faster the elongate member manipulator inserts/rolls. When the operator is not exerting any force, the slave remains still. This configuration allows for a master with a small (near zero) range of motion to control a very large (up to infinite) range of motion on the slave. In further variations, multiple types of input signals can be combined so that arbitrarily complex dynamics between the master and slave can be introduced.

Another configuration may use discrete events such as but not limited to a button press or activation of a switch as an input to the master sending a specified task to the slave. Various types of buttons may be used, as illustrated in FIG. 117J. In this configuration, a button press of one or several different buttons can be used to command the execution of a potentially complex task. In one example for one degree of freedom, holding down of a single first button may cause a motion in a pre-defined direction at a pre-defined speed and release of the button would cease motion. A second button could be used in same manner to cause motion in an opposite direction at the same pre-defined speed. Using the elongate member manipulator as an example, holding down the first button may cause the elongate member to be inserted at a set speed until the user releases the button. Holding down the second button may cause the elongate member to be retracted at the same speed until the button is released. A second pair of buttons could be used for roll in the clockwise and counterclockwise directions. Alternatively, the same configuration could be used where a first single button push may start motion and a second push may stop motion or one button could start motion and a second button could stop motion. In another variation, a button push could cause the elongate member manipulator to move in a pre-determined direction, by a pre-determined amount, at a pre-determined speed. The pre-determined amount could be a set distance or a distance based on a relative position of the elongate member, for example, distance from the elongate member to tissue or distance to the end of a guide catheter if the elongate member was traveling co-axially down the lumen of said guide catheter. Alternatively, the speed could be based on the duration of time a button is pushed such that as the button is held longer, the speed gradually increases or after being pushed for a fixed duration of time, the speed increases from one predetermined amount to another. Alternatively, the movement could be based on a pre-determined force, for example the elongate member may insert until it makes contact with an object and a pre-set threshold of distal tip force is reached.

Multiple combinations of buttons, switches, and other types of on/off input devices could be used with multiple combinations of elongate member movement. It should be understood that the aforementioned combinations are by way of example and not limitation and any combination of inputs to motion including equivalents well known in the art may be used.

In the variation shown in FIGS. 1-2 which includes the operator workstation 22, the controller 55, and the instrument driver 16, the operator workstation includes the input controls in the form of a joystick type master input device 1212 and pendant 8. This variation may be used in a configuration shown in FIG. 119 which displays the sheath catheter assembly 1040, the guide catheter assembly 1050, and the elongate member manipulator 1300 mounted to the instrument driver 1016 with an elongate member in the form of a guide wire 1060 loaded in the elongate member manipulator 1300. The guide wire 1060 is sized to be inserted co-axially into the lumen of the guide catheter 1054, which in turn is sized to be inserted co-axially into the lumen of the sheath catheter 1044.

As previously described, the two degrees by which an elongate member, such as a guide wire 1060 may be manipulated using the elongate member manipulator 1300 are insertion/retraction and roll. Due to the remote nature of a catheterization treatment, the elongate member manipulator 1300 will be located a large distance from the tip of the guide catheter 1054. The insert function assumes the guide wire has high axial stiffness relative to frictional forces between the guide wire and the inner wall of the guide catheter 1054 as well as forces due to contact with tissue. Thus moving the wire a certain distance proximally should correspond directly to motion distal to the catheter tip. FIG. 120 illustrates a control scheme for control of the elongate member manipulator 1300. The control scheme is a more generalized version of the previously described control schemes shown in FIGS. 118A-D. In FIG. 120, the elongate member manipulator inserts and rolls a guide wire according to commands from a master input device. In the currently described variation, the master input device is the joystick and control console. The controller translates the desired actions into voltages and currents which are applied to the guide wire manipulator motor.

As described in detail in the aforementioned incorporated references, both the sheath catheter assembly 1040 and guide catheter assembly 1050 may be mounted on separate carriages that are motor actuated to provide a propelling motion in the insert and retract directions of the guide catheter 1054 and sheath catheter 1044. In one variation, the elongate member manipulator 1300 is fixably mounted to the same carriage as the guide catheter assembly 1050. By mounting the elongate member manipulator in this fashion, buckling of the guide wire can be minimized by locating the elongate member manipulator 1300 as close to the proximal end of the guide catheter 1054 as possible and/or maintaining a constant gap between the elongate member manipulator 1300 and guide catheter 1054 proximal end. The constant gap also avoids an inadvertent collision between the elongate member manipulator 1300 and guide catheter assembly 1050. FIGS. 121A-B illustrate a block diagram showing a variation where an elongate member manipulator 1300 is coupled to the guide catheter assembly 1050 and the sheath catheter assembly 1040. The sheath catheter assembly 1040 may be independently actuated in the insert and retract direction from the guide catheter assembly 1050 and the elongate member manipulator 1300. The elongate member manipulator 1300 and guide catheter assembly may be coupled to the same carriage and thus are inserted or retracted on that carriage simultaneously.

An example of a controls scheme will be described herein for this configuration of a guide wire, guide catheter, and sheath catheter. A guide wire is a thin flexible elongated rod. In one example, the guide wire is sized at roughly half a millimeter in diameter and about a meter long used during non-invasive vascular catheterization procedures, generally for medical treatment. It typically has an extremely flexible distal tip which prevents interaction trauma by deflecting against tissue rather than scraping or piercing tissue when inserted through a patient's vasculature. One possible mode of operation for use of a guide wire includes positioning the guide wire, holding it in a statically fixed position, and then sliding a catheter over the guide wire. When the guide wire is used in conjunction with the robotically steerable guide catheter 1054 and sheath catheter 1044 as in this variation, it is convenient for the operator to have the guide wire be controllable by the robotic system to allow for coordinated motion of the elongate member manipulator 1300 with the guide catheter 1054 and sheath catheter 1044. FIG. 122 shows a controller flow diagram for the construction of a movable carriage and a coupled elongate member manipulator as shown in FIG. 121B. The desired action from the master device is coordinated with the actions of other instrument driver 1016 axes to create a joint command for the insert/retract and roll motors. Finally, these commands are applied to the elongate member manipulator motors with a servo controller to achieve the desired position.

Because the guide catheter assembly 1050 is coupled to the elongate member manipulator 1300, as the guide catheter is inserted, the guide wire is inserted an identical distance. In order to maintain a static position of the guide wire 1060 while sliding the guide catheter 1054 over the guide wire 1060, the guide wire may be retracted an equal distance using the guide wire manipulator actuation previously described and shown in FIG. 120. FIG. 121A shows the insert distances traveled as, $x_S$, $x_G$, and $x_{wd}$. Where:

$x_S$=insert distance for sheath catheter
$x_G$=insert distance for guide catheter
$x_{wd}$=insert distance for guide wire In order for the position of the guide wire 1060 to remain constant such that the guide wire 1060 is static, $\Delta x_{wd}=0$ and the commanded guide wire position ($x_{wp}$) can be represented as:

$$x_{wp}=x_{wd}-x_G \quad (1)$$

The movement of the sheath catheter is independent of the guide carriage so is not included in this calculation.

In another variation shown in FIG. 121B, the elongate member manipulator 1300 and guide catheter assembly 1050 can be mounted to the same carriage as the sheath catheter assembly 1040. Thus as the sheath catheter 1044 is inserted, the guide catheter 1054, and guide wire 1060 are inserted the same amount. Additionally, if the guide carriage is independently inserted, the guide catheter 1054 and guide wire 1060 are independently inserted a separate amount. Thus in order for the position of the guide wire 1060 to be static, $\Delta x_{wd}=0$ and the commanded guide wire position ($x_{wp}$) can be represented as:

$$x_{wp}=x_{wd}-x_G-x_S \quad (2)$$

In one variation, the elongate member manipulator may not retract the guide wire behind the distal tip of the guide catheter such that the guide wire will be immediately available for guiding when desired by the operator. If the guide wire is retracted within the catheter tip, it will need to recover this distance before being available to the physician. This requires the actual guide wire insert position, and guide catheter insert position to be known relative to one another and controlled precisely. Various sensors have been previously described to measure insert of both the guide catheter and the guide wire.

Static friction between the guide wire and the guide catheter can impede distal rotational motion of the guide wire when the proximal end is rolled. Because of the moderate torsional stiffness of guide wires, there can be multiple revolutions of angular difference between the distal and proximal ends of the wire just due to frictional forces. Once the static friction releases, the wire may rotate rapidly until friction stops the motion again creating an undesirable whipping motion. One method of overcoming the static portion of friction is to dither the guide wire insertion while rolling by using the propelling actuation provided by the elongate member manipulator to repeatedly insert and retract the guide wire 1060 a small distance. The axial stiffness will translate motion through the length of the wire and proximal rotation should translate more directly to distal rotation. The dithering motion could be configured to avoid inserting the wire past the point commanded by the operator during the insert dithering.

Manually operated guide wires include an inherent feedback to the operator as resistance to insert and roll felt by the operator's hands. Thus it could be desirable to provide feedback to the operator during robotic control. Feedback could include but not be limited to visual, audible and haptic feedback. Live fluoroscopic images showing the location of the guide wire and catheters relative to patient anatomy could be provided on the display as well as a virtual guide wire image. By monitoring the position of the guide wire in relation to the position of the catheter, i.e. registering the guide wire to the catheter frame, the guide wire position may be displayed. One method of determining relative positions would be to display a virtual wire extended beyond the catheter tip, to scale with the virtual diameters. A numerical distance could replace or accompany such a display. Also, the virtual wire could be striped or otherwise patterned to indicate movement as displayed in FIG. 123. Another method of registration could include the use of position sensors including but not limited to EM or fiber sensors as described in detail in the aforementioned incorporated references.

As previously described, insert force can be measured by the elongate member manipulator. Measured force may be simply displayed for the operator to see how much force the manipulator is applying to move the wire. Further, if the wire inputs are provided with a haptic device, this force could be conveyed to the operator in a way such as with a direct force resistance in the haptic device or with a vibration proportional to force. The force may also be used to detect anomalous insertion conditions in order to avoid or compensate. High insertion forces may cause the wire to buckle between the manipulator and catheter. When force exceeds a threshold, the insertion should be halted to avoid buckling or abrading the surfaces of the wire or catheter. Force may also be used to scale motion in an analog manner. For example, slave motion may correspond directly to master commands, so the master motion may be de-scaled to result in less slave motion as described in detail in aforementioned incorporated references.

Additionally, any feedback sensors including but not limited to position, force, and encoders including redundant encoders as well as kinematic data for commanded guide wire position can all be continuously monitored to detect errors if there is a data mismatch.

The above variations of systems and manipulators may be used with guide wires and/or any other elongate member or instrument.

IX. Instinctive Drive

Referring to FIG. 128A, an overview of an embodiment of a controls system flow is depicted. A master computer 2400 running master input device software, visualization software, instrument localization software, and software to interface with operator control station buttons and/or switches is depicted. In one embodiment, the master input device software is a proprietary module packaged with an off-the-shelf master input device system, such as the Phantom™ from Sensible Devices Corporation, which is configured to communicate with the Phantom™ hardware at a relatively high frequency as prescribed by the manufacturer. Other suitable master input devices are available from suppliers such as Force Dimension of Lausanne, Switzerland. The master input device 12 may also have haptics capability to facilitate feedback to the operator, and the software modules pertinent to such functionality may also be operated on the master computer 2400. Preferred embodiments of haptics feedback to the operator are discussed in further detail below.

The term "localization" is used in the art in reference to systems for determining and/or monitoring the position of objects, such as medical instruments, in a reference coordinate system. In one embodiment, the instrument localization software is a proprietary module packaged with an off-theshelf or custom instrument position tracking system, such as those available from Ascension Technology Corporation, Biosense Webster, Inc., Endocardial Solutions, Inc., Boston Scientific (EP Technologies), Medtronic, Inc., and others. Such systems may be capable of providing not only real-time or near real-time positional information, such as X-Y-Z coordinates in a Cartesian coordinate system, but also orientation information relative to a given coordinate axis or system. Some of the commercially-available localization systems use electromagnetic relationships to determine position and/or orientation, while others, such as some of those available from Endocardial Solutions, Inc.—St Jude Medical, utilize potential difference or voltage, as measured between a conductive sensor located on the pertinent instrument and conductive portions of sets of patches placed against the skin, to determine position and/or orientation. Referring to FIGS. 128B and 128C, various localization sensing systems may be utilized with the various embodiments of the robotic catheter system disclosed herein. In other embodiments not comprising a localization system to determine the position of various components, kinematic and/or geometric relationships between various components of the system may be utilized to predict the position of one component relative to the position of another. Some embodiments may utilize both localization data and kinematic and/or geometric relationships to determine the positions of various components.

As shown in FIG. 128B, one preferred localization system comprises an electromagnetic field transmitter 2406 and an electromagnetic field receiver 2402 positioned within the central lumen of a guide catheter 2090 (which may be one or more of the embodiments of the catheter described herein). The transmitter 2406 and receiver 2402 are interfaced with a computer operating software configured to detect the position of the detector relative to the coordinate system of the transmitter 2406 in real or near-real time with high degrees of accuracy. Referring to FIG. 128C, a similar embodiment is depicted with a receiver 2404 embedded within the guide catheter 2090 construction. Preferred receiver structures may comprise three or more sets of very small coils spatially configured to sense orthogonal aspects of magnetic fields emitted by a transmitter. Such coils may be embedded in a custom configuration within or around the walls of a preferred catheter construct. For example, in one embodiment, two orthogonal coils are embedded within a thin polymeric layer at two slightly flattened surfaces of a catheter 2090 body approximately ninety degrees orthogonal to each other about the longitudinal axis of the catheter 2090 body, and a third coil is embedded in a slight polymer-encapsulated protrusion from the outside of the catheter 2090 body, perpendicular to the other two coils. Due to the very small size of the pertinent coils, the protrusion of the third coil may be minimized. Electronic leads for such coils may also be embedded in the catheter wall, down the length of the catheter body to a position, preferably adjacent an instrument driver, where they may be routed away from the instrument to a computer running localization software and interfaced with a pertinent transmitter.

In another similar embodiment (not shown), one or more conductive rings may be electronically connected to a potential-difference-based localization/orientation system, along with multiple sets, preferably three sets, of conductive skin patches, to provide localization and/or orientation data utilizing a system such as those available from Endocardial Solutions—St. Jude Medical. The one or more conductive rings may be integrated into the walls of the instrument at various longitudinal locations along the instrument, or set of instruments. For example, a guide instrument may have several conductive rings longitudinally displaced from each other toward the distal end of the guide instrument, while a coaxially-coupled sheath instrument may similarly have one or more conductive rings longitudinally displaced from each other toward the distal end of the sheath instrument—to provide precise data regarding the location and/or orientation of the distal ends of each of such instruments.

Referring back to FIG. 128A, in one embodiment, visualization software runs on the master computer 2400 to facilitate real-time driving and navigation of one or more steerable instruments. In one embodiment, visualization software provides an operator at an operator control station, such as that depicted in FIG. 1, with a digitized "dashboard" or "windshield" display to enhance instinctive drivability of the pertinent instrumentation within the pertinent tissue structures. Referring to FIG. 128D, a simple illustration is useful to explain one embodiment of a preferred relationship between visualization and navigation with a master input device 12. In the depicted embodiment, two display views 2410, 2412 are shown. One preferably represents a primary 2410 navigation view, and one may represent a secondary 2412 navigation view. To facilitate instinctive operation of the system, it is preferable to have the master input device coordinate system at least approximately synchronized with the coordinate system of at least one of the two views. Further, it is preferable to provide the operator with one or more secondary views which may be helpful in navigating through challenging tissue structure pathways and geometries.

Using the operation of an automobile as an example, if the master input device is a steering wheel and the operator desires to drive a car in a forward direction using one or more views, his first priority is likely to have a view straight out the windshield, as opposed to a view out the back window, out one of the side windows, or from a car in front of the car that he is operating. The operator might prefer to have the forward windshield view as his primary display view, such that a right turn on the steering wheel takes him right as he observes his primary display, a left turn on the steering wheel takes him left, and so forth. If the operator of the automobile is trying to park the car adjacent another car parked directly in front of him, it might be preferable to also have a view from a camera positioned, for example, upon the sidewalk aimed perpendicularly through the space between the two cars (one driven by the operator and one parked in front of the driven car), so the operator can see the gap closing between his car and the car in front of him as he parks. While the driver might not prefer to have to completely operate his vehicle with the sidewalk perpendicular camera view as his sole visualization for navigation purposes, this view is helpful as a secondary view.

Referring still to FIG. 128D, if an operator is attempting to navigate a steerable catheter in order to, for example, contact a particular tissue location with the catheter's distal tip, a useful primary navigation view 2410 may comprise a three dimensional digital model of the pertinent tissue structures 2414 through which the operator is navigating the catheter with the master input device 12, along with a representation of the catheter distal tip location 2416 as viewed along the longitudinal axis of the catheter near the distal tip. This embodiment illustrates a representation of a targeted tissue structure location 2418, which may be desired in addition to the tissue digital model 2414 information. A useful secondary view 2412, displayed upon a different monitor, in a different window upon the same monitor, or within the same user interface window, for example, comprises an orthogonal view depicting the catheter tip representation 2416, and also perhaps a catheter body representation 2420, to facilitate the operator's driving of the catheter tip toward the desired targeted tissue location 2418.

In one embodiment, subsequent to development and display of a digital model of pertinent tissue structures, an operator may select one primary and at least one secondary view to facilitate navigation of the instrumentation. By selecting which view is a primary view, the user can automatically toggle a master input device 12 coordinate system to synchronize with the selected primary view. In an embodiment with the leftmost depicted view 2410 selected as the primary view, to navigate toward the targeted tissue site 2418, the operator should manipulate the master input device 12 forward, to the right, and down. The right view will provide valued navigation information, but will not be as instinctive from a "driving" perspective.

To illustrate: if the operator wishes to insert the catheter tip toward the targeted tissue site 2418 watching only the rightmost view 2412 without the master input device 12 coordinate system synchronized with such view, the operator would have to remember that pushing straight ahead on the master input device will make the distal tip representation 2416 move to the right on the rightmost display 2412. Should the operator decide to toggle the system to use the rightmost view 2412 as the primary navigation view, the coordinate system of the master input device 12 is then synchronized with that of the rightmost view 2412, enabling the operator to move the catheter tip 2416 closer to the desired targeted tissue location 2418 by manipulating the master input device 12 down and to the right.

Instinctive drive techniques have been described in U.S. patent application Ser. No. 11/176,598, filed on Jul. 6, 2005, the entire disclosure of which is expressly incorporated by reference herein for all purposes.

The synchronization of coordinate systems described herein may be conducted using fairly conventional mathematic relationships. For example, in one embodiment, the orientation of the distal tip of the catheter may be measured using a 6-axis position sensor system such as those available from Ascension Technology Corporation, Biosense Webster, Inc., Endocardial Solutions, Inc., Boston Scientific (EP Technologies), and others. A 3-axis coordinate frame, C, for locating the distal tip of the catheter, is constructed from this orientation information. The orientation information is used to construct the homogeneous transformation matrix, $T_{C0}^{G0}$, which transforms a vector in the Catheter coordinate frame "C" to the fixed Global coordinate frame "G" in which the sensor measurements are done (the subscript $C_0$ and superscript $G_0$ are used to represent the O'th, or initial, step). As a registration step, the computer graphics view of the catheter is rotated until the master input and the computer graphics view of the catheter distal tip motion are coordinated and aligned with the camera view of the graphics scene. The 3-axis coordinate frame transformation matrix $T_{Gref}^{G0}$ for the camera position of this initial view is stored (subscripts $G_{ref}$ and superscript $C_{ref}$ stand for the global and camera "reference" views). The corresponding catheter "reference view" matrix for the catheter coordinates is obtained as:

$$T_{Cref}^{C0} = T_{G0}^{C0} T_{Gref}^{G0} T_{Cref}^{Gref} = (T_{C0G0})^{-1} T_{Gref}^{G0} T_{C1}$$

Also note that the catheter's coordinate frame is fixed in the global reference frame G, thus the transformation matrix between the global frame and the catheter frame is the same in all views, i.e., $T_{C0}^{G0} = T_{Cref}^{Gref} = T_{Ci}^{Gi}$ for any arbitrary view i. The coordination between primary view and master input device coordinate systems is achieved by transforming the master input as follows: Given any arbitrary computer graphics view of the representation, e.g. the i'th view, the 3-axis coordinate frame transformation matrix $T_{Gi}^{G0}$ of the camera view of the computer graphics scene is obtained from the computer graphics software. The corresponding catheter transformation matrix is computed in a similar manner as above:

$$T_{Ci}^{C0} = T_{G0}^{C0} T_{Gi}^{G0} T_{Ci}^{Gi} = (T_{C0}^{G0})^{-1} T_{Gi}^{G0} T_{Ci}^{Gi}$$

The transformation that needs to be applied to the master input which achieves the view coordination is the one that transforms from the reference view that was registered above, to the current ith view, i.e., $T_{Cref}^{Ci}$. Using the previously computed quantities above, this transform is computed as:

$$T_{Cref}^{Ci} = T_{C0}^{Ci} T_{Cref}^{C0}$$

The master input is transformed into the commanded catheter input by application of the transformation $T_{Cref}^{Ci}$. Given a command input $$r_{master} = \begin{bmatrix} x_{master} \\ y_{master} \\ z_{master} \end{bmatrix},$$

one may calculate:

$$r_{catheter} = \begin{bmatrix} x_{catheter} \\ y_{catheter} \\ z_{catheter} \end{bmatrix} = T_{Cref}^{Ci} \begin{bmatrix} x_{master} \\ y_{master} \\ z_{master} \end{bmatrix}.$$

Under such relationships, coordinate systems of the primary view and master input device may be aligned for instinctive operation.

In one or more of the embodiments, the user interface of the robotic system may be configured to allow a user to register (or align) a real image of a catheter (e.g., a fluoroscopic image) with an image of a computer model of the catheter. This results in the real image catheter being in a same orientation as that of the model image, thereby allowing a user to instinctively drive the catheter (e.g., so that a command to move the catheter model to the right will result in the catheter moving to the right in the reference frame of the real image). The model image may be generated using different techniques in different embodiments. In some embodiments, the model image may be generated by a processor using kinematic information (e.g., stress, strain, curvature, amounts of tensions in respective pull wires inside the catheter, etc.) regarding the catheter. In other embodiments, the model image may be generated using a light signal transmitted through a fiber optic that extends along a length of the catheter. Techniques for determining a geometric configuration of an elongated member using light transmitted through a fiber optic have been describe in U.S. patent application Ser. No. 14/690,116, filed on Mar. 22, 2007, now abandoned, the entire disclosure of which is expressly incorporated by reference herein. In further embodiments, the model image of the catheter may be generated (e.g., by a processor) based at least in part on localization data obtained from electromagnetic sensors. Electromagnetic sensors for obtaining localization data for a medical device are well known in the art, and therefore, will not be described in detail herein.

The act of registration (or alignment) between a real image of the device and a model image may be carried out in different manners in different embodiments. For example, in some embodiments, an alignment process may be performed, wherein the user adjusts one or a few inputs to line up a graphic on screen with a fluoro image of the actual catheter. In one such embodiment, the user can adjust one slider on a touchscreen (or a control at a station) to rotate a virtual representation of the catheter within the plane of the fluoro image to align its heading direction at a prescribed location (e.g., location of a control ring in the leader) to that of the real catheter in the fluoro image, and a second slider (or a second control at the station) to rotate the virtual catheter in or out of plane to align its tilt angle to that of the real catheter. In order to align the roll angle, the user may put a slight bend on the catheter (e.g., so that a length of the catheter may appear as a straight line when looking from a proximal or distal end) and rotate it until the bend is aligned with a bend of an actual catheter. For example, the virtual representation of the catheter (in a bent configuration) may be moved using a control (e.g., slider in a touch screen) to align its roll with a roll of the actual catheter that also has a bent configuration. In further embodiments, instead of rotating the catheter, in order to avoid unnecessary catheter movements inside the body, the user may rotate the fluoro C-arm until the catheter bend is in the imaging plane, pointing either to the left or right in that plane. Variations on this process include using other user interfaces or input devices, such as using the trackball on the pendant instead of touchscreen sliders to align the heading and/or tilt angles of the catheter. In further embodiments, the alignment process described above may not be needed. For example, in some cases, if localization information for the catheter is available, then the alignment process may not be performed (unless the localization is imperfect and needs to be adjusted).

Referring back to embodiment of FIG. 128A, the master computer 2400 also comprises software and hardware interfaces to operator control station buttons, switches, and other input devices which may be utilized, for example, to "freeze" the system by functionally disengaging the master input device as a controls input, or provide toggling between various scaling ratios desired by the operator for manipulated inputs at the master input device 12. The master computer 2400 has two separate functional connections with the control and instrument driver computer 2422: one 2426 for passing controls and visualization related commands, such as desired XYZ (in the catheter coordinate system) commands, and one 2428 for passing safety signal commands. Similarly, the control and instrument driver computer 2422 has two separate functional connections with the instrument and instrument driver hardware 2424: one 2430 for passing control and visualization related commands such as required-torque-related voltages to the amplifiers to drive the motors and encoders, and one 2432 for passing safety signal commands.

In some cases, during use of the robotic system, it may or may not be possible to place the catheter at a desired position, depending on how the catheter is driven. This may be illustrated in the example shown in FIGS. 128E and 128F. The catheter tip is shown in a same Cartesian position relative to a reference frame (which may be a distal tip of the sheath, or any location along a length of the catheter or the sheath) in both FIGS. 128E and 128F, while in very different joint configurations. If the catheter were in the configuration shown in FIG. 128E, and the user wants to reach a position incrementally to the left of the catheter tip, but the catheter is already at its maximum articulation, then the desired position of the catheter tip could not be achieved by incrementally moving the tip of the catheter to the left. However, because the desired position is still in the overall workspace, it could be achieved by decreasing the articulation of the catheter, and the insertion, in order to achieve the configuration shown in FIG. 128F. In one approach, an extra constraint is added, such as by keeping a constant catheter insertion. In this approach, the user is haptically constrained to the surface of a "dome", as shown in FIG. 128G, and may orient the catheter but not insert or deinsert it. In this implementation, a proxy position is computed using the haptic implicit-surface (e.g., a cardiod-shaped implicit surface intersected with a plane) proxy algorithm, and a force is returned based on a vector between the device position and the proxy position regardless of whether the device position is inside or outside of the implicit surface. In some embodiments, an artificial limit (e.g., a prescribed velocity limit) for the commanded catheter's articulation motion may be provided to prevent the catheter from moving faster than the robot can command/control it. The difference in position between the proxy and the catheter may then be use to provide force feedback that the user is trying to move the catheter too quickly.

In some embodiments, a two-handed driving technique may be provided, in which the user may insert or deinsert the catheter using a first control (e.g., a pendant button), and orient (e.g., steer) it using a second control (e.g., IMC). The two controls may be configured to allow the user to operate them simultaneously, or one after the other. In one implementation, the user interface is configured to allow the user to control both the pendant-based insertion and the IMC-based orientation simultaneously. In another embodiment, two functional modes for IMC driving may be provided. In one mode, the user orients the catheter as previously described. In the other mode, the user may insert or deinsert the catheter by pushing against the haptic constraint(s). In some cases, the IMC is haptically constrained to a line when in this operation mode because the user may "slip" along the convex top of the dome when trying to push inward to de-insert the catheter.

In other embodiments, a haptic "divot" may be placed in the workspace when de-inserting. Various techniques may be used to allow switching between the different modes. For example, in some embodiments, when clutching the IMC, the user may start out in the orientation mode, but when the force applied against the workspace exceeds a certain threshold, the user may be switched into the insert-deinsert mode. In other embodiments, the mode may be controlled by a secondary IMC button or a foot pedal or a pendant button.

In some embodiments, as the user is driving the catheter using the robotic system, the user interface displays an image of the catheter (which may be a real image, or a computer generated model), and the haptic dome of FIG. 27 that follows the distal end of the catheter. The dome represents a constraint for the distal end of the catheter so that at least a part (e.g., the distal tip) of the distal end of the catheter is required to be on an outline of the dome regardless of how the catheter is driven. For example, in one implementation, the user interface provides a first control for allowing the user to advance or retract the catheter, and a second control for allowing the user to steer the catheter. In such cases, if the user attempts to advance or retract the catheter, the tip of the catheter will be constrained to follow the outline of the dome. As a result, the tip of the catheter may "slide" along the outline of the dome in response to the command to advance or retract the catheter. Similarly, if the user attempts to steer the tip of the catheter, the tip of the catheter will also be constrained to follow the outline of the dome, thereby causing the tip of the catheter to "slide" along the outline of the dome in response to the command to steer the catheter. In some embodiments, advancement or retraction of the catheter will change the size of the doom as it is displayed in the screen, while a steering of the catheter will not change the size of the doom. In some embodiments, the dome may have a cardiod shape. In other embodiments, the dome may have other shapes. In some cases, the system is configured to also provide force feedback at the user interface for the user based on the haptic dome. For example, if the processor determines that a command for positioning (advancement, retraction, and/or steering) of the catheter may result in the distal tip of the catheter being away from the outline of the dome, then the user interface will provide a force feedback to indicate to the user that the tip of the catheter is being "pulled" or "compressed" by the outline of the dome. If the user "feels" a restraining force from the user interface as he/she is commanding the catheter to move, the image of the haptic dome will allow the user to see why that may be the case.

In some of the embodiments described herein, the system may also provide speed control for positioning the catheter so that the tip of the catheter cannot be positioned (e.g., advanced, retracted, and/or steered) too fast. In one implementation, a speed limit may be entered into the system. In such cases, if the user attempts to position the catheter in a way that exceeds the speed limit, the processor may control the positioning of the catheter so that it stays below the speed limit, and may cause the user interface to provide a tactile feedback indicating that the speed of the catheter is being controlled.

In some embodiments, the dome reflects the kinematic articulation workspace of the elongate member. The dome is not limited to any particular shape, and may have a cardioid shape, a spherical shape, a cone shape, or any of other shapes. In some embodiments, the dome shape may be user defined. In other embodiments, the dome shape may be determined by the processor. In one implementation, in order to calculate the shape of the dome, the software starts with a cardioid shape (or another arbitrary shape), then searches around that surface for the true limits of the reach by the elongate member.

X. Sterile Adaptor

As described in detail in application Ser. No. 12/614,349 issued as U.S. Pat. No. 8,720,448 on May 13, 2014, previously incorporated by reference, during surgical robotic procedures, common practice is to place a sterile drape over a robotic assembly such as the previously described instrument driver, then attach sterilized tools onto the robotic assembly over the drape. In this way, the robotic side of the drape is in a non-sterile environment while the surgical side is in a sterile environment. It is often desirable to remove a tool and replace it with an alternative tool which serves an alternative function, then exchange the tools again such that the original tool is replaced. However, once a tool is initially engaged onto the non-sterile robot, it breaks the sterile field making the tool non-sterile, preventing a user from re-installing it without re-sterilizing it. Thus in practice, a user must either sterilize a tool before re-installing it or must treat the tool as a disposable without the capability of re-installation. Re-sterilization is an impractical solution during a procedure and while a disposable tool can be sterilized and used on a later date, it could be costly to continue using new tools during the procedure. Additionally, liquids such as blood or saline are often spilled onto the drape during tool exchange. While tools are removed from anatomy, they are often contaminated with blood that spills specifically in the area where the tool is coupled to the robotic assembly. It is preferable that liquids do not leak into the robotic assembly which may cause a loss of functionality in the electro-mechanical assemblies within the robot. Thus an interface apparatus that prevents fluid ingress while transferring drive motion across a sterile barrier without breaking the sterile barrier may be desirable.

One variation of a drive interface apparatus is illustrated with reference to FIGS. 129a-129c. FIG. 129a illustrates a version of the previously described instrument driver 16 which includes a sheath output plate 3006 and guide output plate 3008. A sheath splayer 3003 and a guide splayer 3005 are each mounted indirectly to the sheath output plate 3006 and guide output plate 3008 respectively. It should be noted that the sheath and guide mounting plates along with the sheath and guide splayers are substantially similar in construction and functionality. By way of example, the sheath splayer and sheath output plate will be later described with the understanding that the same construction and functionality can apply to the guide splayer and guide output plate.

FIG. 129b shows a zoomed in view of a front portion of the instrument driver 16 better illustrating the sheath splayer 3003, a drive interface apparatus 3004, a drape assembly 1900, and the sheath output plate 3006. FIG. 129c illustrates an exploded view of the assembly of FIG. 129b. The sheath splayer 3003 is removably coupled to the interface apparatus 3004 which in turn is removably coupled to the sheath output plate 3006. The drape assembly 1900 is compressed between the drive interface apparatus 3004 and the sheath output plate 3006. For clarity, only portions of the drape assembly 1900 are shown. The full drape assembly 1900 will be described in detail later FIGS. 130a and 130b illustrate a top and bottom view respectively of a variation of the sheath output plate 3006. FIG. 130c illustrates a bottom exploded view of the sheath output plate 3006 which includes a base plate 3010, sliding latches 3012, four sliding springs 3014, and two retaining plates 3016. FIGS. 131a-b illustrates a top and bottom perspective view of the base plate 3010 which includes drive interface alignment holes 3026, contact pin holes 3028, cutouts 3018, latch walls 3020, and latch pins 3022. The sliding latches 3012 can fit into the cutout 3018 in the bottom of the base plate 3010 with the two sliding springs 3014 each compressed between a ridge of the sliding latch 3012 and the latch wall 3020 in the cutout 3018. The retaining plates 3016 can be fixed to the base plate 3010 with screws (not shown in the figures) holding the sliding latches 3012 and sliding springs 3014 in place. By way of example, the base plate 3010 can be made of 6061-T6 aluminum, the latches can be made of 316 stainless steel, and the retaining plates 3016 can be made of high hardness stainless steel.

FIG. 131c illustrates a variation of the guide output plate 3008 which can utilize an alternatively shaped guide output base plate 3024 configured to provide a mount for a clamp holding the handle of a working catheter. The main body 3025 of the guide output plate 3008 can remain substantially identical to that of the sheath output plate 3006. Thus the same type of spring loaded sliding latch mechanisms described for the sheath output plate 3006 can be used for the guide output plate 3008. For both the guide and sheath output plates 3008,3006 the sliding latches can be used to attach and detach the drive interface apparatus 3004 as will be described in detail later.

FIG. 132a-132b illustrate top and bottom perspective views of the drive interface apparatus 3004 while FIG. 132c illustrates an exploded view. The drive interface apparatus 3004 can include a drive interface base 3030, drive interface pulley shafts 3048, drive interface shaft pins 3050, conductive spring loaded EEPROM pins 3052, and a splash deflector 3054.

FIG. 133a-133b illustrates top and bottom perspective views of the drive interface base 3030 which includes top static latches 3032, bottom static latches 3034, pulley holes 3036, pin holes 3038, splayer holes 3040, and output plate alignment pins 3042. The top and bottom static latches 3032, 3034 can be non-adjustable, non-movable protrusions which as will be described in detail later could be used to lock the splayer 3002 to the drive interface apparatus 3004 and the drive interface apparatus 3004 to either the sheath or guide output plates 3006,3008. The splayer holes 3040 and output plate alignment pins 3042 can be used to help with installation of the drive interface apparatus 3004 and the sheath splayer 3003.

FIGS. 134a-134b illustrate top and bottom views of the drive interface base 3030 with the drive interface pulley shafts 3048 and EEPROM pins 3052 installed into the pulley holes 3036 and pin holes 3038 respectively. The bottom portions of drive interface pulley shafts 3038 and EEPROM pins 3052 protrude through the drive interface base 3030 while resting within the drive interface base 3030. Referring back to FIGS. 4132a and 132c, the splash deflector 3044 which is illustrated with cutouts that provide clearance for the top static latches 3032, drive interface pulley shafts 3048, and EEPROM pins 3052 can be installed onto the drive interface base 3030. The splash deflector 3044 not only provides for exclusion of debris and liquids but it also constrains the drive interface pulley shafts 3048 from movement in the vertical and horizontal plane while allowing free rotational movement about their respective axes.

FIG. 135a-135c illustrates perspective and zoomed in views of the drape assembly 1900. Among other components that operate with a guide wire manipulator which will be described later, the drape assembly includes a drape body 1901, a sheath foam pad 1902, a guide foam pad 1904, protective tabs 1906, and an alignment aid 1908. The sheath foam pad 1902 is similar in construction to the guide foam pad 1904, each provided with cutouts to mate with guide or sheath output plates 3008, 3006 as well as the drive interface apparatus 3004. The sheath and guide foam pads 1902, 1904 can be constructed from any number of compressible materials including but not limited to polyurethane foam while the protective tabs and alignment aid can be made of High-density polyethylene (HDPE). The drape body 1901 can be constructed of any type of sheer plastic including but not limited to polyethelene.

FIGS. 136a-b illustrate different types of splayers that may be used in conjunction with the previously described drive interface apparatus. FIG. 136a illustrates a perspective view of a variation of the sheath splayer 3003 while FIG. 136b illustrates a perspective view of a variation of the guide splayer 3005. The sheath splayer 3003 includes a splayer body 3002, a sheath active valve assembly 3080, a sheath anti-buckling interface 3074, and a sheath catheter 3000. The guide splayer 3005 includes a splayer body 3002, a guide flush assembly 3082, a guide anti-buckling interface 3076, and a guide catheter 3001.

Referring to FIG. 136c the sheath splayer 3003 is shown with a sheath cover 3062 exploded from the remaining components of the sheath splayer to illustrate how the sheath active valve 3080, sheath catheter 3000 and sheath anti-buckling interface 3074 are integrated with the splayer body 3002. The sheath splayer 3003 has a substantially identical splayer body 3002 to the guide splayer 3005 so integration of the guide flush assembly 3082, the guide anti-buckling interface 3076, and the guide catheter 3001 is similar.

Referring to FIG. 137a-c, the splayer body 3002 will be described in more detail. FIG. 137a illustrates a top perspective view, FIG. 137b illustrates a bottom perspective view, and FIG. 137c illustrates an exploded view. The splayer body 3002 can include a splayer base 3060, a splayer cover 3062, splayer pulley assemblies 3064, a splayer ID chip 3066, an ID chip cover 3070, a splayer presence magnet 3072, and splayer body screws 1073.

The splayer cover 3062 shown in FIG. 138 can include a pair of splayer latches 3084 coupled to pair of urethane based compliant members 3086 allowing the latches to be repositioned with applied manual forces. Perspective and exploded views of the splayer pulley assembly 3064 are illustrated in FIGS. 138a-138b respectively. The pulley assembly 3064 includes a pulley 3102, a set of outer races 3104, a set of ball cages 3110, a set of ball bearings 3108, and a set of retainer clips 3106. The pulley 3102 can be constructed of plastic and provided with an internal spline 3112 profile and with a feature 3114 for coupling with a pull wire crimp ball located at the end of a catheter pull wire or control wire (well known in the art and described in detail in applications previously incorporated by reference). The retainer clips 3106 fit onto the pulley 3102 to hold the crimp balls (not shown) and bearings 3108 in place. The inner races of the ball bearings are integrated into the pulley in order to achieve a low profile package and minimize assembly processes. The pull wire (not shown) is wound around the pulley 3102 and is run down the length of a catheter shaft as previously described. The splayer ID chip 3066 includes a pair of pogo pins 3068. The magnet can be constructed of various materials including but not limited to a single neodymium magnet. The splayer base 3060 illustrated in FIGS. 139a-b can be configured with pulley pockets 3092, an ID chip pocket 3094, a magnet pocket 3096, cover mounting holes 3090, and latch holes 3091. The bottom of the splayer base 3060 can also include splayer alignment pins 3088.

FIGS. 140a-b illustrate the splayer base 3060 with the splayer pulley assemblies 3064, splayer ID chip 3066, and splayer presence magnet 3072 installed. The splayer pulley assemblies 3064 rest within the pulley pockets 3092 in a manner that allows the each pulley 3102 to rotate about its own axis within the ball bearing 3108. The splayer presence magnet 3072 rests in the magnet pocket 3096. The ID chip pocket 3094 is sized to recess the ID chip 3094 allowing for a low overall splayer profile. The ID chip cover 3070 is installed over the splayer ID chip 3066, protecting the ID chip while allowing the pogo pins 3068 to protrude through. To hold the pulley assemblies 3064 in place, the splayer cover 3062 is mounted to the splayer base 3060 with the splayer body screws 3073 which fit through the cover mounting holes 3090. The splayer latches 3084 fit through the latch holes 3091, protruding out of the bottom of the splayer base 3060. While four pulley assemblies 3064 are illustrated, alternative variations can include any number of pulley assemblies 3064 leaving any number of pulley pockets 3092 empty. The ID chip 3094 is used to transfer device information to the instrument driver (not shown) while the presence magnet 3072 detects when the splayer 3003 is installed on the instrument driver.

Referring to FIG. 141a one method of installation of the drape assembly 1900 onto the instrument driver 16 is shown.

As shown in FIG. 141b the drape assembly 1900 is placed on top of the instrument driver 16 aligning the sheath foam pad 1902 and to the sheath output plate 3006 so that the holes in the foam pad 1902 line up with the holes in the output plate 3006. The same method can be performed for the guide foam pad 1904 and the guide output plate 3008.

A first and second drive interface apparatus can now be installed over the drape assembly 1900 onto the sheath output plate 3006 and guide output plate 3008. The following will illustrate a method of installation for the sheath output plate 3006 but it should be understood that substantially identical methods may be implemented for the guide output plate 3008. FIGS. 142a and 142b illustrate the drive interface apparatus 3004 uninstalled and installed respectively onto the instrument driver 16 with the drape assembly 1900 installed onto the sheath output plate 3006. FIGS. 143a-143c illustrate top and bottom views of only the sterile face apparatus 3004 uninstalled on the sheath output plate 3006 and drape assembly 1900. The drive interface apparatus 3004 can be installed over the sheath foam pad 1902 inserting the drive interface pulley shafts 3048 through the holes in the sterile drape foam pad 1902 and output plate 3006 as shown in FIG. 143. The foam pad 1902 is compressed between the drive interface apparatus and the output plates 3004, 3006 creating a seal preventing liquid ingress. The drive interface pulley shafts 3048 couple to the sleeve receptacles 56b by engaging the drive interface shaft pins 3050 into notches in the sleeve receptacles 56b as shown in FIGS. 144a-d. To aid in alignment of the drive interface apparatus 3004 with the sheath output plate 3006, the output plate alignment pins 3042 fit into the drive interface alignment holes 3026. As the drive interface apparatus 3004 is pressed down onto the output plate 3006, the ramped bottom static latches 3034 on the drive interface base 3030 force the spring loaded sliding latches 3012 apart allowing the bottom static latches to insert into the latch holes 3011. The sliding springs 3014 force the sliding latches apart locking the bottom static latches 3034 to the output plate 3006. The sliding springs 3014 are sized to compress easily enough to allow a one handed press installation of the drive interface apparatus 3004 while being strong enough to expand locking the static latches in place. To un-install the drive interface apparatus 3004 from the output plate 3006, the sliding latches 3012 on the output plate 3006 can be pressed towards the center of the output plate 3006, releasing the bottom static latches 3034 from the output plate 3006.

Once the drive interface apparatus is installed as described above, the guide or sheath splayer 3005, 3003 can be installed and easily uninstalled onto the drive interface apparatus 3004 without breaking the sterile barrier created by the sterile drape assembly 1900. Referring to FIG. 145a-b, one method of installation of the sheath splayer 3003 to the drive interface apparatus 3004 is shown. For clarity, the instrument driver and drape assembly are not shown. The sheath splayer 3003 can be installed to the drive interface apparatus 3004 coupling the splayer pulleys 3102 to the drive interface shafts 3048. The splayer pulleys 3102 are free to rotate within the splayer 3003 before installation onto the drive interface apparatus 3004. Once engaged with the drive interface pulley shafts 3048, the splayer pulley assemblies 3064 lock onto the drive interface pulley shafts 3048. The splayer pulleys 3102 are configured in a similar manner as VHS type with internal splines 3112 that are shaped to ensure consistent self alignment of the pulley 3102 to the interface pulley shaft 3048 and to aid in minimizing insertion and removal force of the splayer 3003 from the drive interface apparatus 3004 as shown in FIGS. 146a-b which illustrates top views of the splayer pulleys 3102 and the interface pulley shafts 3048. For further illustration, FIGS. 147a-b provide various perspective views of a single splayer pulley 3102 and interface pulley shaft 3048.

To aide in alignment of the sheath splayer to the drive interface apparatus, the splayer alignment pins 3088 on the bottom of the splayer 3003 can mate with the splayer holes 3040 on the drive interface apparatus 3004. To lock the splayer 3003 to drive interface apparatus 3004 force applied to the top of the splayer 3003 will force the splayer latches 3084 to displace until they lock with the top static latches 3032 on the drive interface apparatus. The spring force of the compliant members 3086 in the splayer cover 3062 force the splayer latches 3084 to return to their nominal positions locking the splayer latches 3084 to the top static latches 3032. In order to remove the splayer 3003 from the system, the splayer latches 3084 are compressed by squeezing either side of the splayer cover 3062, re-positioning the compliant members 3086 and releasing the splayer latches 3084 from the drive interface top static latches 3032.

Referring to FIGS. 148a-148b, the transfer of motion from the instrument driver 16 to the sheath splayer 3003 actuating bending of the sheath catheter 3000 will be shown. FIG. 148a-b illustrates a top and bottom view respectively of the instrument driver 16 with its cover removed. As previously described, various articulation mechanics 3029 including motors, pulleys belts and gears can drive the motorized rotation of sleeve receptacles 56b which couple to the drive interface pulley shafts 3048. As was illustrated in FIGS. 144a-16d, the drive interface pulleys shafts 3038 can each be provided with drive interface shaft pins 3040 that allow the shafts 3038 to be coupled to the sleeve receptacles 56b. In turn the splayer pulley assemblies 3064 couple to the drive interface pulley shafts 3038. Thus motorized rotation of the sleeve receptacles ultimately actuates rotation of the splayer pulley assemblies. As previously described, pull wires that run the length of the catheter are controlled by the rotation of the splayer pulley assemblies 3064 to actuate bending at the distal tips of the catheter.

FIGS. 148a-148b also illustrate the EEPROM pins 3052 of the drive interface apparatus 3004 which can pass through holes 3028 in the output plate 3006 in order to couple to a circuit mounted (not shown) beneath the output plate 3006. Once the splayer 3003 is installed, the pogo pins 3068 on the splayer ID chip 3066 make contact with the conductive contacts 3052 shown allowing the ID chip 3066 to connect to the circuit and transmit catheter parameter data to the robotic system. Also a splayer presence magnet 3072 shown in FIG. 9c is included on the splayer 3003 that is detected by a switch (not shown) on the instrument driver 16. The presence magnet 3072 can be sized appropriately for detection by a switch mounted within the instrument driver 16 through the drive interface apparatus 3004.

Referring back to FIGS. 135a-135c, the drape can be provided with protective tabs to prevent accidental removal of the drive interface apparatus during the removal of the splayer. As shown in FIG. 135b-135c, protective tabs 1906 can be provided on the drape body 1901 to cover the sliding latches 3012 on the output plate 3006 preventing the user from accidentally compressing the sliding latches 3006 during a procedure when the intention is to release the splayer latches 3084. The drape assembly 1900 also includes an alignment aid 1908 that may be used to aid in positioning of the instrument driver 16 to a patient entry site. When the instrument driver 16 is positioned near the patient, the alignment aid 1908 can be positioned such that its distal tip makes contact with the patient skin setting the distance between the instrument driver nose and the patient. The alignment aid 1908 can be configured such that its overall length is longer than the length of an anti-buckling mechanism (previously described) in its fully compressed state. Thus the distance between the instrument driver and patient will be sufficient to allow for installation of the anti-buckling device without causing undesired force of the anti-buckling device on the patient tissue. The alignment aid may also include an alignment line which coincides with the centerline of the instrument driver 16. The alignment line can be used as a visual aid in alignment of the instrument driver to an introducer or guide wire inserted in a patient vessel. Since the introducer or guide wire will tend to naturally align with the vessel, alignment of the instrument driver to the introducer or guide wire will help with better alignment with the patient vessel. The position of the instrument driver 16 can be saved in the system memory and the alignment aid can be removed from the drape for the remainder of the surgical procedure.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present application. Also, any of the features described herein with reference to a robotic system is not limited to being implemented in a robotic system, and may be implemented in any non-robotic system, such as a device operated manually.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that described herein (in which case what is present herein shall prevail). The referenced items are provided solely for their disclosure prior to the filing date of the present application. Nothing herein is to be construed as an admission that any claimed invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art in the field of this application.

Although particular embodiments have been shown and described, it will be understood that they are not intended to limit the claimed inventions, and it will be obvious to those skilled in the art having the benefit of this disclosure that various changes and modifications may be made. The specification and drawings are, accordingly, to be regarded in an illustrative rather than restrictive sense. The claimed inventions are intended to cover alternatives, modifications, and equivalents.

The invention claimed is:

1. A robotic medical system, comprising:
    a first elongate member defining a working lumen;
    a second elongate member at least partially surrounding the first elongate member and configured to move with the first elongate member in a telescoping configuration;
    at least one robotic driver configured to removably couple to the first and second elongate members, the at least one robotic driver configured to advance the first and second elongate members toward a target anatomy; and
    an energy delivery device configured to be delivered through the first and second elongate members via the working lumen, the energy delivery device being actuatable to treat the target anatomy.

2. The system of claim 1, wherein the first elongate member and the second elongate member are each independently actuatable by the at least one robotic driver.

3. The system of claim 1, wherein the energy delivery device is configured to be actuated manually by an operator and robotically by the at least one robotic driver.

4. The system of claim 1, wherein the first elongate member comprises a catheter and the second elongate member comprises a sheath.

5. The system of claim 1, wherein the first elongate member includes one or more pullwires to articulate a distal tip of the first elongate member.

6. The system of claim 5, wherein the second elongate member includes one or more pullwires to articulate a distal tip of the second elongate member.

7. The system of claim 1, wherein the at least one robotic driver comprises a drive assembly configured to advance the second elongate member distally relative to the first elongate member.

8. The system of claim 7, further comprising a sterile barrier between the drive assembly and at least one of the first elongate member or the second elongate member.

9. The system of claim 1, wherein the energy delivery device comprises a radiofrequency (RF) electrode, a laser, or an ultrasound device.

10. The system of claim 1, wherein the at least one robotic driver comprises a first splayer coupled to the first elongate member and a second splayer coupled to the second elongate member.

11. The system of claim 10, wherein the first splayer is coupled to a first set of motors and the second splayer is coupled to a second set of motors.

12. The system of claim 1, wherein the first elongate member and the second elongate member are each robotically controlled.

13. A robotic medical system, comprising:
    a first elongate instrument configured to be advanced toward a target anatomy;
    a second elongate instrument, wherein the first elongate instrument is positioned within the second elongate instrument and configured to move with the second elongate instrument in a telescoping configuration; and
    an energy delivery device configured to be delivered through the first and second elongate instruments, the energy delivery device being actuatable to treat the target anatomy.

14. The system of claim 13, further comprising at least one robotic instrument driver configured to removably couple to the first and second elongate instruments, the at least one robotic instrument driver configured to advance the first and second elongate instruments toward the target anatomy.

15. The system of claim 14, wherein the energy delivery device is configured to be actuated manually by an operator and robotically by the at least one robotic instrument driver.

16. The system of claim 14, wherein the at least one robotic instrument driver is configured to advance the second elongate instrument distally relative to the first elongate instrument.

17. The system of claim 13, wherein the first elongate instrument comprises a catheter and the second elongate instrument comprises a sheath.

18. The system of claim 13, wherein the energy delivery device comprises at least one of a radiofrequency (RF) electrode, a laser, or an ultrasound device.

19. A robotic medical system, comprising:

a robot;

an outer steerable instrument configured to be advanced by the robot towards a tissue structure within a patient;

an inner steerable instrument configured to be advanced by the robot towards the tissue structure within the outer steerable instrument in a telescoping configuration, the inner steerable instrument defining a working lumen; and an energy delivery device configured to be delivered through the outer and inner steerable instruments via the working lumen, the energy delivery device being operable to treat the tissue structure.

20. The system of claim 19, wherein the energy delivery device comprises at least one of a radiofrequency (RF) electrode, a laser, or an ultrasound device.

* * * * *